US009493522B2

(12) United States Patent
Wells et al.

(10) Patent No.: US 9,493,522 B2
(45) Date of Patent: Nov. 15, 2016

(54) DISCOVERY OF CANDIDATE BIOMARKERS OF IN VIVO APOPTOSIS BY GLOBAL PROFILING OF CASPASE CLEAVAGE SITES

(75) Inventors: James A. Wells, Burlingame, CA (US); Sami Mahrus, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 351 days.

(21) Appl. No.: 13/016,710

(22) Filed: Jan. 28, 2011

(65) Prior Publication Data

US 2012/0028266 A1 Feb. 2, 2012

Related U.S. Application Data

(63) Continuation of application No. PCT/US2009/052297, filed on Jul. 30, 2009.

(60) Provisional application No. 61/084,845, filed on Jul. 30, 2008.

(51) Int. Cl.
| | |
|---|---|
| *G01N 31/00* | (2006.01) |
| *G01N 33/53* | (2006.01) |
| *C07K 14/47* | (2006.01) |
| *C12Q 1/37* | (2006.01) |
| *G01N 33/573* | (2006.01) |
| *G01N 33/574* | (2006.01) |
| *G01N 33/68* | (2006.01) |

(52) U.S. Cl.
CPC ........... *C07K 14/47* (2013.01); *C07K 14/4747* (2013.01); *C12Q 1/37* (2013.01); *G01N 33/573* (2013.01); *G01N 33/574* (2013.01); *G01N 33/6848* (2013.01); *G01N 2333/96466* (2013.01); *G01N 2510/00* (2013.01)

(58) Field of Classification Search
CPC ................... A61K 31/00; A61K 38/00; A61K 39/00; C07K 14/705; C07K 16/18; G01N 33/582; G01N 33/6893
See application file for complete search history.

(56) References Cited

U.S. PATENT DOCUMENTS 6,019,944 A 2/2000 Buechler

FOREIGN PATENT DOCUMENTS

| WO | WO 00/17648 A1 | 3/2000 |
| WO | WO 03/026861 A1 | 4/2003 |
| WO | WO 2008/054597 A2 | 5/2008 |

OTHER PUBLICATIONS

E Solary et al. (Cell Biology and Toxicology, 1998, vol. 14, pp. 121-132).*
Utz and Anderson (Cell Death and Differentiation (2000) vol. 7, pp. 589-602).*
Mahrus et al. (Cell, Sep. 5, 2008, vol. 134, No. 5, pp. 866-876).*
Widmann et al. (Journal of Biological Chemistry, 1998, vol. 27, pp. 7141-7147).*
Widmann et al., Journal of Biological Chemistry, 1998, vol. 27, pp. 7141-7147).*
Mahrus et al. Cell, 2008, vol. 134, No. 5, pp. 866-876.*
Widmann et al., Journal of Biological Chemistry, 1998, vol. 27, pp. 7141-7147.*
Mahrus et al. Cell, 2008, vol. 134, No. 5, pp. 866-876.*
Tascilar et al. (Annals of Oncology 10,Suppl. 4:S107-S110, 1999).*
Tockman et al. (Cancer Research 52:2711s-2718s, 1992).*
Abrahmsen et al., "Engineering Subtilisin and Its Substrates for Efficient Ligation of Peptide Bonds in Aqueous Solution", *Biochemistry*, 1991, 30(17):4151-4159.
Addona et al., "Multi-site assessment of the precision and reproducibility of multiple reaction monitoring-based measurements of proteins in plasma", *Nature Biotechnology*, 2009, 27(7):633-644.
Altschul et al., "Basic Local Alignment Search Tool", *Journal of Molecular Biology*, 1990, 215:403-410.
Altschul et al., "Gapped BLAST and PSI-BLAST: a new generation of protein database search programs", *Nucleic Acids Research*, 1997, 25(17):3389-3402.
Anderson et al., The Human Plasma Proteome: History, Character, and Diagnostic Prospects, *Molecular & Cellular Proteomics* 1.11, 2002, 1:845-867.
Anderson et al., "Mass Spectrometric Quantitation of Peptides and Proteins Using Stable Isotope Standards and Capture by Anti-Peptide Antibodies (SISCAPA)", *Journal of Proteome Research*, 2004, 3:235-244.
Atwell, S. and Wells, J.A., "Selection for improved subtiligases by phage display", *Proc. Natl. Acad. Sci. U.S.A.*, 1999, 96: 9497-9502.
Bao, J. J., "Capillary electrophoretic immunoassays", *Journal of Chromatography B*, 699, 1997, 463-480.
Barrett et al., *The Handbook of Proteolytic Enzymes*, 2nd ed. Academic Press, 2003 (Book).
Batzer et al., "Enhanced evolutionary PCR using oligonucleotides with inosine at the 3'-terminus", *Nucleic Acid Research*, 1991, 19(18):5081.
Beachy, S.H. and Repasky, E.A., "Using extracellular biomarkers for monitoring efficacy of therapeutics in cancer patients: an update", *Cancer Immunol Immunother*, 2008, 57:759-775.

(Continued)

*Primary Examiner* — Lisa Cook
(74) *Attorney, Agent, or Firm* — Mintz Levin Cohn Ferris Glovsky and Popeo, P.C.

(57) ABSTRACT

The present invention relates to the discovery of novel biomarkers of in vivo apoptosis based on a large number of caspase-like cleavage sites. These biomarkers are useful for detection and quantification of apoptosis in a biological sample. The invention also provides synthetic peptides and proteins corresponding to neo-epitopes created by proteolytic processing of these cleavage sites. The synthetic peptides can be used as standards to enable identification and quantitation of these biomarkers using mass spectrometry. The synthetic proteins can be used to generate antibodies and other binding reagents specific for these biomarkers. Methods for detecting apoptosis as well as for diagnosing or for providing a prognosis for a disease or disease state characterized by apoptosis are also provided herein. Finally, the invention provides compositions and kits for performing the methods of the invention.

3 Claims, 20 Drawing Sheets

(56) References Cited

OTHER PUBLICATIONS

Beckers et al., "Distinct pharmacological properties of second generation HDAC inhibitors with the benzamide or hydroxamate head group", *Int. J. Cancer*, 2007, 121(5):1138-1148.
Braisted et al., "Synthesis of Proteins by Subtiligase", *Methods in Enzymology*,1997, 289:298-313.
Brown, J.L. and Roberts, W.K., "Evidence that Approximately Eighty per Cent of the Soluble Proteins from Ehrlich Ascites Cells are $N^{\alpha}$-Acetylated*", *The Journal of Biological Chemistry*, 1976, 251(4):1009-1014.
Chang et al., "Subtiligase: A tool for semisynthesis of proteins", *Proc. Natl. Acad. Sci. USA*, 1994, 91:12544-12548.
*Current Protocols in Molecular Biology* (Ausubel et al., eds. 1987-2005, Wiley Interscience), 18 pages.
De Haas et al., "Clinical Evaluation of M30 and M65 ELISA Cell Death Assays as Circulating Biomarkers in a Drug-Sensitive Tumor, Testicular Cancer[1] ", *Neoplasia*, 2008, 10(10):1041-1048.
Elbashir et al., "Functional anatomy of siRNAs for mediating efficient RNAi *Drosophila melanogaster* embryo lysate", *The EMBO Journal*, 2001, 20(23):6877-6888.
Fink et al., "Measurement of Proteins with the Behring Nephelometer A Multicentre Evaluation", *J. Clin. Chem. Clin. Biochem.*, 1989, 27:261-276.
*Harrison's Principles of Internal Medicine*, (Kasper, et al., eds., 16th ed., 2005) Chapter 70, 21 pages.
Henikoff, S. and Henikoff J.G., "Amino acid substitution matrices from protein blocks", *Proc. Natl. Acad. Sci. USA*, 1989, 89:10915-10919.
Kaufmann, S.H. and Earnshaw, W.C., "Minireview: Induction of Apoptosis by Cancer Chemotherapy", *Experimental Cell Research*, 2000, 256:42-49.
Kramer et al., "Docetaxel induces apoptosis in hormone refractory prostate carcinomas during multiple treatment cycles", *British Journal of Cancer*, 2006, 94:1592-1598.
Ku et al., "Keratins Let Liver Live: Mutations Predispose to Liver Disease and Crosslinking Generates Mallory-Denk Bodies," *Hepatology*, 2007, 46(5):1639-1649.
Linder et al., "Determining tumor apoptosis and necrosis in patient serum using cytokeratin 18 as a biomarker", *Cancer Letters*, 2004, 1-9.
Lüthi, A. and Martin, S.J., "The CASBAH: a searchable database of caspase substrates", *Cell Death and Differentiation*, 2007, 14:641-650.
Mahrus et al., "Degradomics: The proteolysis of cell death," *Molecular & Cellular Proteomics*, 2007, 6(8):51.
McCafferty et al., "Phage antibodies: filamentous phage displaying antibody variable domains", *Nature*, 1990, 348:552-554.
McIntosh, M. and Fitzgibbon, M., "Biomarker validation by targeted mass spectrometry", *Nature Biotechnology*, 2009, 27(7):622-623.
Needleman, S.B. and Wunsch, C.D., "A General Method Applicable to the Search of Similarities in the Amino Acid Sequence of Two Proteins", *J. Mol. Biol.*, 1970, 48:443-453.
Ng, J.H. and Ilag, L.L., "Biomedical applications of protein chips", *J. Cell Mol. Med.*, 2002, 6(3):329-340.
Ohtsuka et al., "An Alternative Approach to Deoxyoligonucleotides as Hybridization Probes by Insertion of Deoxyinosine at Ambiguous Codon Positions*", *The Journal of Biological Chemistry*, 1985, 260(5):2605-2608.
Olofsson et al., "Cytokeratin-18 is a Useful Serum Biomarker for Early Determination of Response of Breast Carcinomas to Chemotherapy", *Clinical Cancer Research*, 2007, 13:3198-3206.
Pearson, W.R. and Lipman, D.J., "Improved tools for biological sequence comparison", *Proc. Nat'l. Acad. Sci. USA*, 1988, 85:2444-2448.
Rifai et al., "Protein biomarker discovery and validation: the long and uncertain path to clinical utility", *Nature Biotechnology*, 2006, 24(8):971-983.
Rigaut et al., "A generic protein purification method for protein complex characterization and proteome exploration", *Nature Biotechnology*, 1999, 17:1030-1032.
Rongen et al., "Liposomes and immunoassays", *Journal of Immunological Methods*, 1997, 204:105-133.
Rossolini et al., "Use of deoxyinosine-containing primers vs degenerate primers for polymerase chain reaction based on ambiguous sequence information", *Molecular and Cellular Probes*, 1994, 8:91-98.
Schilling, O. and Overall, C.M., "Proteomic discovery of protease substrates," *Current Opinion in Chemical Biology*, 2007, 11(1):36-45.
Schilling, O. and Overall, C.M., "Proteome-derived, database-searchable peptide libraries for identifying protease cleavage sites", *Nature Biotechology*, 2008, 26(6):685-694.
Schmalzing, D. and Nashabeh, W., "Capillary electrophoresis based immunoassays: A critical review", *Electrophoresis*, 1997,18:2184-2193.
Self, C.H. and Cook, D.B., "Advances in immunoassay technology", *Curr. Opin. Biotechnol.*, 1996, 7:60-65.
Shi, Yigong, "Caspase Activation: Revisiting the Induced Proximity Model", *Cell*, 2004, 117:855-858.
Simon et al., "Comparative Assessment of Large-Scale Proteomic Studies of Apoptotic Proteolysis," *ACS Chemical Biology*, 2009, 4(6):401-408.
Smith, T.F. and Waterman, M.S., "Comparison of Biosequences", *Advances in Applied Mathematics*, 1981, 2:482-489.
Stennicke et al., "Internally quenched fluorescent peptide substrates disclose the subsite preferences of human caspases 1, 3, 6, 7 and 8", *Biochem J.*, 2000, 350:563-568.
Taylor et al., "Apoptosis: controlled demolition at the cellular level", *Nature Reviews Molecular Cell Biology*, 2008, 9:231-241.
Thornberry et al., "A Combinatorial Approach Defines Specificities of Members of the Caspase Family and Granzyme B: Functional Relationships Established for Key Mediators of Apoptosis", *The Journal of Biological Chemistry*, 1997, 272(29):17907-1791.
Thornberry, N.A. and Lazebnik, Y., "Caspases: Enemies Within", Thornberry, *Science*, 1998, 281:1312-1316.
Ulukaya et al., "The levels of caspase-cleaved cytokeratin 18 are elevated in serum from patients with lung cancer and helpful to predict the survival," *Lung Cancer, Elsevier*, 2007, 56(3):399-404.
Wells et al., "Clonging, sequencing, and secretion of *Bacillus amyloliquefaciens* subtilisin in *Bacillus sutilis*", *Nucleic Acids Research*, 1983,11(22):7911-7925.
Yamazaki et al., "Nonsteroidal Anti-inflammatory Drugs Induce Apoptosis in Association with Activation of Preoxisome Proliferator-Activated Receptor γ in Rheumatoid Synovial Cells", *The Journal of Pharmacology and Experimental Therapeutics*, 2002, 302(1):18-25.
International Preliminary Report on Patentability and Written Opinion dated Feb. 1, 2011 for International Application No. PCT/US2009/052297, 8 pages.
International Search Report dated Mar. 15, 2010 for International Application No. PCT/US2009/052297, 7 pages.
U.S. Appl. No. 12/524,557, filed on Jul. 24, 2009.

* cited by examiner

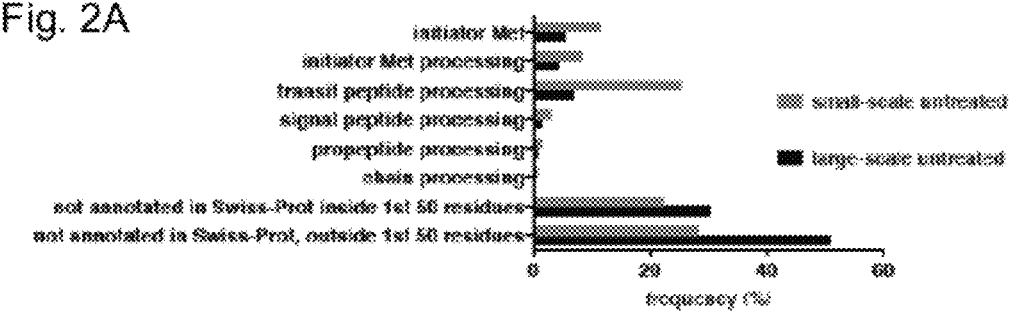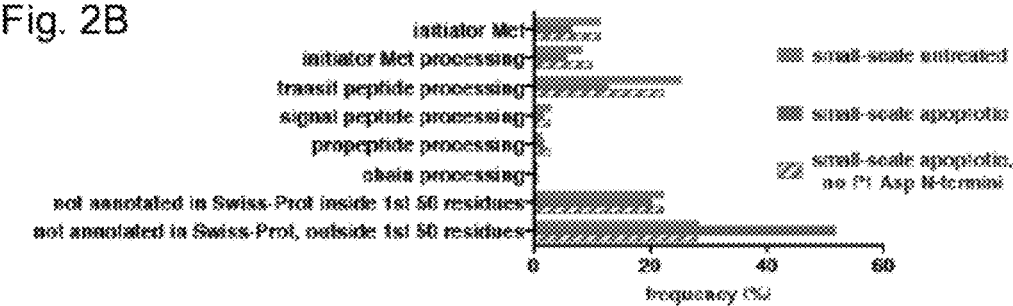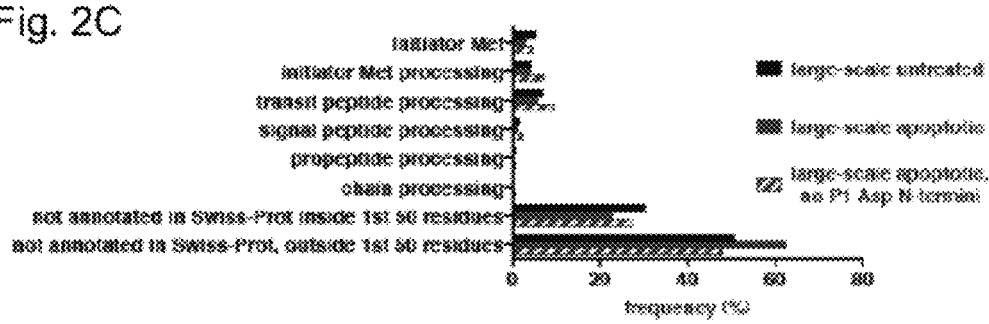

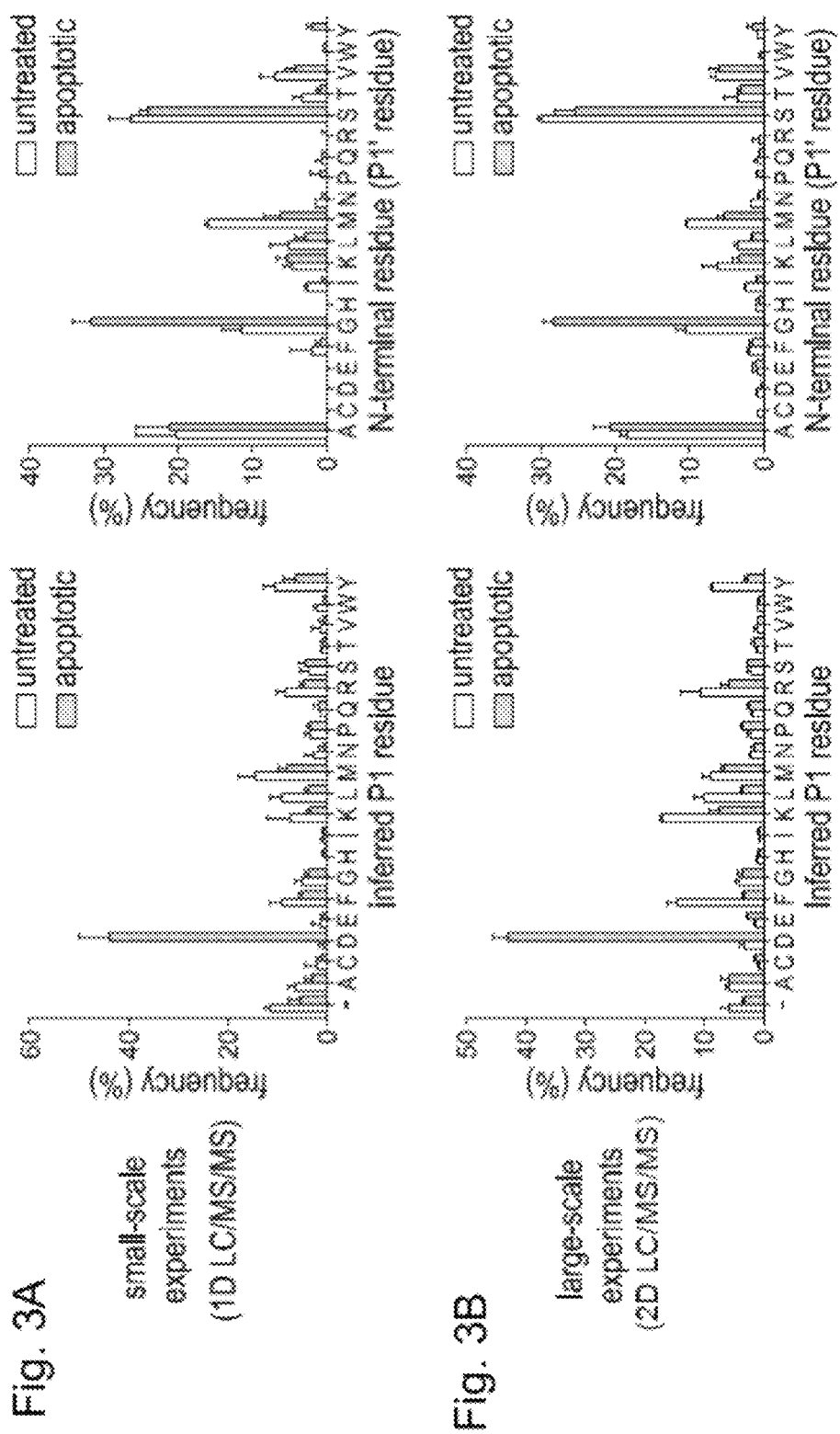
Fig. 3A small-scale experiments (1D LC/MS/MS)
Fig. 3B large-scale experiments (2D LC/MS/MS)

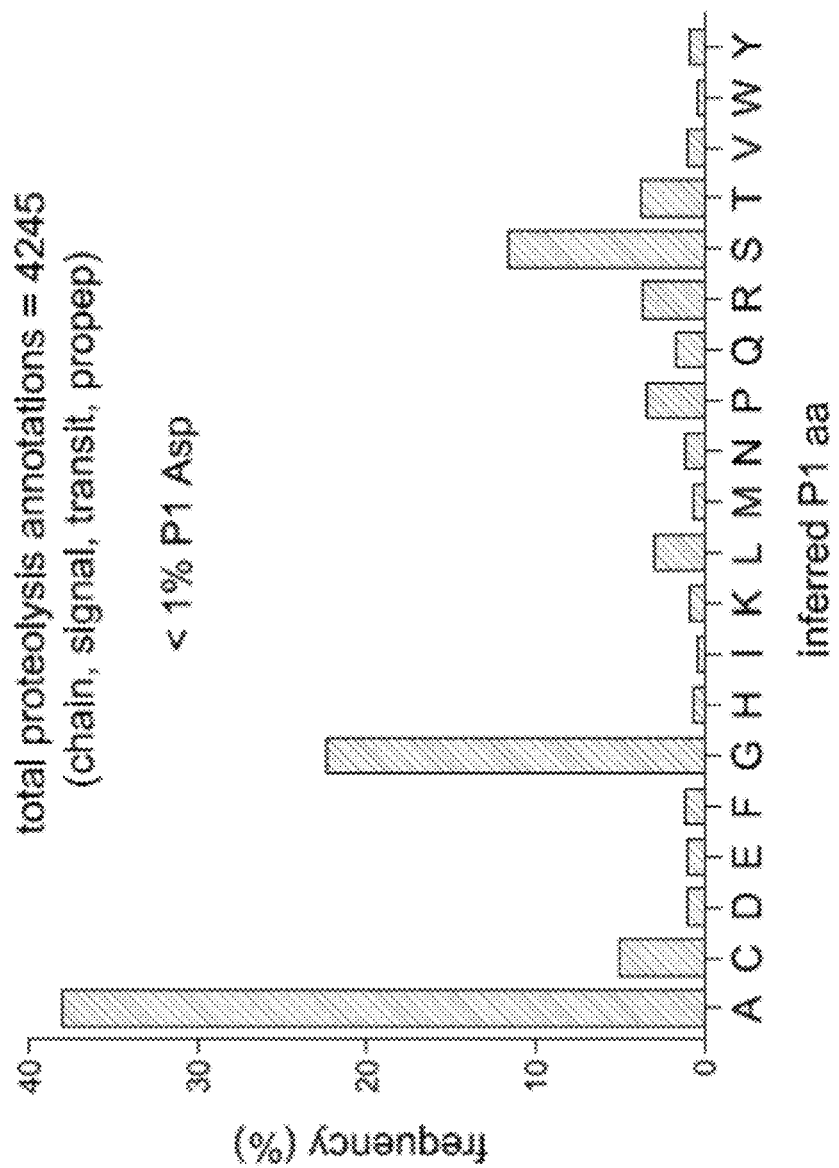

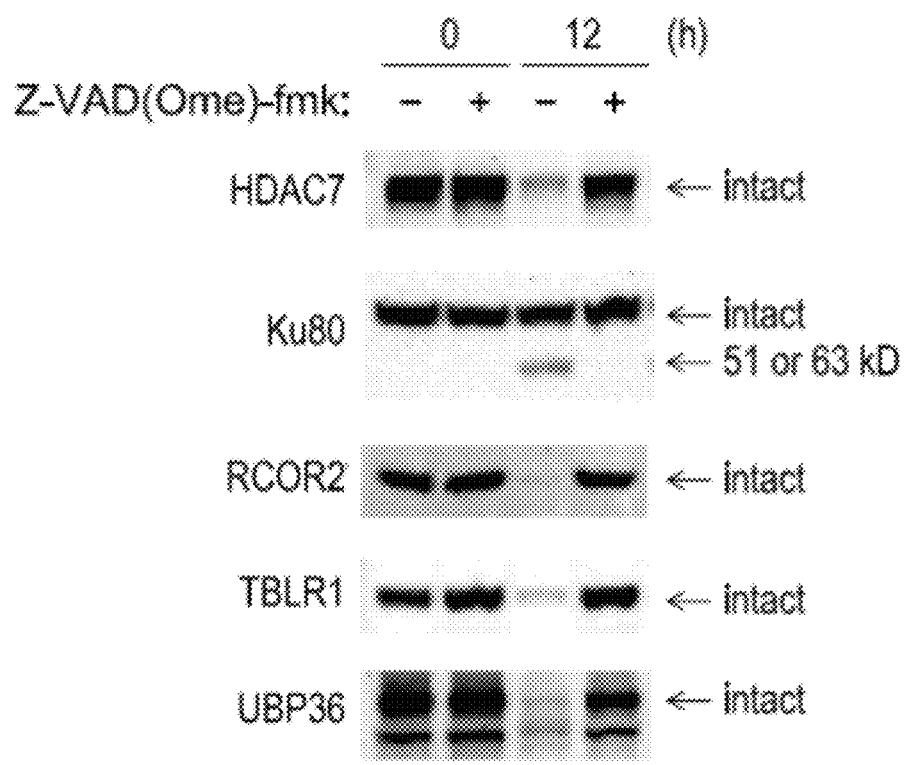

caspase-1 (inflammatory)

caspase-3 (executioner)

caspase-8 (initiator)

SEQUENCE LISTING

<160> NUMBER OF SEQ ID NOS: 438

<210> SEQ ID NO 1
<211> LENGTH: 22
<212> TYPE: PRT
<213> ORGANISM: Homo sapiens

<400> SEQUENCE: 1

Ala Ala Gln Ala Pro Ala Glu Gln Pro His Ser Ser Ser Asp Ala Ala
1               5                   10                  15

Gln Ala Pro Cys Pro Arg

20

<210> SEQ ID NO 2
<211> LENGTH: 10
<212> TYPE: PRT
<213> ORGANISM: Homo sapiens

<400> SEQUENCE: 2

Ala Val Ala Glu Pro Ala Asn Ala Val Lys
1               5                   10

<210> SEQ ID NO 3
<211> LENGTH: 14
<212> TYPE: PRT
<213> ORGANISM: Homo sapiens

<400> SEQUENCE: 3

Ala Val Ala Glu Pro Ala Asn Ala Val Lys Gly Ala Gly Lys
1               5                   10

<210> SEQ ID NO 4
<211> LENGTH: 17
<212> TYPE: PRT
<213> ORGANISM: Homo sapiens

<400> SEQUENCE: 4

Ala Val Ala Glu Pro Ala Asn Ala Val Lys Gly Ala Gly Lys Glu Met
1               5                   10                  15

Lys

<210> SEQ ID NO 5
<211> LENGTH: 23
<212> TYPE: PRT
<213> ORGANISM: Homo sapiens

<400> SEQUENCE: 5

Gly Leu Val Ser Pro Ser Asn Asn Ser Lys Glu Asp Ala Phe Ser Gly
1               5                   10                  15

Thr Asp Trp Met Leu Glu Lys
            20

<210> SEQ ID NO 6
<211> LENGTH: 14
<212> TYPE: PRT
<213> ORGANISM: Homo sapiens

<400> SEQUENCE: 6

Gly Ser Gly Met Leu Asp Glu Asp Glu Asp Leu Gln Arg
1               5                   10

<210> SEQ ID NO 7
<211> LENGTH: 11
<212> TYPE: PRT
<213> ORGANISM: Homo sapiens

<400> SEQUENCE: 7

Ser Val Thr Asp Thr Glu Pro Glu Asp Glu Lys
1               5                   10

<210> SEQ ID NO 8
<211> LENGTH: 17
<212> TYPE: PRT
<213> ORGANISM: Homo sapiens

```
<400> SEQUENCE: 8

Ser Val Thr Asp Thr Glu Pro Glu Asp Glu Lys Val Val Ser Tyr Ser
1               5                   10                  15

Lys

<210> SEQ ID NO 9
<211> LENGTH: 25
<212> TYPE: PRT
<213> ORGANISM: Homo sapiens

<400> SEQUENCE: 9

Tyr Val Val Pro Val Glu Asp Asn Asp Glu Asn Tyr Ile His Pro Thr
1               5                   10                  15

Glu Ser Ser Ser Pro Pro Pro Glu Lys
            20                  25

<210> SEQ ID NO 10
<211> LENGTH: 21
<212> TYPE: PRT
<213> ORGANISM: Homo sapiens

<400> SEQUENCE: 10

Met His Gly Asp Ser Glu Tyr Asn Ile Met Phe Gly Pro Asp Ile Cys
1               5                   10                  15

Gly Pro Gly Thr Lys
            20

<210> SEQ ID NO 11
<211> LENGTH: 14
<212> TYPE: PRT
<213> ORGANISM: Homo sapiens

<400> SEQUENCE: 11

Gly Ser Asp Val Val Ser Asp Leu Glu His Glu Glu Met Lys
1               5                   10

<210> SEQ ID NO 12
<211> LENGTH: 12
<212> TYPE: PRT
<213> ORGANISM: Homo sapiens

<400> SEQUENCE: 12

Gly Gly Pro Pro Cys Ala Pro Gly Gly Thr Ala Lys
1               5                   10

<210> SEQ ID NO 13
<211> LENGTH: 41
<212> TYPE: PRT
<213> ORGANISM: Homo sapiens

<400> SEQUENCE: 13

Gly Phe Gln Ser Glu Ser Pro Glu Lys Leu Asp Pro Val Glu Gln Gly
1               5                   10                  15

Gln Glu Asp Thr Val Ala Pro Glu Val Ala Ala Glu Lys Pro Val Gly
            20                  25                  30

Ala Leu Leu Gly Pro Gly Ala Glu Arg
            35                  40

<210> SEQ ID NO 14
<211> LENGTH: 19
<212> TYPE: PRT
<213> ORGANISM: Homo sapiens
```

<400> SEQUENCE: 14

Gly Gly Gly Asp Asn Lys Glu Gly Glu Asp Ser Ser Val Ile His Tyr
1               5                   10                  15

Asp Asp Lys

<210> SEQ ID NO 15
<211> LENGTH: 23
<212> TYPE: PRT
<213> ORGANISM: Homo sapiens

<400> SEQUENCE: 15

Gly Gly Gly Asp Asn Lys Glu Gly Glu Asp Ser Ser Val Ile His Tyr
1               5                   10                  15

Asp Asp Lys Ala Ile Glu Arg
            20

<210> SEQ ID NO 16
<211> LENGTH: 18
<212> TYPE: PRT
<213> ORGANISM: Homo sapiens

<400> SEQUENCE: 16

Gly Phe Tyr Met Glu Asp Gly Asp Pro Ser Val Ala Gln Leu Leu His
1               5                   10                  15

Glu Arg

<210> SEQ ID NO 17
<211> LENGTH: 10
<212> TYPE: PRT
<213> ORGANISM: Homo sapiens

<400> SEQUENCE: 17

Gly Thr Leu Ser Thr Ile Glu Phe Gln Arg
1               5                   10

<210> SEQ ID NO 18
<211> LENGTH: 25
<212> TYPE: PRT
<213> ORGANISM: Homo sapiens

<400> SEQUENCE: 18

Gly Ser Leu Gly Asp Asp Phe Asp Ala Asn Asp Glu Pro Asp His Thr
1               5                   10                  15

Ala Val Gly Asp His Glu Glu Phe Arg
            20                  25

<210> SEQ ID NO 19
<211> LENGTH: 16
<212> TYPE: PRT
<213> ORGANISM: Homo sapiens

<400> SEQUENCE: 19

Gly Phe Val Glu Ala Thr Glu Gly Leu Gly Asp Asp Ala Leu Gly Lys
1               5                   10                  15

<210> SEQ ID NO 20
<211> LENGTH: 10
<212> TYPE: PRT
<213> ORGANISM: Homo sapiens

<400> SEQUENCE: 20

```
Leu Phe Gly Thr Thr Asp Ala Val Val Lys
1               5                   10
```

```
<210> SEQ ID NO 21
<211> LENGTH: 19
<212> TYPE: PRT
<213> ORGANISM: Homo sapiens

<400> SEQUENCE: 21

Gly Val Ala Asp Ser Thr Val Ile Ser Ser Met Pro Cys Leu Leu Met
1               5                   10                  15

Glu Leu Arg
```

```
<210> SEQ ID NO 22
<211> LENGTH: 20
<212> TYPE: PRT
<213> ORGANISM: Homo sapiens

<400> SEQUENCE: 22

Gly Val Ala Asp Ser Thr Val Ile Ser Ser Met Pro Cys Leu Leu Met
1               5                   10                  15

Glu Leu Arg Arg
            20
```

```
<210> SEQ ID NO 23
<211> LENGTH: 14
<212> TYPE: PRT
<213> ORGANISM: Homo sapiens

<400> SEQUENCE: 23

Gly Lys Gly Gln Glu Val Glu Thr Ser Val Thr Tyr Tyr Arg
1               5                   10
```

```
<210> SEQ ID NO 24
<211> LENGTH: 22
<212> TYPE: PRT
<213> ORGANISM: Homo sapiens

<400> SEQUENCE: 24

Ala Leu Pro Asp Asp Thr Val Ile Glu Ser Glu Ala Leu Pro Ser Asp
1               5                   10                  15

Ile Ala Ala Glu Ala Arg
            20
```

```
<210> SEQ ID NO 25
<211> LENGTH: 11
<212> TYPE: PRT
<213> ORGANISM: Homo sapiens

<400> SEQUENCE: 25

Ala Val Ala Thr Glu Ala Ala Thr Ile Asp Arg
1               5                   10
```

```
<210> SEQ ID NO 26
<211> LENGTH: 11
<212> TYPE: PRT
<213> ORGANISM: Homo sapiens

<400> SEQUENCE: 26

Ala Leu Leu Glu Glu Gly Leu Cys Ala Pro Lys
1               5                   10
```

```
<210> SEQ ID NO 27
```

```
<211> LENGTH: 28
<212> TYPE: PRT
<213> ORGANISM: Homo sapiens

<400> SEQUENCE: 27

Ser Met Gly Ala Asp Pro Gly Pro Asp Glu Lys Asp Pro Leu Gly
1               5                   10                  15

Ala Glu Ala Ala Pro Gly Ala Leu Gly Gln Val Lys
            20                  25

<210> SEQ ID NO 28
<211> LENGTH: 30
<212> TYPE: PRT
<213> ORGANISM: Homo sapiens

<400> SEQUENCE: 28

Ser Met Gly Ala Asp Pro Gly Pro Asp Glu Lys Asp Pro Leu Gly
1               5                   10                  15

Ala Glu Ala Ala Pro Gly Ala Leu Gly Gln Val Lys Ala Lys
            20                  25                  30

<210> SEQ ID NO 29
<211> LENGTH: 20
<212> TYPE: PRT
<213> ORGANISM: Homo sapiens

<400> SEQUENCE: 29

Ser Val Pro Gly Pro Ala Val Ala Ala Ser Lys Glu Asn Leu Pro Val
1               5                   10                  15

Leu Asn Thr Arg
            20

<210> SEQ ID NO 30
<211> LENGTH: 17
<212> TYPE: PRT
<213> ORGANISM: Homo sapiens

<400> SEQUENCE: 30

Val Val Met Ala Ala Thr Glu Pro Glu Leu Leu Asp Asp Gln Glu Ala
1               5                   10                  15

Lys

<210> SEQ ID NO 31
<211> LENGTH: 18
<212> TYPE: PRT
<213> ORGANISM: Homo sapiens

<400> SEQUENCE: 31

Val Val Met Ala Ala Thr Glu Pro Glu Leu Leu Asp Asp Gln Glu Ala
1               5                   10                  15

Lys Arg

<210> SEQ ID NO 32
<211> LENGTH: 20
<212> TYPE: PRT
<213> ORGANISM: Homo sapiens

<400> SEQUENCE: 32

Met Trp Val Glu Pro Glu Ala Ala Ala Tyr Ala Pro Pro Pro Pro Ala
1               5                   10                  15

Lys Lys Pro Arg
            20
```

<210> SEQ ID NO 33
<211> LENGTH: 10
<212> TYPE: PRT
<213> ORGANISM: Homo sapiens

<400> SEQUENCE: 33

Ala Ile Gly Gln Thr Leu Val Asp Pro Lys
1               5                   10

<210> SEQ ID NO 34
<211> LENGTH: 16
<212> TYPE: PRT
<213> ORGANISM: Homo sapiens

<400> SEQUENCE: 34

Ala Ile Gly Gln Thr Leu Val Asp Pro Lys Gln Pro Leu Gln Ala Arg
1               5                   10                  15

<210> SEQ ID NO 35
<211> LENGTH: 26
<212> TYPE: PRT
<213> ORGANISM: Homo sapiens

<400> SEQUENCE: 35

Ser Leu Val Ala Pro Asp Thr Pro Ile Gln Phe Asp Ile Ile Ser Pro
1               5                   10                  15

Val Cys Glu Asp Gln Pro Gly Gln Ala Lys
            20                  25

<210> SEQ ID NO 36
<211> LENGTH: 17
<212> TYPE: PRT
<213> ORGANISM: Homo sapiens

<400> SEQUENCE: 36

His Tyr Val Gly Pro Ala Gln Pro Val Pro Gly Gly Pro Pro Pro Ser
1               5                   10                  15

Arg

<210> SEQ ID NO 37
<211> LENGTH: 24
<212> TYPE: PRT
<213> ORGANISM: Homo sapiens

<400> SEQUENCE: 37

His Tyr Val Gly Pro Ala Gln Pro Val Pro Gly Gly Pro Pro Pro Ser
1               5                   10                  15

Arg Gly Ser Val Pro Val Leu Arg
            20

<210> SEQ ID NO 38
<211> LENGTH: 9
<212> TYPE: PRT
<213> ORGANISM: Homo sapiens

<400> SEQUENCE: 38

Gly Ile Gly Tyr Val Glu Asp Gly Arg
1               5

<210> SEQ ID NO 39
<211> LENGTH: 11
<212> TYPE: PRT

<213> ORGANISM: Homo sapiens

<400> SEQUENCE: 39

Gly Cys Pro Ala Asn Leu Leu Ser Ser His Arg
1               5                   10

<210> SEQ ID NO 40
<211> LENGTH: 22
<212> TYPE: PRT
<213> ORGANISM: Homo sapiens

<400> SEQUENCE: 40

Ser Leu Gly Ala Asp Gly Thr His Gly Ala Gly Ala Met Glu Ser Ala
1               5                   10                  15

Ala Gly Val Leu Ile Lys
            20

<210> SEQ ID NO 41
<211> LENGTH: 16
<212> TYPE: PRT
<213> ORGANISM: Homo sapiens

<400> SEQUENCE: 41

Ser Val Gly Asn Asp Val Asp Val Val Ser Asp Ser Glu Asn Ile Lys
1               5                   10                  15

<210> SEQ ID NO 42
<211> LENGTH: 17
<212> TYPE: PRT
<213> ORGANISM: Homo sapiens

<400> SEQUENCE: 42

Ser Val Gly Asn Asp Val Asp Val Val Ser Asp Ser Glu Asn Ile Lys
1               5                   10                  15

Lys

<210> SEQ ID NO 43
<211> LENGTH: 23
<212> TYPE: PRT
<213> ORGANISM: Homo sapiens

<400> SEQUENCE: 43

Ser Ser Ala Glu Leu Gln Ser Leu Glu Gln Gln Leu Glu Glu Ala Gln
1               5                   10                  15

Thr Glu Asn Phe Asn Ile Lys
            20

<210> SEQ ID NO 44
<211> LENGTH: 28
<212> TYPE: PRT
<213> ORGANISM: Homo sapiens

<400> SEQUENCE: 44

Gly Leu Val Thr Asp Ser Ser Ala Glu Leu Gln Ser Leu Glu Gln Gln
1               5                   10                  15

Leu Glu Glu Ala Gln Thr Glu Asn Phe Asn Ile Lys
            20                  25

<210> SEQ ID NO 45
<211> LENGTH: 15
<212> TYPE: PRT
<213> ORGANISM: Homo sapiens

<400> SEQUENCE: 45

Leu Phe Gly Ser Asp Asp Glu Glu Ser Glu Glu Ala Lys Arg
1               5                   10                  15

<210> SEQ ID NO 46
<211> LENGTH: 14
<212> TYPE: PRT
<213> ORGANISM: Homo sapiens

<400> SEQUENCE: 46

Leu Phe Gly Ser Asp Asp Glu Glu Ser Glu Glu Ala Lys
1               5                   10

<210> SEQ ID NO 47
<211> LENGTH: 26
<212> TYPE: PRT
<213> ORGANISM: Homo sapiens

<400> SEQUENCE: 47

Ser Gln Gln Pro Pro Gly Gly Ser Ser Pro Ser Glu Glu Pro Pro
1               5                   10                  15

Ser Pro Gly Glu Glu Ala Gly Leu Gln Arg
            20                  25

<210> SEQ ID NO 48
<211> LENGTH: 20
<212> TYPE: PRT
<213> ORGANISM: Homo sapiens

<400> SEQUENCE: 48

Asn Trp Asp Asp Asp Asp Asp Glu Lys Lys Glu Glu Ala Glu Val Lys
1               5                   10                  15

Pro Glu Val Lys
            20

<210> SEQ ID NO 49
<211> LENGTH: 14
<212> TYPE: PRT
<213> ORGANISM: Homo sapiens

<400> SEQUENCE: 49

Gly Ile Pro Glu Val Met Glu Thr Gln Gln Val Gln Glu Lys
1               5                   10

<210> SEQ ID NO 50
<211> LENGTH: 22
<212> TYPE: PRT
<213> ORGANISM: Homo sapiens

<400> SEQUENCE: 50

Gly Arg Pro Pro Glu Glu Ser Ala His Glu Met Met Glu Glu Glu Glu
1               5                   10                  15

Glu Ile Pro Lys Pro Lys
            20

<210> SEQ ID NO 51
<211> LENGTH: 14
<212> TYPE: PRT
<213> ORGANISM: Homo sapiens

<400> SEQUENCE: 51

Gly Thr Ser Glu Leu Glu Glu Pro Leu Gly Glu Asp Pro Arg
1               5                   10

<210> SEQ ID NO 52
<211> LENGTH: 23
<212> TYPE: PRT
<213> ORGANISM: Homo sapiens

<400> SEQUENCE: 52

Ala Ala Ala Ala Thr Pro Ala Ala Pro Ser Pro Ala Ser Leu Pro Leu
1               5                   10                  15

Ala Pro Gly Cys Ala Leu Arg
            20

<210> SEQ ID NO 53
<211> LENGTH: 11
<212> TYPE: PRT
<213> ORGANISM: Homo sapiens

<400> SEQUENCE: 53

Gly His Arg Ala Pro Pro Leu Val Gln Arg
1               5                   10

<210> SEQ ID NO 54
<211> LENGTH: 13
<212> TYPE: PRT
<213> ORGANISM: Homo sapiens

<400> SEQUENCE: 54

Ala Ala Ser Gln Pro Ser Lys Gly Gly Leu Leu Glu Arg
1               5                   10

<210> SEQ ID NO 55
<211> LENGTH: 25
<212> TYPE: PRT
<213> ORGANISM: Homo sapiens

<400> SEQUENCE: 55

Gly Leu Met Ala Thr Thr Ala Ser Gly Asp Ile Thr Asn Gln Asn Ser
1               5                   10                  15

Leu Ala Gly Gly Lys Asn Gln Gly Lys
            20                  25

<210> SEQ ID NO 56
<211> LENGTH: 21
<212> TYPE: PRT
<213> ORGANISM: Homo sapiens

<400> SEQUENCE: 56

Gly Ser Pro Val Pro Ser Ser Pro Phe Gln Val Pro Val Thr Glu Gly
1               5                   10                  15

Cys Asp Pro Ser Arg
            20

<210> SEQ ID NO 57
<211> LENGTH: 23
<212> TYPE: PRT
<213> ORGANISM: Homo sapiens

<400> SEQUENCE: 57

Gly Ser Pro Val Pro Ser Ser Pro Phe Gln Val Pro Val Thr Glu Gly
1               5                   10                  15

Cys Asp Pro Ser Arg Val Arg
            20

```
<210> SEQ ID NO 58
<211> LENGTH: 21
<212> TYPE: PRT
<213> ORGANISM: Homo sapiens

<400> SEQUENCE: 58

Gly Val Pro Val Pro Gly Ser Pro Phe Pro Leu Glu Ala Val Ala Pro
1               5                   10                  15

Thr Lys Pro Ser Lys
            20

<210> SEQ ID NO 59
<211> LENGTH: 23
<212> TYPE: PRT
<213> ORGANISM: Homo sapiens

<400> SEQUENCE: 59

Gly Val Pro Val Pro Gly Ser Pro Phe Pro Leu Glu Ala Val Ala Pro
1               5                   10                  15

Thr Lys Pro Ser Lys Val Lys
            20

<210> SEQ ID NO 60
<211> LENGTH: 39
<212> TYPE: PRT
<213> ORGANISM: Homo sapiens

<400> SEQUENCE: 60

Gly Val Pro Val Pro Gly Ser Pro Phe Pro Leu Glu Ala Val Ala Pro
1               5                   10                  15

Thr Lys Pro Ser Lys Val Lys Ala Phe Gly Pro Gly Leu Gln Gly Gly
            20                  25                  30

Ser Ala Gly Ser Pro Ala Arg
            35

<210> SEQ ID NO 61
<211> LENGTH: 19
<212> TYPE: PRT
<213> ORGANISM: Homo sapiens

<400> SEQUENCE: 61

Ser Ala Val Ala Gly Ala Ala Pro Ala Leu Val Ala Ala Ala Ala Ala
1               5                   10                  15

Ser Val Arg

<210> SEQ ID NO 62
<211> LENGTH: 33
<212> TYPE: PRT
<213> ORGANISM: Homo sapiens

<400> SEQUENCE: 62

Gly Leu Val His Pro Pro Thr Ser Ala Ala Pro Val Thr Pro Leu
1               5                   10                  15

Arg Pro Pro Gly Leu Gly Ser Ala Ser Leu His Gly Gly Pro Ala
            20                  25                  30

Arg

<210> SEQ ID NO 63
<211> LENGTH: 14
<212> TYPE: PRT
<213> ORGANISM: Homo sapiens
```

<400> SEQUENCE: 63

Ser Ile Ser Ser Gln Leu Gly Pro Ile His Pro Pro Pro Arg
1               5                   10

<210> SEQ ID NO 64
<211> LENGTH: 14
<212> TYPE: PRT
<213> ORGANISM: Homo sapiens

<400> SEQUENCE: 64

Ser Asn Ser Thr Ile Gln Glu Ile Leu Ile Pro Ala Ser Lys
1               5                   10

<210> SEQ ID NO 65
<211> LENGTH: 16
<212> TYPE: PRT
<213> ORGANISM: Homo sapiens

<400> SEQUENCE: 65

Gly Lys Glu Phe Ser Gly Asn Pro Ile Lys Val Ser Phe Ala Thr Arg
1               5                   10                  15

<210> SEQ ID NO 66
<211> LENGTH: 10
<212> TYPE: PRT
<213> ORGANISM: Homo sapiens

<400> SEQUENCE: 66

Gly Lys Glu Phe Ser Gly Asn Pro Ile Lys
1               5                   10

<210> SEQ ID NO 67
<211> LENGTH: 23
<212> TYPE: PRT
<213> ORGANISM: Homo sapiens

<400> SEQUENCE: 67

Gly Ala Gly Asn Leu Asp Glu Glu Gln Asp Ser Glu Gly Glu Thr Tyr
1               5                   10                  15

Glu Asp Ile Glu Ala Ser Lys
            20

<210> SEQ ID NO 68
<211> LENGTH: 25
<212> TYPE: PRT
<213> ORGANISM: Homo sapiens

<400> SEQUENCE: 68

Gly Ala Gly Asn Leu Asp Glu Glu Gln Asp Ser Glu Gly Glu Thr Tyr
1               5                   10                  15

Glu Asp Ile Glu Ala Ser Lys Glu Arg
            20                  25

<210> SEQ ID NO 69
<211> LENGTH: 16
<212> TYPE: PRT
<213> ORGANISM: Homo sapiens

<400> SEQUENCE: 69

Ser Ala Ser Gln Ala Ala His Pro Gln Asp Ser Ala Phe Ser Tyr Arg
1               5                   10                  15

```
<210> SEQ ID NO 70
<211> LENGTH: 19
<212> TYPE: PRT
<213> ORGANISM: Homo sapiens

<400> SEQUENCE: 70

Ser Ala Ser Gln Ala Ala His Pro Gln Asp Ser Ala Phe Ser Tyr Arg
1               5                   10                  15

Asp Ala Lys

<210> SEQ ID NO 71
<211> LENGTH: 13
<212> TYPE: PRT
<213> ORGANISM: Homo sapiens

<400> SEQUENCE: 71

Ser Ala Ser Val His Asp Met Asp Tyr Val Asn Pro Arg
1               5                   10

<210> SEQ ID NO 72
<211> LENGTH: 20
<212> TYPE: PRT
<213> ORGANISM: Homo sapiens

<400> SEQUENCE: 72

Ser Ser Glu Lys Glu Leu Glu Pro Glu Ala Ala Glu Glu Ala Leu Glu
1               5                   10                  15

Asn Gly Pro Lys
            20

<210> SEQ ID NO 73
<211> LENGTH: 16
<212> TYPE: PRT
<213> ORGANISM: Homo sapiens

<400> SEQUENCE: 73

Gly Leu Gly Leu Ser Tyr Leu Ser Ser His Ile Ala Asn Val Glu Arg
1               5                   10                  15

<210> SEQ ID NO 74
<211> LENGTH: 25
<212> TYPE: PRT
<213> ORGANISM: Homo sapiens

<400> SEQUENCE: 74

Thr Ala Ser Thr Glu Glu Thr Asp Pro Glu Thr Ser Gln Pro Glu Pro
1               5                   10                  15

Asn Arg Pro Ser Glu Leu Asp Leu Arg
            20                  25

<210> SEQ ID NO 75
<211> LENGTH: 20
<212> TYPE: PRT
<213> ORGANISM: Homo sapiens

<400> SEQUENCE: 75

Gly Gly Gly Glu Val Ser Ser Gln Gly Pro Glu Asp Ser Leu Leu Gly
1               5                   10                  15

Thr Gln Ser Arg
            20

<210> SEQ ID NO 76
<211> LENGTH: 12
```

-continued

```
<212> TYPE: PRT
<213> ORGANISM: Homo sapiens

<400> SEQUENCE: 76

Ser Ala Met Glu Pro Thr Gly Pro Thr Gln Glu Arg
1               5                   10

<210> SEQ ID NO 77
<211> LENGTH: 30
<212> TYPE: PRT
<213> ORGANISM: Homo sapiens

<400> SEQUENCE: 77

Ser Ala Met Glu Pro Thr Gly Pro Thr Gln Glu Arg Tyr Lys Asp Gly
1               5                   10                  15

Val Val Thr Ile Gly Cys Val Gly Phe Pro Asn Val Gly Lys
            20                  25                  30

<210> SEQ ID NO 78
<211> LENGTH: 18
<212> TYPE: PRT
<213> ORGANISM: Homo sapiens

<400> SEQUENCE: 78

Ser Leu Ser Met Ser Thr Arg Pro Thr Cys Ser Glu Ser Val Pro Ser
1               5                   10                  15

Ala Lys

<210> SEQ ID NO 79
<211> LENGTH: 13
<212> TYPE: PRT
<213> ORGANISM: Homo sapiens

<400> SEQUENCE: 79

Gly Ala Gly Pro Ser Pro Glu Glu Lys Asp Phe Leu Lys
1               5                   10

<210> SEQ ID NO 80
<211> LENGTH: 9
<212> TYPE: PRT
<213> ORGANISM: Homo sapiens

<400> SEQUENCE: 80

Gly Ala Gly Pro Ser Pro Glu Glu Lys
1               5

<210> SEQ ID NO 81
<211> LENGTH: 18
<212> TYPE: PRT
<213> ORGANISM: Homo sapiens

<400> SEQUENCE: 81

Gly Ala Gly Pro Ser Pro Glu Glu Lys Asp Phe Leu Lys Thr Val Glu
1               5                   10                  15

Gly Arg

<210> SEQ ID NO 82
<211> LENGTH: 16
<212> TYPE: PRT
<213> ORGANISM: Homo sapiens

<400> SEQUENCE: 82

Gly Gln Ile Gln Gly Ser Val Glu Leu Ala Ala Pro Gly Gln Ala Lys
```

```
                1               5                   10                  15
```

<210> SEQ ID NO 83
<211> LENGTH: 16
<212> TYPE: PRT
<213> ORGANISM: Homo sapiens

<400> SEQUENCE: 83

```
Gly Val Pro Ala Glu Gly Ala Phe Thr Glu Asp Phe Gln Gly Leu Arg
1               5                   10                  15
```

<210> SEQ ID NO 84
<211> LENGTH: 11
<212> TYPE: PRT
<213> ORGANISM: Homo sapiens

<400> SEQUENCE: 84

```
Asn Ile Gln Gly Ile Thr Lys Pro Ala Ile Arg
1               5                   10
```

<210> SEQ ID NO 85
<211> LENGTH: 11
<212> TYPE: PRT
<213> ORGANISM: Homo sapiens

<400> SEQUENCE: 85

```
Phe Val Asn Asp Ile Ser Glu Lys Glu Gln Arg
1               5                   10
```

<210> SEQ ID NO 86
<211> LENGTH: 8
<212> TYPE: PRT
<213> ORGANISM: Homo sapiens

<400> SEQUENCE: 86

```
Phe Val Asn Asp Ile Ser Glu Lys
1               5
```

<210> SEQ ID NO 87
<211> LENGTH: 15
<212> TYPE: PRT
<213> ORGANISM: Homo sapiens

<400> SEQUENCE: 87

```
Gly Gly Gly Pro Gly Gln Val Val Asp Asp Gly Leu Glu His Arg
1               5                   10                  15
```

<210> SEQ ID NO 88
<211> LENGTH: 22
<212> TYPE: PRT
<213> ORGANISM: Homo sapiens

<400> SEQUENCE: 88

```
Thr Ala Val Ile Thr Pro Ala Met Leu Glu Glu Glu Glu Gln Leu Glu
1               5                   10                  15

Ala Ala Gly Leu Glu Arg
            20
```

<210> SEQ ID NO 89
<211> LENGTH: 13
<212> TYPE: PRT
<213> ORGANISM: Homo sapiens

<400> SEQUENCE: 89

```
Leu Ile Ser Asn Asn Glu Gln Leu Pro Met Leu Gly Arg
1               5                   10
```

<210> SEQ ID NO 90
<211> LENGTH: 16
<212> TYPE: PRT
<213> ORGANISM: Homo sapiens

<400> SEQUENCE: 90

```
Gly Ser Val Gln Ala Ala Trp Gly Pro Glu Leu Pro Ser His Arg
1               5                   10                  15
```

<210> SEQ ID NO 91
<211> LENGTH: 36
<212> TYPE: PRT
<213> ORGANISM: Homo sapiens

<400> SEQUENCE: 91

```
Gly Gly Ala Gly Ala Ser Ala Phe Glu Gln Ala Asp Leu Asn Gly Met
1               5                   10                  15

Thr Pro Glu Leu Pro Val Ala Val Pro Ser Gly Pro Phe Arg His Glu
            20                  25                  30

Gly Leu Ser Lys
        35
```

<210> SEQ ID NO 92
<211> LENGTH: 15
<212> TYPE: PRT
<213> ORGANISM: Homo sapiens

<400> SEQUENCE: 92

```
Ala Gly Cys Leu Pro Ala Glu Glu Val Asp Val Leu Leu Gln Arg
1               5                   10                  15
```

<210> SEQ ID NO 93
<211> LENGTH: 18
<212> TYPE: PRT
<213> ORGANISM: Homo sapiens

<400> SEQUENCE: 93

```
Ala Val Phe Pro Gly Pro Ser Leu Glu Pro Pro Ala Gly Ser Ser Gly
1               5                   10                  15

Val Lys
```

<210> SEQ ID NO 94
<211> LENGTH: 25
<212> TYPE: PRT
<213> ORGANISM: Homo sapiens

<400> SEQUENCE: 94

```
Gly Gly Tyr Gly Gly Phe Asp Asp Tyr Gly Gly Tyr Asn Asn Tyr Gly
1               5                   10                  15

Tyr Gly Asn Asp Gly Phe Asp Asp Arg
            20                  25
```

<210> SEQ ID NO 95
<211> LENGTH: 10
<212> TYPE: PRT
<213> ORGANISM: Homo sapiens

<400> SEQUENCE: 95

```
Gly His Tyr Ala Met Asp Asn Ile Thr Arg
1               5                   10
```

<210> SEQ ID NO 96
<211> LENGTH: 25
<212> TYPE: PRT
<213> ORGANISM: Homo sapiens

<400> SEQUENCE: 96

Ala Ser Glu Lys Pro Ala Glu Ala Thr Ala Gly Ser Gly Gly Val Asn
1               5                   10                  15

Gly Gly Glu Glu Gln Gly Leu Gly Lys
            20                  25

<210> SEQ ID NO 97
<211> LENGTH: 26
<212> TYPE: PRT
<213> ORGANISM: Homo sapiens

<400> SEQUENCE: 97

Ala Ser Glu Lys Pro Ala Glu Ala Thr Ala Gly Ser Gly Gly Val Asn
1               5                   10                  15

Gly Gly Glu Glu Gln Gly Leu Gly Lys Arg
            20                  25

<210> SEQ ID NO 98
<211> LENGTH: 11
<212> TYPE: PRT
<213> ORGANISM: Homo sapiens

<400> SEQUENCE: 98

Ala Val Glu Cys Leu Asn Tyr Gln His Tyr Lys
1               5                   10

<210> SEQ ID NO 99
<211> LENGTH: 20
<212> TYPE: PRT
<213> ORGANISM: Homo sapiens

<400> SEQUENCE: 99

Ala Val Glu Cys Leu Asn Tyr Gln His Tyr Lys Gly Ser Asp Phe Asp
1               5                   10                  15

Cys Glu Leu Arg
            20

<210> SEQ ID NO 100
<211> LENGTH: 31
<212> TYPE: PRT
<213> ORGANISM: Homo sapiens

<400> SEQUENCE: 100

Ser Ala Ile Asp Thr Trp Ser Pro Ser Glu Trp Gln Met Ala Tyr Glu
1               5                   10                  15

Pro Gln Gly Gly Ser Gly Tyr Asp Tyr Ser Tyr Ala Gly Gly Arg
            20                  25                  30

<210> SEQ ID NO 101
<211> LENGTH: 7
<212> TYPE: PRT
<213> ORGANISM: Homo sapiens

<400> SEQUENCE: 101

Tyr Ser Tyr Ala Gly Gly Arg
1               5

<210> SEQ ID NO 102
<211> LENGTH: 19
<212> TYPE: PRT
<213> ORGANISM: Homo sapiens

<400> SEQUENCE: 102

Tyr Thr Asn Pro Asn Leu Ser Gly Gln Gly Asp Pro Gly Ser Asn Pro
1               5                   10                  15

Asn Lys Arg

<210> SEQ ID NO 103
<211> LENGTH: 15
<212> TYPE: PRT
<213> ORGANISM: Homo sapiens

<400> SEQUENCE: 103

Ser Leu Ser Pro Glu Thr Tyr Gly Asn Phe Asp Ser Gln Ser Arg
1               5                   10                  15

<210> SEQ ID NO 104
<211> LENGTH: 24
<212> TYPE: PRT
<213> ORGANISM: Homo sapiens

<400> SEQUENCE: 104

Ala Gly Gly Glu Pro Asp Ser Leu Gly Gln Gln Pro Thr Asp Thr Pro
1               5                   10                  15

Tyr Glu Trp Asp Leu Asp Lys Lys
            20

<210> SEQ ID NO 105
<211> LENGTH: 29
<212> TYPE: PRT
<213> ORGANISM: Homo sapiens

<400> SEQUENCE: 105

Ala Gly Gly Glu Pro Asp Ser Leu Gly Gln Gln Pro Thr Asp Thr Pro
1               5                   10                  15

Tyr Glu Trp Asp Leu Asp Lys Lys Ala Trp Phe Pro Lys
            20                  25

<210> SEQ ID NO 106
<211> LENGTH: 15
<212> TYPE: PRT
<213> ORGANISM: Homo sapiens

<400> SEQUENCE: 106

Gly Ala Ser Ser Ser Thr Ala Asn Val Glu Asp Val His Ala Arg
1               5                   10                  15

<210> SEQ ID NO 107
<211> LENGTH: 11
<212> TYPE: PRT
<213> ORGANISM: Homo sapiens

<400> SEQUENCE: 107

Gly Leu Pro Glu Glu Gln Pro Gln Thr Thr Lys
1               5                   10

<210> SEQ ID NO 108
<211> LENGTH: 8
<212> TYPE: PRT
<213> ORGANISM: Homo sapiens

<400> SEQUENCE: 108

Met Asn Ala Ser Pro Leu Val Arg
1               5

<210> SEQ ID NO 109
<211> LENGTH: 11
<212> TYPE: PRT
<213> ORGANISM: Homo sapiens

<400> SEQUENCE: 109

Ser Ala Val Ala Ile Ser Gly Ala Asp Ser Arg
1               5                   10

<210> SEQ ID NO 110
<211> LENGTH: 18
<212> TYPE: PRT
<213> ORGANISM: Homo sapiens

<400> SEQUENCE: 110

Ser Val Leu Ala Val Met Pro Pro Asp Ile Ala Ala Glu Ala Gln Ala
1               5                   10                  15

Leu Arg

<210> SEQ ID NO 111
<211> LENGTH: 16
<212> TYPE: PRT
<213> ORGANISM: Homo sapiens

<400> SEQUENCE: 111

Ala Leu Ser Ser Asp Phe Thr Cys Gly Ser Pro Thr Ala Ala Gly Lys
1               5                   10                  15

<210> SEQ ID NO 112
<211> LENGTH: 17
<212> TYPE: PRT
<213> ORGANISM: Homo sapiens

<400> SEQUENCE: 112

Ala Leu Ser Ser Asp Phe Thr Cys Gly Ser Pro Thr Ala Ala Gly Lys
1               5                   10                  15

Lys

<210> SEQ ID NO 113
<211> LENGTH: 14
<212> TYPE: PRT
<213> ORGANISM: Homo sapiens

<400> SEQUENCE: 113

Ser Ser Ser Ala Pro Ser Lys Glu Gln Leu Glu Gln Glu Lys
1               5                   10

<210> SEQ ID NO 114
<211> LENGTH: 26
<212> TYPE: PRT
<213> ORGANISM: Homo sapiens

<400> SEQUENCE: 114

Ser Ser Ser Ala Pro Ser Lys Glu Gln Leu Glu Gln Glu Lys Gln Leu
1               5                   10                  15

Leu Leu Ser Phe Lys Pro Val Met Gln Lys
            20                  25

```
<210> SEQ ID NO 115
<211> LENGTH: 16
<212> TYPE: PRT
<213> ORGANISM: Homo sapiens

<400> SEQUENCE: 115

Ser Leu Lys Glu Ala Leu Thr Tyr Asp Gly Ala Leu Leu Gly Asp Arg
1               5                   10                  15

<210> SEQ ID NO 116
<211> LENGTH: 18
<212> TYPE: PRT
<213> ORGANISM: Homo sapiens

<400> SEQUENCE: 116

Gly Leu Thr Pro Gln Leu Glu Glu Asp Glu Glu Leu Gln Gly His Leu
1               5                   10                  15

Gly Arg

<210> SEQ ID NO 117
<211> LENGTH: 19
<212> TYPE: PRT
<213> ORGANISM: Homo sapiens

<400> SEQUENCE: 117

Gly Leu Thr Pro Gln Leu Glu Glu Asp Glu Glu Leu Gln Gly His Leu
1               5                   10                  15

Gly Arg Arg

<210> SEQ ID NO 118
<211> LENGTH: 21
<212> TYPE: PRT
<213> ORGANISM: Homo sapiens

<400> SEQUENCE: 118

Gly Ser Gly Ile Tyr Asp Pro Cys Glu Lys Glu Ala Thr Asp Ala Ile
1               5                   10                  15

Gly His Leu Asp Arg
            20

<210> SEQ ID NO 119
<211> LENGTH: 9
<212> TYPE: PRT
<213> ORGANISM: Homo sapiens

<400> SEQUENCE: 119

Cys Phe Leu Glu Glu Ile Met Thr Lys
1               5

<210> SEQ ID NO 120
<211> LENGTH: 23
<212> TYPE: PRT
<213> ORGANISM: Homo sapiens

<400> SEQUENCE: 120

Ala Val Thr Pro Gly Pro Gln Pro Thr Leu Glu Gln Leu Glu Glu Gly
1               5                   10                  15

Gly Pro Arg Pro Leu Glu Arg
            20

<210> SEQ ID NO 121
<211> LENGTH: 24
```

<212> TYPE: PRT
<213> ORGANISM: Homo sapiens

<400> SEQUENCE: 121

Ala Val Thr Pro Gly Pro Gln Pro Thr Leu Glu Gln Leu Glu Glu Gly
1               5                   10                  15

Gly Pro Arg Pro Leu Glu Arg Arg
            20

<210> SEQ ID NO 122
<211> LENGTH: 17
<212> TYPE: PRT
<213> ORGANISM: Homo sapiens

<400> SEQUENCE: 122

Gly Leu Gly Val Ala Arg Pro His Tyr Gly Ser Val Leu Asp Asn Glu
1               5                   10                  15

Arg

<210> SEQ ID NO 123
<211> LENGTH: 26
<212> TYPE: PRT
<213> ORGANISM: Homo sapiens

<400> SEQUENCE: 123

Gly Leu Gly Val Ala Arg Pro His Tyr Gly Ser Val Leu Asp Asn Glu
1               5                   10                  15

Arg Leu Thr Ala Glu Glu Met Asp Glu Arg
            20                  25

<210> SEQ ID NO 124
<211> LENGTH: 12
<212> TYPE: PRT
<213> ORGANISM: Homo sapiens

<400> SEQUENCE: 124

Gly Val Ile Val Pro Leu Glu Gln Glu Tyr Glu Lys
1               5                   10

<210> SEQ ID NO 125
<211> LENGTH: 13
<212> TYPE: PRT
<213> ORGANISM: Homo sapiens

<400> SEQUENCE: 125

Gly Val Ile Val Pro Leu Glu Gln Glu Tyr Glu Lys Lys
1               5                   10

<210> SEQ ID NO 126
<211> LENGTH: 15
<212> TYPE: PRT
<213> ORGANISM: Homo sapiens

<400> SEQUENCE: 126

Gly Ala Glu Val Pro Asn Pro Asp Ser Val Thr Asp Asp Leu Lys
1               5                   10                  15

<210> SEQ ID NO 127
<211> LENGTH: 19
<212> TYPE: PRT
<213> ORGANISM: Homo sapiens

<400> SEQUENCE: 127

```
Gly Ala Glu Val Pro Asn Pro Asp Ser Val Thr Asp Asp Leu Lys Val
1               5                   10                  15

Ser Glu Lys

<210> SEQ ID NO 128
<211> LENGTH: 10
<212> TYPE: PRT
<213> ORGANISM: Homo sapiens

<400> SEQUENCE: 128

Ala Val Gln Met Ala Asn Glu Glu Leu Arg
1               5                   10

<210> SEQ ID NO 129
<211> LENGTH: 12
<212> TYPE: PRT
<213> ORGANISM: Homo sapiens

<400> SEQUENCE: 129

His Val Thr Ser Asp Ala Val Glu Leu Ala Asn Arg
1               5                   10

<210> SEQ ID NO 130
<211> LENGTH: 22
<212> TYPE: PRT
<213> ORGANISM: Homo sapiens

<400> SEQUENCE: 130

Gly Gly Leu Gly Ser Cys Gln Ala Leu Glu Asp His Ser Ala Leu Ala
1               5                   10                  15

Glu Thr Gln Glu Asp Arg
                20

<210> SEQ ID NO 131
<211> LENGTH: 21
<212> TYPE: PRT
<213> ORGANISM: Homo sapiens

<400> SEQUENCE: 131

Gly Ser Pro Ala Gly Ala Glu Asp Ser Leu Glu Glu Ala Ser Ser
1               5                   10                  15

Glu Gly Glu Pro Arg
                20

<210> SEQ ID NO 132
<211> LENGTH: 13
<212> TYPE: PRT
<213> ORGANISM: Homo sapiens

<400> SEQUENCE: 132

Ser Ile Gly Ala Val Leu Asn Ser Lys Asp Glu Gln Arg
1               5                   10

<210> SEQ ID NO 133
<211> LENGTH: 19
<212> TYPE: PRT
<213> ORGANISM: Homo sapiens

<400> SEQUENCE: 133

Ser Ile Gly Ala Val Leu Asn Ser Lys Asp Glu Gln Arg Glu Ile Ala
1               5                   10                  15

Glu Thr Arg
```

<210> SEQ ID NO 134
<211> LENGTH: 9
<212> TYPE: PRT
<213> ORGANISM: Homo sapiens

<400> SEQUENCE: 134

Ser Ile Gly Ala Val Leu Asn Ser Lys
1               5

<210> SEQ ID NO 135
<211> LENGTH: 17
<212> TYPE: PRT
<213> ORGANISM: Homo sapiens

<400> SEQUENCE: 135

Ala Gly Ala Glu Pro Ile Thr Ala Asp Ser Asp Pro Ala Tyr Ser Ser
1               5                   10                  15

Lys

<210> SEQ ID NO 136
<211> LENGTH: 21
<212> TYPE: PRT
<213> ORGANISM: Homo sapiens

<400> SEQUENCE: 136

Ala Thr Val Gly Gly Pro Ala Pro Thr Pro Leu Leu Pro Pro Ser Ala
1               5                   10                  15

Thr Ala Ser Val Lys
            20

<210> SEQ ID NO 137
<211> LENGTH: 22
<212> TYPE: PRT
<213> ORGANISM: Homo sapiens

<400> SEQUENCE: 137

Gly Ala Asp Cys Ile Met Leu Ser Gly Glu Thr Ala Lys Gly Asp Tyr
1               5                   10                  15

Pro Leu Glu Ala Val Arg
            20

<210> SEQ ID NO 138
<211> LENGTH: 13
<212> TYPE: PRT
<213> ORGANISM: Homo sapiens

<400> SEQUENCE: 138

Gly Ala Asp Cys Ile Met Leu Ser Gly Glu Thr Ala Lys
1               5                   10

<210> SEQ ID NO 139
<211> LENGTH: 9
<212> TYPE: PRT
<213> ORGANISM: Homo sapiens

<400> SEQUENCE: 139

Gly Trp Lys Glu Pro Ala Phe Ser Lys
1               5

<210> SEQ ID NO 140
<211> LENGTH: 14
<212> TYPE: PRT
<213> ORGANISM: Homo sapiens

```
<400> SEQUENCE: 140

Gly Trp Lys Glu Pro Ala Phe Ser Lys Glu Asp Asn Pro Arg
1               5                   10

<210> SEQ ID NO 141
<211> LENGTH: 21
<212> TYPE: PRT
<213> ORGANISM: Homo sapiens

<400> SEQUENCE: 141

Ala Ala Leu Glu Val Ser Pro Gly Val Ile Ala Asn Pro Phe Ala Ala
1               5                   10                  15

Gly Ile Gly His Arg
            20

<210> SEQ ID NO 142
<211> LENGTH: 13
<212> TYPE: PRT
<213> ORGANISM: Homo sapiens

<400> SEQUENCE: 142

Ala Ile Asn Trp Pro Thr Pro Gly Glu Ile Ala His Lys
1               5                   10

<210> SEQ ID NO 143
<211> LENGTH: 13
<212> TYPE: PRT
<213> ORGANISM: Homo sapiens

<400> SEQUENCE: 143

Phe Ser Gln Leu Leu Asn Cys Pro Glu Phe Val Pro Arg
1               5                   10

<210> SEQ ID NO 144
<211> LENGTH: 19
<212> TYPE: PRT
<213> ORGANISM: Homo sapiens

<400> SEQUENCE: 144

Gly Leu Asn Gln Thr Thr Ile Pro Val Ser Pro Ser Thr Thr Lys
1               5                   10                  15

Pro Ser Arg

<210> SEQ ID NO 145
<211> LENGTH: 20
<212> TYPE: PRT
<213> ORGANISM: Homo sapiens

<400> SEQUENCE: 145

Leu Ala Lys Glu Pro Cys Leu His Pro Leu Glu Pro Asp Glu Val Glu
1               5                   10                  15

Tyr Glu Pro Arg
            20

<210> SEQ ID NO 146
<211> LENGTH: 18
<212> TYPE: PRT
<213> ORGANISM: Homo sapiens

<400> SEQUENCE: 146

Gly Val Leu Asp Ile Asn His Glu Gln Glu Asn Thr Pro Ser Thr Ser
1               5                   10                  15
```

Gly Lys

<210> SEQ ID NO 147
<211> LENGTH: 19
<212> TYPE: PRT
<213> ORGANISM: Homo sapiens

<400> SEQUENCE: 147

Gly Val Leu Asp Ile Asn His Glu Gln Glu Asn Thr Pro Ser Thr Ser
1               5                   10                  15

Gly Lys Arg

<210> SEQ ID NO 148
<211> LENGTH: 15
<212> TYPE: PRT
<213> ORGANISM: Homo sapiens

<400> SEQUENCE: 148

Ser Ala Gln Ala Ser Asp Met Gly Gly Glu Ser Pro Gly Ser Arg
1               5                   10                  15

<210> SEQ ID NO 149
<211> LENGTH: 17
<212> TYPE: PRT
<213> ORGANISM: Homo sapiens

<400> SEQUENCE: 149

Ala Val Ser Gly Gln Leu Pro Asp Pro Thr Thr Asn Pro Ser Ala Gly
1               5                   10                  15

Lys

<210> SEQ ID NO 150
<211> LENGTH: 29
<212> TYPE: PRT
<213> ORGANISM: Homo sapiens

<400> SEQUENCE: 150

Ala Val Ser Gly Gln Leu Pro Asp Pro Thr Thr Asn Pro Ser Ala Gly
1               5                   10                  15

Lys Asp Gly Pro Ser Leu Leu Val Val Glu Gln Val Arg
            20                  25

<210> SEQ ID NO 151
<211> LENGTH: 12
<212> TYPE: PRT
<213> ORGANISM: Homo sapiens

<400> SEQUENCE: 151

Ser Val Val Ser Pro Leu Pro Val Thr Thr Val Lys
1               5                   10

<210> SEQ ID NO 152
<211> LENGTH: 19
<212> TYPE: PRT
<213> ORGANISM: Homo sapiens

<400> SEQUENCE: 152

Ser Ala Gly Leu Leu Ser Asp Glu Asp Cys Met Ser Val Pro Gly Lys
1               5                   10                  15

Thr His Arg

```
<210> SEQ ID NO 153
<211> LENGTH: 11
<212> TYPE: PRT
<213> ORGANISM: Homo sapiens

<400> SEQUENCE: 153

Gly Phe Asp Val Ala Ser Val Gln Gln Gln Arg
1               5                   10

<210> SEQ ID NO 154
<211> LENGTH: 31
<212> TYPE: PRT
<213> ORGANISM: Homo sapiens

<400> SEQUENCE: 154

Ala Ala Val Leu Thr Ser Pro Pro Ala Pro Ala Pro Pro Val Thr Pro
1               5                   10                  15

Ser Lys Pro Met Ala Gly Thr Thr Asp Arg Glu Glu Ala Thr Arg
            20                  25                  30

<210> SEQ ID NO 155
<211> LENGTH: 20
<212> TYPE: PRT
<213> ORGANISM: Homo sapiens

<400> SEQUENCE: 155

Gly Tyr Met Gly Val Asn Gln Ala Pro Glu Lys Leu Asp Lys Gln Cys
1               5                   10                  15

Glu Met Met Lys
            20

<210> SEQ ID NO 156
<211> LENGTH: 14
<212> TYPE: PRT
<213> ORGANISM: Homo sapiens

<400> SEQUENCE: 156

Gly Tyr Met Gly Val Asn Gln Ala Pro Glu Lys Leu Asp Lys
1               5                   10

<210> SEQ ID NO 157
<211> LENGTH: 11
<212> TYPE: PRT
<213> ORGANISM: Homo sapiens

<400> SEQUENCE: 157

Gly Tyr Met Gly Val Asn Gln Ala Pro Glu Lys
1               5                   10

<210> SEQ ID NO 158
<211> LENGTH: 12
<212> TYPE: PRT
<213> ORGANISM: Homo sapiens

<400> SEQUENCE: 158

Ser Val Ile Gly Val Ser Pro Ala Val Met Ile Arg
1               5                   10

<210> SEQ ID NO 159
<211> LENGTH: 11
<212> TYPE: PRT
<213> ORGANISM: Homo sapiens

<400> SEQUENCE: 159
```

Gly Phe Ala Glu Glu Ala Pro Ser Thr Ser Arg
1               5                   10

<210> SEQ ID NO 160
<211> LENGTH: 28
<212> TYPE: PRT
<213> ORGANISM: Homo sapiens

<400> SEQUENCE: 160

Gly Phe Ala Glu Glu Ala Pro Ser Thr Ser Arg Gly Pro Gly Gly Ser
1               5                   10                  15

Gln Gly Ser Gln Gly Pro Ser Pro Gln Gly Ala Arg
            20                  25

<210> SEQ ID NO 161
<211> LENGTH: 23
<212> TYPE: PRT
<213> ORGANISM: Homo sapiens

<400> SEQUENCE: 161

Ser Val Val Ala Ala Val Gln Glu Gly Ala Ala Glu Leu Glu Gly Gly
1               5                   10                  15

Pro Tyr Ser Pro Leu Gly Lys
            20

<210> SEQ ID NO 162
<211> LENGTH: 26
<212> TYPE: PRT
<213> ORGANISM: Homo sapiens

<400> SEQUENCE: 162

Ser Val Val Ala Ala Val Gln Glu Gly Ala Ala Glu Leu Glu Gly Gly
1               5                   10                  15

Pro Tyr Ser Pro Leu Gly Lys Asp Tyr Arg
            20                  25

<210> SEQ ID NO 163
<211> LENGTH: 27
<212> TYPE: PRT
<213> ORGANISM: Homo sapiens

<400> SEQUENCE: 163

Ser Val Val Ala Ala Val Gln Glu Gly Ala Ala Glu Leu Glu Gly Gly
1               5                   10                  15

Pro Tyr Ser Pro Leu Gly Lys Asp Tyr Arg Lys
            20                  25

<210> SEQ ID NO 164
<211> LENGTH: 17
<212> TYPE: PRT
<213> ORGANISM: Homo sapiens

<400> SEQUENCE: 164

Gly Gln Ser Asp Glu Asn Lys Asp Asp Tyr Thr Ile Pro Asp Glu Tyr
1               5                   10                  15

Arg

<210> SEQ ID NO 165
<211> LENGTH: 12
<212> TYPE: PRT
<213> ORGANISM: Homo sapiens

<400> SEQUENCE: 165

Leu Ala Asn Leu Gly Asp Val Ala Ser Asp Gly Lys
1               5                   10

<210> SEQ ID NO 166
<211> LENGTH: 13
<212> TYPE: PRT
<213> ORGANISM: Homo sapiens

<400> SEQUENCE: 166

Leu Ala Asn Leu Gly Asp Val Ala Ser Asp Gly Lys Lys
1               5                   10

<210> SEQ ID NO 167
<211> LENGTH: 20
<212> TYPE: PRT
<213> ORGANISM: Homo sapiens

<400> SEQUENCE: 167

Ser Phe Asp Asp Arg Gly Pro Ser Leu Asn Pro Val Leu Asp Tyr Asp
1               5                   10                  15

His Gly Ser Arg
            20

<210> SEQ ID NO 168
<211> LENGTH: 15
<212> TYPE: PRT
<213> ORGANISM: Homo sapiens

<400> SEQUENCE: 168

Tyr Tyr Thr Thr Thr Pro Ala Leu Val Phe Gly Lys Pro Val Arg
1               5                   10                  15

<210> SEQ ID NO 169
<211> LENGTH: 18
<212> TYPE: PRT
<213> ORGANISM: Homo sapiens

<400> SEQUENCE: 169

Leu Ala Asn Leu Gly Asp Val Ala Ser Asp Gly Lys Lys Glu Pro Ser
1               5                   10                  15

Asp Lys

<210> SEQ ID NO 170
<211> LENGTH: 21
<212> TYPE: PRT
<213> ORGANISM: Homo sapiens

<400> SEQUENCE: 170

Ser Tyr Asp Pro Tyr Asp Phe Ser Asp Thr Glu Glu Glu Met Pro Gln
1               5                   10                  15

Val His Thr Pro Lys
            20

<210> SEQ ID NO 171
<211> LENGTH: 17
<212> TYPE: PRT
<213> ORGANISM: Homo sapiens

<400> SEQUENCE: 171

Gly Ala Ala Ala Glu Asp Ile Val Ala Ser Glu Gln Ser Leu Gly Gln
1               5                   10                  15

Lys

<210> SEQ ID NO 172
<211> LENGTH: 15
<212> TYPE: PRT
<213> ORGANISM: Homo sapiens

<400> SEQUENCE: 172

Ser Phe Gly Gly Asp Ala Gln Ala Asp Glu Gly Gln Ala Arg Lys
1               5                   10                  15

<210> SEQ ID NO 173
<211> LENGTH: 14
<212> TYPE: PRT
<213> ORGANISM: Homo sapiens

<400> SEQUENCE: 173

Ser Phe Gly Gly Asp Ala Gln Ala Asp Glu Gly Gln Ala Arg
1               5                   10

<210> SEQ ID NO 174
<211> LENGTH: 11
<212> TYPE: PRT
<213> ORGANISM: Homo sapiens

<400> SEQUENCE: 174

Gly Tyr Glu Thr Glu Gly Ile Arg Gly Leu Arg
1               5                   10

<210> SEQ ID NO 175
<211> LENGTH: 8
<212> TYPE: PRT
<213> ORGANISM: Homo sapiens

<400> SEQUENCE: 175

Gly Tyr Glu Thr Glu Gly Ile Arg
1               5

<210> SEQ ID NO 176
<211> LENGTH: 23
<212> TYPE: PRT
<213> ORGANISM: Homo sapiens

<400> SEQUENCE: 176

Ala Leu Ser Pro Glu Gln Pro Ala Ser His Glu Ser Gln Gly Ser Val
1               5                   10                  15

Pro Ser Pro Leu Glu Ala Arg
            20

<210> SEQ ID NO 177
<211> LENGTH: 11
<212> TYPE: PRT
<213> ORGANISM: Homo sapiens

<400> SEQUENCE: 177

Ala Leu Tyr Val Ala Cys Gln Gly Gln Pro Lys
1               5                   10

<210> SEQ ID NO 178
<211> LENGTH: 19
<212> TYPE: PRT
<213> ORGANISM: Homo sapiens

<400> SEQUENCE: 178

Gly Ser Ala Val Asn Gly Thr Ser Ser Ala Glu Thr Asn Leu Glu Ala

```
1               5                  10                 15

Leu Gln Lys

<210> SEQ ID NO 179
<211> LENGTH: 20
<212> TYPE: PRT
<213> ORGANISM: Homo sapiens

<400> SEQUENCE: 179

Gly Ser Ala Val Asn Gly Thr Ser Ser Ala Glu Thr Asn Leu Glu Ala
1               5                   10                  15

Leu Gln Lys Lys
            20

<210> SEQ ID NO 180
<211> LENGTH: 12
<212> TYPE: PRT
<213> ORGANISM: Homo sapiens

<400> SEQUENCE: 180

Ala Ala Leu Leu Ala Pro Glu Glu Ile Lys Glu Lys
1               5                   10

<210> SEQ ID NO 181
<211> LENGTH: 10
<212> TYPE: PRT
<213> ORGANISM: Homo sapiens

<400> SEQUENCE: 181

Ala Ala Leu Leu Ala Pro Glu Glu Ile Lys
1               5                   10

<210> SEQ ID NO 182
<211> LENGTH: 14
<212> TYPE: PRT
<213> ORGANISM: Homo sapiens

<400> SEQUENCE: 182

Ala Ile Glu Pro Ala Pro Pro Ser Gln Gly Ala Glu Ala Lys
1               5                   10

<210> SEQ ID NO 183
<211> LENGTH: 9
<212> TYPE: PRT
<213> ORGANISM: Homo sapiens

<400> SEQUENCE: 183

Thr Thr Ala Ala Gln Gln Glu Leu Arg
1               5

<210> SEQ ID NO 184
<211> LENGTH: 9
<212> TYPE: PRT
<213> ORGANISM: Homo sapiens

<400> SEQUENCE: 184

Ser Thr Ala Thr Gln Gln Glu Leu Arg
1               5

<210> SEQ ID NO 185
<211> LENGTH: 9
<212> TYPE: PRT
<213> ORGANISM: Homo sapiens
```

<400> SEQUENCE: 185

Ser Thr Ala Ala Gln Gln Glu Leu Arg
1               5

<210> SEQ ID NO 186
<211> LENGTH: 15
<212> TYPE: PRT
<213> ORGANISM: Homo sapiens

<400> SEQUENCE: 186

Ser Leu Thr Ser Asp Lys Ala Ser Val Pro Ile Val Leu Glu Lys
1               5                   10                  15

<210> SEQ ID NO 187
<211> LENGTH: 25
<212> TYPE: PRT
<213> ORGANISM: Homo sapiens

<400> SEQUENCE: 187

Lys Ile Glu Asp Val Pro Ala Pro Ser Thr Ser Ala Asp Lys Val Glu
1               5                   10                  15

Ser Leu Asp Val Asp Ser Glu Ala Lys
            20                  25

<210> SEQ ID NO 188
<211> LENGTH: 15
<212> TYPE: PRT
<213> ORGANISM: Homo sapiens

<400> SEQUENCE: 188

Ser Ala Ser Pro Ala Asp Asp Ser Phe Val Asp Pro Gly Glu Arg
1               5                   10                  15

<210> SEQ ID NO 189
<211> LENGTH: 12
<212> TYPE: PRT
<213> ORGANISM: Homo sapiens

<400> SEQUENCE: 189

Ala Ala Ala Ser Ala Pro Gln Met Asp Val Ser Lys
1               5                   10

<210> SEQ ID NO 190
<211> LENGTH: 17
<212> TYPE: PRT
<213> ORGANISM: Homo sapiens

<400> SEQUENCE: 190

Gly Thr Ser Leu Val Gly Val Thr Gln Ser Phe Ala Ala Ser Val Leu
1               5                   10                  15

Arg

<210> SEQ ID NO 191
<211> LENGTH: 17
<212> TYPE: PRT
<213> ORGANISM: Homo sapiens

<400> SEQUENCE: 191

Ala Val Ala Glu Gln Gly His Leu Pro Pro Pro Ser Ala Pro Ala Gly
1               5                   10                  15

Arg

```
<210> SEQ ID NO 192
<211> LENGTH: 31
<212> TYPE: PRT
<213> ORGANISM: Homo sapiens

<400> SEQUENCE: 192

Gly Gly Leu Gln Ile Asn Val Asp Glu Glu Pro Phe Val Leu Pro Pro
1               5                   10                  15

Ala Gly Glu Met Glu Gln Asp Ala Gln Ala Pro Asp Leu Gln Arg
            20                  25                  30

<210> SEQ ID NO 193
<211> LENGTH: 35
<212> TYPE: PRT
<213> ORGANISM: Homo sapiens

<400> SEQUENCE: 193

Gly Gly Leu Gln Ile Asn Val Asp Glu Glu Pro Phe Val Leu Pro Pro
1               5                   10                  15

Ala Gly Glu Met Glu Gln Asp Ala Gln Ala Pro Asp Leu Gln Arg Val
            20                  25                  30

His Lys Arg
        35

<210> SEQ ID NO 194
<211> LENGTH: 9
<212> TYPE: PRT
<213> ORGANISM: Homo sapiens

<400> SEQUENCE: 194

Gly Leu Ile Pro Gly Val Glu Pro Arg
1               5

<210> SEQ ID NO 195
<211> LENGTH: 15
<212> TYPE: PRT
<213> ORGANISM: Homo sapiens

<400> SEQUENCE: 195

Gly Leu Val Glu Thr Pro Thr Gly Tyr Ile Glu Ser Leu Pro Arg
1               5                   10                  15

<210> SEQ ID NO 196
<211> LENGTH: 19
<212> TYPE: PRT
<213> ORGANISM: Homo sapiens

<400> SEQUENCE: 196

Gly Leu Val Glu Thr Pro Thr Gly Tyr Ile Glu Ser Leu Pro Arg Val
1               5                   10                  15

Val Lys Arg

<210> SEQ ID NO 197
<211> LENGTH: 11
<212> TYPE: PRT
<213> ORGANISM: Homo sapiens

<400> SEQUENCE: 197

Gly Val Pro Ser Asp Ser Val Glu Ala Ala Lys
1               5                   10

<210> SEQ ID NO 198
<211> LENGTH: 18
```

<212> TYPE: PRT
<213> ORGANISM: Homo sapiens

<400> SEQUENCE: 198

Gly Val Pro Ser Asp Ser Val Glu Ala Ala Lys Asn Ala Ser Asn Thr
1               5                   10                  15

Glu Lys

<210> SEQ ID NO 199
<211> LENGTH: 28
<212> TYPE: PRT
<213> ORGANISM: Homo sapiens

<400> SEQUENCE: 199

Gly Val Pro Ser Asp Ser Val Glu Ala Ala Lys Asn Ala Ser Asn Thr
1               5                   10                  15

Glu Lys Leu Thr Asp Gln Val Met Gln Asn Pro Arg
            20                  25

<210> SEQ ID NO 200
<211> LENGTH: 15
<212> TYPE: PRT
<213> ORGANISM: Homo sapiens

<400> SEQUENCE: 200

Asn Val Pro His Thr Pro Ser Ser Tyr Ile Glu Thr Leu Pro Lys
1               5                   10                  15

<210> SEQ ID NO 201
<211> LENGTH: 25
<212> TYPE: PRT
<213> ORGANISM: Homo sapiens

<400> SEQUENCE: 201

Gly Gln Lys Val Glu Val Pro Gln Pro Leu Ser Trp Tyr Pro Glu Glu
1               5                   10                  15

Leu Ala Trp His Thr Asn Leu Ser Arg
            20                  25

<210> SEQ ID NO 202
<211> LENGTH: 26
<212> TYPE: PRT
<213> ORGANISM: Homo sapiens

<400> SEQUENCE: 202

Gly Gln Lys Val Glu Val Pro Gln Pro Leu Ser Trp Tyr Pro Glu Glu
1               5                   10                  15

Leu Ala Trp His Thr Asn Leu Ser Arg Lys
            20                  25

<210> SEQ ID NO 203
<211> LENGTH: 14
<212> TYPE: PRT
<213> ORGANISM: Homo sapiens

<400> SEQUENCE: 203

Gly Gly Phe Glu Gly Asp His Gln Leu Leu Cys Asp Ile Arg
1               5                   10

<210> SEQ ID NO 204
<211> LENGTH: 18
<212> TYPE: PRT
<213> ORGANISM: Homo sapiens

<400> SEQUENCE: 204

Phe Thr Gln Glu Ser Glu Pro Ser Tyr Ile Ser Asp Val Gly Pro Pro
1               5                   10                  15

Gly Arg

<210> SEQ ID NO 205
<211> LENGTH: 15
<212> TYPE: PRT
<213> ORGANISM: Homo sapiens

<400> SEQUENCE: 205

Ala Ile Asn Gln Gly Met Asp Glu Glu Leu Glu Arg Asp Glu Lys
1               5                   10                  15

<210> SEQ ID NO 206
<211> LENGTH: 11
<212> TYPE: PRT
<213> ORGANISM: Homo sapiens

<400> SEQUENCE: 206

Ala Ala Val Ala Asp Pro Asp Glu Phe Glu Arg
1               5                   10

<210> SEQ ID NO 207
<211> LENGTH: 12
<212> TYPE: PRT
<213> ORGANISM: Homo sapiens

<400> SEQUENCE: 207

Gly Ala Ile Glu Asp Pro Glu Leu Glu Ala Ile Lys
1               5                   10

<210> SEQ ID NO 208
<211> LENGTH: 14
<212> TYPE: PRT
<213> ORGANISM: Homo sapiens

<400> SEQUENCE: 208

Gly Ala Ile Glu Asp Pro Glu Leu Glu Ala Ile Lys Ala Arg
1               5                   10

<210> SEQ ID NO 209
<211> LENGTH: 17
<212> TYPE: PRT
<213> ORGANISM: Homo sapiens

<400> SEQUENCE: 209

Ala Tyr Ser Ile Gln Gly Gln His Thr Ile Ser Pro Leu Asp Leu Ala
1               5                   10                  15

Lys

<210> SEQ ID NO 210
<211> LENGTH: 22
<212> TYPE: PRT
<213> ORGANISM: Homo sapiens

<400> SEQUENCE: 210

Ala Ser Thr Gln Thr Thr His Glu Leu Thr Ile Pro Asn Asn Leu Ile
1               5                   10                  15

Gly Cys Ile Ile Gly Arg
            20

```
<210> SEQ ID NO 211
<211> LENGTH: 15
<212> TYPE: PRT
<213> ORGANISM: Homo sapiens

<400> SEQUENCE: 211

Gly Arg Gly Glu Pro Ala Met Glu Ser Ser Gln Ile Val Ser Arg
1               5                   10                  15

<210> SEQ ID NO 212
<211> LENGTH: 12
<212> TYPE: PRT
<213> ORGANISM: Homo sapiens

<400> SEQUENCE: 212

Ala Tyr Thr Ala Pro Ala Leu Pro Ser Ser Ile Arg
1               5                   10

<210> SEQ ID NO 213
<211> LENGTH: 8
<212> TYPE: PRT
<213> ORGANISM: Homo sapiens

<400> SEQUENCE: 213

Cys Val Gly Pro Glu Val Glu Lys
1               5

<210> SEQ ID NO 214
<211> LENGTH: 25
<212> TYPE: PRT
<213> ORGANISM: Homo sapiens

<400> SEQUENCE: 214

Cys Val Gly Pro Glu Val Glu Lys Ala Cys Ala Asn Pro Ala Ala Gly
1               5                   10                  15

Ser Val Ile Leu Leu Glu Asn Leu Arg
            20                  25

<210> SEQ ID NO 215
<211> LENGTH: 19
<212> TYPE: PRT
<213> ORGANISM: Homo sapiens

<400> SEQUENCE: 215

Ser Ile Thr Ser Gln Glu Ser Lys Glu Pro Val Phe Ile Ala Ala Gly
1               5                   10                  15

Asp Ile Arg

<210> SEQ ID NO 216
<211> LENGTH: 20
<212> TYPE: PRT
<213> ORGANISM: Homo sapiens

<400> SEQUENCE: 216

Ser Ile Thr Ser Gln Glu Ser Lys Glu Pro Val Phe Ile Ala Ala Gly
1               5                   10                  15

Asp Ile Arg Arg
            20

<210> SEQ ID NO 217
<211> LENGTH: 17
<212> TYPE: PRT
<213> ORGANISM: Homo sapiens
```

-continued

```
<400> SEQUENCE: 217

Gly His Pro Ala Ser Ser Pro Leu Leu Pro Val Ser Leu Leu Gly Pro
1               5                   10                  15

Lys

<210> SEQ ID NO 218
<211> LENGTH: 14
<212> TYPE: PRT
<213> ORGANISM: Homo sapiens

<400> SEQUENCE: 218

Ala Asp Ile Lys Pro Pro Glu Asn Val Leu Phe Val Cys Lys
1               5                   10

<210> SEQ ID NO 219
<211> LENGTH: 21
<212> TYPE: PRT
<213> ORGANISM: Homo sapiens

<400> SEQUENCE: 219

Gly Asp Pro Ser Asp Arg Met Glu Val Gln Glu Gln Glu Asp Ile
1               5                   10                  15

Ser Ser Leu Ile Arg
            20

<210> SEQ ID NO 220
<211> LENGTH: 19
<212> TYPE: PRT
<213> ORGANISM: Homo sapiens

<400> SEQUENCE: 220

Val Ala Lys Pro Ser Glu Glu Glu Gln Lys Glu Leu Asp Glu Ile Thr
1               5                   10                  15

Ala Lys Arg

<210> SEQ ID NO 221
<211> LENGTH: 8
<212> TYPE: PRT
<213> ORGANISM: Homo sapiens

<400> SEQUENCE: 221

Gly Ile Gly Glu Glu Val Leu Lys
1               5

<210> SEQ ID NO 222
<211> LENGTH: 17
<212> TYPE: PRT
<213> ORGANISM: Homo sapiens

<400> SEQUENCE: 222

Gly Ile Gly Glu Glu Val Leu Lys Met Ser Thr Glu Glu Ile Ile Gln
1               5                   10                  15

Arg

<210> SEQ ID NO 223
<211> LENGTH: 9
<212> TYPE: PRT
<213> ORGANISM: Homo sapiens

<400> SEQUENCE: 223

Gly Phe Asp Gln Asn Val Asn Val Lys
```

```
1               5
```

<210> SEQ ID NO 224
<211> LENGTH: 19
<212> TYPE: PRT
<213> ORGANISM: Homo sapiens

<400> SEQUENCE: 224

```
Ser Ile Gly Ser Ser Arg Leu Glu Gly Gly Ser Gly Gly Asp Ser Glu
1               5                   10                  15

Val Gln Arg
```

<210> SEQ ID NO 225
<211> LENGTH: 11
<212> TYPE: PRT
<213> ORGANISM: Homo sapiens

<400> SEQUENCE: 225

```
Ser Phe Met Asp Pro Ala Ser Ala Leu Tyr Arg
1               5                   10
```

<210> SEQ ID NO 226
<211> LENGTH: 8
<212> TYPE: PRT
<213> ORGANISM: Homo sapiens

<400> SEQUENCE: 226

```
Tyr Ser Ala Thr Val Asp Gln Arg
1               5
```

<210> SEQ ID NO 227
<211> LENGTH: 9
<212> TYPE: PRT
<213> ORGANISM: Homo sapiens

<400> SEQUENCE: 227

```
Ser Val Ile Thr Gln Val Leu Asn Lys
1               5
```

<210> SEQ ID NO 228
<211> LENGTH: 12
<212> TYPE: PRT
<213> ORGANISM: Homo sapiens

<400> SEQUENCE: 228

```
Gly Val Asp Gln Gln Leu Leu Asp Asp Phe His Arg
1               5                   10
```

<210> SEQ ID NO 229
<211> LENGTH: 24
<212> TYPE: PRT
<213> ORGANISM: Homo sapiens

<400> SEQUENCE: 229

```
Gly Gly Pro Asn Thr Gly Gly Met Gly Ala Tyr Cys Pro Ala Pro Gln
1               5                   10                  15

Val Ser Asn Asp Leu Leu Leu Lys
                20
```

<210> SEQ ID NO 230
<211> LENGTH: 17
<212> TYPE: PRT
<213> ORGANISM: Homo sapiens

```
<400> SEQUENCE: 230

Gly Ile Ile Ala Pro Gly Tyr Glu Glu Glu Ala Leu Thr Ile Leu Ser
1               5                   10                  15

Lys

<210> SEQ ID NO 231
<211> LENGTH: 25
<212> TYPE: PRT
<213> ORGANISM: Homo sapiens

<400> SEQUENCE: 231

Gly Gln Gln Ser Ala Pro Gln Ala Asp Glu Pro Pro Leu Pro Pro Pro
1               5                   10                  15

Pro Pro Pro Pro Gly Glu Leu Ala Arg
            20                  25

<210> SEQ ID NO 232
<211> LENGTH: 20
<212> TYPE: PRT
<213> ORGANISM: Homo sapiens

<400> SEQUENCE: 232

Gly Thr Leu Asn Leu Asp Ser Asp Glu Gly Glu Glu Pro Ser Pro Glu
1               5                   10                  15

Ala Leu Val Arg
            20

<210> SEQ ID NO 233
<211> LENGTH: 35
<212> TYPE: PRT
<213> ORGANISM: Homo sapiens

<400> SEQUENCE: 233

Ser Val Asp Pro Val Glu Pro Met Pro Thr Met Thr Asp Gln Thr Thr
1               5                   10                  15

Leu Val Pro Asn Glu Glu Glu Ala Phe Ala Leu Glu Pro Ile Asp Ile
            20                  25                  30

Thr Val Lys
        35

<210> SEQ ID NO 234
<211> LENGTH: 38
<212> TYPE: PRT
<213> ORGANISM: Homo sapiens

<400> SEQUENCE: 234

Ser Val Asp Pro Val Glu Pro Met Pro Thr Met Thr Asp Gln Thr Thr
1               5                   10                  15

Leu Val Pro Asn Glu Glu Glu Ala Phe Ala Leu Glu Pro Ile Asp Ile
            20                  25                  30

Thr Val Lys Glu Thr Lys
        35

<210> SEQ ID NO 235
<211> LENGTH: 11
<212> TYPE: PRT
<213> ORGANISM: Homo sapiens

<400> SEQUENCE: 235

Val Ala Gln Gln Phe Ser Leu Asn Gln Ser Arg
1               5                   10
```

<210> SEQ ID NO 236
<211> LENGTH: 15
<212> TYPE: PRT
<213> ORGANISM: Homo sapiens

<400> SEQUENCE: 236

Ser Asp Lys Gly Glu Phe Gly Gly Phe Gly Ser Val Thr Gly Lys
1               5                   10                  15

<210> SEQ ID NO 237
<211> LENGTH: 12
<212> TYPE: PRT
<213> ORGANISM: Homo sapiens

<400> SEQUENCE: 237

Gly Val Glu Glu Glu Val Phe Glu Gln Glu Ala Lys
1               5                   10

<210> SEQ ID NO 238
<211> LENGTH: 18
<212> TYPE: PRT
<213> ORGANISM: Homo sapiens

<400> SEQUENCE: 238

Gly Tyr Asn Pro Glu Ala Pro Ser Ile Thr Asn Thr Ser Arg Pro Met
1               5                   10                  15

Tyr Arg

<210> SEQ ID NO 239
<211> LENGTH: 15
<212> TYPE: PRT
<213> ORGANISM: Homo sapiens

<400> SEQUENCE: 239

Ala Ser Ser Ala Ser Ser Phe Leu Asp Ser Asp Glu Leu Glu Arg
1               5                   10                  15

<210> SEQ ID NO 240
<211> LENGTH: 25
<212> TYPE: PRT
<213> ORGANISM: Homo sapiens

<400> SEQUENCE: 240

Ala Ser Ser Ala Ser Ser Phe Leu Asp Ser Asp Glu Leu Glu Arg Thr
1               5                   10                  15

Gly Ile Asp Leu Gly Thr Thr Gly Arg
            20                  25

<210> SEQ ID NO 241
<211> LENGTH: 13
<212> TYPE: PRT
<213> ORGANISM: Homo sapiens

<400> SEQUENCE: 241

Ser Val Glu Gln Asp Gly Asp Glu Pro Gly Pro Gln Arg
1               5                   10

<210> SEQ ID NO 242
<211> LENGTH: 28
<212> TYPE: PRT
<213> ORGANISM: Homo sapiens

<400> SEQUENCE: 242

Gly Gly Ser Ala His Gly Asp Asp Asp Asp Gly Pro His Phe Glu
1               5                   10                  15

Pro Val Val Pro Leu Pro Asp Lys Ile Glu Val Lys
            20                  25

<210> SEQ ID NO 243
<211> LENGTH: 20
<212> TYPE: PRT
<213> ORGANISM: Homo sapiens

<400> SEQUENCE: 243

Gly Thr Gly Gly Gln Ser Ile Tyr Gly Asp Lys Phe Glu Asp Glu Asn
1               5                   10                  15

Phe Asp Val Lys
            20

<210> SEQ ID NO 244
<211> LENGTH: 9
<212> TYPE: PRT
<213> ORGANISM: Homo sapiens

<400> SEQUENCE: 244

Ser Ile Asp Ser Phe Glu Thr Gln Arg
1               5

<210> SEQ ID NO 245
<211> LENGTH: 19
<212> TYPE: PRT
<213> ORGANISM: Homo sapiens

<400> SEQUENCE: 245

Gly Val Asn Lys Asp Tyr Glu Glu Thr Glu Leu Ile Ser Thr Thr Ala
1               5                   10                  15

Asn Tyr Arg

<210> SEQ ID NO 246
<211> LENGTH: 7
<212> TYPE: PRT
<213> ORGANISM: Homo sapiens

<400> SEQUENCE: 246

Tyr Val Pro Ser Thr Thr Lys
1               5

<210> SEQ ID NO 247
<211> LENGTH: 10
<212> TYPE: PRT
<213> ORGANISM: Homo sapiens

<400> SEQUENCE: 247

Tyr Val Pro Ser Thr Thr Lys Thr Pro Arg
1               5                   10

<210> SEQ ID NO 248
<211> LENGTH: 11
<212> TYPE: PRT
<213> ORGANISM: Homo sapiens

<400> SEQUENCE: 248

Gly Tyr Tyr Glu Ala Glu Phe Gly Gln Glu Arg
1               5                   10

<210> SEQ ID NO 249
<211> LENGTH: 15
<212> TYPE: PRT
<213> ORGANISM: Homo sapiens

<400> SEQUENCE: 249

Ser Phe Thr Ser Asp Pro Glu Gln Ile Gly Ser Asn Val Thr Arg
1               5                   10                  15

<210> SEQ ID NO 250
<211> LENGTH: 19
<212> TYPE: PRT
<213> ORGANISM: Homo sapiens

<400> SEQUENCE: 250

Ser Asn Ile Ala Pro Ala Asp Pro Asp Thr Ala Ile Val His Pro Val
1               5                   10                  15

Pro Ile Arg

<210> SEQ ID NO 251
<211> LENGTH: 21
<212> TYPE: PRT
<213> ORGANISM: Homo sapiens

<400> SEQUENCE: 251

Gly Tyr Ser Ser Ser Asp Ser Phe Thr Ser Asp Pro Glu Gln Ile Gly
1               5                   10                  15

Ser Asn Val Thr Arg
            20

<210> SEQ ID NO 252
<211> LENGTH: 9
<212> TYPE: PRT
<213> ORGANISM: Homo sapiens

<400> SEQUENCE: 252

Gly Ser Ser Leu Glu Ala Leu Leu Arg
1               5

<210> SEQ ID NO 253
<211> LENGTH: 8
<212> TYPE: PRT
<213> ORGANISM: Homo sapiens

<400> SEQUENCE: 253

Gly Met Ala Gly Asn Glu Asp Arg
1               5

<210> SEQ ID NO 254
<211> LENGTH: 19
<212> TYPE: PRT
<213> ORGANISM: Homo sapiens

<400> SEQUENCE: 254

Gly Met Ala Gly Asn Glu Asp Arg Gly Gly Ile Gln Glu Leu Ile Gly
1               5                   10                  15

Leu Ile Lys

<210> SEQ ID NO 255
<211> LENGTH: 32
<212> TYPE: PRT
<213> ORGANISM: Homo sapiens

<400> SEQUENCE: 255

```
Ser Phe Ser Ser Met Thr Ser Asp Ser Thr Thr Ser Pro Thr Gly
1               5                   10                  15

Gln Gln Pro Ser Asp Ala Phe Pro Glu Asp Ser Ser Lys Val Pro Arg
                20                  25                  30
```

<210> SEQ ID NO 256
<211> LENGTH: 16
<212> TYPE: PRT
<213> ORGANISM: Homo sapiens

<400> SEQUENCE: 256

```
Gly Cys Leu Cys Pro Cys Ser Leu Gly Leu Gly Gly Val Gly Met Arg
1               5                   10                  15
```

<210> SEQ ID NO 257
<211> LENGTH: 27
<212> TYPE: PRT
<213> ORGANISM: Homo sapiens

<400> SEQUENCE: 257

```
Ser Ile Glu Ala Ala Glu Gly Glu Gln Glu Pro Glu Ala Glu Ala Leu
1               5                   10                  15

Gly Gly Thr Asn Ser Glu Pro Gly Thr Pro Arg
                20                  25
```

<210> SEQ ID NO 258
<211> LENGTH: 14
<212> TYPE: PRT
<213> ORGANISM: Homo sapiens

<400> SEQUENCE: 258

```
Ser Leu Glu Asn Ile Pro Glu Lys Trp Thr Pro Glu Val Lys
1               5                   10
```

<210> SEQ ID NO 259
<211> LENGTH: 9
<212> TYPE: PRT
<213> ORGANISM: Homo sapiens

<400> SEQUENCE: 259

```
Gly Thr Glu Ile Ala Val Ser Pro Arg
1               5
```

<210> SEQ ID NO 260
<211> LENGTH: 16
<212> TYPE: PRT
<213> ORGANISM: Homo sapiens

<400> SEQUENCE: 260

```
Gly Gln Pro Gly Ala Phe Thr Cys Tyr Leu Asp Ala Gly Leu Ala Arg
1               5                   10                  15
```

<210> SEQ ID NO 261
<211> LENGTH: 13
<212> TYPE: PRT
<213> ORGANISM: Homo sapiens

<400> SEQUENCE: 261

```
Gly Val Arg Glu Glu Asp Leu Ala Pro Phe Ser Leu Arg
1               5                   10
```

<210> SEQ ID NO 262
<211> LENGTH: 12

<212> TYPE: PRT
<213> ORGANISM: Homo sapiens

<400> SEQUENCE: 262

Ser Val Lys Pro Gly Ala His Leu Thr Val Lys Lys
1               5                   10

<210> SEQ ID NO 263
<211> LENGTH: 17
<212> TYPE: PRT
<213> ORGANISM: Homo sapiens

<400> SEQUENCE: 263

Ser Phe Asn Gly His Pro Pro Gln Gly Cys Ala Ser Thr Pro Val Ala
1               5                   10                  15

Arg

<210> SEQ ID NO 264
<211> LENGTH: 10
<212> TYPE: PRT
<213> ORGANISM: Homo sapiens

<400> SEQUENCE: 264

Ser Met Ser Ala Ala Leu Gln Asp Glu Arg
1               5                   10

<210> SEQ ID NO 265
<211> LENGTH: 30
<212> TYPE: PRT
<213> ORGANISM: Homo sapiens

<400> SEQUENCE: 265

Ser Thr Ala Gly Thr Thr Lys Gln Pro Ser Lys Glu Glu Glu Glu
1               5                   10                  15

Glu Glu Glu Glu Gln Leu Asn Gln Thr Leu Ala Glu Met Lys
                20                  25                  30

<210> SEQ ID NO 266
<211> LENGTH: 27
<212> TYPE: PRT
<213> ORGANISM: Homo sapiens

<400> SEQUENCE: 266

Gly Asn Lys Met Glu Glu Glu Gly Ala Lys Gly Glu Asp Glu Glu
1               5                   10                  15

Met Ala Asp Pro Met Glu Asp Val Ile Ile Arg
                20                  25

<210> SEQ ID NO 267
<211> LENGTH: 8
<212> TYPE: PRT
<213> ORGANISM: Homo sapiens

<400> SEQUENCE: 267

Ser Phe Val Gln Gln Thr Phe Arg
1               5

<210> SEQ ID NO 268
<211> LENGTH: 13
<212> TYPE: PRT
<213> ORGANISM: Homo sapiens

<400> SEQUENCE: 268

Gly Tyr Gly Glu Asp Leu Met Gly Asp Glu Glu Asp Arg
1               5                   10

<210> SEQ ID NO 269
<211> LENGTH: 15
<212> TYPE: PRT
<213> ORGANISM: Homo sapiens

<400> SEQUENCE: 269

Gly Tyr Gly Glu Asp Leu Met Gly Asp Glu Glu Asp Arg Ala Arg
1               5                   10                  15

<210> SEQ ID NO 270
<211> LENGTH: 12
<212> TYPE: PRT
<213> ORGANISM: Homo sapiens

<400> SEQUENCE: 270

Thr Tyr Leu Thr His Asp Ser Pro Ser Val Arg Lys
1               5                   10

<210> SEQ ID NO 271
<211> LENGTH: 11
<212> TYPE: PRT
<213> ORGANISM: Homo sapiens

<400> SEQUENCE: 271

Thr Tyr Leu Thr His Asp Ser Pro Ser Val Arg
1               5                   10

<210> SEQ ID NO 272
<211> LENGTH: 10
<212> TYPE: PRT
<213> ORGANISM: Homo sapiens

<400> SEQUENCE: 272

Ala Ile Asp Phe Ser Asp Asn Glu Ile Arg
1               5                   10

<210> SEQ ID NO 273
<211> LENGTH: 22
<212> TYPE: PRT
<213> ORGANISM: Homo sapiens

<400> SEQUENCE: 273

Ser Thr Ala Pro Ser Ser Glu Leu Gly Lys Asp Asp Leu Glu Glu Leu
1               5                   10                  15

Ala Ala Ala Ala Gln Lys
            20

<210> SEQ ID NO 274
<211> LENGTH: 9
<212> TYPE: PRT
<213> ORGANISM: Homo sapiens

<400> SEQUENCE: 274

Ala Tyr Gly Glu Asp Asp Phe Ser Arg
1               5

<210> SEQ ID NO 275
<211> LENGTH: 19
<212> TYPE: PRT
<213> ORGANISM: Homo sapiens

<400> SEQUENCE: 275

Ser Tyr Ser Ser Ala Ala Ser Tyr Thr Asp Ser Ser Asp Asp Glu Val
1               5                   10                  15

Ser Pro Arg

<210> SEQ ID NO 276
<211> LENGTH: 21
<212> TYPE: PRT
<213> ORGANISM: Homo sapiens

<400> SEQUENCE: 276

Ser Tyr Ser Ser Ala Ala Ser Tyr Thr Asp Ser Ser Asp Asp Glu Val
1               5                   10                  15

Ser Pro Arg Glu Lys
            20

<210> SEQ ID NO 277
<211> LENGTH: 11
<212> TYPE: PRT
<213> ORGANISM: Homo sapiens

<400> SEQUENCE: 277

Val Tyr Cys Glu Val Cys Glu Phe Leu Val Lys
1               5                   10

<210> SEQ ID NO 278
<211> LENGTH: 15
<212> TYPE: PRT
<213> ORGANISM: Homo sapiens

<400> SEQUENCE: 278

Val Tyr Cys Glu Val Cys Glu Phe Leu Val Lys Glu Val Thr Lys
1               5                   10                  15

<210> SEQ ID NO 279
<211> LENGTH: 10
<212> TYPE: PRT
<213> ORGANISM: Homo sapiens

<400> SEQUENCE: 279

Tyr Ser Leu Asp Ser Pro Gly Pro Glu Lys
1               5                   10

<210> SEQ ID NO 280
<211> LENGTH: 14
<212> TYPE: PRT
<213> ORGANISM: Homo sapiens

<400> SEQUENCE: 280

Ser Val Ser Arg Pro Gln Leu Glu Ser Leu Ser Gly Thr Lys
1               5                   10

<210> SEQ ID NO 281
<211> LENGTH: 16
<212> TYPE: PRT
<213> ORGANISM: Homo sapiens

<400> SEQUENCE: 281

Ser Thr Gly Tyr Tyr Asp Gln Glu Ile Tyr Gly Gly Ser Asp Ser Arg
1               5                   10                  15

<210> SEQ ID NO 282
<211> LENGTH: 14
<212> TYPE: PRT

<213> ORGANISM: Homo sapiens

<400> SEQUENCE: 282

Gly Ser Glu Thr Pro Gln Leu Phe Thr Val Leu Pro Glu Lys
1               5                   10

<210> SEQ ID NO 283
<211> LENGTH: 15
<212> TYPE: PRT
<213> ORGANISM: Homo sapiens

<400> SEQUENCE: 283

Gly Ser Glu Thr Pro Gln Leu Phe Thr Val Leu Pro Glu Lys Arg
1               5                   10                  15

<210> SEQ ID NO 284
<211> LENGTH: 28
<212> TYPE: PRT
<213> ORGANISM: Homo sapiens

<400> SEQUENCE: 284

Gly Leu Pro Gly Glu Ala Ala Glu Asp Asp Leu Ala Gly Ala Pro Ala
1               5                   10                  15

Leu Ser Gln Ala Ser Ser Gly Thr Cys Phe Pro Arg
            20                  25

<210> SEQ ID NO 285
<211> LENGTH: 20
<212> TYPE: PRT
<213> ORGANISM: Homo sapiens

<400> SEQUENCE: 285

Ser Phe Cys Ser Asp Gln Asn Glu Ser Glu Val Glu Pro Ser Val Asn
1               5                   10                  15

Ala Asp Leu Lys
            20

<210> SEQ ID NO 286
<211> LENGTH: 14
<212> TYPE: PRT
<213> ORGANISM: Homo sapiens

<400> SEQUENCE: 286

Gly Gly Ser Pro Pro Gly Pro Gly Asp Leu Ala Glu Glu Arg
1               5                   10

<210> SEQ ID NO 287
<211> LENGTH: 19
<212> TYPE: PRT
<213> ORGANISM: Homo sapiens

<400> SEQUENCE: 287

Ala Ala Ala Pro Ala Asp Ala Pro Ser Gly Leu Glu Ala Glu Leu Glu
1               5                   10                  15

His Leu Arg

<210> SEQ ID NO 288
<211> LENGTH: 23
<212> TYPE: PRT
<213> ORGANISM: Homo sapiens

<400> SEQUENCE: 288

Gly Glu Val Thr Val Ala Glu Gln Lys Pro Gly Glu Ile Ala Glu Glu

```
1               5                   10                  15
Leu Ala Ser Ser Tyr Glu Arg
            20
```

<210> SEQ ID NO 289
<211> LENGTH: 23
<212> TYPE: PRT
<213> ORGANISM: Homo sapiens

<400> SEQUENCE: 289

```
Gly Val Ala Asp Val Ser Ile Glu Asp Ser Val Ile Ser Leu Ser Gly
1               5                   10                  15

Asp His Cys Ile Ile Gly Arg
            20
```

<210> SEQ ID NO 290
<211> LENGTH: 14
<212> TYPE: PRT
<213> ORGANISM: Homo sapiens

<400> SEQUENCE: 290

```
Ser Val Ile Ser Leu Ser Gly Asp His Cys Ile Ile Gly Arg
1               5                   10
```

<210> SEQ ID NO 291
<211> LENGTH: 19
<212> TYPE: PRT
<213> ORGANISM: Homo sapiens

<400> SEQUENCE: 291

```
Ser Phe Leu Lys Phe Asp Ser Glu Pro Ser Ala Val Ala Leu Glu Leu
1               5                   10                  15

Pro Thr Arg
```

<210> SEQ ID NO 292
<211> LENGTH: 19
<212> TYPE: PRT
<213> ORGANISM: Homo sapiens

<400> SEQUENCE: 292

```
Ser Ala Gly Ile Gln Leu His Pro Gly Glu Asn Ala Asp Ser Pro Ala
1               5                   10                  15

Asp Ile Arg
```

<210> SEQ ID NO 293
<211> LENGTH: 12
<212> TYPE: PRT
<213> ORGANISM: Homo sapiens

<400> SEQUENCE: 293

```
Ser Phe Ala Ser Thr Gln Pro Thr His Ser Trp Lys
1               5                   10
```

<210> SEQ ID NO 294
<211> LENGTH: 10
<212> TYPE: PRT
<213> ORGANISM: Homo sapiens

<400> SEQUENCE: 294

```
Ser Tyr Ile Glu Val Leu Asp Gly Ser Arg
1               5                   10
```

```
<210> SEQ ID NO 295
<211> LENGTH: 26
<212> TYPE: PRT
<213> ORGANISM: Homo sapiens

<400> SEQUENCE: 295

Gly Ala Pro Leu Glu Asp Val Asp Gly Ile Pro Ile Asp Ala Thr Pro
1               5                   10                  15
Ile Asp Asp Leu Asp Gly Val Pro Ile Lys
            20                  25

<210> SEQ ID NO 296
<211> LENGTH: 23
<212> TYPE: PRT
<213> ORGANISM: Homo sapiens

<400> SEQUENCE: 296

Gly Val Pro Ile Lys Ser Leu Asp Asp Leu Asp Gly Val Pro Leu
1               5                   10                  15
Asp Ala Thr Glu Asp Ser Lys
            20

<210> SEQ ID NO 297
<211> LENGTH: 24
<212> TYPE: PRT
<213> ORGANISM: Homo sapiens

<400> SEQUENCE: 297

Gly Val Pro Ile Lys Ser Leu Asp Asp Leu Asp Gly Val Pro Leu
1               5                   10                  15
Asp Ala Thr Glu Asp Ser Lys Lys
            20

<210> SEQ ID NO 298
<211> LENGTH: 11
<212> TYPE: PRT
<213> ORGANISM: Homo sapiens

<400> SEQUENCE: 298

Gly Val Pro Leu Asp Ala Thr Glu Asp Ser Lys
1               5                   10

<210> SEQ ID NO 299
<211> LENGTH: 12
<212> TYPE: PRT
<213> ORGANISM: Homo sapiens

<400> SEQUENCE: 299

Gly Val Pro Leu Asp Ala Thr Glu Asp Ser Lys Lys
1               5                   10

<210> SEQ ID NO 300
<211> LENGTH: 18
<212> TYPE: PRT
<213> ORGANISM: Homo sapiens

<400> SEQUENCE: 300

Gly Val Pro Leu Asp Ala Thr Glu Asp Ser Lys Lys Asn Glu Pro Ile
1               5                   10                  15
Phe Lys

<210> SEQ ID NO 301
<211> LENGTH: 22
```

```
<212> TYPE: PRT
<213> ORGANISM: Homo sapiens

<400> SEQUENCE: 301

Gly Phe Pro Ala Gly Glu Gly Glu Ala Gly Arg Pro Gly Ala Glu
1               5                   10                  15

Asp Glu Glu Met Ser Arg
            20

<210> SEQ ID NO 302
<211> LENGTH: 22
<212> TYPE: PRT
<213> ORGANISM: Homo sapiens

<400> SEQUENCE: 302

Gly Phe Pro Ala Gly Glu Gly Glu Ala Gly Arg Pro Gly Ala Glu
1               5                   10                  15

Asp Glu Glu Met Ser Arg
            20

<210> SEQ ID NO 303
<211> LENGTH: 9
<212> TYPE: PRT
<213> ORGANISM: Homo sapiens

<400> SEQUENCE: 303

Ser Val Val Ser Leu Glu Ser Gln Lys
1               5

<210> SEQ ID NO 304
<211> LENGTH: 17
<212> TYPE: PRT
<213> ORGANISM: Homo sapiens

<400> SEQUENCE: 304

Ser Val Val Ser Leu Glu Ser Gln Lys Thr Pro Ala Asp Pro Lys Leu
1               5                   10                  15

Lys

<210> SEQ ID NO 305
<211> LENGTH: 20
<212> TYPE: PRT
<213> ORGANISM: Homo sapiens

<400> SEQUENCE: 305

Ala His Gln Thr Glu Thr Ser Ser Gln Val Lys Asp Asn Lys Pro
1               5                   10                  15

Leu Val Glu Arg
            20

<210> SEQ ID NO 306
<211> LENGTH: 12
<212> TYPE: PRT
<213> ORGANISM: Homo sapiens

<400> SEQUENCE: 306

Ala His Gln Thr Glu Thr Ser Ser Gln Val Lys
1               5                   10

<210> SEQ ID NO 307
<211> LENGTH: 9
<212> TYPE: PRT
<213> ORGANISM: Homo sapiens
```

<400> SEQUENCE: 307

Ser Asn Ser Leu Leu Gly Gln Ser Arg
1               5

<210> SEQ ID NO 308
<211> LENGTH: 14
<212> TYPE: PRT
<213> ORGANISM: Homo sapiens

<400> SEQUENCE: 308

Val Leu Asn Pro Met Pro Ala Cys Phe Tyr Thr Val Ser Arg
1               5                   10

<210> SEQ ID NO 309
<211> LENGTH: 33
<212> TYPE: PRT
<213> ORGANISM: Homo sapiens

<400> SEQUENCE: 309

Gly Ala Asn Thr Met Ile Glu His Asp Asp Thr Leu Pro Ser Gln Leu
1               5                   10                  15

Gly Thr Met Val Ile Asn Ala Glu Asp Glu Glu Glu Gly Thr Met
            20                  25                  30

Lys

<210> SEQ ID NO 310
<211> LENGTH: 34
<212> TYPE: PRT
<213> ORGANISM: Homo sapiens

<400> SEQUENCE: 310

Gly Ala Asn Thr Met Ile Glu His Asp Asp Thr Leu Pro Ser Gln Leu
1               5                   10                  15

Gly Thr Met Val Ile Asn Ala Glu Asp Glu Glu Glu Gly Thr Met
            20                  25                  30

Lys Arg

<210> SEQ ID NO 311
<211> LENGTH: 35
<212> TYPE: PRT
<213> ORGANISM: Homo sapiens

<400> SEQUENCE: 311

Gly Ala Asn Thr Met Ile Glu His Asp Asp Thr Leu Pro Ser Gln Leu
1               5                   10                  15

Gly Thr Met Val Ile Asn Ala Glu Asp Glu Glu Glu Gly Thr Met
            20                  25                  30

Lys Arg Arg
        35

<210> SEQ ID NO 312
<211> LENGTH: 10
<212> TYPE: PRT
<213> ORGANISM: Homo sapiens

<400> SEQUENCE: 312

Ser Leu Thr Tyr Asp Ile Ala Asn Asn Lys
1               5                   10

<210> SEQ ID NO 313

```
<211> LENGTH: 14
<212> TYPE: PRT
<213> ORGANISM: Homo sapiens

<400> SEQUENCE: 313

Ser Leu Thr Tyr Asp Ile Ala Asn Asn Lys Asp Ala Leu Arg
1               5                   10

<210> SEQ ID NO 314
<211> LENGTH: 15
<212> TYPE: PRT
<213> ORGANISM: Homo sapiens

<400> SEQUENCE: 314

Ser Leu Thr Tyr Asp Ile Ala Asn Asn Lys Asp Ala Leu Arg Lys
1               5                   10                  15

<210> SEQ ID NO 315
<211> LENGTH: 15
<212> TYPE: PRT
<213> ORGANISM: Homo sapiens

<400> SEQUENCE: 315

Ser Ile Glu Ala Asn Val Glu Ser Ser Glu Val His Val Glu Arg
1               5                   10                  15

<210> SEQ ID NO 316
<211> LENGTH: 22
<212> TYPE: PRT
<213> ORGANISM: Homo sapiens

<400> SEQUENCE: 316

Ser Ile Glu Ala Asn Val Glu Asn Ala Glu Val His Val Gln Gln Ala
1               5                   10                  15

Asn Gln Gln Leu Ser Arg
            20

<210> SEQ ID NO 317
<211> LENGTH: 16
<212> TYPE: PRT
<213> ORGANISM: Homo sapiens

<400> SEQUENCE: 317

Ala Leu Ile Asp Glu Asp Pro Gln Ala Ala Leu Glu Glu Leu Thr Lys
1               5                   10                  15

<210> SEQ ID NO 318
<211> LENGTH: 17
<212> TYPE: PRT
<213> ORGANISM: Homo sapiens

<400> SEQUENCE: 318

Ser Ala Glu Glu Gly Ser Leu Ala Ala Ala Ala Glu Leu Ala Ala Gln
1               5                   10                  15

Lys

<210> SEQ ID NO 319
<211> LENGTH: 18
<212> TYPE: PRT
<213> ORGANISM: Homo sapiens

<400> SEQUENCE: 319

Ser Ala Glu Glu Gly Ser Leu Ala Ala Ala Ala Glu Leu Ala Ala Gln
1               5                   10                  15
```

Lys Arg

<210> SEQ ID NO 320
<211> LENGTH: 13
<212> TYPE: PRT
<213> ORGANISM: Homo sapiens

<400> SEQUENCE: 320

Phe Val Asp Pro Trp Thr Val Gln Thr Ser Ser Ala Lys
1               5                   10

<210> SEQ ID NO 321
<211> LENGTH: 20
<212> TYPE: PRT
<213> ORGANISM: Homo sapiens

<400> SEQUENCE: 321

Ala Phe Gln Glu Arg Glu Glu Gly His Ala Gly Pro Asp Asp Asn Glu
1               5                   10                  15

Glu Val Met Arg
            20

<210> SEQ ID NO 322
<211> LENGTH: 17
<212> TYPE: PRT
<213> ORGANISM: Homo sapiens

<400> SEQUENCE: 322

Gly His Ala Thr Asp Glu Glu Lys Leu Ala Ser Thr Ser Cys Gly Gln
1               5                   10                  15

Lys

<210> SEQ ID NO 323
<211> LENGTH: 8
<212> TYPE: PRT
<213> ORGANISM: Homo sapiens

<400> SEQUENCE: 323

Gly His Ala Thr Asp Glu Glu Lys
1               5

<210> SEQ ID NO 324
<211> LENGTH: 15
<212> TYPE: PRT
<213> ORGANISM: Homo sapiens

<400> SEQUENCE: 324

Gly Ile Pro Glu Glu Thr Asp Gly Asp Ala Asp Val Asp Leu Lys
1               5                   10                  15

<210> SEQ ID NO 325
<211> LENGTH: 10
<212> TYPE: PRT
<213> ORGANISM: Homo sapiens

<400> SEQUENCE: 325

Ala Val Met Pro Asp Val Val Gln Thr Arg
1               5                   10

<210> SEQ ID NO 326
<211> LENGTH: 17
<212> TYPE: PRT

-continued

<400> SEQUENCE: 326

Gly Lys Gln Glu Ala Lys Pro Gln Gln Ala Ala Gly Met Leu Ser Pro
1               5                   10                  15

Lys

<210> SEQ ID NO 327
<211> LENGTH: 15
<212> TYPE: PRT
<213> ORGANISM: Homo sapiens

<400> SEQUENCE: 327

Gly Leu Ser Val Ser Gln Ala Pro Ala Ile Leu Pro Val Ser Lys
1               5                   10                  15

<210> SEQ ID NO 328
<211> LENGTH: 20
<212> TYPE: PRT
<213> ORGANISM: Homo sapiens

<400> SEQUENCE: 328

Ala Phe Ile Ala Ala Gly Glu Ser Ser Ala Pro Thr Pro Pro Arg Pro
1               5                   10                  15

Ala Leu Pro Arg
            20

<210> SEQ ID NO 329
<211> LENGTH: 35
<212> TYPE: PRT
<213> ORGANISM: Homo sapiens

<400> SEQUENCE: 329

Ala Asn Gln Cys Cys Thr Ser Cys Glu Asp Asn Ala Pro Ala Thr Ser
1               5                   10                  15

Tyr Cys Val Glu Cys Ser Glu Pro Leu Cys Glu Thr Cys Val Glu Ala
            20                  25                  30

His Gln Arg
        35

<210> SEQ ID NO 330
<211> LENGTH: 18
<212> TYPE: PRT
<213> ORGANISM: Homo sapiens

<400> SEQUENCE: 330

Ser Thr Phe Ser Leu Asp Gln Pro Gly Gly Thr Leu Asp Leu Thr Leu
1               5                   10                  15

Ile Arg

<210> SEQ ID NO 331
<211> LENGTH: 17
<212> TYPE: PRT
<213> ORGANISM: Homo sapiens

<400> SEQUENCE: 331

Ser Val Val Pro Phe Asp Ala Ser Glu Val Pro Val Glu Glu Gln
1               5                   10                  15

Arg

<210> SEQ ID NO 332
<211> LENGTH: 17

<212> TYPE: PRT
<213> ORGANISM: Homo sapiens

<400> SEQUENCE: 332

Ser Val Asn Leu Ala Glu Pro Met Glu Gln Asn Pro Pro Gln Gln Gln
1               5                   10                  15

Arg

<210> SEQ ID NO 333
<211> LENGTH: 15
<212> TYPE: PRT
<213> ORGANISM: Homo sapiens

<400> SEQUENCE: 333

Ser Met Arg Gly Glu Ala Pro Gly Ala Glu Thr Pro Ser Leu Arg
1               5                   10                  15

<210> SEQ ID NO 334
<211> LENGTH: 17
<212> TYPE: PRT
<213> ORGANISM: Homo sapiens

<400> SEQUENCE: 334

Ser Ile Lys Pro Glu Glu Thr Glu Gln Glu Val Ala Ala Asp Glu Thr
1               5                   10                  15

Arg

<210> SEQ ID NO 335
<211> LENGTH: 17
<212> TYPE: PRT
<213> ORGANISM: Homo sapiens

<400> SEQUENCE: 335

Ser Ile Leu Lys Ser Glu Leu Gly Asn Gln Ser Pro Ser Thr Ser Ser
1               5                   10                  15

Arg

<210> SEQ ID NO 336
<211> LENGTH: 10
<212> TYPE: PRT
<213> ORGANISM: Homo sapiens

<400> SEQUENCE: 336

Met Leu Ser Pro Ile His Thr Pro Gln Arg
1               5                   10

<210> SEQ ID NO 337
<211> LENGTH: 31
<212> TYPE: PRT
<213> ORGANISM: Homo sapiens

<400> SEQUENCE: 337

Gly Cys Ser Thr Pro Ser Arg Glu Glu Gly Gly Cys Ser Leu Ala Ser
1               5                   10                  15

Thr Pro Ala Thr Thr Leu His Leu Leu Gln Leu Ser Gly Gln Arg
            20                  25                  30

<210> SEQ ID NO 338
<211> LENGTH: 10
<212> TYPE: PRT
<213> ORGANISM: Homo sapiens

<400> SEQUENCE: 338

```
Ser Ser Gln Pro Ser Leu Pro Leu Val Arg
1               5                   10
```

<210> SEQ ID NO 339
<211> LENGTH: 34
<212> TYPE: PRT
<213> ORGANISM: Homo sapiens

<400> SEQUENCE: 339

```
Ser Ala Gly Thr Ser Pro Thr Ala Val Leu Ala Ala Gly Glu Glu Val
1               5                   10                  15

Gly Ala Gly Gly Gly Pro Gly Gly Arg Pro Gly Ala Gly Thr Pro
            20                  25                  30

Leu Arg
```

<210> SEQ ID NO 340
<211> LENGTH: 47
<212> TYPE: PRT
<213> ORGANISM: Homo sapiens

<400> SEQUENCE: 340

```
Ser Ala Gly Thr Ser Pro Thr Ala Val Leu Ala Ala Gly Glu Glu Val
1               5                   10                  15

Gly Ala Gly Gly Gly Pro Gly Gly Arg Pro Gly Ala Gly Thr Pro
            20                  25                  30

Leu Arg Gln Thr Leu Trp Pro Leu Ser Ile His Asp Pro Thr Arg
            35                  40                  45
```

<210> SEQ ID NO 341
<211> LENGTH: 17
<212> TYPE: PRT
<213> ORGANISM: Homo sapiens

<400> SEQUENCE: 341

```
Ser Phe Asp Glu Asp Leu Ala Arg Pro Ser Gly Leu Leu Ala Gln Glu
1               5                   10                  15

Arg
```

<210> SEQ ID NO 342
<211> LENGTH: 20
<212> TYPE: PRT
<213> ORGANISM: Homo sapiens

<400> SEQUENCE: 342

```
Gly Ser Asn Val Thr Val Thr Pro Gly Pro Gly Glu Gln Thr Val Asp
1               5                   10                  15

Val Glu Pro Arg
            20
```

<210> SEQ ID NO 343
<211> LENGTH: 24
<212> TYPE: PRT
<213> ORGANISM: Homo sapiens

<400> SEQUENCE: 343

```
Gly Val Pro Ser Thr Ser Pro Met Glu Val Leu Asp Arg Leu Ile Gln
1               5                   10                  15

Gln Gly Ala Asp Ala His Ser Lys
            20
```

```
<210> SEQ ID NO 344
<211> LENGTH: 13
<212> TYPE: PRT
<213> ORGANISM: Homo sapiens

<400> SEQUENCE: 344

Gly Val Pro Ser Thr Ser Pro Met Glu Val Leu Asp Arg
1               5                   10

<210> SEQ ID NO 345
<211> LENGTH: 10
<212> TYPE: PRT
<213> ORGANISM: Homo sapiens

<400> SEQUENCE: 345

Ala Val Asp Asp Met Glu Glu Gly Leu Lys
1               5                   10

<210> SEQ ID NO 346
<211> LENGTH: 14
<212> TYPE: PRT
<213> ORGANISM: Homo sapiens

<400> SEQUENCE: 346

Ala Val Asp Asp Met Glu Glu Gly Leu Lys Val Leu Met Lys
1               5                   10

<210> SEQ ID NO 347
<211> LENGTH: 12
<212> TYPE: PRT
<213> ORGANISM: Homo sapiens

<400> SEQUENCE: 347

Ser Thr Gly Arg Pro Leu Val Ile Leu Pro Gln Arg
1               5                   10

<210> SEQ ID NO 348
<211> LENGTH: 13
<212> TYPE: PRT
<213> ORGANISM: Homo sapiens

<400> SEQUENCE: 348

Ser Thr Gly Arg Pro Leu Val Ile Leu Pro Gln Arg Lys
1               5                   10

<210> SEQ ID NO 349
<211> LENGTH: 18
<212> TYPE: PRT
<213> ORGANISM: Homo sapiens

<400> SEQUENCE: 349

Gly Leu Ala Val Thr Pro Thr Pro Val Pro Val Val Gly Ser Gln Met
1               5                   10                  15

Thr Arg

<210> SEQ ID NO 350
<211> LENGTH: 19
<212> TYPE: PRT
<213> ORGANISM: Homo sapiens

<400> SEQUENCE: 350

Gly Val Pro Gln Val Val Glu Tyr Ser Glu Ile Ser Pro Glu Thr Ala
1               5                   10                  15

Gln Leu Arg
```

<210> SEQ ID NO 351
<211> LENGTH: 16
<212> TYPE: PRT
<213> ORGANISM: Homo sapiens

<400> SEQUENCE: 351

Ala Leu Glu Cys Leu Pro Glu Asp Lys Glu Val Leu Thr Glu Asp Lys
1               5                   10                  15

<210> SEQ ID NO 352
<211> LENGTH: 29
<212> TYPE: PRT
<213> ORGANISM: Homo sapiens

<400> SEQUENCE: 352

Gly Ser Ala Ser Pro Val Glu Met Gln Asp Glu Gly Ala Glu Glu Pro
1               5                   10                  15

His Glu Ala Gly Glu Gln Leu Pro Pro Phe Leu Leu Lys
            20                  25

<210> SEQ ID NO 353
<211> LENGTH: 32
<212> TYPE: PRT
<213> ORGANISM: Homo sapiens

<400> SEQUENCE: 353

Gly Ser Ala Ser Pro Val Glu Met Gln Asp Glu Gly Ala Glu Glu Pro
1               5                   10                  15

His Glu Ala Gly Glu Gln Leu Pro Pro Phe Leu Leu Lys Glu Gly Arg
            20                  25                  30

<210> SEQ ID NO 354
<211> LENGTH: 35
<212> TYPE: PRT
<213> ORGANISM: Homo sapiens

<400> SEQUENCE: 354

Gly Ser Ala Ser Pro Val Glu Met Gln Asp Glu Gly Ala Glu Glu Pro
1               5                   10                  15

His Glu Ala Gly Glu Gln Leu Pro Pro Phe Leu Leu Lys Glu Gly Arg
            20                  25                  30

Asp Asp Arg
        35

<210> SEQ ID NO 355
<211> LENGTH: 20
<212> TYPE: PRT
<213> ORGANISM: Homo sapiens

<400> SEQUENCE: 355

Ser Phe Ile Asp Asn Ser Glu Ala Tyr Asp Glu Leu Val Pro Ala Ser
1               5                   10                  15

Leu Thr Thr Lys
        20

<210> SEQ ID NO 356
<211> LENGTH: 14
<212> TYPE: PRT
<213> ORGANISM: Homo sapiens

<400> SEQUENCE: 356

Gly Arg Pro Asp Glu Val Val Ala Glu Glu Ala Trp Gln Arg
1               5                   10

<210> SEQ ID NO 357
<211> LENGTH: 14
<212> TYPE: PRT
<213> ORGANISM: Homo sapiens

<400> SEQUENCE: 357

Gly Ser Leu Ala Ser Asn Pro Tyr Ser Gly Asp Leu Thr Lys
1               5                   10

<210> SEQ ID NO 358
<211> LENGTH: 16
<212> TYPE: PRT
<213> ORGANISM: Homo sapiens

<400> SEQUENCE: 358

Gly His Asn Thr Ala Glu Glu Asp Met Glu Asp Asp Thr Ser Trp Arg
1               5                   10                  15

<210> SEQ ID NO 359
<211> LENGTH: 11
<212> TYPE: PRT
<213> ORGANISM: Homo sapiens

<400> SEQUENCE: 359

Ser Val Ala Gly Glu His Ser Val Ser Gly Arg
1               5                   10

<210> SEQ ID NO 360
<211> LENGTH: 11
<212> TYPE: PRT
<213> ORGANISM: Homo sapiens

<400> SEQUENCE: 360

Gly Phe Arg Asp Phe Gln Thr Glu Thr Ile Arg
1               5                   10

<210> SEQ ID NO 361
<211> LENGTH: 17
<212> TYPE: PRT
<213> ORGANISM: Homo sapiens

<400> SEQUENCE: 361

Gly Phe Arg Asp Phe Gln Thr Glu Thr Ile Arg Gln Glu Gln Glu Leu
1               5                   10                  15

Arg

<210> SEQ ID NO 362
<211> LENGTH: 18
<212> TYPE: PRT
<213> ORGANISM: Homo sapiens

<400> SEQUENCE: 362

Ser Arg Pro Ala Asp Glu Asp Met Trp Asp Glu Thr Glu Leu Gly Leu
1               5                   10                  15

Tyr Lys

<210> SEQ ID NO 363
<211> LENGTH: 26
<212> TYPE: PRT
<213> ORGANISM: Homo sapiens

```
<400> SEQUENCE: 363

Ser Arg Pro Ala Asp Glu Asp Met Trp Asp Glu Thr Glu Leu Gly Leu
1               5                   10                  15

Tyr Lys Val Asn Glu Tyr Val Asp Ala Arg
            20                  25

<210> SEQ ID NO 364
<211> LENGTH: 9
<212> TYPE: PRT
<213> ORGANISM: Homo sapiens

<400> SEQUENCE: 364

Ser Leu Thr Thr Ile Pro Glu Leu Lys
1               5

<210> SEQ ID NO 365
<211> LENGTH: 13
<212> TYPE: PRT
<213> ORGANISM: Homo sapiens

<400> SEQUENCE: 365

Ser Leu Thr Thr Ile Pro Glu Leu Lys Asp His Leu Arg
1               5                   10

<210> SEQ ID NO 366
<211> LENGTH: 7
<212> TYPE: PRT
<213> ORGANISM: Homo sapiens

<400> SEQUENCE: 366

Ala Ile Asn Thr Glu Phe Lys
1               5

<210> SEQ ID NO 367
<211> LENGTH: 10
<212> TYPE: PRT
<213> ORGANISM: Homo sapiens

<400> SEQUENCE: 367

Ala Ile Asn Thr Glu Phe Lys Asn Thr Arg
1               5                   10

<210> SEQ ID NO 368
<211> LENGTH: 11
<212> TYPE: PRT
<213> ORGANISM: Homo sapiens

<400> SEQUENCE: 368

Ala Leu Lys Gly Thr Asn Glu Ser Leu Glu Arg
1               5                   10

<210> SEQ ID NO 369
<211> LENGTH: 12
<212> TYPE: PRT
<213> ORGANISM: Homo sapiens

<400> SEQUENCE: 369

Phe Ser Leu Ala Asp Ala Ile Asn Thr Glu Phe Lys
1               5                   10

<210> SEQ ID NO 370
<211> LENGTH: 15
<212> TYPE: PRT
<213> ORGANISM: Homo sapiens
```

<400> SEQUENCE: 370

Phe Ser Leu Ala Asp Ala Ile Asn Thr Glu Phe Lys Asn Thr Arg
1               5                   10                  15

<210> SEQ ID NO 371
<211> LENGTH: 13
<212> TYPE: PRT
<213> ORGANISM: Homo sapiens

<400> SEQUENCE: 371

Val Asp Val Ser Lys Pro Asp Leu Thr Ala Ala Leu Arg
1               5                   10

<210> SEQ ID NO 372
<211> LENGTH: 16
<212> TYPE: PRT
<213> ORGANISM: Homo sapiens

<400> SEQUENCE: 372

Val Asp Val Ser Lys Pro Asp Leu Thr Ala Ala Leu Arg Asp Val Arg
1               5                   10                  15

<210> SEQ ID NO 373
<211> LENGTH: 11
<212> TYPE: PRT
<213> ORGANISM: Homo sapiens

<400> SEQUENCE: 373

Val Ser Lys Pro Asp Leu Thr Ala Ala Leu Arg
1               5                   10

<210> SEQ ID NO 374
<211> LENGTH: 14
<212> TYPE: PRT
<213> ORGANISM: Homo sapiens

<400> SEQUENCE: 374

Val Ser Lys Pro Asp Leu Thr Ala Ala Leu Arg Asp Val Arg
1               5                   10

<210> SEQ ID NO 375
<211> LENGTH: 11
<212> TYPE: PRT
<213> ORGANISM: Homo sapiens

<400> SEQUENCE: 375

Ser Val Gly Thr Tyr Leu Pro Gly Ala Ser Arg
1               5                   10

<210> SEQ ID NO 376
<211> LENGTH: 15
<212> TYPE: PRT
<213> ORGANISM: Homo sapiens

<400> SEQUENCE: 376

Ser Leu Cys Gly Ser Arg Asn Glu Asn Glu Ser Glu Ala Ala Arg
1               5                   10                  15

<210> SEQ ID NO 377
<211> LENGTH: 16
<212> TYPE: PRT
<213> ORGANISM: Homo sapiens

<400> SEQUENCE: 377

Ser Leu Cys Gly Ser Arg Asn Glu Asn Glu Ser Glu Ala Ala Arg Arg
1               5                   10                  15

<210> SEQ ID NO 378
<211> LENGTH: 19
<212> TYPE: PRT
<213> ORGANISM: Homo sapiens

<400> SEQUENCE: 378

Gly Ile Gly Gly Leu Gly Ile Gly Glu Gly Ala Pro Glu Ile Val Thr
1               5                   10                  15

Gly Ser Arg

<210> SEQ ID NO 379
<211> LENGTH: 14
<212> TYPE: PRT
<213> ORGANISM: Homo sapiens

<400> SEQUENCE: 379

Gly Ile Pro Asn Asp Ser Ser Asp Ser Glu Met Glu Asp Lys
1               5                   10

<210> SEQ ID NO 380
<211> LENGTH: 26
<212> TYPE: PRT
<213> ORGANISM: Homo sapiens

<400> SEQUENCE: 380

Gly Asn Gly Val Gly Gln Ser Gln Ala Gly Ser Gly Ser Thr Pro Ser
1               5                   10                  15

Glu Pro His Pro Val Leu Glu Lys Leu Arg
            20                  25

<210> SEQ ID NO 381
<211> LENGTH: 12
<212> TYPE: PRT
<213> ORGANISM: Homo sapiens

<400> SEQUENCE: 381

Gly Gln Ser Ala Phe Ala Asn Glu Thr Leu Asn Lys
1               5                   10

<210> SEQ ID NO 382
<211> LENGTH: 27
<212> TYPE: PRT
<213> ORGANISM: Homo sapiens

<400> SEQUENCE: 382

Gly Gln Ser Ala Phe Ala Asn Glu Thr Leu Asn Lys Ala Pro Gly Met
1               5                   10                  15

Asn Thr Ile Asp Gln Gly Met Ala Ala Leu Lys
            20                  25

<210> SEQ ID NO 383
<211> LENGTH: 39
<212> TYPE: PRT
<213> ORGANISM: Homo sapiens

<400> SEQUENCE: 383

Gly Gln Ser Ala Phe Ala Asn Glu Thr Leu Asn Lys Ala Pro Gly Met
1               5                   10                  15

Asn Thr Ile Asp Gln Gly Met Ala Ala Leu Lys Leu Gly Ser Thr Glu

```
                 20                  25                  30

Val Ala Ser Asn Val Pro Lys
                 35

<210> SEQ ID NO 384
<211> LENGTH: 15
<212> TYPE: PRT
<213> ORGANISM: Homo sapiens

<400> SEQUENCE: 384

Gly Ser Ile Ser Pro Val Ser Ser Glu Cys Ser Val Val Glu Arg
1               5                  10                  15

<210> SEQ ID NO 385
<211> LENGTH: 35
<212> TYPE: PRT
<213> ORGANISM: Homo sapiens

<400> SEQUENCE: 385

Gly Val Pro Ser Pro Pro Gly Tyr Met Ser Asp Gln Glu Glu Asp Met
1               5                  10                  15

Cys Phe Glu Gly Met Lys Pro Val Asn Gln Thr Ala Ala Ser Asn Lys
                 20                  25                  30

Gly Leu Arg
         35

<210> SEQ ID NO 386
<211> LENGTH: 10
<212> TYPE: PRT
<213> ORGANISM: Homo sapiens

<400> SEQUENCE: 386

Gly Val Ala Thr Asp Ile Thr Ser Thr Arg
1               5                  10

<210> SEQ ID NO 387
<211> LENGTH: 12
<212> TYPE: PRT
<213> ORGANISM: Homo sapiens

<400> SEQUENCE: 387

Ser Leu Ser Asp Val Thr Ser Thr Thr Ser Ser Arg
1               5                  10

<210> SEQ ID NO 388
<211> LENGTH: 17
<212> TYPE: PRT
<213> ORGANISM: Homo sapiens

<400> SEQUENCE: 388

Thr Val Leu Glu Pro Tyr Ala Asp Pro Tyr Tyr Asp Tyr Glu Ile Glu
1               5                  10                  15

Arg

<210> SEQ ID NO 389
<211> LENGTH: 12
<212> TYPE: PRT
<213> ORGANISM: Homo sapiens

<400> SEQUENCE: 389

Gly Glu Thr Glu Val Gly Glu Ile Gln Gln Asn Lys
1               5                  10
```

<210> SEQ ID NO 390
<211> LENGTH: 22
<212> TYPE: PRT
<213> ORGANISM: Homo sapiens

<400> SEQUENCE: 390

Ala Ala Asp Cys Glu Gly Val Pro Glu Asp Asp Leu Pro Thr Asp Gln
1               5                   10                  15
Thr Val Leu Pro Gly Arg
            20

<210> SEQ ID NO 391
<211> LENGTH: 8
<212> TYPE: PRT
<213> ORGANISM: Homo sapiens

<400> SEQUENCE: 391

Gly Thr Cys Pro Glu Val Ile Lys
1               5

<210> SEQ ID NO 392
<211> LENGTH: 13
<212> TYPE: PRT
<213> ORGANISM: Homo sapiens

<400> SEQUENCE: 392

Gly Thr Cys Pro Glu Val Ile Lys Val Tyr Ile Phe Lys
1               5                   10

<210> SEQ ID NO 393
<211> LENGTH: 30
<212> TYPE: PRT
<213> ORGANISM: Homo sapiens

<400> SEQUENCE: 393

Ser Thr Glu Ser Ile Pro Val Ser Asp Glu Ser Asp Ala Met Val
1               5                   10                  15
Asp Asp Pro Asn Asp Glu Asp Phe Val Pro Phe Arg Pro Arg
            20                  25                  30

<210> SEQ ID NO 394
<211> LENGTH: 11
<212> TYPE: PRT
<213> ORGANISM: Homo sapiens

<400> SEQUENCE: 394

Ser Phe Gly Ser Pro Leu Gly Leu Asp Lys Arg
1               5                   10

<210> SEQ ID NO 395
<211> LENGTH: 12
<212> TYPE: PRT
<213> ORGANISM: Homo sapiens

<400> SEQUENCE: 395

Ser Phe Gly Ser Pro Leu Gly Leu Asp Lys Arg Lys
1               5                   10

<210> SEQ ID NO 396
<211> LENGTH: 20
<212> TYPE: PRT
<213> ORGANISM: Homo sapiens

<400> SEQUENCE: 396

```
Ala Ile Asp Asp Gln Lys Cys Asp Ile Leu Val Gln Glu Glu Leu Leu
1               5                   10                  15

Ala Ser Pro Lys
            20

<210> SEQ ID NO 397
<211> LENGTH: 21
<212> TYPE: PRT
<213> ORGANISM: Homo sapiens

<400> SEQUENCE: 397

Ala Ile Asp Asp Gln Lys Cys Asp Ile Leu Val Gln Glu Glu Leu Leu
1               5                   10                  15

Ala Ser Pro Lys Lys
            20

<210> SEQ ID NO 398
<211> LENGTH: 16
<212> TYPE: PRT
<213> ORGANISM: Homo sapiens

<400> SEQUENCE: 398

Ser Ile Leu Ile Ile Pro Thr Pro Asp Glu Glu Glu Lys Ile Leu Arg
1               5                   10                  15

<210> SEQ ID NO 399
<211> LENGTH: 13
<212> TYPE: PRT
<213> ORGANISM: Homo sapiens

<400> SEQUENCE: 399

Ser Ile Leu Ile Ile Pro Thr Pro Asp Glu Glu Glu Lys
1               5                   10

<210> SEQ ID NO 400
<211> LENGTH: 11
<212> TYPE: PRT
<213> ORGANISM: Homo sapiens

<400> SEQUENCE: 400

Ser Leu Ser Ser Leu Leu Asp Asp Met Thr Lys
1               5                   10

<210> SEQ ID NO 401
<211> LENGTH: 18
<212> TYPE: PRT
<213> ORGANISM: Homo sapiens

<400> SEQUENCE: 401

Ser Leu Ser Ser Leu Leu Asp Asp Met Thr Lys Asn Asp Pro Phe Lys
1               5                   10                  15

Ala Arg

<210> SEQ ID NO 402
<211> LENGTH: 14
<212> TYPE: PRT
<213> ORGANISM: Homo sapiens

<400> SEQUENCE: 402

Ser Tyr Ala Ala Ala Ser Ala Pro Gln Met Asp Val Ser Lys
1               5                   10
```

```
<210> SEQ ID NO 403
<211> LENGTH: 7
<212> TYPE: PRT
<213> ORGANISM: Homo sapiens

<400> SEQUENCE: 403

Leu Val Asp Ala Ala Ala Ser
1               5

<210> SEQ ID NO 404
<211> LENGTH: 12
<212> TYPE: PRT
<213> ORGANISM: Homo sapiens

<400> SEQUENCE: 404

Ser Tyr Gly Leu Ser Glu Gln Glu Asn Asn Glu Lys
1               5                   10

<210> SEQ ID NO 405
<211> LENGTH: 8
<212> TYPE: PRT
<213> ORGANISM: Homo sapiens

<400> SEQUENCE: 405

Glu Ile Ile Asp Gly Leu Ser Glu
1               5

<210> SEQ ID NO 406
<211> LENGTH: 17
<212> TYPE: PRT
<213> ORGANISM: Homo sapiens

<400> SEQUENCE: 406

Ser Tyr Gly Thr Ala Glu Glu Thr Glu Arg Glu Gln Ala Thr Pro
1               5                   10                  15

Arg

<210> SEQ ID NO 407
<211> LENGTH: 8
<212> TYPE: PRT
<213> ORGANISM: Homo sapiens

<400> SEQUENCE: 407

Asp Lys Ile Asp Gly Thr Ala Glu
1               5

<210> SEQ ID NO 408
<211> LENGTH: 16
<212> TYPE: PRT
<213> ORGANISM: Homo sapiens

<400> SEQUENCE: 408

Ser Tyr Gly Asp Val Glu Ile Pro Pro Asn Lys Ala Val Val Leu Arg
1               5                   10                  15

<210> SEQ ID NO 409
<211> LENGTH: 8
<212> TYPE: PRT
<213> ORGANISM: Homo sapiens

<400> SEQUENCE: 409

Met Glu Val Asp Gly Asp Val Glu
1               5
```

```
<210> SEQ ID NO 410
<211> LENGTH: 12
<212> TYPE: PRT
<213> ORGANISM: Homo sapiens

<400> SEQUENCE: 410

Ser Tyr Ala Val Met Pro Asp Val Val Gln Thr Arg
1               5                   10

<210> SEQ ID NO 411
<211> LENGTH: 8
<212> TYPE: PRT
<213> ORGANISM: Homo sapiens

<400> SEQUENCE: 411

Ser Leu Ile Asp Ala Val Met Pro
1               5

<210> SEQ ID NO 412
<211> LENGTH: 17
<212> TYPE: PRT
<213> ORGANISM: Homo sapiens

<400> SEQUENCE: 412

Ser Tyr Gly Gly Gly Pro Gly Gln Val Val Asp Asp Gly Leu Glu His
1               5                   10                  15

Arg

<210> SEQ ID NO 413
<211> LENGTH: 8
<212> TYPE: PRT
<213> ORGANISM: Homo sapiens

<400> SEQUENCE: 413

Leu Glu Thr Asp Gly Gly Gly Pro
1               5

<210> SEQ ID NO 414
<211> LENGTH: 14
<212> TYPE: PRT
<213> ORGANISM: Homo sapiens

<400> SEQUENCE: 414

Ser Tyr Ser Ile Gln Glu Pro Val Val Leu Phe His Ser Arg
1               5                   10

<210> SEQ ID NO 415
<211> LENGTH: 8
<212> TYPE: PRT
<213> ORGANISM: Homo sapiens

<400> SEQUENCE: 415

Ser Thr Thr Asp Ser Ile Gln Glu
1               5

<210> SEQ ID NO 416
<211> LENGTH: 17
<212> TYPE: PRT
<213> ORGANISM: Homo sapiens

<400> SEQUENCE: 416

Ser Tyr Ser Asp Lys Gly Glu Phe Gly Gly Phe Gly Ser Val Thr Gly
1               5                   10                  15

Lys
```

<210> SEQ ID NO 417
<211> LENGTH: 8
<212> TYPE: PRT
<213> ORGANISM: Homo sapiens

<400> SEQUENCE: 417

Ser His Cys Asp Ser Asp Lys Gly
1               5

<210> SEQ ID NO 418
<211> LENGTH: 17
<212> TYPE: PRT
<213> ORGANISM: Homo sapiens

<400> SEQUENCE: 418

Ala Ala Asn Ser Asn Gly Pro Phe Gln Pro Val Val Leu Leu His Ile
1               5                   10                  15

Arg

<210> SEQ ID NO 419
<211> LENGTH: 8
<212> TYPE: PRT
<213> ORGANISM: Homo sapiens

<400> SEQUENCE: 419

Ala Gly Ser Arg Met Val Val Asp
1               5

<210> SEQ ID NO 420
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 420

Glu Asn Leu Tyr Phe Gln Ser Tyr
1               5

<210> SEQ ID NO 421
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 421

Glu Asn Leu Tyr Phe Gln Ser Lys
1               5

<210> SEQ ID NO 422
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 422

Glu Asn Leu Tyr Phe Gln Ser Ala
1               5

<210> SEQ ID NO 423
<211> LENGTH: 4
<212> TYPE: PRT

```
<213> ORGANISM: Artificial sequence
<220> FEATURE:
<223> OTHER INFORMATION: Synthetic polypeptide

<400> SEQUENCE: 423

Ala Ala Pro Tyr
1

<210> SEQ ID NO 424
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 424

Ala Ala Pro Lys
1

<210> SEQ ID NO 425
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 425

Ala Ala Pro Ala
1

<210> SEQ ID NO 426
<211> LENGTH: 7
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa can be Thr or Val

<400> SEQUENCE: 426

Glu Xaa Leu Phe Gln Gly Pro
1               5

<210> SEQ ID NO 427
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 427

Asp Asp Asp Asp Lys
1               5

<210> SEQ ID NO 428
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 428

Leu Val Pro Arg
1
```

```
<210> SEQ ID NO 429
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 429

Ile Glu Pro Asp
1

<210> SEQ ID NO 430
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 430

Asp Glu Val Asp
1

<210> SEQ ID NO 431
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 431

Ser Tyr Gly Ser Ala Val Asn Gly Thr Ser Ser Ala Glu Thr Asn Leu
1               5                   10                  15

Glu Ala Leu Gln Lys
            20

<210> SEQ ID NO 432
<211> LENGTH: 50
<212> TYPE: PRT
<213> ORGANISM: Homo sapiens

<400> SEQUENCE: 432

Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu
    50

<210> SEQ ID NO 433
<211> LENGTH: 8
<212> TYPE: PRT
<213> ORGANISM: Homo sapiens

<400> SEQUENCE: 433

Pro Ala Pro Asp Gly Ser Ala Val
1               5

<210> SEQ ID NO 434
<211> LENGTH: 10
<212> TYPE: PRT
<213> ORGANISM: Artificial sequence
<220> FEATURE:
<223> OTHER INFORMATION: Synthetic polypeptide
```

```
<220> FEATURE:
<221> NAME/KEY: MOD_RES
<222> LOCATION: (1)..(1)
<223> OTHER INFORMATION: Glycine modified at N-terminal amine by bond to
      biotin label through linker
<220> FEATURE:
<221> NAME/KEY: MOD_RES
<222> LOCATION: (10)..(10)
<223> OTHER INFORMATION: Tyrosine modified at C-terminal carboxyl by
      ester bond to end cap

<400> SEQUENCE: 434

Gly Thr Glu Asn Leu Tyr Phe Gln Ser Tyr
1               5                   10

<210> SEQ ID NO 435
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Lysine modified at side chain amine by amide
      bond to biotin label through linker
<220> FEATURE:
<221> NAME/KEY: MOD_RES
<222> LOCATION: (10)..(10)
<223> OTHER INFORMATION: Glutamine modified at C-terminal carboxyl by
      amide bond to end cap

<400> SEQUENCE: 435

Lys Gly Gly Thr Glu Asn Leu Tyr Phe Gln
1               5                   10

<210> SEQ ID NO 436
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: VARIANT
<222> LOCATION: (7)..(7)
<223> OTHER INFORMATION: Residue at position 7 is S, G or A

<400> SEQUENCE: 436

Glu Xaa Xaa Tyr Xaa Gln Xaa
1               5

<210> SEQ ID NO 437
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 437

Arg Xaa Xaa Arg
1
```

```
<210> SEQ ID NO 438
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 438

Asp Xaa Xaa Asp
1
```

DISCOVERY OF CANDIDATE BIOMARKERS OF IN VIVO APOPTOSIS BY GLOBAL PROFILING OF CASPASE CLEAVAGE SITES

CROSS-REFERENCES TO RELATED APPLICATIONS

This application is a continuation of International Application No. PCT/US2009/052297, filed Jul. 30, 2009, which claims priority benefit of U.S. Provisional Application Ser. No. 61/084,845 filed on Jul. 30, 2008, the disclosure of which is incorporated by reference in its entirety for all purposes.

STATEMENT AS TO RIGHTS TO INVENTIONS MADE UNDER FEDERALLY SPONSORED RESEARCH AND DEVELOPMENT

This invention was made with Government support under grant nos. R01 GM081051 and F32 GM074458, awarded by the National Institutes of Health. The Government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 81906-797932_ST25.TXT, created on Apr. 14, 2013, 98,022 bytes, machine format IBM-PC, MS-Windows operating system, is hereby incorporated by reference.

BACKGROUND OF THE INVENTION

The 600 or so proteases encoded in the human genome are involved in a diversity of biological processes. Some function as nonspecific degradative enzymes associated with protein catabolism, indiscriminately and exhaustively cleaving many protein substrates at many sites. In contrast, several others function as selective post-translational modifiers, cleaving a limited set of protein substrates, usually at only one or a few sites. Apoptosis is an important example of a biological process regulated by widespread but specific intracellular proteolysis, predominantly carried out by the caspase family of proteases. This genetically programmed and non-inflammatory form of cell death is a central component of homeostasis, tissue turnover, and development. Since apoptotic turnover of cells lies in direct opposition to the uncontrolled growth of tumor cells, a strong link also exists between apoptosis and cancer. Indeed, the terminal cellular effect of most chemotherapeutic compounds is induction of apoptosis (Kaufmann et al., Exp Cell Res, 2000, 256, 42-9).

The widespread intracellular proteolysis that is a hallmark of apoptosis is predominantly mediated by a family of aspartate-specific proteases termed caspases (Taylor et al., Nat Rev Mol Cell Biol, 2008, 9, 231-41). Apoptosis can be induced by extracellular death ligands, such as Fas ligand, TNF-α, or TRAIL, via the extrinsic pathway to activate caspase-8. It can also be induced by agents such as cytotoxic compounds, radiation, and other environmental stresses via the intrinsic pathway with release of proapoptotic factors from mitochondria to activate caspase-9. Initiator caspases-8 and -9 in turn activate downstream executioner caspases, among them caspases-3 and -7. Caspases then catalyze the inactivation of a multitude of prosurvival/antiapoptotic proteins and activation of antisurvival/proapoptotic proteins. The combined proteolytic events culminate in apoptotic cell death and clearance by phagocytes.

As a specific illustration, after receiving a cell death signal, apoptotic cells execute a cellular program that results in widespread and dramatic cellular changes that can include: (1) cell shrinkage and rounding due to the breakdown of the proteinaceous cytoskeleton; (2) the appearance of a dense cytoplasm and tight packing of cell organelles; (3) chromatin condensation into compact patches against the nuclear envelope; (4) discontinuity of the nuclear envelope and DNA fragmentation; (5) breakdown of the nucleus into several discrete chromatin bodies or nucleosomal units due to the degradation of DNA; (6) blebbing of the cell membrane into irregular buds. Near the conclusion of the apoptotic program, the cell breaks apart into several vesicles called apoptotic bodies, which are then typically phagocytosed.

Because the study of apoptotic pathways has ramifications for development of therapies for treatment of cancer, there is significant interest in gaining a better understanding of caspase proteolysis during apoptosis. For example, identification of new targets of proteolysis in apoptosis can lead to discovery of prosurvival/antiapoptotic factors, which can in turn serve as novel targets for cancer chemotherapy. A number of caspase substrates are active or established drug targets for treating cancer, including topoisomerases I and II, androgen receptor, thymidylate synthase, Bcl-2, IAPs, Mdm2 or Hdm2, PARP, HSP90, HDACs, the proteasome, Akt, MEK, Abl, EGFR, HER2, and VEGF, to name a few.

Products of caspase proteolysis may also serve as useful biomarkers of in vivo apoptosis. For example, serum levels of the caspase cleavage product of cytokeratin-18 have been used as a marker of chemotherapeutic efficacy in prostate, breast, and testicular cancers (Kramer et al., Br J Cancer, 2006, 94, 1592-8; Olofsson et al, Clin Cancer Res, 2007, 13, 3198-208; de Haas et al, Neoplasia, 2008, 10, 1041-8). Although apoptotic cells are typically cleared by phagocytes such as macrophages, it has been hypothesized that local clearance mechanisms are overloaded in cases of high cellular turnover and death, causing dying apoptotic cells to undergo secondary necrosis (Linder et al, Cancer Lett, 2004, 1, 1-9). While the plasma membrane remains intact during apoptosis, it is compromised and ruptured during secondary necrosis. Such secondary necrosis of dying tumor cells is consistent with the observation of what are normally intracellular components such as cytochrome c, DNA, nucleosomes, and cytokeratin-18 in the vasculature of cancer patients during chemotherapy (Beachy et al., Cancer Immunol Immunother, 2008, 57, 759-75).

A logical extension of these findings is that other caspase-derived neo-epitopes besides caspase-cleaved cytokeratin-18 are released into the vasculature of cancer patients undergoing chemotherapy. Such additional caspase-proteolyzed proteins may represent novel prognostic, diagnostic, or pharmacodynamic biomarkers of in vivo apoptosis, predicting likely patient outcome, indicating the most suitable therapeutic regimen, or serving as markers of therapeutic response. Because of tumor and patient heterogeneity, the clinical utility of single biomarker assays can be limited (Anderson et al., Mol Cell Proteomics, 2002, 1, 845-67). A multiparameter diagnostic assay of in vivo apoptosis based on a panel of caspase-derived neo-epitopes would likely be more sensitive and specific for a given type of cancer or therapeutic regimen. Great utility therefore exists in the identification of physiologically relevant caspase cleavage sites. Knowledge of such cleavage sites is required for the preparation of both peptide standards corresponding to neo-epitopes and antibodies that specifically bind to neo-epitopes. These reagents will enable identification and quantitation of caspase-derived neo-epitopes in biological samples such as serum, plasma, or tissue biopsies, and for validation of a given set of caspase-derived neo-epitopes as clinically useful biomarkers of in vivo apoptosis.

BRIEF SUMMARY OF THE INVENTION

The present invention relates generally to 1356 experimentally determined and physiologically relevant caspase-like cleavage sites, a method for discovering additional physiologically relevant caspase cleavage sites, discovery of biomarkers of in vivo apoptosis based on any of these caspase-like cleavage sites, and methods and compositions for detecting and quantitating protein neo-epitopes corresponding to these biomarkers in biological samples, using either peptide standards and mass spectrometry, or antibodies specific to neo-epitopes, or both. The invention also provides compositions and kits for performing the methods of the invention.

Direct and selective labeling of protein α-amines or α-carboxylates is a powerful approach for profiling proteolysis in complex mixtures since it permits direct identification of cleavage sites in protein substrates. Approximately 80% of mammalian proteins are known to be N-terminally acetylated (Brown et al., J Biol. Chem. 1976; 251(4):1009-14). Thus, greater signal over background can be achieved through N-terminal instead of C-terminal labeling. However, such labeling must still be extremely selective for α-amines over lysine ε-amines, which are approximately 25 times more abundant in an average protein. To achieve this selectivity, we have adopted an enzymological approach that makes use of the rationally designed protein ligase subtiligase. This engineered enzyme exhibits absolute selectivity for modification of α-amines (Abrahmsén et al., Biochemistry. 1991; 30(17):4151-9; Chang et al., Proc Natl Acad Sci USA. 1994; 91(26):12544-8).

We have developed a proteomic method utilizing subtiligase that enables capture and sequencing of N-terminal peptides found in complex biochemical mixtures (FIGS. 1A-1 and 1A-2). Proteins in biological samples are N-terminally biotinylated by treatment with subtiligase and peptide glycolate ester substrates specially tailored to our proteomic workflow (FIGS. 1B-1 and 1B-2). Biotinylated samples are exhaustively digested with trypsin, and N-terminal peptides are captured using avidin affinity media. The peptide ester substrate contains a tobacco etch virus (TEV) protease cleavage site to permit facile recovery of captured peptides. An important aspect of our workflow is that recovered peptides retain an N-terminal serinyl-tyrosyl dipeptide modification or 2-aminobutyryl modification, providing a key hallmark to distinguish labeled peptides from contaminating unlabeled peptides using tandem mass spectrometry (LC/MS/MS). In standard protease nomenclature, substrates are cleaved between the P1 (N-terminal) and P1' (C-terminal) residues, with Pn and Pn' residues increasing in count by one in both directions away from the scissile bond (Schechter and Berger, 1968). Thus, the Pn' residues of a cleavage site correspond to N-terminal residues of the labeled peptide identified, while the Pn residues of a cleavage site can be inferred from the protein sequence preceding the identified peptide.

Over 300 publications describing a wide variety of cell types and apoptotic inducers have reported the proteolysis of approximately 360 human proteins in apoptosis, but only approximately 300 caspase cleavage sites in human protein substrates have been reported (Lüthi et al., Cell Death Differ. 2007; 14(4):641-50). We have carried out studies in a number of cancer cell lines, including Jurkat, an acute lymphocytic leukemia cell line, DB, a diffuse large B cell lymphoma cell line, and RPMI 8228, a multiple myeloma cell line, using a variety of apoptotic inducers including etoposide, doxorubicin, staurosporine, and TRAIL. Our combined studies to date have resulted in the identification of approximately 1360 caspase cleavage sites in a approximately 1040 protein substrates. These caspase cleavage sites and additional caspase cleavage sites yet to be discovered in other model systems of human cancers represent a wealth of knowledge and an excellent starting point for discovery of novel biomarkers of in vivo apoptosis, and for preparation of reagents for detection and quantitation of such biomarkers in biological samples.

The present invention provides proteolytic polypeptide biomarkers for the detection and quantitation of apoptosis. In one embodiment of the invention, these biomarkers comprise proteolytic polypeptides generated in response to an apoptotic stimulus. The biomarkers of the present invention may be generated in response to a specific apoptotic stimulus or conversely may be generated by multiple or general apoptotic stimuli. In some embodiments, the proteolytic polypeptide biomarkers of the present invention are generated by the action of a single protease, or by the action of a limited set of proteases activated in response to a specific apoptotic stimulus. In other embodiments, the biomarkers may be generated by the action of a plurality of apoptotic proteases. In a particular embodiment, the proteolytic apoptotic polypeptide biomarkers comprise N-termini or C-termini selected from those found in Table 1.

In one embodiment, the proteolytic biomarkers of the present invention are useful for the detection of apoptosis in an individual. In a specific embodiment, the proteolytic biomarkers are useful for the diagnosis in an individual of a disease characterized by apoptosis. In another embodiment, these biomarkers are useful for providing a prognosis for an individual suffering from a disease characterized by apoptosis. In yet other embodiments, these biomarkers are useful for determining the extent of apoptosis in an individual or the severity, stage, or other relevant characteristics of a disease characterized by apoptosis in an individual. In one particular embodiment, the proteolytic apoptotic biomarkers of the present invention are useful in determining the efficacy of a drug in vitro or in vivo.

In another embodiment, the present invention provides novel proteolytic apoptotic cleavage junctions. In certain embodiments, these cleavage junctions comprise amino acids that are cleavage substrates for proteases activated in response to an apoptotic stimulus. In a particular embodiment, the proteolytic apoptotic cleavage junctions comprise an amino acid sequence selected from those found in Table 3. In a first embodiment, the cleavage junctions of the present invention are useful for detecting apoptosis in a biological sample. In a second embodiment, the cleavage junctions are useful for diagnosing or providing a prognosis for a disease state associated with apoptosis in an individual, or for assessing response to a particular line of therapy. For instance, a protein or polypeptide comprising the cleavage junction can be used in an assay to measure apoptotic protease (e.g., a caspase) activity or levels in a sample. The peptides or polypeptides comprising the junction may be of a variety of lengths, preferably from 7 to 40, 7 to 20, or 10 to 30 amino acids in length.

The present invention also provides proteolytic apoptotic signatures. In one embodiment, the apoptotic signatures of the invention comprise at least one proteolytic polypeptide generated in response to an apoptotic stimulus. In another embodiment of the invention, the apoptotic signatures comprise the levels of one or more proteolytic polypeptides. In a particular embodiment, the apoptotic signatures of the present invention comprise the presence or particular level of one or more proteolytic polypeptides comprising N-termini or C-termini selected from those found in Table 1. In yet other embodiments, the apoptotic signatures of the present invention may comprise one or more ratios of cleaved to uncleaved apoptotic proteolytic sites. In a particular embodiment of the present invention, the apoptotic proteolytic sites are selected from those found in Table 3. In some embodiments, the proteolytic apoptotic signatures of the present invention may correspond to the presence or absence of a disease state in an individual. In other embodiments of the present invention, the proteolytic apoptotic signatures may correspond to a particular level of apoptosis in an individual or in a sample from an individual suffering from a disease characterized by apoptosis. In another embodiment of the present invention, the proteolytic apoptotic signatures may correspond to a prognosis for an individual suffering from a disease characterized by apoptosis. In yet other embodiments, the apoptotic signatures may correspond to a level of efficacy for a drug or to a response level in an individual taking a drug or receiving a treatment for a disease characterized by apoptosis.

In one embodiment, the present invention provides reagents for detecting the proteolytic apoptotic polypeptide biomarkers of the invention. In one embodiment, the reagents comprise synthetic peptides corresponding to an N-terminal or C-terminal sequence selected from those found in Table 1. In a particular embodiment, these synthetic peptides have the same sequence as either an unmodified or modified peptide found in Table 1. In another embodiment, these synthetic peptides contain six or more consecutive residues from a sequence of previous residues found in Table 1, starting from the most C-terminal residue, and possibly extending to further than eight prior residues in the sequence of the full-length protein. In one embodiment, these peptides correspond to the most N-terminal peptide obtained after digestion with trypsin of the C-terminal fragment of the full-length protein following proteolysis during apoptosis at one the cleavage sites found in Table 2. In another embodiment, these peptides correspond to the most C-terminal peptide obtained after digestion with trypsin of the N-terminal fragment of the full-length protein following proteolysis during apoptosis at one the cleavage sites found in Table 1 or 2. In another embodiment, these peptides correspond to the peptides that would be obtained following digestion of the N- and C-terminal fragments of the protein substrate with a protease other than trypsin, including, but not limited to, chymotrypsin, V8, Lys-C, Lys-N, Arg-C, Asp-N, Asp-C, pepsin, and thermolysin. In another particular embodiment, these peptides correspond to the peptides that would be obtained following treatment of the N- and C-terminal fragments of the protein substrate with a chemical cleavage agent such as cyanogen bromide. In a specific embodiment, the synthetic peptides contain stable heavy isotopes of carbon or nitrogen (e.g., $^{13}C$ or $^{15}N$), incorporated by use of the appropriately heavy isotope-labeled amino acid during preparation of the synthetic or modified peptides. In a particular embodiment, the light and heavy versions of the peptides are used as standards in a mass spectrometry approach such as selected reaction monitoring (SRM) or multiple reaction monitoring (MRM) to optimize detection of corresponding peptides in biological samples derived from proteolytic apoptotic polypeptides, and to permit quantitation of such peptides in biological samples.

In another embodiment, the present invention provides reagents for detecting the proteolytic apoptotic polypeptide biomarkers of the invention. In one embodiment, the reagents comprise proteins that bind to the biomarkers with high affinity and specificity. In a particular embodiment, the reagents comprise antibodies, or fragments thereof, generated against the proteolytic apoptotic polypeptides of the present invention. In a specific embodiment, the present invention provides antibodies that bind to a proteolytic apoptotic polypeptide comprising an N-terminal or C-terminal sequence selected from those found in Table 1. In one embodiment, an antibody of the present invention binds to the target proteolytic fragment, but does not substantially bind to the full-length protein or intact proteolytic cleavage junction. In other embodiments, the reagents comprise antibodies generated against antigens comprising apoptotic cleavage sites or junctions. In a specific embodiment, the present invention provides antibodies that bind to an apoptotic cleavage site selected from those listed in Table 3. In one embodiment, the antibodies of the present invention bind to an intact proteolytic cleavage junction, but do not substantially bind to the N-terminal or C-terminal proteolytic polypeptide generated in response to an apoptotic stimulus. In another particular embodiment of the invention, antibodies are provided that bind to the N-terminus or C-terminus of a proteolytic polypeptide comprising a sequence selected from those found in Table 1.

In another embodiment, the present invention provides methods of generating binding reagents to one or more proteolytic apoptotic polypeptide biomarker. In one embodiment of the invention, methods are provided for generating a binding reagent to a single proteolytic polypeptide. In other embodiments, the present invention provides methods of simultaneously generating binding reagents against more than one proteolytic polypeptides of the present invention. In a particular embodiment, the present invention provides methods of generating antibodies against one or more proteolytic apoptotic polypeptide of the invention.

In one embodiment, the present invention provides methods of detecting apoptosis or determining the level of apoptosis in an individual or in a sample from an individual. In one embodiment, the methods comprise detecting a proteolytic apoptotic polypeptide biomarker generated in response to an apoptotic stimulus in a biological sample. In certain embodiments, the methods of the present invention comprise detecting one or more biomarkers comprising an N-terminal or C-terminal sequence selected from those found in Table 1. In other embodiments of the present invention, methods are provided for detecting or determining a proteolytic apoptotic signature. In certain embodiments of the invention, detecting or determining a proteolytic apoptotic signature comprises detecting or determining the level of one or more proteolytic apoptotic polypeptide biomarkers generated in response to an apoptotic signature. In other embodiments, the methods further comprise comparing a first proteolytic apoptotic signature detected in an individual with a second apoptotic signature corresponding to a predetermined apoptotic level or disease state. In certain embodiments of the invention, said second apoptotic signature comprises an average or conglomerate apoptotic signature determined from samples taken from a plurality of individuals suffering from the same disease or disease state associated with apoptosis. In yet other embodiments, the methods of the present invention comprise determining the ratio of the levels of at least one proteolytic apoptotic polypeptide to the levels of at least one intact proteolytic cleavage junction.

In another embodiment, the present invention provides methods for diagnosing or providing a prognosis for a disease associated with apoptosis in an individual, or for tracking therapeutic progress in an individual. In some embodiments of the present invention, the methods comprise detecting one or more proteolytic apoptotic polypeptide biomarkers in a sample from said individual. In other embodiments, the methods of the present invention comprise detecting a proteolytic apoptotic signature in a sample from an individual. In particular embodiments, the methods of the present invention comprise comparing the level of one or more proteolytic apoptotic polypeptide or apoptotic signature in an individual with one or more proteolytic apoptotic signature corresponding to a predetermined disease or disease state. In yet other embodiments, the methods of diagnosing and providing a prognosis provided by the present invention comprise determining the ratio of the levels of at least one proteolytic apoptotic polypeptide to the levels of at least one intact proteolytic cleavage junction. In particular embodiments, these methods further comprise comparing said ratios to predetermined values corresponding to a particular diagnosis or prognosis for a disease state associated with apoptosis. In another embodiment, the methods comprise comparing levels of apoptotic signatures in a patient before the start of therapy, and during the course of therapy.

In one embodiment, the present invention provides kits for use in the detection of proteolytic apoptotic polypeptides. In some embodiments, the kits of the present invention comprise a plurality of light- or heavy-labeled synthetic peptides corresponding to N- and/or C-terminal sequences found in Table 1 that can be used for optimizing detection of corresponding peptides in biological samples derived from proteolytic apoptotic polypeptides, and to permit quantitation of such peptides in biological samples, using mass spectrometry. In other embodiments, the kits of the present invention comprise a plurality of binding reagents that specifically bind to proteolytic polypeptides that are generated in response to an apoptotic stimulus. In a specific embodiment, the kits of the present invention comprise a plurality of binding reagents that bind to polypeptides comprising an N-terminal or C-terminal sequence found in Table 1. In certain embodiments, the binding reagents are antibodies, including polyclonal antibodies, monoclonal antibodies, and fragments thereof. In certain embodiments, the kits of the present invention are useful in the diagnosis or prognosis of a disease characterized by apoptosis in an individual, or for tracking therapeutic progress in an individual that is characterized by an increased level of apoptosis. In yet other embodiments, the present invention provides kits comprising a plurality of binding reagents that specifically bind to proteolytic apoptotic cleavage junctions. In a particular embodiment, the proteolytic apoptotic cleavage junctions comprise amino acid sequences found in Table 3. In still other embodiments, the kits of the present invention comprise at least one binding reagent that specifically binds to a proteolytic apoptotic polypeptide and at least one binding reagent that specifically binds to a proteolytic apoptotic cleavage junction. In other certain embodiments, the kits comprise binding reagents that specifically bind to peptides generated from proteolytic apoptotic polypeptides after treatment with proteases such as trypsin, chymotrypsin, V8, Lys-C, Lys-N, Arg-C, Asp-N, Asp-C, pepsin, or thermolysin, or reagents such as cyanogen bromide, permitting enrichment of these peptides for detection and quantitation using mass spectrometry.

In another aspect, the invention provides a method of modulation apoptosis by administering a siRNA or a shRNA corresponding to an mRNA encoding a protein of Table 1. In this first aspect, the invention also provides a pharmaceutical composition comprising the siRNA molecule or the shRNA molecule and/or an siRNA or shRNA expression vector which comprises a portion of a nucleotide sequence complementary to an mRNA encoding a protein of Table 1. In some embodiments, the siRNA is at least about 15-50 nucleotides in length (e.g., each complementary sequence of the double stranded siRNA is 15-50 nucleotides in length, and the double stranded siRNA is about 15-50 base pairs in length). In some further embodiments still, the length of the siRNA molecule is about 20-30 base nucleotides, about 20-25 or about 24-29 nucleotides in length, e.g., 20, 21, 22, 23, 24, 25, 26, 27, 28, 29, or 30 nucleotides in length. In still further embodiments, the siRNA is a small hairpin loop or small hairpin RNA, known as shRNA. In some embodiments, the invention provides a method of treating cancer or inducing apoptosis in a subject in need thereof by administering the siRNA or shRNA or siRNA vector or shRNA vector to the subject. In some embodiments of any of the above the siRNA or shRNA is directed toward a protein having a M value from Table 1 greater than 1, 2, 4, or 8. In other embodiments, siRNA corresponding to a protein of Table 1 or 3 having a plurality of such cleavage sites is used.

BRIEF DESCRIPTION OF THE DRAWINGS

(FIGS. 1A-1 and 1A-2) Workflow for biotinylation of protein N-termini in complex mixtures using subtiligase and a biotinylated peptide ester that contains a TEV protease cleavage site, trypsinization of labeled proteins, capture of biotinylated N-terminal peptides with immobilized avidin, recovery of captured peptides using TEV protease, and analysis of N-terminal peptides by 1D or 2D LC/MS/MS for identification of corresponding proteins and cleavage sites. The representative MS/MS spectrum corresponds to semitryptic peptide GSAVNGTSSAETNLEALQK from MEK1 (MP2K1 HUMAN) (SEQ ID NO:178) and identifies a previously unknown caspase-like cleavage site at Asp 16. The $a^2$ and $b_2$ ions at m/z 223 and 251 are characteristic hallmarks of a ligated, serinyl-tyrosyl dipeptive-bearing, N-terminal peptide. (FIGS. 1B-1 and 1B-2) Structure of two biotinylated peptide glycolate esters used in the proteomic workflow. Sequences: (FIG. 1A-2) SYGSAVNGTSSAETNLEALQK (SEQ ID NO:431); MEK1 protein sequence (SEQ ID NO:432); cleavage site (SEQ ID NO:433), (FIG. 1B-1) Ester1 (SEQ ID NO:434), (FIG. 1B-2) Ester2 (SEQ ID NO:435), (FIG. 1A-1) TENLYFQSY (fragment of SEQ ID NO:434).

FIGS. 2A, 2B, and 2C. Classification of unique N-termini identified in untreated and apoptotic Jurkat cells according to Swiss-Prot annotation. (FIG. 2A) Classification of N-termini identified in small-scale and large-scale experiments with untreated cells (131 and 661 unique N-termini, respectively, combined from two experiments in both cases). (FIG. 2B) Classification N-termini identified in small-scale experiments with untreated cells (131 unique N-termini combined from two experiments) and apoptotic cells (244 unique N-termini combined from four experiments). (FIG. 2C)

Classification N-termini identified in large-scale experiments with untreated cells (661 unique N-termini combined from two experiments) and apoptotic cells (733 unique N-termini combined from three experiments).

FIGS. 3A and 3B. N-termini derived from caspase-like proteolytic processing are a hallmark of apoptotic cells. (FIG. 3A) Frequencies of P1 and P1' amino acid residues corresponding to non-homologous N-termini identified in small-scale 1D LC/MS/MS experiments with untreated and apoptotic Jurkat cells. Data are represented as mean±SD (n=2 for untreated and n=4 for apoptotic). (FIG. 3B) Frequencies of P1 and P1' amino acid residues corresponding to non-homologous N-termini identified in large-scale 2D LC/MS/MS experiments with untreated and apoptotic Jurkat cells. Data are represented as mean±SD (n=2 for untreated and n=3 for apoptotic). " " indicates lack of a putative P1 residue in cases where the P1' residue is an initiator methionine.

FIG. 4. Inferred P1 residues for all N-termini annotated in the human Swiss-Prot database originating from chain, signal peptide, transit peptide, or propeptide processing.

Figure 5A:
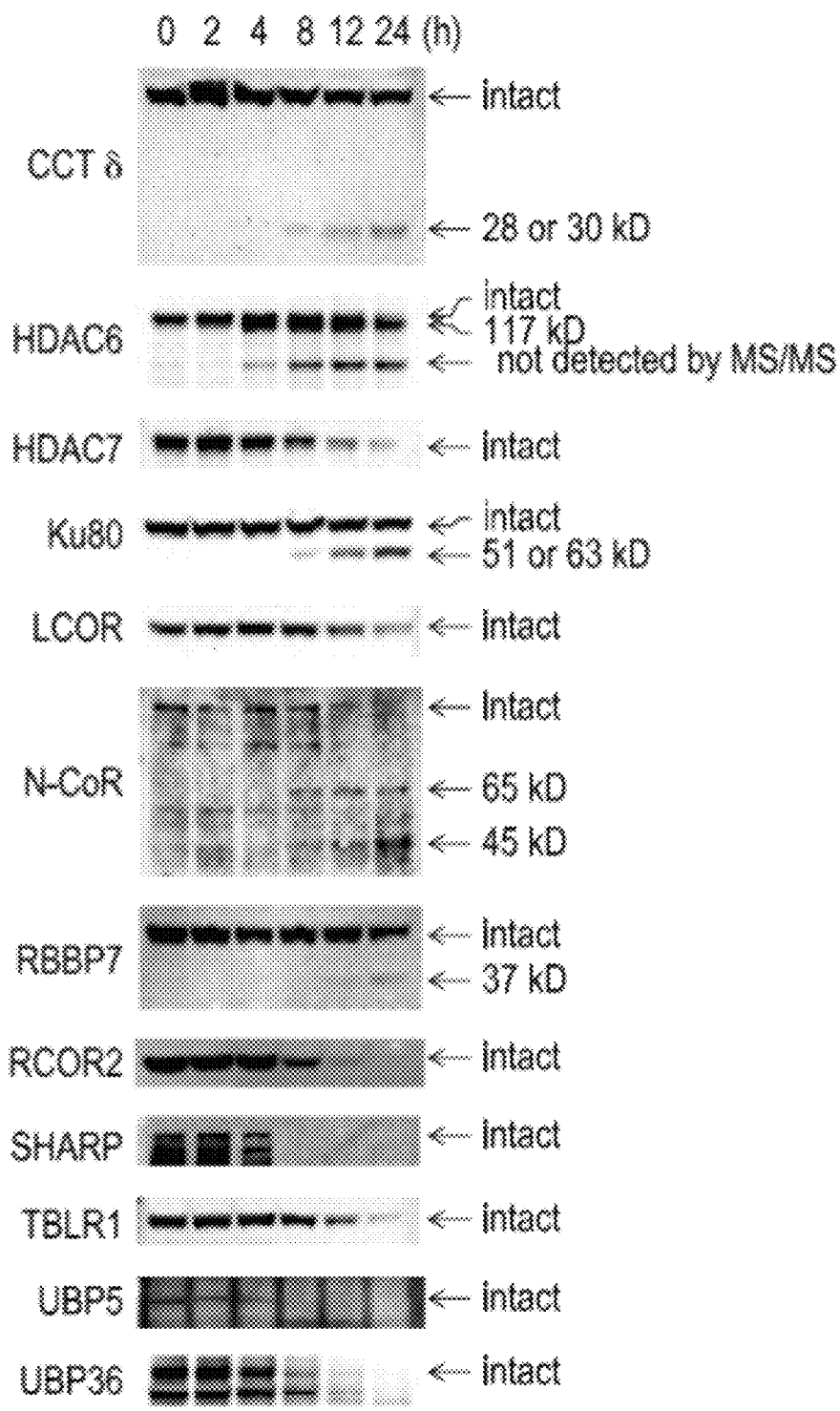

FIGS. 5A and 5B. Analysis of proteolysis of selected proteins, all identified as caspase substrates in proteomic studies, during apoptosis in Jurkat cells following treatment with 50 μM etoposide. Black arrows indicate full-length proteins. Red arrows indicate expected cleavage products for cleavage at the sites identified in our studies. Cleavage products were not detected in all cases. (FIG. 5A) Time courses for the proteolysis of CCTδ, HDAC6, HDAC7, Ku80, LCOR, N-CoR, RBBP7, RCOR2, SHARP, TBLR1, UBP5, and UBP36 indicates full cleavage of HDAC6, HDAC7, N-CoR, RCOR2, SHARP, TBLR1, UBP5, and UBP36, and partial cleavage of CCTδ, Ku80, LCOR, and RBBP7. (FIG. 5B) The cleavage of a representative set of substrates identified in our studies, HDAC7, Ku80, RCOR2, TBLR1, and UBP36, is blocked by the broad-spectrum caspase inhibitor Z-VAD(OMe)-fmk and is thus dependent on caspase activity.

FIGS. 6A, 6B, 6C, 6D, and 6E. Substrate specificity of the caspase-like proteolytic activity in etoposide-treated Jurkat cells. (FIG. 6A) Sequence logo representation (Crooks et al., 2004) of the frequency of amino acid residues in the identified caspase cleavage sites. (FIG. 6B) Sequence logo representation of the in vitro substrate specificity of caspase-3 (Stennicke et al., 2000; Thornberry et al., 1997). (FIG. 6C) Sequence logo representation of the frequency of amino acid residues in known human and human ortholog of rodent caspase cleavage sites (Liithi and Martin, 2007). (FIG. 6D) Frequency of P4-P1 motifs in the identified caspase cleavage sites. (FIG. 6E) Receiver operator characteristic curves showing the discrimination ability of HMMs constructed from three different cleavage site training sets (Jurkat, literature, and merged). Three representative HMM score threshold values for the merged dataset are indicates (TPR=true positive rate, FPR=false positive rate). Sequence: DEVD (SEQ ID NO:430).

Figure 7A:
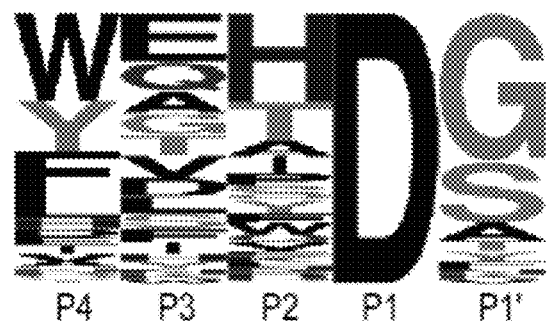
Figure 7B:
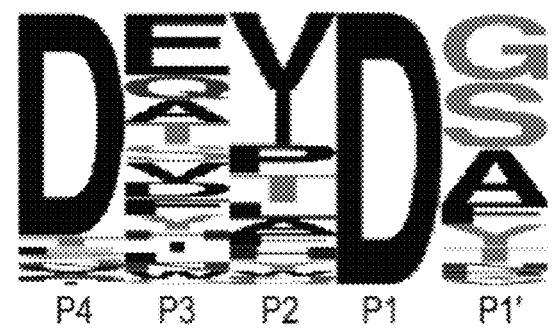
Figure 7C:
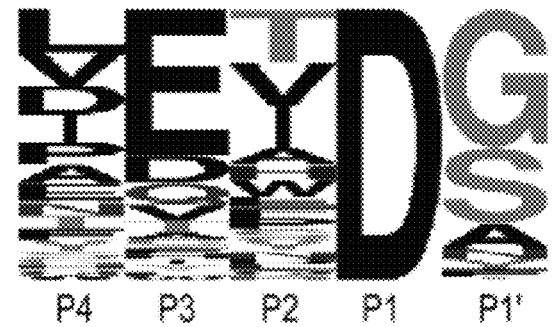

FIGS. 7A, 7B, and 7C. Sequence logo representations of prototypical inflammatory, executioner, and initiator caspase substrate specificities. These are exemplified by (FIG. 7A) caspase-1, (FIG. 7B) caspase-3, and (FIG. 7C) caspase-8, based on P4-P1 data adapted from Thornberry et al. (Thornberry et al., J Biol Chem. 1997; 272(29):17907-11) and P1' data adapted from Stennicke et al. (Stennicke et al., Biochem J. 2000; 350 Pt 2:563-8).

Figure 8:
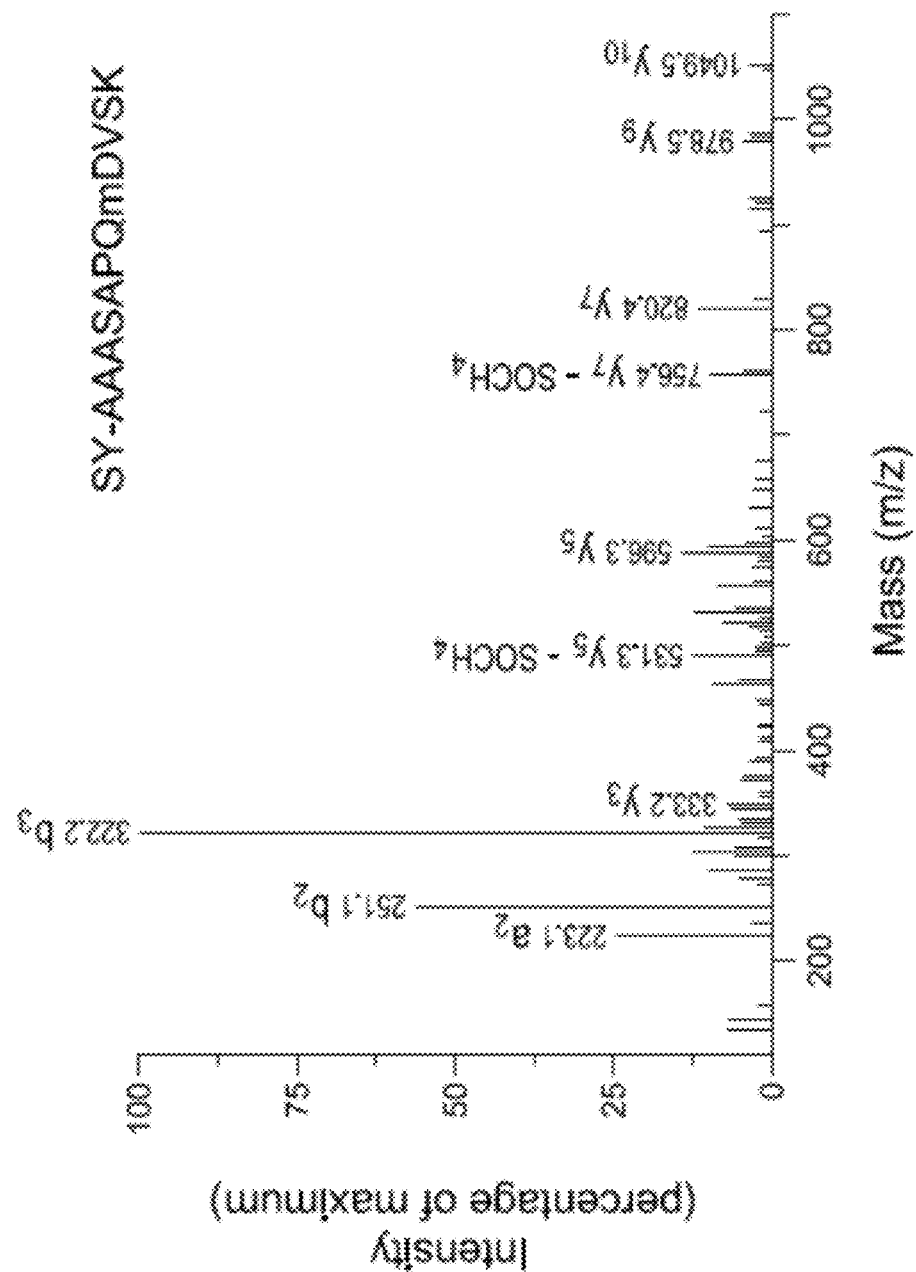

FIG. 8. CID spectrum of the SY-labeled N-terminal peptide AAASAPQM(Oxidation)DVSK from N-CoR (NCOR1_HUMAN) (SEQ ID NO:402) corresponding to the P4-P4' cleavage site LVD(1826)/AAAS (SEQ ID NO:403).

Figure 9:
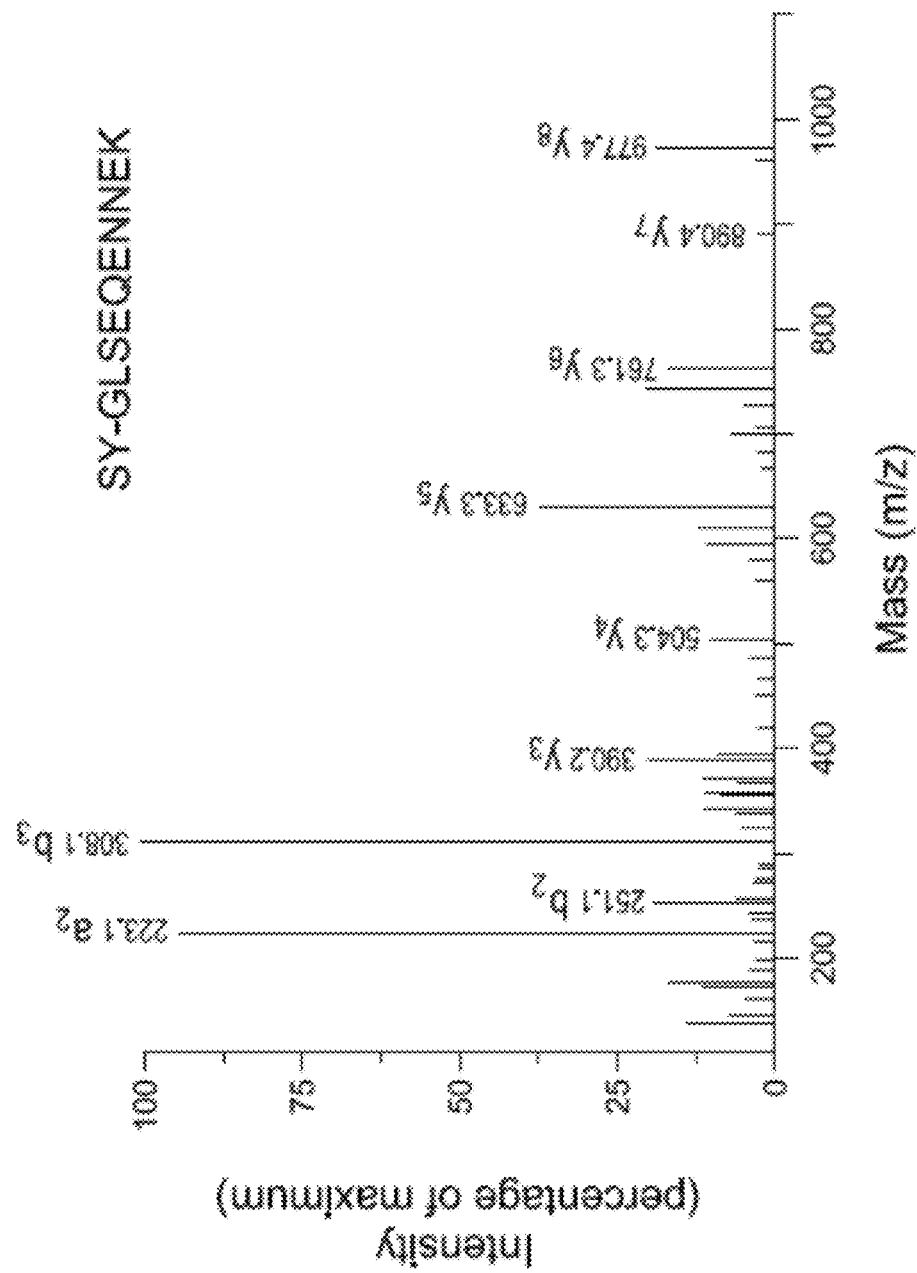

FIG. 9. CID spectrum of the SY-labeled N-terminal peptide GLSEQENNEK from N-CoR (NCOR1_HUMAN) (SEQ ID NO:404) corresponding to the P4-P4' cleavage site EIID(385)/GLSE (SEQ ID NO:405).

Figure 10:
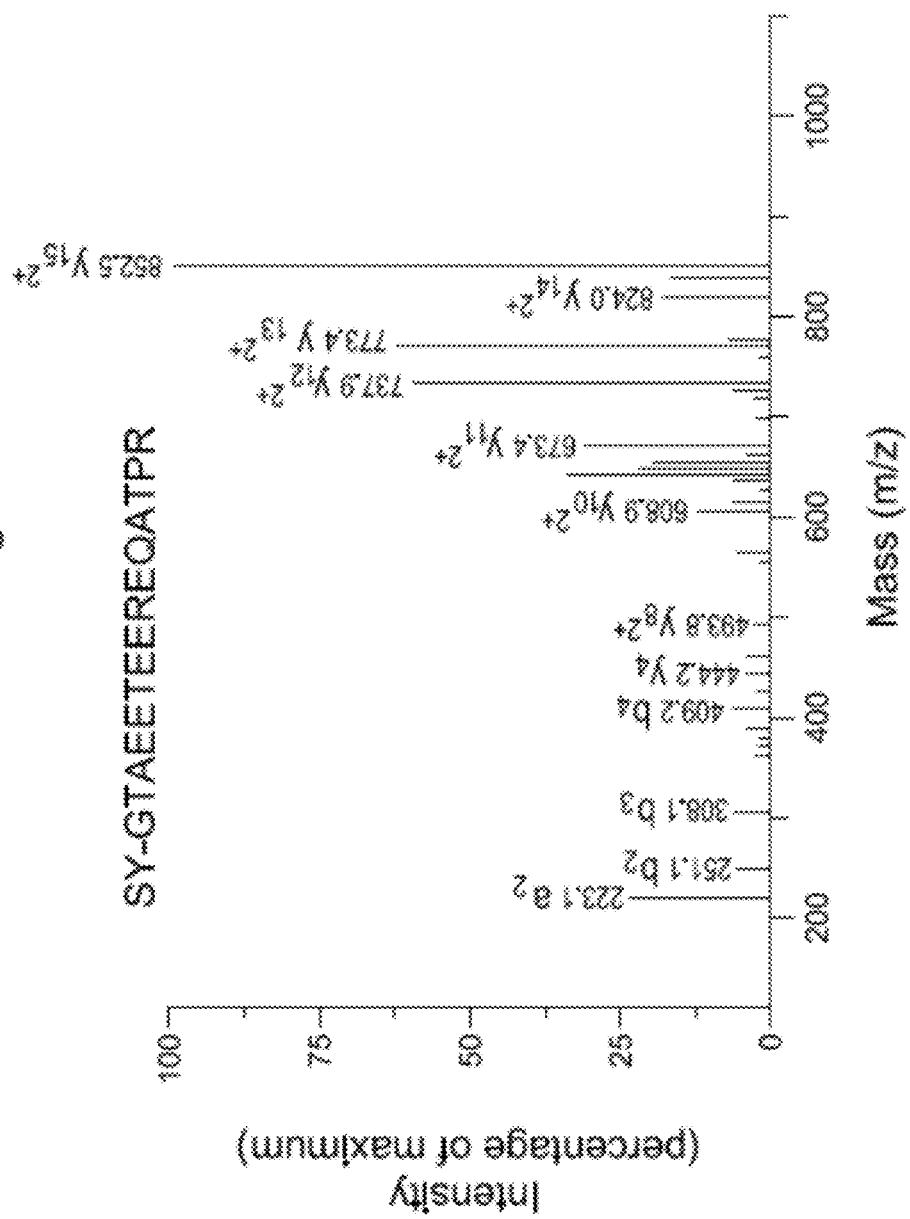

FIG. 10. CID spectrum of the SY-labeled N-terminal peptide GTAEETEEREQATPR from N-CoR (NCOR1_HUMAN) (SEQ ID NO:406) corresponding to the P4-P4' cleavage site DKID(555)/GTAE (SEQ ID NO:407).

Figure 11:
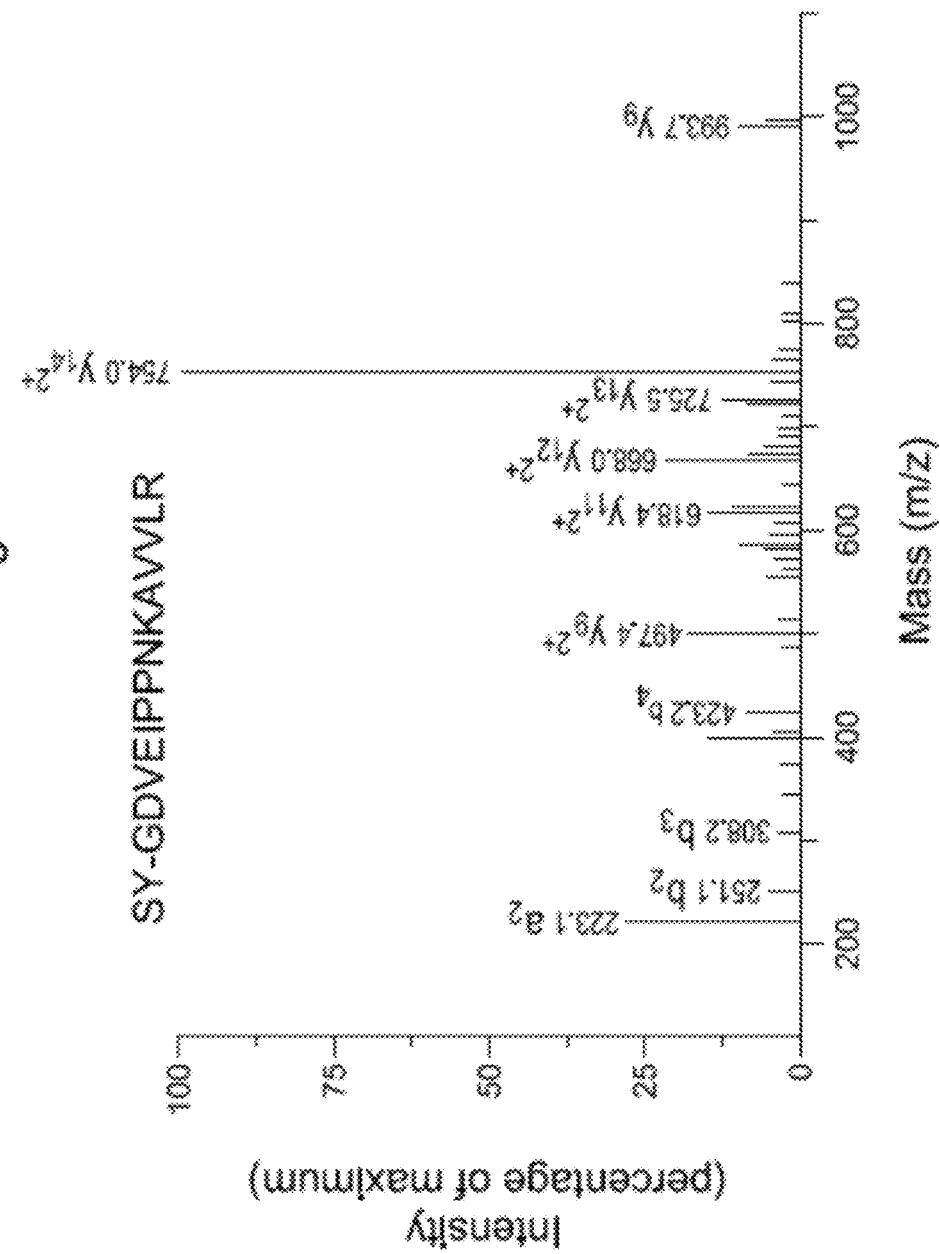

FIG. 11. CID spectrum of the SY-labeled N-terminal peptide GDVEIPPNKAVVLR from TBLR1 (TBL1R_HUMAN) (SEQ ID NO:408) corresponding to the P4-P4' cleavage site MEVD(152)/GDVE (SEQ ID NO:409).

Figure 12:
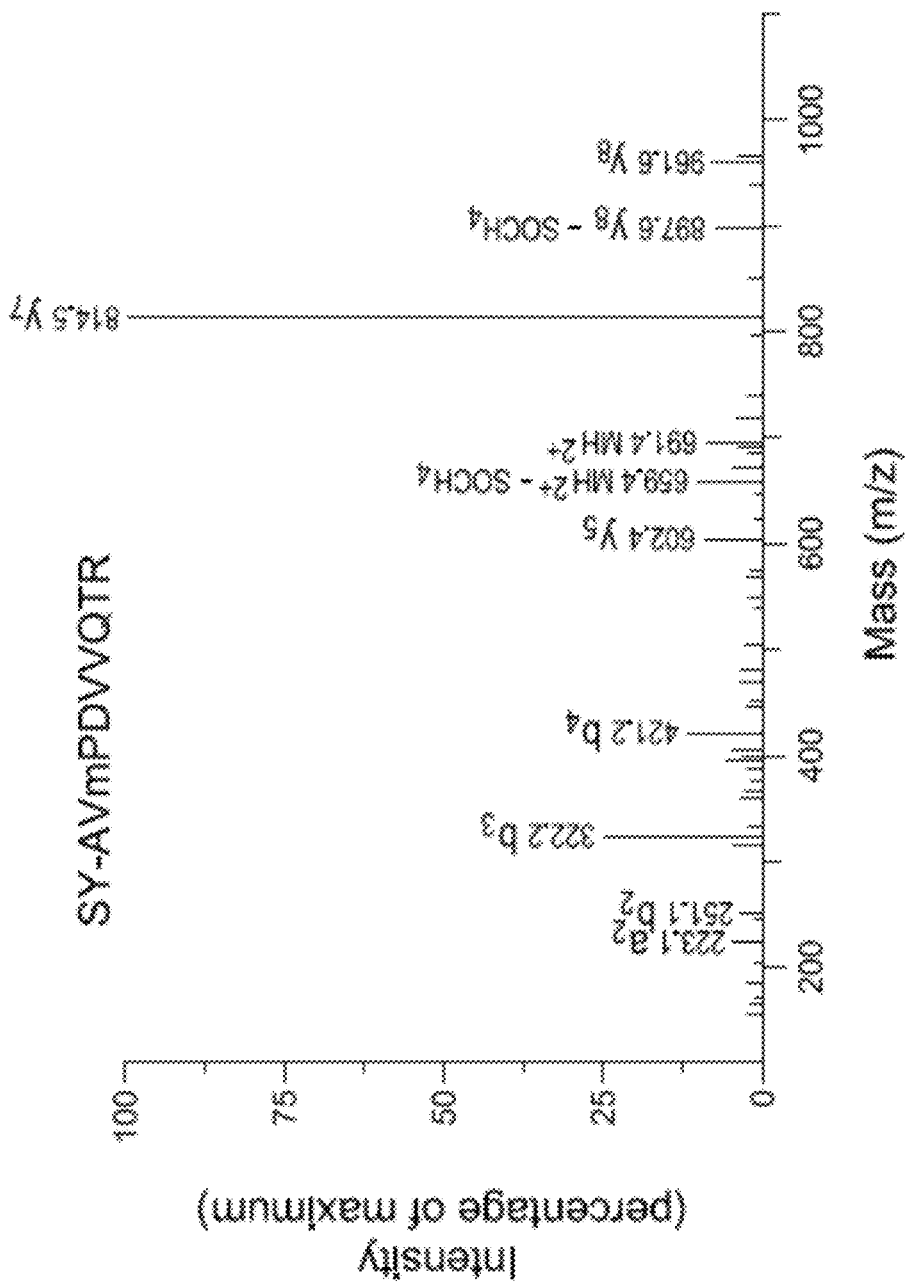

FIG. 12. CID spectrum of the SY-labeled homologous N-terminal peptide AVM(Oxidized)PDVVQTR from either TBLR1 (TBL1R_HUMAN) or TBL1X (TBL1X_HUMAN) (SEQ ID NO:410) corresponding to the P4-P4' cleavage site SLID(86)/AVMP (SEQ ID NO:411).

Figure 13:
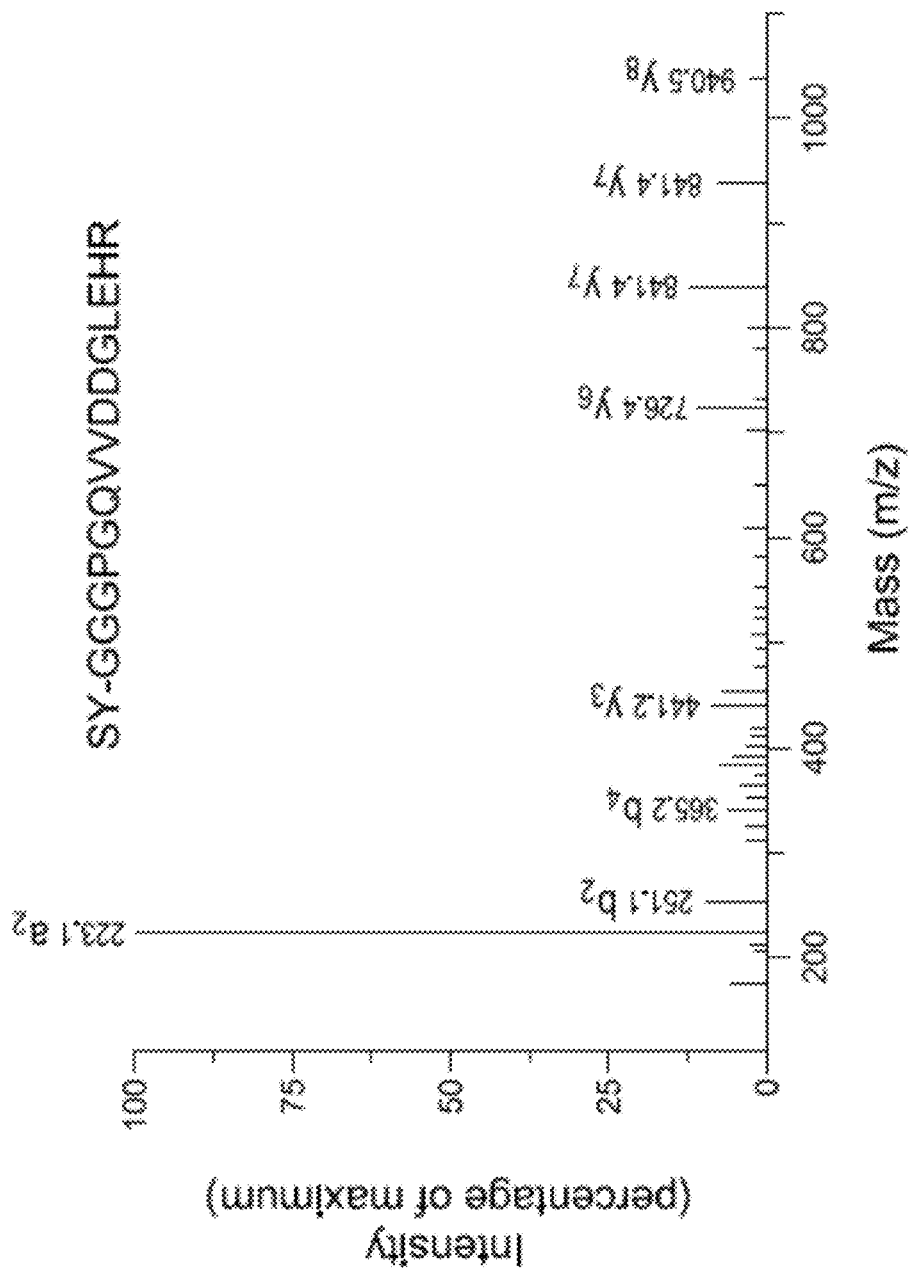

FIG. 13. CID spectrum of the SY-labeled N-terminal peptide GGGPGQVVDDGLEHR from HDAC7 (HDAC7_HUMAN) (SEQ ID NO:412) corresponding to the P4-P4' cleavage site LETD(412)/GGGP (SEQ ID NO:413).

Figure 14:
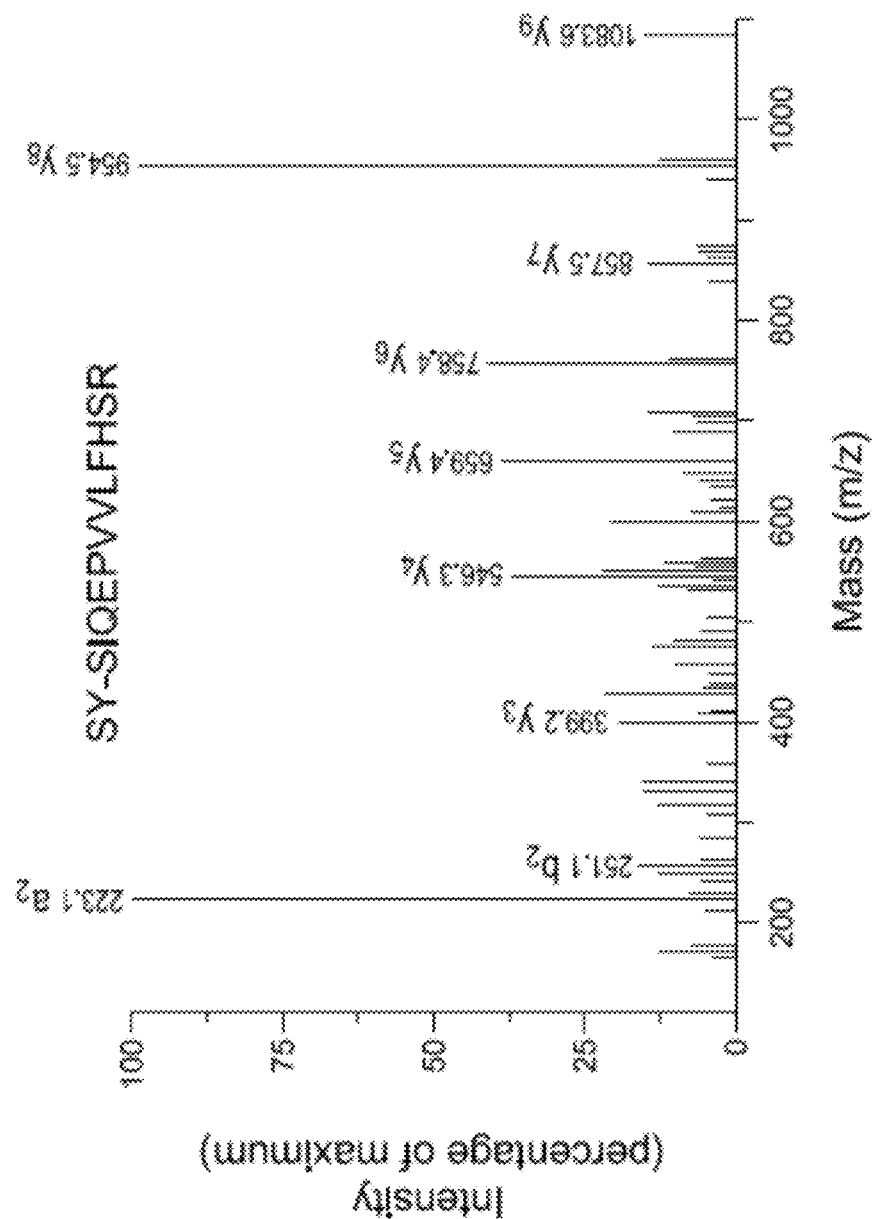

FIG. 14. CID spectrum of the SY-labeled N-terminal peptide SIQEPVVLFHSR from SHARP (MINT_HUMAN) (SEQ ID NO:414) corresponding to P4-P4' caspase-like cleavage site STTD(1574)/SIQE (SEQ ID NO:415).

Figure 15:
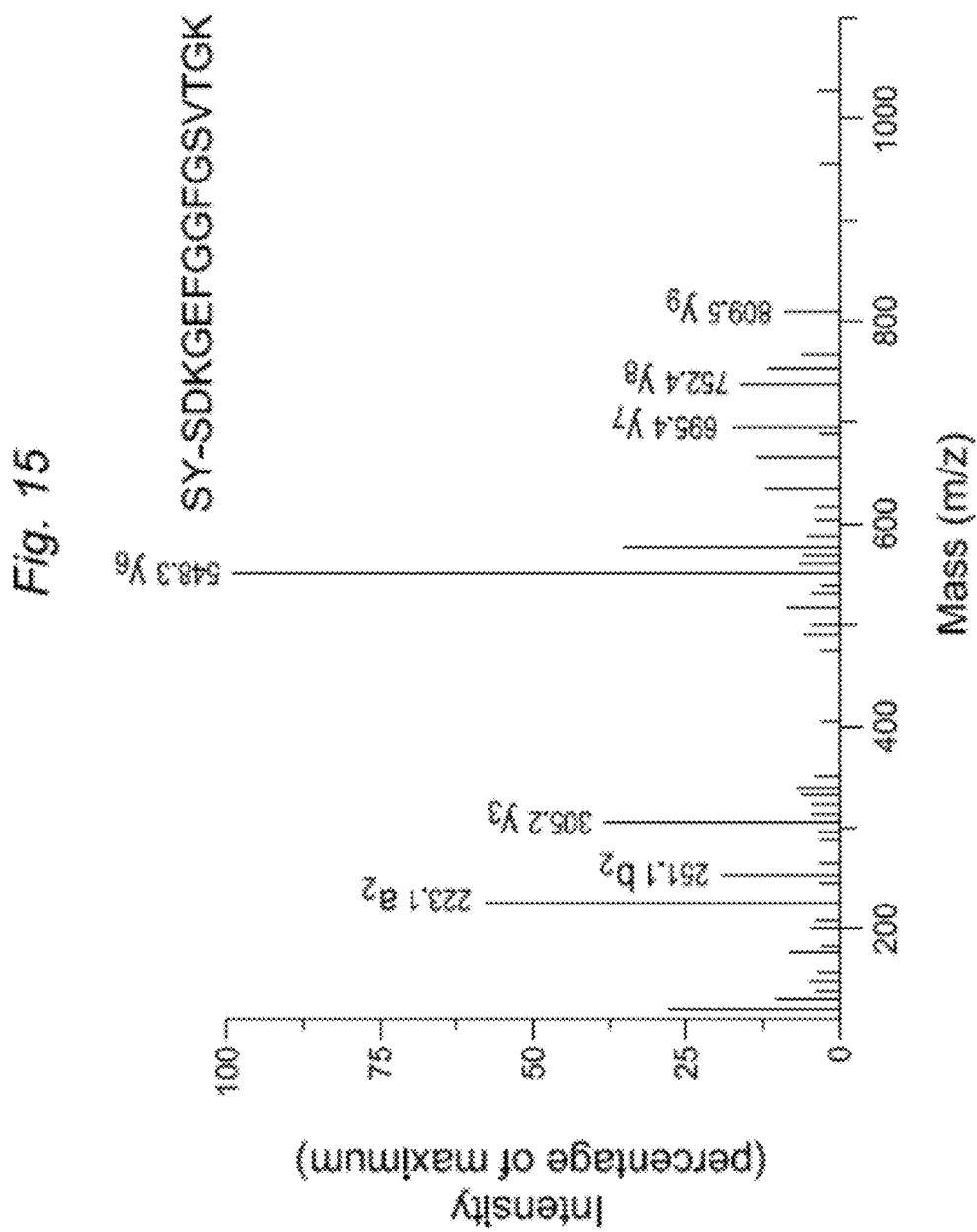

FIG. 15. CID spectrum of the SY-labeled N-terminal peptide SDKGEFGGFGSVTGK from RBBP7 (RBBP7_HUMAN) (SEQ ID NO:416) corresponding to P4-P4' caspase-like cleavage site SHCD(98)/SDKG (SEQ ID NO:417).

DETAILED DESCRIPTION OF THE INVENTION

The present invention provides novel proteolytic apoptotic polypeptide biomarkers. In one embodiment of the invention, the proteolytic apoptotic polypeptide biomarkers are generated in response to an apoptotic stimulus. In certain embodiments, the apoptotic stimulus may be endogenous to the cell, tissue, organ, or organism of interest. In other embodiments, the apoptotic stimulus may be exogenous or induced, such as in tissue culture. In some embodiments, apoptosis may be induced by the treatment of cells, tissues, organs, or organisms with a drug known to cause apoptosis, such as etoposide, camptothecin, anisomycin, and the like. In a specific embodiment, the proteolytic apoptotic polypeptide biomarkers of the present invention comprise N-terminal or C-terminal sequences selected from those found in Table 1.

In certain embodiments of the invention, the proteolytic apoptotic polypeptide biomarkers comprise proteolytic fragments that are generated by cleavage of a full length protein of Table 1 or an intact proteolytic apoptotic cleavage junction of Table 1 by the action of a suitable protease. Suitable proteases will be obvious to the skilled artisan. In one particular embodiment, the protease is an enzyme known to function in the apoptotic pathway of a cell such as a caspase. In one embodiment of the present invention, a proteolytic apoptotic polypeptide biomarker of the present invention will have a sequence selected from those found in Table 1 at its N-terminus or C-terminus. In some embodiments of any of the above polypeptide biomarker corresponds to a protein having a M value from Table 1 of 1 or greater than 1, 2, 4, or 8. In other embodiments, the biomarker corresponds to a protein of Table 1 or 3 having a plurality of such apoptotic polypeptide biomarkers or cleavage sites. In yet another embodiment, a plurality of biomarkers from Table 1 are used in assessing apoptosis or a particular apoptosis pathway in which the biomarkers correspond to apoptotic cleavages of multiple protein substrates of a single apoptotic protease (e.g., caspase) of interest. In other embodiments, the biomarkers from Table 1 are selected so as to include biomarkers for the activity of a plurality of apoptotic proteases of interest.

In certain embodiments, a proteolytic apoptotic polypeptide biomarker of the invention may further comprise a recombinant sequence N-terminal or C-terminal to a sequence found in Table 1. For example, a biomarker of the invention may further comprise a fusion tag used to facilitate purification, detection, or both purification and detection of the polypeptide. Many fusion tags suitable for use with the present invention are well known in the art and include without limitation, polyhistidine tags, GST tags, biotin, calmodulin binding protein tags, chitin binding protein tags, TAP tags, Strep tags, Myc tags, HA tags, and the like. Other suitable recombinant sequences may further comprise a linker between the fusion tag and the polypeptide. Linker sequences may comprise a protease recognition site, such as a TEV cleavage site.

The present invention also provides proteolytic apoptotic cleavage junctions. In certain embodiments, a cleavage junction of the present invention may comprise an amino acid sequence targeted by a protease in response to an apoptotic stimulus. In a particular embodiment, the cleavage junctions of the present invention comprise sequences selected from those found in Table 3. In one embodiment, a cleavage junction of the invention comprises a full length protein containing a sequence identical to a sequence listed in Table 3. In a second embodiment, a cleavage junction of the present invention may comprise a protein fragment containing a sequence found in Table 3, that is competent for cleavage by a protease involved in apoptosis. In certain embodiments, the protein fragment may comprise about 8, 9, 10, 11, 12, 13, 14, 15, 16, 17, 18, 19, 20, 25, 30, 35, 40, 45, 50, 60, 70, 80, 90, 100, 125, 150, 175, 200, 250, 300, 400, 500, 600, 700, 800, 900, 1000, or more amino acids of a protein identified by a Swiss-Prot ID found in Table 3. In some embodiments, the peptide is preferably at least about 6 amino acids long, 7 amino acids long, 8 amino acids long, 10 amino acids long and less than 50 amino acids long and can comprise or consist of an amino acid sequence (previous amino acid or C-terminal amino acid sequence, unmodified or identified amino acid, or N-terminal amino acid sequence, modified identified amino acid sequence, or protein) of Table 1. Preferred peptides for measuring the activity of apoptotic protease include the cleavage junction corresponding to a previous amino acid sequence of Table 1 and its corresponding immediately following identified or unmodified peptide of Table 1. A preferred ranged of peptide lengths is from about 7 to 50 amino acids in length and may include the full sequences of both the previous and identified or unmodified polypeptides of Table 1. Other suitable lengths range from 7 to 25, 7 to 15, 10 to 30, 15 to 35, and 15 to 25.

The apoptotic biomarkers of the present invention find use in the detection and quantification of apoptosis in a biological sample. In certain embodiments, the biomarkers can be used to detect apoptosis in a sample from an organism suffering from a disease characterized by apoptosis. In one embodiment, the biomarkers of the present invention can be used to diagnose or provide a prognosis for a disease characterized by apoptosis in an individual. In other embodiments the biomarkers can be used to determine the extent of apoptosis or the extent of a disease state in an individual or in a sample from an individual. In yet other embodiments, the biomarkers of the present invention are useful for determining the efficacy of a drug or for monitoring treatment in a patient. The biomarkers are particularly useful for determining the efficacy of drugs that induce apoptosis or for monitoring a treatment in a patient that results in apoptosis.

In one embodiment, the present invention provides proteolytic apoptotic signatures or profiles. In a specific embodiment, the apoptotic signatures of the present invention comprise one or more proteolytic polypeptide that is generated in response to an apoptotic stimulus. In another embodiment, an apoptotic signature of the invention comprises the level of at least one proteolytic apoptotic polypeptide biomarker in a biological sample. In one specific embodiment of the invention, an apoptotic signature comprises the level of at least one, preferably at least 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 125, 150, 175, 200, 250, 300, or more proteolytic apoptotic polypeptides comprising an N-terminus or C-terminus selected from those found in Table 1, in a biological sample. In some embodiments, the N-terminus or C-terminus is that formed by the cleavage of a polypeptide by an apoptotic protease. In another embodiment of the invention, an apoptotic signature or profile comprises a plurality, or the level of a plurality, of proteolytic apoptotic cleavage junctions. In a specific embodiment, an apoptotic signature comprises the level of at least one, preferably at least 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 125, 150, 175, 200, 250, 300, or more proteolytic apoptotic cleavage junctions, in a biological sample, selected from those found in Table 3. In further embodiments of the present invention, a proteolytic apoptotic signature may comprise a mixture of proteolytic apoptotic polypeptides and proteolytic apoptotic cleavage junctions, or the levels thereof, in a biological sample. In yet another embodiment, a proteolytic apoptotic signature comprises one or more ratio of a proteolytic apoptotic polypeptide to its corresponding intact proteolytic apoptotic cleavage junction in a biological sample. For example, a proteolytic apoptotic signature of the present invention may comprise at least one, preferably at least 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 125, 150, 175, 200, 250, 300, or more ratios of cut to uncut proteolytic apoptotic cleavage junctions selected from those found in Table 3, or corresponding to the proteins identified by a Swiss-Prot ID found in Table 3, in a biological sample.

In certain embodiments, the present invention provides proteolytic apoptotic signatures that correspond to a specific level or degree of apoptosis in a biological sample, or in an individual. In other embodiments, the proteolytic apoptotic signatures of the present invention correspond to the level of apoptosis in a mammal suffering from a disease characterized by apoptosis. In yet other embodiments of the invention, a proteolytic apoptotic signature may correspond to a specific disease state or to a specific prognosis for a disease in an individual suffering with a disease characterized by apoptosis. In further embodiments, the proteolytic apoptotic signatures of the present invention may correspond to a specific efficacy for a drug administered to an individual or to a predicted response to a drug administered to an individual. The proteolytic apoptotic signatures of the present invention may be derived from a single biological sample from an individual or from a plurality of samples taken a group of individuals suffering from a disease characterized by apoptosis. In certain embodiments, the apoptotic signature may comprise an average of apoptotic signatures determined from a study or disease cohort.

In some embodiments, the present invention provides apoptotic signatures that correspond to healthy subjects, i.e. individuals that are not suffering from a disease, individuals that are suffering from a disease, individuals that have undergone therapy for a specific disease, individuals that have a good prognosis, individuals that have a bad prognosis, individuals with cancer, individuals with a high likelihood of developing metastatic cancer, individuals with a particular disease state, i.e. stage of cancer, severity of disease, benign tumor, and the like. As such, the various apoptotic signatures of the present invention find use in the diagnosis and prognosis of various diseases and disease states, as well as for monitoring the progression of a disease or the progression of a disease treatment regime.

In some embodiments, the invention provides synthetic peptides or polypeptides which are labeled with heavy isotopes of C, N, H, or O. For instance, $^{13}$C or $^{15}$N labeled peptides can be used as internal standards in the assay methods as known to one of ordinary skill in the art. By adding a known quantity of a heavy isotope-labeled peptide to a sample and then calculating the amount of the labeled polypeptide detected, it is possible to estimate the concentration of an unlabeled endogenous corresponding polypeptide in a sample by use of an analytical technique such as mass spectrometry (see, PCT Patent Publications WO 03026861 and WO 2008/054597), and see also, Carr et al., Clinical Chemistry 54:11 1749-1752 (2008) the contents of each of which are incorporated herein by reference in their entirety with respect to methods of quantitating proteins or polypeptides in a biological sample. Anderson et al., Journal of Proteome Research 2004, 3, 235-244; Carr et al., Nature Biotechnology 24(8):971 (2006); and Addona et al., Nature Biotechnology 27(7): 633 (2009); and McIntosh et al. Nature Biotechnology 27(7):622 (2009) are also each incorporated by reference in their entirety with respect to their disclosures of methods for detecting biomarkers in biological samples by targeted mass spectrometry. For instance, detection methods using selected reaction monitoring (SRM) or multiple reaction monitoring (MRM are contemplated.

An isotopically labeled peptide is preferably at least about 6 amino acids long, 7 amino acids long, 8 amino acids long, 10 amino acids long and less than 50 amino acids long and can comprise an amino acid sequence (previous amino acid or C-terminal amino acid sequence, identified or unmodified amino acid or N-terminal amino acid sequence, or the modified identified amino acid sequence of Table 1. Preferred labeled peptides for measuring the activity of apoptotic protease comprise a previous amino acid sequence of Table 1 with its corresponding immediately following identified or unmodified peptide of Table 1. A preferred ranged of labeled peptide lengths is from about 7 to 50 amino acids in length and may include the full sequences of both the previous and identified or unmodified polypeptides of Table 1.

The method detects and quantifies a target protein in a sample by introducing a known quantity of at least one heavy-isotope labeled peptide standard into a digested biological sample. By comparing to the peptide standard, one may readily determine the quantity of a peptide having the same sequence and protein modification(s) in the biological sample. Briefly, the methodology has two stages: (1) peptide internal standard selection and validation; method development; and (2) implementation using validated peptide internal standards to detect and quantify a target protein in a sample. The method is a powerful technique for detecting and quantifying a given peptide/protein within a complex biological mixture, such as a biological sample, a cell lysate, tissue section, or serum and may be used, e.g., to quantify change in protein as a result of drug treatment, or to quantify a protein in different biological states.

Generally, to develop a suitable internal standard, a particular peptide (or modified peptide) within a target protein sequence is chosen based on its amino acid sequence and a particular protease for digestion. The peptide can then generated by solid-phase peptide synthesis such that one residue is replaced with that same residue containing stable isotopes (e.g., $^{13}$C, $^{15}$N). The result is a peptide that is chemically identical to its native counterpart formed by proteolysis, but is easily distinguishable by MS via a mass shift. A newly synthesized internal standard peptide is then evaluated by the detection method. This process provides qualitative information about peptide retention by the detection method.

The second stage of the strategy is its implementation to measure the amount of a protein or the modified form of the protein from complex mixtures. A biological sample such as a cell lysate, tissue section lysate, or serum may be extensively digested with a protease such as trypsin. Labeled peptides can then be spiked in to the complex peptide mixture obtained by digestion of the biological sample with a proteolytic enzyme, either before or after an optional affinity purification of a subset of the peptides in the mixture, as described above. The retention time and fragmentation pattern of the native peptide formed by digestion (e.g., trypsinization) is identical to that 25 of the labeled internal standard peptide determined previously; thus, the use of isotopically labeled peptides results in the highly specific and sensitive measurement of both internal standard and analyte directly from extremely complex peptide mixtures. Because an absolute amount of the labeled peptide is added, the ratio of the amount of endogenous peptide detected to the amount of labeled peptide detected can be used to determine the precise levels of a polypeptide, or more specifically, a proteolytic apoptotic polypeptide, in a sample.

In addition, the internal or labeled polypeptide standard when present during digestion and chromatography, such that peptide extraction efficiencies and absolute losses during sample handling (including vacuum centrifugation), and variability during introduction into the detection system do not affect the determined ratio of native and labeled polypeptide abundances.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. Thus, peptides longer than about 20 amino acids are not preferred. The preferred ranged is about 7 to 15 amino acids. A peptide sequence is also selected that is not likely to be chemically reactive during mass spectrometry, thus sequences comprising cysteine, tryptophan, or methionine are avoided.

The peptide is labeled using one or more labeled amino acids (i.e. the label is an actual part of the peptide) or less preferably, labels may be attached after synthesis according to standard methods. Preferably, the label is a mass-altering label selected based on the following considerations: The mass should be unique to shift fragment masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum. Preferably, the ion mass signature component imparts a mass to a protein fragment that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^{13}C$, $^{15}N$, $^{17}O$, $^{18}O$, or $^{34}S$, are among preferred labels. Pairs of peptide internal standards that incorporate a different isotope label may also be prepared.

Peptide internal standards are characterized according to their mass-to-charge (m/z) ratio, and preferably, also according to their behavior in chromatographic columns (e.g. an HPLC column). Internal standards that co-elute with unlabeled peptides of identical sequence are selected as optimal internal standards. The internal standard can then analyzed be fragmenting the peptide by any suitable means, for example by collision-induced dissociation (CID) using, e.g., argon or helium as a collision gas. The fragments can then be analyzed, for example, by multi-stage mass spectrometry ($MS^n$) to obtain a fragment ion spectrum, to obtain a peptide fragmentation signature. Preferably, peptide fragments have significant differences in m/z ratios to enable peaks corresponding to each fragment to be well separated, and a signature that is unique for the target peptide is obtained. If a suitable fragment signature is not obtained at the first stage, additional stages of MS are performed until a unique signature is obtained.

Fragment ions in the MS/MS and MS spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts are preferably used. Generally, the sample may have at least 0.01 mg of protein, typically a concentration of 0.1-10 mg/mL, and may be adjusted to a desired buffer concentration and pH.

Accordingly, internal peptide standards (heavy-isotope or light isotope labeled peptides) may be produced, as described above, for any of the novel polypeptides of the invention (see Table 1). These peptides may then be further used in assessing apoptotic enzyme activities in samples as described herein.

Quantitation of Corresponding Peptides Derived from the Neo-Epitopes in Samples.

In one embodiment, the present invention provides reagents for detecting the proteolytic apoptotic polypeptide biomarkers of the invention. In one embodiment, the reagents comprise proteins that bind to the biomarkers with high affinity and specificity. In another embodiment, the invention provides binding reagents for detecting proteolytic apoptotic cleavage junctions. In a particular embodiment, the reagents comprise antibodies, or fragments thereof, generated against the proteolytic apoptotic polypeptides or proteolytic apoptotic cleavage junctions of the present invention. Suitable antibody fragment types include without limitation, F(ab')2, F(ab), Fv, scFv, and the like. Antibodies can be generated by a number of well known methods including, without limitation, animal immunization, molecular display techniques, including phage display and ribosomal or mRNA display, rational design, and the like. In certain embodiments of the present invention, the binding reagents further comprise a detectable moiety and/or a tag to facilitate purification of the binding reagent or binding reagent-biomarker complex.

In another embodiment, the present invention provides methods for generating binding reagents to one or more apoptotic biomarkers. In certain embodiments the apoptotic biomarkers comprise N-terminal or C-terminal sequences selected form those found in Table 3. In other embodiments, the apoptotic biomarkers comprise cleavage junctions selected from those found in Table 3. In a specific embodiment, the methods of the present invention comprise the steps of: (a) generating a plurality of proteolytic apoptotic polypeptides; (b) generating one or more binding reagents to said plurality of proteolytic apoptotic polypeptides; and (c) purifying at least one of said binding reagents. Pluralities of proteolytic apoptotic polypeptides can be generated, for example, by heterologous gene expression, in vitro translation, synthetic peptide synthesis, purification of proteolytic polypeptides from a biological sample, or in vitro proteolysis of peptides containing a proteolytic apoptosis cleavage junction. In one embodiment, the binding reagents comprise proteins or antibodies that specifically bind to either a proteolytic apoptotic polypeptide or to an intact cleavage junction corresponding to a proteolytic apoptotic polypeptide, but do not substantially bind to both.

In certain embodiments, the methods of the present invention for generating one or more antibodies comprise the steps of (a) simultaneously immunizing a mammal with a plurality of apoptotic proteolytic polypeptides; (b) collecting the immune serum from said mammal; (c) affinity purifying a first antibody to a first proteolytic polypeptide, (d) affinity purifying at least a second antibody to at least a second proteolytic polypeptide from the supernatant of step (c), (e) removing antibodies that bind to the cleavage junction corresponding to said first proteolytic polypeptide by affinity means from said first antibody purification, and (f) removing antibodies that bind to the cleavage junction corresponding to said at least second proteolytic polypeptide by affinity means from said second antibody purification, thereby generating at least two antibodies to proteolytic apoptotic polypeptides. These methods find use in generating a plurality of antibodies that bind to a proteolytic apoptotic polypeptide, but that do not substantially bind to the cleavage junction corresponding to said proteolytic polypeptide. In certain embodiments, the methods can be altered in order to generate a plurality of antibodies that bind to a proteolytic apoptotic cleavage junction, but that do not substantially bind to the corresponding proteolytic polypeptides generated in response to an apoptotic stimulus. In further embodiments, the methods of the present invention can be performed using molecular display techniques.

In yet other embodiments, the present invention provides methods of generating an antibody to the N-terminus or C-terminus of a proteolytic polypeptide, the method comprising the steps of: (a) Generating the N-terminal or C-terminal apoptotic product, by means of heterologous gene expression, in vitro transcription-translation, or synthetic methods, or by producing the full length protein and cleaving it with a protease to generate the N-terminal and C-terminal pieces and purification of the N-terminal proteolytic fragment, C-terminal proteolytic fragment, or any combination thereof; (b) using the N-terminal or C-terminal apoptotic fragment to generate one or more antibodies, either by immunization of animal, or in vitro selection methods such as phage display, ribosome display or other suitable display or selection methods, or to generate other suitable binding protein or proteins, either by in vitro selection methods such as phage display, ribosome display or other suitable display or selection methods The present invention also provides methods of detecting proteolytic apoptotic biomarkers, including both proteolytic apoptotic polypeptides and proteolytic apoptotic cleavage junctions, in a biological sample. In one embodiment, the method comprises contacting a biological sample with a binding reagent that specifically binds to a proteolytic apoptotic biomarker of the present invention and detecting the binding reagent, thereby detecting the biomarker. In a second embodiment, the present invention provides methods of quantitating the amount of a proteolytic apoptotic biomarker in a biological sample, the method comprising the steps of contacting a biological sample with a binding reagent of the present invention, and determining the amount of biomarker is said sample. Methods of detecting and quantitating the amount of a polypeptide in a sample are well known in the art and include, without limitation, ELISA, immunohistochemical techniques, mass spectrometry, Luminex® xMAP technology, and the like.

In another embodiment, the present invention provides methods of detecting apoptosis in an individual. In one embodiment, the methods comprise detecting at least one proteolytic apoptotic polypeptide in a biological sample from an individual. In another specific embodiment, the methods comprise detecting an increased ratio of the level of at least a first proteolytic apoptotic polypeptide biomarker to the level of at least one first proteolytic apoptotic cleavage junction biomarker that corresponds to said first proteolytic apoptotic polypeptide. In some embodiments, the present methods comprise the detection or quantitation of at least about 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 125, 150, 175, 200, 250, 300, or more proteolytic apoptotic biomarkers of the present invention, or corresponding ratios thereof. In a second embodiment, the methods of the present invention comprise the detection of a proteolytic apoptotic signature in a biological sample from an individual, thereby detecting the presence of apoptosis is said individual. In yet another embodiment, the present invention provides methods of detecting a proteolytic apoptotic signature in a subject, the methods comprising the steps of: (a) determining the level of at least two proteolytic polypeptides in a biological sample from said subject; and (b) comparing said levels of at least two proteolytic polypeptides to a proteolytic apoptotic signature, thereby detecting a proteolytic signature in the subject, wherein said at least two proteolytic polypeptides comprise N-terminal or C-terminal sequences selected from those found in Table 1.

In one embodiment, the present invention provides methods of determining the level of apoptosis in an individual. In a particular embodiment, the methods comprise the steps of: (a) determining the level of at least one proteolytic polypeptide that is generated in response to an apoptotic stimulus in a biological sample from said subject; and (b) comparing said level of at least one proteolytic polypeptide to a biological signature corresponding to no apoptosis, thereby determining the level of apoptosis in the subject, wherein said at least one proteolytic polypeptide comprises an N-terminal or C-terminal sequence selected from those found in Table 1. In a related embodiment, the method further comprises the step of (c) comparing said level of at least one proteolytic polypeptide to at least one biological signature corresponding to a predetermined level of apoptosis. In a second embodiment, the methods comprise the steps of: (a) determining the level of at least one intact proteolytic apoptotic cleavage junction in a biological sample from said subject; (b) determining the level of at least one of the N-terminal or C-terminal proteolytic polypeptides corresponding to said at least one intact proteolytic apoptotic cleavage junction in said biological sample; and (c) determining the ratio of proteolytic polypeptides to intact proteolytic apoptotic cleavage junctions in said biological sample, thereby determining the level of apoptosis in the subject, wherein said proteolytic polypeptides are generated in response to an apoptotic stimulus.

In another embodiment, the invention provides methods of diagnosing or providing a prognosis for a disease characterized by apoptosis in an individual. In a specific embodiment, the methods comprise the steps of: (a) detecting a first proteolytic apoptotic signature in a biological sample from said individual; and (b) comparing said first proteolytic apoptotic signature to at least a second proteolytic apoptotic signature corresponding to a diagnosis or prognosis for a disease characterized by apoptosis, thereby diagnosing or providing a prognosis for a disease characterized by apoptosis in said individual. In other embodiments, the methods further comprise the steps of: (c) comparing said first apoptotic signature to at least a third apoptotic signature corresponding to a diagnosis of no disease or a second prognosis for said disease; and (d) determining which apoptotic signature said first apoptotic most highly correlates to, thereby diagnosing or providing a prognosis for a disease characterized by apoptosis in said individual.

Many correlation methodologies may be employed for the comparison of both individual proteolytic apoptotic biomarker levels and proteolytic apoptotic signatures or profiles in the present invention. Non-limiting examples of these correlation methods include parametric and non-parametric methods as well as methodologies based on mutual information and non-linear approaches. Examples of parametric approaches include without limitation, Pearson correlation (or Pearson r, also referred to as linear or product-moment correlation) and cosine correlation. Non-limiting examples of non-parametric methods include Spearman's R (or rank-order) correlation, Kendall's Tau correlation, and the Gamma statistic. Each correlation methodology can be used to determine the level of correlation between the levels or ratios of individual biomarkers in the data set. The correlation of all biomarkers with all other biomarkers is most readily considered as a matrix. Using Pearson's correlation as a non-limiting example, the correlation coefficient r in the method is used as the indicator of the level of correlation. When other correlation methods are used, the correlation coefficient analogous to r may be used, along with the recognition of equivalent levels of correlation corresponding to r being at or about 0.25 to being at or about 0.5. The correlation coefficient may be selected as desired to reduce the number of correlated biomarkers to various numbers. In particular embodiments of the invention using r, the selected coefficient value may be of about 0.25 or higher, about 0.3 or higher, about 0.35 or higher, about 0.4 or higher, about 0.45 or higher, or about 0.5 or higher.

In another embodiment, the present invention provides methods of monitoring the progression of therapy for a disease in an individual. In certain embodiments, the methods comprise determining the level of a proteolytic apoptotic biomarker or an apoptotic signature at different time points in a sample from an individual undergoing therapy for a disease. In some embodiments, the method will comprise comparing the levels of biomarkers or signatures at different times during the course of a disease treatment. Typically, a disease that is characterized by increased apoptosis, such as auto-imune diseases, will result in a decrease in apoptosis, as measured by the levels of biomarkers or signatures in a biological sample from an individual, during the course of a successful treatment regime. Conversely, a disease that is characterized by decreased apoptosis, such as cancer, will typically result in increased apoptosis, as measured by the levels of biomarkers or signatures in a biological sample from an individual, during the course of a successful treatment regime. In this fashion a biological sample from a patient that is responding favorably to a treatment regime will show a change, either increase or decrease, in the level of apoptosis over time, as measured by the methods of the present invention. In a particular embodiment, the methods of the present invention are useful for monitoring the progression of cancer therapy in an individual. The methods of the invention are compatible with all types of cancer therapy including, without limitation, chemotherapy, hormone therapy, biologic therapy, radiation therapy, surgical therapy, and the like.

In one embodiment, the present invention provides methods of determining the efficacy of a drug. In a specific embodiment, the methods comprise the steps of: (a) determining the level of at least one proteolytic polypeptide generated in response to an apoptotic stimulus in a biological sample from a first subject receiving a dose of said drug; (b) determining the level of at least one proteolytic polypeptide generated in response to an apoptotic stimulus in a biological sample from a second subject not receiving a dose of said drug; and (c) comparing said first and said second levels of said at least one proteolytic polypeptide, thereby determining the efficacy of said drug, wherein said at least one proteolytic polypeptide comprises an N-terminal or C-terminal sequence selected from those found in Table 1. In yet other embodiments of the invention, the method comprises determining a proteolytic apoptotic signature and comparing said signature to a second proteolytic apoptotic signature corresponding to a specific level of apoptosis. Drugs particularly well suited for use with the above methods include both drugs that induce apoptosis and anti-apoptotic drugs.

Many pharmaceuticals are known to cause apoptosis in vivo including, without limitation, nonsteroidal anti-inflammatory drugs (NSAIDs) (Yamazaki et al., *Journal of Pharmacology and Experimental Therapeutics* 302(1): 18-25 (2002)) and chemotherapeutic drugs. Examples of NSAIDs include, without limitation, Salicylates (including Acetylsalicylic acid (Aspirin), Amoxiprin Benorylate/Benorilate, Choline magnesium salicylate, Diflunisal, Ethenzamide, Faislamine, Methyl salicylate, Magnesium salicylate, Salicyl salicylate, and Salicylamide), Arylalkanoic acids (including Diclofenac, Aceclofenac, Acemetacin, Alclofenac, Bromfenac, Etodolac, Indometacin, Nabumetone, Oxametacin, Proglumetacin, Sulindac, and Tolmetin), 2-Arylpropionic acids (profens) (including Ibuprofen, Alminoprofen, Benoxaprofen, Carprofen, Dexibuprofen, Dexketoprofen, Fenbufen, Fenoprofen, Flunoxaprofen, Flurbiprofen, Ibuproxam, Indoprofen, Ketoprofen, Ketorolac, Loxoprofen, Naproxen, Oxaprozin, Pirprofen, Suprofen, and Tiaprofenic acid), N-Arylanthranilic acids (fenamic acids) (including Mefenamic acid, Flufenamic acid, Meclofenamic acid, and Tolfenamic acid), Pyrazolidine derivatives (including Phenylbutazone, Ampyrone, Azapropazone, Clofezone, Kebuzone, Metamizole, Mofebutazone, Oxyphenbutazone, Phenazone, Phenylbutazone, and Sulfinpyrazone), Oxicams (including Piroxicam, Droxicam, Lornoxicam, Meloxicam, and Tenoxicam), COX-2 inhibitors (including Celecoxib, Etoricoxib, Lumiracoxib, Parecoxib, Rofecoxib, Valdecoxib), Sulphonanilides including Nimesulide, histone deacetylase inhibitors (including Trichostatin A, cyclic tetrapeptides, benzamides, electrophilic ketones, phenylbutyrate, valproic acid, SAHA (approved by the FDA in 2007 for leukemia therapy under the name Vorinostat), Belinostat/PXD101, MS275, LAQ824/LBH589, CI994, MGCD0103 (Beckers et al., *Int. J. Cancer* 121(5): 1138-48 (2007)) nicotinamide, dihydrocoumarin, naphthopyranone, 2-hydroxynaphaldehydes, and the like). While not all NSAIDs induce apoptosis, one of skill in the art will know which drugs are appropriate for use in the present invention. Drugs that do not induce apoptosis, including some NSAIDs and some chemotherapeutic agents, may be used in combination with other drugs that do induce apoptosis in certain embodiments of the present invention.

Examples of chemotherapeutic anti-cancer drugs include, without limitation, Aminopterin, Methotrexate, Pemetrexed, Raltitrexed, Cladribine, Clofarabine, Fludarabine, Mercaptopurine, Pentostatin, Thioguanine, Cytarabine, Decitabine, Fluorouracil/Capecitabine, Floxuridine, Gemcitabine, Sapacitabine, Chlorambucil, Chlormethine, Cyclophosphamide, Ifosfamide, Melphalan, Bendamustine, Trofosfamide, Uramustine, Carmustine, Fotemustine, Lomustine, Nimustine, Prednimustine, Ranimustine, Semustine, Streptozocin, Carboplatin, Cisplatin, Nedaplatin, Oxaliplatin, Triplatin tetranitrate, Satraplatin, Busulfan, Mannosulfan, Treosulfan, Procarbazine, Dacarbazine, Temozolomide, Carboquone, ThioTEPA, Triaziquone, Triethylenemelamine, Docetaxel, Larotaxel, Ortataxel, Paclitaxel, Tesetaxel, Vinblastine, Vincristine, Vinflunine, Vindesine, Vinorelbine, Ixabepilone, Aclarubicin, Daunorubicin, Doxorubicin, Epirubicin, Idarubicin, Amrubicin, Pirarubicin, Mitoxantrone, Pixantrone, Valrubicin, Zorubicin, Actinomycin, Bleomycin, Mitomycin, Plicamycin, Hydroxyurea, Camptothecin, Topotecan, Irinotecan, Rubitecan, Belotecan, Etoposide, Teniposide, Altretamine, Amsacrine, Bexarotene, Estramustine, Irofulven, Trabectedin, Cetuximab, Panitumumab, Trastuzumab, Rituximab, Tositumomab, Alemtuzumab, Bevacizumab, Edrecolomab, Gemtuzumab, Axitinib, Bosutinib, Cediranib, Dasatinib, Erlotinib, Gefitinib, Imatinib, Lapatinib, Lestaurtinib, Nilotinib, Semaxanib, Sorafenib, Sunitinib, Vandetanib, Alvocidib, Seliciclib, Aflibercept, Denileukin diftitox, Aminolevulinic acid, Efaproxiral, Methyl aminolevulinate, Porfimer sodium, Temoporfin, Verteporfin, Alitretinoin, Tretinoin, Anagrelide, Arsenic trioxide, Pegaspargase, Atrasentan, Bortezomib, Carmofur, Celecoxib, Demecolcine, Elesclomol, Elsamitrucin, Etoglucid, Lonidamine, Lucanthone, Masoprocol, Mitobronitol, Mitoguazone, Mitotane, Oblimersen, Omacetaxine, Sitimagene ceradenovec, Testolactone, Tiazofurine, Tipifarnib, and the like. While not all chemotherapeutic drugs induce apoptosis, one of skill in the art will know which drugs are appropriate for use in the present invention.

The invention also provides RNA interference, or RNAi, by use of siRNA or shRNA molecules directed toward a protein of Table 1. An "siRNA" or "shRNA" refers to a nucleic acid that forms a double stranded RNA, which double stranded RNA has the ability to reduce or inhibit expression of a gene or target gene when the siRNA expressed in the same cell as the gene or target gene. "siRNA" or "shRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length. The siRNA find use in moulating apoptosis, treating cancer by promoting apoptosis, and in treating conditions in which the modulation or promotion of apoptosis would be beneficial, or in treating disease or conditions characterized by apoptosis. The subjects are preferably human.

The design and making of siRNA molecules and vectors are well known to those of ordinary skill in the art. For instance, an efficient process for designing a suitable siRNA is to start at the AUG start codon of the mRNA transcript and scan for AA dinucleotide sequences (see, Elbashir et al. EMBO J. 20: 6877-6888 (2001). Each AA and the 3' adjacent nucleotides are potential siRNA target sites. The length of the adjacent site sequence will determine the length of the siRNA. For instance, 19 adjacent sites would give a 21 nucleotide long siRNA siRNAs with 3' overhanging UU dinucleotides are often the most effective. This approach is also compatible with using RNA pol III to transcribe hairpin siRNAs. RNA pol III terminates transcription at 4-6 nucleotide poly(T) tracts to create RNA molecules having a short poly(U) tail. However, siRNAs with other 3' terminal dinucleotide overhangs can also effectively induce RNAi and the sequence may be empirically selected. For selectivity, target sequences with more than 16-17 contiguous base pairs of homology to other coding sequences can be avoided by conducting a BLAST search (see, www.ncbi.nlm.nih.gov/BLAST).

The siRNA or shRNA can be administered directly or an siRNA or shRNA expression vector can be used to induce RNAi. A vector can have inserted two inverted repeats separated by a short spacer sequence and ending with a string of T's which serve to terminate transcription. The expressed RNA transcript is predicted to fold into a short hairpin shRNA. The selection of shRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary. A preferred order of the shRNA expression cassette is sense strand, short spacer, and antisense strand. shRNAs with these various stem lengths (e.g., 15 to 30) are suitable. The length of the loops linking sense and antisense strands of the shRNA can have varying lengths (e.g., 3 to 9 nucleotides, or longer). The vectors may contain promoters and expression enhancers or other regulatory elements which are operably linked to the nucleotide sequence encoding the shRNA.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. These control elements may be designed to allow the clinician to turn of or on the expression of the gene by adding or controlling external factors to which the regulatory elements are responsive.

In yet another embodiment, the present invention provides kits for detecting or quantitating the biomarkers of the present invention. In certain embodiments, these kits comprise binding reagents, such as antibodies or proteins, that specifically bind the biomarkers of the invention. In other embodiments, the kits of the present invention comprise protein binding arrays for the detection or quantitation of the biomarkers of the invention. In one embodiment, the kits of the present invention are useful in the detection or quantitation of apoptosis in a biological sample. In a second embodiment, the kits of the invention are useful for diagnosing or for providing a prognosis for a disease characterized by apoptosis in an individual.

The present invention also provides novel enzymatic approaches for positive selection of protein fragments containing unblocked α-amines, characteristically produced in proteolysis. This approach makes use of an engineered peptide ligase termed subtiligase to selectively biotinylate unblocked protein α-amines in complex samples with great selectivity over ε-amines of lysine side chains. Site-specific biotinylation permits subsequent purification and identification of corresponding N-terminal peptides using tandem mass spectrometry (LC/MS/MS).

Figures 1, 1A:
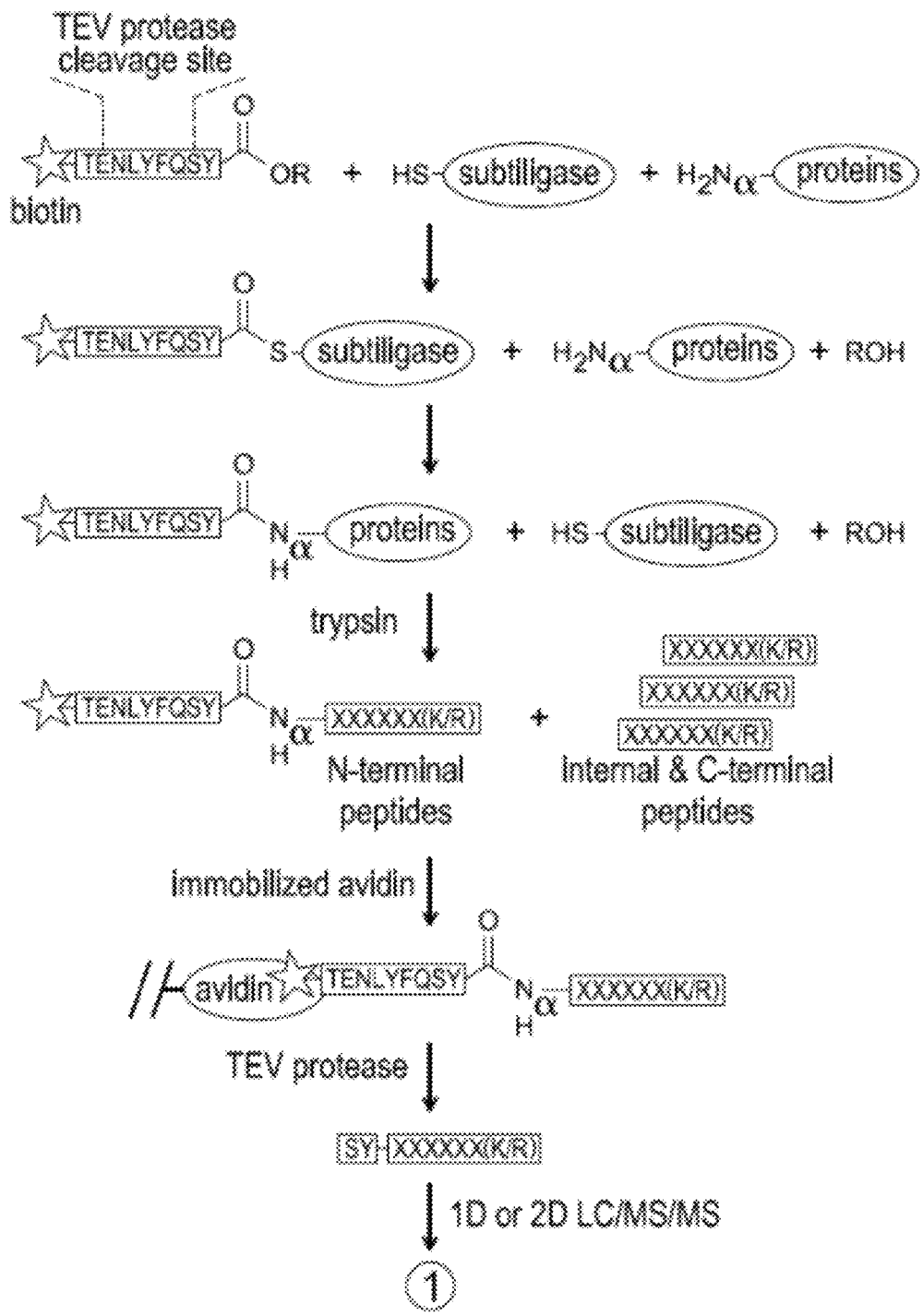
FIGS. 1A-1, 1A-2, 1B-1, and 1B-2. A subtiligase subtiligase-based method for positive selection of peptides corresponding to N-termini of proteins from complex mixtures.
Figures 1, 1A, 2:
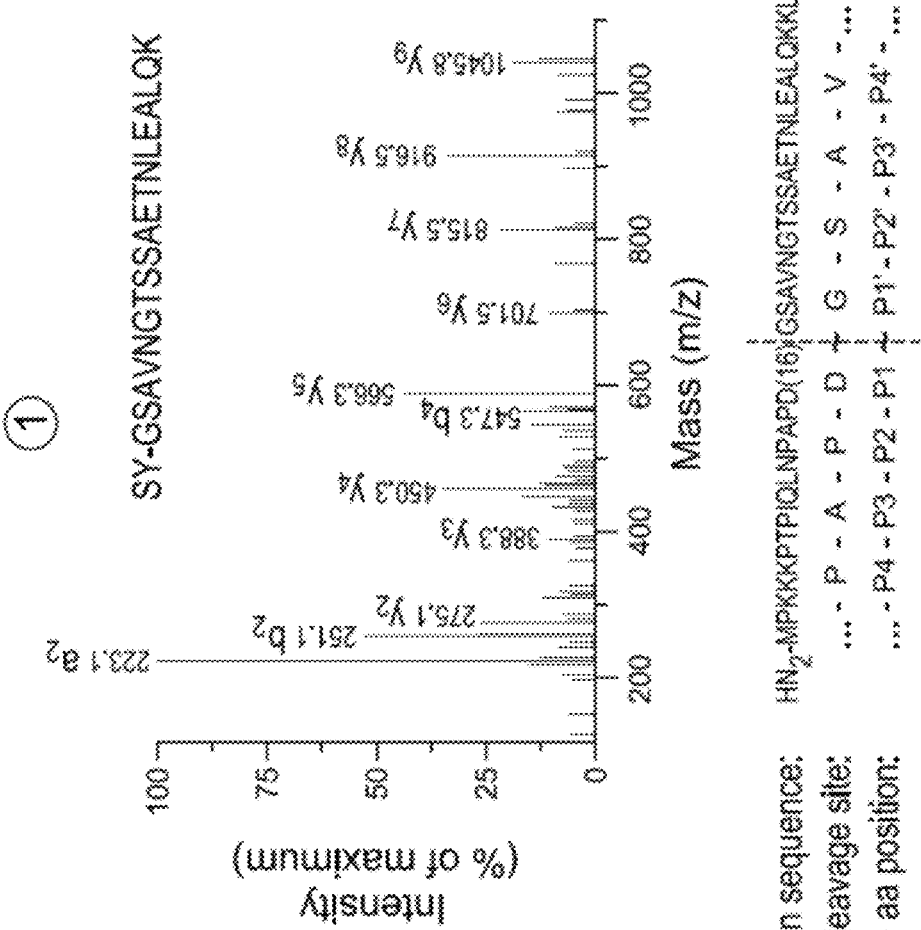
Figures 1, 1B:
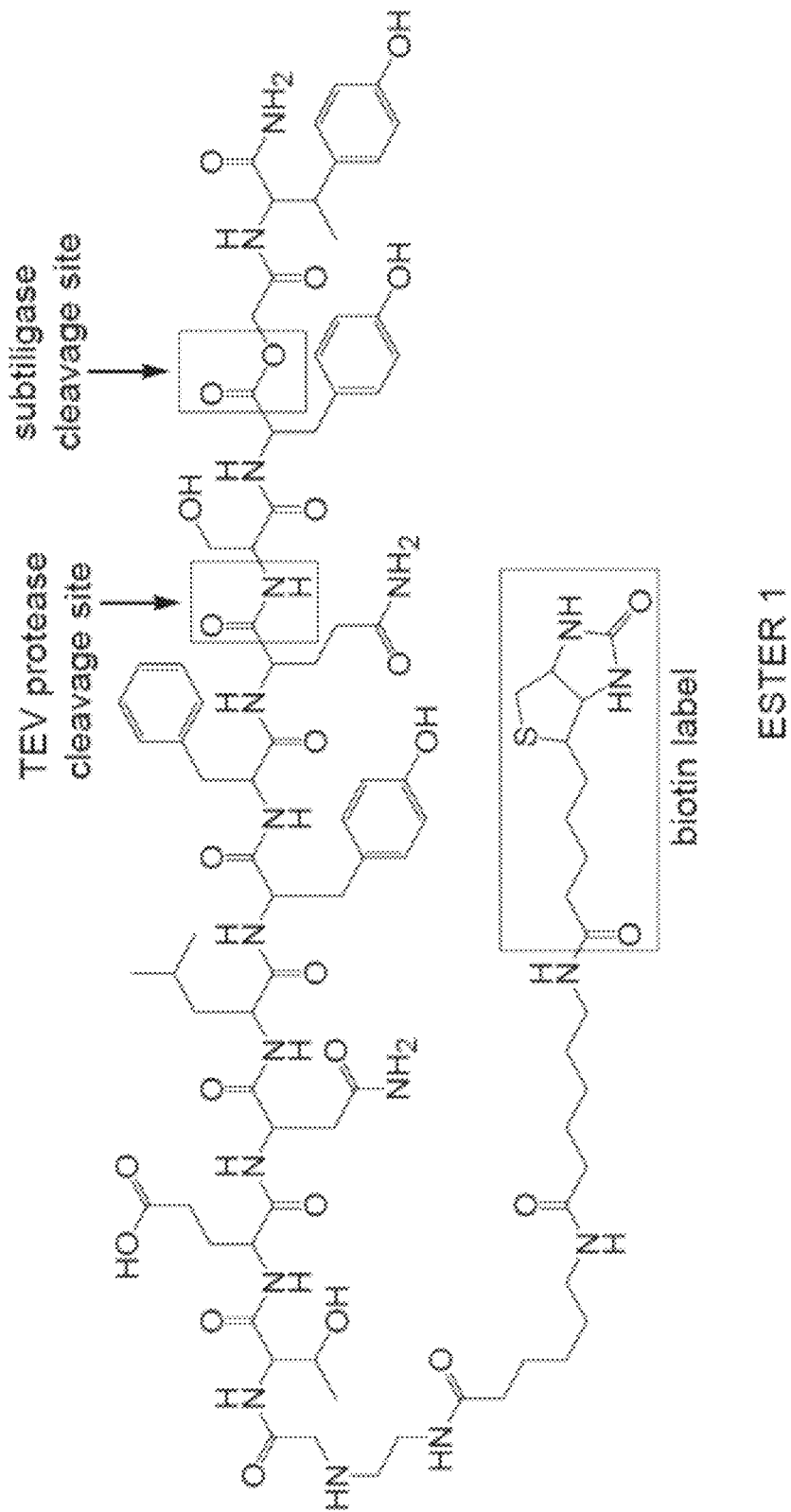
Figures 1, 1B, 2:
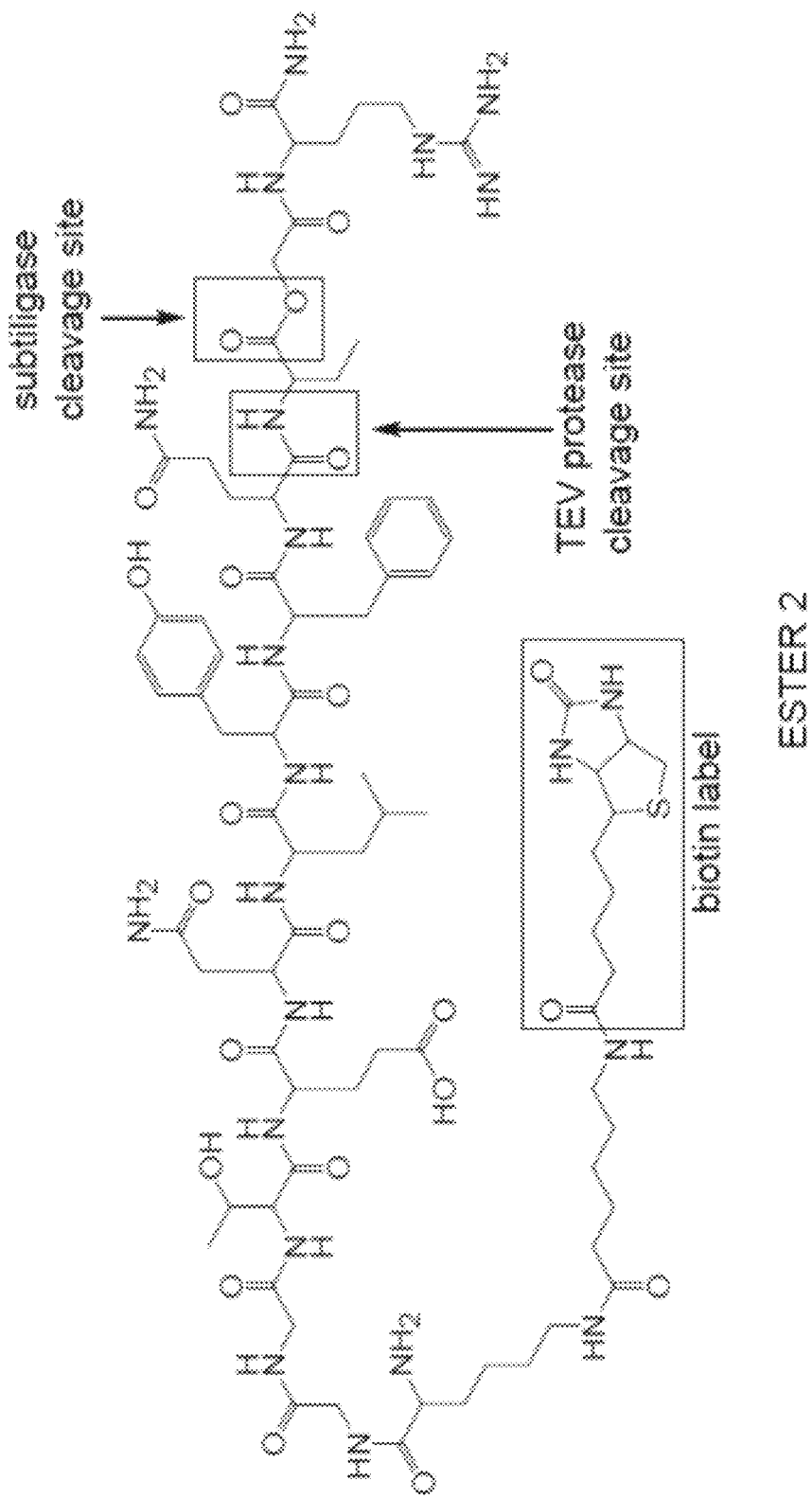

The present invention provides a proteomic workflow utilizing subtiligase that enables biotinylation of protein α-amines in complex mixtures and subsequent cataloguing of N-termini in a given sample (FIGS. 1A-1 and 1A-2). Detergent lysates of either normal or apoptotic cells are first prepared in the presence of protease inhibitors to quench all protease activity. Proteins in these lysates are then N-terminally biotinylated by treatment with subtiligase and a peptide glycolate ester substrate specially tailored to the proteomic workflow (FIGS. 1B-1 and 1B-2). Biotinylated samples are then exhaustively digested with trypsin, and N-terminal peptides are captured using avidin affinity media. The peptide ester substrate contains a tobacco etch virus (TEV) protease cleavage site between biotin and the site of ligation to permit facile recovery of captured peptides (Rigaut et al., 1999). An important aspect of the workflow is that all labeled peptides recovered using TEV protease retain an N-terminal SY-dipeptide modification. This modification provides a key hallmark to distinguish ligated peptides from contaminating unligated ones using LC/MS/MS. Identification of recovered SY-peptides permits identification of corresponding proteins, native N-termini, and localization of proteolytic processing sites.

DEFINITIONS

"Subtiligase" refers generally to proteins which have the enzymatic activity of being able to ligate esterified peptides site-specifically onto the N termini of proteins or peptides. An example of such a subtiligase is one derived from the enzyme subtilisin BPN' by site directed mutagenesis to effect the double substitution Ser221Cys and Pro225Ala, as described herein. Also described herein are additional subtiligases which have been engineered to exhibit other advantageous features, such as enhanced stability.

A "substrate" used in the context of subtiligase refers generally to any chemical moiety that is capable of being utilized during the enzymatic action of subtiligase that results in the specific labeling of the N termini of proteins or peptides by subtiligase. Examples of such substrates include peptide esters as described in greater detail herein.

"A complex mixture" refers generally to any composition that is composed of at least two or more proteins or peptides containing α-amines. A complex mixture can have at least two different proteins encoded by different genes; a complex mixture can be naturally occurring (e.g., a cell extract) or prepared (e.g., a formulation); a complex mixture can have recombinant, synthetic, or naturally occurring proteins or a mixture thereof. In many cases, a complex sample is one which displays a high degree of heterogeneity of proteins or peptides. Examples of complex mixtures include whole cells, cell extracts, partially purified cell extracts, tissues, bodily fluids, and animals, among others. Accordingly, in some embodiments, such complex mixtures comprise the naturally occurring proteins found in cells and tissues encoded by, for instance, different genes as found in the genomes of the source of the complex mixture (e.g., a cell or tissue extract or a bodily fluid such as serum). However, a complex mixture can also contain, as a component thereof, a recombinant protein or a purified protein or polypeptide either as an endogenous component (in the case of a recombinant protein), or as one added exogenously to the composition.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "cleavable linker" when used in the context of a peptide ester of the present invention refers generally to any element contained within the peptide that can serve as a spacer and is labile to cleavage upon suitable manipulation. Accordingly, a cleavable linker may comprise any of a number of chemical entities, including amino acids, nucleic acids, or small molecules, among others. A cleavable linker may be cleaved by, for instance, chemical, enzymatic, or physical means. Non-limiting examples of cleavable linkers include protease cleavage sites and nucleic acid sequences cleaved by nucleases. Further, a nucleic acid sequence may form a cleavable linker between multiple entities in double stranded form by complementary sequence hybridization, with cleavage effected by, for instance, application of a suitable temperature increase to disrupt hybridization of complementary strands. Examples of chemical cleavage sites include the incorporation photolabile, acid-labile, or base-labile functional groups into peptides.

"Proteases" (or "proteinases", "peptidases", or "proteolytic" enzymes) generally refer to a class of enzymes that cleave peptide bonds between amino acids of proteins. Because proteases use a molecule of water to effect hydrolysis of peptide bonds, these enzymes can also be classified as hydrolases. Six classes of proteases are presently known: serine proteases, threonine proteases, cysteine proteases, aspartic acid proteases, metalloproteases, and glutamic acid proteases (see, e.g., Barrett A. J. et al. The Handbook of Proteolytic Enzymes, 2nd ed. Academic Press, 2003).

Proteases are involved in a multitude of physiological reactions from simple digestion of food proteins to highly regulated cascades (e.g., the cell cycle, the blood clotting cascade, the complement system, and apoptosis pathways). It is well known to the skilled artisan that proteases can break either specific peptide bonds, depending on the amino acid sequence of a protein, or break down a polypeptide to constituent amino acids.

Among the proteases of this invention are "caspases", a family of cysteine proteases, which cleave other proteins after an aspartic acid residue. Many of the caspases are held in an inactive form as a zymogen until they are activated by proteolytic cleavage, which converts the inactive caspase into an active conformation, allowing caspase cleavage of downstream targets. Caspases serve an essential role in apoptosis, in which a cascade of sequential caspase activation is responsible executing programmed cell death. See, e.g., Thornberry, N. L. and Lazebnik, Y., *Science,* 281:1312-1316 (1998); Shi, Y., *Cell,* 117:855-8 (2004) for reviews. As an example of this regulatory hierarchy, caspase-3 is processed into an active form through its proteolysis by caspases-8, -9, and -10. Upon activation, caspase 3 is then able to activate caspases-6 and -7 via proteolysis. Caspases-3, -6, and -7 are then able to proteolyze cellular substrates such as nuclear lamins. Caspases can also become inappropriately and acutely activated during stroke, myocardial infarction, or Parkinson's disease.

"Apoptosis" refers generally to a process of programmed cell death and involves a series of ordered molecular events leading to characteristic changes in cell morphology and death, as distinguished from general cell death or necrosis that results from exposure of cells to non-specific toxic events such as metabolic poisons or ischemia. Cells undergoing apoptosis show characteristic morphological changes such as chromatin condensation and fragmentation and breakdown of the nuclear envelope. As apoptosis proceeds, the plasma membrane is seen to form blebbings, and the apoptotic cells are either phagocytosed or else break up into smaller vesicles which are then phagocytosed. Typical assays used to detect and measure apoptosis include microscopic examination of cellular morphology, TUNEL assays for DNA fragmentation, caspase activity assays, annexin-V externalization assays, and DNA laddering assays, among others. It is well known to the skilled artisan that the process of apoptosis is controlled by a diversity of cell signals which includes extracellular signals such as hormones, growth factors, cytokines, and nitric oxide, among others. These signals may positively or negatively induce apoptosis. Other effectors of apoptosis include oncogenes (e.g., c-myc) and exposure of cancer cells to chemotherapeutic agents, among other examples.

"Inducing apoptosis" or "inducer of apoptosis" refers to an agent or process which causes a cell to undergo the program of cell death described above for apoptosis.

A "cell signal" refers to any agent which may initiate or stimulate directly or indirectly proteolysis within a cell. Examples of cell signals include agents that cause cells to undergo apoptosis such as those discussed above. In the context of this invention, a cell signal may include introduction of an activated or overexpressed oncogene, such as c-myc, or any other protein that causes a proteolytic event to occur within cells, as well as, externally applied agents (e.g., chemotherapeutic drugs, etc.).

A "peptide ester" refers generally to any peptide in which one carboxyl group of the peptide is esterified, i.e., is of the structure —CO—O—R. In embodiments of this invention, a peptide ester can serve as a substrate for subtiligase such that the peptide is added to the α-amino group of polypeptides to form the structure —CO—NH—R, thus labeling the polypeptide. In some embodiments of this invention, a peptide ester can carry a detectable label and a site for proteolysis or another form of chemical cleavage (e.g., through introduction of photolabile, acid-labile, or base-labile functional groups).

A "label" or "detectable label" or "tag" is a composition detectable by mass spectrometric, spectroscopic, photochemical, biochemical, immunochemical, or chemical means. For example, useful labels include radioactive isotopes (e.g., 3H, 35S, 32P, 51Cr, or 125I), stable isotopes (e.g., $^{13}C$ or $^{15}N$), fluorescent dyes, electron-dense reagents, enzymes (e.g., alkaline phosphatase, horseradish peroxidase, or others commonly used in an ELISA), biotin, digoxigenin, or haptens or epitopes and proteins for which antisera or monoclonal antibodies are available. In general, a label as used in the context of the present invention is any entity that may be used to detect or isolate the product of the subtiligase ligation reaction. Thus, any entity that is capable of binding to another entity maybe used in the practice of this invention, including without limitation, epitopes for antibodies, ligands for receptors, and nucleic acids, which may interact with a second entity through means such as complementary base pair hybridization.

"Biological sample" as used herein is a sample of cells, biological tissue, or fluid that is to be tested for the occurrence of proteolysis or the presence, more generally, of polypeptides of interest in the sample. Among the cells that can be examined are cancer cells, cells stimulated to under apoptosis, and cells at different stages of development, among others. The biological tissues of this invention include any of the tissues that comprise the organs of an organism. The biological sample can be derived from any species including bacteria, yeasts, plants, invertebrates, and vertebrate organisms. The fluid of this invention can be any fluid associated with a cell or tissue. Such fluids may include the media in which cells are cultured as well as the fluid surrounding tissues and organs, as well as the fluid comprising the circulatory system of invertebrates and vertebrates (e.g., body fluids such as whole blood, serum, plasma, cerebrospinal fluid, urine, lymph fluids, and various external secretions of the respiratory, intestinal and genitourinary tracts, tears, saliva, milk, white blood cells, myelomas, and the like). An "extracellular fluid" refers generally to any fluid found exterior to cells. Such fluids may include all of the fluids described above. In certain embodiments, such fluids may further include cellular debris, for example from lysed cells, including membrane-bound and cytosolic proteins. A biological sample used in the present invention may be from a suitable organism, for example a mammal such as a mouse, rat, hamster, guinea pig, rabbit, sheep, goat, pig, monkey, human, and the like.

A "negative control" has the definition recognized by the skilled artisan and generally refers to an experiment in which the desired result is no effect. Conversely, a "positive control" is a control experiment in which the desired outcome is a well-defined or well-known effect. In the context of this invention, a negative control may be a biological sample which is not treated with an agent that provides a cell signal to stimulate proteolysis or may be a sample treated with a placebo.

"Secreted protein" refers generally to any protein that is synthesized by a cell for export to the exterior of the cell membrane, for instance, secretion to the extracellular fluid. A variety of secreted proteins are recognized by the skilled artisan including: hormones, growth factors, antibiotics, antibodies, neuropeptides, toxins, cytokines, apolipoproteins, proteases and protease inhibitors, among others.

"Disease" or "disease state" refers generally to any derangement of normal physiology. Examples of diseases relevant to the practice of this invention include, without limitation: inflammatory diseases such as rheumatoid arthritis, osteoporosis, inflammatory bowel syndrome, asthma; cardiovascular diseases such as ischemia, stroke, myocardial infarction, congestive heart failure, atherosclerosis; type I and II diabetes and diabetes related diseases such as hyperglycemia, diabetic retinopathy, peripheral neuropathy; thrombotic disorders, such as diseases affecting blood clotting or complement fixation; neurodegenerative diseases such as Alzheimer's disease, Parkinson's disease, Huntington's disease, age-related dementia; liver diseases, such as liver infection, fibrosis, cirrhosis; kidney infection, fibrosis, and cirrhosis; muscular dystrophy; multiple sclerosis; lung diseases, such as lung fibrosis; schizophrenia and other mental disorders; and disorders of cell proliferation such as psoriasis and cancer (see below). (See, generally, Harrison's Principles of Internal Medicine, 16th edition, 2004.)

"Cancer" and "cancer cells" refers generally to human and animal cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas) and Hodgkin's lymphoma, leukemia (including AML, ALL, and CML), multiple myeloma, mantle cell lymphoma, Waldenstrom's macrogobulinemia, and Philadelphia positive cancers, among others.

"Chemotherapeutic drugs or agents" include conventional chemotherapeutic reagents such as alkylating agents, antimetabolites, plant alkaloids, antibiotics, and miscellaneous compounds e.g., cis-platinum, CDDP, methotrexate, vincristine, adriamycin, bleomycin, and hydroxyurea, as well as biologics, such as therapeutic antibodies. Chemotherapeutic agents can include other therapeutic approaches known in the art for treating cancer, such as radiation therapy. Chemotherapeutic drugs or agents can be used alone or in combination in the practice of the present invention. The methods of the present invention are useful in combination with adjuvant cancer therapies, including hormone therapy, chemotherapy, biologic therapy (i.e. antibody therapy), radiation therapy, immunotherapy, surgery, and the like.

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins)

"Metastasis" refers to spread of a cancer from the primary tumor or origin to other tissues and parts of the body, such as the lymph nodes.

"Providing a prognosis" refers to providing a prediction of the likelihood of metastasis, predictions of disease free and overall survival, the probable course and outcome of cancer therapy, or the likelihood of recovery from the cancer, in a subject.

"Diagnosis" refers to identification of a disease state, such as cancer, in a subject. The methods of diagnosis provided by the present invention can be combined with other methods of diagnosis well known in the art. Non-limiting examples of other methods of diagnosis include, detection of previously known disease biomarkers, including protein and nucleic acid biomarkers, radiography, co-axial tomography (CAT) scans, positron emission tomography (PET), radionuclide scanning, and the like.

The terms "cancer-associated antigen", or "tumor-specific marker", or "tumor marker", or "biomarker" interchangeably refer to a molecule (typically nucleic acid, protein, proteolytic fragment, carbohydrate, or lipid) that is present in a biological sample, from a subject with cancer, expressed in a cancer cell, expressed on the surface of a cancer cell, or secreted by a cancer cell differentially in comparison to a biological sample from a subject without cancer or a non-cancer cell, and which is useful for the diagnosis of cancer, for providing a prognosis, or for preferential targeting of a pharmacological agent to the cancer cell. In the context of the present invention, a cancer-associated antigen may be a proteolytic fragment, for example one that is generated in response to an apoptotic stimulus, that is present in a biological sample, such as a blood sample, tumor biopsy, tissue, and the like, from a patient suffering from a disease, such as cancer, at an elevated level, for example, 10% greater level, 20%, 50%, 75%, 100% or greater level, than found in an biological sample from an individual not suffering from the disease. In other cases, the proteolytic fragment may be present at about 1-fold, 2, 3, 4, 5, 6, 7, 8, 9, 10, 20, 30, 40, 50, 75, 100, 250, 500, or 1000-fold greater level in a sample from a patient suffering from the disease as compared to a sample from an individual not suffering from the disease, or a control sample. In some embodiments, a biomarker of the present invention may be a proteolytic fragment that is present in a biological sample from a patient suffering from a disease, such as cancer, but not present, or present at a minimal level, in a sample from an individual not suffering from the disease. In other embodiments, a cancer-associated antigen is a molecule that is overexpressed in a biological sample from a subject with cancer or a cancer cell in comparison to a biological sample from a subject without cancer or a non-cancer cell, for instance, 1-fold over expression, 2-fold overexpression, 3-fold overexpression or more in comparison. Oftentimes, a cancer-associated antigen is a molecule that is inappropriately synthesized in a cancer cell or present in a biological sample from a subject with cancer, for instance, a molecule that contains deletions, additions or mutations in comparison to the molecule expressed in a biological sample from a subject without cancer or in a non-cancer cell.

The "proteolytic apoptotic polypeptide biomarkers" of the present invention generally relate to proteolytic polypeptides that are generated in response to an apoptotic stimulus. Typically, these fragments are formed by the cleavage of a "pro-apoptotic polypeptide" or "proteolytic apoptotic cleavage junction" by a protease involved in an apoptotic pathway. Typically, two proteolytic apoptotic polypeptide biomarkers are generated by every cleavage. For example, one proteolytic polypeptide may comprise an N-terminal sequence selected from those found in Table 1. I.e., cleavage of Serine/threonine-protein phosphatase 2A 56 kDa regulatory subunit gamma isoform, Swiss-Prot accession number Q13362, results in a proteolytic apoptotic polypeptide biomarkers comprising the sequence AANSNGPFQPVVLL-HIR (SEQ ID NO:418), wherein AAN are the first three, or N-terminal, residues of the biomarker. A second proteolytic apoptotic polypeptide biomarker formed by a cleavage reaction may comprise a C-terminal sequence also found in Table 1. I.e., cleavage of Serine/threonine-protein phosphatase 2A 56 kDa regulatory subunit gamma isoform, Swiss-Prot accession number Q13362, will also result in a proteolytic apoptotic polypeptide biomarkers comprising the sequence AGSRMVVD (SEQ ID NO:419), wherein VVD are the last three, or C-terminal, residues of the biomarkers. In certain embodiments, proteolytic apoptotic polypeptide biomarkers of the invention may further comprise a fusion sequence N-terminal or C-terminal to a sequence found in Table 1, in order to facilitate purification or detection of the biomarker. Proteolytic apoptotic polypeptide biomarkers of the present invention may comprise polypeptides spanning from the cleavage site (P1 or P1' residue) to the N- or C-terminus of the parent protein. In other embodiments, the proteolytic apoptotic polypeptide biomarkers of the invention may undergo further proteolysis prior to detection or quantitation. As such, a proteolytic apoptotic polypeptide biomarker may comprise at least about 4, 5, 6, 7, 8, 9, 10, 11, 12, 13, 14, 15, 16, 17, 18, 19, 20, 25, 30, 35, 40, 45, 50, 55, 60, 70, 80, 90, 100, 125, 150, 175, 200, 250, 300, 400, 500, or more of the parent protein, including the identified N- or C-terminal sequence, for example those found in Table 1.

A "proteolytic apoptotic cleavage junction", or "cleavage junction", or "intact cleavage junction", in the context of the present invention, refers to an amino acid sequence, or polypeptide containing said sequence, that contains a recognition motif that is cleaved by a protease under certain conditions. In one embodiment, a cleavage junction of the invention is cleaved in response to an apoptotic stimulus. In a particular embodiment, the cleavage junctions comprise a sequence selected from those found in Table 3. A cleavage junction is said to correspond to a proteolytic polypeptide or a proteolytic apoptotic polypeptide biomarker if said proteolytic polypeptide is formed or generated by the proteolysis of the cleavage junction. Thus, typically a cleavage junction of the present invention will result in the formation of two proteolytic apoptotic polypeptide biomarkers that correspond to said intact cleavage junction. In one embodiment, a cleavage junction comprising a sequence selected from those found in Table 3, with a given Swiss-Prot accession number, will correspond to two proteolytic polypeptides, one comprising an N-terminal sequence selected from those found in Table 1 and one comprising a C-terminal sequence selected from those found in Table 1, with the same Swiss-Prot accession number. For example, a cleavage junction of Table 3, Swiss-Prot accession number Q13362, would correspond to both a proteolytic polypeptide comprising a N-terminal sequence of the corresponding unmodified polypeptide sequence and a proteolytic polypeptide comprising an C-terminal sequence of the corresponding previous amino acid sequence.

In certain embodiments, the cleaved products of the present invention may be further trimmed in vivo or in vitro by exoproteases after capsase-based proteolysis. The present invention, in one embodiment, includes fragments of the biomarkers identified herein that have been further processed by such exoproteases, which may serve as biomarkers of apoptosis equivalent to their predecessor fragments. In other embodiments, the detection of either an N-terminal or C-terminal proteolytic fragment, in the absence of the other, will provide diagnostic or prognostic power for the detection of spoptosis in a biological sample.

An "apoptotic stimulus" generally refers to a signal or condition that causes or induces a cell to undergo apoptosis. Apoptotic signals may originate intracellularly, as per the action of an intrinsic inducer, or extracellularly, as in the action of an extrinsic inducer. Extracellular signals may include, without limitation, toxins, hormones, growth factors, nitric oxide, cytokines, cytotoxic dugs, and the like. Intracellular apoptotic signalling is typically initiated in response to stress. These stimuli include, without limitation, the binding of nuclear receptors by glucocorticoids, heat, radiation, nutrient deprivation, viral infection, hypoxia, and the like. In certain embodiments of the invention, apoptosis may be induced through the use of cytotoxic drugs or by environmental conditioning of the cells.

"Biological sample" includes sections of tissues such as biopsy and autopsy samples, and frozen sections taken for histologic purposes. Such samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, Mouse; rabbit; or a bird; reptile; or fish A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., tongue, colon, prostate, kidney, bladder, lymph node, liver, bone marrow, blood cell, etc.), the size and type of the tumor (e.g., solid or suspended, blood or ascites), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally obtains a suspension of cells from within the tumor mass. Biopsy techniques are discussed, for example, in *Harrison's Principles of Internal Medicine*, Kasper, et al., eds., 16th ed., 2005, Chapter 70, and throughout Part V.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1987-2005, Wiley Interscience)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of cancer antigens. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., supra.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of a target protein or polypeptide.

The phrase "specifically (or selectively) binds" to or "specifically (or selectively) immunoreactive with" an antibody or binding reagent, when referring to a protein or peptide, refers to a binding reaction that is determinative of the presence of the protein, often in a heterogeneous population of proteins and other biologics. Similarly, an antibody or binding reagent is considered to "substantially bind" to an epitope, when the antibody or binding reagent binds to said epitope in a specific or selective fashion. Thus, under designated immunoassay conditions, the specified antibodies or binding reagents bind to a particular protein at least two times the background and more typically more than 10 to 100 times background. Specific binding to an antibody or binding reagent under such conditions requires an antibody or binding reagent that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies or binding reagents specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

A binding reagent or antibody that "binds with a lower affinity" to a second polypeptide or to a background polypeptide will generally bind specifically to a first target polypeptide of interest with a greater affinity as compared to the binding affinity to said second polypeptide. In certain embodiments, the binding reagent or antibody will bind to the second polypeptide with at least a two fold lower affinity, or more typically at least about 10-fold, 100-fold, or 1000-fold lower affinity as compared to the binding affinity of the first or target polypeptide. In this fashion, a binding reagent or polypeptide that binds with a lower affinity to a second polypeptide can discriminate between a first target polypeptide and a second polypeptide, even when the second polypeptide is a derivative of the first polypeptide. For example, an antibody specific for a proteolytic polypeptide of the present invention may bind with a lower affinity to the corresponding proteolytic cleavage junction, or a polypeptide containing said cleavage junction, such that the target proteolytic polypeptide, or the level thereof, can be discriminated from said cleavage junction in a biological sample.

In the context of the present invention, a disease is "characterized by apoptosis" if said disease results in altered levels of apoptosis in an individual suffering from the disease. A disease may be considered to be characterized by apoptosis, for example, if levels of apoptosis are reduced or increased in an individual suffering from the disease as compared to levels in individuals not suffering from said disease. In one embodiment of the present invention, apoptosis levels may be reduced or increased by at least about 5%, or at least about 10, 15, 20, 25, 30, 35, 40, 45, 50, 60, 70, 80, 90, or 100% as compared to levels in an individual not suffering from said disease. In other embodiments, the level of apoptosis may be reduced or increased by at least about 1-fold, 2-fold, 3-fold, 4-fold, 5-fold, 6-fold, 7-fold, 8-fold, 9-fold, 10-fold or more as compared to levels in individuals not suffering from the disease. In yet other embodiments, apoptosis may be reduced or increased by at least about 1 order of magnitude, or at least about 2, 3, 4, 5, 6, 7, 8, 9, 10, or more orders of magnitude as compared to levels in an individual not suffering from the disease. Non-limiting examples of diseases that are characterized by apoptosis include, cancer, auto-imune diseases (such as Graves' disease, Lupus erythematosus, Rheumatoid arthritis, Sjögren's syndrome, multiple sclerosis, type-I diabetes mellitus, Hashimoto thyroiditis, and the like), neurodegenerative diseases (such as Parkinson's or Alzheimer's Diseases), preeclampsia, acute and chronic liver diseases, and the like.

Diagnostic Methods

The present invention provides methods of diagnosing a disease characterized by apoptosis, by examining proteolytic apoptotic biomarkers, including proteolytic polypeptides comprising an N-terminal or C-terminal sequence found in Table 1 and proteolytic apoptotic cleavage junctions comprising a sequence found in Table 3, in biological samples, including wild-type, truncated or alternatively spliced forms. Diagnosis involves determining the level of a polypeptide of the invention in a patient and then comparing the level to a baseline or range. Typically, the baseline value is representative of a polypeptide of the invention in a healthy person not suffering from the disease, as measured using biological sample such as blood, serum, saliva, urine, a tissue sample (e.g., tongue or lymph tissue), or a biopsy. Variation of the levels of a polypeptide of the invention from the baseline range (either up or down) indicates that the patient has a disease characterized by apoptosis or is at risk of developing a disease characterized by apoptosis.

Analysis of a protein can be achieved, for example, by high pressure liquid chromatography (HPLC), alone or in combination with mass spectrometry (e.g., MALDI/MS, MALDI-TOF/MS, tandem MS, etc.).

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used (see, e.g., Self et al., *Curr. Opin. Biotechnol.*, 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing et al., *Electrophoresis*, 18:2184-93 (1997); Bao, *J. Chromatogr. B. Biomed. Sci.*, 699:463-80 (1997)). Liposome immunoassays, such as flow-injection liposome immunoassays and liposome immunosensors, are also suitable for use in the present invention (see, e.g., Rongen et al., *J. Immunol. Methods*, 204:105-133 (1997)). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., *J. Clin. Chem. Clin. Biochem.*, 27:261-276 (1989)).

Specific immunological binding of the antibody or binding reagent to a protein can be detected directly or indirectly. Direct labels include fluorescent or luminescent tags, metals, dyes, radionuclides, and the like, attached to the antibody.

An antibody labeled with iodine-125 ($^{125}$I) can be used. A chemiluminescence assay using a chemiluminescent antibody specific for the protein marker is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies or binding reagents can be immobilized onto a variety of solid supports, such as polystyrene beads, magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Useful physical formats comprise surfaces having a plurality of discrete, addressable locations for the detection of a plurality of different biomarkers. Such formats include protein microarrays, or "protein chips" (see, e.g., Ng et al., J. Cell Mol. Med., 6:329-340 (2002)) and certain capillary devices (see, e.g., U.S. Pat. No. 6,019,944). In these embodiments, each discrete surface location may comprise antibodies to immobilize one or more protein markers for detection at each location. Surfaces may alternatively comprise one or more discrete particles (e.g., microparticles or nanoparticles) immobilized at discrete locations of a surface, where the microparticles comprise antibodies to immobilize one or more protein markers for detection.

The analysis can be carried out in a variety of physical formats. For example, the use of microtiter plates or automation could be used to facilitate the processing of large numbers of test samples. Alternatively, single sample formats could be developed to facilitate diagnosis or prognosis in a timely fashion.

Compositions, Kits and Integrated Systems

The invention provides compositions, kits and integrated systems for practicing the assays described herein using polypeptides of the invention, antibodies or binding reagents specific for polypeptides of the invention, etc.

The invention provides assay compositions for use in solid phase assays; such compositions can include, for example, one or more antibodies or binding reagents specific for the polypeptide biomarkers of the invention immobilized on a solid support, and a labeling reagent. In each case, the assay compositions can also include additional reagents that are desirable for hybridization.

The invention also provides kits for carrying out the diagnostic or prognostic assays of the invention. The kits typically include a probe that comprises an antibody or binding reagent that specifically binds to polypeptides of the invention, and a label for detecting the presence of the probe. The kits may include several antibodies specific for the polypeptides of the invention. In one embodiment, the kits of the invention comprise at least 2, or at least about 3, 4, 5, 6, 7, 8, 9, 10, 15, 20, 25, 30, 40, 50, 60, 70, 80, 90, 100, 125, 150, 175, 200, 250, 300 or more antibodies or binding reagents.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical images.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen are sampled to obtain light intensity readings for each position. Multiple pixels are processed in parallel to increase speed. The apparatus and methods of the invention are easily used for viewing any sample, e.g., by fluorescent or dark field microscopic techniques.

N-Terminal Labeling of Polypeptides

In general, any method of making an extract from cells or tissues from a biological sample that preserves the ability to label the N-termini of polypeptides with the reagents described below may be used in the practice of this invention. Any of a number of such methods are known in the art and are described in standard sources (see, e.g., Scopes, Protein Purification: Principles and Practice (1982)). In general, cells are disrupted to release and solubilize intracellular contents, followed by centrifugation to remove insoluble material, such as cell membranes and organelles. For tissue culture cells, a lysis buffer which may contain a detergent (e.g., TRITON X-100 detergent, NP-40, among others) may be used. For adherent tissue culture cells, cell disruption can be accomplished by the process of scraping cells in the presence of the lysis buffer from culture plates using, for example, a rubber policeman. Other mechanical means can also be used to effect cell disruption. For example, cells can be lysed using a Dounce homogenizer. As recognized by the skilled artisan, additional mechanical means may be needed to prepare cell extracts from tissues, such as homogenization in a blender or sonication. (See, generally, e.g., Scopes, Protein Purification: Principles and Practice (1982).)

The labeling of polypeptides can be accomplished using any method that labels the N-terminus (i.e., α-amino group) of a polypeptide present in a complex mixture.

In one embodiment of this invention, the labeling is accomplished using the enzyme subtiligase, which is derived from the enzyme subtilisin BPN' by converting the catalytic residue, Ser-221, to a cysteine residue, and Pro-225 to an alanine residue. The resulting double mutant protein provides the enzymatic activity of ligation of esterified peptides site-specifically onto the N termini of proteins or peptides (see, e.g., Chang, T. K. et al., Proc. Natl. Acad. Sci. U.S.A., 91, 12544-12548 (1994)). Furthermore, additional forms of subtiligase that exhibit increased stability have been generated through the introduction of additional site directed mutations into the sequence (e.g., Met-50 to Phe, Asn-76 to Asp, Asn-109 to Ser, Lys-213 to Arg, and Asn-218 to Ser). Such mutant enzymes have also been termed stabiligases and may also may be used in the practice of the present invention (see, e.g., Chang, T. K. et al., Proc. Natl. Acad. Sci. U.S.A., 91, 12544-12548 (1994)).

All of the earlier work describing the use of subtiligase and its variants disclosed the ligation of peptides and proteins in non-complex samples composed of single purified polypeptides. In this earlier work, two examples of the application of subtiligase to the ligation of proteins that were recombinantly expressed on the surface of phage particles were shown. For example, the work of Chang et al. demonstrated the ligation of phage-displayed human growth hormone variants that were randomized at the first three residues (Chang, T. K. et al., Proc. Natl. Acad. Sci. U.S.A., 91, 12544-12548 (1994)). The work of Atwell et al. demonstrated the autoligation of phage-displayed subtiligase variants that contained an N-terminal extension and were randomized at up to five different residues outside of this N-terminal extension (Atwell S. et al., Proc. Natl. Acad. Sci. U.S.A., 96, 9497-9502 (1999)). In contrast, the present invention represents a major advance, as it applies subtiligase to the ligation of polypeptides in complex mixtures of endogenous proteins as found in a variety of biological samples, not merely to simple formulations of recombinant proteins, as shown by the earlier studies. The modest amount of sample complexity in the earlier reported phage display experiments arises from minor genetic manipulations of either the human growth hormone gene or the subtiligase gene. In contrast, the complexity found in the biological samples of the present invention arises from the fact that the component polypeptides of the complex mixtures of the invention are products of a plurality of endogenous genes, which are subject to transcriptional, translational, and post-translational modulation of expression.

Furthermore, the work of Chang et al. demonstrated that subtiligase is very dependent on the primary and secondary structure of polypeptide substrates. Although subtiligase was found to exhibit broad specificity for peptide substrates, some N-terminal residues in these substrates were found to be exceedingly more preferred than others. Structural occlusion of N-termini in a protein substrate was also found to drastically affect ligation efficiency. This earlier work indicated limitations to this approach for labeling a plurality of polypeptides in complex mixtures and provided no indication of applicability to more complex samples, as the only substrates used in addition to short peptides were recombinant human growth hormone and subtiligase. In fact, those of skill in the art recognized several potential pitfalls in the implementation of subtiligase as a tool for selective labeling of polypeptide α-amines in complex mixtures. First, it was believed that only the most abundant proteins in the sample would be labeled. Second, the previous data indicated the possibility that only the most efficient substrates, based on the identity of N-terminal residues, would be labeled. Third, there existed the possibility of poor labeling of mixtures due to structural occlusion of N-termini. Fourth, there was a strong possibility that complex samples would contain inhibitors of subtiligase. Fifth, there was a prevalent concern that the peptide glycolate ester reagents would not be stable in biological samples because of the action of endogenous esterases and proteases.

However, as demonstrated below, the inventors have surprisingly found that these many pitfalls could be circumvented and have demonstrated that subtiligase may be used to efficiently label the N-termini of a plurality of polypeptides in complex mixtures, such as cell extracts and serum. For example, the inventors show that addition of a cocktail of inhibitors sufficiently blocks endogenous proteases and esterases without inhibiting subtiligase, thus, allowing for sufficient substrate to be available for ligation. Another advantage imparted by the present invention is the nature of the labeled peptide ester reagents used here. The inventors have designed versions of these reagents that are optimized for use in proteomic studies. Among other innovations, they have found that incorporation of a cleavable linker into these reagents greatly facilitates purification of labeled polypeptides from complex mixtures and subsequent analysis by tandem mass spectrometry for identification of the corresponding proteins.

Additional variants of subtiligase enzymes that have enhanced activity have also been selected through the application of phage display methods (see, e.g., Atwell, S. et al., Proc. Natl. Acad. Sci. U.S.A., 96:9497-502 (1999)). Such variants may also be used in the practice of the present invention. Furthermore, other subtilisin-like enzymes and their variants may also be engineered to be used in the practice of this invention.

Subtiligase has been used to incorporate a variety of label moieties into proteins and polypeptides, including affinity handles (e.g., biotin), immunoprobes, isotopic labels, heavy-atom derivatives, PEG moieties, and other non-natural constituents (see, e.g., Chang, T. K. et al., Proc. Natl. Acad. Sci. U.S.A., 91, 12544-12548 (1994)). The skilled artisan will recognize that this is not an exhaustive list, as for instance, any detectable label that can be incorporated into a substrate (e.g., biotin labeled peptide esters) to be used to label a free N-terminus (e.g., α-amino group of a polypeptide generated through proteolysis) may be used. In particular, any of the labels disclosed above may be used in the practice of the present invention.

The reaction by which subtiligase may be used to label a free N-terminus of a polypeptide is illustrated in FIGS. 1A-1, 1A-2, 1B-1, and 1B-2 with a biotin labeled peptide ester as the substrate for the introduction of a biotin label onto a protein. In the first step of this reaction, a free sulfhydryl group on subtiligase serves as a nucleophile to effect a nucleophilic attack on the carbonyl carbon atom of the ester moiety of the substrate peptide ester, resulting in the release of an alcohol leaving group. In a second step, the carbonyl carbon of the thioester linkage between the peptide substrate and the subtiligase enzyme is then subject to nucleophilic attack by the α-amino group of a protein or peptide. This reaction results in a covalent adduct comprising the biotin labeled peptide linked to the α-amino group on a protein or peptide via an amide bond. Accordingly, the biotin label then can serve as an affinity handle to allow the identification and isolation of polypeptides that have a free N-terminus or free α-amino group (e.g., protein fragments that have resulted from proteolysis, or native non-acetylated or otherwise N-terminally blocked proteins).

In general, any peptide ester with the following generic elements may be used in the practice of the present invention: label-linker-peptide sequence-esterified carboxyl terminus. The skilled artisan will recognize that the location of the label within this structure may be varied without affecting the operation of the present invention. The generic structure of these elements may optionally contain a protease cleavage site or other cleavable moiety to facilitate the ready removal of the label added to the α-amino group of a protein or polypeptide. Such removal also greatly facilitates downstream mass spectrometric analysis of labeled proteins or polypeptides. FIG. 6 shows a representative peptide ester that may be used in the practice of the invention. In this example, there is a biotin label at the N-terminus of the peptide ester, a site for a protease cleavage (TEV protease), and an esterified carboxyl terminus, which serves as a subtiligase cleavage site (i.e., the site for the nucleophilic attack by a free sulfhydryl group on subtiligase as described above). Among the peptide sequences that may be used in the practice of the invention include, but are not limited to: ENLYFQSY (SEQ ID NO:420), ENLYFQSK (SEQ ID NO:421), ENLYFQSA (SEQ ID NO:422), AAPY (SEQ ID NO:423), AAPK (SEQ ID NO:424), and AAPA (SEQ ID NO:425), among others. Optional protease cleavage sites that may be used in the practice of this invention include, but are not limited to: the site for TEV protease: EXXYXQ(S/G/A) (SEQ ID NO:436), where X corresponds to any amino acid; the site for rhinovirus 3C protease: E(T/V)LFQGP (SEQ ID NO:426); the site for enterokinase: DDDDK (SEQ ID NO:427); the site for Factor Xa: I(D/E)GR; the site for thrombin: LVPR (SEQ ID NO:428); the site for furin: RXXR (SEQ ID NO:437), where X corresponds to any amino acid; and the site for Granzyme B: IEPD (SEQ ID NO:429). Some examples of the many possible moieties that may be used to esterify the carboxyl terminus of the peptide are: HO—CH2-CO—X, where X is any amino acid, in the case of glycolate esters; HO—CHCH3-CO—X, where X is any amino acid, in the case of lactate esters; HO—R, where R is an alkyl or aryl substituent; and HS—R, where R is an alkyl or aryl substituent. A number of label moieties may be used, including radioisotopes, stable isotopes, flurophores, heavy metals, and biotin, among others.

In general, any reaction conditions that favor nucleophilic attack of a carbonyl group at an ester or thioester linkage to result in the release of the relevant leaving group (e.g., an alcohol in step one or the —SH group of subtiligase in step two) may be used in the practice of this invention for the labeling of free α-amino groups. Generally, any conditions under which ester reagents are stable to degradation and hydrolysis in complex samples; conditions under which subtiligase is stable and active; and conditions under which protein and polypeptide N-termini are free and available to react with the thioester linkage formed after the reaction of subtiligase with ester reagents are favored for the practice of this invention.

In some embodiments of this invention, the pre-existing unblocked α-amino groups of polypeptides may be blocked with a suitable N-termini blocking agent before an experimental treatment. Thus, for instance, the free, unblocked N-termini of cellular proteins may be blocked with any reagent that reacts with free α-amino groups prior to exposure of a biological sample to an agent, such as a chemotherapeutic agent, which promotes a physiological response of interest, such as apoptosis. After the experimental treatment, the newly exposed N termini which have resulted from the proteolytic events that accompany apoptosis can then be labeled using subtiligase and the ester substrates of the present invention. Examples of such blocking agents include: amine-reactive reagents such as succinimidyl esters, isothiocyanates, sulfonyl chlorides, and aldehydes, among others, provided these reagents do not contain primary or secondary amine moieties. In one embodiment, the blocking reaction can be accomplished using subtiligase and an acetylated ester.

It will be appreciated by the skilled artisan that a variety of complex samples can be labeled using the methods and compositions of the present invention. Such samples may include, without limitation, whole cells, cell extracts, media from cell cultures, serum from humans or animals, and other bodily fluids, among others. For example, the culture medium of cells stimulated with an agent that causes polypeptide secretion can be labeled using the methods of the present invention to identify polypeptides that have been secreted. As another example, proteins found on the surfaces of intact cells may be labeled to identify cell surface proteins, such as membrane proteins. The comparison of the cell surface proteins labeled in normal versus transformed cells can be used to identify, for example, tumor specific antigens. As a further example, serum or other bodily fluids from normal subjects and patients suffering from various diseases can be labeled to identify proteins that are unique to the serum of a patient population. The proteins so identified can serve as easily detected disease markers to be used in disease diagnostics. U.S. patent application Ser. No. 12/524,557 filed on Jul. 24, 2009, assigned to the same assignee as the present invention, the disclosure of which is incorporated by reference in its entirety and with particularity with reference to its teachings concerning methods for the specific N-terminal labeling and detection of peptides and proteins in complex mixtures.

EXAMPLES

Example 1

This example demonstrates the identification and profiling of N-termini in normal Jurkat cells.

As a validation of a method provided by the present invention, endogenous N-termini in non-apoptotic Jurkat cells were analysed in two small-scale experiments using one-dimensional reversed-phase (1D) LC/MS/MS and two large-scale experiments using two-dimensional strong cation exchange/reversed-phase (2D) LC/MS/MS. Comparison of data obtained in both types of experiments is informative since 1D LC/MS/MS typically results in identification of abundant N-termini, whereas the increased proteomic coverage afforded by 2D LC/MS/MS results in additional identification of lower abundance N-termini. Of the combined 131 unique N-termini identified in small-scale experiments, 72% are either annotated in Swiss-Prot as native protein N-termini, or correspond to cleavages within the first 50 residues of proteins as would be expected for N-terminal signal or transit peptide processing (FIG. 2A). The remaining 28% correspond to cleavages outside the first 50 residues, arising from additional processing or constitutive protein degradation. In support of the latter notion, 51% of the combined 661 unique N-termini identified in large-scale experiments correspond to cleavages outside the first 50 residues (FIG. 2A). The increased frequency of such N-termini in large-scale experiments is consistent with the expected lower abundance for products of constitutive protein degradation.

Example 2

This example provides degradomic analysis of apoptotic Jurkat cells.

For analysis of apoptosis in Jurkat cells, several small-scale (1D) and large-scale (2D) LC/MS/MS experiments were carried out using cells treated with the topoisomerase II poison etoposide. The experiments with untreated cells described above serve as respective controls for the small- and large-scale experiments with apoptotic cells, in which a combined 244 and 733 unique N-termini, respectively, were identified. Caspases are known to exhibit strict substrate specificity for aspartate at P1, and for glycine>serine>alanine at P1' (Schilling et al., Nat. Biotechnol. 2008; 26(6):685-94; Stennicke et al., Biochem J. 2000; 350 Pt 2:563-8). In small-scale experiments, 43% of N-termini identified in apoptotic cells were derived from P1 aspartate cleavages, in contrast to less than 1% in untreated cells (FIG. 3A). In large-scale experiments, 43% of N-termini identified in apoptotic cells were derived from P1 aspartate cleavages, in contrast to 3% in untreated cells (FIG. 3B). An increased frequency of glycine at the first position of N-termini is also observed in apoptotic cells relative to untreated cells at both experimental scales (FIGS. 3A and 3B). The N-termini uniquely identified in apoptotic Jurkat cells are thus consistent with induction of caspase-like activity.

Of the 3% P1 aspartate N-termini detected in large-scale experiments with untreated cells (FIG. 3B), 55% correspond to reported caspase substrates (Lüthi et al., Cell Death Differ. 2007; 14(4):641-50). Thus, it is likely that these originate from the small number of apoptotic cells typically present in untreated cultures. The detection of 3% P1 aspartate N-termini in large-scale experiments with untreated cells and less than 1% in small-scale experiments is consistent with the low abundance of such N-termini in cultures of normal cells. Additionally, if one considers that N-termini annotated in Swiss-Prot are representative of native N-termini in healthy cells, it is notable that <1% are derived from proteolytic processing following an aspartate residue (FIG. 4). In apoptotic samples, the increased frequency of N-termini located beyond the first 50 residues is solely attributable to P1 aspartate N-termini (FIGS. 2B and 2C). Thus, the vast majority of proteolysis we observe in apoptosis is attributable to caspases or proteases with caspase-like substrate specificity.

Among the total 1099 SY-labeled peptides identified in etoposide-treated Jurkat cells, 418 follow aspartate in corresponding protein sequences. These peptides correspond to 333 P1 aspartate N-termini and caspase-like cleavage sites. In turn, these cleavage sites map to 282 unique substrates and 10 additional others that cannot be distinguished from homologs containing the same identified cleavage site. Approximately 16 of the proteins identified as caspase substrates in these studies have been verified to be cleaved during apoptosis using immunoblotting (representative examples are indicated in FIG. 5A). The proteolysis of a representative set of substrates is also blocked by the broad-spectrum caspase inhibitor Z-VAD(OMe)-fmk, consistent with this proteolysis being caspase-dependent (FIG. 5B). Representative CID spectra for P1 aspartate peptides are included (FIGS. 8-15).

Figure 6A:
Figure 6B:
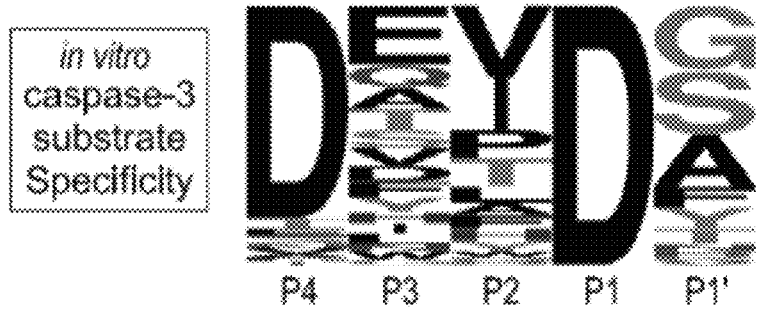
Figure 6C:
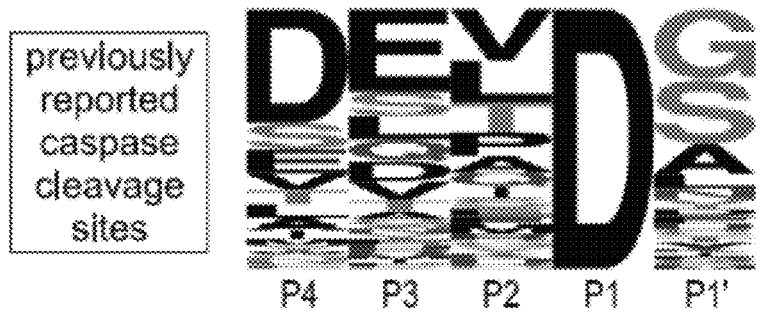
Figure 6D:
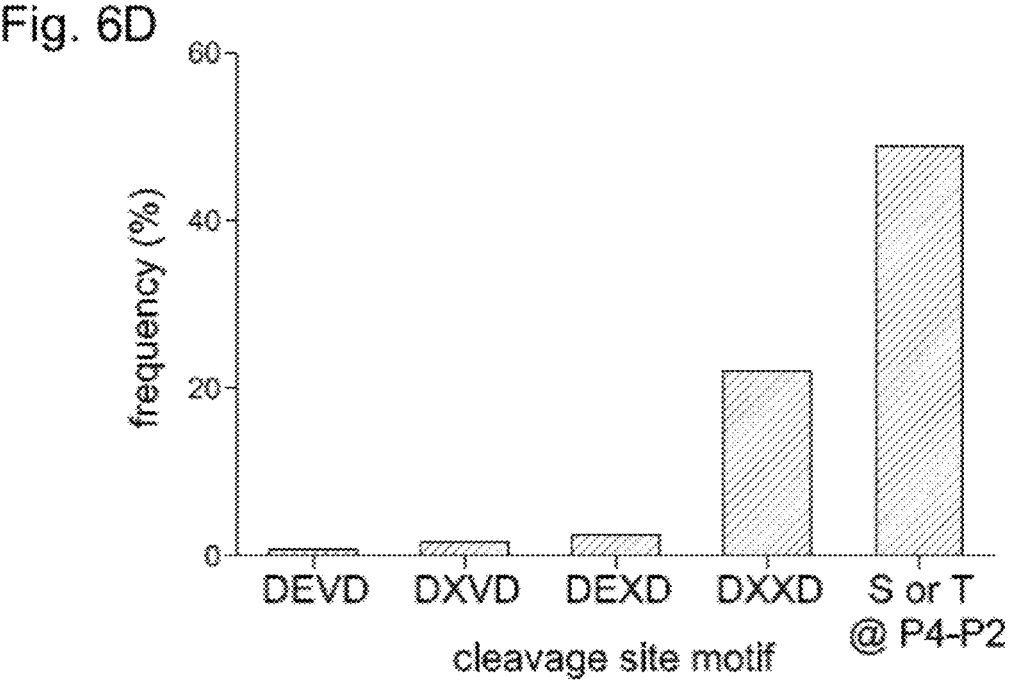

The most frequent residues at the P4, P3, P2, and P1' positions of the caspase-like cleavage sites identified in apoptotic Jurkat cells are aspartate, glutamate, valine, and glycine, respectively (FIG. 6A). Thus, an averaged composite of these cleavage sites indicates that the most common caspase activity in apoptotic cells exhibits a specificity that is most similar to the substrate specificity of executioner caspases-3 and -7, as determined using peptide substrates (FIG. 6B) (Thornberry et al., J Biol Chem. 1997; 272(29): 17907-11). However, there are significant differences between the cellular cleavage sites and the in vitro specificity profiles. Notably, the canonical DEVD (SEQ ID NO:430) cleavage site motif is found in less than 1% of the caspase-like cleavage sites observed in apoptotic Jurkat cells, and the broader DXXD (SEQ ID NO:438) motif is still only found in 22% of the identified cleavage sites (FIG. 6D). A distinct difference in the composite cellular profile is the high frequency of serine and threonine residues at P4, P3, and P2, which is not observed in vitro for any of the caspases (FIG. 7). Interestingly, a composite of all previously reported human and human ortholog of rodent caspase cleavage sites (Lüthi et al., Cell Death Differ. 2007; 14(4): 641-50) is very similar to the Jurkat cellular profile reported here (FIG. 6C).

Figure 6E:
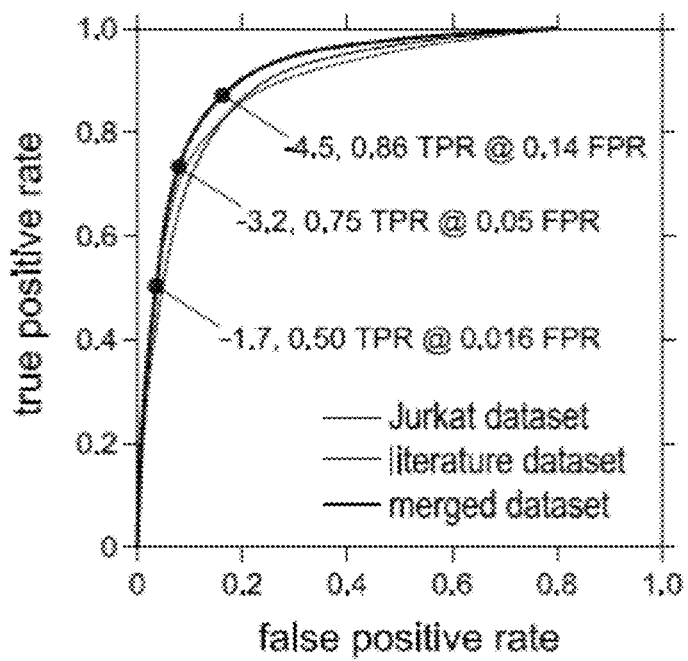

These observations suggest that caspase substrate specificity determined using peptide substrates has limited value as a predictor of physiological caspase cleavage sites. To investigate the predictive value of a large set of known physiological caspase cleavage sites, we constructed three profile hidden Markov models (HMMs) using the cleavage sites identified in our studies, previously reported cleavage sites, and the union of these two datasets. The accuracy of these HMMs was estimated using jackknifing and plotted in a receiver operator characteristic (ROC) plot, showing the true positive rate versus the false positive rate at different HMM score thresholds. While all three HMMs predict caspase cleavage sites relatively accurately, the HMM built from the merged substrate set performed most accurately (FIG. 6E).

Example 5

Cell Culture, Induction of Apoptosis, and Cell Lysate Preparation

Jurkat clone E6-1 (ATCC) cells were grown in RPMI-1640 supplemented with 10% fetal bovine serum, sodium pyruvate, and antibiotics. Normal cells were harvested for experiments at a density of $1 \times 10^6$ cells/ml. For apoptotic samples, cells at a density of $1 \times 10^6$ cells/ml were treated with etoposide (50 µM) for 12 hours prior to harvesting. Harvested cells (0.1 to 1 billion) were pelleted at 2,000×g and 25° C. for 5 minutes, washed twice with phosphate buffered saline, and lysed at a typical concentration of $2 \times 10^8$ cells/ml in 1.0% TRITON X-100 detergent, 100 mM BICINE pH 8.0, 100 µM Z-VAD-FMK, 100 µM E-64, 1 mM PMSF, 1 mM AEBSF, and 5 mM EDTA. Cell lysates were incubated at room temperature for 1 hour to allow complete inhibition of endogenous protease and esterase activity, and centrifuged at 21,000×g and 4° C. for 15 minutes to pellet insoluble material. Clarified supernatant was immediately used in ligation reactions at a protein concentration of approximately 20 mg/ml, as determined by Bradford assay (Bio-Rad).

Example 6

Sample Biotinylation, Denaturation, Reduction, Alkylation, and Gel Filtration Subtiligase (1 µM), biotinylated peptide ester (1 mM), and DTT (2 mM) were added to either control or apoptotic cell lysate. Ligation reactions were typically left to proceed at room temperature for 60 minutes. Samples were then denatured by direct addition of solid guanidine hydrochloride to a final concentration of 6 M, reduced by addition of neutralized TCEP (2 mM), heated at 95° C. for 15 minutes, cooled to room temperature, and alkylated by addition of iodoacetamide (6 mM) and incubation at room temperature in the dark for 1 hour. The alkylation reaction was quenched by addition of DTT (10 mM), the sample was passed through a 0.8 µm filter, and subjected to gel filtration chromatography using a Superdex 30 16/60 column (GE Healthcare) on an ÄKTA FPLC system (GE Healthcare). The mobile phase was 100 mM BICINE pH 8.0, 200 mM NaCl, and 1 M guanidine hydrochloride. Fractions containing protein (corresponding to polypeptides greater than 5 kDa) were collected and pooled for a final volume of approximately 30 ml.

Example 7

Trypsinization and Recovery of Biotinylated Peptides

The gel-filtered material was supplemented with $CaCl_2$ (20 mM) and digested with sequencing grade modified trypsin (100 µg, Promega) by incubation at 37° C. for 12 hours. Trypsinized samples were clarified by centrifugation, supplemented with benzamidine (500 mM), and NeutrAvidin agarose (250 µl bed volume, Pierce) was added for affinity capture of biotinylated N-terminal peptides. After 12 hours of gentle agitation, NeutrAvidin agarose resin was pelleted and washed with 100 mM BICINE pH 8.0 and AEBSF (1 mM), 100 mM BICINE pH 8.0, 5 M NaCl, and again with a few washes of 100 mM BICINE pH 8.0. More stringent washes using either 1 M or 5 M guanidine hydrochloride were used in some cases. Captured peptides were released from NeutrAvidin agarose resin by treatment with TEV protease (1 µM) in 100 mM BICINE pH 8.0 and DTT (1 mM). Recovered peptides were concentrated and desalted using ZipTip$_{C18}$ pipette tips, or a $C_{18}$ Macrotrap (Michrom) trap column on a 2796 HPLC system (Waters). TEV protease was sometimes depleted from samples using an SCX Macrotrap (Michrom) trap column.

Example 9

Expression and Purification of Subtiligase

The expression construct for subtiligase was prepared using the *B. subtilis/E. coli* shuttle vector pBS42 (ATCC) (Wells et al., Nucleic Acids Res. 1983; 11(22):7911-25). The variant of subtiligase used corresponds to subtilisin BPN' containing point mutations S221C, P225A, M124L, and S125A for ligase activity (Abrahmsen et al., Biochemistry. 1991; 30(17):4151-9; Atwell et al., Proc Natl Acad Sci USA. 1999; 96(17):9497-502), and point mutations M50F, N76D, N109S, K213R, AND N218S for increased stability (Chang et al., Proc Natl Acad Sci USA. 1994; 91(26):12544-8). Recombinant subtiligase was prepared in *B. subtilis* strain 168 (ATCC). Subtiligase expression and purification was carried out essentially as described (Abrahmsen et al., Biochemistry. 1991; 30(17):4151-9). The purified enzyme was stored at −80° C. in 100 mM BICINE, pH 8.0 and 10 mM DTT or TCEP.

Example 12

Synthesis of Peptide Ester Substrates

Peptide glycolate ester substrates for subtiligase were prepared by solid-phase peptide synthesis using Fmoc chemistry as previously described (Braisted et al., Methods Enzymol. 1997; 289:298-313). Peptides were purified using 10×50 mm XTerra Prep MS $C_{18}$ ODB columns on a Parallex Flex HPLC system (Biotage). Purity and identity of peptides was verified by LC/MS analysis using a 4.6×50 mm XTerra MS $C_{18}$ column on a 2795 HPLC (Waters) system equipped with a ZQ quadrupole MS detector (Waters).

Example 13

Sample Fractionation Using Strong Cation Exchange (SCX) Chromatography

For larger scale experiments, samples were fractionated by SCX chromatography prior to LC/MS/MS analysis using a 2.1×200 mm PolySULFOETHYL Aspartamide column (The Nest Group) at a flow rate of 0.3 ml/min on a 2796 HPLC system (Waters). Buffer A consisted of 25 mM ammonium formate pH 2.8 and 30% acetonitrile, and buffer B consisted of 500 mM ammonium formate pH 2.8 and 30% acetonitrile. Approximately 25 fractions were collected during a 40 minute gradient block from 0% to 75% buffer B. Solvent from fractions was removed using an EZ-2 Plus evaporator (GeneVac), and remaining ammonium formate salt was removed by lyophilization. Some samples were also fractionated using a phosphate buffer and KCl salt system, in which case each fraction was subjected to automated desalting using a C is Microtrap (Michrom) trap column on a 2796 HPLC system (Waters) before solvent removal.

Example 14

Nano-LC-ESI-Qq-TOF MS/MS Analysis

Desalted fractionated or unfractionated samples were separated using a 75 µm×15 cm $C_{18}$ column (LC Packings) at a flow rate of 350 nl/min, with a 60 minute gradient of 3 to 30% acetonitrile in 0.1% formic acid, on a 1100 series HPLC system (Agilent). The LC eluent was coupled to a microion spray source attached to a QSTAR Pulsar or QSTAR XL mass spectrometer (Applied Biosystems). Peptides were analyzed in positive ion mode. MS spectra were acquired for 1 s. For each MS spectrum, either the single most intense or the two most intense multiply charged peaks were selected for generation of subsequent CID mass spectra, depending on the analysis method used. The CID collision energy was automatically adjusted based upon peptide charge and m/z ratio. A dynamic exclusion window was applied that prevented the same m/z from being selected for 3 min after its initial acquisition. Representative CID spectra are included as FIGS. 11-18. Additional CID figures will be made available upon request.

Example 15

Interpretation of MS/MS Spectra

Data were analyzed using Analyst QS software (version 1.1), and MS/MS centroid peak lists were generated using the Mascot.dll script (version 1.6b16). Data were searched against the Swiss-Prot human database (March 2008 release) using Protein Prospector 5.0 (University of California, San Francisco). Initial peptide tolerances in MS and MS/MS modes were 200 ppm and 300 ppm, respectively. The digest protease specified was trypsin, allowing for non-specific cleavage at N-termini in searches for N-terminally labeled semitryptic peptides, and trypsin allowing for non-specific cleavage at 0 N-termini in searches for unlabeled fully tryptic peptide contaminants. Two missed cleavages were typically allowed in searches. An N-terminal SY modification was specified as a fixed modification in searches for Nterminal peptides, but not in searches for unlabeled peptides. Cysteine carbamidomethylation was specified as a fixed modification and methionine oxidation was specified as a variable modification in all searches. High scoring peptide identifications from individual LC/MS/MS runs were then used to internally recalibrate MS parent ion m/z values within each run. Recalibrated data files were then searched again with an MS peptide tolerance of 100 ppm. Peptides with scores of greater than or equal to 22 and expectation values of less than or equal to 0.05 were considered positively identified. False positive rates for peptide identifications were estimated by conducting searches using a concatenated database containing the original Swiss-Prot human database, as well as a version of each original database entry where the sequence had been randomized. The overall false positive rate for N-terminal peptides identified was found to be 2.09%, while the false positive rate for peptides following aspartic acid in corresponding protein sequences was found to be 0.71%. A representative sampling of SY-labeled peptide identifications, particularly those based on expectation values near 0.05, was also manually validated.

Example 16

Immunoblotting and DNA Fragmentation Analysis

Jurkat cells at a density of 1×10$^6$ cells/ml were treated with etoposide (50 µM) for 0, 2, 4, 8, 12, and 24 hours prior to harvesting. Harvested cells were pelleted at 2,000×g and 25° C. for 5 minutes, washed twice with phosphate buffered saline, and lysed at a concentration of 2×10$^7$ cells/ml in 1.0% SDS, phosphate buffered saline, 100 µM Z-VAD-FMK, 100 µM E-64, 1 mM PMSF, 1 mM AEBSF, 5 mM EDTA, and 10 mM sodium butyrate. Whole cell lysates were sonicated to shear genomic DNA, normalized to a protein concentration of approximately 2 mg/ml, as determined by BCA assay (Pierce). Cell lysates for each apoptotic timepoint were then analyzed by SDS-PAGE and Western blot. Mouse monoclonal anti-caspase-3 (#9668) and rabbit polyclonal anti-HDAC3 (#2632) antibodies were purchased from Cell Signaling Technology. Mouse monoclonal anti-DFF45 (#611036) antibody was purchased from BD Transduction Laboratories. Goat polyclonal anti-N-Cor (#sc-1611) and rabbit polyclonal anti-HDAC7 (#sc-11412) antibodies were purchased from Santa Cruz Biotechnology. Rabbit polyclonal anti-TBLR1 (#A300-408A), rabbit polyclonal anti-SHARP (#A301-119A), and rabbit polyclonal anti-RBBP7 (#A300-959A) antibodies were purchased from Bethyl Laboratories. Rabbit polyclonal anti-SMRTe (#06-891) antibody was purchased from Millipore. Western blots were imaged using SuperSignal West Femto Substrate (Pierce) with a Fluor Chem SP imager (Alpha Innotech). DNA fragmentation of whole cell DNA was analyzed by agarose gel with the Apoptotic DNA Ladder Kit (Roche).

Example 17

Identification of protein N-termini in serum. Serum and plasma can be labeled by N-terminal protein biotinylation by a process similar to that described in Example 6. For example, two milliliters of human serum (NHS) supplemented with 100 mM BICINE pH 8.0, 1 mM EDTA, 1 mM PMSF, and 10% DMSO are labeled with 1 mM of biotinylated peptide ester using 1 µM subtiligase at room temperature for 15 to 120 minutes. Peptides corresponding to protein N termini of serum or plasma proteins are then recovered and identified as described in the Examples above. As a result of such an analysis, 79 nonredundant peptides can be identified in a single LC/MS/MS run, corresponding to 34 unique proteins. 68% of the peptides corresponded to annotated N termi resulting from signal cleavage or other known functional proteolytic processing. The 32% of N-terminal peptides with unknown origin indicate the potential of this technique to identify previously unknown posttranslational modifications in serum proteins. The abundances of identified proteins can span five orders of magnitude, from the processed N terminus of serum albumin (~20 mg/ml) to insulin-like growth factor II (~500 ng/ml). Low abundance serum proteins can be identified despite no effort being made to deplete highabundance proteins prior to analysis, illustrating the power of this labeling technique to partially neutralize dynamic range problems that confound serum proteomics. These results can be obtained without pre-fractionation of the labeled serum peptides. Significantly improved depth of coverage can be obtained with SCX fractionation.

TABLE 1

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | 2A5G_HUMAN | Q13362 | | 15 | 1 | Serine/threonine-protein phosphatase 2A 56 kDa regulatory subunit gamma isoform |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 1 | 3MG_HUMAN | P29372 | AAQAPAEQPHSSS DAAQAPCPR | 37 | 1 | DNA-3-methyladenine glycosylase |
|  | 41_HUMAN | P11171 |  | 551 | 1 | Protein 4.1 |
|  | 41_HUMAN | P11171 |  | 551 | 1 | Protein 4.1 |
|  | 4EBP1_HUMAN | Q13541 |  | 26 | 1 | Eukaryotic translation initiation factor 4E-binding protein 1 |
|  | 4EBP2_HUMAN | Q13542 |  | 27 | 1 | Eukaryotic translation initiation factor 4E-binding protein 2 |
|  | A26CA_HUMAN | Q6S8J3 |  | 945 | 10 | ANKRD26-like family C member 1A |
|  | A26CB_HUMAN | A5A3E0 |  | 945 |  | ANKRD26-like family C member 1B |
|  | ACTA_HUMAN | P62736 |  | 247 |  | Actin, aortic smooth muscle |
|  | ACTBL_HUMAN | Q562R1 |  | 246 |  | Beta-actin-like protein 2 |
|  | ACTB_HUMAN | P60709 |  | 245 |  | Actin, cytoplasmic 1 |
|  | ACTC_HUMAN | P68032 |  | 247 |  | Actin, alpha cardiac muscle 1 |
|  | ACTG_HUMAN | P63261 |  | 245 |  | Actin, cytoplasmic 2 |
|  | ACTH_HUMAN | P63267 |  | 246 |  | Actin, gamma-enteric smooth muscle |
|  | ACTK_HUMAN | Q9BYX7 |  | 245 |  | Kappa-actin |
|  | ACTS_HUMAN | P68133 |  | 247 |  | Actin, alpha skeletal muscle |
|  | A26CA_HUMAN | Q6S8J3 |  | 945 | 10 | ANKRD26-like family C member 1A |
|  | A26CB_HUMAN | A5A3E0 |  | 945 |  | ANKRD26-like family C member 1B |
|  | ACTA_HUMAN | P62736 |  | 247 |  | Actin, aortic smooth muscle |
|  | ACTBL_HUMAN | Q562 |  | 246 |  | Beta-actin-like protein 2 |
|  | ACTB_HUMAN | P60709 |  | 245 |  | Actin, cytoplasmic 1 |
|  | ACTC_HUMAN | P68032 |  | 247 |  | Actin, alpha cardiac muscle 1 |
|  | ACTG_HUMAN | P63261 |  | 245 |  | Actin, cytoplasmic 2 |
|  | ACTH_HUMAN | P63267 |  | 246 |  | Actin, gamma-enteric smooth muscle |
|  | ACTK_HUMAN | Q9BYX7 |  | 245 |  | Kappa-actin |
|  | ACTS_HUMAN | P68133 |  | 247 |  | Actin, alpha skeletal muscle |
|  | A26CA_HUMAN | Q6S8J3 |  | 923 | 3 | ANKRD26-like family C member 1A |
|  | ACTB_HUMAN | P60709 |  | 223 |  | Actin, cytoplasmic 1 |
|  | ACTG_HUMAN | P63261 |  | 223 |  | Actin, cytoplasmic 2 |
|  | AASD1_HUMAN | Q9BTE6 |  | 81 | 1 | Alanyl-tRNA synthetase domain-containing protein 1 |
|  | ABL1_HUMAN | P00519 |  | 940 | 1 | Proto-oncogene tyrosine-protein kinase ABL1 |
|  | ABLM1_HUMAN | O14639 |  | 568 | 1 | Actin-binding LIM protein 1 |
|  | ACAP3_HUMAN | Q96P50 |  | 589 | 1 | ArfGAP with coiled-coil, ANK repeat and PH domain-containing protein 3 |
|  | ACINU_HUMAN | Q9UKV3 |  | 664 | 1 | Apoptotic chromatin condensation inducer in the nucleus |
|  | ACINU_HUMAN | Q9UKV3 |  | 512 | 1 | Apoptotic chromatin condensation inducer in the nucleus |
|  | ACINU_HUMAN | Q9UKV3 |  | 69 | 1 | Apoptotic chromatin condensation inducer in the nucleus |
|  | ACINU_HUMAN | Q9UKV3 |  | 664 | 1 | Apoptotic chromatin condensation inducer in the nucleus |
|  | ACOC_HUMAN | P21399 |  | 674 | 1 | Cytoplasmic aconitate hydratase |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | ACSL3_HUMAN | O95573 | | 572 | 2 | Long-chain-fatty-acid--CoA ligase 3 |
| | ACSL4_HUMAN | O60488 | | 563 | | Long-chain-fatty-acid--CoA ligase 4 |
| | ACTA_HUMAN | P62736 | | 54 | 6 | Actin, aortic smooth muscle |
| | ACTB_HUMAN | P60709 | | 52 | | Actin, cytoplasmic 1 |
| | ACTC_HUMAN | P68032 | | 54 | | Actin, alpha cardiac muscle 1 |
| | ACTG_HUMAN | P63261 | | 52 | | Actin, cytoplasmic 2 |
| | ACTH_HUMAN | P63267 | | 53 | | Actin, gamma-enteric smooth muscle |
| | ACTS_HUMAN | P68133 | | 54 | | Actin, alpha skeletal muscle |
| | ACTA_HUMAN | P62736 | | 54 | 6 | Actin, aortic smooth muscle |
| | ACTB_HUMAN | P60709 | | 52 | | Actin, cytoplasmic 1 |
| | ACTC_HUMAN | P68032 | | 54 | | Actin, alpha cardiac muscle 1 |
| | ACTG_HUMAN | P63261 | | 52 | | Actin, cytoplasmic 2 |
| | ACTH_HUMAN | P63267 | | 53 | | Actin, gamma-enteric smooth muscle |
| | ACTS_HUMAN | P68133 | | 54 | | Actin, alpha skeletal muscle |
| | ACTB_HUMAN | P60709 | | 155 | 2 | Actin, cytoplasmic 1 |
| | ACTG_HUMAN | P63261 | | 155 | | Actin, cytoplasmic 2 |
| | ACTB_HUMAN | P60709 | | 158 | 2 | Actin, cytoplasmic 1 |
| | ACTG_HUMAN | P63261 | | 158 | | Actin, cytoplasmic 2 |
| | ACTN1_HUMAN | P12814 | | 6 | 1 | Alpha-actinin-1 |
| | ACTN1_HUMAN | P12814 | | 6 | 1 | Alpha-actinin-1 |
| | ACTN1_HUMAN | P12814 | | 23 | 4 | Alpha-actinin-1 |
| | ACTN2_HUMAN | P35609 | | 30 | | Alpha-actinin-2 |
| | ACTN3_HUMAN | Q08043 | | 37 | | Alpha-actinin-3 |
| | ACTN4_HUMAN | O43707 | | 42 | | Alpha-actinin-4 |
| | ADDA_HUMAN | P35611 | | 634 | 1 | Alpha-adducin |
| | AEBP2_HUMAN | Q6ZN18 | | 234 | 1 | Zinc finger protein AEBP2 |
| | AEDO_HUMAN | Q96SZ5 | | 35 | 1 | 2-aminoethanethiol dioxygenase |
| | AF1L2_HUMAN | Q8N4X5 | | 631 | 1 | Actin filament-associated protein 1-like 2 |
| | AF1L2_HUMAN | Q8N4X5 | | 631 | 1 | Actin filament-associated protein 1-like 2 |
| | AF1L2_HUMAN | Q8N4X5 | | 313 | 1 | Actin filament-associated protein 1-like 2 |
| | AFTIN_HUMAN | Q6ULP2 | | 340 | 1 | Aftiphilin |
| | AGGF1_HUMAN | Q8N302 | | 149 | 1 | Angiogenic factor with G patch and FHA domains 1 |
| | AGGF1_HUMAN | Q8N302 | | 149 | 1 | Angiogenic factor with G patch and FHA domains 1 |
| | AGGF1_HUMAN | Q8N302 | | 149 | 1 | Angiogenic factor with G patch and FHA domains 1 |
| | AHNK_HUMAN | Q09666 | | 3719 | 1 | Neuroblast differentiation-associated protein AHNAK |
| | AHNK_HUMAN | Q09666 | | 1425 | 1 | Neuroblast differentiation-associated protein AHNAK |
| | AHNK_HUMAN | Q09666 | | 2712 | 1 | Neuroblast differentiation-associated protein AHNAK |
| | AHNK_HUMAN | Q09666 | | 3719 | 1 | Neuroblast differentiation-associated protein AHNAK |
| | AHNK_HUMAN | Q09666 | | 5581 | 1 | Neuroblast differentiation-associated protein AHNAK |
| | AHNK_HUMAN | Q09666 | | 576 | 1 | Neuroblast differentiation-associated protein AHNAK |
| | AHNK_HUMAN | Q09666 | | 3494 | 1 | Neuroblast differentiation-associated protein AHNAK |
| | AHNK_HUMAN | Q09666 | | 738 | 1 | Neuroblast differentiation-associated protein AHNAK |
| | AHNK_HUMAN | Q09666 | | 866 | 1 | Neuroblast differentiation-associated protein AHNAK |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | AHNK_HUMAN | Q09666 | | 1584 | 1 | Neuroblast differentiation-associated protein AHNAK |
| | AHNK_HUMAN | Q09666 | | 740 | 1 | Neuroblast differentiation-associated protein AHNAK |
| | AHNK_HUMAN | Q09666 | | 3465 | 1 | Neuroblast differentiation-associated protein AHNAK |
| | AHNK_HUMAN | Q09666 | | 920 | 1 | Neuroblast differentiation-associated protein AHNAK |
| | AHNK_HUMAN | Q09666 | | 2883 | 1 | Neuroblast differentiation-associated protein AHNAK |
| | AHNK_HUMAN | Q09666 | | 4359 | 1 | Neuroblast differentiation-associated protein AHNAK |
| | AHNK_HUMAN | Q09666 | | 1169 | 1 | Neuroblast differentiation-associated protein AHNAK |
| | AHSA1_HUMAN | O95433 | | 255 | 1 | Activator of 90 kDa heat shock protein ATPase homolog 1 |
| | AHSA1_HUMAN | O95433 | | 255 | 1 | Activator of 90 kDa heat shock protein ATPase homolog 1 |
| | AHSA1_HUMAN | O95433 | | 19 | 1 | Activator of 90 kDa heat shock protein ATPase homolog 1 |
| | AHTF1_HUMAN | Q8WYP5 | | 1368 | 1 | AT-hook-containing transcription factor 1 |
| | AIM1_HUMAN | Q9Y4K1 | | 68 | 1 | Absent in melanoma 1 protein |
| | AIM1_HUMAN | Q9Y4K1 | | 68 | 1 | Absent in melanoma 1 protein |
| | AKA12_HUMAN | Q02952 | | 452 | 1 | A-kinase anchor protein 12 |
| | AKAP2_HUMAN | Q9Y2D5 | | 473 | 1 | A-kinase anchor protein 2 |
| | AKAP9_HUMAN | Q99996 | | 1034 | 1 | A-kinase anchor protein 9 |
| | AKAP9_HUMAN | Q99996 | | 1034 | 1 | A-kinase anchor protein 9 |
| | AKNA_HUMAN | Q7Z591 | | 800 | 1 | AT-hook-containing transcription factor |
| | AKP13_HUMAN | Q12802 | | 545 | 1 | A-kinase anchor protein 13 |
| | AKP13_HUMAN | Q12802 | | 545 | 1 | A-kinase anchor protein 13 |
| | AKP13_HUMAN | Q12802 | | 830 | 1 | A-kinase anchor protein 13 |
| | AKP13_HUMAN | Q12802 | | 906 | 1 | A-kinase anchor protein 13 |
| | AKP13_HUMAN | Q12802 | | 1056 | 1 | A-kinase anchor protein 13 |
| | AKP13_HUMAN | Q12802 | | 1540 | 1 | A-kinase anchor protein 13 |
| | AKP8L_HUMAN | Q9ULX6 | | 109 | 1 | A-kinase anchor protein 8-like |
| | ALMS1_HUMAN | Q8TCU4 | | 428 | 1 | Alstrom syndrome protein 1 |
| | ALMS1_HUMAN | Q8TCU4 | | 780 | 1 | Alstrom syndrome protein 1 |
| | ALMS1_HUMAN | Q8TCU4 | | 591 | 1 | Alstrom syndrome protein 1 |
| 2 | ALO17_HUMAN | Q9HCF4 | AVAEPANAVK | 274 | 1 | Protein ALO17 |
| 3 | ALO17_HUMAN | Q9HCF4 | AVAEPANAVKGAGK | 274 | 1 | Protein ALO17 |
| 4 | ALO17_HUMAN | Q9HCF4 | AVAEPANAVKGAGKEMK | 274 | 1 | Protein ALO17 |
| | AMPD3_HUMAN | Q01432 | | 37 | 1 | AMP deaminase 3 |
| | AMPM1_HUMAN | P53582 | | 13 | 1 | Methionine aminopeptidase 1 |
| | ANKH1_HUMAN | Q8IWZ3 | | 1049 | 1 | Ankyrin repeat and KH domain-containing protein 1 |
| | ANKH1_HUMAN | Q8IWZ3 | | 5 | 1 | Ankyrin repeat and KH domain-containing protein 1 |
| | ANKS6_HUMAN | Q68DC2 | | 276 | 1 | Ankyrin repeat and SAM domain-containing protein 6 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | ANS1A_HUMAN | Q92625 | | 530 | 1 | Ankyrin repeat and SAM domain-containing protein 1A |
| | ANXA2_HUMAN | P07355 | | 17 | 2 | Annexin A2 |
| | AXA2L_HUMAN | A6NMY6 | | 17 | | Putative annexin A2-like protein |
| | AP1G1_HUMAN | O43747 | | 690 | 1 | AP-1 complex subunit gamma-1 |
| | AP1G2_HUMAN | O75843 | | 632 | 1 | AP-1 complex subunit gamma-like 2 |
| | AP2A2_HUMAN | O94973 | | 691 | 1 | AP-2 complex subunit alpha-2 |
| | AP3B2_HUMAN | Q13367 | | 844 | 1 | AP-3 complex subunit beta-2 |
| | AP3B2_HUMAN | Q13367 | | 844 | 1 | AP-3 complex subunit beta-2 |
| | APBB2_HUMAN | Q92870 | | 280 | 1 | Amyloid beta A4 precursor protein-binding family B member 2 |
| | APC_HUMAN | P25054 | | 1499 | 1 | Adenomatous polyposis coli protein |
| | APMAP_HUMAN | Q9HDC9 | | 23 | 1 | Adipocyte plasma membrane-associated protein |
| | APTX_HUMAN | Q7Z2E3 | | 142 | 1 | Aprataxin |
| | AR13B_HUMAN | Q3SXY8 | | 242 | 1 | ADP-ribosylation factor-like protein 13B |
| | ARBK1_HUMAN | P25098 | | 528 | 1 | Beta-adrenergic receptor kinase 1 |
| | ARBK1_HUMAN | P25098 | | 482 | 2 | Beta-adrenergic receptor kinase 1 |
| | ARBK2_HUMAN | P35626 | | 482 | | Beta-adrenergic receptor kinase 2 |
| | ARBK1_HUMAN | P25098 | | 482 | 2 | Beta-adrenergic receptor kinase 1 |
| | ARBK2_HUMAN | P35626 | | 482 | | Beta-adrenergic receptor kinase 2 |
| | ARHG1_HUMAN | Q92888 | | 293 | 1 | Rho guanine nucleotide exchange factor 1 |
| | ARHG2_HUMAN | Q92974 | | 627 | 1 | Rho guanine nucleotide exchange factor 2 |
| | ARHGA_HUMAN | O15013 | | 1247 | 1 | Rho guanine nucleotide exchange factor 10 |
| | ARI1A_HUMAN | O14497 | | 607 | 1 | AT-rich interactive domain-containing protein 1A |
| | ARI1A_HUMAN | O14497 | | 607 | 1 | AT-rich interactive domain-containing protein 1A |
| | ARI1A_HUMAN | O14497 | | 76 | 1 | AT-rich interactive domain-containing protein 1A |
| | ARI4A_HUMAN | P29374 | | 1031 | 1 | AT-rich interactive domain-containing protein 4A |
| | ARI4B_HUMAN | Q4LE39 | | 1073 | 1 | AT-rich interactive domain-containing protein 4B |
| | ARID2_HUMAN | Q68CP9 | | 626 | 1 | AT-rich interactive domain-containing protein 2 |
| | ARID2_HUMAN | Q68CP9 | | 630 | 1 | AT-rich interactive domain-containing protein 2 |
| | ARM10_HUMAN | Q8N2F6 | | 87 | 1 | Armadillo repeat-containing protein 10 |
| | ARMC6_HUMAN | Q6NXE6 | | 83 | 1 | Armadillo repeat-containing protein 6 |
| | ARMC6_HUMAN | Q6NXE6 | | 83 | 1 | Armadillo repeat-containing protein 6 |
| | ARNT_HUMAN | P27540 | | 152 | 1 | Aryl hydrocarbon receptor nuclear translocator |
| | ARP21_HUMAN | Q9UBL0 | | 495 | 1 | cAMP-regulated phosphoprotein 21 |
| | ARP2_HUMAN | P61160 | | 162 | 1 | Actin-related protein 2 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | ARP3_HUMAN | P61158 | | 60 | 1 | Actin-related protein 3 |
| | ARPC5_HUMAN | O15511 | | 30 | 1 | Actin-related protein 2/3 complex subunit 5 |
| | ARPC5_HUMAN | O15511 | | 33 | 1 | Actin-related protein 2/3 complex subunit 5 |
| | ARS2_HUMAN | Q9BXP5 | | 162 | 1 | Arsenite-resistance protein 2 |
| | ASB13_HUMAN | Q8WXK3 | | 52 | 1 | Ankyrin repeat and SOCS box protein 13 |
| | ASCC1_HUMAN | Q8N9N2 | | 35 | 1 | Activating signal cointegrator 1 complex subunit 1 |
| | ASCC2_HUMAN | Q9H1I8 | | 622 | 1 | Activating signal cointegrator 1 complex subunit 2 |
| | ASHWN_HUMAN | Q9BVC5 | | 106 | 1 | Ashwin |
| | ASPP2_HUMAN | Q13625 | | 528 | 1 | Apoptosis-stimulating of p53 protein 2 |
| | ATAD5_HUMAN | Q96QE3 | | 285 | 1 | ATPase family AAA domain-containing protein 5 |
| | ATD2B_HUMAN | Q9ULI0 | | 78 | 1 | ATPase family AAA domain-containing protein 2B |
| | ATF1_HUMAN | P18846 | | 47 | 1 | Cyclic AMP-dependent transcription factor ATF-1 |
| 5 | ATF4_HUMAN | P18848 | GLVSPSNNSKEDAFSGTDWMLEK | 66 | 1 | Cyclic AMP-dependent transcription factor ATF-4 |
| | ATF7_HUMAN | P17544 | | 44 | 1 | Cyclic AMP-dependent transcription factor ATF-7 |
| | ATF7_HUMAN | P17544 | | 44 | 1 | Cyclic AMP-dependent transcription factor ATF-7 |
| | ATG3_HUMAN | Q9NT62 | | 105 | 1 | Autophagy-related protein 3 |
| | ATG3_HUMAN | Q9NT62 | | 105 | 1 | Autophagy-related protein 3 |
| | ATG4B_HUMAN | Q9Y4P1 | | 3 | 1 | Cysteine protease ATG4B |
| | ATRX_HUMAN | P46100 | | 920 | 1 | Transcriptional regulator ATRX |
| | ATX1L_HUMAN | P0C7T5 | | 309 | 1 | Ataxin-1-like |
| | ATX2L_HUMAN | Q8WWM7 | | 585 | 1 | Ataxin-2-like protein |
| | ATX2L_HUMAN | Q8WWM7 | | 585 | 1 | Ataxin-2-like protein |
| | ATX2_HUMAN | Q99700 | | 843 | 1 | Ataxin-2 |
| 6 | ATX3_HUMAN | P54252 | GSGMLDEDEEDLQR | 218 | 1 | Ataxin-3 |
| | AZI1_HUMAN | Q9UPN4 | | 549 | 1 | 5-azacytidine-induced protein 1 |
| | BA2D1_HUMAN | Q9Y520 | | 889 | 1 | BAT2 domain-containing protein 1 |
| | BA2D1_HUMAN | Q9Y520 | | 2190 | 1 | BAT2 domain-containing protein 1 |
| | BAP1_HUMAN | Q92560 | | 312 | 1 | Ubiquitin carboxyl-terminal hydrolase BAP1 |
| | BAP31_HUMAN | P51572 | | 165 | 1 | B-cell receptor-associated protein 31 |
| | BAP31_HUMAN | P51572 | | 165 | 1 | B-cell receptor-associated protein 31 |
| | BASP_HUMAN | P80723 | | 166 | 1 | Brain acid soluble protein 1 |
| | BASP_HUMAN | P80723 | | 172 | 1 | Brain acid soluble protein 1 |
| | BAT3_HUMAN | P46379 | | 1002 | 1 | Large proline-rich protein BAT3 |
| | BAT3_HUMAN | P46379 | | 1002 | 1 | Large proline-rich protein BAT3 |
| | BAZ1A_HUMAN | Q9NRL2 | | 500 | 1 | Bromodomain adjacent to zinc finger domain protein 1A |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 7 | BCAP_HUMAN | Q6ZUJ8 | SVTDTEPEDEK | 149 | 1 | Phosphoinositide 3-kinase adapter protein 1 |
| 8 | BCAP_HUMAN | Q6ZUJ8 | SVTDTEPEDEKVVSYSK | 149 | 1 | Phosphoinositide 3-kinase adapter protein 1 |
|  | BCLF1_HUMAN | Q9NYF8 |  | 325 | 1 | Bcl-2-associated transcription factor 1 |
|  | BCLF1_HUMAN | Q9NYF8 |  | 383 | 1 | Bcl-2-associated transcription factor 1 |
|  | BCR_HUMAN | P11274 |  | 244 | 1 | Breakpoint cluster region protein |
|  | BDP1_HUMAN | A6H8Y1 |  | 526 | 1 | Transcription factor TFIIIB component B" homolog |
|  | BID_HUMAN | P55957 |  | 76 | 1 | BH3-interacting domain death agonist |
|  | BIG3_HUMAN | Q5TH69 |  | 293 | 1 | Brefeldin A-inhibited guanine nucleotide-exchange protein 3 |
|  | BIN1_HUMAN | O00499 |  | 302 | 1 | Myc box-dependent-interacting protein 1 |
|  | BIRC6_HUMAN | Q9NR09 |  | 462 | 1 | Baculoviral IAP repeat-containing protein 6 |
|  | BL1S3_HUMAN | Q6QNY0 |  | 65 | 1 | Biogenesis of lysosome-related organelles complex 1 subunit 3 |
| 9 | BLNK_HUMAN | Q8WV28 | YVVPVEDNDENYIHPTESSSPPPEK | 178 | 1 | B-cell linker protein |
|  | BNIP2_HUMAN | Q12982 |  | 84 | 1 | BCL2/adenovirus E1B 19 kDa protein-interacting protein 2 |
|  | BPTF_HUMAN | Q12830 |  | 1626 | 1 | Nucleosome-remodeling factor subunit BPTF |
|  | BRD1_HUMAN | O95696 |  | 922 | 1 | Bromodomain-containing protein 1 |
|  | BRD4_HUMAN | O60885 |  | 338 | 1 | Bromodomain-containing protein 4 |
|  | BRD8_HUMAN | Q9H0E9 |  | 561 | 1 | Bromodomain-containing protein 8 |
|  | BTB14_HUMAN | Q96RE7 |  | 175 | 1 | BTB/POZ domain-containing protein 14B |
|  | BUB1_HUMAN | O43683 |  | 396 | 1 | Mitotic checkpoint serine/threonine-protein kinase BUB1 |
|  | BUB1_HUMAN | O43683 |  | 396 | 1 | Mitotic checkpoint serine/threonine-protein kinase BUB1 |
|  | BUD13_HUMAN | Q9BRD0 |  | 274 | 1 | BUD13 homolog |
|  | C170L_HUMAN | Q96L14 |  | 51 | 1 | Cep170-like protein |
|  | C1QBP_HUMAN | Q07021 |  | 186 | 1 | Complement component 1 Q sub component-binding protein, mitochondrial |
|  | C2C2L_HUMAN | O14523 |  | 443 | 1 | C2 domain-containing protein 2-like |
|  | C2D1A_HUMAN | Q6P1N0 |  | 31 | 1 | Coiled-coil and C2 domain-containing protein 1A |
|  | C2D1A_HUMAN | Q6P1N0 |  | 31 | 1 | Coiled-coil and C2 domain-containing protein 1A |
|  | C2D1B_HUMAN | Q5T0F9 |  | 461 | 1 | Coiled-coil and C2 domain-containing protein 1B |
|  | CA059_HUMAN | Q5T8I9 |  | 14 | 1 | UPF0486 protein C1orf59 |
|  | CA059_HUMAN | Q5T8I9 |  | 14 | 1 | UPF0486 protein C1orf59 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | CA103_HUMAN | Q5T3J3 | | 516 | 1 | Uncharacterized protein C1orf103 |
| | CA103_HUMAN | Q5T3J3 | | 516 | 1 | Uncharacterized protein C1orf103 |
| | CA163_HUMAN | Q96BR5 | | 121 | 1 | Hcp beta-lactamase-like protein C1orf163 |
| | CA165_HUMAN | Q7L4P6 | | 104 | 1 | Coiled-coil domain-containing protein C1orf165 |
| | CA170_HUMAN | Q5SV97 | | 43 | 1 | Uncharacterized protein C1orf170 |
| | CA175_HUMAN | Q68CQ1 | | 412 | 1 | Uncharacterized protein C1orf175 |
| | CA1L1_HUMAN | Q08AD1 | | 422 | 1 | Calmodulin-regulated spectrin-associated protein 1-like protein 1 |
| | CABL2_HUMAN | Q9BTV7 | | 59 | 1 | CDK5 and ABL1 enzyme substrate 2 |
| | CACO1_HUMAN | Q9P1Z2 | | 135 | 1 | Calcium-binding and coiled-coil domain-containing protein 1 |
| | CADH2_HUMAN | P19022 | | 800 | 1 | Cadherin-2 |
| | CADH2_HUMAN | P19022 | | 800 | 1 | Cadherin-2 |
| | CAF1A_HUMAN | Q13111 | | 615 | 1 | Chromatin assembly factor 1 subunit A |
| | CAF1A_HUMAN | Q13111 | | 111 | 1 | Chromatin assembly factor 1 subunit A |
| | CAF1A_HUMAN | Q13111 | | 111 | 1 | Chromatin assembly factor 1 subunit A |
| | CALR_HUMAN | P27797 | | 259 | 1 | Calreticulin |
| | CALR_HUMAN | P27797 | | 329 | 1 | Calreticulin |
| 10 | CALR_HUMAN | P27797 | MHGDSEYNIMFGPDICGPGTK | 122 | 1 | Calreticulin |
| | CAMKV_HUMAN | Q8NCB2 | | 408 | 1 | CaM kinase-like vesicle-associated protein |
| | CAMLG_HUMAN | P49069 | | 10 | 1 | Calcium signal-modulating cyclophilin ligand |
| | CAMLG_HUMAN | P49069 | | 10 | 1 | Calcium signal-modulating cyclophilin ligand |
| | CAMLG_HUMAN | P49069 | | 116 | 1 | Calcium signal-modulating cyclophilin ligand |
| | CAMP1_HUMAN | Q5T5Y3 | | 752 | 1 | Calmodulin-regulated spectrin-associated protein 1 |
| | CAMP1_HUMAN | Q5T5Y3 | | 1255 | 1 | Calmodulin-regulated spectrin-associated protein 1 |
| | CAMP1_HUMAN | Q5T5Y3 | | 1255 | 1 | Calmodulin-regulated spectrin-associated protein 1 |
| | CAPR1_HUMAN | Q14444 | | 95 | 1 | Caprin-1 |
| | CAPZB_HUMAN | P47756 | | 150 | 1 | F-actin-capping protein subunit beta |
| | CASC3_HUMAN | O15234 | | 390 | 1 | Protein CASC3 |
| | CASC5_HUMAN | Q8NG31 | | 1195 | 1 | Protein CASC5 |
| | CASP3_HUMAN | P42574 | | 29 | 1 | Caspase-3 |
| | CASP3_HUMAN | P42574 | | 176 | 1 | Caspase-3 |
| | CASP3_HUMAN | P42574 | | 176 | 1 | Caspase-3 |
| | CASP7_HUMAN | P55210 | | 199 | 1 | Caspase-7 |
| | CASP_HUMAN | Q13948 | | 388 | 2 | Protein CASP |
| | CUX1_HUMAN | P39880 | | 377 | | Homeobox protein cut-like 1 |
| | CATB_HUMAN | P07858 | | 78 | 1 | Cathepsin B |
| | CB044_HUMAN | Q9H6R7 | | 509 | 1 | WD repeat-containing protein C2orf44 |
| | CBL_HUMAN | P22681 | | 807 | 1 | E3 ubiquitin-protein ligase CBL |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | CBWD1_HUMAN | Q9BRT8 | | 185 | 6 | COBW domain-containing protein 1 |
| | CBWD2_HUMAN | Q8IUF1 | | 185 | | COBW domain-containing protein 2 |
| | CBWD3_HUMAN | Q5JTY5 | | 185 | | COBW domain-containing protein 3 |
| | CBWD5_HUMAN | Q5RIA9 | | 185 | | COBW domain-containing protein 5 |
| | CBWD6_HUMAN | Q4V339 | | 185 | | COBW domain-containing protein 6 |
| | CBWD7_HUMAN | A6NM15 | | 37 | | COBW domain-containing protein 7 |
| | CC104_HUMAN | Q96G28 | | 142 | 1 | Coiled-coil domain-containing protein 104 |
| 11 | CC104_HUMAN | Q96G28 | GSDVVSDLEHEEMK | 142 | 1 | Coiled-coil domain-containing protein 104 |
| | CC104_HUMAN | Q96G28 | | 145 | 1 | Coiled-coil domain-containing protein 104 |
| | CC104_HUMAN | Q96G28 | | 145 | 1 | Coiled-coil domain-containing protein 104 |
| | CC124_HUMAN | Q96CT7 | | 150 | 1 | Coiled-coil domain-containing protein 124 |
| | CC131_HUMAN | O60293 | | 336 | 1 | Coiled-coil domain-containing protein 131 |
| 12 | CC50A_HUMAN | Q9NV96 | GGPPCAPGGTAK | 13 | 1 | Cell cycle control protein 50A |
| | CCD43_HUMAN | Q96MW1 | | 17 | 1 | Coiled-coil domain-containing protein 43 |
| | CCD53_HUMAN | Q9Y3C0 | | 5 | 1 | Coiled-coil domain-containing protein 53 |
| | CCD91_HUMAN | Q7Z6B0 | | 100 | 1 | Coiled-coil domain-containing protein 91 |
| | CCD97_HUMAN | Q96F63 | | 53 | 1 | Coiled-coil domain-containing protein 97 |
| | CCDC9_HUMAN | Q9Y3X0 | | 300 | 1 | Coiled-coil domain-containing protein 9 |
| | CCDC9_HUMAN | Q9Y3X0 | | 300 | 1 | Coiled-coil domain-containing protein 9 |
| | CCNT2_HUMAN | O60583 | | 455 | 1 | Cyclin-T2 |
| | CCNT2_HUMAN | O60583 | | 455 | 1 | Cyclin-T2 |
| | CD2L1_HUMAN | P21127 | | 406 | 1 | PITSLRE serine/threonine-protein kinase CDC2L1 |
| | CD2L1_HUMAN | P21127 | | 406 | 1 | PITSLRE serine/threonine-protein kinase CDC2L1 |
| | CD2L5_HUMAN | Q14004 | | 1354 | 1 | Cell division cycle 2-like protein kinase 5 |
| | CDC27_HUMAN | P30260 | | 237 | 1 | Cell division cycle protein 27 homolog |
| | CDC27_HUMAN | P30260 | | 244 | 1 | Cell division cycle protein 27 homolog |
| | CDC5L_HUMAN | Q99459 | | 392 | 1 | Cell division cycle 5-like protein |
| | CDCA7_HUMAN | Q9BWT1 | | 40 | 1 | Cell division cycle-associated protein 7 |
| | CDV3_HUMAN | Q9UKY7 | | 123 | 1 | Protein CDV3 homolog |
| 13 | CDYL1_HUMAN | Q9Y232 | GFQSESPEKLDPVEQGQEDTVAPEVAAEKPVGALLGPGAER | 211 | 1 | Chromodomain Y-like protein |
| | CE022_HUMAN | Q49AR2 | | 197 | 1 | UPF0489 protein C5orf22 |
| | CE152_HUMAN | O94986 | | 63 | 1 | Centrosomal protein of 152 kDa |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | CE170_HUMAN | Q5SW79 | | 1325 | 1 | Centrosomal protein of 170 kDa |
| | CE170_HUMAN | Q5SW79 | | 1325 | 1 | Centrosomal protein of 170 kDa |
| | CE170_HUMAN | Q5SW79 | | 937 | 1 | Centrosomal protein of 170 kDa |
| | CEBPZ_HUMAN | Q03701 | | 918 | 1 | CCAAT/enhancer-binding protein zeta |
| | CEBPZ_HUMAN | Q03701 | | 775 | 1 | CCAAT/enhancer-binding protein zeta |
| | CEBPZ_HUMAN | Q03701 | | 956 | 1 | CCAAT/enhancer-binding protein zeta |
| | CH041_HUMAN | Q6NXR4 | | 5 | 1 | Uncharacterized protein C8orf41 |
| | CH082_HUMAN | Q6P1X6 | | 26 | 1 | UPF0598 protein C8orf82 |
| | CH60_HUMAN | P10809 | | 505 | 1 | 60 kDa heat shock protein, mitochondrial |
| | CH60_HUMAN | P10809 | | 112 | 1 | 60 kDa heat shock protein, mitochondrial |
| | CH60_HUMAN | P10809 | | 453 | 1 | 60 kDa heat shock protein, mitochondrial |
| | CH60_HUMAN | P10809 | | 453 | 1 | 60 kDa heat shock protein, mitochondrial |
| | CHD3_HUMAN | Q12873 | | 373 | 3 | Chromodomain-helicase-DNA-binding protein 3 |
| | CHD4_HUMAN | Q14839 | | 364 | | Chromodomain-helicase-DNA-binding protein 4 |
| | CHD5_HUMAN | Q8TDI0 | | 337 | | Chromodomain-helicase-DNA-binding protein 5 |
| 14 | CHD4_HUMAN | Q14839 | GGGDNKEGEDSSVIHYDDK | 1234 | 1 | Chromodomain-helicase-DNA-binding protein 4 |
| 15 | CHD4_HUMAN | Q14839 | GGGDNKEGEDSSVIHYDDKAIER | 1234 | 1 | Chromodomain-helicase-DNA-binding protein 4 |
| 16 | CHD7_HUMAN | Q9P2D1 | GFYMEDGDPSVAQLLHER | 2286 | 1 | Chromodomain-helicase-DNA-binding protein 7 |
| 17 | CHM4B_HUMAN | Q9H444 | GTLSTIEFQR | 84 | 3 | Charged multivesicular body protein 4b |
| 17 | CHM4C_HUMAN | Q96CF2 | GTLSTIEFQR | 84 | | Charged multivesicular body protein 4c |
| | CI080_HUMAN | Q9NRY2 | | 58 | 1 | Uncharacterized protein C9orf80 |
| | CJ018_HUMAN | Q5VWN6 | | 1208 | 1 | Uncharacterized protein C10orf18 |
| | CJ047_HUMAN | Q86WR7 | | 110 | 1 | Uncharacterized protein C10orf47 |
| | CK059_HUMAN | Q6IAA8 | | 73 | 1 | UPF0404 protein C11orf59 |
| | CK059_HUMAN | Q6IAA8 | | 73 | 1 | UPF0404 protein C11orf59 |
| | CL035_HUMAN | Q9HCM1 | | 360 | 1 | Uncharacterized protein C12orf35 |
| | CL035_HUMAN | Q9HCM1 | | 502 | 1 | Uncharacterized protein C12orf35 |
| | CL043_HUMAN | Q96C57 | | 73 | 1 | Uncharacterized protein C12orf43 |
| | CL043_HUMAN | Q96C57 | | 205 | 1 | Uncharacterized protein C12orf43 |
| | CL043_HUMAN | Q96C57 | | 205 | 1 | Uncharacterized protein C12orf43 |
| | CL043_HUMAN | Q96C57 | | 205 | 1 | Uncharacterized protein C12orf43 |
| | CLAP1_HUMAN | Q7Z460 | | 1219 | 1 | CLIP-associating protein 1 |
| | CLAP1_HUMAN | Q7Z460 | | 1219 | 1 | CLIP-associating protein 1 |
| | CLCA_HUMAN | P09496 | | 77 | 1 | Clathrin light chain A |
| | CLCA_HUMAN | P09496 | | 77 | 1 | Clathrin light chain A |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | CLCA_HUMAN | P09496 | | 93 | 1 | Clathrin light chain A |
| | CLIC1_HUMAN | O00299 | | 142 | 1 | Chloride intracellular channel protein 1 |
| | CLIP1_HUMAN | P30622 | | 398 | 1 | CAP-Gly domain-containing linker protein 1 |
| | CLSPN_HUMAN | Q9HAW4 | | 564 | 1 | Claspin |
| | CND2_HUMAN | Q15003 | | 200 | 1 | Condensin complex subunit 2 |
| 18 | CND2_HUMAN | Q15003 | GSLGDDFDANDEPDHTAVGDHEEFR | 367 | 1 | Condensin complex subunit 2 |
| | CND2_HUMAN | Q15003 | | 381 | 1 | Condensin complex subunit 2 |
| | CND2_HUMAN | Q15003 | | 171 | 1 | Condensin complex subunit 2 |
| | CND2_HUMAN | Q15003 | | 200 | 1 | Condensin complex subunit 2 |
| | CNDH2_HUMAN | Q6IBW4 | | 460 | 1 | Condensin-2 complex subunit H2 |
| | CO6A3_HUMAN | P12111 | | 2616 | 1 | Collagen alpha-3(VI) chain |
| | COBL1_HUMAN | Q53SF7 | | 984 | 1 | Cordon-bleu protein-like 1 |
| 19 | COPA_HUMAN | P53621 | GFVEATEGLGDDALGK | 857 | 1 | Coatomer subunit alpha |
| 20 | COPA_HUMAN | P53621 | LFGTTDAVVK | 189 | 1 | Coatomer subunit alpha |
| | COPB2_HUMAN | P35606 | | 855 | 1 | Coatomer subunit beta' |
| | COR1A_HUMAN | P31146 | | 395 | 2 | Coronin-1A |
| | CP088_HUMAN | Q1ED39 | | 183 | 1 | Protein C16orf88 |
| | CP110_HUMAN | Q7Z7A1 | | 1396 | 1 | Centriolin |
| | CP110_HUMAN | Q7Z7A1 | | 802 | 1 | Centriolin |
| | CPIN1_HUMAN | Q6FI81 | | 215 | 1 | Anamorsin |
| | CPNE1_HUMAN | Q99829 | | 465 | 1 | Copine-1 |
| | CPNE3_HUMAN | O75131 | | 429 | 1 | Copine-3 |
| | CPSF6_HUMAN | Q16630 | | 55 | 1 | Cleavage and polyadenylation specificity factor subunit 6 |
| | CPSF7_HUMAN | Q8N684 | | 325 | 1 | Cleavage and polyadenylation specificity factor subunit 7 |
| | CPSF7_HUMAN | Q8N684 | | 30 | 1 | Cleavage and polyadenylation specificity factor subunit 7 |
| | CPSF7_HUMAN | Q8N684 | | 34 | 1 | Cleavage and polyadenylation specificity factor subunit 7 |
| | CPZIP_HUMAN | Q6JBY9 | | 273 | 1 | Capz-interacting protein |
| | CQ056_HUMAN | Q96N21 | | 381 | 1 | Uncharacterized protein C17orf56 |
| | CQ085_HUMAN | Q53F19 | | 158 | 1 | Uncharacterized protein C17orf85 |
| | CQ085_HUMAN | Q53F19 | | 232 | 1 | Uncharacterized protein C17orf85 |
| | CR025_HUMAN | Q96B23 | | 45 | 1 | Uncharacterized protein C18orf25 |
| | CR025_HUMAN | Q96B23 | | 45 | 1 | Uncharacterized protein C18orf25 |
| | CR025_HUMAN | Q96B23 | | 45 | 1 | Uncharacterized protein C18orf25 |
| 21 | CR025_HUMAN | Q96B23 | GVADSTVISSMPCLLMELR | 45 | 1 | Uncharacterized protein C18orf25 |
| 22 | CR025_HUMAN | Q96B23 | GVADSTVISSMPCLLMELRR | 45 | 1 | Uncharacterized protein C18orf25 |
| | CREB1_HUMAN | P16220 | | 230 | 1 | cAMP response element-binding protein |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | CREB1_HUMAN | P16220 | | 117 | 1 | cAMP response element-binding protein |
| | CREB1_HUMAN | P16220 | | 117 | 1 | cAMP response element-binding protein |
| | CROCC_HUMAN | Q5TZA2 | | 579 | 1 | Rootletin |
| | CS043_HUMAN | Q9BQ61 | | 63 | 1 | Uncharacterized protein C19orf43 |
| | CS044_HUMAN | Q9H6X5 | | 369 | 1 | Uncharacterized protein C19orf44 |
| | CSN1_HUMAN | Q13098 | | 95 | 1 | COP9 signalosome complex subunit 1 |
| | CSRN2_HUMAN | Q9H175 | | 40 | 1 | Cysteine/serine-rich nuclear protein 2 |
| | CSTF3_HUMAN | Q12996 | | 577 | 1 | Cleavage stimulation factor 77 kDa subunit |
| | CTBL1_HUMAN | Q8WYA6 | | 67 | 1 | Beta-catenin-like protein 1 |
| | CTCF_HUMAN | P49711 | | 47 | 1 | Transcriptional repressor CTCF |
| | CTCF_HUMAN | P49711 | | 47 | 1 | Transcriptional repressor CTCF |
| | CTCF_HUMAN | P49711 | | 47 | 1 | Transcriptional repressor CTCF |
| | CTNB1_HUMAN | P35222 | | 116 | 1 | Catenin beta-1 |
| | CTND1_HUMAN | O60716 | | 162 | 1 | Catenin delta-1 |
| | CTR9_HUMAN | Q6PD62 | | 1121 | 1 | RNA polymerase-associated protein CTR9 homolog |
| | CUL4B_HUMAN | Q13620 | | 26 | 1 | Cullin-4B |
| | CUTC_HUMAN | Q9NTM9 | | 34 | 1 | Copper homeostasis protein cutC homolog |
| | CUX1_HUMAN | P39880 | | 1340 | 1 | Homeobox protein cut-like 1 |
| 23 | CYB5B_HUMAN | O43169 | GKGQEVETSVTYYR | 11 | 1 | Cytochrome b5 type B |
| | DBPA_HUMAN | P16989 | | 270 | 1 | DNA-binding protein A |
| | DBPA_HUMAN | P16989 | | 162 | 1 | DNA-binding protein A |
| | DBPA_HUMAN | P16989 | | 145 | 1 | DNA-binding protein A |
| | DBPA_HUMAN | P16989 | | 138 | 3 | DNA-binding protein A |
| | YBOX1_HUMAN | P67809 | | 106 | | Nuclease-sensitive element-binding protein 1 |
| | YBOX2_HUMAN | Q9Y2T7 | | 141 | | Y-box-binding protein 2 |
| | DCNL2_HUMAN | Q6PH85 | | 43 | 1 | DCN1-like protein 2 |
| | DCTN1_HUMAN | Q14203 | | 303 | 1 | Dynactin subunit 1 |
| | DD19A_HUMAN | Q9NUU7 | | 5 | 1 | ATP-dependent RNA helicase DDX19A |
| | DDX1_HUMAN | Q92499 | | 440 | 1 | ATP-dependent RNA helicase DDX1 |
| 24 | DDX24_HUMAN | Q9GZR7 | ALPDDTVIESEALPSDIAAEAR | 297 | 1 | ATP-dependent RNA helicase DDX24 |
| | DDX46_HUMAN | Q7L014 | | 872 | 1 | Probable ATP-dependent RNA helicase DDX46 |
| | DDX46_HUMAN | Q7L014 | | 923 | 1 | Probable ATP-dependent RNA helicase DDX46 |
| | DDX46_HUMAN | Q7L014 | | 872 | 1 | Probable ATP-dependent RNA helicase DDX46 |
| | DDX46_HUMAN | Q7L014 | | 872 | 1 | Probable ATP-dependent RNA helicase DDX46 |
| 25 | DDX59_HUMAN | Q5T1V6 | AVATEAATIDR | 44 | 1 | Probable ATP-dependent RNA helicase DDX59 |
| | DESM_HUMAN | P17661 | | 265 | 1 | Desmin |
| | DESM_HUMAN | P17661 | | 265 | 1 | Desmin |
| | DFFA_HUMAN | O00273 | | 7 | 1 | DNA fragmentation factor subunit alpha |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | DFFA_HUMAN | O00273 | | 222 | 1 | DNA fragmentation factor subunit alpha |
| | DFFA_HUMAN | O00273 | | 222 | 1 | DNA fragmentation factor subunit alpha |
| 26 | DGCR8_HUMAN | Q8WYQ5 | ALLEEGLCAPK | 249 | 1 | Protein DGCR8 |
| | DGCR8_HUMAN | Q8WYQ5 | | 397 | 1 | Protein DGCR8 |
| 27 | DGCR8_HUMAN | Q8WYQ5 | SMGADPGPPDEKDPLGAEAAPGALGQVK | 397 | 1 | Protein DGCR8 |
| 28 | DGCR8_HUMAN | Q8WYQ5 | SMGADPGPPDEKDPLGAEAAPGALGQVKAK | 397 | 1 | Protein DGCR8 |
| | DGKH_HUMAN | Q86XP1 | | 583 | 1 | Diacylglycerol kinase eta |
| 29 | DGKH_HUMAN | Q86XP1 | SVPGPAVAASKENLPVLNTR | 699 | 1 | Diacylglycerol kinase eta |
| | DGLB_HUMAN | Q8NCG7 | | 549 | 1 | Sn1-specific diacylglycerol lipase beta |
| | DHAK_HUMAN | Q3LXA3 | | 363 | 1 | Dihydroxyacetone kinase |
| | DHAK_HUMAN | Q3LXA3 | | 363 | 1 | Dihydroxyacetone kinase |
| | DHX30_HUMAN | Q7L2E3 | | 207 | 1 | Putative ATP-dependent RNA helicase DHX30 |
| | DHX37_HUMAN | Q8IY37 | | 574 | 1 | Probable ATP-dependent RNA helicase DHX37 |
| | DHX9_HUMAN | Q08211 | | 168 | 1 | ATP-dependent RNA helicase A |
| | DHX9_HUMAN | Q08211 | | 97 | 1 | ATP-dependent RNA helicase A |
| | DHX9_HUMAN | Q08211 | | 97 | 1 | ATP-dependent RNA helicase A |
| | DIAP1_HUMAN | O60610 | | 649 | 1 | Protein diaphanous homolog 1 |
| | DIDO1_HUMAN | Q9BTC0 | | 1251 | 1 | Death-inducer obliterator 1 |
| | DIDO1_HUMAN | Q9BTC0 | | 1519 | 1 | Death-inducer obliterator 1 |
| | DIDO1_HUMAN | Q9BTC0 | | 1353 | 1 | Death-inducer obliterator 1 |
| | DIDO1_HUMAN | Q9BTC0 | | 1353 | 1 | Death-inducer obliterator 1 |
| | DIDO1_HUMAN | Q9BTC0 | | 988 | 1 | Death-inducer obliterator 1 |
| | DLG1_HUMAN | Q12959 | | 413 | 1 | Disks large homolog 1 |
| | DNJC7_HUMAN | Q99615 | | 9 | 1 | DnaJ homolog subfamily C member 7 |
| | DNJC7_HUMAN | Q99615 | | 9 | 1 | DnaJ homolog subfamily C member 7 |
| 30 | DNJC7_HUMAN | Q99615 | VVMAATEPELLDDQEAK | 9 | 1 | DnaJ homolog subfamily C member 7 |
| 31 | DNJC7_HUMAN | Q99615 | VVMAATEPELLDDQEAKR | 9 | 1 | DnaJ homolog subfamily C member 7 |
| | DNM1L_HUMAN | O00429 | | 580 | 1 | Dynamin-1-like protein |
| | DNM1L_HUMAN | O00429 | | 504 | 1 | Dynamin-1-like protein |
| | DNM1L_HUMAN | O00429 | | 504 | 1 | Dynamin-1-like protein |
| | DNM1L_HUMAN | O00429 | | 504 | 1 | Dynamin-1-like protein |
| | DNM1L_HUMAN | O00429 | | 504 | 1 | Dynamin-1-like protein |
| 32 | DNM3A_HUMAN | Q9Y6K1 | MWVEPEAAAYAPPPPAKKPR | 439 | 1 | DNA (cytosine-5)-methyltransferase 3A |
| | DOC10_HUMAN | Q96BY6 | | 328 | 1 | Dedicator of cytokinesis protein 10 |
| 33 | DOHH_HUMAN | Q9BU89 | AIGQTLVDPK | 9 | 1 | Deoxyhypusine hydroxylase |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 34 | DOHH_HUMAN | Q9BU89 | AIGQTLVDPKQPLQAR | 9 | 1 | Deoxyhypusine hydroxylase |
|  | DOT1L_HUMAN | Q8TEK3 |  | 1334 | 1 | Histone-lysine N-methyltransferase, H3 lysine-79 specific |
| 35 | DP13A_HUMAN | Q9UKG1 | SLVAPDTPIQFDIISPVCEDQPGQAK | 445 | 1 | DCC-interacting protein 13-alpha |
| 36 | DPOD1_HUMAN | P28340 | HYVGPAQPVPGGPPPSR | 103 | 1 | DNA polymerase delta catalytic subunit |
| 37 | DPOD1_HUMAN | P28340 | HYVGPAQPVPGGPPPSRGSVPVLR | 103 | 1 | DNA polymerase delta catalytic subunit |
| 38 | DPOLA_HUMAN | P09884 | GIGYVEDGR | 84 | 1 | DNA polymerase alpha catalytic subunit |
|  | DPP9_HUMAN | Q86TI2 |  | 14 | 1 | Dipeptidyl peptidase 9 |
|  | DPYL4_HUMAN | O14531 |  | 457 | 1 | Dihydropyrimidinase-related protein 4 |
|  | DREB_HUMAN | Q16643 |  | 341 | 1 | Drebrin |
|  | DREB_HUMAN | Q16643 |  | 478 | 1 | Drebrin |
|  | DSRAD_HUMAN | P55265 |  | 215 | 1 | Double-stranded RNA-specific adenosine deaminase |
|  | DTL_HUMAN | Q9NZJ0 |  | 579 | 1 | Denticleless protein homolog |
|  | DTL_HUMAN | Q9NZJ0 |  | 579 | 1 | Denticleless protein homolog |
|  | DTX3L_HUMAN | Q8TDB6 |  | 218 | 1 | Protein deltex-3-like |
|  | DYHC1_HUMAN | Q14204 |  | 4368 | 1 | Cytoplasmic dynein 1 heavy chain 1 |
|  | DYHC1_HUMAN | Q14204 |  | 4221 | 1 | Cytoplasmic dynein 1 heavy chain 1 |
|  | E400N_HUMAN | Q6ZTU2 |  | 184 | 2 | EP400 N-terminal-like protein |
|  | EP400_HUMAN | Q96L91 |  | 195 |  | E1A-binding protein p400 |
|  | E41L2_HUMAN | O43491 |  | 913 | 1 | Band 4.1-like protein 2 |
|  | EAP1_HUMAN | Q9H1B7 |  | 133 | 1 | Enhanced at puberty protein 1 |
|  | EBP2_HUMAN | Q99848 |  | 212 | 1 | Probable rRNA-processing protein EBP2 |
|  | ECE1_HUMAN | P42892 |  | 34 | 1 | Endothelin-converting enzyme 1 |
| 39 | ECT2_HUMAN | Q9H8V3 | GCPANLLSSHR | 629 | 1 | Protein ECT2 |
|  | EDC4_HUMAN | Q6P2E9 |  | 797 | 1 | Enhancer of mRNA-decapping protein 4 |
|  | EDC4_HUMAN | Q6P2E9 |  | 663 | 1 | Enhancer of mRNA-decapping protein 4 |
|  | EDC4_HUMAN | Q6P2E9 |  | 663 | 1 | Enhancer of mRNA-decapping protein 4 |
|  | EDC4_HUMAN | Q6P2E9 |  | 491 | 1 | Enhancer of mRNA-decapping protein 4 |
|  | EDC4_HUMAN | Q6P2E9 |  | 486 | 1 | Enhancer of mRNA-decapping protein 4 |
| 40 | EDC4_HUMAN | Q6P2E9 | SLGADGTHGAGAMESAAGVLIK | 486 | 1 | Enhancer of mRNA-decapping protein 4 |
|  | EDC4_HUMAN | Q6P2E9 |  | 58 | 1 | Enhancer of mRNA-decapping protein 4 |
| 41 | EDRF1_HUMAN | Q3B7T1 | SVGNDVDVVSDSENIK | 116 | 1 | Erythroid differentiation-related factor 1 |
| 42 | EDRF1_HUMAN | Q3B7T1 | SVGNDVDVVSDSENIKK | 116 | 1 | Erythroid differentiation-related factor 1 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 43 | EEA1_HUMAN | Q15075 | SSAELQSLEQQLE EAQTENFNIK | 133 | 1 | Early endosome antigen 1 |
| 44 | EEA1_HUMAN | Q15075 | GLVTDSSAELQSL EQQLEEAQTENF NIK | 128 | 1 | Early endosome antigen 1 |
|  | EF1A1_HUMAN | P68104 |  | 399 | 2 | Elongation factor 1-alpha 1 |
|  | EF1A3_HUMAN | Q5VTE0 |  | 399 |  | Putative elongation factor 1-alpha-like 3 |
|  | EF1A1_HUMAN | P68104 |  | 404 | 2 | Elongation factor 1-alpha 1 |
|  | EF1A3_HUMAN | Q5VTE0 |  | 404 |  | Putative elongation factor 1-alpha-like 3 |
|  | EF1A1_HUMAN | P68104 |  | 404 | 2 | Elongation factor 1-alpha 1 |
|  | EF1A3_HUMAN | Q5VTE0 |  | 404 |  | Putative elongation factor 1-alpha-like 3 |
|  | EF1A1_HUMAN | P68104 |  | 200 | 2 | Elongation factor 1-alpha 1 |
|  | EF1A3_HUMAN | Q5VTE0 |  | 200 |  | Putative elongation factor 1-alpha-like 3 |
|  | EF1A1_HUMAN | P68104 |  | 234 | 2 | Elongation factor 1-alpha 1 |
|  | EF1A3_HUMAN | Q5VTE0 |  | 234 |  | Putative elongation factor 1-alpha-like 3 |
|  | EF1A1_HUMAN | P68104 |  | 404 | 2 | Elongation factor 1-alpha 1 |
|  | EF1A3_HUMAN | Q5VTE0 |  | 404 |  | Putative elongation factor 1-alpha-like 3 |
| 45 | EF1B_HUMAN | P24534 | LFGSDDEEESEEA KR | 103 | 1 | Elongation factor 1-beta |
| 46 | EF1B_HUMAN | P24534 | LFGSDDEEESEEAK | 103 | 1 | Elongation factor 1-beta |
|  | EF1D_HUMAN | P29692 |  | 159 | 1 | Elongation factor 1-delta |
|  | EF1D_HUMAN | P29692 |  | 159 | 1 | Elongation factor 1-delta |
|  | EF2_HUMAN | P13639 |  | 612 | 1 | Elongation factor 2 |
| 47 | EH1L1_HUMAN | Q8N3D4 | SQQPPGGSSPSEE PPPSPGEEAGLQR | 1330 | 1 | EH domain-binding protein 1-like protein 1 |
|  | EHBP1_HUMAN | Q8NDI1 |  | 275 | 1 | EH domain-binding protein 1 |
|  | EHD1_HUMAN | Q9H4M9 |  | 416 | 1 | EH domain-containing protein 1 |
|  | EHMT1_HUMAN | Q9H9B1 |  | 330 | 1 | Histone-lysine N-methyltransferase, H3 lysine-9 specific 5 |
|  | EHMT1_HUMAN | Q9H9B1 |  | 482 | 1 | Histone-lysine N-methyltransferase, H3 lysine-9 specific 5 |
|  | EHMT2_HUMAN | Q96KQ7 |  | 454 | 1 | Histone-lysine N-methyltransferase, H3 lysine-9 specific 3 |
|  | EIF3B_HUMAN | P55884 |  | 4 | 1 | Eukaryotic translation initiation factor 3 subunit B |
|  | EIF3B_HUMAN | P55884 |  | 185 | 1 | Eukaryotic translation initiation factor 3 subunit B |
|  | EIF3G_HUMAN | O75821 |  | 8 | 1 | Eukaryotic translation initiation factor 3 subunit G |
| 48 | EIF3J_HUMAN | O75822 | NWDDDDDEKKE EAEVKPEVK | 51 | 1 | Eukaryotic translation initiation factor 3 subunit J |
|  | ELF1_HUMAN | P32519 |  | 146 | 1 | ETS-related transcription factor Elf-1 |
| 49 | ELF1_HUMAN | P32519 | GIPEVMETQQVQ EK | 146 | 1 | ETS-related transcription factor Elf-1 |
|  | ENOA_HUMAN | P06733 |  | 204 | 1 | Alpha-enolase |
|  | ENPL_HUMAN | P14625 |  | 60 | 1 | Endoplasmin |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide.
"M" indicates the number of matches.

| SEQ ID NO. | Swiss-Prot ID | Swiss-Prot acc # | unmodified peptide | SR | M | protein name |
|---|---|---|---|---|---|---|
| | ENPL_HUMAN | P14625 | | 29 | 1 | Endoplasmin |
| | ENPL_HUMAN | P14625 | | 29 | 1 | Endoplasmin |
| | EP15R_HUMAN | Q9UBC2 | | 570 | 1 | Epidermal growth factor receptor substrate 15-like 1 |
| | EP15_HUMAN | P42566 | | 619 | 1 | Epidermal growth factor receptor substrate 15 |
| | EPC1_HUMAN | Q9H2F5 | | 28 | 1 | Enhancer of polycomb homolog 1 |
| | EPN1_HUMAN | Q9Y6I3 | | 461 | 1 | Epsin-1 |
| | EPN2_HUMAN | O95208 | | 340 | 1 | Epsin-2 |
| | ERC6L_HUMAN | Q2NKX8 | | 802 | 1 | DNA excision repair protein ERCC-6-like |
| | ERCC6_HUMAN | Q03468 | | 53 | 1 | DNA excision repair protein ERCC-6 |
| | ERF3A_HUMAN | P15170 | | 40 | 1 | Eukaryotic peptide chain release factor GTP-binding subunit ERF3A |
| | ERF3A_HUMAN | P15170 | | 40 | 1 | Eukaryotic peptide chain release factor GTP-binding subunit ERF3A |
| | ERF3A_HUMAN | P15170 | | 40 | 1 | Eukaryotic peptide chain release factor GTP-binding subunit ERF3A |
| 50 | ERF3A_HUMAN | P15170 | GRPPEESAHEMMEEEEEIPKPK | 40 | 1 | Eukaryotic peptide chain release factor GTP-binding subunit ERF3A |
| 51 | ERF_HUMAN | P50548 | GTSELEEPLGEDPR | 192 | 1 | ETS domain-containing transcription factor ERF |
| | ERIC1_HUMAN | Q86X53 | | 277 | 1 | Glutamate-rich protein 1 |
| | ESYT2_HUMAN | A0FGR8 | | 760 | 1 | Extended synaptotagmin-2 |
| | ETUD1_HUMAN | Q7Z2Z2 | | 933 | 1 | Elongation factor Tu GTP-binding domain-containing protein 1 |
| | ETUD1_HUMAN | Q7Z2Z2 | | 933 | 1 | Elongation factor Tu GTP-binding domain-containing protein 1 |
| | EXDL2_HUMAN | Q9NVH0 | | 199 | 1 | Exonuclease 3'-5' domain-like-containing protein 2 |
| 52 | F101B_HUMAN | Q8N5W9 | AAAATPAAPSPASLPLAPGCALR | 62 | 1 | Protein FAM101B |
| | F107B_HUMAN | Q9H098 | | 6 | 1 | Protein FAM107B |
| 53 | F117B_HUMAN | Q6P1L5 | GHRAPPPLVQR | 375 | 1 | Protein FAM117B |
| 54 | F125A_HUMAN | Q96EY5 | AASQPSKGGLLER | 173 | 1 | Protein FAM125A |
| | F169A_HUMAN | Q9Y6X4 | | 447 | 1 | UPF0611 protein FAM169A |
| | FA13A_HUMAN | O94988 | | 595 | 1 | Protein FAM13A1 |
| | FA13A_HUMAN | O94988 | | 595 | 1 | Protein FAM13A1 |
| | FA21A_HUMAN | Q641Q2 | | 1135 | 4 | Protein FAM21A |
| | FA21B_HUMAN | Q5SNT6 | | 1047 | | Protein FAM21B |
| | FA21C_HUMAN | Q9Y4E1 | | 1114 | | Protein FAM21C |
| | FA21D_HUMAN | Q5SRD0 | | 102 | | Protein FAM21D |
| | FA29A_HUMAN | Q7Z4H7 | | 569 | 1 | Protein FAM29A |
| 55 | FA44A_HUMAN | Q8NFC6 | GLMATTASGDITNQNSLAGGKNQGK | 2045 | 1 | Protein FAM44A |
| | FA44A_HUMAN | Q8NFC6 | | 1484 | 1 | Protein FAM44A |
| | FA44A_HUMAN | Q8NFC6 | | 2045 | 1 | Protein FAM44A |
| | FA44A_HUMAN | Q8NFC6 | | 2045 | 1 | Protein FAM44A |
| | FA44A_HUMAN | Q8NFC6 | | 2045 | 1 | Protein FAM44A |
| | FA44A_HUMAN | Q8NFC6 | | 1709 | 1 | Protein FAM44A |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | FAS_HUMAN | P49327 | | 1166 | 1 | Fatty acid synthase |
| | FETUA_HUMAN | P02765 | | 134 | 1 | Alpha-2-HS-glycoprotein |
| | FIP1_HUMAN | Q6UN15 | | 159 | 1 | Pre-mRNA 3'-end-processing factor FIP1 |
| | FKB15_HUMAN | Q5T1M5 | | 307 | 1 | FK506-binding protein 15 |
| | FKB15_HUMAN | Q5T1M5 | | 307 | 1 | FK506-binding protein 15 |
| | FLI1_HUMAN | Q01543 | | 21 | 1 | Friend leukemia integration 1 transcription factor |
| 56 | FLNA_HUMAN | P21333 | GSPVPSSPFQVPV TEGCDPSR | 1337 | 1 | Filamin-A |
| 57 | FLNA_HUMAN | P21333 | GSPVPSSPFQVPV TEGCDPSRVR | 1337 | 1 | Filamin-A |
| | FLNA_HUMAN | P21333 | | 2537 | 1 | Filamin-A |
| | FLNA_HUMAN | P21333 | | 26 | 1 | Filamin-A |
| | FLNA_HUMAN | P21333 | | 1505 | 1 | Filamin-A |
| 58 | FLNA_HUMAN | P21333 | GVPVPGSPFPLEA VAPTKPSK | 1049 | 1 | Filamin-A |
| 59 | FLNA_HUMAN | P21333 | GVPVPGSPFPLEA VAPTKPSKVK | 1049 | 1 | Filamin-A |
| 60 | FLNA_HUMAN | P21333 | GVPVPGSPFPLEA VAPTKPSKVKAF GPGLQGGSAGSP AR | 1049 | 1 | Filamin-A |
| | FLNA_HUMAN | P21333 | | 35 | 3 | Filamin-A |
| | FLNB_HUMAN | O75369 | | 8 | | Filamin-B |
| | FLNC_HUMAN | Q14315 | | 28 | | Filamin-C |
| | FLNB_HUMAN | O75369 | | 479 | 1 | Filamin-B |
| | FLNB_HUMAN | O75369 | | 1022 | 1 | Filamin-B |
| | FLNB_HUMAN | O75369 | | 1477 | 1 | Filamin-B |
| | FLNB_HUMAN | O75369 | | 1477 | 1 | Filamin-B |
| | FNBP1_HUMAN | Q96RU3 | | 520 | 1 | Formin-binding protein 1 |
| | FNBP1_HUMAN | Q96RU3 | | 520 | 1 | Formin-binding protein 1 |
| | FNBP4_HUMAN | Q8N3X1 | | 154 | 1 | Formin-binding protein 4 |
| | FNBP4_HUMAN | Q8N3X1 | | 426 | 1 | Formin-binding protein 4 |
| | FNBP4_HUMAN | Q8N3X1 | | 778 | 1 | Formin-binding protein 4 |
| | FOXJ2_HUMAN | Q9P0K8 | | 213 | 1 | Forkhead box protein J2 |
| 61 | FOXK1_HUMAN | P85037 | SAVAGAAPALVA AAAASVR | 81 | 1 | Forkhead box protein K1 |
| | FOXO3_HUMAN | O43524 | | 55 | 1 | Forkhead box protein O3 |
| 62 | FOXP4_HUMAN | Q8IVH2 | GLVHPPTSAAAPV TPLRPPGLGSASL HGGGPAR | 407 | 1 | Forkhead box protein P4 |
| | FRAP_HUMAN | P42345 | | 2460 | 1 | FKBP12-rapamycin complex-associated protein |
| | FRAP_HUMAN | P42345 | | 2460 | 1 | FKBP12-rapamycin complex-associated protein |
| | FRYL_HUMAN | O94915 | | 1513 | 1 | Protein furry homolog-like |
| | FUBP1_HUMAN | Q96AE4 | | 182 | 1 | Far upstream element-binding protein 1 |
| | FUBP1_HUMAN | Q96AE4 | | 84 | 1 | Far upstream element-binding protein 1 |
| | FUBP1_HUMAN | Q96AE4 | | 140 | 2 | Far upstream element-binding protein 1 |
| | FUBP2_HUMAN | Q92945 | | 184 | | Far upstream element-binding protein 2 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide.
"M" indicates the number of matches.

| SEQ ID NO. | Swiss-Prot ID | Swiss-Prot acc # | unmodified peptide | SR | M | protein name |
|---|---|---|---|---|---|---|
| 63 | FUBP2_HUMAN | Q92945 | SISSQLGPIHPPPR | 129 | 1 | Far upstream element-binding protein 2 |
| 64 | FUBP3_HUMAN | Q96I24 | SNSTIQEILIPASK | 160 | 1 | Far upstream element-binding protein 3 |
| | FUBP3_HUMAN | Q96I24 | | 35 | 1 | Far upstream element-binding protein 3 |
| 65 | FUS_HUMAN | P35637 | GKEFSGNPIKVSFATR | 356 | 1 | RNA-binding protein FUS |
| 66 | FUS_HUMAN | P35637 | GKEFSGNPIK | 356 | 1 | RNA-binding protein FUS |
| | FXR2_HUMAN | P51116 | | 562 | 1 | Fragile X mental retardation syndrome-related protein 2 |
| | FYB_HUMAN | O15117 | | 656 | 1 | FYN-binding protein |
| 67 | FYB_HUMAN | O15117 | GAGNLDEEQDSEGETYEDIEASK | 447 | 1 | FYN-binding protein |
| 68 | FYB_HUMAN | O15117 | GAGNLDEEQDSEGETYEDIEASKER | 447 | 1 | FYN-binding protein |
| | FYN_HUMAN | P06241 | | 20 | 1 | Proto-oncogene tyrosine-protein kinase Fyn |
| | FYTD1_HUMAN | Q96QD9 | | 327 | 2 | Forty-two-three domain-containing protein 1 |
| | THOC4_HUMAN | Q86V81 | | | | THO complex subunit 4 |
| | FYV1_HUMAN | Q9Y2I7 | | 1608 | 1 | FYVE finger-containing phosphoinositide kinase |
| | FYV1_HUMAN | Q9Y2I7 | | 1608 | 1 | FYVE finger-containing phosphoinositide kinase |
| | FYV1_HUMAN | Q9Y2I7 | | 990 | 1 | FYVE finger-containing phosphoinositide kinase |
| | G3P_HUMAN | P04406 | | 90 | 1 | Glyceraldehyde-3-phosphate dehydrogenase |
| | GABP1_HUMAN | Q06547 | | 304 | 1 | GA-binding protein subunit beta-1 |
| | GABP1_HUMAN | Q06547 | | 304 | 1 | GA-binding protein subunit beta-1 |
| | GABP2_HUMAN | Q8TAK5 | | 305 | 1 | GA-binding protein subunit beta-2 |
| | GALT_HUMAN | P07902 | | 19 | 1 | Galactose-1-phosphate uridylyltransferase |
| 69 | GAPD1_HUMAN | Q14C86 | SASQAAHPQDSAFSYR | 1103 | 1 | GTPase-activating protein and VPS9 domain-containing protein 1 |
| 70 | GAPD1_HUMAN | Q14C86 | SASQAAHPQDSAFSYRDAK | 1103 | 1 | GTPase-activating protein and VPS9 domain-containing protein 1 |
| | GATA2_HUMAN | P23769 | | 47 | 1 | Endothelial transcription factor GATA-2 |
| 71 | GBF1_HUMAN | Q92538 | SASVHDMDYVNPR | 369 | 1 | Golgi-specific brefeldin A-resistance guanine nucleotide exchange factor 1 |
| | GBF1_HUMAN | Q92538 | SASVHDMDYVNPR | 369 | 1 | Golgi-specific brefeldin A-resistance guanine nucleotide exchange factor 1 |
| | GCFC_HUMAN | Q9Y5B6 | | 222 | 1 | GC-rich sequence DNA-binding factor homolog |
| | GCP2_HUMAN | Q9BSJ2 | | 773 | 1 | Gamma-tubulin complex component 2 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | GCP60_HUMAN | Q9H3P7 | | 16 | 1 | Golgi resident protein GCP60 |
| 72 | GCP60_HUMAN | Q9H3P7 | SSEKELEPEAAEEALENGPK | 344 | 1 | Golgi resident protein GCP60 |
| | GDIR2_HUMAN | P52566 | | 20 | 1 | Rho GDP-dissociation inhibitor 2 |
| | GDIR2_HUMAN | P52566 | | 20 | 1 | Rho GDP-dissociation inhibitor 2 |
| | GDIR2_HUMAN | P52566 | | 56 | 1 | Rho GDP-dissociation inhibitor 2 |
| | GELS_HUMAN | P06396 | | 640 | 1 | Gelsolin |
| 73 | GELS_HUMAN | P06396 | GLGLSYLSSHIANVER | 404 | 1 | Gelsolin |
| 74 | GEMI5_HUMAN | Q8TEQ6 | TASTEETDPETSQPEPNRPSELDLR | 1320 | 1 | Gem-associated protein 5 |
| | GEMI8_HUMAN | Q9NWZ8 | | 170 | 1 | Gem-associated protein 8 |
| | GEN_HUMAN | Q17RS7 | | 624 | 1 | Flap endonuclease GEN homolog 1 |
| | GFPT1_HUMAN | Q06210 | | 261 | 1 | Glucosamine--fructose-6-phosphate aminotransferase [isomerizing] 1 |
| | GGA3_HUMAN | Q9NZ52 | | 334 | 1 | ADP-ribosylation factor-binding protein GGA3 |
| | GGA3_HUMAN | Q9NZ52 | | 518 | 1 | ADP-ribosylation factor-binding protein GGA3 |
| | GIT1_HUMAN | Q9Y2X7 | | 633 | 1 | ARF GTPase-activating protein GIT1 |
| | GIT1_HUMAN | Q9Y2X7 | | 419 | 1 | ARF GTPase-activating protein GIT1 |
| | GIT1_HUMAN | Q9Y2X7 | | 419 | 1 | ARF GTPase-activating protein GIT1 |
| | GIT1_HUMAN | Q9Y2X7 | | 633 | 1 | ARF GTPase-activating protein GIT1 |
| | GIT2_HUMAN | Q14161 | | 626 | 1 | ARF GTPase-activating protein GIT2 |
| | GLGB_HUMAN | Q04446 | | 308 | 1 | 1,4-alpha-glucan-branching enzyme |
| | GLRX3_HUMAN | O76003 | | 102 | 1 | Glutaredoxin-3 |
| | GLRX3_HUMAN | O76003 | | 102 | 1 | Glutaredoxin-3 |
| | GLU2B_HUMAN | P14314 | | 102 | 1 | Glucosidase 2 subunit beta |
| | GLU2B_HUMAN | P14314 | | 102 | 1 | Glucosidase 2 subunit beta |
| | GLU2B_HUMAN | P14314 | | 227 | 1 | Glucosidase 2 subunit beta |
| | GLU2B_HUMAN | P14314 | | 95 | 1 | Glucosidase 2 subunit beta |
| 75 | GMIP_HUMAN | Q9P107 | GGGEVSSQGPEDSLLGTQSR | 843 | 1 | GEM-interacting protein |
| | GMIP_HUMAN | Q9P107 | | 425 | 1 | GEM-interacting protein |
| | GMIP_HUMAN | Q9P107 | | 473 | 1 | GEM-interacting protein |
| 76 | GNL1_HUMAN | P36915 | SAMEPTGPTQER | 344 | 1 | Guanine nucleotide-binding protein-like 1 |
| 77 | GNL1_HUMAN | P36915 | SAMEPTGPTQERYKDGVVTIGCVGFPNVGK | 344 | 1 | Guanine nucleotide-binding protein-like 1 |
| | GNL1_HUMAN | P36915 | | 53 | 1 | Guanine nucleotide-binding protein-like 1 |
| | GNL1_HUMAN | P36915 | | 344 | 1 | Guanine nucleotide-binding protein-like 1 |
| | GNL1_HUMAN | P36915 | | 50 | 1 | Guanine nucleotide-binding protein-like 1 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | GOGB1_HUMAN | Q14789 | | 1246 | 1 | Golgin subfamily B member 1 |
| | GOGB1_HUMAN | Q14789 | | 1802 | 1 | Golgin subfamily B member 1 |
| 78 | GOGB1_HUMAN | Q14789 | SLSMSTRPTCSESVPSAK | 1802 | 1 | Golgin subfamily B member 1 |
| | GON4L_HUMAN | Q3T8J9 | | 482 | 1 | GON-4-like protein |
| 79 | GPKOW_HUMAN | Q92917 | GAGPSPEEKDFLK | 38 | 1 | G patch domain and KOW motifs-containing protein |
| 80 | GPKOW_HUMAN | Q92917 | GAGPSPEEK | 38 | 1 | G patch domain and KOW motifs-containing protein |
| 81 | GPKOW_HUMAN | Q92917 | GAGPSPEEKDFLKTVEGR | 38 | 1 | G patch domain and KOW motifs-containing protein |
| | GPKOW_HUMAN | Q92917 | | 99 | 1 | G patch domain and KOW motifs-containing protein |
| | GPKOW_HUMAN | Q92917 | | 99 | 1 | G patch domain and KOW motifs-containing protein |
| | GPN1_HUMAN | Q9HCN4 | | 312 | 1 | GPN-loop GTPase 1 |
| | GPTC8_HUMAN | Q9UKJ3 | | 883 | 1 | G patch domain-containing protein 8 |
| | GRDN_HUMAN | Q3V6T2 | | 220 | 1 | Girdin |
| | GRDN_HUMAN | Q3V6T2 | | 485 | 1 | Girdin |
| | GRIN1_HUMAN | Q7Z2K8 | | 307 | 1 | G protein-regulated inducer of neurite outgrowth 1 |
| 82 | GSDMD_HUMAN | P57764 | GQIQGSVELAAPGQAK | 88 | 1 | Gasdermin-D |
| 83 | GSDMD_HUMAN | P57764 | GVPAEGAFTEDFQGLR | 276 | 1 | Gasdermin-D |
| | GSTP1_HUMAN | P09211 | | 92 | 1 | Glutathione S-transferase P |
| | GSTP1_HUMAN | P09211 | | 92 | 1 | Glutathione S-transferase P |
| | GTF2I_HUMAN | P78347 | | 106 | 1 | General transcription factor II-I |
| | GTF2I_HUMAN | P78347 | | 106 | 1 | General transcription factor II-I |
| | H2AY_HUMAN | O75367 | | 173 | 1 | Core histone macro-H2A.1 |
| | H4_HUMAN | P62805 | | 70 | 1 | Histone H4 |
| | H4_HUMAN | P62805 | | 70 | 1 | Histone H4 |
| | H4_HUMAN | P62805 | | 70 | 1 | Histone H4 |
| 84 | H4_HUMAN | P62805 | NIQGITKPAIR | 26 | 1 | Histone H4 |
| | HAP28_HUMAN | Q13442 | | 25 | 1 | 28 kDa heat- and acid-stable phosphoprotein |
| | HAP28_HUMAN | Q13442 | | 25 | 1 | 28 kDa heat- and acid-stable phosphoprotein |
| | HBS1L_HUMAN | Q9Y450 | | 30 | 1 | HBS1-like protein |
| 85 | HCLS1_HUMAN | P14317 | FVNDISEKEQR | 27 | 1 | Hematopoietic lineage cell-specific protein |
| 86 | HCLS1_HUMAN | P14317 | FVNDISEK | 27 | 1 | Hematopoietic lineage cell-specific protein |
| | HDAC4_HUMAN | P56524 | | 9 | 1 | Histone deacetylase 4 |
| | HDAC4_HUMAN | P56524 | | 290 | 1 | Histone deacetylase 4 |
| | HDAC6_HUMAN | Q9UBN7 | | 1089 | 1 | Histone deacetylase 6 |
| | HDAC6_HUMAN | Q9UBN7 | | 1089 | 1 | Histone deacetylase 6 |
| 87 | HDAC7_HUMAN | Q8WUI4 | GGGPGQVVDDGLEHR | 413 | 1 | Histone deacetylase 7 |
| | HDC_HUMAN | Q9UBI9 | | 324 | 1 | Headcase protein homolog |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide.
"M" indicates the number of matches.

| SEQ ID NO. | Swiss-Prot ID | Swiss-Prot acc # | unmodified peptide | SR | M | protein name |
|---|---|---|---|---|---|---|
| | HDGR2_HUMAN | Q7Z4V5 | | 31 | 1 | Hepatoma-derived growth factor-related protein 2 |
| | HDGR2_HUMAN | Q7Z4V5 | | 242 | 1 | Hepatoma-derived growth factor-related protein 2 |
| | HDGR2_HUMAN | Q7Z4V5 | | 242 | 1 | Hepatoma-derived growth factor-related protein 2 |
| | HDGR2_HUMAN | Q7Z4V5 | | 31 | 1 | Hepatoma-derived growth factor-related protein 2 |
| | HECD1_HUMAN | Q9ULT8 | | 1493 | 1 | E3 ubiquitin-protein ligase HECTD1 |
| 88 | HELLS_HUMAN | Q9NRZ9 | TAVITPAMLEEEE QLEAAGLER | 23 | 1 | Lymphoid-specific helicase |
| | HG2A_HUMAN | P04233 | | 23 | 1 | HLA class II histocompatibility antigen gamma chain |
| 89 | HG2A_HUMAN | P04233 | LISNNEQLPMLGR | 23 | 1 | HLA class II histocompatibility antigen gamma chain |
| | HIRP3_HUMAN | Q9BW71 | | 111 | 1 | HIRA-interacting protein 3 |
| 90 | HJURP_HUMAN | Q8NCD3 | GSVQAAAWGPEL PSHR | 92 | 1 | Holliday junction recognition protein |
| 91 | HMHA1_HUMAN | Q92619 | GGAGASAFEQAD LNGMTPELPVAV PSGPFRHEGLSK | 663 | 1 | Minor histocompatibility protein HA-1 |
| 92 | HMHA1_HUMAN | Q92619 | AGCLPAEEVDVL LQR | 263 | 1 | Minor histocompatibility protein HA-1 |
| 93 | HMHA1_HUMAN | Q92619 | AVFPGPSLEPPAG SSGVK | 40 | 1 | Minor histocompatibility protein HA-1 |
| | HMOX2_HUMAN | P30519 | | 252 | 1 | Heme oxygenase 2 |
| | HMOX2_HUMAN | P30519 | | 252 | 1 | Heme oxygenase 2 |
| | HMOX2_HUMAN | P30519 | | 252 | 1 | Heme oxygenase 2 |
| | HNRH1_HUMAN | P31943 | | 341 | 1 | Heterogeneous nuclear ribonucleoprotein H |
| | HNRH1_HUMAN | P31943 | | 95 | 2 | Heterogeneous nuclear ribonucleoprotein H |
| | HNRH2_HUMAN | P55795 | | 95 | | Heterogeneous nuclear ribonucleoprotein H2 |
| | HNRH1_HUMAN | P31943 | | 95 | 2 | Heterogeneous nuclear ribonucleoprotein H |
| | HNRH2_HUMAN | P55795 | | 95 | | Heterogeneous nuclear ribonucleoprotein H2 |
| | HNRH1_HUMAN | P31943 | | 252 | 2 | Heterogeneous nuclear ribonucleoprotein H |
| | HNRH2_HUMAN | P55795 | | 252 | | Heterogeneous nuclear ribonucleoprotein H2 |
| | HNRH2_HUMAN | P55795 | | 341 | 1 | Heterogeneous nuclear ribonucleoprotein H2 |
| 94 | HNRH3_HUMAN | P31942 | GGYGGFDDYGGY NNYGYGNDGFDDR | 145 | 1 | Heterogeneous nuclear ribonucleoprotein H3 |
| | HNRL1_HUMAN | Q9BUJ2 | | 97 | 1 | Heterogeneous nuclear ribonucleoprotein U-like protein 1 |
| 95 | HNRL1_HUMAN | Q9BUJ2 | GHYAMDNITR | 97 | 1 | Heterogeneous nuclear ribonucleoprotein U-like protein 1 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 96 | HNRL2_HUMAN | Q1KMD3 | ASEKPAEATAGSGGVNGGEEQGLGK | 127 | 1 | Heterogeneous nuclear ribonucleoprotein U-like protein 2 |
| 97 | HNRL2_HUMAN | Q1KMD3 | ASEKPAEATAGSGGVNGGEEQGLG | 127 | 1 | Heterogeneous nuclear ribonucleoprotein U-like protein 2 |
|  | HNRLL_HUMAN | Q8WVV9 |  | 290 | 1 | Heterogeneous nuclear ribonucleoprotein L-like |
|  | HNRPD_HUMAN | Q14103 |  | 70 | 1 | Heterogeneous nuclear ribonucleoprotein D0 |
|  | HNRPF_HUMAN | P52597 |  | 252 | 1 | Heterogeneous nuclear ribonucleoprotein F |
|  | HNRPG_HUMAN | P38159 |  | 284 | 1 | Heterogeneous nuclear ribonucleoprotein G |
|  | HNRPG_HUMAN | P38159 |  | 234 | 1 | Heterogeneous nuclear ribonucleoprotein G |
| 98 | HNRPK_HUMAN | P61978 | AVECLNYQHYK | 129 | 1 | Heterogeneous nuclear ribonucleoprotein K |
| 99 | HNRPK_HUMAN | P61978 | AVECLNYQHYKGSDFDCELR | 129 | 1 | Heterogeneous nuclear ribonucleoprotein K |
| 100 | HNRPK_HUMAN | P61978 | SAIDTWSPSEWQMAYEPQGGSGYDYSYAGGR | 347 | 1 | Heterogeneous nuclear ribonucleoprotein K |
| 101 | HNRPK_HUMAN | P61978 | YSYAGGR | 371 | 2 | Heterogeneous nuclear ribonucleoprotein K |
| 102 | HNRPL_HUMAN | P14866 | YTNPNLSGQGDPGSNPNKR | 285 | 1 | Heterogeneous nuclear ribonucleoprotein L |
|  | HNRPQ_HUMAN | O60506 |  | 469 | 1 | Heterogeneous nuclear ribonucleoprotein Q |
|  | HOOK1_HUMAN | Q9UJC3 |  | 234 | 1 | Protein Hook homolog 1 |
|  | HOOK1_HUMAN | Q9UJC3 |  | 234 | 1 | Protein Hook homolog 1 |
| 103 | HOOK2_HUMAN | Q96ED9 | SLSPETYGNFDSQSR | 161 | 1 | Protein Hook homolog 2 |
|  | HPS4_HUMANM | Q9NQG7 |  | 496 | 1 | Hermansky-Pudlak syndrome 4 protein |
|  | HRX_HUMAN | Q03164 |  | 2719 | 1 | Histone-lysine N-methyltransferase HRX |
|  | HRX_HUMAN | Q03164 |  | 2719 | 1 | Histone-lysine N-methyltransferase HRX |
|  | HRX_HUMAN | Q03164 |  | 2385 | 1 | Histone-lysine N-methyltransferase HRX |
|  | HS105_HUMAN | Q92598 |  | 548 | 1 | Heat shock protein 105 kDa |
|  | HS105_HUMAN | Q92598 |  | 548 | 1 | Heat shock protein 105 kDa |
|  | HS105_HUMAN | Q92598 |  | 548 | 1 | Heat shock protein 105 kDa |
|  | HS71L_HUMAN | P34931 |  | 228 | 6 | Heat shock 70 kDa protein 1L |
|  | HSP71_HUMAN | P08107 |  | 226 |  | Heat shock 70 kDa protein 1 |
|  | HSP72_HUMAN | P54652 |  | 229 |  | Heat shock-related 70 kDa protein 2 |
|  | HSP76_HUMAN | P17066 |  | 228 |  | Heat shock 70 kDa protein 6 |
|  | HSP77_HUMAN | P48741 |  | 228 |  | Putative heat shock 70 kDa protein 7 |
|  | HSP7C_HUMAN | P11142 |  | 226 |  | Heat shock cognate 71 kDa protein |
|  | HSP74_HUMAN | P34932 |  | 728 | 1 | Heat shock 70 kDa protein 4 |
|  | HSP7C_HUMAN | P11142 |  | 81 | 1 | Heat shock cognate 71 kDa protein |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | HTF4_HUMAN | Q99081 | | 23 | 1 | Transcription factor 12 |
| 104 | HTSF1_HUMAN | O43719 | AGGEPDSLGQQP TDTPYEWDLDKK | 34 | 1 | HIV Tat-specific factor 1 |
| 105 | HTSF1_HUMAN | O43719 | AGGEPDSLGQQP TDTPYEWDLDKK AWFPK | 34 | 1 | HIV Tat-specific factor 1 |
| 106 | HTSF1_HUMAN | O43719 | GASSSTANVEDV HAR | 81 | 1 | HIV Tat-specific factor 1 |
| | HTSF1_HUMAN | O43719 | | 40 | 1 | HIV Tat-specific factor 1 |
| | HUWE1_HUMAN | Q7Z6Z7 | | 2360 | 1 | E3 ubiquitin-protein ligase HUWE1 |
| 107 | HUWE1_HUMAN | Q7Z6Z7 | GLPEEQPQTTK | 3665 | 1 | E3 ubiquitin-protein ligase HUWE1 |
| 108 | HUWE1_HUMAN | Q7Z6Z7 | MNASPLVR | 2474 | 1 | E3 ubiquitin-protein ligase HUWE1 |
| 109 | HUWE1_HUMAN | Q7Z6Z7 | SAVAISGADSR | 2931 | 1 | E3 ubiquitin-protein ligase HUWE1 |
| | HUWE1_HUMAN | Q7Z6Z7 | | 2018 | 1 | E3 ubiquitin-protein ligase HUWE1 |
| 110 | HUWE1_HUMAN | Q7Z6Z7 | SVLAVMPPDIAAE AQALR | 3080 | 1 | E3 ubiquitin-protein ligase HUWE1 |
| | I2BP2_HUMAN | Q7Z5L9 | | 496 | 1 | Interferon regulatory factor 2-binding protein 2 |
| | I5P2_HUMAN | P32019 | | 264 | 1 | Type II inositol-1,4,5-trisphosphate 5-phosphatase |
| | IASPP_HUMAN | Q8WUF5 | | 295 | 1 | RelA-associated inhibitor |
| 111 | ICAL_HUMAN | P20810 | ALSSDFTCGSPTA AGK | 234 | 1 | Calpastatin |
| 112 | ICAL_HUMAN | P20810 | ALSSDFTCGSPTA AGKK | 234 | 1 | Calpastatin |
| | ICAL_HUMAN | P20810 | | 514 | 1 | Calpastatin |
| | ICAL_HUMAN | P20810 | | 349 | 1 | Calpastatin |
| | ICAL_HUMAN | P20810 | | 660 | 1 | Calpastatin |
| | IF2BL_HUMAN | A6NK07 | | 119 | 2 | Eukaryotic translation initiation factor 2 subunit 2-like protein |
| | IF2B_HUMAN | P20042 | | 119 | | Eukaryotic translation initiation factor 2 subunit 2 |
| | IF2P_HUMAN | O60841 | | 21 | 1 | Eukaryotic translation initiation factor 5B |
| | IF2P_HUMAN | O60841 | | 21 | 1 | Eukaryotic translation initiation factor 5B |
| | IF2P_HUMAN | O60841 | | 21 | 1 | Eukaryotic translation initiation factor 5B |
| | IF4A2_HUMAN | Q14240 | | 22 | 1 | Eukaryotic initiation factor 4A-II |
| | IF4A2_HUMAN | Q14240 | | 22 | 1 | Eukaryotic initiation factor 4A-II |
| | IF4B_HUMAN | P23588 | | 60 | 1 | Eukaryotic translation initiation factor 4B |
| | IF4B_HUMAN | P23588 | | 51 | 1 | Eukaryotic translation initiation factor 4B |
| | IF4G1_HUMAN | Q04637 | | 533 | 1 | Eukaryotic translation initiation factor 4 gamma 1 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | IF4G1_HUMAN | Q04637 | | 666 | 1 | Eukaryotic translation initiation factor 4 gamma 1 |
| | IF4G1_HUMAN | Q04637 | | 415 | 1 | Eukaryotic translation initiation factor 4 gamma 1 |
| 113 | IF4G2_HUMAN | P78344 | SSSAPSKEQLEQEK | 793 | 1 | Eukaryotic translation initiation factor 4 gamma 2 |
| 114 | IF4G2_HUMAN | P78344 | SSSAPSKEQLEQEKQLLLSFKPVMQK | 793 | 1 | Eukaryotic translation initiation factor 4 gamma 2 |
| | IF4G3_HUMAN | O43432 | | 479 | 1 | Eukaryotic translation initiation factor 4 gamma 3 |
| | IF4G3_HUMAN | O43432 | | 479 | 1 | Eukaryotic translation initiation factor 4 gamma 3 |
| 115 | IF4H_HUMAN | Q15056 | SLKEALTYDGALLGDR | 94 | 1 | Eukaryotic translation initiation factor 4H |
| | IF5A1_HUMAN | P63241 | | 97 | 1 | Eukaryotic translation initiation factor 5A-1 |
| | IF5A1_HUMAN | P63241 | | 12 | 2 | Eukaryotic translation initiation factor 5A-1 |
| | IF5AL_HUMAN | Q6IS14 | | 12 | | Eukaryotic translation initiation factor 5A-1-like |
| | IF5A1_HUMAN | P63241 | | 12 | 2 | Eukaryotic translation initiation factor 5A-1 |
| | IF5AL_HUMAN | Q6IS14 | | 12 | | Eukaryotic translation initiation factor 5A-1-like |
| | IF5A1_HUMAN | P63241 | | 12 | 2 | Eukaryotic translation initiation factor 5A-1 |
| | IF5AL_HUMAN | Q6IS14 | | 12 | | Eukaryotic translation initiation factor 5A-1-like |
| | IF5A1_HUMAN | P63241 | | 7 | 2 | Eukaryotic translation initiation factor 5A-1 |
| | IF5AL_HUMAN | Q6IS14 | | 7 | | Eukaryotic translation initiation factor 5A-1-like |
| | IF5A1_HUMAN | P63241 | | 12 | 2 | Eukaryotic translation initiation factor 5A-1 |
| | IF5AL_HUMAN | Q6IS14 | | 12 | | Eukaryotic translation initiation factor 5A-1-like |
| | IF5A1_HUMAN | P63241 | | 7 | 2 | Eukaryotic translation initiation factor 5A-1 |
| | IF5AL_HUMAN | Q6IS14 | | 7 | | Eukaryotic translation initiation factor 5A-1-like |
| | IF5A1_HUMAN | P63241 | | 7 | 2 | Eukaryotic translation initiation factor 5A-1 |
| | IF5AL_HUMAN | Q6IS14 | | 7 | | Eukaryotic translation initiation factor 5A-1-like |
| | IF5A1_HUMAN | P63241 | | 7 | 2 | Eukaryotic translation initiation factor 5A-1 |
| | IF5AL_HUMAN | Q6IS14 | | 7 | | Eukaryotic translation initiation factor 5A-1-like |
| | IF5A2_HUMAN | Q9GZV4 | | 7 | 1 | Eukaryotic translation initiation factor 5A-2 |
| | IF5A2_HUMAN | Q9GZV4 | | 7 | 1 | Eukaryotic translation initiation factor 5A-2 |
| | IKBB_HUMAN | Q15653 | | 160 | 1 | NF-kappa-B inhibitor beta |
| 116 | IKBL2_HUMAN | Q96HA7 | GLTPQLEEDEELQGHLGR | 499 | 1 | NF-kappa-B inhibitor-like protein 2 |
| 117 | IKBL2_HUMAN | Q96HA7 | GLTPQLEEDEELQGHLGRR | 499 | 1 | NF-kappa-B inhibitor-like protein 2 |
| | IKZF1_HUMAN | Q13422 | | 368 | 1 | DNA-binding protein Ikaros |
| | IKZF2_HUMAN | Q9UKS7 | | 8 | 1 | Zinc finger protein Helios |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | IKZF5_HUMAN | Q9H5V7 | | 226 | 1 | Zinc finger protein Pegasus |
| 118 | ILF3_HUMAN | Q12906 | GSGIYDPCEKEATDAIGHLDR | 288 | 1 | interleukin enhancer-binding factor 3 |
| | ILF3_HUMAN | Q12906 | | 440 | 1 | Interleukin enhancer-binding factor 3 |
| | ILF3_HUMAN | Q12906 | | 440 | 1 | Interleukin enhancer-binding factor 3 |
| | ILKAP_HUMAN | Q9H0C8 | | 40 | 1 | Integrin-linked kinase-associated serine/threonine phosphatase 2C |
| | IMA1_HUMAN | P52294 | | 65 | 1 | Importin subunit alpha-1 |
| | IMA1_HUMAN | P52294 | | 65 | 1 | Importin subunit alpha-1 |
| | IMA7_HUMAN | O60684 | | 70 | 1 | Importin subunit alpha-7 |
| 119 | IMDH2_HUMAN | P12268 | CFLEEIMTK | 173 | 1 | Inosine-5'-monophosphate dehydrogenase 2 |
| | IN80D_HUMAN | Q53TQ3 | | 679 | 1 | INO80 complex subunit D |
| 120 | INF2_HUMAN | Q27J81 | AVTPGPQPTLEQLEEGGPRPLER | 1052 | 1 | Inverted formin-2 |
| 121 | INF2_HUMAN | Q27J81 | AVTPGPQPTLEQLEEGGPRPLERR | 1052 | 1 | Inverted formin-2 |
| | INF2_HUMAN | Q27J81 | | 1147 | 1 | Inverted formin-2 |
| | IPO9_HUMAN | Q96P70 | | 964 | 1 | Importin-9 |
| | IQEC1_HUMAN | Q6DN90 | | 235 | 1 | IQ motif and SEC7 domain-containing protein 1 |
| 122 | IQGA1_HUMAN | P46940 | GLGVARPHYGSVLDNER | 9 | 1 | Ras GTPase-activating-like protein IQGAP1 |
| 123 | IQGA1_HUMAN | P46940 | GLGVARPHYGSVLDNERLTAEEMDER | 9 | 1 | Ras GTPase-activating-like protein IQGAP1 |
| | IRF2_HUMAN | P14316 | | 238 | 1 | Interferon regulatory factor 2 |
| | IRS4_HUMAN | O14654 | | 717 | 1 | Insulin receptor substrate 4 |
| 124 | ISY1_HUMAN | Q9ULR0 | GVIVPLEQEYEK | 168 | 1 | Pre-mRNA-splicing factor ISY1 homolog |
| 125 | ISY1_HUMAN | Q9ULR0 | GVIVPLEQEYEKK | 168 | 1 | Pre-mRNA-splicing factor ISY1 homolog |
| | IWS1_HUMAN | Q96ST2 | | 348 | 1 | Protein IWS1 homolog |
| | IWS1_HUMAN | Q96ST2 | | 348 | 1 | Protein IWS1 homolog |
| 126 | JHD3C_HUMAN | Q9H3R0 | GAEVPNPDSVTDDLK | 397 | 1 | JmjC domain-containing histone demethylation protein 3C |
| 127 | JHD3C_HUMAN | Q9H3R0 | GAEVPNPDSVTDDLKVSEK | 397 | 1 | JmjC domain-containing histone demethylation protein 3C |
| | JIP4_HUMAN | O60271 | | 214 | 1 | C-jun-amino-terminal kinase-interacting protein 4 |
| | JIP4_HUMAN | O60271 | | 6 | 1 | C-jun-amino-terminal kinase-interacting protein 4 |
| | JIP4_HUMAN | O60271 | | 6 | 1 | C-jun-amino-terminal kinase-interacting protein 4 |
| | JIP4_HUMAN | O60271 | | 285 | 1 | C-jun-amino-terminal kinase-interacting protein 4 |
| | JKIP1_HUMAN | Q96N16 | | 18 | 1 | Janus kinase and microtubule-interacting protein 1 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 128 | JKIP1_HUMAN | Q96N16 | AVQMANEELR | 18 | 1 | Janus kinase and microtubule-interacting protein 1 |
| | JMY_HUMAN | Q8N9B5 | | 723 | 1 | Junction-mediating and -regulatory protein |
| | JMY_HUMAN | Q8N9B5 | | 723 | 1 | Junction-mediating and -regulatory protein |
| 129 | JOSD3_HUMAN | Q9H5J8 | HVTSDAVELANR | 11 | 1 | Protein JOSD3 |
| 130 | JSPR1_HUMAN | Q96MG2 | GGLGSCQALEDH SALAETQEDR | 13 | 1 | Junctional sarcoplasmic reticulum protein 1 |
| | K0174_HUMAN | P53990 | | 198 | 1 | Uncharacterized protein KIAA0174 |
| | K0174_HUMAN | P53990 | | 198 | 1 | Uncharacterized protein KIAA0174 |
| | K0232_HUMAN | Q92628 | | 557 | 1 | Uncharacterized protein KIAA0232 |
| | K0515_HUMAN | Q5JSZ5 | | 1083 | 1 | Uncharacterized protein KIAA0515 |
| | K0515_HUMAN | Q5JSZ5 | | 1236 | 1 | Uncharacterized protein KIAA0515 |
| | K0831_HUMAN | Q6ZNE5 | | 29 | 1 | Uncharacterized protein KIAA0831 |
| | K0831_HUMAN | Q6ZNE5 | | 227 | 1 | Uncharacterized protein KIAA0831 |
| | K1462_HUMAN | Q9P266 | | 1180 | 1 | Uncharacterized protein KIAA1462 |
| 131 | K1543_HUMAN | Q9P1Y5 | GSPAGAEDSLEEE ASSEGEPR | 862 | 1 | Uncharacterized protein KIAA1543 |
| 132 | K1627_HUMAN | Q9HCE5 | SIGAVLNSKDEQR | 30 | 1 | Methyltransferase-like protein KIAA1627 |
| 133 | K1627_HUMAN | Q9HCE5 | SIGAVLNSKDEQR EIAETR | 30 | 1 | Methyltransferase-like protein KIAA1627 |
| 134 | K1627_HUMAN | Q9HCE5 | SIGAVLNSK | 30 | 1 | Methyltransferase-like protein KIAA1627 |
| | K1704_HUMAN | Q8IXQ4 | | 89 | 1 | Uncharacterized protein KIAA1704 |
| 135 | K1967_HUMAN | Q8N163 | AGAEPITADSDPA YSSK | 293 | 1 | Protein KIAA1967 |
| | K1967_HUMAN | Q8N163 | | 769 | 1 | Protein KIAA1967 |
| | K1967_HUMAN | Q8N163 | | 619 | 1 | Protein KIAA1967 |
| 136 | KHDR1_HUMAN | Q07666 | ATVGGPAPTPLLP PSATASVK | 76 | 1 | KH domain-containing, RNA-binding, signal transduction-associated protein 1 |
| | KI67_HUMAN | P46013 | | 2148 | 1 | Antigen KI-67 |
| | KI67_HUMAN | P46013 | | 411 | 1 | Antigen KI-67 |
| | KI67_HUMAN | P46013 | | 174 | 1 | Antigen KI-67 |
| | KIF15_HUMAN | Q9NS87 | | 1134 | 1 | Kinesin-like protein KIF15 |
| | KKCC1_HUMAN | Q8N5S9 | | 33 | 1 | Calcium/calmodulin-dependent protein kinase Kinase 1 |
| | KLF12_HUMAN | Q9Y4X4 | | 74 | 1 | Krueppel-like factor 12 |
| 137 | KPYM_HUMAN | P14618 | GADCIMLSGETA KGDYPLEAVR | 355 | 1 | Pyruvate kinase isozymes M1/M2 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 138 | KPYM_HUMAN | P14618 | GADCIMLSGETAK | 355 | 2 | Pyruvate kinase isozymes M1/M2 |
| 138 | KPYR_HUMAN | P30613 | GADCIMLSGETAK | 398 | | Pyruvate kinase isozymes R/L |
| | KRI1_HUMAN | Q8N9T8 | | 313 | 1 | Protein KRI1 homolog |
| 139 | KRR1_HUMAN | Q13601 | GWKEPAFSK | 39 | 1 | KRR1 small subunit processome component homolog |
| 140 | KRR1_HUMAN | Q13601 | GWKEPAFSKEDNPR | 39 | 1 | KRR1 small subunit processome component homolog |
| | KS6A4_HUMAN | O75676 | | 378 | 1 | Ribosomal protein S6 kinase alpha-4 |
| | KU86_HUMAN | P13010 | | 456 | 1 | ATP-dependent DNA helicase 2 subunit 2 |
| | KU86_HUMAN | P13010 | | 456 | 1 | ATP-dependent DNA helicase 2 subunit 2 |
| | KU86_HUMAN | P13010 | | 557 | 1 | ATP-dependent DNA helicase 2 subunit 2 |
| | LAGE3_HUMAN | Q14657 | | 29 | 1 | L antigen family member 3 |
| | LAMB1_HUMAN | P07942 | | 1359 | 1 | Laminin subunit beta-1 |
| | LAP2A_HUMAN | P42166 | | 487 | 1 | Lamina-associated polypeptide 2, isoform alpha |
| | LAP2A_HUMAN | P42166 | | 442 | 1 | Lamina-associated polypeptide 2, isoform alpha |
| 141 | LAP4_HUMAN | Q14160 | AALEVSPGVIANPFAAGIGHR | 1198 | 1 | Protein LAP4 |
| | LAP4_HUMAN | Q14160 | | 502 | 1 | Protein LAP4 |
| | LAP4_HUMAN | Q14160 | | 636 | 1 | Protein LAP4 |
| 142 | LARP1_HUMAN | Q6PKG0 | AINWPTPGEIAHK | 173 | 1 | La-related protein 1 |
| 143 | LARP1_HUMAN | Q6PKG0 | FSQLLNCPEFVPR | 496 | 1 | La-related protein 1 |
| 144 | LARP4_HUMAN | Q71RC2 | GLNQTTIPVSPPSTTKPSR | 574 | 1 | La-related protein 4 |
| | LARP5_HUMAN | Q92615 | | 136 | 1 | La-related protein 5 |
| | LAT_HUMAN | O43561 | | 168 | 1 | Linker for activation of T-cells family member 1 |
| 145 | LCAP_HUMAN | Q9UIQ6 | LAKEPCLHPLEPDEVEYEPR | 30 | 1 | Leucyl-cystinyl aminopeptidase |
| | LCORL_HUMAN | Q8N3X6 | | 230 | 2 | Ligand-dependent nuclear receptor corepressor-like protein |
| | LCOR_HUMAN | Q96JN0 | | 81 | | Ligand-dependent corepressor |
| | LIMA1_HUMAN | Q9UHB6 | | 346 | 1 | LIM domain and actin-binding protein 1 |
| | LIN37_HUMAN | Q96GY3 | | 24 | 1 | Protein lin-37 homolog |
| | LIN7C_HUMAN | Q9NUP9 | | 63 | 1 | Lin-7 homolog C |
| 146 | LIPA1_HUMAN | Q13136 | GVLDINHEQENTPSTSGK | 219 | 1 | Liprin-alpha-1 |
| 147 | LIPA1_HUMAN | Q13136 | GVLDINHEQENTPSTSGKR | 219 | 1 | Liprin-alpha-1 |
| | LIPB2_HUMAN | Q8ND30 | | 32 | 1 | Liprin-beta-2 |
| | LMNB1_HUMAN | P20700 | | 147 | 1 | Lamin-B1 |
| | LMO7_HUMAN | Q8WWI1 | | 963 | 1 | LIM domain only protein 7 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | LMTK2_HUMAN | Q8IWU2 | | 901 | 1 | Serine/threonine-protein kinase LMTK2 |
| | LNP_HUMAN | Q9C0E8 | | 369 | 1 | Protein lunapark |
| | LPP_HUMAN | Q93052 | | 404 | 1 | Lipoma-preferred partner |
| | LPP_HUMAN | Q93052 | | 404 | 1 | Lipoma-preferred partner |
| | LRBA_HUMAN | P50851 | | 1757 | 1 | Lipopolysaccharide-responsive and beige-like anchor protein |
| 148 | LRBA_HUMAN | P50851 | SAQASDMGGESPGSR | 1757 | 1 | Lipopolysaccharide-responsive and beige-like anchor protein |
| | LRBA_HUMAN | P50851 | | 1785 | 1 | Lipopolysaccharide-responsive and beige-like anchor protein |
| | LRBA_HUMAN | P50851 | | 1785 | 1 | Lipopolysaccharide-responsive and beige-like anchor protein |
| 149 | LRC47_HUMAN | Q8N1G4 | AVSGQLPDPTTNPSAGK | 526 | 1 | Leucine-rich repeat-containing protein 47 |
| 150 | LRC47_HUMAN | Q8N1G4 | AVSGQLPDPTTNPSAGKDGPSLLVVEQVR | 526 | 1 | Leucine-rich repeat-containing protein 47 |
| | LRCH1_HUMAN | Q9Y2L9 | | 406 | 1 | Leucine-rich repeat and calponin homology domain-containing protein 1 |
| | LRCH1_HUMAN | Q9Y2L9 | | 406 | 1 | Leucine-rich repeat and calponin homology domain-containing protein 1 |
| | LRCH2_HUMAN | Q5VUJ6 | | 604 | 1 | Leucine-rich repeat and calponin homology domain-containing protein 2 |
| | LRCH3_HUMAN | Q96II8 | | 643 | 1 | Leucine-rich repeat and calponin homology domain-containing protein 3 |
| | LRCH4_HUMAN | O75427 | | 359 | 1 | Leucine-rich repeat and calponin homology domain-containing protein 4 |
| 151 | LRMP_HUMAN | Q12912 | SVVSPLPVTTVK | 182 | 1 | Lymphoid-restricted membrane protein |
| | LRRF1_HUMAN | Q32MZ4 | | 416 | 1 | Leucine-rich repeat flightless-interacting protein 1 |
| | LRRF2_HUMAN | Q9Y608 | | 532 | 1 | Leucine-rich repeat flightless-interacting protein 2 |
| | LSM11_HUMAN | P83369 | | 306 | 1 | U7 snRNA-associated Sm-like protein LSm11 |
| | LSM3_HUMAN | P62310 | | 7 | 1 | U6 snRNA-associated Sm-like protein LSm3 |
| | LSP1_HUMAN | P33241 | | 103 | 1 | Lymphocyte-specific protein 1 |
| 152 | LTV1_HUMAN | Q96GA3 | SAGLLSDEDCMSVPGKTHR | 206 | 1 | Protein LTV1 homolog |
| | LYRIC_HUMAN | Q86UE4 | | 184 | 1 | Protein LYRIC |
| 153 | M6PBP_HUMAN | O60664 | GFDVASVQQQR | 220 | 1 | Mannose-6-phosphate receptor-binding protein 1 |
| | M6PBP_HUMAN | O60664 | | 10 | 1 | Mannose-6-phosphate receptor-binding protein 1 |
| | M6PBP_HUMAN | O60664 | | 223 | 1 | Mannose-6-phosphate receptor-binding protein 1 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | MA7D1_HUMAN | Q3KQU3 | | 571 | 1 | MAP7 domain-containing protein 1 |
| 154 | MA7D1_HUMAN | Q3KQU3 | AAVLTSPPAPAPP VTPSKPMAGTTD REEATR | 571 | 1 | MAP7 domain-containing protein 1 |
| | MACF1_HUMAN | Q9UPN3 | | 1524 | 1 | Microtubule-actin cross-linking factor 1, isoforms 1/2/3/5 |
| | MACF1_HUMAN | Q9UPN3 | | 3021 | 2 | Microtubule-actin cross-linking factor 1, isoforms 1/2/3/5 |
| | MACF4_HUMAN | Q96PK2 | | 3523 | | Microtubule-actin cross-linking factor 1, isoform 4 |
| | MACF1_HUMAN | Q9UPN3 | | 3021 | 2 | Microtubule-actin cross-linking factor 1, isoforms 1/2/3/5 |
| | MACF4_HUMAN | Q96PK2 | | 3523 | | Microtubule-actin cross-linking factor 1, isoform 4 |
| 155 | MACF1_HUMAN | Q9UPN3 | GYMGVNQAPEKL DKQCEMMK | 1727 | 2 | Microtubule-actin cross-linking factor 1, isoforms 1/2/3/5 |
| 155 | MACF4_HUMAN | Q96PK2 | GYMGVNQAPEKL DKQCEMMK | 2229 | | Microtubule-actin cross-linking factor 1, isoform 4 |
| | MACF1_HUMAN | Q9UPN3 | | 1727 | 2 | Microtubule-actin cross-linking factor 1, isoforms 1/2/3/5 |
| | MACF4_HUMAN | Q96PK2 | | 2229 | | Microtubule-actin cross-linking factor 1, isoform 4 |
| | MACF1_HUMAN | Q9UPN3 | | 1727 | 2 | Microtubule-actin cross-linking factor 1, isoforms 1/2/3/5 |
| | MACF4_HUMAN | Q96PK2 | | 2229 | | Microtubule-actin cross-linking factor 1, isoform 4 |
| 156 | MACF1_HUMAN | Q9UPN3 | GYMGVNQAPEKL DK | 1727 | 2 | Microtubule-actin cross-linking factor 1, isoforms 1/2/3/5 |
| 156 | MACF4_HUMAN | Q96PK2 | GYMGVNQAPEKL DK | 2229 | | Microtubule-actin cross-linking factor 1, isoform 4 |
| 157 | MACF1_HUMAN | Q9UPN3 | GYMGVNQAPEK | 1727 | 2 | Microtubule-actin cross-linking factor 1, isoforms 1/2/3/5 |
| 157 | MACF4_HUMAN | Q96PK2 | GYMGVNQAPEK | 2229 | | Microtubule-actin cross-linking factor 1, isoform 4 |
| 158 | MADD_HUMAN | Q8WXG6 | SVIGVSPAVMIR | 1178 | 1 | MAP kinase-activating death domain protein |
| | MAGD1_HUMAN | Q9Y5V3 | | 223 | 1 | Melanoma-associated antigen D1 |
| 159 | MAGG1_HUMAN | Q96MG7 | GFAEEAPSTSR | 42 | 1 | Melanoma-associated antigen G1 |
| 160 | MAGG1_HUMAN | Q96MG7 | GFAEEAPSTSRGP GGSQGSQGPSPQ GAR | 42 | 1 | Melanoma-associated antigen G1 |
| | MAOM_HUMAN | P23368 | | 380 | 1 | NAD-dependent malic enzyme, mitochondrial |
| 161 | MAP1A_HUMAN | P78559 | SVVAAVQEGAAE LEGGPYSPLGK | 1885 | 1 | Microtubule-associated protein 1A |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 162 | MAP1A_HUMAN | P78559 | SVVAAVQEGAAELEGGPYSPLGKDYR | 1885 | 1 | Microtubule-associated protein 1A |
| 163 | MAP1A_HUMAN | P78559 | SVVAAVQEGAAELEGGPYSPLGKDYRK | 1885 | 1 | Microtubule-associated protein 1A |
| | MAP4_HUMAN | P27816 | | 9 | 1 | Microtubule-associated protein 4 |
| | MAP4_HUMAN | P27816 | | 9 | 1 | Microtubule-associated protein 4 |
| | MAP4_HUMAN | P27816 | | 250 | 1 | Microtubule-associated protein 4 |
| | MAP4_HUMAN | P27816 | | 152 | 1 | Microtubule-associated protein 4 |
| | MAP4_HUMAN | P27816 | | 328 | 1 | Microtubule-associated protein 4 |
| | MAP4_HUMAN | P27816 | | 47 | 1 | Microtubule-associated protein 4 |
| | MAP9_HUMAN | Q49MG5 | | 120 | 1 | Microtubule-associated protein 9 |
| | MARE1_HUMAN | Q15691 | | 117 | 1 | Microtubule-associated protein RP/EB family member 1 |
| | MARK1_HUMAN | Q9P0L2 | | 23 | 1 | Serine/threonine-protein kinase MARK1 |
| 164 | MATR3_HUMAN | P43243 | GQSDENKDDYTIPDEYR | 764 | 1 | Matrin-3 |
| 165 | MATR3_HUMAN | P43243 | LANLGDVASDGK | 681 | 1 | Matrin-3 |
| 166 | MATR3_HUMAN | P43243 | LANLGDVASDGKK | 681 | 1 | Matrin-3 |
| 167 | MATR3_HUMAN | P43243 | SFDDRGPSLNPVLDYDHGSR | 188 | 1 | Matrin-3 |
| 168 | MATR3_HUMAN | P43243 | YYTTTPALVFGKPVR | 453 | 1 | Matrin-3 |
| | MATR3_HUMAN | P43243 | | 704 | 1 | Matrin-3 |
| 169 | MATR3_HUMAN | P43243 | LANLGDVASDGKKEPSDK | 681 | 1 | Matrin-3 |
| | MAVS_HUMAN | Q7Z434 | | 491 | 1 | Mitochondrial antiviral-signaling protein |
| | MAVS_HUMAN | Q7Z434 | | 491 | 1 | Mitochondrial antiviral-signaling protein |
| | MAX_HUMAN | P61244 | | 49 | 1 | Protein max |
| | MBB1A_HUMAN | Q9BQG0 | | 750 | 1 | Myb-binding protein 1A |
| | MCM2_HUMAN | P49736 | | 89 | 1 | DNA replication licensing factor MCM2 |
| | MCM2_HUMAN | P49736 | | 69 | 1 | DNA replication licensing factor MCM2 |
| 170 | MCM3_HUMAN | P25205 | SYDPYDFSDTEEEMPQVHTPK | 704 | 1 | DNA replication licensing factor MCM3 |
| 171 | MCM4_HUMAN | P33991 | GAAAEDIVASEQSLGQK | 133 | 1 | DNA replication licensing factor MCM4 |
| 172 | MCM5_HUMAN | P33992 | SFGGDAQADEGQARK | 14 | 1 | DNA replication licensing factor MCM5 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 173 | MCM5_HUMAN | P33992 | SFGGDAQADEGQAR | 14 | 1 | DNA replication licensing factor MCM5 |
| 174 | MCM6_HUMAN | Q14566 | GYETEGIRGLR | 275 | 1 | DNA replication licensing factor MCM6 |
| 175 | MCM6_HUMAN | Q14566 | GYETEGIR | 275 | 1 | DNA replication licensing factor MCM6 |
|  | MDC1_HUMAN | Q14676 |  | 1036 | 1 | Mediator of DNA damage checkpoint protein 1 |
|  | MDC1_HUMAN | Q14676 |  | 1036 | 1 | Mediator of DNA damage checkpoint protein 1 |
|  | MDN1_HUMAN | Q9NU22 |  | 5128 | 1 | Midasin |
|  | MED14_HUMAN | O60244 |  | 995 | 1 | Mediator of RNA polymerase II transcription subunit 14 |
|  | MED1_HUMAN | Q15648 |  | 931 | 1 | Mediator of RNA polymerase II transcription subunit 1 |
|  | MED1_HUMAN | Q15648 |  | 1485 | 1 | Mediator of RNA polymerase II transcription subunit 1 |
|  | MED26_HUMAN | O95402 |  | 408 | 1 | Mediator of RNA polymerase II transcription subunit 26 |
|  | MEF2C_HUMAN | Q06413 |  | 106 | 1 | Myocyte-specific enhancer factor 2C |
|  | MEF2C_HUMAN | Q06413 |  | 106 | 1 | Myocyte-specific enhancer factor 2C |
|  | METK2_HUMAN | P31153 |  | 40 | 1 | S-adenosylmethionine synthetase isoform type-2 |
|  | MEX3B_HUMAN | Q6ZN04 |  | 355 | 1 | RNA-binding protein MEX3B |
|  | MGAP_HUMAN | Q8IWI9 |  | 681 | 1 | MAX gene-associated protein |
|  | MGAP_HUMAN | Q8IWI9 |  | 340 | 1 | MAX gene-associated protein |
|  | MGAP_HUMAN | Q8IWI9 |  | 340 | 1 | MAX gene-associated protein |
|  | MGAP_HUMAN | Q8IWI9 |  | 572 | 1 | MAX gene-associated protein |
|  | MIA3_HUMAN | Q5JRA6 |  | 710 | 1 | Melanoma inhibitory activity protein 3 |
|  | MIER1_HUMAN | Q8N108 |  | 52 | 1 | Mesoderm induction early response protein 1 |
|  | MINT_HUMAN | Q96T58 |  | 1575 | 1 | Msx2-interacting protein |
|  | MINT_HUMAN | Q96T58 |  | 2008 | 1 | Msx2-interacting protein |
|  | MINT_HUMAN | Q96T58 |  | 2860 | 1 | Msx2-interacting protein |
|  | MISSL_HUMAN | Q8NDC0 |  | 10 | 1 | MAPK-interacting and spindle-stabilizing protein-like |
| 176 | MKL1_HUMAN | Q969V6 | ALSPEQPASHESQGSVPSPLEAR | 122 | 1 | MKL/myocardin-like protein 1 |
|  | MKL2_HUMAN | Q9ULH7 |  | 183 | 1 | MKL/myocardin-like protein 2 |
| 177 | MLL2_HUMAN | O14686 | ALYVACQGQPK | 387 | 1 | Histone-lysine N-methyltransferase MLL2 |
|  | MLL2_HUMAN | O14686 |  | 1866 | 1 | Histone-lysine N-methyltransferase MLL2 |
|  | MLL3_HUMAN | Q8NEZ4 |  | 2189 | 1 | Histone-lysine N-methyltransferase MLL3 |
|  | MOBL3_HUMAN | Q9Y3A3 |  | 35 | 1 | Mps one binder kinase activator-like 3 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | MOES_HUMAN | P26038 | | 115 | 1 | Moesin |
| | MORC3_HUMAN | Q14149 | | 665 | 1 | MORC family CW-type zinc finger protein 3 |
| | MORC3_HUMAN | Q14149 | | 752 | 1 | MORC family CW-type zinc finger protein 3 |
| | MOT1_HUMAN | P53985 | | 470 | 1 | Monocarboxylate transporter 1 |
| | MP2K1_HUMAN | Q02750 | | 283 | 1 | Dual specificity mitogen-activated protein kinase kinase 1 |
| 178 | MP2K1_HUMAN | Q02750 | GSAVNGTSSAETNLEALQK | 17 | 1 | Dual specificity mitogen-activated protein kinase kinase 1 |
| 179 | MP2K1_HUMAN | Q02750 | GSAVNGTSSAETNLEALQKK | 17 | 1 | Dual specificity mitogen-activated protein kinase kinase 1 |
| 180 | MPP10_HUMAN | O00566 | AALLAPEEIKEK | 546 | 1 | U3 small nucleolar ribonucleoprotein protein MPP10 |
| 181 | MPP10_HUMAN | O00566 | AALLAPEEIK | 546 | 1 | U3 small nucleolar ribonucleoprotein protein MPP10 |
| | MPP8_HUMAN | Q99549 | | 20 | 1 | M-phase phosphoprotein 8 |
| | MPP8_HUMAN | Q99549 | | 502 | 1 | M-phase phosphoprotein 8 |
| | MPP8_HUMAN | Q99549 | | 517 | 1 | M-phase phosphoprotein 8 |
| 182 | MRP_HUMAN | P49006 | AIEPAPPSQGAEAK | 64 | 1 | MARCKS-related protein |
| | MSPD2_HUMAN | Q8NHP6 | | 275 | 1 | Motile sperm domain-containing protein 2 |
| | MTA70_HUMAN | Q86U44 | | 335 | 1 | N6-adenosine-methyltransferase 70 kDa subunit |
| | MYH10_HUMAN | P35580 | | 1310 | 1 | Myosin-10 |
| 183 | MYH10_HUMAN | P35580 | TTAAQQELR | 1161 | 1 | Myosin-10 |
| 184 | MYH11_HUMAN | P35749 | STATQQELR | 1161 | 1 | Myosin-11 |
| | MYH9_HUMAN | P35579 | | 1376 | 1 | Myosin-9 |
| 185 | MYH9_HUMAN | P35579 | STAAQQELR | 1154 | 1 | Myosin-9 |
| 186 | MYO9B_HUMAN | Q13459 | SLTSDKASVPIVLEK | 1704 | 1 | Myosin-IXb |
| | MYPT1_HUMAN | O14974 | | 886 | 1 | Protein phosphatase 1 regulatory subunit 12A |
| | N4BP1_HUMAN | O75113 | | 491 | 1 | NEDD4-binding protein 1 |
| | NACA_HUMAN | Q13765 | | 43 | 1 | Nascent polypeptide-associated complex subunit alpha |
| | NACA_HUMAN | Q13765 | | 43 | 1 | Nascent polypeptide-associated complex subunit alpha |
| | NADAP_HUMAN | Q9BWU0 | | 538 | 1 | Kanadaptin |
| | NADAP_HUMAN | Q9BWU0 | | 538 | 1 | Kanadaptin |
| | NADAP_HUMAN | Q9BWU0 | | 538 | 1 | Kanadaptin |
| | NAG_HUMAN | A2RRP1 | | 637 | 1 | Neuroblastoma-amplified gene protein |
| | NAG_HUMAN | A2RRP1 | | 637 | 1 | Neuroblastoma-amplified gene protein |
| | NAIF1_HUMAN | Q69YI7 | | 103 | 1 | Nuclear apoptosis-inducing factor 1 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | NARF_HUMAN | Q9UHQ1 | | 292 | 1 | Nuclear prelamin A recognition factor |
| | NARF_HUMAN | Q9UHQ1 | | 273 | 1 | Nuclear prelamin A recognition factor |
| 187 | NASP_HUMAN | P49321 | KIEDVPAPSTSADKVESLDVDSEAK | 20 | 1 | Nuclear autoantigenic sperm protein |
| | NASP_HUMAN | P49321 | | 33 | 1 | Nuclear autoantigenic sperm protein |
| | NASP_HUMAN | P49321 | | 33 | 1 | Nuclear autoantigenic sperm protein |
| 188 | NCK1_HUMAN | P16333 | SASPADDSFVDPGER | 89 | 1 | Cytoplasmic protein NCK1 |
| | NCOA3_HUMAN | Q9Y6Q9 | | 1013 | 1 | Nuclear receptor coactivator 3 |
| | NCOA5_HUMAN | Q9HCD5 | | 381 | 1 | Nuclear receptor coactivator 5 |
| | NCOA5_HUMAN | Q9HCD5 | | 154 | 1 | Nuclear receptor coactivator 5 |
| | NCOA6_HUMAN | Q14686 | | 1462 | 1 | Nuclear receptor coactivator 6 |
| | NCOR1_HUMAN | O75376 | | 1827 | 1 | Nuclear receptor corepressor 1 |
| | NCOR1_HUMAN | O75376 | | 386 | 1 | Nuclear receptor corepressor 1 |
| | NCOR1_HUMAN | O75376 | | 556 | 1 | Nuclear receptor corepressor 1 |
| 189 | NCOR1_HUMAN | O75376 | AAASAPQMDVSK | 1827 | 1 | Nuclear receptor corepressor 1 |
| | NCOR1_HUMAN | O75376 | | 386 | 1 | Nuclear receptor corepressor 1 |
| | NCOR1_HUMAN | O75376 | | 556 | 1 | Nuclear receptor corepressor 1 |
| | NCOR2_HUMAN | Q9Y618 | | 378 | 1 | Nuclear receptor corepressor 2 |
| | NCOR2_HUMAN | Q9Y618 | | 1927 | 1 | Nuclear receptor corepressor 2 |
| | NDRG1_HUMAN | Q92597 | | 10 | 1 | Protein NDRG1 |
| 190 | NEB2_HUMAN | Q96SB3 | GTSLVGVTQSFAASVLR | 552 | 1 | Neurabin-2 |
| 191 | NED4L_HUMAN | Q96PU5 | AVAEQGHLPPPSAPAGR | 346 | 1 | E3 ubiquitin-protein ligase NEDD4-like |
| | NEDD1_HUMAN | Q8NHV4 | | 435 | 1 | Protein NEDD1 |
| | NEDD4_HUMAN | P46934 | | 280 | 1 | E3 ubiquitin-protein ligase NEDD4 |
| | NEK1_HUMAN | Q96PY6 | | 950 | 1 | Serine/threonine-protein kinase Nek1 |
| | NEK4_HUMAN | P51957 | | 381 | 1 | Serine/threonine-protein kinase Nek4 |
| | NEK9_HUMAN | Q8TD19 | | 842 | 1 | Serine/threonine-protein kinase Nek9 |
| | NELFA_HUMAN | Q9H3P2 | | 300 | 1 | Negative elongation factor A |
| | NFAC1_HUMAN | O95644 | | 111 | 1 | Nuclear factor of activated T-cells, cytoplasmic 1 |
| | NFAC2_HUMAN | Q13469 | | 67 | 1 | Nuclear factor of activated T-cells, cytoplasmic 2 |
| | NFKB2_HUMAN | Q00653 | | 11 | 1 | Nuclear factor NF-kappa-B p100 subunit |
| | NFRKB_HUMAN | Q6P4R8 | | 497 | 1 | Nuclear factor related to kappa-B-binding protein |
| | NFRKB_HUMAN | Q6P4R8 | | 6 | 1 | Nuclear factor related to kappa-B-binding protein |
| | NHERF_HUMAN | O14745 | | 5 | 1 | Ezrin-radixin-moesin-binding phosphoprotein 50 |
| | NIPA_HUMAN | Q86WB0 | | 450 | 1 | Nuclear-interacting partner of ALK |
| | NIPA_HUMAN | Q86WB0 | | 296 | 1 | Nuclear-interacting partner of ALK |
| | NIPBL_HUMAN | Q6KC79 | | 473 | 1 | Nipped-B-like protein |
| | NIPBL_HUMAN | Q6KC79 | | 473 | 1 | Nipped-B-like protein |
| | NKTR_HUMAN | P30414 | | 960 | 1 | NK-tumor recognition protein |

TABLE 1-continued

Identified caspase-derived peptides. Previous residues indicates the inferred
P8-P1 residues in the given protein substrate that directly precede the
sequence of residues corresponding to the identified peptide. Unmodified
peptide indicates the sequence of residues corresponding to the identified
peptide. Modified peptide indicates the peptide as identified, sometimes
containing chemical modifications such as oxidized methionine and
carbamidomethylated cysteine, and always containing either an N-terminal serinyl-
glycyl dipeptide (SerTyr) modification or an N-terminal 2-aminobutyryl (Abu)
modification. Start residue(SR) indicates the residue number in the full-length
protein sequence of the first residue of the unmodified peptide.
"M" indicates the number of matches.

| SEQ ID NO. | Swiss-Prot ID | Swiss-Prot acc # | unmodified peptide | SR | M | protein name |
|---|---|---|---|---|---|---|
| | NOL1_HUMAN | P46087 | | 231 | 1 | Putative RNA methyltransferase NOL1 |
| | NOL1_HUMAN | P46087 | | 208 | 1 | Putative RNA methyltransferase NOL1 |
| 192 | NOL1_HUMAN | P46087 | GGLQINVDEEPFVLPPAGEMEQDAQAPDLQR | 208 | 1 | Putative RNA methyltransferase NOL1 |
| 193 | NOL1_HUMAN | P46087 | GGLQINVDEEPFVLPPAGEMEQDAQAPDLQRVHKR | 208 | 1 | Putative RNA methyltransferase NOL1 |
| 194 | NOL5_HUMAN | Q9Y2X3 | GLIPGVEPR | 125 | 1 | Nucleolar protein 5 |
| | NOP14_HUMAN | P78316 | | 320 | 1 | Nucleolar protein 14 |
| | NOP14_HUMAN | P78316 | | 320 | 1 | Nucleolar protein 14 |
| 195 | NP1L1_HUMAN | P55209 | GLVETPTGYIESLPR | 58 | 1 | Nucleosome assembly protein 1-like 1 |
| 196 | NP1L1_HUMAN | P55209 | GLVETPTGYIESLPRVVKR | 58 | 1 | Nucleosome assembly protein 1-like 1 |
| | NP1L1_HUMAN | P55209 | | 184 | 1 | Nucleosome assembly protein 1-like 1 |
| 197 | NP1L4_HUMAN | Q99733 | GVPSDSVEAAK | 9 | 1 | Nucleosome assembly protein 1-like 4 |
| 198 | NP1L4_HUMAN | Q99733 | GVPSDSVEAAKNASNTEK | 9 | 1 | Nucleosome assembly protein 1-like 4 |
| | NP1L4_HUMAN | Q99733 | | 9 | 1 | Nucleosome assembly protein 1-like 4 |
| 199 | NP1L4_HUMAN | Q99733 | GVPSDSVEAAKNASNTEKLTDQVMQNPR | 9 | 1 | Nucleosome assembly protein 1-like 4 |
| 200 | NP1L4_HUMAN | Q99733 | NVPHTPSSYIETLPK | 47 | 1 | Nucleosome assembly protein 1-like 4 |
| | NP60_HUMAN | Q49A26 | | 256 | 1 | Nuclear protein NP60 |
| | NPAT_HUMAN | Q14207 | | 734 | 1 | Protein NPAT |
| | NPM_HUMAN | P06748 | | 7 | 1 | Nucleophosmin |
| | NPM_HUMAN | P06748 | | 4 | 1 | Nucleophosmin |
| | NS1BP_HUMAN | Q9Y6Y0 | | 239 | 1 | Influenza virus NS1A-binding protein |
| | NSBP1_HUMAN | P82970 | | 58 | 1 | Nucleosome-binding protein 1 |
| 201 | NSUN2_HUMAN | Q08J23 | GQKVEVPQPLSWYPEELAWHTNLSR | 109 | 1 | tRNA (cytosine-5-)-methyltransferase NSUN2 |
| 202 | NSUN2_HUMAN | Q08J23 | GQKVEVPQPLSWYPEELAWHTNLSRK | 109 | 1 | tRNA (cytosine-5-)-methyltransferase NSUN2 |
| | NSUN2_HUMAN | Q08J23 | | 500 | 1 | tRNA (cytosine-5-)-methyltransferase NSUN2 |
| | NSUN2_HUMAN | Q08J23 | | 500 | 1 | tRNA (cytosine-5-)-methyltransferase NSUN2 |
| | NSUN2_HUMAN | Q08J23 | | 665 | 1 | tRNA (cytosine-5-)-methyltransferase NSUN2 |
| | NU153_HUMAN | P49790 | | 359 | 1 | Nuclear pore complex protein Nup153 |
| | NUCB2_HUMAN | P80303 | | 259 | 1 | Nucleobindin-2 |
| | NUCB2_HUMAN | P80303 | | 238 | 1 | Nucleobindin-2 |
| | NUCKS_HUMAN | Q9H1E3 | | 30 | 3 | Nuclear ubiquitous casein |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | | | | | | and cyclin-dependent kinases substrate |
| | NUCL_HUMAN | P19338 | | 637 | 1 | Nucleolin |
| | NUDC3_HUMAN | Q8IVD9 | | 126 | 1 | NudC domain-containing protein 3 |
| | NUDC3_HUMAN | Q8IVD9 | | 126 | 1 | NudC domain-containing protein 3 |
| | NUDC3_HUMAN | Q8IVD9 | | 120 | 1 | NudC domain-containing protein 3 |
| | NUFP2_HUMAN | Q7Z417 | | 452 | 1 | Nuclear fragile X mental retardation-interacting protein 2 |
| | NUMA1_HUMAN | Q14980 | | 1748 | 1 | Nuclear mitotic apparatus protein 1 |
| | NUMA1_HUMAN | Q14980 | | 1748 | 1 | Nuclear mitotic apparatus protein 1 |
| | NUMA1_HUMAN | Q14980 | | 1830 | 1 | Nuclear mitotic apparatus protein 1 |
| 203 | NUP43_HUMAN | Q8NFH3 | GGFEGDHQLLCDIR | 59 | 1 | Nucleoporin Nup43 |
| | NUP50_HUMAN | Q9UKX7 | | 127 | 1 | Nucleoporin 50 kDa |
| 204 | NUP93_HUMAN | Q8N1F7 | FTQESEPSYISDVGPPGR | 158 | 1 | Nuclear pore complex protein Nup93 |
| 205 | ODPB_HUMAN | P11177 | AINQGMDEELERDEK | 38 | 1 | Pyruvate dehydrogenase E1 component subunit beta, mitochondrial |
| | OFD1_HUMAN | O75665 | | 854 | 1 | Oral-facial-digital syndrome 1 protein |
| | ORAV1_HUMAN | Q8WV07 | | 10 | 1 | Oral cancer overexpressed protein 1 |
| | OSBL8_HUMAN | Q9BZF1 | | 807 | 1 | Oxysterol-binding protein-related protein 8 |
| | OTU6B_HUMAN | Q8N6M0 | | 81 | 1 | OTU domain-containing protein 6B |
| | OTUD4_HUMAN | Q01804 | | 10 | 1 | OTU domain-containing protein 4 |
| | OXR1_HUMAN | Q8N573 | | 450 | 1 | Oxidation resistance protein 1 |
| | OXR1_HUMAN | Q8N573 | | 450 | 1 | Oxidation resistance protein 1 |
| | P4R3A_HUMAN | Q6IN85 | | 693 | 1 | Serine/threonine-protein phosphatase 4 regulatory subunit 3A |
| | P66B_HUMAN | Q8WXI9 | | 345 | 1 | Transcriptional repressor p66-beta |
| 206 | PA24A_HUMAN | P47712 | AAVADPDEFER | 523 | 1 | Cytosolic phospholipase A2 |
| 207 | PABP2_HUMAN | Q86U42 | GAIEDPELEAIK | 112 | 1 | Polyadenylate-binding protein 2 |
| 208 | PABP2_HUMAN | Q86U42 | GAIEDPELEAIKAR | 112 | 1 | Polyadenylate-binding protein 2 |
| | PAIRB_HUMAN | Q8NC51 | | 338 | 1 | Plasminogen activator inhibitor 1 RNA-binding protein |
| | PAK1_HUMAN | Q13153 | | 91 | 2 | Serine/threonine-protein kinase PAK 1 |
| | PAK2_HUMAN | Q13177 | | 90 | | Serine/threonine-protein kinase PAK 2 |
| | PAK2_HUMAN | Q13177 | | 149 | 1 | Serine/threonine-protein kinase PAK 2 |
| | PALLD_HUMAN | Q8WX93 | | 433 | 1 | Palladin |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | PARG_HUMAN | Q86W56 | | 257 | 1 | Poly(ADP-ribose) glycohydrolase |
| | PARP1_HUMAN | P09874 | | 215 | 1 | Poly [ADP-ribose] polymerase 1 |
| | PARP1_HUMAN | P09874 | | 215 | 1 | Poly [ADP-ribose] polymerase 1 |
| | PARP1_HUMAN | P09874 | | 215 | 1 | Poly [ADP-ribose] polymerase 1 |
| | PARP1_HUMAN | P09874 | | 73 | 1 | Poly [ADP-ribose] polymerase 1 |
| | PAWR_HUMAN | Q96IZ0 | | 132 | 1 | PRKC apoptosis WT1 regulator protein |
| | PAXI_HUMAN | P49023 | | 103 | 1 | Paxillin |
| | PAXI_HUMAN | P49023 | | 6 | 1 | Paxillin |
| | PAXI_HUMAN | P49023 | | 336 | 1 | Paxillin |
| | PB1_HUMAN | Q86U86 | | 22 | 1 | Protein polybromo-1 |
| | PCBP1_HUMAN | Q15365 | | 204 | 1 | Poly(rC)-binding protein 1 |
| 209 | PCBP1_HUMAN | Q15365 | AYSIQGQHTISPLDLAK | 221 | 1 | Poly(rC)-binding protein 1 |
| 210 | PCBP1_HUMAN | Q15365 | ASTQTTHELTIPNNLIGCIIGR | 276 | 1 | Poly(rC)-binding protein 1 |
| | PCBP2_HUMAN | Q15366 | | 283 | 1 | Poly(rC)-binding protein 2 |
| | PCF11_HUMAN | O94913 | | 1289 | 1 | Pre-mRNA cleavage complex 2 protein Pcf11 |
| 211 | PCM1_HUMAN | Q15154 | GRGEPAMESSQIVSR | 194 | 1 | Pericentriolar material 1 protein |
| | PCM1_HUMAN | Q15154 | | 1552 | 1 | Pericentriolar material 1 protein |
| | PCNT_HUMAN | O95613 | | 81 | 1 | Pericentrin |
| 212 | PDIP3_HUMAN | Q9BY77 | AYTAPALPSSIR | 235 | 1 | Polymerase delta-interacting protein 3 |
| | PDLI1_HUMAN | O00151 | | 55 | 1 | PDZ and LIM domain protein 1 |
| | PDXD1_HUMAN | Q6P996 | | 585 | 1 | Pyridoxal-dependent decarboxylase domain-containing protein 1 |
| | PEBB_HUMAN | Q13951 | | 121 | 1 | Core-binding factor subunit beta |
| | PFTK1_HUMAN | O94921 | | 57 | 1 | Serine/threonine-protein kinase PFTAIRE-1 |
| 213 | PGK1_HUMAN | P00558 | CVGPEVEK | 99 | 1 | Phosphoglycerate kinase 1 |
| 214 | PGK1_HUMAN | P00558 | CVGPEVEKACANPAAGSVILLENLR | 99 | 1 | Phosphoglycerate kinase 1 |
| | PGK1_HUMAN | P00558 | | 286 | 1 | Phosphoglycerate kinase 1 |
| | PGK1_HUMAN | P00558 | | 69 | 1 | Phosphoglycerate kinase 1 |
| | PGK1_HUMAN | P00558 | | 160 | 2 | Phosphoglycerate kinase 1 |
| | PGK2_HUMAN | P07205 | | 160 | | Phosphoglycerate kinase 2 |
| | PHAR4_HUMAN | Q8IZ21 | | 21 | 1 | Phosphatase and actin regulator 4 |
| | PHF3_HUMAN | Q92576 | | 1627 | 1 | PHD finger protein 3 |
| | PHF3_HUMAN | Q92576 | | 1100 | 1 | PHD finger protein 3 |
| | PHF3_HUMAN | Q92576 | | 1158 | 1 | PHD finger protein 3 |
| | PHF3_HUMAN | Q92576 | | 1398 | 1 | PHD finger protein 3 |
| | PHTNS_HUMAN | Q6NYC8 | | 496 | 1 | Phostensin |
| 215 | PI4KB_HUMAN | Q9UBF8 | SITSQESKEPVFIAAGDIR | 489 | 1 | Phosphatidylinositol 4-kinase beta |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 216 | PI4KB_HUMAN | Q9UBF8 | SITSQESKEPVFIAAGDIRR | 489 | 1 | Phosphatidylinositol 4-kinase beta |
| 217 | PIAS1_HUMAN | O75925 | GHPASSPLLPVSLLGPK | 101 | 1 | E3 SUMO-protein ligase PIAS1 |
|  | PICAL_HUMAN | Q13492 |  | 277 | 1 | Phosphatidylinositol-binding clathrin assembly protein |
|  | PITM1_HUMAN | O00562 |  | 379 | 1 | Membrane-associated phosphatidylinositol transfer protein 1 |
|  | PJA2_HUMAN | O43164 |  | 87 | 1 | E3 ubiquitin-protein ligase Praja2 |
|  | PKHG1_HUMAN | Q9ULL1 |  | 436 | 1 | Pleckstrin homology domain-containing family G member 1 |
|  | PKP4_HUMAN | Q99569 |  | 804 | 1 | Plakophilin-4 |
|  | PLCG1_HUMAN | P19174 |  | 771 | 1 | 1-phosphatidylinositol-4,5-bisphosphate phosphodiesterase gamma-1 |
|  | PLDN_HUMAN | Q9UL45 |  | 11 | 1 | Pallidin |
|  | POGZ_HUMAN | Q7Z3K3 |  | 28 | 1 | Pogo transposable element with ZNF domain |
|  | POMP_HUMAN | Q9Y244 |  | 13 | 1 | Proteasome maturation protein |
|  | PP1RA_HUMAN | Q96QC0 |  | 377 | 1 | Serine/threonine-protein phosphatase 1 regulatory subunit 10 |
|  | PP1RA_HUMAN | Q96QC0 |  | 294 | 1 | Serine/threonine-protein phosphatase 1 regulatory subunit 10 |
|  | PP1RA_HUMAN | Q96QC0 |  | 367 | 1 | Serine/threonine-protein phosphatase 1 regulatory subunit 10 |
|  | PP4R1_HUMAN | Q8TF05 |  | 445 | 1 | Serine/threonine-protein phosphatase 4 regulatory subunit 1 |
|  | PPIA_HUMAN | P62937 |  | 10 | 1 | Peptidyl-prolyl cis-trans isomerase A |
| 218 | PPIL4_HUMAN | Q8WUA2 | ADIKPPENVLFVCK | 233 | 1 | Peptidyl-prolyl cis-trans isomerase-like 4 |
|  | PPR3D_HUMAN | O95685 |  | 32 | 1 | Protein phosphatase 1 regulatory subunit 3D |
|  | PR40A_HUMAN | O75400 |  | 134 | 1 | Pre-mRNA-processing factor 40 homolog A |
|  | PRD15_HUMAN | P57071 |  | 1270 | 1 | PR domain zinc finger protein 15 |
|  | PRD15_HUMAN | P57071 |  | 1270 | 1 | PR domain zinc finger protein 15 |
| 219 | PRKDC_HUMAN | P78527 | GDPSDRMEVQEQEEDISSLIR | 3212 | 1 | DNA-dependent protein kinase catalytic subunit |
|  | PROF1_HUMAN | P07737 |  | 20 | 1 | Profilin-1 |
|  | PROF1_HUMAN | P07737 |  | 82 | 1 | Profilin-1 |
|  | PROF1_HUMAN | P07737 |  | 82 | 1 | Profilin-1 |
|  | PROF1_HUMAN | P07737 |  | 15 | 1 | Profilin-1 |
|  | PRP17_HUMAN | O60508 |  | 56 | 1 | Pre-mRNA-processing factor 17 |
| 220 | PRP17_HUMAN | O60508 | VAKPSEEEQKELDEITAKR | 205 | 1 | Pre-mRNA-processing factor 17 |
|  | PRP17_HUMAN | O60508 |  | 191 | 1 | Pre-mRNA-processing factor 17 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | PRP17_HUMAN | O60508 | | 205 | 1 | Pre-mRNA-processing factor 17 |
| | PRP17_HUMAN | O60508 | | 205 | 1 | Pre-mRNA-processing factor 17 |
| | PRP31_HUMAN | Q8WWY3 | | 387 | 1 | U4/U6 small nuclear ribonucleoprotein Prp31 |
| | PRR12_HUMAN | Q9ULL5 | | 116 | 1 | Proline-rich protein 12 |
| | PRR3_HUMAN | P79522 | | 32 | 1 | Proline-rich protein 3 |
| | PRS10_HUMAN | P62333 | | 266 | 1 | 26S protease regulatory subunit S10B |
| 221 | PRS6A_HUMAN | P17980 | GIGEEVLK | 28 | 1 | 26S protease regulatory subunit 6A |
| | PRS6A_HUMAN | P17980 | | 28 | 1 | 26S protease regulatory subunit 6A |
| 222 | PRS6A_HUMAN | P17980 | GIGEEVLKMSTEEIIQR | 28 | 1 | 26S protease regulatory subunit 6A |
| | PRS6A_HUMAN | P17980 | | 319 | 1 | 26S protease regulatory subunit 6A |
| 223 | PRS6B_HUMAN | P43686 | GFDQNVNVK | 298 | 1 | 26S protease regulatory subunit 6B |
| 224 | PRS8_HUMAN | P62195 | SIGSSRLEGGSGGDSEVQR | 253 | 1 | 26S protease regulatory subunit 8 |
| | PSA5_HUMAN | P28066 | | 72 | 1 | Proteasome subunit alpha type-5 |
| | PSA7L_HUMAN | Q8TAA3 | | 16 | 2 | Proteasome subunit alpha type-7-like |
| | PSA7_HUMAN | O14818 | | 14 | | Proteasome subunit alpha type-7 |
| | PSB1_HUMAN | P20618 | | 48 | 1 | Proteasome subunit beta type-1 |
| 225 | PSB4_HUMAN | P28070 | SFMDPASALYR | 30 | 1 | Proteasome subunit beta type-4 |
| | PSB7_HUMAN | Q99436 | | 54 | 1 | Proteasome subunit beta type-7 |
| 226 | PSD12_HUMAN | O00232 | YSATVDQR | 20 | 1 | 26S proteasome non-ATPase regulatory subunit 12 |
| | PSD4_HUMAN | Q8NDX1 | | 83 | 1 | PH and SEC7 domain-containing protein 4 |
| | PSD4_HUMAN | Q8NDX1 | | 536 | 1 | PH and SEC7 domain-containing protein 4 |
| | PSIP1_HUMAN | O75475 | | 31 | 1 | PC4 and SFRS1-interacting protein |
| | PSIP1_HUMAN | O75475 | | 31 | 1 | PC4 and SFRS1-interacting protein |
| 227 | PSIP1_HUMAN | O75475 | SVITQVLNK | 434 | 1 | PC4 and SFRS1-interacting protein |
| | PSME3_HUMAN | P61289 | | 78 | 1 | Proteasome activator complex subunit 3 |
| | PTBP1_HUMAN | P26599 | | 3 | 1 | Polypyrimidine tract-binding protein 1 |
| | PTBP1_HUMAN | P26599 | | 3 | 1 | Polypyrimidine tract-binding protein 1 |
| | PTBP1_HUMAN | P26599 | | 173 | 1 | Polypyrimidine tract-binding protein 1 |
| | PTBP1_HUMAN | P26599 | | 173 | 1 | Polypyrimidine tract-binding protein 1 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | PTBP1_HUMAN | P26599 | | 173 | 1 | Polypyrimidine tract-binding protein 1 |
| | PTBP1_HUMAN | P26599 | | 173 | 1 | Polypyrimidine tract-binding protein 1 |
| | PTBP1_HUMAN | P26599 | | 140 | 2 | Polypyrimidine tract-binding protein 1 |
| | PTCA_HUMAN | Q14761 | | 121 | 1 | Protein tyrosine phosphatase receptor type C-associated protein |
| | PTCA_HUMAN | Q14761 | | 121 | 1 | Protein tyrosine phosphatase receptor type C-associated protein |
| | PTCA_HUMAN | Q14761 | | 117 | 1 | Protein tyrosine phosphatase receptor type C-associated protein |
| | PTMA_HUMAN | P06454 | | 4 | 1 | Prothymosin alpha |
| | PTMA_HUMAN | P06454 | | 4 | 1 | Prothymosin alpha |
| | PTMA_HUMAN | P06454 | | 8 | 1 | Prothymosin alpha |
| | PTMA_HUMAN | P06454 | | 8 | 1 | Prothymosin alpha |
| 228 | PTN3_HUMAN | P26045 | GVDQQLLDDFHR | 472 | 1 | Tyrosine-protein phosphatase non-receptor type 3 |
| 229 | PUR2_HUMAN | P22102 | GGPNTGGMGAYCPAPQVSNDLLLK | 226 | 1 | Trifunctional purine biosynthetic protein adenosine-3 |
| | PUR2_HUMAN | P22102 | | 206 | 1 | Trifunctional purine biosynthetic protein adenosine-3 |
| | PUR2_HUMAN | P22102 | | 444 | 1 | Trifunctional purine biosynthetic protein adenosine-3 |
| | PUR6_HUMAN | P22234 | | 320 | 1 | Multifunctional protein ADE2 |
| | PUR6_HUMAN | P22234 | | 27 | 1 | Multifunctional protein ADE2 |
| 230 | PUR9_HUMAN | P31939 | GIIAPGYEEEALTILSK | 340 | 1 | Bifunctional purine biosynthesis protein PURH |
| | PUS7_HUMAN | Q96PZ0 | | 51 | 1 | Pseudouridylate synthase 7 homolog |
| | PUS7_HUMAN | Q96PZ0 | | 23 | 1 | Pseudouridylate synthase 7 homolog |
| 231 | PWP2A_HUMAN | Q96N64 | GQQSAPQADEPPLPPPPPPPGELAR | 56 | 1 | PWWP domain-containing protein 2A |
| | PYR1_HUMAN | P27708 | | 1139 | 1 | CAD protein |
| | QKI_HUMAN | Q96PU8 | | 75 | 1 | Protein quaking |
| | QN1_HUMAN | Q5TB80 | | 248 | 1 | Protein QN1 homolog |
| | QSER1_HUMAN | Q2KHR3 | | 1322 | 1 | Glutamine and serine-rich protein 1 |
| 232 | QSK_HUMAN | Q9Y2K2 | GTLNLDSDEGEEPSPEALVR | 384 | 1 | Serine/threonine-protein kinase QSK |
| | R3HD1_HUMAN | Q15032 | | 500 | 1 | R3H domain-containing protein 1 |
| | R3HD1_HUMAN | Q15032 | | 500 | 1 | R3H domain-containing protein 1 |
| | RA1L3_HUMAN | P0C7M2 | | 158 | 3 | Putative heterogeneous nuclear ribonucleoprotein A1-like protein 3 |
| | ROA1L_HUMAN | Q32P51 | | 158 | | Heterogeneous nuclear ribonucleoprotein A1-like protein |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | ROA1_HUMAN | P09651 | | 158 | | Heterogeneous nuclear ribonucleoprotein A1 |
| | RA1L3_HUMAN | P0C7M2 | | 95 | 3 | Putative heterogeneous nuclear ribonucleoprotein A1-like protein 3 |
| | ROA1L_HUMAN | Q32P51 | | 95 | | Heterogeneous nuclear ribonucleoprotein A1-like protein |
| | ROA1_HUMAN | P09651 | | 95 | | Heterogeneous nuclear ribonucleoprotein A1 |
| | RA1L3_HUMAN | P0C7M2 | | 70 | 2 | Putative heterogeneous nuclear ribonucleoprotein A1-like protein 3 |
| | ROA1_HUMAN | P09651 | | 70 | | Heterogeneous nuclear ribonucleoprotein A1 |
| | RA1L3_HUMAN | P0C7M2 | | 158 | 2 | Putative heterogeneous nuclear ribonucleoprotein A1-like protein 3 |
| | ROA1_HUMAN | P09651 | | 158 | | Heterogeneous nuclear ribonucleoprotein A1 |
| | RA1L3_HUMAN | P0C7M2 | | 70 | 2 | Putative heterogeneous nuclear ribonucleoprotein A1-like protein 3 |
| | ROA1_HUMAN | P09651 | | 70 | | Heterogeneous nuclear ribonucleoprotein A1 |
| 233 | RAD21_HUMAN | O60216 | SVDPVEPMPTMTDQTTLVPNEEEAFALEPIDITVK | 280 | 1 | Double-strand-break repair protein rad21 homolog |
| | RAD21_HUMAN | O60216 | | 280 | 1 | Double-strand-break repair protein rad21 homolog |
| 234 | RAD21_HUMAN | O60216 | SVDPVEPMPTMTDQTTLVPNEEEAFALEPIDITVKETK | 280 | 1 | Double-strand-break repair protein rad21 homolog |
| 235 | RAD21_HUMAN | O60216 | VAQQFSLNQSR | 129 | 1 | Double-strand-break repair protein rad21 homolog |
| | RADIL_HUMAN | Q96JH8 | | 842 | 1 | Ras-associating and dilute domain-containing protein |
| | RADIL_HUMAN | Q96JH8 | | 842 | 1 | Ras-associating and dilute domain-containing protein |
| | RANG_HUMAN | P43487 | | 128 | 1 | Ran-specific GTPase-activating protein |
| | RB3GP_HUMAN | Q15042 | | 253 | 1 | Rab3 GTPase-activating protein catalytic subunit |
| | RBBP4_HUMAN | Q09028 | | 362 | 2 | Histone-binding protein RBBP4 |
| | RBBP7_HUMAN | Q16576 | | 361 | | Histone-binding protein RBBP7 |
| | RBBP6_HUMAN | Q7Z6E9 | | 973 | 1 | Retinoblastoma-binding protein 6 |
| | RBBP6_HUMAN | Q7Z6E9 | | 1679 | 1 | Retinoblastoma-binding protein 6 |
| | RBBP6_HUMAN | Q7Z6E9 | | 1268 | 1 | Retinoblastoma-binding protein 6 |
| | RBBP6_HUMAN | Q7Z6E9 | | 1268 | 1 | Retinoblastoma-binding protein 6 |
| 236 | RBBP7_HUMAN | Q16576 | SDKGEFGGFGSVTGK | 99 | 1 | Histone-binding protein RBBP7 |
| | RBBP7_HUMAN | Q16576 | | 94 | 1 | Histone-binding protein RBBP7 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | RBBP8_HUMAN | Q99708 | | 743 | 1 | Retinoblastoma-binding protein 8 |
| | RBM15_HUMAN | Q96T37 | | 751 | 1 | Putative RNA-binding protein 15 |
| 237 | RBM16_HUMAN | Q9UPN6 | GVEEEVFEQEAK | 381 | 1 | Putative RNA-binding protein 16 |
| | RBM16_HUMAN | Q9UPN6 | | 776 | 1 | Putative RNA-binding protein 16 |
| | RBM25_HUMAN | P49756 | | 634 | 1 | Probable RNA-binding protein 25 |
| | RBM26_HUMAN | Q5T8P6 | | 432 | 1 | RNA-binding protein 26 |
| 238 | RBM26_HUMAN | Q5T8P6 | GYNPEAPSITNTSRPMYR | 432 | 1 | RNA-binding protein 26 |
| | RBM26_HUMAN | Q5T8P6 | | 281 | 1 | RNA-binding protein 26 |
| | RBM26_HUMAN | Q5T8P6 | | 281 | 1 | RNA-binding protein 26 |
| | RBM27_HUMAN | Q9P2N5 | | 488 | 1 | RNA-binding protein 27 |
| | RBM28_HUMAN | Q9NW13 | | 245 | 1 | RNA-binding protein 28 |
| | RBM33_HUMAN | Q96EV2 | | 999 | 1 | RNA-binding protein 33 |
| 239 | RBM39_HUMAN | Q14498 | ASSASSFLDSDELER | 332 | 1 | RNA-binding protein 39 |
| 240 | RBM39_HUMAN | Q14498 | ASSASSFLDSDELERTGIDLGTTGR | 332 | 1 | RNA-binding protein 39 |
| | RBM8A_HUMAN | Q9Y5S9 | | 7 | 1 | RNA-binding protein 8A |
| | RBM8A_HUMAN | Q9Y5S9 | | 7 | 1 | RNA-binding protein 8A |
| | RBM8A_HUMAN | Q9Y5S9 | | 7 | 1 | RNA-binding protein 8A |
| | RBM8A_HUMAN | Q9Y5S9 | | 7 | 1 | RNA-binding protein 8A |
| | RBM8A_HUMAN | Q9Y5S9 | | 7 | 1 | RNA-binding protein 8A |
| 241 | RBM8A_HUMAN | Q9Y5S9 | SVEQDGDEPGPQR | 56 | 1 | RNA-binding protein 8A |
| | RBM9_HUMAN | O43251 | | 103 | 1 | RNA-binding protein 9 |
| | RBP2_HUMAN | P49792 | | 2491 | 1 | E3 SUMO-protein ligase RanBP2 |
| 242 | RBP2_HUMAN | P49792 | GGSAHGDDDDGPHFEPVVPLPDKIEVK | 1158 | 1 | E3 SUMO-protein ligase RanBP2 |
| 243 | RBP2_HUMAN | P49792 | GTGGQSIYGDKFEDENFDVK | 3132 | 1 | E3 SUMO-protein ligase RanBP2 |
| | RBP2_HUMAN | P49792 | | 2861 | 1 | E3 SUMO-protein ligase RanBP2 |
| | RBP2_HUMAN | P49792 | | 1158 | 1 | E3 SUMO-protein ligase RanBP2 |
| | RBP2_HUMAN | P49792 | | 2307 | 7 | E3 SUMO-protein ligase RanBP2 |
| | RGPD1_HUMAN | Q68DN6 | | 1316 | | RANBP2-like and GRIP domain-containing protein 1 |
| | RGPD3_HUMAN | A6NKT7 | | 1332 | | RANBP2-like and GRIP domain-containing protein 3 |
| | RGPD4_HUMAN | Q7Z3J3 | | 1332 | | RANBP2-like and GRIP domain-containing protein 4 |
| | RGPD5_HUMAN | Q99666 | | 1331 | | RANBP2-like and GRIP domain-containing protein 5 |
| | RGPD6_HUMAN | Q53T03 | | 1331 | | RANBP2-like and GRIP domain-containing protein 6 |
| | RGPD8_HUMAN | O14715 | | 321 | | RANBP2-like and GRIP domain-containing protein 8 (Fragment) |
| | RBP2_HUMAN | P49792 | | 2237 | 6 | E3 SUMO-protein ligase RanBP2 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | RGPD3_HUMAN | A6NKT7 | | 1262 | | RANBP2-like and GRIP domain-containing protein 3 |
| | RGPD4_HUMAN | Q7Z3J3 | | 1262 | | RANBP2-like and GRIP domain-containing protein 4 |
| | RGPD5_HUMAN | Q99666 | | 1261 | | RANBP2-like and GRIP domain-containing protein 5 |
| | RGPD6_HUMAN | Q53T03 | | 1261 | | RANBP2-like and GRIP domain-containing protein 6 |
| | RGPD8_HUMAN | O14715 | | 251 | | RANBP2-like and GRIP domain-containing protein 8 (Fragment) |
| | RBP56_HUMAN | Q92804 | | 141 | 1 | TATA-binding protein-associated factor 2N |
| | RBTN1_HUMAN | P25800 | | 9 | 1 | Rhombotin-1 |
| | RBY1B_HUMAN | A6NDE4 | | 467 | 3 | RNA-binding motif protein, Y chromosome, family 1 member B |
| | RBY1F_HUMAN | Q15415 | | 467 | | RNA-binding motif protein, Y chromosome, family 1 member F/J |
| | RBY1H_HUMAN | Q15378 | | 327 | | Putative RNA-binding motif protein, Y chromosome, family 1 member H |
| 244 | RB_HUMAN | P06400 | SIDSFETQR | 347 | 1 | Retinoblastoma-associated protein |
| | RCAN1_HUMAN | P53805 | | 4 | 1 | Calcipressin-1 |
| | RCC2_HUMAN | Q9P258 | | 61 | 1 | Protein RCC2 |
| | RCC2_HUMAN | Q9P258 | | 61 | 1 | Protein RCC2 |
| | RCN2_HUMAN | Q14257 | | 204 | 1 | Reticulocalbin-2 |
| | RCOR2_HUMAN | Q8IZ40 | | 392 | 1 | REST corepressor 2 |
| | RCOR2_HUMAN | Q8IZ40 | | 392 | 1 | REST corepressor 2 |
| | RCOR2_HUMAN | Q8IZ40 | | 392 | 1 | REST corepressor 2 |
| | RCOR2_HUMAN | Q8IZ40 | | 392 | 1 | REST corepressor 2 |
| | RD23B_HUMAN | P54727 | | 166 | 1 | UV excision repair protein RAD23 homolog B |
| 245 | RED_HUMAN | Q13123 | GVNKDYEETELISTTANYR | 109 | 1 | Protein Red |
| 246 | RED_HUMAN | Q13123 | YVPSTTK | 325 | 2 | Protein Red |
| 247 | RED_HUMAN | Q13123 | YVPSTTKTPR | 325 | 1 | Protein Red |
| 248 | REL_HUMAN | Q04864 | GYYEAEFGQER | 87 | 1 | C-Rel proto-oncogene protein |
| | RENT1_HUMAN | Q92900 | | 76 | 1 | Regulator of nonsense transcripts 1 |
| 249 | REPS1_HUMAN | Q96D71 | SFTSDPEQIGSNVTR | 466 | 1 | RalBP1-associated Eps domain-containing protein 1 |
| 250 | REPS1_HUMAN | Q96D71 | SNIAPADPDTAIVHPVPIR | 387 | 1 | RalBP1-associated Eps domain-containing protein 1 |
| 251 | REPS1_HUMAN | Q96D71 | GYSSSDSFTSDPEQIGSNVTR | 460 | 1 | RalBP1-associated Eps domain-containing protein 1 |
| | REQU_HUMAN | Q92785 | | 244 | 1 | Zinc finger protein ubi-d4 |
| 252 | REQU_HUMAN | Q92785 | GSSLEALLR | 116 | 1 | Zinc finger protein ubi-d4 |
| | REST_HUMAN | Q13127 | | 942 | 1 | RE1-silencing transcription factor |
| | RFC1_HUMAN | P35251 | | 724 | 1 | Replication factor C subunit 1 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 253 | RFC1_HUMAN | P35251 | GMAGNEDR | 724 | 1 | Replication factor C subunit 1 |
| 254 | RFC1_HUMAN | P35251 | GMAGNEDRGGIQELIGLIK | 724 | 1 | Replication factor C subunit 1 |
| | RFC1_HUMAN | P35251 | | 168 | 1 | Replication factor C subunit 1 |
| | RFX7_HUMAN | Q2KHR2 | | 480 | 1 | DNA-binding protein RFX7 |
| | RGAP1_HUMAN | Q9H0H5 | | 274 | 1 | Rac GTPase-activating protein 1 |
| | RGAP1_HUMAN | Q9H0H5 | | 274 | 1 | Rac GTPase-activating protein 1 |
| | RGPD1_HUMAN | Q68DN6 | | 1500 | 7 | RANBP2-like and GRIP domain-containing protein 1 |
| | RGPD2_HUMAN | P0C839 | | 765 | | RANBP2-like and GRIP domain-containing protein 2 |
| | RGPD3_HUMAN | A6NKT7 | | 1516 | | RANBP2-like and GRIP domain-containing protein 3 |
| | RGPD4_HUMAN | Q7Z3J3 | | 1516 | | RANBP2-like and GRIP domain-containing protein 4 |
| | RGPD5_HUMAN | Q99666 | | 1515 | | RANBP2-like and GRIP domain-containing protein 5 |
| | RGPD6_HUMAN | Q53T03 | | 1515 | | RANBP2-like and GRIP domain-containing protein 6 |
| | RGPD8_HUMAN | O14715 | | 505 | | RANBP2-like and GRIP domain-containing protein 8 (Fragment) |
| | RGS10_HUMAN | O43665 | | 15 | 1 | Regulator of G-protein signaling 10 |
| | RGS10_HUMAN | O43665 | | 13 | 1 | Regulator of G-protein signaling 10 |
| | RHG04_HUMAN | P98171 | | 404 | 1 | Rho GTPase-activating protein 4 |
| | RHG04_HUMAN | P98171 | | 404 | 1 | Rho GTPase-activating protein 4 |
| 255 | RHG25_HUMAN | P42331 | SFSSMTSDSDTTSPTGQQPSDAFPEDSSKVPR | 388 | 1 | Rho GTPase-activating protein 25 |
| | RHG25_HUMAN | P42331 | | 398 | 1 | Rho GTPase-activating protein 25 |
| 256 | RHG30_HUMAN | Q7Z6I6 | GCLCPCSLGLGGVGMR | 908 | 1 | Rho GTPase-activating protein 30 |
| | RHG30_HUMAN | Q7Z6I6 | | 593 | 1 | Rho GTPase-activating protein 30 |
| 257 | RHG30_HUMAN | Q7Z6I6 | SIEAAEGEQEPEAEALGGTNSEPGTPR | 364 | 1 | Rho GTPase-activating protein 30 |
| | RHGBA_HUMAN | Q6P4F7 | | 257 | 1 | Rho GTPase-activating protein 11A |
| 258 | RHOA_HUMAN | P61586 | SLENIPEKWTPEVK | 91 | 2 | Transforming protein RhoA |
| 258 | RHOC_HUMAN | P08134 | SLENIPEKWTPEVK | 91 | | Rho-related GTP-binding protein RhoC |
| | RIF1_HUMAN | Q5UIP0 | | 1810 | 1 | Telomere-associated protein RIF1 |
| | RIF1_HUMAN | Q5UIP0 | | 2001 | 1 | Telomere-associated protein RIF1 |
| | RIMB1_HUMAN | O95153 | | 1808 | 1 | Peripheral-type benzodiazepine receptor-associated protein 1 |
| | RIMB1_HUMAN | O95153 | | 45 | 1 | Peripheral-type benzodiazepine receptor-associated protein 1 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 259 | RING1_HUMAN | Q06587 | GTEIAVSPR | 32 | 1 | E3 ubiquitin-protein ligase RING1 |
| | RIOK1_HUMAN | Q9BRS2 | | 130 | 1 | Serine/threonine-protein kinase RIO1 |
| | RIOK1_HUMAN | Q9BRS2 | | 130 | 1 | Serine/threonine-protein kinase RIO1 |
| | RIPK1_HUMAN | Q13546 | | 559 | 1 | Receptor-interacting serine/threonine-protein kinase 1 |
| | RIR2_HUMAN | P31350 | | 30 | 1 | Ribonucleoside-diphosphate reductase subunit M2 |
| | RL17_HUMAN | P18621 | | 111 | 1 | 60S ribosomal protein L17 |
| 260 | RL5_HUMAN | P46777 | GQPGAFTCYLDAGLAR | 137 | 1 | 60S ribosomal protein L5 |
| | RL5_HUMAN | P46777 | | 169 | 1 | 60S ribosomal protein L5 |
| | RN168_HUMAN | Q8IYW5 | | 251 | 1 | RING finger protein 168 |
| 261 | RN213_HUMAN | Q63HN8 | GVREEDLAPFSLR | 356 | 1 | RING finger protein 213 |
| | RN219_HUMAN | Q5W0B1 | | 434 | 1 | RING finger protein 219 |
| | RN220_HUMAN | Q5VTB9 | | 414 | 1 | RING finger protein 220 |
| | RNF5_HUMAN | Q99942 | | 9 | 1 | E3 ubiquitin-protein ligase RNF5 |
| | RNZ1_HUMAN | Q9H777 | | 280 | 1 | Zinc phosphodiesterase ELAC protein 1 |
| | ROA0_HUMAN | Q13151 | | 63 | 1 | Heterogeneous nuclear ribonucleoprotein A0 |
| | ROA0_HUMAN | Q13151 | | 74 | 1 | Heterogeneous nuclear ribonucleoprotein A0 |
| | ROA0_HUMAN | Q13151 | | 63 | 1 | Heterogeneous nuclear ribonucleoprotein A0 |
| | ROA0_HUMAN | Q13151 | | 63 | 1 | Heterogeneous nuclear ribonucleoprotein A0 |
| | ROA2_HUMAN | P22626 | | 77 | 1 | Heterogeneous nuclear ribonucleoproteins A2/B1 |
| | ROA2_HUMAN | P22626 | | 77 | 1 | Heterogeneous nuclear ribonucleoproteins A2/B1 |
| | ROA2_HUMAN | P22626 | | 77 | 1 | Heterogeneous nuclear ribonucleoproteins A2/B1 |
| | ROA2_HUMAN | P22626 | | 131 | 1 | Heterogeneous nuclear ribonucleoproteins A2/B1 |
| | ROA3_HUMAN | P51991 | | 91 | 1 | Heterogeneous nuclear ribonucleoprotein A3 |
| 262 | ROA3_HUMAN | P51991 | SVKPGAHLTVKK | 116 | 1 | Heterogeneous nuclear ribonucleoprotein A3 |
| | ROA3_HUMAN | P51991 | | 179 | 1 | Heterogeneous nuclear ribonucleoprotein A3 |
| | ROA3_HUMAN | P51991 | | 91 | 1 | Heterogeneous nuclear ribonucleoprotein A3 |
| | ROA3_HUMAN | P51991 | | 116 | 1 | Heterogeneous nuclear ribonucleoprotein A3 |
| | ROCK1_HUMAN | Q13464 | | 1114 | 1 | Rho-associated protein kinase 1 |
| | RPAP3_HUMAN | Q9H6T3 | | 125 | 1 | RNA polymerase II-associated protein 3 |
| | RPAP3_HUMAN | Q9H6T3 | | 452 | 1 | RNA polymerase II-associated protein 3 |
| | RPAP3_HUMAN | Q9H6T3 | | 452 | 1 | RNA polymerase II-associated protein 3 |
| | RPB9_HUMAN | P36954 | | 5 | 1 | DNA-directed RNA polymerase II subunit RPB9 |
| | RPC4_HUMAN | P05423 | | 132 | 1 | DNA-directed RNA polymerase III subunit RPC4 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 263 | RPC5_HUMAN | Q9NVU0 | SFNGHPPQGCASTPVAR | 544 | 1 | DNA-directed RNA polymerase III subunit RPC5 |
| | RPGF6_HUMAN | Q8TEU7 | | 1283 | 1 | Rap guanine nucleotide exchange factor 6 |
| 264 | RPGF6_HUMAN | Q8TEU7 | SMSAALQDER | 1283 | 1 | Rap guanine nucleotide exchange factor 6 |
| | RREB1_HUMAN | Q92766 | | 1174 | 1 | RAS-responsive element-binding protein 1 |
| 265 | RRMJ3_HUMAN | Q8IY81 | STAGTTKQPSKEEEEEEEEQLNQTLAEMK | 347 | 1 | Putative rRNA methyltransferase 3 |
| | RRP12_HUMAN | Q5JTH9 | | 1162 | 1 | RRP12-like protein |
| | RRP12_HUMAN | Q5JTH9 | | 1162 | 1 | RRP12-like protein |
| | RRP12_HUMAN | Q5JTH9 | | 1162 | 1 | RRP12-like protein |
| 266 | RRP12_HUMAN | Q5JTH9 | GNKMEEEEGAKGEDEEMADPMEDVIIR | 1162 | 1 | RRP12-like protein |
| | RRP12_HUMAN | Q5JTH9 | | 557 | 1 | RRP12-like protein |
| | RRP1B_HUMAN | Q14684 | | 276 | 1 | Ribosomal RNA processing protein 1 homolog B |
| | RS20_HUMAN | P60866 | | 6 | 1 | 40S ribosomal protein S20 |
| | RS23_HUMAN | P62266 | | 89 | 1 | 40S ribosomal protein S23 |
| | RS23_HUMAN | P62266 | | 89 | 1 | 40S ribosomal protein S23 |
| | RS28_HUMAN | P62857 | | 55 | 1 | 40S ribosomal protein S28 |
| | RS3_HUMAN | P23396 | | 33 | 1 | 40S ribosomal protein S3 |
| 267 | RSRC1_HUMAN | Q96IZ7 | SFVQQTFR | 239 | 1 | Arginine/serine-rich coiled-coil protein 1 |
| | RTF1_HUMAN | Q92541 | | 141 | 1 | RNA polymerase-associated protein RTF1 homolog |
| 268 | RTF1_HUMAN | Q92541 | GYGEDLMGDEEDR | 141 | 1 | RNA polymerase-associated protein RTF1 homolog |
| 269 | RTF1_HUMAN | Q92541 | GYGEDLMGDEEDRAR | 141 | 1 | RNA polymerase-associated protein RTF1 homolog |
| | RTN4_HUMAN | Q9NQC3 | | 85 | 1 | Reticulon-4 |
| | RTN4_HUMAN | Q9NQC3 | | 906 | 1 | Reticulon-4 |
| 270 | RU1C_HUMAN | P09234 | TYLTHDSPSVRK | 11 | 1 | U1 small nuclear ribonucleoprotein C |
| 271 | RU1C_HUMAN | P09234 | TYLTHDSPSVR | 11 | 1 | U1 small nuclear ribonucleoprotein C |
| 272 | RU2A_HUMAN | P09661 | AIDFSDNEIR | 46 | 1 | U2 small nuclear ribonucleoprotein A' |
| 273 | RUSD2_HUMAN | Q8IZ73 | STAPSSELGKDDLEELAAAAQK | 442 | 1 | RNA pseudouridylate synthase domain-containing protein 2 |
| | RUXF_HUMAN | P62306 | | 53 | 1 | Small nuclear ribonucleoprotein F |
| | S11IP_HUMAN | Q8N1F8 | | 373 | 1 | Serine/threonine kinase 11-interacting protein |
| | S12A2_HUMAN | P55011 | | 67 | 1 | Solute carrier family 12 member 2 |
| | S2546_HUMAN | Q96AG3 | | 11 | 1 | Solute carrier family 25 member 46 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 274 | S30BP_HUMAN | Q9UHR5 | AYGEDDFSR | 45 | 1 | SAP30-binding protein |
| | SAFB1_HUMAN | Q15424 | | 147 | 1 | Scaffold attachment factor B1 |
| | SAFB1_HUMAN | Q15424 | | 797 | 2 | Scaffold attachment factor B1 |
| | SAFB2_HUMAN | Q14151 | | 821 | | Scaffold attachment factor B2 |
| | SAFB1_HUMAN | Q15424 | | 263 | 2 | Scaffold attachment factor B |
| | SAFB2_HUMAN | Q14151 | | 262 | | Scaffold attachment factor B2 |
| | SAFB1_HUMAN | Q15424 | | 263 | 2 | Scaffold attachment factor B1 |
| | SAFB2_HUMAN | Q14151 | | 262 | | Scaffold attachment factor B2 |
| | SAFB1_HUMAN | Q15424 | | 263 | 2 | Scaffold attachment factor B1 |
| | SAFB2_HUMAN | Q14151 | | 262 | | Scaffold attachment factor B2 |
| | SAFB1_HUMAN | Q15424 | | 361 | 2 | Scaffold attachment factor B1 |
| | SAFB2_HUMAN | Q14151 | | 360 | | Scaffold attachment factor B2 |
| | SAFB1_HUMAN | Q15424 | | 797 | 2 | Scaffold attachment factor B1 |
| | SAFB2_HUMAN | Q14151 | | 821 | | Scaffold attachment factor B2 |
| | SAFB2_HUMAN | Q14151 | | 184 | 1 | Scaffold attachment factor B2 |
| | SAFB2_HUMAN | Q14151 | | 154 | 1 | Scaffold attachment factor B2 |
| | SAFB2_HUMAN | Q14151 | | 154 | 1 | Scaffold attachment factor B2 |
| | SAHH2_HUMAN | O43865 | | 6 | 1 | Putative adenosylhomocysteinase 2 |
| 275 | SAHH2_HUMAN | O43865 | SYSSAASYTDSSDDEVSPR | 74 | 1 | Putative adenosylhomocysteinase 2 |
| 276 | SAHH2_HUMAN | O43865 | SYSSAASYTDSSDDEVSPREK | 74 | 1 | Putative adenosylhomocysteinase 2 |
| | SAHH2_HUMAN | O43865 | | 6 | 1 | Putative adenosylhomocysteinase 2 |
| | SAHH2_HUMAN | O43865 | | 6 | 1 | Putative adenosylhomocysteinase 2 |
| | SAHH2_HUMAN | O43865 | | 6 | 1 | Putative adenosylhomocysteinase 2 |
| | SAHH2_HUMAN | O43865 | | 84 | 1 | Putative adenosylhomocysteinase 2 |
| | SAHH3_HUMAN | Q96HN2 | | 110 | 1 | Putative adenosylhomocysteinase 3 |
| | SAM4B_HUMAN | Q5PRF9 | | 413 | 1 | Sterile alpha motif domain-containing protein 4B |
| | SAPS1_HUMAN | Q9UPN7 | | 359 | 1 | Serine/threonine-protein phosphatase 6 regulatory subunit 1 |
| 277 | SAP_HUMAN | P07602 | VYCEVCEFLVK | 313 | 1 | Proactivator polypeptide |
| 278 | SAP_HUMAN | P07602 | VYCEVCEFLVKEVTK | 313 | 1 | Proactivator polypeptide |
| | SAP_HUMAN | P07602 | | 406 | 1 | Proactivator polypeptide |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 279 | SASH3_HUMAN | O75995 | YSLDSPGPEK | 116 | 1 | SAM and SH3 domain-containing protein 3 |
| | SASH3_HUMAN | O75995 | | 56 | 1 | SAM and SH3 domain-containing protein 3 |
| | SATB1_HUMAN | Q01826 | | 255 | 1 | DNA-binding protein SATB1 |
| | SATT_HUMAN | P43007 | | 13 | 1 | Neutral amino acid transporter A |
| | SC16A_HUMAN | O15027 | | 838 | 1 | Protein transport protein Sec16A |
| | SC16A_HUMAN | O15027 | | 342 | 1 | Protein transport protein Sec16A |
| | SC24B_HUMAN | O95487 | | 296 | 1 | Protein transport protein Sec24B |
| | SCAM3_HUMAN | O14828 | | 40 | 1 | Secretory carrier-associated membrane protein 3 |
| | SCMH1_HUMAN | Q96GD3 | | 512 | 1 | Polycomb protein SCMH1 |
| | SCO1_HUMAN | O75880 | | 189 | 1 | Protein SCO1 homolog, mitochondrial |
| | SCO1_HUMAN | O75880 | | 189 | 1 | Protein SCO1 homolog, mitochondrial |
| | SCOC_HUMAN | Q9UIL1 | | 88 | 1 | Short coiled-coil protein |
| | SCOC_HUMAN | Q9UIL1 | | 88 | 1 | Short coiled-coil protein |
| | SDCG1_HUMAN | O60524 | | 780 | 1 | Serologically defined colon cancer antigen 1 |
| | SEC13_HUMAN | P55735 | | 15 | 1 | Protein SEC13 homolog |
| | SEC20_HUMAN | Q12981 | | 33 | 1 | Vesicle transport protein SEC20 |
| | SENP6_HUMAN | Q9GZR1 | | 50 | 1 | Sentrin-specific protease 6 |
| | SEPT9_HUMAN | Q9UHD8 | | 283 | 1 | Septin-9 |
| | SETD2_HUMAN | Q9BYW2 | | 648 | 1 | Histone-lysine N-methyltransferase SETD2 |
| | SETD2_HUMAN | Q9BYW2 | | 1170 | 1 | Histone-lysine N-methyltransferase SETD2 |
| | SETD2_HUMAN | Q9BYW2 | | 1170 | 1 | Histone-lysine N-methyltransferase SETD2 |
| 280 | SETX_HUMAN | Q7Z333 | SVSRPQLESLSGTK | 1535 | 1 | Probable helicase senataxin |
| | SF01_HUMAN | Q15637 | | 449 | 1 | Splicing factor 1 |
| | SF3A1_HUMAN | Q15459 | | 504 | 1 | Splicing factor 3 subunit 1 |
| | SF3A1_HUMAN | Q15459 | | 504 | 1 | Splicing factor 3 subunit 1 |
| | SF3A1_HUMAN | Q15459 | | 33 | 1 | Splicing factor 3 subunit 1 |
| 281 | SF3B1_HUMAN | O75533 | STGYYDQEIYGGSDSR | 35 | 1 | Splicing factor 3B subunit 1 |
| | SF3B2_HUMAN | Q13435 | | 292 | 1 | Splicing factor 3B subunit 2 |
| 282 | SF3B2_HUMAN | Q13435 | GSETPQLFTVLPEK | 754 | 1 | Splicing factor 3B subunit 2 |
| 283 | SF3B2_HUMAN | Q13435 | GSETPQLFTVLPEKR | 754 | 1 | Splicing factor 3B subunit 2 |
| | SF3B4_HUMAN | Q15427 | | 13 | 1 | Splicing factor 3B subunit 4 |
| | SFPQ_HUMAN | P23246 | | 526 | 1 | Splicing factor, proline- and glutamine-rich |
| | SFR14_HUMAN | Q8IX01 | | 733 | 1 | Putative splicing factor, arginine/serine-rich 14 |
| | SFR14_HUMAN | Q8IX01 | | 902 | 1 | Putative splicing factor, arginine/serine-rich 14 |
| 284 | SFR14_HUMAN | Q8IX01 | GLPGEAAEDDLAGAPALSQASSGTCFPR | 923 | 1 | Putative splicing factor, arginine/serine-rich 14 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 285 | SFRIP_HUMAN | Q99590 | SFCSDQNESEVEPSVNADLK | 408 | 1 | SFRS2-interacting protein |
| | SFRS2_HUMAN | Q01130 | | 71 | 1 | Splicing factor, arginine/serine-rich 2 |
| | SFRS2_HUMAN | Q01130 | | 71 | 1 | Splicing factor, arginine/serine-rich 2 |
| | SFRS2_HUMAN | Q01130 | | 74 | 1 | Splicing factor, arginine/serine-rich 2 |
| | SFRS2_HUMAN | Q01130 | | 74 | 1 | Splicing factor, arginine/serine-rich 2 |
| | SFRS3_HUMAN | P84103 | | 5 | 1 | Splicing factor, arginine/serine-rich 3 |
| | SFRS5_HUMAN | Q13243 | | 53 | 1 | Splicing factor, arginine/serine-rich 5 |
| | SFRS6_HUMAN | Q13247 | | 168 | 1 | Splicing factor, arginine/serine-rich 6 |
| | SGOL1_HUMAN | Q5FBB7 | | 207 | 1 | Shugoshin-like 1 |
| | SH2D3_HUMAN | Q8N5H7 | | 376 | 1 | SH2 domain-containing protein 3C |
| | SHOT1_HUMAN | A0MZ66 | | 130 | 1 | Shootin-1 |
| 286 | SIPA1_HUMAN | Q96FS4 | GGSPPGPGDLAEER | 815 | 1 | Signal-induced proliferation-associated protein 1 |
| | SIX4_HUMAN | Q9UIU6 | | 297 | 1 | Homeobox protein SIX4 |
| 287 | SKI_HUMAN | P12755 | AAAPADAPSGLEAELEHLR | 528 | 1 | Ski oncogene |
| | SKT_HUMAN | Q5T5P2 | | 610 | 1 | Sickle tail protein homolog |
| | SLD5_HUMAN | Q9BRT9 | | 7 | 1 | DNA replication complex GINS protein SLD5 |
| | SLK_HUMAN | Q9H2G2 | | 404 | 1 | STE20-like serine/threonine-protein kinase |
| | SLMAP_HUMAN | Q14BN4 | | 465 | 1 | Sarcolemmal membrane-associated protein |
| | SLU7_HUMAN | O95391 | | 8 | 1 | Pre-mRNA-splicing factor SLU7 |
| | SLU7_HUMAN | O95391 | | 8 | 1 | Pre-mRNA-splicing factor SLU7 |
| | SLU7_HUMAN | O95391 | | 8 | 1 | Pre-mRNA-splicing factor SLU7 |
| | SLU7_HUMAN | O95391 | | 8 | 1 | Pre-mRNA-splicing factor SLU7 |
| | SMC2_HUMAN | O95347 | | 1117 | 1 | Structural maintenance of chromosomes protein 2 |
| | SMCA4_HUMAN | P51532 | | 1382 | 1 | Probable global transcription activator SNF2L4 |
| | SMCE1_HUMAN | Q969G3 | | 265 | 1 | SWI/SNF-related matrix-associated actin-dependent regulator of chromatin subfamily E member 1 |
| | SMHD1_HUMAN | A6NHR9 | | 6 | 1 | Structural maintenance of chromosomes flexible hinge domain-containing protein 1 |
| | SMRC2_HUMAN | Q8TAQ2 | | 815 | 1 | SWI/SNF complex subunit SMARCC2 |
| | SMRD2_HUMAN | Q92925 | | 136 | 1 | SWI/SNF-related matrix-associated actin-dependent regulator of chromatin subfamily D member 2 |
| | SNPC4_HUMAN | Q5SXM2 | | 1169 | 1 | snRNA-activating protein complex subunit 4 |
| | SNX12_HUMAN | Q9UMY4 | | 22 | 1 | Sorting nexin-12 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 288 | SNX29_HUMAN | Q8TEQ0 | GEVTVAEQKPGEIAEELASSYER | 183 | 1 | Sorting nexin-29 |
|  | SNX2_HUMAN | O60749 |  | 85 | 1 | Sorting nexin-2 |
|  | SNX3_HUMAN | O60493 |  | 33 | 1 | Sorting nexin-3 |
|  | SNX6_HUMAN | Q9UNH7 |  | 11 | 1 | Sorting nexin-6 |
|  | SNX6_HUMAN | Q9UNH7 |  | 11 | 1 | Sorting nexin-6 |
|  | SOBP_HUMAN | A7XYQ1 |  | 299 | 1 | Sine oculis-binding protein homolog |
| 289 | SODC_HUMAN | P00441 | GVADVSIEDSVISLSGDHCIIGR | 94 | 1 | Superoxide dismutase [Cu–Zn] |
| 290 | SODC_HUMAN | P00441 | SVISLSGDHCIIGR | 103 | 1 | Superoxide dismutase [Cu–Zn] |
|  | SON_HUMAN | P18583 |  | 1641 | 1 | SON protein |
| 291 | SON_HUMAN | P18583 | SFLKFDSEPSAVALELPTR | 154 | 1 | SON protein |
|  | SON_HUMAN | P18583 |  | 1719 | 1 | SON protein |
|  | SON_HUMAN | P18583 |  | 1641 | 1 | SON protein |
|  | SON_HUMAN | P18583 |  | 353 | 1 | SON protein |
|  | SP110_HUMAN | Q9HB58 |  | 354 | 1 | Sp110 nuclear body protein |
|  | SP110_HUMAN | Q9HB58 |  | 354 | 1 | Sp110 nuclear body protein |
|  | SP1_HUMAN | P08047 |  | 200 | 1 | Transcription factor Sp1 |
|  | SP3_HUMAN | Q02447 |  | 276 | 1 | Transcription factor Sp3 |
| 292 | SP3_HUMAN | Q02447 | SAGIQLHPGENADSPADIR | 531 | 1 | Transcription factor Sp3 |
|  | SPAS2_HUMAN | Q86XZ4 |  | 146 | 1 | Spermatogenesis-associated serine-rich protein 2 |
|  | SPAST_HUMAN | Q9UBP0 |  | 471 | 1 | Spastin |
|  | SPD2B_HUMAN | A1X283 |  | 683 | 1 | SH3 and PX domain-containing protein 2B |
|  | SPEC1_HUMAN | Q5M775 |  | 214 | 1 | Sperm antigen with calponin homology and coiled-coil domains 1 |
|  | SPEE_HUMAN | P19623 |  | 7 | 1 | Spermidine synthase |
|  | SPF27_HUMAN | O75934 |  | 15 | 1 | Pre-mRNA-splicing factor SPF27 |
| 293 | SPF30_HUMAN | O75940 | SFASTQPTHSWK | 63 | 1 | Survival of motor neuron-related-splicing factor 30 |
|  | SPG20_HUMAN | Q8N0X7 |  | 497 | 1 | Spartin |
|  | SPG20_HUMAN | Q8N0X7 |  | 497 | 1 | Spartin |
|  | SPG20_HUMAN | Q8N0X7 |  | 497 | 1 | Spartin |
|  | SPS2L_HUMAN | Q9NUQ6 |  | 120 | 1 | SPATS2-like protein |
| 294 | SPT6H_HUMAN | Q7KZ85 | SYIEVLDGSR | 1048 | 1 | Transcription elongation factor SPT6 |
|  | SPTA2_HUMAN | Q13813 |  | 1479 | 1 | Spectrin alpha chain, brain |
|  | SPTA2_HUMAN | Q13813 |  | 501 | 1 | Spectrin alpha chain, brain |
|  | SPTN2_HUMAN | O15020 |  | 1753 | 1 | Spectrin beta chain, brain 2 |
| 295 | SR140_HUMAN | O15042 | GAPLEDVDGIPIDATPIDDLDGVPIK | 705 | 1 | U2-associated protein SR140 |
|  | SR140_HUMAN | O15042 |  | 713 | 1 | U2-associated protein SR140 |
| 296 | SR140_HUMAN | O15042 | GVPIKSLDDDLDGVPLDATEDSK | 726 | 1 | U2-associated protein SR140 |
| 297 | SR140_HUMAN | O15042 | GVPIKSLDDDLDGVPLDATEDSKK | 726 | 1 | U2-associated protein SR140 |
| 298 | SR140_HUMAN | O15042 | GVPLDATEDSK | 738 | 1 | U2-associated protein SR140 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 299 | SR140_HUMAN | O15042 | GVPLDATEDSKK | 738 | 1 | U2-associated protein SR140 |
| 300 | SR140_HUMAN | O15042 | GVPLDATEDSKKNEPIFK | 738 | 1 | U2-associated protein SR140 |
| 301 | SRCAP_HUMAN | Q6ZRS2 | GFPAGEGEEAGRPGAEDEEMSR | 2276 | 1 | Helicase SRCAP |
| 302 | SRCAP_HUMAN | Q6ZRS2 | GFPAGEGEEAGRPGAEDEEMSR | 2276 | 1 | Helicase SRCAP |
|  | SRC_HUMAN | P12931 |  | 46 | 1 | Proto-oncogene tyrosine-protein kinase Src |
| 303 | SRFB1_HUMAN | Q8NEF9 | SVVSLESQK | 212 | 1 | Serum response factor-binding protein 1 |
| 304 | SRFB1_HUMAN | Q8NEF9 | SVVSLESQKTPADPKLK | 212 | 1 | Serum response factor-binding protein 1 |
| 305 | SRP68_HUMAN | Q9UHB9 | AHQTETSSSQVKDNKPLVER | 538 | 1 | Signal recognition particle 68 kDa protein |
| 306 | SRP68_HUMAN | Q9UHB9 | AHQTETSSSQVK | 538 | 1 | Signal recognition particle 68 kDa protein |
|  | SRPK1_HUMAN | Q96SB4 |  | 413 | 1 | Serine/threonine-protein kinase SRPK1 |
|  | SRRM2_HUMAN | Q9UQ35 |  | 148 | 1 | Serine/arginine repetitive matrix protein 2 |
| 307 | SRRM2_HUMAN | Q9UQ35 | SNSLLGQSR | 1150 | 1 | Serine/arginine repetitive matrix protein 2 |
|  | SRRM2_HUMAN | Q9UQ35 |  | 148 | 1 | Serine/arginine repetitive matrix protein 2 |
|  | SSA27_HUMAN | O60232 |  | 82 | 1 | Sjoegren syndrome/scleroderma autoantigen 1 |
|  | SSBP3_HUMAN | Q9BWW4 |  | 287 | 1 | Single-stranded DNA-binding protein 3 |
|  | SSF1_HUMAN | Q9NQ55 |  | 246 | 1 | Suppressor of SWI4 1 homolog |
|  | SSFA2_HUMAN | P28290 |  | 628 | 1 | Sperm-specific antigen 2 |
|  | SSH2_HUMAN | Q76I76 |  | 964 | 1 | Protein phosphatase Slingshot homolog 2 |
|  | SSRP1_HUMAN | Q08945 |  | 174 | 1 | FACT complex subunit SSRP1 |
|  | STAP1_HUMAN | Q9ULZ2 |  | 171 | 1 | Signal-transducing adaptor protein 1 |
| 308 | STAP1_HUMAN | Q9ULZ2 | VLNPMPACFYTVSR | 171 | 1 | Signal-transducing adaptor protein 1 |
|  | STK10_HUMAN | O94804 |  | 333 | 1 | Serine/threonine-protein kinase 10 |
|  | STK24_HUMAN | Q9Y6E0 |  | 326 | 1 | Serine/threonine-protein kinase 24 |
|  | STK24_HUMAN | Q9Y6E0 |  | 326 | 1 | Serine/threonine-protein kinase 24 |
|  | STK39_HUMAN | Q9UEW8 |  | 436 | 1 | STE20/SPS1-related proline-alanine-rich protein kinase |
| 309 | STK4_HUMAN | Q13043 | GANTMIEHDDTLPSQLGTMVINAEDEEEEGTMK | 350 | 1 | Serine/threonine-protein kinase 4 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 310 | STK4_HUMAN | Q13043 | GANTMIEHDDTL PSQLGTMVINAED EEEEGTMKR | 350 | 1 | Serine/threonine-protein kinase 4 |
| 311 | STK4_HUMAN | Q13043 | GANTMIEHDDTL PSQLGTMVINAED EEEEGTMKRR | 350 | 1 | Serine/threonine-protein kinase 4 |
|  | STRN_HUMAN | O43815 |  | 36 | 1 | Striatin |
| 312 | STRN_HUMAN | O43815 | SLTYDIANNK | 437 | 1 | Striatin |
| 313 | STRN_HUMAN | O43815 | SLTYDIANNKDALR | 437 | 1 | Striatin |
| 314 | STRN_HUMAN | O43815 | SLTYDIANNKDAL RK | 437 | 1 | Striatin |
|  | STX10_HUMAN | O60499 |  | 197 | 1 | Syntaxin-10 |
|  | STX10_HUMAN | O60499 |  | 139 | 1 | Syntaxin-10 |
| 315 | STX12_HUMAN | Q86Y82 | SIEANVESSEVHV ER | 218 | 1 | Syntaxin-12 |
|  | STX17_HUMAN | P56962 |  | 202 | 1 | Syntaxin-17 |
|  | STX17_HUMAN | P56962 |  | 202 | 1 | Syntaxin-17 |
| 316 | STX7_HUMAN | O15400 | SIEANVENAEVHV QQANQQLSR | 205 | 1 | Syntaxin-7 |
| 317 | SUGT1_HUMAN | Q9Y2Z0 | ALIDEDPQAALEE LTK | 21 | 1 | Suppressor of G2 allele of SKP1 homolog |
|  | SYAP1_HUMAN | Q96A49 |  | 282 | 1 | Synapse-associated protein 1 |
|  | SYEP_HUMAN | P07814 |  | 930 | 1 | Bifunctional aminoacyl-tRNA synthetase |
| 318 | SYF2_HUMAN | O95926 | SAEEGSLAAAAEL AAQK | 13 | 1 | Pre-mRNA-splicing factor SYF2 |
| 319 | SYF2_HUMAN | O95926 | SAEEGSLAAAAEL AAQKR | 13 | 1 | Pre-mRNA-splicing factor SYF2 |
|  | SYG_HUMAN | P41250 |  | 57 | 1 | Glycyl-tRNA synthetase |
|  | SYMPK_HUMAN | Q92797 |  | 29 | 1 | Symplekin |
|  | SYNC_HUMAN | O43776 |  | 410 | 1 | Asparaginyl-tRNA synthetase, cytoplasmic |
|  | SYNE1_HUMAN | Q8NF91 |  | 8280 | 1 | Nesprin-1 |
|  | SYNE2_HUMAN | Q8WXH0 |  | 4216 | 1 | Nesprin-2 |
| 320 | SYWC_HUMAN | P23381 | FVDPWTVQTSSAK | 84 | 1 | Tryptophanyl-tRNA synthetase, cytoplasmic |
|  | T106B_HUMAN | Q9NUM4 |  | 20 | 1 | Transmembrane protein 106B |
|  | T106B_HUMAN | Q9NUM4 |  | 20 | 1 | Transmembrane protein 106B |
|  | T106C_HUMAN | Q9BVX2 |  | 24 | 1 | Transmembrane protein 106C |
|  | T2EA_HUMAN | P29083 |  | 304 | 1 | General transcription factor IIE subunit 1 |
| 321 | T2EA_HUMAN | P29083 | AFQEREEGHAGP DDNEEVMR | 304 | 1 | General transcription factor IIE subunit 1 |
|  | T2FA_HUMAN | P35269 |  | 273 | 1 | General transcription factor IIF subunit 1 |
|  | T2FA_HUMAN | P35269 |  | 273 | 1 | General transcription factor IIF subunit 1 |
|  | TACC1_HUMAN | O75410 |  | 324 | 1 | Transforming acidic coiled-coil-containing protein 1 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 322 | TACC1_HUMAN | O75410 | GHATDEEKLASTSCGQK | 501 | 1 | Transforming acidic coiled-coil-containing protein 1 |
| 323 | TACC1_HUMAN | O75410 | GHATDEEK | 501 | 1 | Transforming acidic coiled-coil-containing protein 1 |
| | TACC2_HUMAN | O95359 | | 372 | 1 | Transforming acidic coiled-coil-containing protein 2 |
| | TACC3_HUMAN | Q9Y6A5 | | 287 | 1 | Transforming acidic coiled-coil-containing protein 3 |
| | TACC3_HUMAN | Q9Y6A5 | | 22 | 1 | Transforming acidic coiled-coil-containing protein 3 |
| | TAD1L_HUMAN | Q96BN2 | | 79 | 1 | Transcriptional adapter 1-like protein |
| 324 | TAF11_HUMAN | Q15544 | GIPEETDGDADVDLK | 35 | 1 | Transcription initiation factor TFIID subunit 11 |
| | TAF7_HUMAN | Q15545 | | 101 | 1 | Transcription initiation factor TFIID subunit 7 |
| | TBA1A_HUMAN | Q71U36 | | 34 | 5 | Tubulin alpha-1A chain |
| | TBA1B_HUMAN | P68363 | | 34 | | Tubulin alpha-1B chain |
| | TBA1C_HUMAN | Q9BQE3 | | 34 | | Tubulin alpha-1C chain |
| | TBA3C_HUMAN | Q13748 | | 34 | | Tubulin alpha-3C/D chain |
| | TBA3E_HUMAN | Q6PEY2 | | 34 | | Tubulin alpha-3E chain |
| | TBA1A_HUMAN | Q71U36 | | 34 | 5 | Tubulin alpha-1A chain |
| | TBA1B_HUMAN | P68363 | | 34 | | Tubulin alpha-1B chain |
| | TBA1C_HUMAN | Q9BQE3 | | 34 | | Tubulin alpha-1C chain |
| | TBA3C_HUMAN | Q13748 | | 34 | | Tubulin alpha-3C/D chain |
| | TBA3E_HUMAN | Q6PEY2 | | 34 | | Tubulin alpha-3E chain |
| | TBA1A_HUMAN | Q71U36 | | 34 | 5 | Tubulin alpha-1A chain |
| | TBA1B_HUMAN | P68363 | | 34 | | Tubulin alpha-1B chain |
| | TBA1C_HUMAN | Q9BQE3 | | 34 | | Tubulin alpha-1C chain |
| | TBA3C_HUMAN | Q13748 | | 34 | | Tubulin alpha-3C/D chain |
| | TBA3E_HUMAN | Q6PEY2 | | 34 | | Tubulin alpha-3E chain |
| | TBA1A_HUMAN | Q71U36 | | 48 | 5 | Tubulin alpha-1A chain |
| | TBA1B_HUMAN | P68363 | | 48 | | Tubulin alpha-1B chain |
| | TBA1C_HUMAN | Q9BQE3 | | 48 | | Tubulin alpha-1C chain |
| | TBA3C_HUMAN | Q13748 | | 48 | | Tubulin alpha-3C/D chain |
| | TBA3E_HUMAN | Q6PEY2 | | 48 | | Tubulin alpha-3E chain |
| | TBA1A_HUMAN | Q71U36 | | 34 | 6 | Tubulin alpha-1A chain |
| | TBA1B_HUMAN | P68363 | | 34 | | Tubulin alpha-1B chain |
| | TBA1C_HUMAN | Q9BQE3 | | 34 | | Tubulin alpha-1C chain |
| | TBA3C_HUMAN | Q13748 | | 34 | | Tubulin alpha-3C/D chain |
| | TBA3E_HUMAN | Q6PEY2 | | 34 | | Tubulin alpha-3E chain |
| | TBA4A_HUMAN | P68366 | | 34 | | Tubulin alpha-4A chain |
| | TBA1A_HUMAN | Q71U36 | | 200 | 7 | Tubulin alpha-1A chain |
| | TBA1B_HUMAN | P68363 | | 200 | | Tubulin alpha-1B chain |
| | TBA1C_HUMAN | Q9BQE3 | | 200 | | Tubulin alpha-1C chain |
| | TBA3C_HUMAN | Q13748 | | 200 | | Tubulin alpha-3C/D chain |
| | TBA3E_HUMAN | Q6PEY2 | | 200 | | Tubulin alpha-3E chain |
| | TBA4A_HUMAN | P68366 | | 200 | | Tubulin alpha-4A chain |
| | TBA8_HUMAN | Q9NY65 | | 200 | | Tubulin alpha-8 chain |
| | TBA1A_HUMAN | Q71U36 | | 246 | 7 | Tubulin alpha-1A chain |
| | TBA1B_HUMAN | P68363 | | 246 | | Tubulin alpha-1B chain |
| | TBA1C_HUMAN | Q9BQE3 | | 246 | | Tubulin alpha-1C chain |
| | TBA3C_HUMAN | Q13748 | | 246 | | Tubulin alpha-3C/D chain |
| | TBA3E_HUMAN | Q6PEY2 | | 246 | | Tubulin alpha-3E chain |
| | TBA4A_HUMAN | P68366 | | 246 | | Tubulin alpha-4A chain |
| | TBA8_HUMAN | Q9NY65 | | 246 | | Tubulin alpha-8 chain |
| | TBB2A_HUMAN | Q13885 | | 115 | 5 | Tubulin beta-2A chain |
| | TBB2B_HUMAN | Q9BVA1 | | 115 | | Tubulin beta-2B chain |
| | TBB2C_HUMAN | P68371 | | 115 | | Tubulin beta-2C chain |
| | TBB3_HUMAN | Q13509 | | 115 | | Tubulin beta-3 chain |
| | TBB5_HUMAN | P07437 | | 115 | | Tubulin beta chain |
| | TBB2A_HUMAN | Q13885 | | 115 | 5 | Tubulin beta-2A chain |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | TBB2B_HUMAN | Q9BVA1 | | 115 | | Tubulin beta-2B chain |
| | TBB2C_HUMAN | P68371 | | 115 | | Tubulin beta-2C chain |
| | TBB3_HUMAN | Q13509 | | 115 | | Tubulin beta-3 chain |
| | TBB5_HUMAN | P07437 | | 115 | | Tubulin beta chain |
| | TBB2C_HUMAN | P68371 | | 115 | 2 | Tubulin beta-2C chain |
| | TBB5_HUMAN | P07437 | | 115 | | Tubulin beta chain |
| | TBCC_HUMAN | Q15814 | | 154 | 1 | Tubulin-specific chaperone C |
| | TBCD4_HUMAN | O60343 | | 273 | 1 | TBC1 domain family member 4 |
| | TBCD4_HUMAN | O60343 | | 276 | 1 | TBC1 domain family member 4 |
| | TBL1R_HUMAN | Q9BZK7 | | 153 | 1 | F-box-like/WD repeat-containing protein TBL1XR1 |
| 325 | TBL1R_HUMAN | Q9BZK7 | AVMPDVVQTR | 86 | 2 | F-box-like/WD repeat-containing protein TBL1XR1 |
| 325 | TBL1X_HUMAN | O60907 | AVMPDVVQTR | 86 | | F-box-like/WD repeat-containing protein TBL1X |
| | TBL1R_HUMAN | Q9BZK7 | | 153 | 2 | F-box-like/WD repeat-containing protein TBL1XR1 |
| | TBL1Y_HUMAN | Q9BQ87 | | 163 | | F-box-like/WD repeat-containing protein TBL1Y |
| | TBL1X_HUMAN | O60907 | | 165 | 1 | F-box-like/WD repeat-containing protein TBL1X |
| | TCEA1_HUMAN | P23193 | | 125 | 1 | Transcription elongation factor A protein 1 |
| | TCF20_HUMAN | Q9UGU0 | | 1220 | 1 | Transcription factor 20 |
| | TCF20_HUMAN | Q9UGU0 | | 1220 | 1 | Transcription factor 20 |
| | TCF20_HUMAN | Q9UGU0 | | 1220 | 1 | Transcription factor 20 |
| | TCOF_HUMAN | Q13428 | | 1243 | 1 | Treacle protein |
| 326 | TCOF_HUMAN | Q13428 | GKQEAKPQQAAGMLSPK | 1243 | 1 | Treacle protein |
| | TCOF_HUMAN | Q13428 | | 1102 | 1 | Treacle protein |
| | TCPD_HUMAN | P50991 | | 457 | 1 | T-complex protein 1 subunit delta |
| | TCPD_HUMAN | P50991 | | 269 | 2 | T-complex protein 1 subunit delta |
| | TCPD_HUMAN | P50991 | | 269 | 2 | T-complex protein 1 subunit delta |
| | TCPE_HUMAN | P48643 | | 66 | 1 | T-complex protein 1 subunit epsilon |
| | TCPE_HUMAN | P48643 | | 154 | 1 | T-complex protein 1 subunit epsilon |
| | TCPZ_HUMAN | P40227 | | 405 | 1 | T-complex protein 1 subunit zeta |
| | TCTP_HUMAN | P13693 | | 26 | 1 | Translationally-controlled tumor protein |
| | TDRD6_HUMAN | O60522 | | 1919 | 1 | Tudor domain-containing protein 6 |
| | TEX2_HUMAN | Q8IWB9 | | 357 | 1 | Testis-expressed sequence 2 protein |
| 327 | TEX2_HUMAN | Q8IWB9 | GLSVSQAPAILPVSK | 97 | 1 | Testis-expressed sequence 2 protein |
| | TF2B_HUMAN | Q00403 | | 208 | 1 | Transcription initiation factor IIB |
| | TF2B_HUMAN | Q00403 | | 208 | 1 | Transcription initiation factor IIB |
| | TF2L1_HUMAN | Q9NZI6 | | 23 | 3 | Transcription factor CP2-like protein 1 |
| | TFCP2_HUMAN | Q12800 | | 43 | | Alpha-globin transcription factor CP2 |
| | UBIP1_HUMAN | Q9NZI7 | | 40 | | Upstream-binding protein 1 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 328 | TF3A_HUMAN | Q92664 | AFIAAGESSAPTPPRPALPR | 19 | 1 | Transcription factor IIIA |
|  | TF65_HUMAN | Q04206 |  | 98 | 1 | Transcription factor p65 |
|  | TGS1_HUMAN | Q96RS0 |  | 344 | 1 | Trimethylguanosine synthase homolog |
|  | TGS1_HUMAN | Q96RS0 |  | 344 | 1 | Trimethylguanosine synthase homolog |
|  | TGS1_HUMAN | Q96RS0 |  | 338 | 1 | Trimethylguanosine synthase homolog |
|  | THOC4_HUMAN | Q86V81 |  | 94 | 1 | THO complex subunit 4 |
|  | THOC5_HUMAN | Q13769 |  | 18 | 1 | THO complex subunit 5 homolog |
|  | THOP1_HUMAN | P52888 |  | 14 | 1 | Thimet oligopeptidase |
|  | TIF1A_HUMAN | O15164 |  | 785 | 1 | Transcription intermediary factor 1-alpha |
| 329 | TIF1B_HUMAN | Q13263 | ANQCCTSCEDNAPATSYCVECSEPLCETCVEAHQR | 149 | 1 | Transcription intermediary factor 1-beta |
|  | TIF1B_HUMAN | Q13263 |  | 106 | 1 | Transcription intermediary factor 1-beta |
| 330 | TIF1B_HUMAN | Q13263 | STFSLDQPGGTLDLTLIR | 727 | 1 | Transcription intermediary factor 1-beta |
|  | TIF1B_HUMAN | Q13263 |  | 686 | 1 | Transcription intermediary factor 1-beta |
|  | TIF1B_HUMAN | Q13263 |  | 689 | 1 | Transcription intermediary factor 1-beta |
| 331 | TIM_HUMAN | Q9UNS1 | SVVPFDAASEVPVEEQR | 580 | 1 | Protein timeless homolog |
|  | TINF2_HUMAN | Q9BSI4 |  | 208 | 1 | TERF1-interacting nuclear factor 2 |
| 332 | TINF2_HUMAN | Q9BSI4 | SVNLAEPMEQNPPQQQR | 208 | 1 | TERF1-interacting nuclear factor 2 |
|  | TLK2_HUMAN | Q86UE8 |  | 133 | 1 | Serine/threonine-protein kinase tousled-like 2 |
|  | TM168_HUMAN | Q9H0V1 |  | 427 | 1 | Transmembrane protein 168 |
|  | TM1L2_HUMAN | Q6ZVM7 |  | 158 | 1 | TOM1-like protein 2 |
|  | TMUB1_HUMAN | Q9BVT8 |  | 61 | 1 | Transmembrane and ubiquitin-like domain-containing protein 1 |
| 333 | TMUB1_HUMAN | Q9BVT8 | SMRGEAPGAETPSLR | 61 | 1 | Transmembrane and ubiquitin-like domain-containing protein 1 |
|  | TNIP2_HUMAN | Q8NFZ5 |  | 195 | 1 | TNFAIP3-interacting protein 2 |
|  | TNR6A_HUMAN | Q8NDV7 |  | 1543 | 1 | Trinucleotide repeat-containing gene 6A protein |
|  | TNR6A_HUMAN | Q8NDV7 |  | 1543 | 1 | Trinucleotide repeat-containing gene 6A protein |
| 334 | TOE1_HUMAN | Q96GM8 | SIKPEETEQEVAADETR | 374 | 1 | Target of EGR1 protein 1 |
|  | TOE1_HUMAN | Q96GM8 |  | 8 | 1 | Target of EGR1 protein 1 |
| 335 | TOIP1_HUMAN | Q5JTV8 | SILKSELGNQSPSTSSR | 305 | 1 | Torsin-1A-interacting protein 1 |
|  | TOIP1_HUMAN | Q5JTV8 |  | 227 | 1 | Torsin-1A-interacting protein 1 |
|  | TOIP1_HUMAN | Q5JTV8 |  | 227 | 1 | Torsin-1A-interacting protein 1 |
|  | TOLIP_HUMAN | Q9H0E2 |  | 37 | 1 | Toll-interacting protein |
|  | TOM1_HUMAN | O60784 |  | 394 | 1 | Target of Myb protein 1 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | TOM1_HUMAN | O60784 | | 185 | 1 | Target of Myb protein 1 |
| | TOM1_HUMAN | O60784 | | 180 | 1 | Target of Myb protein 1 |
| | TOM1_HUMAN | O60784 | | 158 | 1 | Target of Myb protein 1 |
| 336 | TOM1_HUMAN | O60784 | MLSPIHTPQR | 158 | 1 | Target of Myb protein 1 |
| | TOP2B_HUMAN | Q02880 | | 1471 | 1 | DNA topoisomerase 2-beta |
| | TP53B_HUMAN | Q12888 | | 212 | 1 | Tumor suppressor p53-binding protein 1 |
| 337 | TP53B_HUMAN | Q12888 | GCSTPSREEGGCSLASTPATTLHLLQLSGQR | 318 | 1 | Tumor suppressor p53-binding protein 1 |
| | TP53B_HUMAN | Q12888 | | 1479 | 1 | Tumor suppressor p53-binding protein 1 |
| | TP53B_HUMAN | Q12888 | | 318 | 1 | Tumor suppressor p53-binding protein 1 |
| 338 | TP53B_HUMAN | Q12888 | SSQPSLPLVR | 830 | 1 | Tumor suppressor p53-binding protein 1 |
| | TPD54_HUMAN | O43399 | | 3 | 1 | Tumor protein D54 |
| 339 | TPRGL_HUMAN | Q5T0D9 | SAGTSPTAVLAAGEEVGAGGGPGGGRPGAGTPLR | 10 | 1 | Tumor protein p63-regulated gene 1-like protein |
| 340 | TPRGL_HUMAN | Q5T0D9 | SAGTSPTAVLAAGEEVGAGGGPGGGRPGAGTPLRQTLWPLSIHDPTR | 10 | 1 | Tumor protein p63-regulated gene 1-like protein |
| | TPR_HUMAN | P12270 | | 1838 | 1 | Nucleoprotein TPR |
| | TPR_HUMAN | P12270 | | 2148 | 1 | Nucleoprotein TPR |
| 341 | TR150_HUMAN | Q9Y2W1 | SFDEDLARPSGLLAQER | 575 | 1 | Thyroid hormone receptor-associated protein 3 |
| | TRBP2_HUMAN | Q15633 | | 235 | 1 | TAR RNA-binding protein 2 |
| 342 | TREF1_HUMAN | Q96PN7 | GSNVTVTPGPGEQTVDVEPR | 761 | 1 | Transcriptional-regulating factor 1 |
| | TRI33_HUMAN | Q9UPN9 | | 830 | 1 | E3 ubiquitin-protein ligase TRIM33 |
| | TRI33_HUMAN | Q9UPN9 | | 830 | 1 | E3 ubiquitin-protein ligase TRIM33 |
| | TRI33_HUMAN | Q9UPN9 | | 830 | 1 | E3 ubiquitin-protein ligase TRIM33 |
| | TRIP4_HUMAN | Q15650 | | 123 | 1 | Activating signal cointegrator 1 |
| | TRIP4_HUMAN | Q15650 | | 289 | 1 | Activating signal cointegrator 1 |
| | TRM1L_HUMAN | Q7Z2T5 | | 45 | 1 | TRM1-like protein |
| | TRS85_HUMAN | Q9Y2L5 | | 854 | 1 | Protein TRS85 homolog |
| | TSC1_HUMAN | Q92574 | | 639 | 1 | Hamartin |
| 343 | TSC1_HUMAN | Q92574 | GVPSTSPMEVLDRLIQQGADAHSK | 639 | 1 | Hamartin |
| 344 | TSC1_HUMAN | Q92574 | GVPSTSPMEVLDR | 639 | 1 | Hamartin |
| | TSR1_HUMAN | Q2NL82 | | 333 | 1 | Pre-rRNA-processing protein TSR1 homolog |
| | TSR1_HUMAN | Q2NL82 | | 333 | 1 | Pre-rRNA-processing protein TSR1 homolog |
| 345 | TSR1_HUMAN | Q2NL82 | AVDDMEEGLK | 333 | 1 | Pre-rRNA-processing protein TSR1 homolog |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | TSR1_HUMAN | Q2NL82 | | 333 | 1 | Pre-rRNA-processing protein TSR1 homolog |
| 346 | TSR1_HUMAN | Q2NL82 | AVDDMEEGLKVLMK | 333 | 1 | Pre-rRNA-processing protein TSR1 homolog |
| | TTC1_HUMAN | Q99614 | | 66 | 1 | Tetratricopeptide repeat protein 1 |
| | TTC4_HUMAN | O95801 | | 255 | 1 | Tetratricopeptide repeat protein 4 |
| 347 | TTF2_HUMAN | Q9UNY4 | STGRPLVILPQR | 827 | 1 | Transcription termination factor 2 |
| 348 | TTF2_HUMAN | Q9UNY4 | STGRPLVILPQRK | 827 | 1 | Transcription termination factor 2 |
| | TYB10_HUMAN | P63313 | | 7 | 1 | Thymosin beta-10 |
| | TYSY_HUMAN | P04818 | | 120 | 1 | Thymidylate synthase |
| | TYY1_HUMAN | P25490 | | 120 | 1 | Transcriptional repressor protein YY1 |
| | U119A_HUMAN | Q13432 | | 45 | 1 | Protein unc-119 homolog A |
| | U119B_HUMAN | A6NIH7 | | 52 | 1 | Protein unc-119 homolog B |
| | U2AF2_HUMAN | P26368 | | 129 | 1 | Splicing factor U2AF 65 kDa subunit |
| 349 | U2AF2_HUMAN | P26368 | GLAVTPTPVPVVGSQMTR | 129 | 1 | Splicing factor U2AF 65 kDa subunit |
| 350 | UAP1L_HUMAN | Q3KQV9 | GVPQVVEYSEISPETAQLR | 300 | 1 | UDP-N-acetylhexosamine pyrophosphorylase-like protein 1 |
| | UAP56_HUMAN | Q13838 | | 26 | 1 | Spliceosome RNA helicase BAT1 |
| 351 | UBA1_HUMAN | P22314 | ALECLPEDKEVLTEDK | 428 | 1 | Ubiquitin-like modifier-activating enzyme 1 |
| | UBA3_HUMAN | Q8TBC4 | | 26 | 1 | NEDD8-activating enzyme E1 catalytic subunit |
| | UBA3_HUMAN | Q8TBC4 | | 26 | 1 | NEDD8-activating enzyme E1 catalytic subunit |
| | UBAP2_HUMAN | Q5T6F2 | | 855 | 1 | Ubiquitin-associated protein 2 |
| | UBAP2_HUMAN | Q5T6F2 | | 202 | 1 | Ubiquitin-associated protein 2 |
| | UBAP2_HUMAN | Q5T6F2 | | 263 | 1 | Ubiquitin-associated protein 2 |
| | UBE2O_HUMAN | Q9C0C9 | | 438 | 1 | Ubiquitin-conjugating enzyme E2 O |
| 352 | UBE2O_HUMAN | Q9C0C9 | GSASPVEMQDEGAEEPHEAGEQLPPFLLK | 438 | 1 | Ubiquitin-conjugating enzyme E2 O |
| 353 | UBE2O_HUMAN | Q9C0C9 | GSASPVEMQDEGAEEPHEAGEQLPPFLLKEGR | 438 | 1 | Ubiquitin-conjugating enzyme E2 O |
| 354 | UBE2O_HUMAN | Q9C0C9 | GSASPVEMQDEGAEEPHEAGEQLPPFLLKEGRDDR | 438 | 1 | Ubiquitin-conjugating enzyme E2 O |
| | UBE2O_HUMAN | Q9C0C9 | | 1226 | 1 | Ubiquitin-conjugating enzyme E2 O |
| | UBFD1_HUMAN | O14562 | | 233 | 1 | Ubiquitin domain-containing protein UBFD1 |
| 355 | UBN1_HUMAN | Q9NPG3 | SFIDNSEAYDELVPASLTTK | 137 | 1 | Ubinuclein |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | UBP10_HUMAN | Q14694 | | 126 | 1 | Ubiquitin carboxyl-terminal hydrolase 10 |
| | UBP10_HUMAN | Q14694 | | 139 | 1 | Ubiquitin carboxyl-terminal hydrolase 10 |
| | UBP10_HUMAN | Q14694 | | 218 | 1 | Ubiquitin carboxyl-terminal hydrolase 10 |
| | UBP14_HUMAN | P54578 | | 77 | 1 | Ubiquitin carboxyl-terminal hydrolase 14 |
| | UBP14_HUMAN | P54578 | | 228 | 1 | Ubiquitin carboxyl-terminal hydrolase 14 |
| 356 | UBP19_HUMAN | O94966 | GRPDEVVAEEAWQR | 620 | 1 | Ubiquitin carboxyl-terminal hydrolase 19 |
| | UBP2L_HUMAN | Q14157 | | 412 | 1 | Ubiquitin-associated protein 2-like |
| | UBP2L_HUMAN | Q14157 | | 299 | 1 | Ubiquitin-associated protein 2-like |
| 357 | UBP2L_HUMAN | Q14157 | GSLASNPYSGDLTK | 851 | 1 | Ubiquitin-associated protein 2-like |
| | UBP34_HUMAN | Q70CQ2 | | 3367 | 1 | Ubiquitin carboxyl-terminal hydrolase 34 |
| | UBP34_HUMAN | Q70CQ2 | | 3367 | 1 | Ubiquitin carboxyl-terminal hydrolase 34 |
| | UBP36_HUMAN | Q9P275 | | 577 | 1 | Ubiquitin carboxyl-terminal hydrolase 36 |
| | UBP42_HUMAN | Q9H9J4 | | 765 | 1 | Ubiquitin carboxyl-terminal hydrolase 42 |
| | UBP5_HUMAN | P45974 | | 768 | 1 | Ubiquitin carboxyl-terminal hydrolase 5 |
| | UBP5_HUMAN | P45974 | | 768 | 1 | Ubiquitin carboxyl-terminal hydrolase 5 |
| | UBP5_HUMAN | P45974 | | 783 | 1 | Ubiquitin carboxyl-terminal hydrolase 5 |
| | UBP5_HUMAN | P45974 | | 135 | 1 | Ubiquitin carboxyl-terminal hydrolase 5 |
| | UBP5_HUMAN | P45974 | | 783 | 1 | Ubiquitin carboxyl-terminal hydrolase 5 |
| | UBP7_HUMAN | Q93009 | | 51 | 1 | Ubiquitin carboxyl-terminal hydrolase 7 |
| 358 | UBP7_HUMAN | Q93009 | GHNTAEEDMEDDTSWR | 51 | 1 | Ubiquitin carboxyl-terminal hydrolase 7 |
| | UBQL1_HUMAN | Q9UMX0 | | 16 | 1 | Ubiquilin-1 |
| 359 | UBR4_HUMAN | Q5T4S7 | SVAGEHSVSGR | 2904 | 1 | E3 ubiquitin-protein ligase UBR4 |
| 360 | UBXN7_HUMAN | O94888 | GFRDFQTETIR | 110 | 1 | UBX domain-containing protein 7 |
| 361 | UBXN7_HUMAN | O94888 | GFRDFQTETIRQEQELR | 110 | 1 | UBX domain-containing protein 7 |
| | UBXN7_HUMAN | O94888 | | 401 | 1 | UBX domain-containing protein 7 |
| | UGPA_HUMAN | Q16851 | | 16 | 1 | UTP--glucose-1-phosphate uridylyltransferase |
| | UH1BL_HUMAN | A0JNW5 | | 1174 | 1 | UHRF1-binding protein 1-like |
| 362 | UHRF1_HUMAN | Q96T88 | SRPADEDMWDETELGLYK | 119 | 1 | E3 ubiquitin-protein ligase UHRF1 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 363 | UHRF1_HUMAN | Q96T88 | SRPADEDMWDETELGLYKVNEYVDAR | 119 | 1 | E3 ubiquitin-protein ligase UHRF1 |
| 364 | URP2_HUMAN | Q86UX7 | SLTTIPELK | 345 | 1 | Fermitin family homolog 3 |
| 365 | URP2_HUMAN | Q86UX7 | SLTTIPELKDHLR | 345 | 1 | Fermitin family homolog 3 |
|  | USE1_HUMAN | Q9NZ43 |  | 130 | 1 | Vesicle transport protein USE1 |
|  | USF2_HUMAN | Q15853 |  | 121 | 1 | Upstream stimulatory factor 2 |
|  | USO1_HUMAN | O60763 |  | 758 | 1 | General vesicular transport factor p115 |
|  | UTRO_HUMAN | P46939 |  | 262 | 1 | Utrophin |
|  | VAMP2_HUMAN | P63027 |  | 69 | 2 | Vesicle-associated membrane protein 2 |
|  | VAMP3_HUMAN | Q15836 |  | 52 |  | Vesicle-associated membrane protein 3 |
|  | VATD_HUMAN | Q9Y5K8 |  | 118 | 1 | V-type proton ATPase subunit D |
| 366 | VIME_HUMAN | P08670 | AINTEFK | 91 | 1 | Vimentin |
| 367 | VIME_HUMAN | P08670 | AINTEFKNTR | 91 | 1 | Vimentin |
| 368 | VIME_HUMAN | P08670 | ALKGTNESLER | 332 | 1 | Vimentin |
| 369 | VIME_HUMAN | P08670 | FSLADAINTEFK | 86 | 1 | Vimentin |
| 370 | VIME_HUMAN | P08670 | FSLADAINTEFKNTR | 86 | 1 | Vimentin |
|  | VIME_HUMAN | P08670 |  | 83 | 1 | Vimentin |
|  | VIME_HUMAN | P08670 |  | 430 | 1 | Vimentin |
| 371 | VIME_HUMAN | P08670 | VDVSKPDLTAALR | 258 | 1 | Vimentin |
| 372 | VIME_HUMAN | P08670 | VDVSKPDLTAALRDVR | 258 | 1 | Vimentin |
| 373 | VIME_HUMAN | P08670 | VSKPDLTAALR | 260 | 1 | Vimentin |
| 374 | VIME_HUMAN | P08670 | VSKPDLTAALRDVR | 260 | 1 | Vimentin |
| 375 | VP13D_HUMAN | Q5THJ4 | SVGTYLPGASR | 2611 | 1 | Vacuolar protein sorting-associated protein 13D |
| 376 | VPS4A_HUMAN | Q9UN37 | SLCGSRNENESEAAR | 231 | 1 | Vacuolar protein sorting-associating protein 4A |
| 377 | VPS4A_HUMAN | Q9UN37 | SLCGSRNENESEAARR | 231 | 1 | Vacuolar protein sorting-associating protein 4A |
|  | VRK1_HUMAN | Q99986 |  | 232 | 1 | Serine/threonine-protein kinase VRK1 |
|  | WAPL_HUMAN | Q7Z5K2 |  | 155 | 1 | Wings apart-like protein homolog |
|  | WASF1_HUMAN | Q92558 |  | 248 | 1 | Wiskott-Aldrich syndrome protein family member 1 |
|  | WASF2_HUMAN | Q9Y6W5 |  | 243 | 1 | Wiskott-Aldrich syndrome protein family member 2 |
|  | WASF2_HUMAN | Q9Y6W5 |  | 412 | 1 | Wiskott-Aldrich syndrome protein family member 2 |
|  | WASH1_HUMAN | A8K0Z3 |  | 299 | 1 | WAS protein family homolog 1 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| | WDR33_HUMAN | Q9C0J8 | | 1184 | 1 | WD repeat-containing protein 33 |
| | WDR44_HUMAN | Q5JSH3 | | 84 | 1 | WD repeat-containing protein 44 |
| | WDR55_HUMAN | Q9H6Y2 | | 21 | 1 | WD repeat-containing protein 55 |
| | WDR62_HUMAN | O43379 | | 1302 | 1 | WD repeat-containing protein 62 |
| 378 | WDR92_HUMAN | Q96MX6 | GIGGLGIGEGAPEIVTGSR | 119 | 1 | WD repeat-containing protein 92 |
| | WFS1_HUMAN | O76024 | | 212 | 1 | Wolframin |
| | WFS1_HUMAN | O76024 | | 76 | 1 | Wolframin |
| | WIPF1_HUMAN | O43516 | | 182 | 1 | WAS/WASL-interacting protein family member 1 |
| | WNK1_HUMAN | Q9H4A3 | | 1070 | 1 | Serine/threonine-protein kinase WNK1 |
| | WNK1_HUMAN | Q9H4A3 | | 1070 | 1 | Serine/threonine-protein kinase WNK1 |
| | WNK1_HUMAN | Q9H4A3 | | 1070 | 1 | Serine/threonine-protein kinase WNK1 |
| | WNK1_HUMAN | Q9H4A3 | | 2026 | 1 | Serine/threonine-protein kinase WNK1 |
| | WNK1_HUMAN | Q9H4A3 | | 653 | 1 | Serine/threonine-protein kinase WNK1 |
| | WNK1_HUMAN | Q9H4A3 | | 1070 | 1 | Serine/threonine-protein kinase WNK1 |
| | WRIP1_HUMAN | Q96S55 | | 193 | 1 | ATPase WRNIP1 |
| | WWC2_HUMAN | Q6AWC2 | | 856 | 1 | Protein WWC2 |
| | XPA_HUMAN | P23025 | | 6 | 1 | DNA repair protein complementing XP-A cells |
| | YAP1_HUMAN | P46937 | | 112 | 1 | 65 kDa Yes-associated protein |
| | YBOX1_HUMAN | P67809 | | 25 | 1 | Nuclease-sensitive element-binding protein 1 |
| | YBOX1_HUMAN | P67809 | | 25 | 1 | Nuclease-sensitive element-binding protein 1 |
| | YBOX1_HUMAN | P67809 | | 113 | 1 | Nuclease-sensitive element-binding protein 1 |
| | YIPF3_HUMAN | Q9GZM5 | | 69 | 1 | Protein YIPF3 |
| | YJ005_HUMAN | Q6ZSR9 | | 118 | 1 | Uncharacterized protein FLJ45252 |
| | YJ005_HUMAN | Q6ZSR9 | | 124 | 1 | Uncharacterized protein FLJ45252 |
| | YM017_HUMAN | A8MX80 | | 224 | 1 | Putative UPF0607 protein ENSP00000383144 |
| 379 | YTDC2_HUMAN | Q9H6S0 | GIPNDSSDSEMEDK | 325 | 1 | YTH domain-containing protein 2 |
| | YTHD1_HUMAN | Q9BYJ9 | | 165 | 1 | YTH domain family protein 1 |
| | YTHD1_HUMAN | Q9BYJ9 | | 165 | 1 | YTH domain family protein 1 |
| | YTHD1_HUMAN | Q9BYJ9 | | 165 | 1 | YTH domain family protein 1 |
| 380 | YTHD2_HUMAN | Q9Y5A9 | GNGVGQSQAGSGSTPSEPHPVLEKLR | 368 | 1 | YTH domain family protein 2 |
| 381 | YTHD2_HUMAN | Q9Y5A9 | GQSAFANETLNK | 167 | 1 | YTH domain family protein 2 |
| 382 | YTHD2_HUMAN | Q9Y5A9 | GQSAFANETLNKAPGMNTIDQGMAALK | 167 | 1 | YTH domain family protein 2 |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
| 383 | YTHD2_HUMAN | Q9Y5A9 | GQSAFANETLNK APGMNTIDQGMA ALKLGSTEVASN VPK | 167 | 1 | YTH domain family protein 2 |
| | YTHD2_HUMAN | Q9Y5A9 | | 368 | 1 | YTH domain family protein 2 |
| | YTHD3_HUMAN | Q7Z739 | | 169 | 1 | YTH domain family protein 3 |
| | YTHD3_HUMAN | Q7Z739 | | 169 | 1 | YTH domain family protein 3 |
| | ZAP70_HUMAN | P43403 | | 291 | 1 | Tyrosine-protein kinase ZAP-70 |
| | ZBT34_HUMAN | Q8NCN2 | | 140 | 1 | Zinc finger and BTB domain-containing protein 34 |
| 384 | ZBT44_HUMAN | Q8NCP5 | GSISPVSSECSVVER | 158 | 1 | Zinc finger and BTB domain-containing protein 44 |
| | ZC11A_HUMAN | O75152 | | 349 | 1 | Zinc finger CCCH domain-containing protein 11A |
| | ZC11A_HUMAN | O75152 | | 531 | 1 | Zinc finger CCCH domain-containing protein 11A |
| | ZC3H4_HUMAN | Q9UPT8 | | 68 | 1 | Zinc finger CCCH domain-containing protein 4 |
| | ZC3H4_HUMAN | Q9UPT8 | | 742 | 1 | Zinc finger CCCH domain-containing protein 4 |
| | ZC3HD_HUMAN | Q5T200 | | 160 | 1 | Zinc finger CCCH domain-containing protein 13 |
| | ZC3HD_HUMAN | Q5T200 | | 160 | 1 | Zinc finger CCCH domain-containing protein 13 |
| 385 | ZC3HE_HUMAN | Q6PJT7 | GVPSPPGYMSDQ EEDMCFEGMKPV NQTAASNKGLR | 524 | 1 | Zinc finger CCCH domain-containing protein 14 |
| 386 | ZCCHV_HUMAN | Q7Z2W4 | GVATDITSTR | 434 | 1 | Zinc finger CCCH-type antiviral protein 1 |
| 387 | ZCCHV_HUMAN | Q7Z2W4 | SLSDVTSTTSSR | 492 | 1 | Zinc finger CCCH-type antiviral protein 1 |
| 388 | ZCH18_HUMAN | Q86VM9 | TVLEPYADPYYD YEIER | 362 | 1 | Zinc finger CCCH domain-containing protein 18 |
| | ZCHC2_HUMAN | Q9C0B9 | | 235 | 1 | Zinc finger CCHC domain-containing protein 2 |
| 389 | ZCHC8_HUMAN | Q6NZY4 | GETEVGEIQQNK | 344 | 1 | Zinc finger CCHC domain-containing protein 8 |
| 390 | ZEB1_HUMAN | P37275 | AADCEGVPEDDL PTDQTVLPGR | 50 | 1 | Zinc finger E-box-binding homeobox 1 |
| | ZF161_HUMAN | O43829 | | 244 | 1 | Zinc finger protein 161 homolog |
| | ZF161_HUMAN | O43829 | | 244 | 1 | Zinc finger protein 161 homolog |
| | ZFAN6_HUMAN | Q6FIF0 | | 107 | 1 | AN1-type zinc finger protein 6 |
| | ZFAN6_HUMAN | Q6FIF0 | | 127 | 1 | AN1-type zinc finger protein 6 |
| | ZFPL1_HUMAN | O95159 | | 172 | 1 | Zinc finger protein-like 1 |
| 391 | ZFX_HUMAN | P17010 | GTCPEVIK | 245 | 1 | Zinc finger X-chromosomal protein |
| 392 | ZFX_HUMAN | P17010 | GTCPEVIKVYIFK | 245 | 1 | Zinc finger X-chromosomal protein |

TABLE 1-continued

Identified caspase-derived peptides. Previous residues indicates the inferred P8-P1 residues in the given protein substrate that directly precede the sequence of residues corresponding to the identified peptide. Unmodified peptide indicates the sequence of residues corresponding to the identified peptide. Modified peptide indicates the peptide as identified, sometimes containing chemical modifications such as oxidized methionine and carbamidomethylated cysteine, and always containing either an N-terminal serinyl-glycyl dipeptide (SerTyr) modification or an N-terminal 2-aminobutyryl (Abu) modification. Start residue(SR) indicates the residue number in the full-length protein sequence of the first residue of the unmodified peptide. "M" indicates the number of matches.

| SEQ ID NO. | Swiss-Prot ID | Swiss-Prot acc # | unmodified peptide | SR | M | protein name |
|---|---|---|---|---|---|---|
|  | ZFY16_HUMAN | Q7Z3T8 |  | 535 | 1 | Zinc finger FYVE domain-containing protein 16 |
|  | ZFY16_HUMAN | Q7Z3T8 |  | 108 | 1 | Zinc finger FYVE domain-containing protein 16 |
|  | ZFY16_HUMAN | Q7Z3T8 |  | 284 | 1 | Zinc finger FYVE domain-containing protein 16 |
| 393 | ZMYM3_HUMAN | Q14202 | STESIPVSDEDSDAMVDDPNDEDFVPFRPR | 256 | 1 | Zinc finger MYM-type protein 3 |
|  | ZMYM4_HUMAN | Q5VZL5 |  | 929 | 1 | Zinc finger MYM-type protein 4 |
|  | ZN143_HUMAN | P52747 |  | 183 | 1 | Zinc finger protein 143 |
|  | ZN143_HUMAN | P52747 |  | 152 | 1 | Zinc finger protein 143 |
|  | ZN200_HUMAN | P98182 |  | 189 | 1 | Zinc finger protein 200 |
|  | ZN264_HUMAN | O43296 |  | 160 | 1 | Zinc finger protein 264 |
|  | ZN277_HUMAN | Q9NRM2 |  | 7 | 1 | Zinc finger protein 277 |
|  | ZN346_HUMAN | Q9UL40 |  | 14 | 1 | Zinc finger protein 346 |
| 394 | ZN644_HUMAN | Q9H582 | SFGSPLGLDKR | 616 | 1 | Zinc finger protein 644 |
| 395 | ZN644_HUMAN | Q9H582 | SFGSPLGLDKRK | 616 | 1 | Zinc finger protein 644 |
|  | ZN646_HUMAN | O15015 |  | 1006 | 1 | Zinc finger protein 646 |
|  | ZN787_HUMAN | Q6DD87 |  | 231 | 1 | Zinc finger protein 787 |
| 396 | ZN828_HUMAN | Q96JM3 | AIDDQKCDILVQEELLASPK | 586 | 1 | Zinc finger protein 828 |
| 397 | ZN828_HUMAN | Q96JM3 | AIDDQKCDILVQEELLASPKK | 586 | 1 | Zinc finger protein 828 |
| 398 | ZNF24_HUMAN | P17028 | SILIIPTPDEEEKILR | 10 | 1 | Zinc finger protein 24 |
| 399 | ZNF24_HUMAN | P17028 | SILIIPTPDEEEK | 10 | 1 | Zinc finger protein 24 |
|  | ZNF76_HUMAN | P36508 |  | 14 | 1 | Zinc finger protein 76 |
|  | ZNHI2_HUMAN | Q9UHR6 |  | 145 | 1 | Zinc finger HIT domain-containing protein 2 |
|  | ZNHI2_HUMAN | Q9UHR6 |  | 145 | 1 | Zinc finger HIT domain-containing protein 2 |
|  | ZYX_HUMAN | Q15942 |  | 150 | 1 | Zyxin |
| 400 | ZYX_HUMAN | Q15942 | SLSSLLDDMTK | 150 | 1 | Zyxin |
| 401 | ZYX_HUMAN | Q15942 | SLSSLLDDMTKNDPFKAR | 150 | 1 | Zyxin |

TABLE 2

Mass spectrometry statistics for identified caspase-derived peptides.

| Swiss-Prot acc # | m/z | z | Error ppm | score | E value |
|---|---|---|---|---|---|
| Q13362 | 695.0352 | 3 | −8.3 | 60.6 | 2.80E−06 |
| P29372 | 833.0408 | 3 | −3.3 | 44.3 | 6.30E−05 |
| P11171 | 756.4105 | 4 | 21 | 51.9 | 4.30E−08 |
| P11171 | 663.9429 | 5 | −2.3 | 62.5 | 2.50E−09 |
| Q13541 | 938.7966 | 3 | 6.1 | 55.9 | 2.30E−07 |
| Q13542 | 952.7778 | 3 | −2.4 | 55 | 1.80E−08 |
| Q6S8J3 | 737.909 | 2 | −1.2 | 24.9 | 0.0013 |
| A5A3E0 |  |  |  |  |  |
| P62736 |  |  |  |  |  |
| Q562R1 |  |  |  |  |  |
| P60709 |  |  |  |  |  |
| P68032 |  |  |  |  |  |
| P63261 |  |  |  |  |  |
| P63267 |  |  |  |  |  |
| Q9BYX7 |  |  |  |  |  |
| P68133 |  |  |  |  |  |

TABLE 2-continued

Mass spectrometry statistics for identified caspase-derived peptides.

| Swiss-Prot acc # | m/z | z | Error ppm | score | E value |
|---|---|---|---|---|---|
| Q6S8J3 | 586.3246 | 2 | −0.82 | 30.7 | 2.60E−04 |
| A5A3E0 | | | | | |
| P62736 | | | | | |
| Q562 | | | | | |
| P60709 | | | | | |
| P68032 | | | | | |
| P63261 | | | | | |
| P63267 | | | | | |
| Q9BYX7 | | | | | |
| P68133 | | | | | |
| Q6S8J3 | 600.9496 | 3 | 1.2 | 43.4 | 9.70E−06 |
| P60709 | | | | | |
| P63261 | | | | | |
| Q9BTE6 | 682.349 | 3 | −6.1 | 48.5 | 4.10E−04 |
| P00519 | 640.3181 | 3 | −5.7 | 56 | 1.70E−05 |
| O14639 | 657.989 | 3 | 5.1 | 45.6 | 8.30E−06 |
| Q96P50 | 836.3983 | 2 | −14 | 42.9 | 5.50E−07 |
| Q9UKV3 | 1144.8881 | 3 | 0.63 | 24.3 | 0.092 |
| Q9UKV3 | 541.5953 | 3 | 3.6 | 39.8 | 2.20E−05 |
| Q9UKV3 | 378.2309 | 3 | 27 | 28.4 | 0.0014 |
| Q9UKV3 | 627.2832 | 2 | 4.8 | 34.5 | 0.009 |
| P21399 | 812.425 | 2 | −1.4 | 23.4 | 4.10E−04 |
| O95573 | 612.8007 | 2 | −8.2 | 39.5 | 0.014 |
| O60488 | | | | | |
| P62736 | 662.8276 | 2 | −0.9 | 34.1 | 3.00E−06 |
| P60709 | | | | | |
| P68032 | | | | | |
| P63261 | | | | | |
| P63267 | | | | | |
| P68133 | | | | | |
| P62736 | 584.7781 | 2 | 0.66 | 38.2 | 5.90E−06 |
| P60709 | | | | | |
| P68032 | | | | | |
| P63261 | | | | | |
| P63267 | | | | | |
| P68133 | | | | | |
| P60709 | 638.5862 | 4 | −2.9 | 42.2 | 1.80E−06 |
| P63261 | | | | | |
| P60709 | 615.0721 | 4 | −11 | 40.9 | 4.10E−07 |
| P63261 | | | | | |
| P12814 | 1108.499 | 3 | 0.83 | 30.6 | 2.10E−04 |
| P12814 | 1103.1478 | 3 | −17 | 22.4 | 0.011 |
| P12814 | 667.8556 | 2 | 3.7 | 41.5 | 0.096 |
| P35609 | | | | | |
| Q08043 | | | | | |
| O43707 | | | | | |
| P35611 | 996.1574 | 3 | −18 | 33.4 | 4.90E−05 |
| Q6ZN18 | 396.7168 | 2 | 6.6 | 28.8 | 0.023 |
| Q96SZ5 | 1006.9929 | 2 | 1.9 | 22.8 | 0.0013 |
| Q8N4X5 | 770.9177 | 2 | −5.7 | 42.4 | 2.80E−04 |
| Q8N4X5 | 604.6598 | 3 | −0.055 | 39.4 | 0.019 |
| Q8N4X5 | 415.2028 | 3 | −1.2 | 28.2 | 0.02 |
| Q6ULP2 | 401.8817 | 3 | 19 | 29.6 | 0.085 |
| Q8N302 | 432.7184 | 2 | 9.9 | 28 | 0.0053 |
| Q8N302 | 439.4802 | 4 | 9.6 | 32.2 | 3.70E−04 |
| Q8N302 | 534.2534 | 3 | −9.1 | 32.4 | 0.0061 |
| Q09666 | 794.9363 | 2 | −2.5 | 23.4 | 9.00E−04 |
| Q09666 | 514.2765 | 2 | 3.8 | 31.7 | 0.0041 |
| Q09666 | 416.5694 | 3 | −4.7 | 31.8 | 0.005 |
| Q09666 | 598.7812 | 2 | −20 | 38.5 | 0.068 |
| Q09666 | 463.9146 | 3 | −5.8 | 44.8 | 0.013 |
| Q09666 | 481.5986 | 2 | −19 | 29.6 | 0.052 |
| Q09666 | 496.2643 | 2 | −25 | 24.4 | 0.058 |
| Q09666 | 388.9439 | 4 | −0.37 | 39.1 | 3.00E−04 |
| Q09666 | 519.9274 | 3 | −1.2 | 48.4 | 5.60E−04 |
| Q09666 | 397.2338 | 3 | −5.9 | 29.2 | 0.0027 |
| Q09666 | 446.888 | 3 | −7 | 30.8 | 0.025 |
| Q09666 | 439.2175 | 3 | −3.9 | 32 | 0.0024 |
| Q09666 | 596.7931 | 2 | −4.6 | 39.1 | 0.055 |
| Q09666 | 514.9217 | 3 | −13 | 40.8 | 0.0015 |
| Q09666 | 583.2912 | 2 | 1.3 | 40.7 | 0.041 |
| Q09666 | 583.2881 | 2 | −4 | 37.2 | 0.048 |
| O95433 | 788.8887 | 2 | −9.6 | 37.5 | 6.50E−05 |
| O95433 | 547.0416 | 4 | 5.6 | 30.2 | 2.80E−04 |
| O95433 | 593.2786 | 3 | 9.7 | 43.6 | 8.50E−05 |
| Q8WYP5 | 960.9803 | 2 | −0.86 | 36.5 | 5.00E−06 |
| Q9Y4K1 | 571.6341 | 3 | 3.7 | 57.2 | 3.60E−06 |
| Q9Y4K1 | 904.4601 | 3 | −1.9 | 26.4 | 0.026 |
| Q02952 | 596.9709 | 3 | −1.9 | 35.8 | 0.02 |
| Q9Y2D5 | 530.78 | 2 | −9.9 | 22.1 | 0.027 |
| Q99996 | 476.256 | 2 | 12 | 34.5 | 4.80E−04 |
| Q99996 | 468.2558 | 2 | 6.9 | 35.5 | 0.0067 |
| Q7Z591 | 438.5817 | 3 | 10 | 42.8 | 2.70E−05 |
| Q12802 | 737.6817 | 3 | −4.9 | 46.5 | 1.60E−04 |
| Q12802 | 772.363 | 4 | −3.1 | 44.8 | 4.50E−05 |
| Q12802 | 562.265 | 3 | −4.8 | 35.9 | 3.00E−04 |
| Q12802 | 474.2589 | 2 | 6.4 | 34.5 | 0.0039 |
| Q12802 | 917.9474 | 2 | −7 | 52.6 | 1.00E−05 |
| Q12802 | 848.4239 | 2 | 2 | 29.9 | 0.052 |
| Q9ULX6 | 707.3197 | 2 | 5.1 | 40.1 | 3.20E−05 |
| Q8TCU4 | 716.8455 | 2 | −0.84 | 39.6 | 6.80E−05 |
| Q8TCU4 | 530.2837 | 4 | −2.8 | 30 | 0.005 |
| Q8TCU4 | 556.8022 | 2 | 2.3 | 25.9 | 3.30E−04 |
| Q9HCF4 | 527.7967 | 2 | −2.9 | 36.4 | 4.40E−04 |
| Q9HCF4 | 684.3854 | 2 | −0.51 | 23.9 | 0.0017 |
| Q9HCF4 | 878.4746 | 2 | −0.13 | 30.8 | 6.10E−05 |
| Q01432 | 1012.9898 | 2 | −14 | 42 | 6.50E−05 |
| P53582 | 608.6207 | 3 | 1.5 | 49.8 | 7.80E−07 |
| Q8IWZ3 | 632.3286 | 5 | 14 | 26.7 | 0.007 |
| Q8IWZ3 | 933.4111 | 2 | −19 | 22 | 2.60E−04 |
| Q68DC2 | 518.28 | 3 | −7.5 | 43 | 0.0026 |
| Q92625 | 440.5292 | 3 | −5.1 | 36 | 7.90E−04 |
| P07355 | 494.2418 | 3 | 2.7 | 38.9 | 1.10E−04 |
| A6NMY6 | | | | | |
| O43747 | 867.4424 | 3 | −4.5 | 51.8 | 5.70E−08 |
| O75843 | 833.4361 | 5 | −5.6 | 34.6 | 0.0022 |
| O94973 | 679.9964 | 3 | −6.4 | 49.5 | 3.40E−06 |
| Q13367 | 608.3474 | 4 | −6.1 | 22.8 | 0.041 |
| Q13367 | 910.0015 | 2 | −0.16 | 39.4 | 7.10E−05 |
| Q92870 | 792.7011 | 3 | −1.8 | 43 | 2.10E−04 |
| P25054 | 957.4693 | 3 | −11 | 52.5 | 4.50E−09 |
| Q9HDC9 | 475.7311 | 2 | −2.9 | 33 | 0.084 |
| Q7Z2E3 | 891.0972 | 3 | −8.3 | 50 | 3.20E−06 |
| Q3SXY8 | 1169.6076 | 3 | 2 | 31.7 | 0.0066 |
| P25098 | 491.9294 | 3 | 5.4 | 36 | 0.0013 |
| P25098 | 619.6332 | 3 | −3.3 | 31.5 | 1.70E−04 |
| P35626 | | | | | |
| P25098 | 779.8454 | 2 | −4.6 | 32.2 | 8.90E−07 |
| P35626 | | | | | |
| Q92888 | 398.8444 | 3 | −47 | 26.6 | 0.0068 |
| Q92974 | 711.8592 | 2 | 4.6 | 32.7 | 1.10E−04 |
| O15013 | 1053.8212 | 3 | −24 | 23.4 | 2.10E−04 |
| O14497 | 830.8775 | 2 | −0.32 | 22.6 | 3.00E−05 |
| O14497 | 822.8813 | 2 | 1.2 | 29.3 | 1.50E−06 |
| O14497 | 774.0026 | 3 | −6.1 | 65.8 | 1.40E−07 |
| P29374 | 796.8669 | 2 | 2.8 | 36.1 | 2.90E−06 |
| Q4LE39 | 1357.619 | 3 | 2.2 | 28.9 | 2.60E−05 |
| Q68CP9 | 710.3607 | 4 | −2.5 | 34.7 | 2.40E−05 |
| Q68CP9 | 652.071 | 4 | −11 | 23.6 | 0.0054 |
| Q8N2F6 | 915.4348 | 2 | 3.9 | 49.2 | 2.40E−04 |
| Q6NXE6 | 969.2285 | 4 | −0.03 | 23.1 | 0.046 |
| Q6NXE6 | 965.2247 | 4 | −5.3 | 42.8 | 1.40E−06 |
| P27540 | 621.6545 | 3 | 17 | 41.6 | 4.50E−04 |
| Q9UBL0 | 663.9974 | 3 | −13 | 43 | 3.50E−06 |
| P61160 | 567.7937 | 4 | −2.9 | 25.9 | 0.0085 |
| P61158 | 694.0126 | 3 | −2 | 34.8 | 1.00E−03 |
| O15511 | 952.3894 | 2 | −20 | 61.5 | 3.90E−08 |
| O15511 | 837.8722 | 2 | −0.95 | 43.1 | 3.90E−08 |
| Q9BXP5 | 406.8858 | 3 | 8.5 | 32.4 | 4.10E−04 |
| Q8WXK3 | 817.952 | 2 | −0.3 | 26.3 | 6.10E−04 |
| Q8N9N2 | 1067.091 | 3 | −15 | 36.1 | 8.00E−07 |
| Q9H1I8 | 709.3174 | 3 | 5.1 | 64.5 | 6.50E−08 |
| Q9BVC5 | 476.7547 | 2 | 7.9 | 27.4 | 0.016 |
| Q13625 | 884.4693 | 3 | −0.001 | 28.5 | 0.0026 |
| Q96QE3 | 990.488 | 2 | 1.2 | 22 | 0.003 |
| Q9ULI0 | 761.9025 | 2 | 0.34 | 27.9 | 2.30E−04 |
| P18846 | 378.2114 | 4 | −17 | 28.1 | 0.0012 |
| P18848 | 866.4062 | 3 | −5.7 | 45.6 | 2.90E−06 |
| P17544 | 742.397 | 2 | −17 | 42 | 0.0031 |
| P17544 | 624.6849 | 3 | −10 | 27.6 | 0.01 |

TABLE 2-continued

Mass spectrometry statistics for identified caspase-derived peptides.

| Swiss-Prot acc # | m/z | z | Error ppm | score | E value |
|---|---|---|---|---|---|
| Q9NT62 | 706.7647 | 5 | 0.57 | 29.7 | 0.0033 |
| Q9NT62 | 790.3876 | 3 | 3.1 | 58.8 | 1.30E−06 |
| Q9Y4P1 | 687.847 | 2 | −2.3 | 43.1 | 0.0069 |
| P46100 | 689.0362 | 3 | 0.84 | 34 | 5.70E−04 |
| P0C7T5 | 631.8268 | 2 | −1.9 | 27 | 7.30E−04 |
| Q8WWM7 | 878.4225 | 2 | −5.3 | 55.1 | 2.70E−07 |
| Q8WWM7 | 870.4253 | 2 | −5 | 50.7 | 3.20E−05 |
| Q99700 | 1189.2343 | 3 | 4.8 | 26.6 | 0.0068 |
| P54252 | 839.8587 | 2 | −7.4 | 40.4 | 3.10E−04 |
| Q9UPN4 | 971.4637 | 3 | −11 | 30.2 | 6.50E−06 |
| Q9Y520 | 832.8634 | 2 | −8.3 | 40.2 | 2.20E−06 |
| Q9Y520 | 716.0153 | 3 | 0.7 | 49.7 | 5.30E−06 |
| Q92560 | 759.3601 | 3 | −2.9 | 31.8 | 0.0062 |
| P51572 | 479.5827 | 3 | −3.1 | 42 | 6.90E−05 |
| P51572 | 552.5266 | 4 | −4.3 | 52.9 | 2.30E−08 |
| P80723 | 660.9797 | 3 | 5.1 | 49.9 | 1.20E−05 |
| P80723 | 494.9073 | 3 | 0.21 | 43.6 | 3.50E−04 |
| P46379 | 1087.21 | 3 | −7 | 37.4 | 3.70E−05 |
| P46379 | 1129.9151 | 3 | −0.73 | 37.4 | 6.60E−06 |
| Q9NRL2 | 678.316 | 3 | −11 | 24.9 | 0.0029 |
| Q6ZUJ8 | 750.3245 | 2 | 2.2 | 57.3 | 4.20E−04 |
| Q6ZUJ8 | 721.6722 | 3 | 2.1 | 49.5 | 1.40E−05 |
| Q9NYF8 | 528.2364 | 2 | 1.5 | 29.8 | 0.021 |
| Q9NYF8 | 437.5387 | 3 | 9 | 32.9 | 3.40E−04 |
| P11274 | 682.3057 | 2 | −6.1 | 24.6 | 6.20E−04 |
| A6H8Y1 | 803.4489 | 2 | −3.3 | 29.3 | 2.90E−04 |
| P55957 | 581.2888 | 2 | −3.7 | 39.6 | 0.0038 |
| Q5TH69 | 385.5289 | 3 | 15 | 28.2 | 0.0034 |
| O00499 | 542.2935 | 2 | 0.33 | 31.9 | 8.20E−04 |
| Q9NR09 | 398.861 | 3 | −5.4 | 26.8 | 0.025 |
| Q6QNY0 | 878.9029 | 2 | −2.2 | 40.9 | 0.0018 |
| Q8WV28 | 1031.4701 | 3 | −1.6 | 34.3 | 4.70E−05 |
| Q12982 | 933.0836 | 3 | −4 | 37.9 | 6.20E−05 |
| Q12830 | 613.3208 | 2 | 2.6 | 44.1 | 0.027 |
| O95696 | 624.8586 | 2 | 21 | 25 | 0.0048 |
| O60885 | 424.5384 | 3 | −0.75 | 32.9 | 0.0026 |
| Q9H0E9 | 597.9905 | 3 | 4.6 | 52 | 8.20E−05 |
| Q96RE7 | 420.8942 | 3 | 10 | 29.4 | 0.037 |
| O43683 | 463.2503 | 2 | 13 | 28.4 | 0.0023 |
| Q43683 | 835.4028 | 2 | −3.2 | 28.7 | 4.70E−06 |
| Q9BRD0 | 740.8795 | 2 | −19 | 46 | 6.20E−04 |
| Q96L14 | 832.4292 | 2 | 0.79 | 24.5 | 3.60E−04 |
| Q07021 | 904.0546 | 3 | −3 | 48.5 | 4.20E−09 |
| O14523 | 567.6593 | 3 | −1.2 | 49.4 | 7.10E−06 |
| Q6P1N0 | 1118.5371 | 3 | −15 | 52.9 | 4.20E−08 |
| Q6P1N0 | 1113.2059 | 3 | −14 | 52 | 2.70E−08 |
| Q5T0F9 | 550.814 | 2 | −9.3 | 39.7 | 0.0015 |
| Q5T8I9 | 516.7592 | 2 | 0.29 | 28.6 | 0.031 |
| Q5T8I9 | 619.8312 | 4 | 1.9 | 30.4 | 0.0013 |
| Q5T3J3 | 741.8712 | 2 | −1.3 | 22.9 | 7.10E−05 |
| Q5T3J3 | 1040.5147 | 2 | 4.5 | 26.6 | 1.70E−04 |
| Q96BR5 | 721.3472 | 2 | −3.2 | 27.7 | 1.10E−04 |
| Q7L4P6 | 579.2901 | 3 | 3.5 | 31.4 | 2.90E−04 |
| Q5SV97 | 881.8479 | 5 | −5.2 | 23 | 0.028 |
| Q68CQ1 | 552.8186 | 2 | −10 | 34.7 | 0.071 |
| Q08AD1 | 578.2992 | 2 | 6.8 | 36.9 | 0.016 |
| Q9BTV7 | 579.3169 | 4 | 22 | 36.9 | 1.50E−04 |
| Q9P1Z2 | 674.3779 | 2 | −2.5 | 47.5 | 2.10E−05 |
| P19022 | 547.86 | 2 | −2.8 | 22.4 | 0.0049 |
| P19022 | 368.5621 | 3 | 13 | 24.2 | 0.0094 |
| Q13111 | 661.5167 | 5 | 16 | 51 | 9.80E−09 |
| Q13111 | 449.2444 | 2 | 3 | 25.6 | 0.021 |
| Q13111 | 919.9718 | 2 | 0.46 | 35.5 | 1.30E−06 |
| P27797 | 631.8193 | 4 | −2.6 | 51.1 | 1.10E−06 |
| P27797 | 911.7541 | 3 | −7.3 | 34.9 | 5.90E−04 |
| P27797 | 870.0258 | 3 | −6.1 | 54.5 | 1.90E−07 |
| Q8NCB2 | 865.9321 | 2 | 0.86 | 25.9 | 2.90E−05 |
| P49069 | 642.0082 | 3 | −0.29 | 26 | 0.0051 |
| P49069 | 644.9868 | 3 | −3.2 | 62.1 | 2.40E−06 |
| P49069 | 747.6898 | 2 | −14 | 48.1 | 1.50E−05 |
| Q5T5Y3 | 487.9148 | 2 | −0.65 | 28.9 | 5.30E−04 |
| Q5T5Y3 | 686.1413 | 5 | 2.1 | 27.1 | 9.90E−04 |
| Q5T5Y3 | 779.045 | 3 | −1.6 | 52.6 | 1.10E−05 |
| Q14444 | 642.6701 | 3 | −0.51 | 51.8 | 2.30E−07 |
| P47756 | 418.2392 | 3 | 11 | 33.5 | 5.90E−04 |
| O15234 | 513.2743 | 3 | 4.9 | 30.6 | 6.70E−05 |
| Q8NG31 | 810.8847 | 2 | −4 | 32.6 | 1.20E−06 |
| P42574 | 667.3261 | 2 | 13 | 41 | 0.0012 |
| P42574 | 500.8599 | 3 | −5.2 | 39.2 | 1.30E−04 |
| P42574 | 495.5289 | 3 | −3.9 | 30.9 | 1.00E−04 |
| P55210 | 671.3188 | 2 | −6.7 | 54.1 | 3.20E−05 |
| Q13948 | 525.3142 | 3 | 5.1 | 29.9 | 4.40E−04 |
| P39880 | | | | | |
| P07858 | 456.5788 | 3 | −7.3 | 36.9 | 0.036 |
| Q9H6R7 | 954.0162 | 2 | 0.98 | 46.1 | 5.70E−07 |
| P22681 | 689.8437 | 4 | −4 | 37 | 3.20E−06 |
| Q9BRT8 | 479.7709 | 2 | 3 | 32.6 | 0.072 |
| Q8IUF1 | | | | | |
| Q5JTY5 | | | | | |
| Q5RIA9 | | | | | |
| Q4V339 | | | | | |
| A6NM15 | | | | | |
| Q96G28 | 559.2568 | 3 | 4.8 | 27.2 | 0.0029 |
| Q96G28 | 553.9217 | 3 | −1.5 | 29.9 | 4.00E−04 |
| Q96G28 | 467.5685 | 3 | 13 | 24.4 | 0.0025 |
| Q96G28 | 527.9086 | 3 | 0.77 | 40.9 | 3.70E−05 |
| Q96CT7 | 546.7925 | 4 | 20 | 27.8 | 0.0032 |
| O60293 | 563.6239 | 3 | 0.51 | 42.9 | 2.20E−05 |
| Q9NV96 | 577.7865 | 2 | 2.9 | 52.4 | 2.10E−04 |
| Q96MW1 | 736.8328 | 2 | 2 | 51.9 | 5.60E−05 |
| Q9Y3C0 | 776.4054 | 2 | −3.3 | 47.6 | 0.007 |
| Q7Z6B0 | 791.9203 | 2 | −1.9 | 38.8 | 0.005 |
| Q96F63 | 734.3549 | 3 | −5.2 | 26.5 | 0.0023 |
| Q9Y3X0 | 616.3044 | 3 | −1.6 | 38.3 | 6.50E−05 |
| Q9Y3X0 | 507.7253 | 4 | −30 | 33 | 8.60E−05 |
| O60583 | 768.8993 | 2 | −0.24 | 34.5 | 4.40E−05 |
| O60583 | 1060.8711 | 3 | −1.4 | 31.1 | 0.0011 |
| P21127 | 807.4354 | 2 | −9.3 | 54.5 | 1.70E−07 |
| P21127 | 737.069 | 3 | −8.6 | 47.5 | 1.10E−07 |
| Q14004 | 628.3353 | 2 | −0.65 | 30.1 | 5.10E−05 |
| P30260 | 1014.5668 | 2 | 2 | 29.5 | 1.10E−04 |
| P30260 | 762.4204 | 2 | 1.3 | 51.1 | 0.001 |
| Q99459 | 571.2824 | 2 | −5.4 | 37.5 | 0.0019 |
| Q9BWT1 | 657.8024 | 2 | −7.4 | 37.5 | 5.80E−05 |
| Q9UKY7 | 725.3042 | 2 | −3.5 | 33.7 | 9.40E−05 |
| Q9Y232 | 1439.7215 | 3 | −0.52 | 42.5 | 3.20E−06 |
| Q49AR2 | 586.9478 | 3 | 8.5 | 41.8 | 2.40E−05 |
| O94986 | 626.0437 | 4 | −6.9 | 36 | 1.90E−04 |
| Q5SW79 | 870.4244 | 3 | −12 | 50.5 | 2.10E−06 |
| Q5SW79 | 1117.558 | 3 | 1.1 | 26.3 | 0.0077 |
| Q5SW79 | 559.9728 | 3 | 1.3 | 24.6 | 0.015 |
| Q03701 | 869.0709 | 3 | 0.25 | 24.2 | 0.001 |
| Q03701 | 445.2475 | 2 | 7.5 | 22.2 | 0.023 |
| Q03701 | 608.79 | 2 | −1.6 | 40 | 0.0048 |
| Q6NXR4 | 1017.8124 | 3 | 1.6 | 25 | 0.016 |
| Q6P1X6 | 774.3731 | 2 | −3.8 | 29.5 | 2.90E−06 |
| P10809 | 698.8351 | 2 | 2.1 | 38 | 5.30E−04 |
| P10809 | 538.3097 | 2 | 1.4 | 33.2 | 0.0055 |
| P10809 | 594.2953 | 2 | −5.8 | 39.6 | 0.0068 |
| P10809 | 528.3024 | 4 | 0.58 | 23.6 | 0.02 |
| Q12873 | 1130.1293 | 3 | −7.1 | 40.5 | 5.50E−07 |
| Q14839 | | | | | |
| Q8TDI0 | | | | | |
| Q14839 | 568.7467 | 4 | 0.63 | 38.4 | 3.10E−06 |
| Q14839 | 686.0461 | 4 | −24 | 34.5 | 3.20E−05 |
| Q9P2D1 | 777.361 | 3 | 12 | 51 | 1.80E−06 |
| Q9BY43 | 618.8337 | 2 | 1.5 | 34.6 | 0.0014 |
| Q9H444 | | | | | |
| Q96CF2 | | | | | |
| Q9NRY2 | 546.9371 | 3 | −0.91 | 40.1 | 3.80E−04 |
| Q5VWN6 | 526.2781 | 2 | 11 | 40.6 | 4.50E−04 |
| Q86WR7 | 931.142 | 3 | 7.8 | 55.6 | 3.50E−09 |
| Q6IAA8 | 598.2323 | 3 | −4.3 | 29.2 | 0.0064 |
| Q6IAA8 | 592.907 | 3 | 6.4 | 23.6 | 0.041 |
| Q9HCM1 | 701.8622 | 2 | −0.14 | 27.8 | 5.00E−05 |
| Q9HCM1 | 741.8753 | 2 | −2.8 | 43.8 | 0.064 |
| Q96C57 | 688.8449 | 2 | 1.5 | 26.1 | 3.70E−04 |
| Q96C57 | 832.9297 | 2 | −0.19 | 27.4 | 7.50E−04 |
| Q96C57 | 824.9339 | 2 | 1.8 | 31.3 | 8.30E−06 |
| Q96C57 | 953.0076 | 2 | −1.6 | 23.2 | 3.70E−04 |

TABLE 2-continued

Mass spectrometry statistics for identified caspase-derived peptides.

| Swiss-Prot acc # | m/z | z | Error ppm | score | E value |
|---|---|---|---|---|---|
| Q7Z460 | 612.289 | 2 | 4.7 | 39.3 | 0.0017 |
| Q7Z460 | 684.6447 | 3 | −8.9 | 39.5 | 7.40E−05 |
| P09496 | 1039.7784 | 3 | −5.5 | 63.1 | 4.30E−10 |
| P09496 | 1034.4414 | 3 | −11 | 59.2 | 1.40E−10 |
| P09496 | 680.3305 | 2 | −0.11 | 40.2 | 6.10E−04 |
| O00299 | 917.4094 | 3 | −18 | 29.1 | 2.90E−04 |
| P30622 | 487.59 | 3 | 4.3 | 24 | 0.038 |
| Q9HAW4 | 940.0497 | 2 | 1.2 | 32.6 | 5.20E−06 |
| Q15003 | 534.2601 | 2 | 8.6 | 40.5 | 8.00E−04 |
| Q15003 | 708.3025 | 4 | 2.1 | 29.7 | 1.50E−05 |
| Q15003 | 461.5532 | 3 | 0.11 | 36.7 | 7.50E−06 |
| Q15003 | 394.2029 | 3 | 17 | 25.1 | 0.02 |
| Q15003 | 624.776 | 2 | 2.7 | 34.2 | 2.60E−05 |
| Q6IBW4 | 578.9792 | 3 | 1.3 | 35.7 | 6.90E−04 |
| P12111 | 1063.8161 | 3 | −21 | 30.7 | 0.0079 |
| Q53SF7 | 889.4591 | 2 | 3.8 | 44 | 6.80E−04 |
| P53621 | 914.9333 | 2 | −0.38 | 53.3 | 5.70E−07 |
| P53621 | 650.848 | 2 | 8 | 29.3 | 0.0038 |
| P35606 | 603.5815 | 4 | 20 | 35 | 0.0012 |
| P31146 | 455.7318 | 2 | −12 | 23.2 | 0.033 |
| Q1ED39 | 484.2491 | 4 | 5.1 | 25.1 | 0.02 |
| Q7Z7A1 | 838.9225 | 2 | −2 | 29.1 | 4.20E−05 |
| Q7Z7A1 | 482.9271 | 3 | −2.3 | 30.2 | 0.017 |
| Q6FI81 | 556.5493 | 4 | 11 | 29.9 | 2.10E−04 |
| Q99829 | 494.2491 | 2 | −9.9 | 31.4 | 0.011 |
| O75131 | 602.3151 | 2 | 1.1 | 23.1 | 6.90E−04 |
| Q16630 | 724.8665 | 2 | −0.77 | 47.3 | 0.027 |
| Q8N684 | 721.3527 | 3 | 0.039 | 26.5 | 1.80E−04 |
| Q8N684 | 682.6449 | 2 | −4.8 | 44.1 | 2.70E−06 |
| Q8N684 | 770.3681 | 2 | 0.24 | 42.4 | 0.0031 |
| Q6JBY9 | 908.7383 | 3 | −4.8 | 61.4 | 1.10E−08 |
| Q96N21 | 1176.6536 | 2 | 3.3 | 24.7 | 2.30E−04 |
| Q53F19 | 666.9666 | 3 | −2.1 | 24.7 | 0.096 |
| Q53F19 | 744.8885 | 2 | −14 | 46.5 | 1.80E−04 |
| Q96B23 | 779.3919 | 3 | −6.8 | 31.3 | 5.20E−04 |
| Q96B23 | 727.367 | 3 | 4.8 | 38.3 | 1.30E−04 |
| Q96B23 | 779.3968 | 3 | −0.56 | 28.3 | 0.0065 |
| Q96B23 | 722.0345 | 3 | 3.7 | 40.8 | 8.90E−05 |
| Q96B23 | 774.055 | 3 | −14 | 40.5 | 3.00E−04 |
| P16220 | 961.8356 | 3 | −14 | 49.5 | 4.30E−07 |
| P16220 | 425.2108 | 2 | −20 | 32.1 | 0.084 |
| P16220 | 503.2726 | 3 | 5.5 | 32.5 | 0.06 |
| Q5TZA2 | 493.88 | 3 | −1.8 | 30.5 | 8.70E−04 |
| Q9BQ61 | 595.811 | 2 | 4.6 | 31.2 | 0.014 |
| Q9H6X5 | 782.024 | 3 | −14 | 32.4 | 2.60E−05 |
| Q13098 | 820.4062 | 2 | −2 | 61.5 | 1.10E−08 |
| Q9H175 | 672.7048 | 3 | −6.2 | 37.6 | 1.30E−05 |
| Q12996 | 652.331 | 4 | −6.2 | 39.9 | 2.20E−04 |
| Q8WYA6 | 781.3392 | 3 | −0.45 | 53.5 | 1.30E−07 |
| P49711 | 1069.8452 | 3 | −6.1 | 38.2 | 1.20E−07 |
| P49711 | 1069.8381 | 3 | −13 | 44.6 | 2.10E−07 |
| P49711 | 1064.5039 | 3 | −15 | 50.7 | 7.00E−09 |
| P35222 | 415.2119 | 3 | 2.6 | 29 | 0.0089 |
| O60716 | 747.7031 | 3 | −8.9 | 56.8 | 3.80E−06 |
| Q6PD62 | 498.719 | 4 | −7.4 | 40.8 | 5.00E−05 |
| Q13620 | 706.335 | 2 | −5.1 | 42.6 | 3.60E−05 |
| Q9NTM9 | 573.7935 | 2 | 4.2 | 40 | 8.60E−04 |
| P39880 | 962.4311 | 2 | 4.9 | 44.1 | 1.30E−05 |
| O43169 | 622.9469 | 2 | −32 | 33.8 | 7.10E−05 |
| P16989 | 510.6162 | 2 | 10 | 46.8 | 1.10E−06 |
| P16989 | 443.2429 | 2 | −0.47 | 27.6 | 0.0021 |
| P16989 | 892.1155 | 3 | 14 | 51.2 | 8.10E−06 |
| P16989 | 761.8609 | 2 | −8.2 | 27.4 | 0.0011 |
| P67809 | | | | | |
| Q9Y2T7 | | | | | |
| Q6PH85 | 533.2533 | 3 | 3.8 | 43.5 | 7.00E−05 |
| Q14203 | 607.9659 | 3 | 6.1 | 45.5 | 3.10E−05 |
| Q9NUU7 | 801.4011 | 2 | −14 | 26.5 | 0.014 |
| Q92499 | 705.915 | 2 | 0.84 | 31.6 | 2.50E−06 |
| Q9GZR7 | 1184.5992 | 2 | 1.4 | 34.7 | 2.00E−05 |
| Q7L014 | 809.1259 | 3 | 1.5 | 36.2 | 1.10E−04 |
| Q7L014 | 424.872 | 3 | 3.7 | 29.6 | 0.063 |
| Q7L014 | 755.8863 | 2 | −2 | 53.1 | 2.50E−05 |
| Q7L014 | 747.891 | 2 | 1 | 39.1 | 2.00E−04 |
| Q5T1V6 | 601.8233 | 2 | 1.4 | 40.5 | 0.0018 |
| P17661 | 490.2534 | 3 | −0.52 | 23.6 | 0.0019 |
| P17661 | 484.9203 | 3 | −3.5 | 29.6 | 0.011 |
| O00273 | 550.2886 | 2 | −3.9 | 28.9 | 0.022 |
| O00273 | 452.2561 | 2 | 17 | 36 | 0.037 |
| O00273 | 667.8635 | 4 | 2.2 | 22 | 0.041 |
| Q8WYQ5 | 643.3443 | 2 | −0.52 | 23.3 | 0.0055 |
| Q8WYQ5 | 926.1158 | 3 | −4.6 | 49.6 | 5.40E−09 |
| Q8WYQ5 | 920.7767 | 3 | −13 | 53 | 2.90E−09 |
| Q8WYQ5 | 987.1671 | 3 | 1.2 | 24 | 0.063 |
| Q86XP1 | 1012.8194 | 3 | −1.8 | 31.6 | 2.40E−04 |
| Q86XP1 | 702.3881 | 3 | −10 | 53.1 | 3.80E−09 |
| Q8NCG7 | 802.0843 | 3 | 1.3 | 63 | 1.10E−07 |
| Q3LXA3 | 543.7521 | 2 | −8.5 | 31.8 | 0.0026 |
| Q3LXA3 | 414.8688 | 3 | −12 | 35.1 | 3.30E−04 |
| Q7L2E3 | 519.2635 | 4 | 8.9 | 24.4 | 2.10E−04 |
| Q8IY37 | 996.1776 | 3 | −11 | 34 | 0.001 |
| Q08211 | 629.989 | 3 | 9.3 | 39.7 | 0.0011 |
| Q08211 | 890.1142 | 3 | −0.28 | 56.1 | 2.20E−09 |
| Q08211 | 884.7845 | 3 | 1.9 | 57.3 | 1.60E−09 |
| O60610 | 918.5204 | 4 | 11 | 35.9 | 9.30E−06 |
| Q9BTC0 | 865.1213 | 3 | −16 | 35.4 | 6.10E−05 |
| Q9BTC0 | 553.7901 | 2 | 16 | 33.1 | 8.20E−04 |
| Q9BTC0 | 796.7609 | 3 | 3.5 | 60.2 | 2.70E−08 |
| Q9BTC0 | 877.7758 | 3 | −26 | 45.1 | 5.70E−07 |
| Q9BTC0 | 399.519 | 3 | 4.9 | 24 | 0.012 |
| Q12959 | 1189.5762 | 3 | −0.17 | 25.8 | 0.0075 |
| Q99615 | 709.0066 | 3 | 2.2 | 34.6 | 5.40E−05 |
| Q99615 | 761.0354 | 3 | −4.4 | 40.5 | 1.00E−05 |
| Q99615 | 703.6769 | 3 | 5.1 | 66 | 1.10E−06 |
| Q99615 | 755.7119 | 3 | 6.4 | 55.9 | 1.10E−06 |
| O00429 | 665.3303 | 2 | −0.93 | 29.1 | 8.40E−05 |
| O00429 | 605.5967 | 3 | −2.2 | 51 | 1.50E−05 |
| O00429 | 657.6226 | 3 | −14 | 34.5 | 1.40E−04 |
| O00429 | 600.2747 | 3 | 14 | 49.7 | 1.40E−05 |
| O00429 | 652.2982 | 3 | −2.9 | 47.1 | 1.40E−04 |
| Q9Y6K1 | 573.5599 | 4 | 7.5 | 38.5 | 1.10E−04 |
| Q96BY6 | 709.3342 | 2 | −6.7 | 30.3 | 3.40E−06 |
| Q9BU89 | 563.8221 | 2 | −8.6 | 29 | 0.0021 |
| Q9BU89 | 607.3488 | 3 | −3.8 | 59.6 | 1.70E−07 |
| Q8TEK3 | 826.1048 | 3 | 2.2 | 30.7 | 0.0027 |
| Q9UKG1 | 1025.8137 | 3 | −23 | 53.4 | 1.20E−07 |
| P28340 | 599.9963 | 3 | 19 | 43.9 | 5.90E−07 |
| P28340 | 627.3408 | 4 | −11 | 36 | 1.80E−05 |
| P09884 | 525.7645 | 2 | 0.34 | 36.6 | 0.0066 |
| Q86TI2 | 604.7786 | 2 | −3.6 | 43.1 | 0.0049 |
| O14531 | 407.887 | 3 | 4.7 | 23.4 | 0.067 |
| Q16643 | 780.8959 | 2 | −1.2 | 23.7 | 0.0024 |
| Q16643 | 1009.9798 | 2 | −2.1 | 47.6 | 2.60E−05 |
| P55265 | 659.9648 | 3 | −5 | 39.8 | 4.40E−06 |
| Q9NZJ0 | 824.8967 | 4 | −7.2 | 41.2 | 3.10E−06 |
| Q9NZJ0 | 720.5584 | 5 | 4.3 | 44.5 | 1.80E−06 |
| Q8TDB6 | 660.31 | 2 | −1.6 | 24.5 | 0.0062 |
| Q14204 | 510.5649 | 3 | 0.026 | 28.9 | 0.0014 |
| Q14204 | 600.2835 | 2 | 1.4 | 35.5 | 0.072 |
| Q6ZTU2 | 936.4917 | 3 | −6.9 | 43 | 7.70E−05 |
| Q96L91 | | | | | |
| O43491 | 1026.8482 | 3 | −4.4 | 24.5 | 0.027 |
| Q9H1B7 | 812.954 | 2 | −0.63 | 34 | 1.70E−06 |
| Q99848 | 551.2859 | 3 | −0.34 | 44 | 4.20E−04 |
| P42892 | 813.3829 | 3 | −1.2 | 46.7 | 1.30E−04 |
| Q9H8V3 | 648.8259 | 2 | −2.4 | 22.2 | 0.013 |
| Q6P2E9 | 1036.5319 | 4 | 25 | 32.1 | 6.80E−04 |
| Q6P2E9 | 833.9083 | 2 | 1.7 | 36 | 1.10E−06 |
| Q6P2E9 | 825.9041 | 2 | −6.5 | 35.5 | 8.70E−07 |
| Q6P2E9 | 557.6229 | 3 | 0.72 | 27.7 | 0.036 |
| Q6P2E9 | 700.021 | 3 | −5.3 | 51.3 | 1.70E−07 |
| Q6P2E9 | 760.3679 | 3 | −3.6 | 55.8 | 6.80E−07 |
| Q6P2E9 | 428.8875 | 2 | −4.9 | 29.4 | 0.0077 |
| Q3B7T1 | 881.4229 | 2 | −6.5 | 39 | 1.50E−05 |
| Q3B7T1 | 945.4758 | 2 | −0.38 | 34.9 | 2.10E−07 |
| Q15075 | 907.7752 | 3 | −3.8 | 22.9 | 0.009 |
| Q15075 | 1124.5314 | 3 | −9.8 | 48.8 | 1.30E−07 |

TABLE 2-continued

Mass spectrometry statistics for identified caspase-derived peptides.

| Swiss-Prot acc # | m/z | z | Error ppm | score | E value |
|---|---|---|---|---|---|
| P68104 Q5VTE0 | 941.1216 | 3 | −7.7 | 44.6 | 1.40E−05 |
| P68104 Q5VTE0 | 790.0424 | 3 | −0.28 | 29.8 | 0.0025 |
| P68104 Q5VTE0 | 784.7067 | 3 | −5.5 | 43.6 | 2.90E−07 |
| P68104 Q5VTE0 | 674.3309 | 3 | 0.44 | 22.5 | 0.076 |
| P68104 Q5VTE0 | 479.2559 | 4 | −13 | 25.3 | 0.018 |
| P68104 Q5VTE0 | 850.3883 | 3 | −0.24 | 43.8 | 3.20E−06 |
| P24534 | 609.2763 | 3 | 3.1 | 45.2 | 4.80E−07 |
| P24534 | 917.8751 | 2 | −3.9 | 43.7 | 2.30E−05 |
| P29692 | 613.2911 | 4 | −0.12 | 33.8 | 1.70E−06 |
| P29692 | 734.3377 | 3 | −0.37 | 43.6 | 2.50E−05 |
| P13639 | 515.6041 | 3 | 4.1 | 63 | 3.40E−05 |
| Q8N3D4 | 951.4455 | 3 | 8.8 | 52.1 | 6.90E−08 |
| Q8NDI1 | 843.3957 | 3 | −2.4 | 45.2 | 1.10E−05 |
| Q9H4M9 | 1034.4543 | 3 | −3.1 | 52.4 | 3.10E−08 |
| Q9H9B1 | 576.9345 | 3 | −2.7 | 40.8 | 9.40E−05 |
| Q9H9B1 | 702.3415 | 2 | −0.92 | 28.2 | 1.10E−04 |
| Q96KQ7 | 491.9357 | 3 | 5.6 | 44 | 1.20E−04 |
| P55884 | 735.3623 | 2 | −3.9 | 42.1 | 0.0024 |
| P55884 | 683.7148 | 2 | −2 | 44 | 1.80E−04 |
| O75821 | 741.8482 | 4 | −2.3 | 38.9 | 1.10E−05 |
| O75822 | 667.7986 | 4 | −6.4 | 39.9 | 6.20E−06 |
| P32519 | 858.9174 | 2 | −12 | 60.5 | 2.40E−06 |
| P32519 | 850.9296 | 2 | −0.21 | 44.1 | 3.40E−06 |
| P06733 | 905.1272 | 3 | −14 | 34.6 | 4.50E−04 |
| P14625 | 554.7924 | 2 | 2.6 | 32.2 | 0.085 |
| P14625 | 599.2788 | 2 | −11 | 32.4 | 0.004 |
| P14625 | 480.912 | 3 | 17 | 30.3 | 1.90E−04 |
| Q9UBC2 | 806.7389 | 3 | 5.3 | 57.4 | 1.20E−06 |
| P42566 | 843.0613 | 3 | 9.5 | 29.7 | 0.0043 |
| Q9H2F5 | 594.3092 | 2 | −4.7 | 24 | 8.10E−05 |
| Q9Y6I3 | 538.6288 | 3 | 4.5 | 37.7 | 0.0043 |
| O95208 | 638.8329 | 2 | 4.2 | 32.2 | 5.10E−04 |
| Q2NKX8 | 551.6196 | 3 | −2.8 | 22.4 | 0.056 |
| Q03468 | 745.3792 | 2 | 5.7 | 23.2 | 0.0012 |
| P15170 | 674.3426 | 4 | −0.88 | 28.4 | 0.0016 |
| P15170 | 533.6556 | 5 | 7.9 | 35.3 | 1.30E−05 |
| P15170 | 569.8814 | 5 | 39 | 25 | 0.0013 |
| P15170 | 712.066 | 4 | −8.1 | 48.1 | 5.00E−06 |
| P50548 | 807.3873 | 2 | 1.2 | 27.3 | 0.0017 |
| Q86X53 | 531.277 | 2 | −0.54 | 26.6 | 0.0036 |
| A0FGR8 | 745.9169 | 2 | 3.5 | 43 | 0.022 |
| Q7Z2Z2 | 390.1911 | 3 | 15 | 31.6 | 3.60E−04 |
| Q7Z2Z2 | 589.2464 | 2 | 2.2 | 40.2 | 0.005 |
| Q9NVH0 | 440.2091 | 3 | 13 | 25.1 | 0.0051 |
| Q8N5W9 | 739.3938 | 3 | −8.5 | 42.5 | 1.00E−06 |
| Q9H098 | 660.663 | 3 | 1.7 | 31.1 | 7.20E−04 |
| Q6P1L5 | 438.2587 | 3 | 1.5 | 32.9 | 5.20E−04 |
| Q96EY5 | 466.9291 | 3 | 2 | 45.8 | 4.70E−04 |
| Q9Y6X4 | 667.8344 | 2 | −5.3 | 23.7 | 9.90E−04 |
| O94988 | 507.2676 | 3 | 3.8 | 31.8 | 0.0025 |
| O94988 | 567.6108 | 3 | −1.3 | 55.4 | 2.50E−06 |
| Q641Q2 Q5SNT6 Q9Y4E1 Q5SRD0 | 809.892 | 2 | 3.7 | 49.8 | 2.60E−05 |
| Q7Z4H7 | 671.3426 | 2 | −1.4 | 41.6 | 0.077 |
| Q8NFC6 | 840.4196 | 3 | −3 | 53.2 | 5.30E−08 |
| Q8NFC6 | 513.9373 | 3 | 6.4 | 40.2 | 3.50E−06 |
| Q8NFC6 | 758.3617 | 3 | −0.36 | 56.7 | 9.50E−08 |
| Q8NFC6 | 900.7601 | 3 | −8.8 | 65.1 | 3.60E−11 |
| Q8NFC6 | 753.034 | 3 | 4.8 | 67.6 | 1.20E−08 |
| Q8NFC6 | 581.7388 | 2 | 7.5 | 26.8 | 0.0022 |
| P49327 | 592.9841 | 3 | 1.5 | 46.1 | 2.00E−04 |
| P02765 | 480.8913 | 2 | −0.56 | 30.6 | 0.0083 |
| Q6UN15 | 438.8746 | 2 | −1.5 | 25.1 | 0.017 |
| Q5T1M5 | 1176.6186 | 3 | 0.9 | 32.4 | 1.60E−04 |
| Q5T1M5 | 994.8491 | 3 | 7.8 | 49 | 1.40E−06 |
| Q01543 | 445.8907 | 3 | −8.7 | 29.2 | 0.0027 |
| P21333 | 1143.0476 | 2 | 0.52 | 42.5 | 1.10E−08 |
| P21333 | 847.4108 | 3 | −15 | 30.1 | 6.30E−04 |
| P21333 | 768.7155 | 3 | −3.5 | 39.7 | 2.50E−05 |
| P21333 | 571.7673 | 2 | 21 | 33 | 0.0063 |
| P21333 | 736.361 | 2 | −1.9 | 41.3 | 4.70E−05 |
| P21333 | 775.7592 | 3 | 6.1 | 56.5 | 4.50E−08 |
| P21333 | 638.8862 | 4 | 43 | 50.2 | 7.30E−10 |
| P21333 | 793.4324 | 5 | 5.1 | 33.9 | 5.30E−06 |
| P21333 | 590.2847 | 2 | −5 | 38.7 | 0.048 |
| O75369 Q14315 | | | | | |
| O75369 | 484.2596 | 3 | 5 | 23.2 | 0.0062 |
| O75369 | 794.721 | 3 | −5.4 | 35.1 | 6.40E−04 |
| O75369 | 816.7023 | 3 | −19 | 62.4 | 1.10E−08 |
| O75369 | 811.3807 | 3 | −6.7 | 35.3 | 1.90E−05 |
| Q96RU3 | 949.8877 | 2 | 4.4 | 50.8 | 7.00E−09 |
| Q96RU3 | 941.8855 | 2 | −0.55 | 58.5 | 1.90E−07 |
| Q8N3X1 | 867.4791 | 3 | 1.3 | 39.8 | 1.60E−06 |
| Q8N3X1 | 459.7417 | 2 | 13 | 34.1 | 0.0046 |
| Q8N3X1 | 535.2756 | 2 | 6.3 | 35.1 | 5.30E−05 |
| Q9P0K8 | 479.7612 | 2 | 9 | 40.5 | 0.0011 |
| P85037 | 625.3471 | 3 | 7.3 | 60.1 | 9.10E−05 |
| O43524 | 1040.3843 | 2 | −15 | 43.7 | 5.70E−07 |
| Q8IVH2 | 636.952 | 5 | −2.6 | 42 | 1.70E−06 |
| P42345 | 429.552 | 3 | 3 | 42.5 | 0.0038 |
| P42345 | 472.2454 | 3 | −7.7 | 44.6 | 0.012 |
| O94915 | 508.5913 | 3 | −0.42 | 37 | 0.001 |
| Q96AE4 | 881.4463 | 2 | 0.8 | 48 | 9.20E−06 |
| Q96AE4 | 664.6509 | 3 | −0.6 | 35.5 | 0.001 |
| Q96AE4 | 483.2372 | 2 | −1.7 | 24 | 0.049 |
| Q92945 | | | | | |
| Q92945 | 579.3093 | 3 | 0.37 | 50.4 | 4.30E−06 |
| Q96I24 | 793.4292 | 2 | −18 | 42.7 | 3.90E−05 |
| Q96I24 | 912.4542 | 3 | −7.1 | 58.7 | 8.70E−07 |
| P35637 | 911.9938 | 2 | −0.33 | 39 | 5.90E−07 |
| P35637 | 442.8908 | 3 | −8.2 | 29.8 | 6.60E−04 |
| P51116 | 728.3358 | 4 | 10 | 32.3 | 7.10E−05 |
| O15117 | 1037.9759 | 2 | 2.9 | 26.4 | 2.70E−05 |
| O15117 | 912.7125 | 3 | −1.8 | 46 | 1.90E−07 |
| O15117 | 1007.7678 | 3 | 5.8 | 72.4 | 1.30E−09 |
| P06241 | 577.2888 | 2 | 9.2 | 41.4 | 1.50E−04 |
| Q96QD9 Q86V81 | 600.7898 | 2 | −7.8 | 41.3 | 0.016 |
| Q9Y2I7 | 663.8579 | 2 | 5.5 | 27.2 | 2.20E−05 |
| Q9Y2I7 | 792.423 | 2 | −0.051 | 41.6 | 9.10E−07 |
| Q9Y2I7 | 801.415 | 3 | −6.1 | 49.2 | 8.30E−07 |
| P04406 | 668.6631 | 3 | 5.8 | 33.8 | 4.90E−06 |
| Q06547 | 903.133 | 3 | −7.1 | 22.6 | 0.0016 |
| Q06547 | 955.1564 | 3 | −18 | 39.6 | 2.10E−04 |
| Q8TAK5 | 591.8463 | 2 | 1.1 | 33.2 | 5.50E−04 |
| P07902 | 479.244 | 2 | 2 | 29.4 | 0.047 |
| Q14C86 | 603.2872 | 3 | 6.2 | 52.3 | 6.50E−08 |
| Q14C86 | 531.257 | 4 | 5.4 | 37 | 5.80E−05 |
| P23769 | 667.8206 | 4 | 10 | 34.6 | 4.80E−05 |
| Q92538 | 788.3685 | 3 | 4.9 | 29.6 | 8.00E−06 |
| Q92538 | 586.2578 | 3 | −0.41 | 43.9 | 2.20E−07 |
| Q9Y5B6 | 369.5298 | 3 | 0.6 | 28.4 | 0.0087 |
| Q9BSJ2 | 857.7569 | 3 | −4.9 | 50.5 | 3.70E−04 |
| Q9H3P7 | 901.5111 | 4 | 48 | 33.2 | 2.80E−05 |
| Q9H3P7 | 803.0445 | 3 | 1.7 | 56 | 7.40E−08 |
| P52566 | 692.8988 | 2 | −3.2 | 23.3 | 4.80E−04 |
| P52566 | 429.0122 | 4 | 12 | 31.5 | 1.90E−04 |
| P52566 | 531.7784 | 2 | 2.7 | 35.2 | 0.014 |
| P06396 | 607.7944 | 2 | −2.1 | 41.5 | 0.0065 |
| P06396 | 656.0097 | 3 | 6 | 55.1 | 1.10E−05 |
| Q8TEQ6 | 962.1116 | 3 | −8.3 | 38.8 | 7.50E−05 |
| Q9NWZ8 | 659.951 | 3 | −0.54 | 42 | 1.70E−06 |
| Q17RS7 | 940.4229 | 2 | −5.6 | 23.4 | 0.0081 |
| Q06210 | 698.3406 | 2 | −6.1 | 37.1 | 3.20E−05 |
| Q9NZ52 | 1129.5866 | 3 | −26 | 37.9 | 1.10E−04 |
| Q9NZ52 | 690.3595 | 2 | 4.6 | 48.7 | 0.0065 |
| Q9Y2X7 | 814.0902 | 3 | −11 | 29.1 | 0.0062 |
| Q9Y2X7 | 807.43 | 2 | 6.6 | 49.5 | 4.00E−04 |
| Q9Y2X7 | 581.3222 | 3 | 8.6 | 42 | 8.70E−05 |
| Q9Y2X7 | 959.9743 | 2 | −12 | 39.5 | 1.60E−04 |
| Q14161 | 789.7401 | 3 | 9.8 | 53.7 | 1.20E−04 |

TABLE 2-continued

Mass spectrometry statistics for identified caspase-derived peptides.

| Swiss-Prot acc # | m/z | z | Error ppm | score | E value |
|---|---|---|---|---|---|
| Q04446 | 454.1991 | 3 | 6.4 | 30 | 6.20E−04 |
| O76003 | 391.8701 | 3 | 5 | 31.2 | 0.0041 |
| O76003 | 434.562 | 3 | −10 | 33.6 | 0.0058 |
| P14314 | 966.4078 | 2 | −1.3 | 33.4 | 1.20E−06 |
| P14314 | 730.3231 | 3 | 2.8 | 56.6 | 7.40E−08 |
| P14314 | 1200.0392 | 4 | −16 | 25.1 | 3.00E−05 |
| P14314 | 1019.0646 | 3 | −1.6 | 38.7 | 3.90E−07 |
| Q9P107 | 1023.4906 | 2 | 0.26 | 35.9 | 8.30E−07 |
| Q9P107 | 460.7289 | 2 | 8 | 38.5 | 0.0034 |
| Q9P107 | 713.3512 | 2 | −4 | 35.2 | 9.90E−05 |
| P36915 | 694.827 | 2 | −0.48 | 36.4 | 6.90E−05 |
| P36915 | 820.6503 | 4 | −10 | 32.4 | 5.60E−04 |
| P36915 | 429.2062 | 3 | −19 | 32.8 | 0.03 |
| P36915 | 785.3473 | 2 | 1.5 | 37.5 | 1.10E−05 |
| P36915 | 530.2459 | 3 | −7.5 | 31.4 | 0.0016 |
| Q14789 | 907.4273 | 3 | −15 | 46.6 | 1.20E−06 |
| Q14789 | 670.6572 | 3 | −3 | 29.8 | 0.0048 |
| Q14789 | 730.9991 | 3 | −8.1 | 49.8 | 2.80E−06 |
| Q3T8J9 | 806.3869 | 2 | −11 | 33.4 | 7.90E−04 |
| Q92917 | 487.2541 | 3 | 3.5 | 40.5 | 1.70E−05 |
| Q92917 | 561.2759 | 2 | 30 | 31.5 | 0.018 |
| Q92917 | 542.5193 | 4 | −5.1 | 40.6 | 1.00E−07 |
| Q92917 | 519.2812 | 2 | −7.2 | 28.6 | 0.0096 |
| Q92917 | 603.3236 | 3 | −13 | 43 | 1.10E−04 |
| Q9HCN4 | 578.3334 | 3 | −5.7 | 33.2 | 1.40E−04 |
| Q9UKJ3 | 892.4116 | 3 | −21 | 43.8 | 8.80E−06 |
| Q3V6T2 | 626.54 | 4 | −4.4 | 51.6 | 4.20E−06 |
| Q3V6T2 | 521.2493 | 2 | 6.4 | 34.8 | 0.061 |
| Q7Z2K8 | 715.8928 | 2 | −4.6 | 23 | 0.0017 |
| P57764 | 819.9452 | 2 | 1.3 | 36.9 | 4.10E−06 |
| P57764 | 889.9305 | 2 | −9.6 | 40 | 4.90E−06 |
| P09211 | 624.7982 | 2 | 0.18 | 30.9 | 0.0026 |
| P09211 | 616.7935 | 2 | −12 | 41 | 5.70E−04 |
| P78347 | 590.8117 | 2 | −4 | 41.8 | 0.042 |
| P78347 | 436.9094 | 3 | −1.5 | 38 | 0.044 |
| O75367 | 898.9377 | 2 | −13 | 44.9 | 2.30E−05 |
| P62805 | 552.7883 | 2 | 0.87 | 22.5 | 0.0064 |
| P62805 | 420.9007 | 3 | 14 | 36.2 | 8.00E−04 |
| P62805 | 463.5985 | 3 | 12 | 37.5 | 4.60E−04 |
| P62805 | 432.605 | 3 | 16 | 39.8 | 2.10E−04 |
| Q13442 | 376.8892 | 3 | 14 | 23.9 | 0.017 |
| Q13442 | 452.5993 | 3 | 5.9 | 28.8 | 0.0026 |
| Q9Y450 | 1007.4704 | 2 | −2 | 40.9 | 7.90E−05 |
| P14317 | 483.9191 | 3 | 6.6 | 46.6 | 3.10E−04 |
| P14317 | 601.2884 | 2 | −3.3 | 35 | 0.048 |
| P56524 | 603.0072 | 3 | 14 | 38 | 9.30E−05 |
| P56524 | 1383.3258 | 3 | 1.1 | 33.9 | 6.30E−05 |
| Q9UBN7 | 596.2706 | 2 | 17 | 34.3 | 0.0016 |
| Q9UBN7 | 580.2673 | 2 | 3.3 | 39 | 0.0016 |
| Q8WUI4 | 581.6054 | 3 | −4.4 | 45.4 | 3.20E−06 |
| Q9UBI9 | 440.8914 | 3 | −7.4 | 35.5 | 0.0021 |
| Q7Z4V5 | 737.1483 | 4 | 0.079 | 22.1 | 0.035 |
| Q7Z4V5 | 464.9002 | 3 | −5.8 | 38.6 | 5.40E−05 |
| Q7Z4V5 | 459.5666 | 3 | −10 | 23.2 | 0.012 |
| Q7Z4V5 | 386.5469 | 3 | −4.4 | 31.6 | 0.0041 |
| Q9ULT8 | 897.4596 | 3 | −2.3 | 28.6 | 0.0036 |
| Q9NRZ9 | 829.0873 | 3 | −0.68 | 35.6 | 3.60E−04 |
| P04233 | 875.9403 | 2 | −3.4 | 48 | 9.20E−05 |
| P04233 | 867.9434 | 2 | −2.7 | 47.9 | 3.30E−04 |
| Q9BW71 | 515.2498 | 2 | −11 | 24.4 | 0.0058 |
| Q8NCD3 | 583.3096 | 3 | 15 | 44 | 9.40E−07 |
| Q92619 | 920.6968 | 4 | −14 | 26.5 | 1.20E−05 |
| Q92619 | 960.4808 | 2 | 0.58 | 43.9 | 1.20E−05 |
| Q92619 | 973.9817 | 2 | −15 | 38.1 | 1.10E−05 |
| P30519 | 369.5154 | 3 | 4.6 | 29.4 | 0.001 |
| P30519 | 527.8961 | 3 | −24 | 35.5 | 3.60E−06 |
| P30519 | 392.1869 | 4 | 6 | 22.9 | 0.0017 |
| P31943 | 871.9425 | 2 | −0.65 | 34.4 | 9.70E−05 |
| P31943 | 513.8811 | 5 | 17 | 32.1 | 2.10E−04 |
| P55795 | | | | | |
| P31943 | 766.0473 | 3 | −8.5 | 44.4 | 7.00E−06 |
| P55795 | | | | | |
| P31943 | 554.7388 | 2 | 0.87 | 33.5 | 2.90E−04 |
| P55795 | | | | | |
| P55795 | 581.6278 | 3 | −5.7 | 24.8 | 0.037 |
| P31942 | 934.0253 | 3 | −7.3 | 40.1 | 3.20E−08 |
| Q9BUJ2 | 481.8748 | 3 | −15 | 42.2 | 1.70E−05 |
| Q9BUJ2 | 476.5497 | 3 | −1.9 | 45.5 | 6.20E−05 |
| Q1KMD3 | 851.0696 | 3 | 1.4 | 62.6 | 7.50E−09 |
| Q1KMD3 | 677.5804 | 4 | 3 | 53.3 | 7.20E−07 |
| Q8WVV9 | 567.6299 | 3 | −0.24 | 37.5 | 0.0035 |
| Q14103 | 499.2117 | 4 | −12 | 41 | 7.40E−07 |
| P52597 | 742.3466 | 2 | 0.49 | 43.3 | 4.60E−04 |
| P38159 | 574.2536 | 2 | −1.3 | 36.1 | 1.50E−05 |
| P38159 | 495.25 | 3 | 1.8 | 31.5 | 0.0024 |
| P61978 | 755.3641 | 2 | 3.7 | 30.5 | 2.80E−05 |
| P61978 | 648.0446 | 2 | 2.7 | 55.5 | 2.80E−10 |
| P61978 | 1167.8252 | 3 | −10 | 22.2 | 7.80E−05 |
| P61978 | 512.2341 | 2 | 7.6 | 26.4 | 0.0056 |
| P14866 | 756.0158 | 3 | −6.8 | 34.1 | 1.90E−04 |
| O60506 | 555.2274 | 3 | −8.2 | 37 | 8.20E−05 |
| Q9UJC3 | 750.3508 | 2 | −4.7 | 47.6 | 5.80E−04 |
| Q9UJC3 | 543.2718 | 3 | 2.9 | 35.7 | 7.70E−04 |
| Q96ED9 | 886.8975 | 2 | −12 | 48.5 | 2.10E−04 |
| Q9NQG7 | 1106.7951 | 3 | −14 | 55.7 | 8.90E−10 |
| Q03164 | 898.9001 | 2 | −12 | 52.9 | 4.30E−07 |
| Q03164 | 642.3179 | 3 | 15 | 53.2 | 1.90E−06 |
| Q03164 | 972.9138 | 2 | −5.2 | 46.5 | 2.70E−06 |
| Q92598 | 770.0305 | 3 | 8.3 | 53.5 | 1.70E−04 |
| Q92598 | 983.132 | 3 | 0.38 | 44 | 3.50E−06 |
| Q92598 | 848.1935 | 4 | 45 | 49 | 2.60E−07 |
| P34931 | 449.2161 | 3 | 15 | 31.2 | 0.0019 |
| P08107 | | | | | |
| P54652 | | | | | |
| P17066 | | | | | |
| P48741 | | | | | |
| P11142 | | | | | |
| P34932 | 451.7001 | 2 | 0.47 | 25.9 | 0.013 |
| P11142 | 481.7543 | 2 | 3.9 | 29.1 | 0.011 |
| Q99081 | 727.3534 | 2 | −10 | 28.4 | 0.0028 |
| O43719 | 911.4252 | 3 | −2.8 | 42 | 4.90E−06 |
| O43719 | 1121.2057 | 3 | 0.38 | 23.7 | 0.092 |
| O43719 | 529.2607 | 3 | 6.9 | 39.2 | 3.90E−07 |
| O43719 | 736.0272 | 3 | 0.37 | 55.5 | 1.70E−08 |
| Q7Z6Z7 | 616.8288 | 2 | −7.3 | 26.6 | 0.0025 |
| Q7Z6Z7 | 656.8401 | 2 | −1.1 | 24.5 | 1.50E−04 |
| Q7Z6Z7 | 486.7675 | 2 | −1.8 | 31.8 | 7.00E−04 |
| Q7Z6Z7 | 559.7913 | 2 | −4.1 | 31.5 | 1.40E−04 |
| Q7Z6Z7 | 826.3566 | 3 | 0.28 | 57.6 | 1.20E−08 |
| Q7Z6Z7 | 701.367 | 3 | −4.1 | 59.6 | 1.10E−07 |
| Q7Z5L9 | 683.3163 | 3 | −0.65 | 57 | 9.60E−05 |
| P32019 | 496.2696 | 2 | 0.067 | 31.9 | 0.07 |
| Q8WUF5 | 581.6511 | 3 | −0.51 | 44.7 | 3.60E−06 |
| P20810 | 827.8799 | 2 | −13 | 56.2 | 1.50E−07 |
| P20810 | 594.9629 | 3 | 2.8 | 54.1 | 4.20E−08 |
| P20810 | 950.9444 | 2 | −5.7 | 50.5 | 1.40E−05 |
| P20810 | 492.0218 | 4 | −7.7 | 39 | 6.40E−07 |
| P20810 | 881.3723 | 2 | −13 | 52.4 | 1.20E−06 |
| A6NK07 | 471.2361 | 2 | −12 | 28.9 | 0.063 |
| P20042 | | | | | |
| O60841 | 628.8424 | 2 | −5.6 | 48.6 | 6.20E−05 |
| O60841 | 666.0137 | 3 | −3.9 | 58.6 | 7.80E−06 |
| O60841 | 553.5485 | 4 | 4.7 | 48.4 | 1.60E−06 |
| Q14240 | 873.395 | 3 | −0.38 | 56.2 | 2.40E−06 |
| Q14240 | 1067.4832 | 3 | −27 | 48 | 8.40E−08 |
| P23588 | 522.9046 | 3 | −35 | 23.3 | 0.051 |
| P23588 | 648.9545 | 3 | 6.7 | 41.1 | 1.00E−04 |
| Q04637 | 1290.1025 | 4 | 0.97 | 22.1 | 0.028 |
| Q04637 | 680.3351 | 2 | −4.5 | 43.7 | 9.10E−04 |
| Q04637 | 782.3865 | 2 | 7.7 | 49.6 | 0.01 |
| P78344 | 544.9423 | 3 | 3 | 49 | 8.90E−06 |
| P78344 | 1015.8857 | 3 | 4.5 | 27.8 | 0.0033 |
| O43432 | 596.9612 | 3 | −1.8 | 44.8 | 3.30E−06 |
| O43432 | 648.9964 | 3 | 0.65 | 38.5 | 0.0019 |
| Q15056 | 903.9804 | 3 | −3.3 | 40.4 | 4.10E−04 |
| P63241 | 761.391 | 2 | −10 | 39 | 3.30E−04 |
| P63241 | 834.8914 | 2 | −4.6 | 30.1 | 1.10E−05 |
| Q6IS14 | | | | | |
| P63241 | 594.304 | 3 | 7.9 | 47.1 | 1.80E−05 |
| Q6IS14 | | | | | |

TABLE 2-continued

Mass spectrometry statistics for identified caspase-derived peptides.

| Swiss-Prot acc # | m/z | z | Error ppm | score | E value |
|---|---|---|---|---|---|
| P63241 Q6IS14 | 826.8934 | 2 | −5.3 | 42.9 | 1.90E−05 |
| P63241 Q6IS14 | 782.6949 | 3 | −6.5 | 54.8 | 2.50E−10 |
| P63241 Q6IS14 | 654.6412 | 3 | −6 | 35 | 3.20E−04 |
| P63241 Q6IS14 | 795.0175 | 3 | 2.1 | 57.1 | 1.90E−06 |
| P63241 Q6IS14 | 832.3709 | 3 | −14 | 60.6 | 2.50E−09 |
| P63241 Q6IS14 | 789.6877 | 3 | 4.4 | 59.2 | 4.20E−07 |
| Q9GZV4 | 778.6994 | 3 | −0.68 | 54.2 | 1.50E−07 |
| Q9GZV4 | 839.0477 | 3 | 2.3 | 35.9 | 4.20E−05 |
| Q15653 | 635.8092 | 2 | 3.8 | 43.4 | 0.0031 |
| Q96HA7 | 702.685 | 3 | −2.8 | 47.6 | 7.60E−08 |
| Q96HA7 | 566.2926 | 4 | 0.63 | 41.3 | 9.40E−06 |
| Q13422 | 718.8969 | 2 | −9.1 | 57.1 | 0.002 |
| Q9UKS7 | 819.8802 | 2 | 6.3 | 38 | 1.50E−05 |
| Q9H5V7 | 541.2358 | 2 | 13 | 27.3 | 0.0031 |
| Q12906 | 598.0347 | 4 | 3.4 | 39.8 | 2.50E−08 |
| Q12906 | 665.7981 | 2 | −1.5 | 47.2 | 5.40E−05 |
| Q12906 | 486.9006 | 3 | 0.88 | 30.9 | 7.80E−05 |
| Q9H0C8 | 1055.1788 | 3 | −7.7 | 33.7 | 2.00E−05 |
| P52294 | 671.91 | 5 | −7.6 | 23.1 | 0.011 |
| P52294 | 1168.8793 | 3 | 8.3 | 56.1 | 1.40E−07 |
| O60684 | 868.9194 | 2 | −1.2 | 48.8 | 1.80E−05 |
| P12268 | 628.3016 | 2 | −8.2 | 27.5 | 0.0019 |
| Q53TQ3 | 592.8169 | 2 | −0.42 | 31.4 | 0.0017 |
| Q27J81 | 852.7746 | 3 | −13 | 28.6 | 4.10E−04 |
| Q27J81 | 678.866 | 4 | −0.28 | 32.1 | 9.10E−05 |
| Q27J81 | 491.5756 | 3 | 10 | 32.8 | 6.10E−06 |
| Q96P70 | 868.9808 | 2 | 6.6 | 46.8 | 1.90E−04 |
| Q6DN90 | 668.841 | 2 | 0.35 | 37.6 | 3.80E−06 |
| P46940 | 523.2617 | 4 | −7.9 | 43 | 1.20E−06 |
| P46940 | 791.8718 | 4 | −13 | 48.2 | 9.70E−10 |
| P14316 | 481.7287 | 4 | −0.69 | 37.4 | 6.40E−07 |
| O14654 | 569.2558 | 3 | −1.8 | 56.2 | 4.30E−05 |
| Q9ULR0 | 744.8934 | 2 | −10 | 35 | 0.002 |
| Q9ULR0 | 594.651 | 3 | 3.6 | 35.8 | 0.0022 |
| Q96ST2 | 495.5329 | 3 | −1.1 | 40.8 | 3.40E−06 |
| Q96ST2 | 367.9039 | 4 | 1.8 | 27.4 | 0.0015 |
| Q9H3R0 | 821.4007 | 2 | −1.5 | 37.8 | 1.40E−06 |
| Q9H3R0 | 695.6855 | 3 | 3.5 | 47 | 1.90E−06 |
| O60271 | 596.8115 | 2 | −4.4 | 42.8 | 0.047 |
| O60271 | 706.6559 | 3 | 4.1 | 46.4 | 3.10E−08 |
| O60271 | 701.3263 | 3 | 7 | 64.2 | 2.30E−08 |
| O60271 | 780.0608 | 3 | −5.7 | 35.4 | 0.035 |
| Q96N16 | 623.3181 | 2 | 2.7 | 36.2 | 0.0012 |
| Q96N16 | 713.8268 | 2 | −12 | 34.1 | 1.30E−04 |
| Q8N9B5 | 657.3692 | 2 | −0.032 | 35.9 | 1.10E−04 |
| Q8N9B5 | 724.3729 | 3 | −6.9 | 55.5 | 8.50E−09 |
| Q9H5J8 | 466.25 | 3 | 13 | 31.1 | 0.0022 |
| Q96MG2 | 865.3917 | 2 | 7 | 52.6 | 1.80E−05 |
| P53990 | 565.7727 | 2 | 1.5 | 25.2 | 0.04 |
| P53990 | 420.2057 | 3 | −23 | 29.6 | 0.097 |
| Q92628 | 502.7451 | 2 | −0.04 | 23.9 | 0.035 |
| Q5JSZ5 | 825.9764 | 2 | −0.66 | 25.7 | 3.50E−04 |
| Q5JSZ5 | 416.8733 | 2 | −5.2 | 29.4 | 0.0034 |
| Q6ZNE5 | 804.3995 | 2 | 0.31 | 29.9 | 7.30E−05 |
| Q6ZNE5 | 632.7896 | 2 | −0.53 | 57.2 | 8.80E−04 |
| Q9P266 | 772.3801 | 3 | −1.3 | 43.4 | 1.10E−05 |
| Q9P1Y5 | 1094.9782 | 2 | 0.65 | 37.3 | 1.80E−07 |
| Q9HCE5 | 501.2751 | 3 | 9.2 | 57.5 | 1.90E−04 |
| Q9HCE5 | 551.0467 | 4 | 6 | 50.3 | 2.00E−07 |
| Q9HCE5 | 569.8155 | 2 | 12 | 34.1 | 0.009 |
| Q8IXQ4 | 742.8841 | 2 | 2.5 | 49.2 | 1.00E−04 |
| Q8N163 | 965.44 | 2 | 0.78 | 51.8 | 9.40E−06 |
| Q8N163 | 771.413 | 3 | 3 | 42.2 | 3.30E−04 |
| Q8N163 | 544.0272 | 4 | −12 | 24.2 | 0.0032 |
| Q07666 | 1009.0557 | 2 | −14 | 51 | 2.30E−08 |
| P46013 | 456.7362 | 4 | −3.1 | 45.5 | 3.00E−06 |
| P46013 | 471.2396 | 3 | −1.6 | 39.3 | 4.40E−04 |
| P46013 | 497.7349 | 4 | −2 | 33.8 | 5.00E−04 |
| Q9NS87 | 640.3066 | 2 | 20 | 36.9 | 0.0064 |
| Q8N5S9 | 482.235 | 2 | 10 | 25.9 | 0.037 |
| Q9Y4X4 | 669.6589 | 3 | −9.8 | 48.2 | 8.50E−05 |
| P14618 | 813.389 | 3 | −6.8 | 33.9 | 5.90E−04 |
| P14618 | 719.3419 | 2 | 3.7 | 24.7 | 5.20E−04 |
| P30613 Q8N9T8 | 365.2104 | 3 | 15 | 22.8 | 0.0065 |
| Q13601 | 433.882 | 3 | −4.2 | 36.2 | 0.0065 |
| Q13601 | 478.4787 | 4 | −5.2 | 41.7 | 3.70E−06 |
| O75676 | 446.5743 | 3 | 12 | 37.8 | 4.00E−04 |
| P13010 | 567.3097 | 2 | −10 | 36.9 | 0.0011 |
| P13010 | 657.839 | 2 | 7.5 | 33.5 | 2.40E−05 |
| P13010 | 406.8455 | 3 | −14 | 31.1 | 1.00E−03 |
| Q14657 | 625.3109 | 3 | −6.5 | 53.5 | 5.80E−07 |
| P07942 | 603.2805 | 3 | −4.7 | 27.7 | 0.074 |
| P42166 | 563.9676 | 3 | 2.1 | 27.5 | 0.0043 |
| P42166 | 763.7119 | 2 | −0.39 | 28.9 | 7.80E−04 |
| Q14160 | 711.3793 | 3 | −18 | 43.8 | 5.20E−06 |
| Q14160 | 462.2459 | 3 | 12 | 34.1 | 0.022 |
| Q14160 | 600.0339 | 4 | −5.6 | 44.1 | 7.30E−09 |
| Q6PKG0 | 561.9504 | 3 | −7.3 | 49.7 | 3.50E−04 |
| Q6PKG0 | 619.6416 | 3 | 5.6 | 53.1 | 3.60E−05 |
| Q71RC2 | 744.3937 | 3 | −0.062 | 49.5 | 1.40E−06 |
| Q92615 | 1019.1531 | 3 | −0.13 | 24.9 | 0.029 |
| O43561 | 1020.0438 | 2 | 1.7 | 22.7 | 4.00E−04 |
| Q9UIQ6 | 627.3172 | 4 | 7.4 | 40.6 | 6.90E−05 |
| Q8N3X6 | 541.7993 | 2 | 17 | 27 | 0.011 |
| Q96JN0 Q9UHB6 | 810.1002 | 3 | −3.4 | 40.6 | 3.00E−06 |
| Q96GY3 | 662.349 | 2 | −5.2 | 40.5 | 0.05 |
| Q9NUP9 | 562.7991 | 2 | 29 | 28.8 | 0.066 |
| Q13136 | 1005.9911 | 2 | 1.1 | 38.3 | 2.30E−07 |
| Q13136 | 1084.037 | 2 | −3.2 | 39.1 | 1.10E−06 |
| Q8ND30 | 1023.8431 | 3 | −0.77 | 26.9 | 0.0098 |
| P20700 | 572.3392 | 2 | −1.8 | 26 | 3.60E−05 |
| Q8WWI1 | 728.8589 | 2 | −12 | 52.3 | 0.0013 |
| Q8IWU2 | 622.8452 | 2 | −1.1 | 39.6 | 3.30E−04 |
| Q9C0E8 | 617.0009 | 3 | 9.8 | 35.9 | 4.70E−04 |
| Q93052 | 763.8397 | 2 | 9.2 | 22.5 | 1.40E−04 |
| Q93052 | 755.8336 | 2 | −2.1 | 27.4 | 8.00E−05 |
| P50851 | 761.3326 | 2 | −1.3 | 31.9 | 9.80E−07 |
| P50851 | 851.8504 | 2 | −2.2 | 51.5 | 5.90E−09 |
| P50851 | 639.3044 | 3 | 15 | 61 | 4.10E−05 |
| P50851 | 633.9662 | 3 | 4.5 | 49.5 | 9.80E−05 |
| Q8N1G4 | 945.4597 | 2 | −6.2 | 46.9 | 2.80E−06 |
| Q8N1G4 | 796.4119 | 4 | −2.2 | 59 | 2.80E−10 |
| Q9Y2L9 | 655.8126 | 2 | −1.4 | 26.2 | 8.30E−05 |
| Q9Y2L9 | 513.2605 | 3 | 5.9 | 29.5 | 6.80E−04 |
| Q5VUJ6 | 395.7015 | 4 | −11 | 39.7 | 7.80E−05 |
| Q96II8 | 474.2556 | 2 | 14 | 36.1 | 0.013 |
| O75427 | 413.8601 | 3 | 4.7 | 27.9 | 0.0014 |
| Q12912 | 738.9125 | 2 | −8.9 | 48.2 | 0.0057 |
| Q32MZ4 | 1070.7324 | 4 | 0.24 | 32.4 | 4.30E−04 |
| Q9Y608 | 1281.3087 | 3 | −2.3 | 30.6 | 0.0028 |
| P83369 | 520.261 | 2 | −1.8 | 22.6 | 7.10E−04 |
| P62310 | 985.5148 | 2 | 1.7 | 26.1 | 7.90E−04 |
| P33241 | 590.7599 | 2 | 6.2 | 35.6 | 0.025 |
| Q96GA3 | 537.006 | 4 | −2 | 22.3 | 0.035 |
| Q86UE4 | 717.348 | 2 | −1.4 | 38 | 9.00E−05 |
| O60664 | 742.8439 | 2 | −22 | 44.9 | 9.60E−06 |
| O60664 | 769.0493 | 3 | 1.2 | 60 | 1.60E−08 |
| O60664 | 583.3055 | 2 | 6.7 | 47.7 | 0.063 |
| Q3KQU3 | 1073.2181 | 3 | −3.9 | 30.4 | 0.0011 |
| Q3KQU3 | 1067.8871 | 3 | −3.3 | 28.9 | 0.005 |
| Q9UPN3 | 829.739 | 3 | −8 | 46.7 | 1.70E−06 |
| Q9UPN3 | 699.8616 | 4 | −1 | 30.7 | 7.80E−04 |
| Q96PK2 Q9UPN3 | 838.0933 | 3 | −1 | 33 | 8.60E−05 |
| Q96PK2 Q9UPN3 | 611.2847 | 4 | −4.7 | 50.5 | 1.10E−08 |
| Q96PK2 Q9UPN3 | 817.9101 | 2 | −4.8 | 34.2 | 2.90E−05 |
| Q96PK2 Q9UPN3 Q96PK2 | 639.8107 | 2 | −0.49 | 37.5 | 1.90E−06 |

TABLE 2-continued

Mass spectrometry statistics for identified caspase-derived peptides.

| Swiss-Prot acc # | m/z | z | Error ppm | score | E value |
|---|---|---|---|---|---|
| Q9UPN3 Q96PK2 | 605.9573 | 3 | −0.38 | 49.3 | 1.50E−06 |
| Q9UPN3 Q96PK2 | 730.334 | 2 | 5.9 | 41 | 6.30E−04 |
| Q8WXG6 | 657.3757 | 2 | −13 | 34.7 | 0.0096 |
| Q9Y5V3 | 714.665 | 3 | 5.1 | 59.6 | 1.10E−06 |
| Q96MG7 | 701.316 | 2 | −2.3 | 48.5 | 2.70E−04 |
| Q96MG7 | 969.7688 | 3 | −12 | 52.3 | 1.20E−07 |
| P23368 | 608.0444 | 3 | 15 | 33.6 | 2.00E−04 |
| P78559 | 1157.6109 | 2 | 9.5 | 38.8 | 1.40E−06 |
| P78559 | 916.7866 | 3 | −14 | 53.3 | 1.60E−06 |
| P78559 | 719.8776 | 4 | 3.4 | 52.3 | 6.50E−08 |
| P27816 | 792.4116 | 2 | −0.25 | 28.1 | 4.50E−04 |
| P27816 | 580.6472 | 3 | 5.6 | 51.1 | 7.80E−06 |
| P27816 | 497.9203 | 3 | −5.6 | 25.8 | 0.028 |
| P27816 | 843.7541 | 3 | −1.2 | 47.2 | 4.40E−05 |
| P27816 | 730.7259 | 3 | −0.99 | 45 | 8.80E−05 |
| P27816 | 727.8715 | 2 | −3.9 | 42 | 0.0061 |
| Q49MG5 | 502.7553 | 2 | −4.7 | 30.1 | 0.041 |
| Q15691 | 547.2662 | 3 | 7.8 | 26.6 | 0.0011 |
| Q9P0L2 | 507.587 | 3 | 5.5 | 38.4 | 1.60E−04 |
| P43243 | 1065.4672 | 2 | 0.62 | 38.4 | 7.70E−09 |
| P43243 | 622.8264 | 2 | −2.2 | 36.2 | 1.30E−06 |
| P43243 | 686.8753 | 2 | 0.15 | 36.4 | 3.30E−06 |
| P43243 | 583.7786 | 4 | −1.2 | 39.6 | 2.10E−05 |
| P43243 | 600.0053 | 3 | 6.5 | 41.5 | 1.20E−05 |
| P43243 | 456.7237 | 2 | −2.3 | 25.6 | 0.018 |
| P43243 | 524.2863 | 4 | 42 | 54.5 | 3.80E−07 |
| Q7Z434 | 401.8584 | 3 | −22 | 30.1 | 0.0099 |
| Q7Z434 | 333.6772 | 4 | 4.1 | 28.2 | 0.031 |
| P61244 | 515.2815 | 2 | −1.7 | 27.2 | 0.072 |
| Q9BQG0 | 726.3666 | 3 | −7.6 | 44.5 | 6.80E−06 |
| P49736 | 837.0505 | 3 | −8.2 | 35.4 | 2.70E−05 |
| P49736 | 645.802 | 2 | −2.1 | 28.9 | 0.014 |
| P25205 | 927.726 | 3 | 4.5 | 45.9 | 9.50E−08 |
| P33991 | 586.9691 | 3 | 3.3 | 48 | 3.90E−07 |
| P33992 | 541.2561 | 3 | −1.6 | 53 | 6.00E−07 |
| P33992 | 829.8377 | 3 | −22 | 48.5 | 2.30E−07 |
| Q14566 | 445.9049 | 3 | −0.98 | 38.8 | 0.0012 |
| Q14566 | 587.765 | 2 | −13 | 32 | 0.0024 |
| Q14676 | 1192.6804 | 4 | 5.2 | 25.9 | 3.50E−04 |
| Q14676 | 935.8055 | 3 | −7.9 | 30.8 | 0.0041 |
| Q9NU22 | 939.4534 | 3 | 7.9 | 45.5 | 7.80E−07 |
| O60244 | 728.3893 | 3 | 1.7 | 49.9 | 1.40E−04 |
| Q15648 | 586.3193 | 2 | −3.7 | 39 | 0.038 |
| Q15648 | 547.283 | 3 | 1.2 | 36.1 | 4.80E−04 |
| O95402 | 487.5985 | 3 | −3.2 | 51.1 | 3.20E−04 |
| Q06413 | 474.5466 | 3 | 5.2 | 32.5 | 8.80E−04 |
| Q06413 | 435.9476 | 4 | −7.9 | 33.2 | 3.70E−06 |
| P31153 | 803.4165 | 2 | 1.7 | 25.7 | 0.001 |
| Q6ZN04 | 1048.8488 | 3 | −9.3 | 26.4 | 3.70E−04 |
| Q8IWI9 | 1088.4852 | 2 | −0.27 | 31.4 | 1.00E−06 |
| Q8IWI9 | 578.8284 | 2 | −6.6 | 36.8 | 0.018 |
| Q8IWI9 | 1041.8352 | 3 | −7.7 | 33 | 2.50E−04 |
| Q8IWI9 | 502.26 | 3 | 3.5 | 57 | 2.80E−05 |
| Q5JRA6 | 525.2844 | 2 | −1.1 | 33.7 | 3.90E−04 |
| Q8N108 | 454.5474 | 3 | 9.1 | 31.6 | 9.90E−05 |
| Q96T58 | 499.6148 | 3 | 5.4 | 40.8 | 9.70E−05 |
| Q96T58 | 668.6869 | 3 | 3.2 | 51.5 | 3.20E−05 |
| Q96T58 | 626.3152 | 2 | 1.3 | 44 | 8.50E−04 |
| Q8NDC0 | 400.5423 | 3 | 5.7 | 27.1 | 0.0033 |
| Q969V6 | 1230.1066 | 2 | −4.2 | 24.9 | 1.30E−05 |
| Q9ULH7 | 840.3932 | 3 | 4.7 | 51.4 | 1.70E−07 |
| O14686 | 660.3398 | 2 | −4.1 | 34.5 | 1.40E−04 |
| O14686 | 820.7642 | 3 | −1.1 | 36.3 | 1.00E−04 |
| Q8NEZ4 | 712.8812 | 2 | 1.3 | 46.4 | 0.019 |
| Q9Y3A3 | 638.0062 | 3 | 6.2 | 53.9 | 5.60E−06 |
| P26038 | 732.3907 | 3 | 7.2 | 25.9 | 0.0026 |
| Q14149 | 736.3953 | 2 | 0.61 | 24.1 | 0.0051 |
| Q14149 | 720.8905 | 3 | 0.28 | 41.8 | 0.0015 |
| P53985 | 431.5621 | 3 | −9.8 | 26.8 | 0.0017 |
| Q02750 | 415.5408 | 3 | −24 | 28.8 | 0.0062 |
| Q02750 | 709.685 | 3 | 9.6 | 47.9 | 7.20E−07 |
| Q02750 | 752.3787 | 3 | 2.9 | 46.7 | 2.00E−06 |
| O00566 | 466.2746 | 3 | 3.3 | 34.2 | 6.70E−04 |
| O00566 | 652.8626 | 2 | 6.3 | 41.4 | 0.022 |
| Q99549 | 844.3957 | 3 | −0.76 | 35.4 | 1.40E−05 |
| Q99549 | 1028.7731 | 3 | −14 | 23.6 | 3.10E−05 |
| Q99549 | 794.3193 | 2 | −1.6 | 55.5 | 3.40E−05 |
| P49006 | 725.8746 | 2 | −8.1 | 40.6 | 4.00E−04 |
| Q8NHP6 | 602.8095 | 4 | −16 | 37.8 | 9.40E−06 |
| Q86U44 | 709.7824 | 2 | 0.83 | 53.3 | 6.20E−06 |
| P35580 | 792.055 | 3 | −9.6 | 25 | 0.018 |
| P35580 | 634.3247 | 2 | 11 | 29.9 | 0.054 |
| P35749 | 642.3197 | 2 | 7.4 | 27.1 | 0.043 |
| P35579 | 521.604 | 3 | 8.5 | 45.1 | 2.10E−04 |
| P35579 | 627.3053 | 2 | −6.9 | 36.9 | 0.0022 |
| Q13459 | 557.99 | 3 | 1.5 | 34 | 0.0017 |
| O14974 | 627.3053 | 4 | −6.9 | 42.9 | 2.90E−06 |
| O75113 | 688.861 | 2 | 6.6 | 36.9 | 2.00E−04 |
| Q13765 | 858.0908 | 3 | −6.1 | 49.1 | 2.10E−05 |
| Q13765 | 924.4515 | 3 | −24 | 31.4 | 0.0042 |
| Q9BWU0 | 472.7181 | 2 | 7.8 | 26.2 | 2.10E−04 |
| Q9BWU0 | 464.7216 | 2 | 10 | 28.1 | 0.0046 |
| Q9BWU0 | 563.2347 | 2 | 2.6 | 41.1 | 0.0018 |
| A2RRP1 | 938.4413 | 2 | −5.6 | 36.5 | 5.80E−05 |
| A2RRP1 | 569.2801 | 4 | −12 | 39.5 | 5.10E−06 |
| Q69YI7 | 863.7732 | 3 | −5.9 | 50.7 | 1.30E−04 |
| Q9UHQ1 | 726.8673 | 2 | −4.8 | 23.9 | 0.001 |
| Q9UHQ1 | 591.296 | 3 | −0.82 | 40.2 | 4.80E−04 |
| P49321 | 679.5959 | 4 | 1.8 | 38.5 | 3.00E−06 |
| P49321 | 523.927 | 3 | 1.4 | 47.7 | 0.0015 |
| P49321 | 425.2185 | 4 | −4.2 | 39.9 | 6.30E−05 |
| P16333 | 817.8674 | 2 | −1 | 41.4 | 3.50E−07 |
| Q9Y6Q9 | 560.5436 | 4 | 4.2 | 35.2 | 4.00E−05 |
| Q9HCD5 | 456.2735 | 2 | 9.8 | 25.8 | 0.018 |
| Q9HCD5 | 492.2351 | 3 | −8.6 | 42.4 | 6.70E−05 |
| Q14686 | 663.6483 | 3 | −13 | 34.3 | 0.0096 |
| O75376 | 630.8125 | 2 | −6 | 44.6 | 1.20E−04 |
| O75376 | 549.9297 | 3 | −0.67 | 53 | 5.80E−05 |
| O75376 | 596.9484 | 3 | −2.8 | 54.4 | 1.60E−05 |
| O75376 | 721.3387 | 2 | 5 | 30.6 | 2.60E−04 |
| O75376 | 699.316 | 2 | 4.8 | 35.5 | 0.015 |
| O75376 | 636.2653 | 2 | −12 | 32.1 | 0.0085 |
| Q9Y618 | 616.3077 | 2 | −6.8 | 39.8 | 0.0015 |
| Q9Y618 | 903.9988 | 2 | 11 | 42.7 | 1.70E−05 |
| Q92597 | 459.2619 | 3 | −8.7 | 43.3 | 0.0064 |
| Q96SB3 | 889.4941 | 2 | 0.17 | 30.7 | 8.60E−06 |
| Q96PU5 | 635.6574 | 3 | −1.9 | 45.6 | 2.10E−04 |
| Q8NHV4 | 832.9363 | 2 | −8.5 | 38.2 | 0.0049 |
| P46934 | 848.4097 | 3 | 1.9 | 26.7 | 0.016 |
| Q96PY6 | 684.826 | 4 | −9.1 | 33.7 | 0.0076 |
| P51957 | 580.2952 | 2 | −2 | 33.9 | 7.50E−04 |
| Q8TD19 | 770.9013 | 2 | 3.9 | 44.2 | 0.045 |
| Q9H3P2 | 561.8099 | 2 | −2.6 | 24.4 | 7.20E−05 |
| O95644 | 491.7674 | 2 | −4.2 | 37.3 | 0.0064 |
| Q13469 | 747.0483 | 3 | −4 | 48.9 | 1.00E−05 |
| Q00653 | 675.3181 | 2 | 2.1 | 25.5 | 0.0063 |
| Q6P4R8 | 413.7458 | 2 | 7.4 | 25.7 | 0.038 |
| Q6P4R8 | 537.7532 | 4 | −2.4 | 47.4 | 3.00E−07 |
| O14745 | 454.7748 | 2 | 12 | 39.5 | 0.0026 |
| Q86WB0 | 549.7813 | 2 | −2.3 | 33.1 | 0.0039 |
| Q86WB0 | 741.0469 | 3 | 0.66 | 46.8 | 1.20E−05 |
| Q6KC79 | 428.9177 | 3 | 9 | 39.1 | 0.012 |
| Q6KC79 | 493.2756 | 4 | 7 | 24.9 | 0.004 |
| P30414 | 530.8812 | 3 | 13 | 24.9 | 0.002 |
| P46087 | 492.2631 | 2 | −8.1 | 26.2 | 0.045 |
| P46087 | 1155.5475 | 3 | −10 | 52.3 | 5.30E−08 |
| P46087 | 1150.2057 | 3 | −19 | 48.5 | 7.50E−08 |
| P46087 | 794.62 | 5 | 20 | 38 | 1.60E−05 |
| Q9Y2X3 | 594.3311 | 2 | 11 | 29.8 | 0.02 |
| P78316 | 435.8993 | 3 | −5.7 | 33.9 | 0.011 |
| P78316 | 438.8914 | 3 | 21 | 30.9 | 0.019 |
| P55209 | 858.9613 | 2 | −0.83 | 44.8 | 3.60E−07 |
| P55209 | 550.5661 | 4 | −3.2 | 31.1 | 3.30E−04 |
| P55209 | 475.2504 | 3 | 8.3 | 22.8 | 0.0092 |
| Q99733 | 572.7957 | 2 | −0.29 | 37.8 | 4.10E−06 |
| Q99733 | 630.3146 | 3 | 2.4 | 56.1 | 1.00E−08 |
| Q99733 | 813.918 | 4 | 33 | 32 | 1.10E−04 |
| Q99733 | 809.8793 | 4 | −16 | 53.4 | 2.20E−09 |

TABLE 2-continued

Mass spectrometry statistics for identified caspase-derived peptides.

| Swiss-Prot acc # | m/z | z | Error ppm | score | E value |
|---|---|---|---|---|---|
| Q99733 | 644.9927 | 3 | −3.5 | 46.4 | 1.80E−06 |
| Q49A26 | 556.9489 | 3 | −7 | 35.5 | 0.0015 |
| Q14207 | 458.7825 | 2 | 13 | 25.1 | 0.046 |
| P06748 | 762.0246 | 3 | −15 | 35.4 | 2.40E−05 |
| P06748 | 873.0628 | 3 | −6.9 | 28.7 | 0.004 |
| Q9Y6Y0 | 702.3287 | 3 | −10 | 43.8 | 9.70E−07 |
| P82970 | 628.3083 | 2 | −5.7 | 46.2 | 7.40E−04 |
| Q08J23 | 763.1407 | 4 | −4 | 36.7 | 1.40E−05 |
| Q08J23 | 636.3339 | 5 | −2.5 | 27.9 | 0.002 |
| Q08J23 | 492.2567 | 2 | 8.5 | 24.8 | 0.0075 |
| Q08J23 | 371.2087 | 3 | 17 | 24.1 | 0.013 |
| Q08J23 | 1021.5092 | 2 | 8.1 | 22.2 | 3.20E−04 |
| P49790 | 530.278 | 2 | −9 | 25.6 | 0.033 |
| P80303 | 862.9316 | 2 | −11 | 32.8 | 6.60E−04 |
| P80303 | 684.3105 | 2 | 1.7 | 26.6 | 0.013 |
| Q9H1E3 | 418.7163 | 2 | 12 | 23.2 | 0.08 |
| P19338 | 721.4094 | 2 | −3.3 | 25.2 | 3.20E−04 |
| Q8IVD9 | 456.2354 | 2 | 5.9 | 26.6 | 0.034 |
| Q8IVD9 | 857.4669 | 2 | −0.98 | 39.5 | 3.10E−06 |
| Q8IVD9 | 519.9218 | 3 | 7.6 | 40 | 2.80E−05 |
| Q7Z417 | 635.6724 | 3 | 1.5 | 32.9 | 1.80E−04 |
| Q14980 | 784.3966 | 2 | −14 | 40.5 | 0.0049 |
| Q14980 | 927.2416 | 4 | −11 | 29.4 | 0.001 |
| Q14980 | 602.7781 | 2 | −8.6 | 41.7 | 5.10E−05 |
| Q8NFH3 | 567.9402 | 3 | 2.8 | 38 | 8.00E−05 |
| Q9UKX7 | 639.3153 | 4 | 0.62 | 43.6 | 5.20E−06 |
| Q8N1F7 | 739.3486 | 3 | 7.6 | 38.8 | 1.10E−05 |
| P11177 | 621.2949 | 3 | 5.7 | 33.6 | 0.0033 |
| O75665 | 701.6811 | 3 | −10 | 36.1 | 0.011 |
| Q8WV07 | 495.2563 | 2 | −3.1 | 27.2 | 0.028 |
| Q9BZF1 | 557.611 | 3 | 12 | 33.7 | 0.0014 |
| Q8N6M0 | 700.7099 | 3 | 3.3 | 57.1 | 8.30E−06 |
| Q01804 | 740.3386 | 3 | −6.1 | 28.2 | 4.80E−04 |
| Q8N573 | 698.8929 | 2 | −0.63 | 28.6 | 0.001 |
| Q8N573 | 435.566 | 3 | −0.84 | 33.3 | 6.20E−04 |
| Q6IN85 | 619.801 | 2 | 3.8 | 40.8 | 0.0034 |
| Q8WXI9 | 541.2675 | 2 | 0.45 | 42.8 | 0.0029 |
| P47712 | 652.8033 | 2 | −9.5 | 35.2 | 5.30E−05 |
| Q86U42 | 685.3593 | 2 | −7 | 39.5 | 0.0063 |
| Q86U42 | 532.9647 | 3 | 13 | 55 | 3.60E−05 |
| Q8NC51 | 432.2047 | 3 | 28 | 22.1 | 0.044 |
| Q13153 | 882.9118 | 2 | −12 | 49.2 | 1.60E−05 |
| Q13177 | | | | | |
| Q13177 | 622.8325 | 2 | −4.6 | 39.4 | 4.70E−06 |
| Q8WX93 | 840.421 | 2 | 1.8 | 34.5 | 0.01 |
| Q86W56 | 740.3677 | 3 | 7.7 | 28.4 | 5.70E−04 |
| P09874 | 401.7048 | 2 | −35 | 25.7 | 0.035 |
| P09874 | 465.7711 | 2 | 10 | 33.5 | 0.017 |
| P09874 | 353.5524 | 3 | 18 | 24.1 | 0.0076 |
| P09874 | 586.9405 | 3 | −0.65 | 28.2 | 0.044 |
| Q96IZ0 | 361.2023 | 4 | 8 | 28.4 | 0.0021 |
| P49023 | 467.7274 | 2 | 6.9 | 31.8 | 0.012 |
| P49023 | 612.6551 | 3 | 6.6 | 46.8 | 6.20E−06 |
| P49023 | 771.8785 | 2 | 1.9 | 42.3 | 8.30E−04 |
| Q86U86 | 490.2353 | 2 | −0.87 | 26.6 | 0.045 |
| Q15365 | 1223.6101 | 3 | −5.1 | 30.1 | 0.0016 |
| Q15365 | 643.0097 | 3 | −7.1 | 53.5 | 4.40E−08 |
| Q15365 | 887.1171 | 3 | −5.2 | 49.4 | 2.30E−06 |
| Q15366 | 906.4588 | 2 | 2.1 | 49.9 | 3.90E−06 |
| O94913 | 1111.7555 | 4 | −7.2 | 22.1 | 0.0019 |
| Q15154 | 563.6162 | 3 | −2.6 | 46.3 | 3.40E−05 |
| Q15154 | 764.7111 | 3 | 3.7 | 44 | 4.90E−06 |
| O95613 | 1011.4802 | 2 | 8.1 | 34.6 | 0.0018 |
| Q9BY77 | 748.8864 | 2 | −5.9 | 45.5 | 8.00E−04 |
| O00151 | 893.912 | 2 | 1.7 | 29.3 | 3.20E−04 |
| Q6P996 | 700.8916 | 2 | 1.1 | 41.4 | 6.70E−04 |
| Q13951 | 714.2997 | 2 | −0.56 | 33.9 | 3.80E−07 |
| O94921 | 568.9773 | 3 | 7.1 | 43.1 | 6.10E−04 |
| P00558 | 501.7499 | 2 | 0.087 | 24.7 | 0.018 |
| P00558 | 918.1347 | 3 | −8.1 | 28.2 | 9.60E−04 |
| P00558 | 490.5819 | 3 | 2.8 | 44.4 | 8.50E−06 |
| P00558 | 686.3663 | 3 | −7.1 | 40.4 | 2.80E−05 |
| P00558 | 478.9172 | 3 | 17 | 24.9 | 0.0089 |
| P07205 | | | | | |
| Q8IZ21 | 726.8483 | 2 | 2.8 | 32.1 | 5.70E−04 |
| Q92576 | 838.9101 | 2 | 6.4 | 27.5 | 1.60E−04 |
| Q92576 | 454.8939 | 3 | 18 | 39.9 | 1.50E−06 |
| Q92576 | 941.1218 | 3 | 3.4 | 41.1 | 1.20E−04 |
| Q92576 | 530.9376 | 3 | 1.9 | 43.8 | 1.40E−04 |
| Q6NYC8 | 442.2755 | 2 | 8.7 | 28.1 | 0.012 |
| Q9UBF8 | 766.7201 | 3 | −6.7 | 53.9 | 2.10E−07 |
| Q9UBF8 | 614.3193 | 4 | −2.9 | 24.9 | 0.0093 |
| O75925 | 585.6803 | 3 | 5.7 | 45.4 | 2.20E−06 |
| Q13492 | 515.9336 | 3 | −2.8 | 44 | 4.50E−04 |
| O00562 | 1007.4763 | 2 | −15 | 52.1 | 3.40E−06 |
| O43164 | 659.8461 | 2 | −3 | 29.6 | 0.0021 |
| Q9ULL1 | 921.9333 | 2 | 0.13 | 25.2 | 0.0011 |
| Q99569 | 505.3024 | 2 | −6.4 | 32.2 | 3.60E−05 |
| P19174 | 589.7828 | 2 | 9.1 | 32.8 | 0.039 |
| Q9UL45 | 1347.968 | 3 | −15 | 29.9 | 1.50E−04 |
| Q7Z3K3 | 670.3166 | 2 | −8.7 | 30.9 | 5.30E−04 |
| Q9Y244 | 747.3844 | 3 | −7.6 | 48.5 | 5.30E−07 |
| Q96QC0 | 620.3147 | 3 | 0.11 | 48.1 | 1.80E−05 |
| Q96QC0 | 658.8625 | 2 | −2.5 | 46.5 | 0.015 |
| Q96QC0 | 938.4655 | 3 | −4.8 | 41.7 | 1.10E−04 |
| Q8TF05 | 704.3491 | 3 | −0.9 | 24.2 | 0.0029 |
| P62937 | 556.3095 | 2 | 1 | 22.2 | 0.0042 |
| Q8WUA2 | 857.9648 | 2 | 1.6 | 29.7 | 1.50E−04 |
| O95685 | 442.2522 | 2 | −2.9 | 31 | 0.033 |
| O75400 | 541.7818 | 2 | 8.1 | 46.6 | 0.011 |
| P57071 | 1206.6293 | 2 | 0.34 | 25 | 0.0053 |
| P57071 | 684.3572 | 4 | −6.9 | 44.8 | 4.20E−06 |
| P78527 | 840.0617 | 3 | −0.86 | 25 | 5.70E−04 |
| P07737 | 667.6942 | 3 | −6.2 | 28.8 | 0.0037 |
| P07737 | 528.2513 | 2 | 12 | 26 | 0.025 |
| P07737 | 520.2524 | 2 | 9.5 | 34.9 | 9.30E−04 |
| P07737 | 854.7551 | 3 | −5.8 | 36.1 | 1.00E−04 |
| O60508 | 443.2527 | 2 | −6.7 | 22.9 | 0.0035 |
| O60508 | 572.0596 | 4 | 8.1 | 39 | 5.20E−05 |
| O60508 | 563.2973 | 2 | 13 | 23.6 | 0.0096 |
| O60508 | 465.5632 | 3 | −3.3 | 36.4 | 0.0026 |
| O60508 | 574.2879 | 4 | −4.3 | 47.2 | 1.70E−07 |
| Q8WWY3 | 573.9644 | 3 | 5 | 35.1 | 5.40E−04 |
| Q9ULL5 | 537.7743 | 2 | −1.3 | 23.6 | 0.016 |
| P79522 | 849.7758 | 3 | 8.5 | 33.3 | 0.0019 |
| P62333 | 365.8465 | 3 | 2.9 | 25.1 | 0.0038 |
| P17980 | 465.2692 | 2 | 0.96 | 29.6 | 0.017 |
| P17980 | 678.3531 | 3 | −6.7 | 52 | 9.60E−07 |
| P17980 | 673.0301 | 3 | 6.2 | 53.9 | 2.30E−06 |
| P17980 | 634.8181 | 2 | 1.5 | 22.6 | 0.04 |
| P43686 | 635.799 | 2 | −12 | 53.2 | 6.90E−04 |
| P62195 | 654.986 | 3 | −2 | 46.3 | 5.70E−06 |
| P28066 | 533.939 | 3 | 2.7 | 34 | 7.20E−04 |
| Q8TAA3 | 623.6471 | 3 | 4.8 | 49.9 | 4.00E−04 |
| O14818 | | | | | |
| P20618 | 532.788 | 2 | −4.5 | 25.5 | 9.40E−04 |
| P28070 | 754.3484 | 2 | 0.66 | 45.6 | 0.0018 |
| Q99436 | 493.7846 | 2 | −1 | 22.2 | 0.0037 |
| O00232 | 595.2774 | 2 | −0.74 | 38.2 | 0.0087 |
| Q8NDX1 | 651.809 | 2 | 0.028 | 41.6 | 0.003 |
| Q8NDX1 | 418.2104 | 4 | −5.7 | 39.9 | 8.30E−06 |
| O75475 | 580.7258 | 5 | 4.6 | 43.8 | 5.00E−07 |
| O75475 | 387.8818 | 3 | 3.9 | 31.4 | 0.0051 |
| O75475 | 626.3578 | 2 | 11 | 49.6 | 0.037 |
| P61289 | 468.2449 | 2 | −0.75 | 28.2 | 0.03 |
| P26599 | 577.8366 | 2 | −10 | 41.2 | 5.60E−04 |
| P26599 | 437.604 | 2 | 14 | 39.6 | 9.10E−06 |
| P26599 | 785.8742 | 2 | 3.8 | 47.7 | 1.20E−06 |
| P26599 | 777.8724 | 2 | −1.8 | 44 | 0.0012 |
| P26599 | 777.8709 | 2 | −3.7 | 45.2 | 9.70E−05 |
| P26599 | 769.871 | 2 | −6.9 | 49.1 | 3.10E−05 |
| P26599 | 505.2334 | 2 | −10 | 24.6 | 0.034 |
| Q14761 | 923.0806 | 3 | −11 | 37.9 | 1.10E−05 |
| Q14761 | 1108.5143 | 3 | 2.7 | 35.1 | 5.60E−05 |
| Q14761 | 1063.8215 | 3 | −0.022 | 37.9 | 6.80E−05 |
| P06454 | 654.3372 | 2 | −1.4 | 41 | 2.30E−07 |
| P06454 | 832.4412 | 2 | 0.093 | 35.2 | 5.90E−05 |
| P06454 | 476.2544 | 2 | 2.2 | 29.9 | 0.006 |
| P06454 | 782.9235 | 2 | −2 | 27.6 | 0.0033 |
| P26045 | 564.9375 | 3 | 0.22 | 47.9 | 6.10E−05 |

TABLE 2-continued

Mass spectrometry statistics for identified caspase-derived peptides.

| Swiss-Prot acc # | m/z | z | Error ppm | score | E value |
|---|---|---|---|---|---|
| P22102 | 834.7403 | 3 | −2 | 57.7 | 1.80E−06 |
| P22102 | 430.2471 | 4 | 29 | 24.1 | 0.0091 |
| P22102 | 591.8156 | 2 | 4.3 | 46 | 0.0065 |
| P22234 | 636.3664 | 2 | −17 | 29.6 | 0.0031 |
| P22234 | 436.2483 | 3 | −4.7 | 24.9 | 0.066 |
| P31939 | 945.0053 | 2 | −12 | 29.8 | 0.041 |
| Q96PZ0 | 765.7245 | 3 | 3.7 | 43.9 | 3.50E−04 |
| Q96PZ0 | 441.9001 | 3 | 5.1 | 39.5 | 9.40E−04 |
| Q96N64 | 876.7814 | 3 | −4.6 | 47.6 | 5.80E−06 |
| P27708 | 974.7468 | 4 | −9.9 | 27.6 | 0.013 |
| Q96PU8 | 716.3922 | 2 | −4.9 | 53.5 | 0.0016 |
| Q5TB80 | 531.7871 | 4 | −1.5 | 53.9 | 1.80E−07 |
| Q2KHR3 | 524.2761 | 2 | −2 | 25.2 | 0.023 |
| Q9Y2K2 | 1107.0348 | 2 | 2.5 | 34.5 | 2.90E−06 |
| Q15032 | 679.3418 | 3 | 9.9 | 38.5 | 1.60E−06 |
| Q15032 | 673.9918 | 3 | −17 | 37.4 | 2.70E−05 |
| P0C7M2 Q32P51 P09651 | 557.8447 | 2 | −0.74 | 23.6 | 0.0054 |
| P0C7M2 Q32P51 P09651 | 481.9217 | 3 | −14 | 29.8 | 0.032 |
| P0C7M2 P09651 | 503.2672 | 3 | −2.6 | 29.9 | 0.0038 |
| P0C7M2 P09651 | 646.0898 | 4 | 2.7 | 28.8 | 0.0037 |
| P0C7M2 P09651 | 422.9679 | 4 | 12 | 31.8 | 7.60E−05 |
| O60216 | 1319.9436 | 3 | −27 | 24.4 | 4.60E−04 |
| O60216 | 1439.373 | 3 | −0.97 | 28.2 | 0.0025 |
| O60216 | 1434.0475 | 3 | 3.3 | 28 | 0.0022 |
| O60216 | 681.8575 | 2 | −3.5 | 24.1 | 5.80E−04 |
| Q96JH8 | 745.3844 | 2 | 2.4 | 30.1 | 2.90E−04 |
| Q96JH8 | 539.2765 | 4 | −1.5 | 36.6 | 5.10E−05 |
| P43487 | 636.9929 | 3 | 6.2 | 39 | 4.60E−05 |
| Q15042 | 791.9123 | 2 | 3.9 | 47.8 | 6.20E−04 |
| Q09028 | 456.7423 | 4 | 1.9 | 25.9 | 0.0013 |
| Q16576 | | | | | |
| Q7Z6E9 | 1041.1916 | 3 | 2.9 | 28.1 | 9.90E−04 |
| Q7Z6E9 | 593.3615 | 2 | 18 | 30.4 | 0.004 |
| Q7Z6E9 | 692.8444 | 2 | 8.1 | 28.4 | 6.30E−06 |
| Q7Z6E9 | 559.9359 | 3 | −8.7 | 34.1 | 8.10E−05 |
| Q16576 | 779.3788 | 2 | −2.5 | 29.2 | 8.90E−06 |
| Q16576 | 573.9941 | 4 | −12 | 29.6 | 9.80E−05 |
| Q99708 | 964.4301 | 2 | −12 | 28.1 | 3.80E−05 |
| Q96T37 | 583.2963 | 2 | 13 | 45.6 | 5.30E−05 |
| Q9UPN6 | 739.8526 | 2 | −2 | 30.8 | 5.50E−05 |
| Q9UPN6 | 460.2171 | 3 | 1.5 | 32.4 | 0.0019 |
| P49756 | 716.6218 | 3 | −5.8 | 59.2 | 5.80E−07 |
| Q5T8P6 | 719.011 | 3 | −2.4 | 33.5 | 4.00E−04 |
| Q5T8P6 | 713.675 | 3 | −8.5 | 38.4 | 4.90E−05 |
| Q5T8P6 | 713.8652 | 3 | −2.1 | 22.3 | 7.60E−04 |
| Q5T8P6 | 705.869 | 2 | −0.17 | 22.7 | 2.80E−04 |
| Q9P2N5 | 760.8699 | 2 | −0.91 | 35.9 | 2.70E−07 |
| Q9NW13 | 984.907 | 2 | −6.3 | 50.6 | 3.80E−07 |
| Q96EV2 | 517.2424 | 3 | −3.6 | 38.6 | 2.90E−04 |
| Q14498 | 849.8904 | 2 | −4.9 | 43.8 | 5.00E−07 |
| Q14498 | 890.7576 | 3 | −10 | 45.9 | 2.00E−06 |
| Q9Y5S9 | 601.5095 | 4 | 5.1 | 43.7 | 4.50E−08 |
| Q9Y5S9 | 726.0813 | 4 | −5.9 | 28.1 | 0.0057 |
| Q9Y5S9 | 597.5048 | 4 | −4.9 | 47.7 | 3.70E−10 |
| Q9Y5S9 | 526.4485 | 5 | 9.6 | 30.6 | 9.60E−04 |
| Q9Y5S9 | 962.4462 | 3 | −0.58 | 40.9 | 5.80E−06 |
| Q9Y5S9 | 749.8414 | 3 | −0.93 | 28.1 | 4.30E−04 |
| O43251 | 937.9043 | 2 | 0.75 | 46.3 | 3.90E−05 |
| P49792 | 869.4243 | 2 | 1.4 | 43 | 4.10E−07 |
| P49792 | 606.2963 | 5 | 6.3 | 39.5 | 1.30E−04 |
| P49792 | 764.3483 | 3 | −6.9 | 27.7 | 0.006 |
| P49792 | 453.7201 | 2 | −3 | 23.4 | 0.017 |
| P49792 | 681.5493 | 4 | −3.7 | 34 | 1.70E−05 |
| P49792 | 1157.9086 | 3 | −9.2 | 26.7 | 0.0099 |
| Q68DN6 A6NKT7 Q7Z3J3 Q99666 | | | | | |
| Q53T03 O14715 P49792 A6NKT7 Q7Z3J3 Q99666 Q53T03 O14715 | 984.5243 | 2 | −4.8 | 33.2 | 2.80E−06 |
| Q92804 | 566.5941 | 3 | 3 | 47.2 | 1.90E−06 |
| P25800 | 661.3486 | 2 | 5.9 | 24.1 | 0.016 |
| A6NDE4 Q15415 Q15378 | 758.0301 | 3 | −3.6 | 22.7 | 0.032 |
| P06400 | 666.792 | 2 | −23 | 35.8 | 9.80E−04 |
| P53805 | 632.3271 | 3 | 2.6 | 43.1 | 8.80E−06 |
| Q9P258 | 397.1981 | 2 | 6.2 | 22.4 | 0.013 |
| Q9P258 | 317.1538 | 3 | −40 | 30.6 | 0.014 |
| Q14257 | 808.9093 | 2 | 9.8 | 34.2 | 1.30E−06 |
| Q8IZ40 | 508.2666 | 3 | 3.8 | 39.4 | 0.0019 |
| Q8IZ40 | 774.3639 | 2 | 3 | 55.4 | 5.30E−07 |
| Q8IZ40 | 568.6037 | 3 | −12 | 28.5 | 0.0019 |
| Q8IZ40 | 766.3689 | 2 | 6.2 | 40.2 | 3.10E−05 |
| P54727 | 523.7205 | 2 | −4.6 | 28.4 | 8.70E−04 |
| Q13123 | 818.3831 | 3 | −4.8 | 50.8 | 1.70E−06 |
| Q13123 | 523.2591 | 2 | −8.7 | 22.9 | 0.011 |
| Q13123 | 467.2408 | 3 | −9.9 | 36.2 | 7.00E−04 |
| Q04864 | 717.3198 | 2 | −0.66 | 35.5 | 3.10E−06 |
| Q92900 | 740.0423 | 3 | 6.1 | 62.6 | 3.80E−07 |
| Q96D71 | 861.908 | 2 | −12 | 51.2 | 6.10E−07 |
| Q96D71 | 690.0421 | 3 | −3.3 | 48.9 | 3.90E−07 |
| Q96D71 | 828.6982 | 3 | 0.13 | 59 | 8.00E−08 |
| Q92785 | 591.3139 | 2 | −5.7 | 33.4 | 0.0012 |
| Q92785 | 598.317 | 2 | −4.2 | 35.6 | 0.0012 |
| Q13127 | 476.2368 | 2 | 2.6 | 25.4 | 0.037 |
| P35251 | 691.3596 | 3 | −7.9 | 39.5 | 2.00E−06 |
| P35251 | 467.708 | 2 | 4.3 | 35.5 | 0.003 |
| P35251 | 686.0367 | 3 | 4.9 | 47.4 | 4.90E−05 |
| P35251 | 632.7869 | 2 | −23 | 37.7 | 0.036 |
| Q2KHR2 | 556.6503 | 3 | 2.2 | 29.9 | 0.0067 |
| Q9H0H5 | 638.3082 | 2 | −1.5 | 48.5 | 3.30E−04 |
| Q9H0H5 | 728.8242 | 2 | −5 | 33.2 | 6.60E−04 |
| Q68DN6 P0C839 A6NKT7 Q7Z3J3 Q99666 Q53T03 O14715 | 856.4174 | 2 | 2.5 | 40.1 | 1.30E−07 |
| O43665 | 452.2108 | 3 | −4.1 | 29.8 | 0.0036 |
| O43665 | 519.5628 | 3 | −5.4 | 44.2 | 4.60E−05 |
| P98171 | 698.8462 | 2 | −7.4 | 37 | 4.00E−04 |
| P98171 | 1136.0371 | 2 | −2.9 | 33.7 | 1.40E−06 |
| P42331 | 1154.517 | 3 | 2.3 | 30.6 | 1.50E−05 |
| P42331 | 744.0015 | 3 | 5.2 | 44.6 | 1.90E−04 |
| Q7Z6I6 | 889.9152 | 2 | 3.5 | 27.4 | 3.60E−04 |
| Q7Z6I6 | 1013.5108 | 4 | −3 | 34 | 0.001 |
| Q7Z6I6 | 992.7758 | 3 | −7.1 | 49.4 | 4.70E−08 |
| Q6P4F7 | 935.4164 | 3 | −13 | 29 | 0.0057 |
| P61586 P08134 | 640.6616 | 3 | −2.5 | 42.4 | 8.10E−04 |
| Q5UIP0 | 481.2801 | 2 | −3.7 | 33.1 | 0.012 |
| Q5UIP0 | 680.6394 | 3 | 12 | 46.5 | 1.30E−05 |
| O95153 | 838.6621 | 4 | −3.7 | 23.1 | 0.049 |
| O95153 | 529.6074 | 3 | −29 | 28.4 | 0.011 |
| Q06587 | 507.7835 | 2 | 1.9 | 29.4 | 0.022 |
| Q9BRS2 | 551.8251 | 2 | −3.4 | 26.2 | 0.0026 |
| Q9BRS2 | 673.3936 | 2 | 0.097 | 25.7 | 0.0016 |
| Q13546 | 507.9304 | 3 | 15 | 41.1 | 1.30E−06 |
| P31350 | 507.5879 | 3 | −14 | 38.8 | 6.40E−05 |
| P18621 | 830.9908 | 3 | −0.077 | 36.8 | 7.20E−07 |
| P46777 | 891.4249 | 2 | −12 | 50.6 | 9.60E−07 |
| P46777 | 416.2192 | 3 | 0.43 | 31.9 | 4.20E−04 |
| Q8IYW5 | 431.8839 | 3 | 7 | 35 | 3.40E−04 |
| Q63HN8 | 525.2821 | 3 | −0.97 | 32.2 | 0.0011 |
| Q5W0B1 | 608.942 | 3 | −5.1 | 22.5 | 0.031 |

TABLE 2-continued

Mass spectrometry statistics for identified caspase-derived peptides.

| Swiss-Prot acc # | m/z | z | Error ppm | score | E value |
|---|---|---|---|---|---|
| Q5VTB9 | 586.2893 | 3 | −0.1 | 47.2 | 5.30E−06 |
| Q99942 | 517.239 | 2 | 0.95 | 24.2 | 0.017 |
| Q9H777 | 651.0489 | 4 | −17 | 23.2 | 0.008 |
| Q13151 | 506.5176 | 4 | 4.8 | 47 | 3.70E−06 |
| Q13151 | 501.2954 | 2 | 9.6 | 38.6 | 0.011 |
| Q13151 | 683.329 | 3 | −1.4 | 44.2 | 1.80E−06 |
| Q13151 | 551.7779 | 4 | 6 | 36.5 | 1.20E−05 |
| P22626 | 664.025 | 3 | −2.4 | 31.1 | 0.0099 |
| P22626 | 405.4502 | 4 | 2.1 | 34.1 | 6.60E−06 |
| P22626 | 401.447 | 4 | −9 | 27.1 | 1.20E−04 |
| P22626 | 593.2562 | 2 | −4.1 | 27.7 | 0.0076 |
| P51991 | 518.5953 | 3 | −4.8 | 28.8 | 0.0016 |
| P51991 | 675.4156 | 2 | −1.8 | 26.1 | 4.70E−04 |
| P51991 | 557.8444 | 2 | −1.3 | 27.9 | 5.20E−04 |
| P51991 | 434.4605 | 4 | 2.3 | 30.2 | 2.30E−04 |
| P51991 | 462.9331 | 3 | 7.9 | 33.6 | 7.70E−04 |
| Q13464 | 429.2267 | 2 | −1.7 | 30.1 | 0.049 |
| Q9H6T3 | 378.523 | 3 | −3.6 | 23.8 | 0.012 |
| Q9H6T3 | 926.4674 | 3 | −2.7 | 55.1 | 9.90E−08 |
| Q9H6T3 | 969.1674 | 3 | −0.9 | 47.6 | 2.60E−06 |
| P36954 | 640.8309 | 2 | −6.9 | 34.8 | 2.00E−04 |
| P05423 | 459.2409 | 3 | 3 | 29.9 | 0.015 |
| Q9NVU0 | 678.3157 | 3 | 1.6 | 45.8 | 1.20E−06 |
| Q8TEU7 | 604.7821 | 2 | −0.54 | 36 | 4.80E−05 |
| Q8TEU7 | 596.7848 | 2 | −0.25 | 28.9 | 8.60E−04 |
| Q92766 | 570.2785 | 2 | −7.2 | 29.4 | 0.004 |
| Q8IY81 | 877.8995 | 4 | −10 | 33.8 | 9.60E−06 |
| Q5JTH9 | 788.8457 | 4 | −3 | 41.8 | 8.20E−06 |
| Q5JTH9 | 788.8351 | 4 | −16 | 40.1 | 9.90E−06 |
| Q5JTH9 | 788.8461 | 4 | −2.4 | 36.9 | 1.60E−05 |
| Q5JTH9 | 1046.1287 | 3 | −1.2 | 39.1 | 1.80E−05 |
| Q5JTH9 | 618.2945 | 2 | −6.8 | 29.1 | 3.60E−04 |
| Q14684 | 769.8537 | 4 | −0.7 | 25.8 | 0.004 |
| P60866 | 446.7393 | 4 | 0.93 | 34.2 | 2.70E−05 |
| P62266 | 742.0295 | 3 | 1.6 | 29.7 | 0.0016 |
| P62266 | 784.7221 | 3 | −5.8 | 25.6 | 0.0015 |
| P62857 | 655.3537 | 2 | 0.21 | 45.2 | 0.086 |
| P23396 | 476.2526 | 2 | 8.9 | 31.4 | 0.0036 |
| Q96IZ7 | 549.2897 | 2 | −1.6 | 35.8 | 6.80E−04 |
| Q92541 | 605.2661 | 3 | 10 | 49 | 4.20E−08 |
| Q92541 | 785.8209 | 2 | 1.2 | 40.5 | 3.90E−06 |
| Q92541 | 599.9287 | 3 | 0.35 | 53 | 3.20E−08 |
| Q9NQC3 | 517.2857 | 2 | 17 | 23.3 | 0.0032 |
| Q9NQC3 | 682.331 | 3 | −11 | 47.5 | 2.20E−05 |
| P09234 | 744.8917 | 2 | −3 | 25 | 7.60E−04 |
| P09234 | 509.2383 | 3 | −18 | 38.6 | 7.00E−05 |
| P09661 | 632.8091 | 2 | −4.6 | 34.1 | 0.0041 |
| Q8IZ73 | 827.7338 | 3 | −4.9 | 49.9 | 1.00E−05 |
| P62306 | 524.6212 | 3 | −3.1 | 36.4 | 0.0019 |
| Q8N1F8 | 536.6424 | 3 | 0.61 | 24.6 | 0.029 |
| P55011 | 558.2956 | 3 | −2.6 | 34 | 0.0074 |
| Q96AG3 | 598.0486 | 4 | 12 | 24.9 | 0.013 |
| Q9UHR5 | 572.7506 | 2 | 3 | 36.2 | 2.10E−05 |
| Q15424 | 718.303 | 3 | 0.43 | 39.1 | 2.70E−05 |
| Q15424 | 389.8636 | 3 | 19 | 28.6 | 0.002 |
| Q14151 | | | | | |
| Q15424 | 876.9452 | 4 | 0.7 | 28.5 | 0.0017 |
| Q14151 | | | | | |
| Q15424 | 670.5357 | 5 | −1.7 | 50 | 5.80E−07 |
| Q14151 | | | | | |
| Q15424 | 613.7926 | 4 | 11 | 58.9 | 7.50E−10 |
| Q14151 | | | | | |
| Q15424 | 666.8127 | 2 | −5.4 | 44.1 | 4.80E−04 |
| Q15424 | 588.7517 | 2 | 0.48 | 45.1 | 0.0033 |
| Q14151 | | | | | |
| Q14151 | 928.9761 | 2 | 3.2 | 38.1 | 6.10E−06 |
| Q14151 | 613.7917 | 2 | 3.2 | 40.8 | 0.0013 |
| Q14151 | 719.6928 | 3 | −0.31 | 49 | 3.40E−06 |
| O43865 | 551.6385 | 3 | −1.8 | 51.6 | 1.20E−06 |
| O43865 | 1054.9309 | 2 | −16 | 45.8 | 3.20E−09 |
| O43865 | 789.3434 | 3 | −4.7 | 32.1 | 1.00E−05 |
| O43865 | 753.8749 | 2 | −5.6 | 31.1 | 0.0013 |
| O43865 | 611.9803 | 3 | −8.2 | 44.8 | 3.90E−06 |
| O43865 | 745.8807 | 2 | −1.2 | 42.4 | 0.006 |
| O43865 | 621.2629 | 2 | −7.7 | 30.5 | 0.012 |
| Q96HN2 | 458.2483 | 2 | −0.03 | 31.2 | 0.052 |
| Q5PRF9 | 785.7272 | 3 | 2.4 | 41.1 | 3.70E−04 |
| Q9UPN7 | 756.6575 | 4 | −6.3 | 47.1 | 3.20E−08 |
| P07602 | 765.863 | 2 | −9.4 | 40.9 | 9.10E−06 |
| P07602 | 663.3343 | 3 | 0.84 | 41.8 | 2.50E−06 |
| P07602 | 603.7409 | 2 | −14 | 38.4 | 0.0013 |
| O75995 | 589.2881 | 2 | −3.9 | 37.5 | 8.30E−05 |
| O75995 | 711.7937 | 2 | −41 | 25.8 | 0.084 |
| Q01826 | 1516.7479 | 3 | 0.93 | 42.1 | 1.70E−07 |
| P43007 | 605.6328 | 3 | 3.2 | 54.9 | 2.70E−05 |
| O15027 | 726.8801 | 2 | −1.7 | 35.8 | 1.40E−05 |
| O15027 | 522.7519 | 2 | 0.83 | 40.2 | 3.00E−04 |
| O95487 | 1144.919 | 3 | 9.5 | 24.5 | 0.023 |
| O14828 | 638.2995 | 2 | −6.9 | 28.6 | 0.027 |
| Q96GD3 | 773.8944 | 2 | −0.26 | 29 | 4.60E−05 |
| O75880 | 1107.1123 | 2 | 4.9 | 24.4 | 0.0014 |
| O75880 | 853.1275 | 3 | −3.2 | 35.1 | 1.60E−04 |
| Q9UIL1 | 637.3021 | 2 | −24 | 32.7 | 0.0016 |
| Q9UIL1 | 510.9325 | 3 | 4.6 | 33.6 | 0.0063 |
| O60524 | 553.6177 | 3 | −6.7 | 36.5 | 0.0019 |
| P55735 | 562.584 | 3 | −2.2 | 32.6 | 2.10E−04 |
| Q12981 | 580.9564 | 3 | 4.3 | 26.8 | 0.046 |
| Q9GZR1 | 703.6621 | 3 | −5.3 | 44.2 | 6.30E−07 |
| Q9UHD8 | 571.7677 | 2 | −20 | 27.9 | 0.018 |
| Q9BYW2 | 402.236 | 3 | 13 | 30.6 | 0.0032 |
| Q9BYW2 | 817.3996 | 3 | 1.9 | 34.7 | 8.20E−05 |
| Q9BYW2 | 883.7687 | 3 | −7.5 | 25.4 | 0.026 |
| Q7Z333 | 787.4313 | 2 | 0.53 | 26.6 | 3.90E−06 |
| Q15637 | 784.8964 | 2 | −13 | 47.5 | 8.40E−06 |
| Q15459 | 356.8125 | 3 | −28 | 24.5 | 9.50E−05 |
| Q15459 | 351.4769 | 3 | −40 | 25 | 1.40E−04 |
| Q15459 | 719.3953 | 3 | −1.7 | 40.2 | 1.30E−04 |
| O75533 | 941.8958 | 2 | −13 | 46.5 | 1.10E−07 |
| Q13435 | 364.2256 | 3 | 14 | 26.9 | 0.055 |
| Q13435 | 898.4512 | 2 | −9 | 46.4 | 1.00E−04 |
| Q13435 | 651.3396 | 3 | −4.1 | 48.5 | 5.60E−06 |
| Q15427 | 618.8253 | 2 | −3 | 38.6 | 5.10E−04 |
| P23246 | 401.2014 | 4 | 1.1 | 30.7 | 0.0017 |
| Q8IX01 | 1310.8661 | 4 | 1.6 | 25.4 | 0.0011 |
| Q8IX01 | 674.3126 | 2 | 0.24 | 45.5 | 0.0011 |
| Q8IX01 | 999.1261 | 3 | −3.4 | 60.5 | 3.30E−10 |
| Q99590 | 835.6921 | 3 | −4.1 | 58.8 | 4.90E−07 |
| Q01130 | 719.8186 | 2 | −0.12 | 28.1 | 1.90E−05 |
| Q01130 | 703.8222 | 2 | −2.2 | 38.3 | 1.90E−04 |
| Q01130 | 545.2738 | 2 | 4.2 | 34.6 | 0.0051 |
| Q01130 | 635.7889 | 2 | −2.2 | 47.8 | 3.50E−04 |
| P84103 | 482.7164 | 2 | 3 | 22.2 | 0.019 |
| Q13243 | 585.2827 | 3 | −5.1 | 49.2 | 9.40E−07 |
| Q13247 | 498.745 | 2 | 8.2 | 28.6 | 0.076 |
| Q5FBB7 | 557.2639 | 3 | 4.1 | 31.6 | 0.0014 |
| Q8N5H7 | 526.9266 | 3 | −2.5 | 40.4 | 0.0014 |
| A0MZ66 | 761.8523 | 3 | −0.94 | 43.8 | 7.40E−07 |
| Q96FS4 | 712.3373 | 2 | −9.7 | 51.2 | 1.70E−06 |
| Q9UIU6 | 928.7876 | 3 | 5.4 | 61.4 | 5.70E−09 |
| P12755 | 668.3472 | 3 | 3.9 | 44.9 | 1.10E−05 |
| Q5T5P2 | 416.5381 | 3 | −1.4 | 29.2 | 0.016 |
| Q9BRT9 | 849.4166 | 3 | −10 | 49.2 | 1.20E−05 |
| Q9H2G2 | 500.2528 | 3 | 7.9 | 28.1 | 2.90E−04 |
| Q14BN4 | 843.8928 | 2 | −13 | 46.8 | 2.00E−05 |
| O95391 | 550.3146 | 2 | 10 | 30.9 | 5.00E−05 |
| O95391 | 681.6812 | 3 | −6.7 | 50.8 | 4.90E−07 |
| O95391 | 543.5403 | 4 | 0.81 | 35.3 | 3.30E−05 |
| O95391 | 742.0353 | 3 | 5.1 | 48.6 | 2.80E−05 |
| O95347 | 618.331 | 3 | 4.6 | 44.6 | 1.30E−06 |
| P51532 | 609.3476 | 2 | −0.79 | 22.4 | 0.01 |
| Q969G3 | 419.8795 | 3 | 1.3 | 32.5 | 0.046 |
| A6NHR9 | 632.291 | 3 | −2.9 | 53.2 | 5.80E−10 |
| Q8TAQ2 | 492.9114 | 3 | −1.3 | 34.4 | 0.0015 |
| Q92925 | 797.8757 | 2 | 6.1 | 42.5 | 3.40E−04 |
| Q5SXM2 | 736.887 | 2 | −13 | 27.7 | 0.057 |
| Q9UMY4 | 914.4595 | 3 | 2.6 | 45.9 | 9.70E−08 |
| Q8TEQ0 | 859.7477 | 3 | −15 | 26.2 | 0.0094 |
| O60749 | 1009.8868 | 3 | 3.2 | 26.1 | 0.0095 |
| O60493 | 599.8294 | 2 | −1.9 | 27.8 | 2.20E−04 |

TABLE 2-continued

Mass spectrometry statistics for identified caspase-derived peptides.

| Swiss-Prot acc # | m/z | z | Error ppm | score | E value |
|---|---|---|---|---|---|
| Q9UNH7 | 490.7423 | 2 | 9.1 | 28.1 | 0.0089 |
| Q9UNH7 | 426.897 | 3 | 5.8 | 35.2 | 0.031 |
| A7XYQ1 | 711.8476 | 2 | −9.3 | 42.9 | 0.015 |
| P00441 | 828.7504 | 3 | −1.3 | 29 | 0.011 |
| P00441 | 533.6151 | 3 | −0.76 | 55 | 1.10E−05 |
| P18583 | 1296.6627 | 3 | 1 | 28.2 | 0.0013 |
| P18583 | 1096.5876 | 2 | 3.7 | 44.5 | 8.70E−09 |
| P18583 | 754.3801 | 4 | −8.9 | 43 | 1.10E−06 |
| P18583 | 803.7332 | 3 | 15 | 34 | 6.70E−05 |
| P18583 | 626.9766 | 3 | −6.1 | 41.9 | 0.0011 |
| Q9HB58 | 398.5299 | 3 | 14 | 30 | 0.0044 |
| Q9HB58 | 458.8638 | 3 | −13 | 28.9 | 0.0014 |
| P08047 | 1047.0821 | 2 | 5.1 | 44.3 | 2.80E−06 |
| Q02447 | 1236.5731 | 3 | 4.8 | 22.3 | 0.026 |
| Q02447 | 733.3483 | 3 | −7.7 | 58.9 | 3.20E−08 |
| Q86XZ4 | 788.4009 | 2 | −18 | 37.1 | 3.30E−04 |
| Q9UBP0 | 577.758 | 2 | 1.3 | 39 | 0.023 |
| A1X283 | 830.4031 | 2 | −5.8 | 35.4 | 1.60E−06 |
| Q5M775 | 766.3726 | 2 | −2.7 | 38 | 9.80E−04 |
| P19623 | 609.3094 | 2 | −13 | 44.2 | 0.0013 |
| O75934 | 644.9756 | 3 | −0.17 | 51.8 | 6.80E−07 |
| O75940 | 731.3598 | 2 | 0.17 | 33.9 | 4.90E−06 |
| Q8N0X7 | 625.3093 | 2 | 6.9 | 22.1 | 8.50E−04 |
| Q8N0X7 | 506.7156 | 4 | 19 | 26.3 | 0.0069 |
| Q8N0X7 | 538.7899 | 4 | 0.5 | 29.9 | 0.0016 |
| Q9NUQ6 | 482.5808 | 3 | −32 | 27.4 | 0.059 |
| Q7KZ85 | 612.3149 | 2 | −3.4 | 33.8 | 0.0015 |
| Q13813 | 872.4677 | 2 | 0.34 | 31.4 | 1.10E−04 |
| Q13813 | 486.8061 | 2 | −4.1 | 23 | 0.011 |
| O15020 | 605.312 | 3 | −4.8 | 45.7 | 1.50E−04 |
| O15042 | 910.7951 | 3 | −14 | 26.2 | 0.091 |
| O15042 | 967.4972 | 2 | −32 | 46.4 | 1.30E−05 |
| O15042 | 828.7499 | 3 | 0.01 | 38 | 2.70E−05 |
| O15042 | 653.8394 | 4 | 2.1 | 38 | 1.30E−04 |
| O15042 | 608.8057 | 2 | −1.1 | 35.2 | 1.80E−07 |
| O15042 | 448.9081 | 3 | 6.8 | 41.1 | 2.60E−07 |
| O15042 | 519.029 | 4 | 3.9 | 48.2 | 7.40E−08 |
| Q6ZRS2 | 788.3406 | 3 | −5.5 | 45.7 | 2.60E−06 |
| Q6ZRS2 | 848.6655 | 3 | −30 | 41.6 | 4.20E−08 |
| P12931 | 860.4475 | 2 | −2.8 | 26.5 | 1.70E−04 |
| Q8NEF9 | 531.2961 | 2 | 1.1 | 27.9 | 0.0016 |
| Q8NEF9 | 478.7739 | 4 | −0.65 | 22.5 | 0.085 |
| Q9UHB9 | 585.5641 | 4 | 17 | 49.3 | 1.30E−07 |
| Q9UHB9 | 518.2524 | 3 | 12 | 38.7 | 0.004 |
| Q96SB4 | 1439.3376 | 3 | 5.3 | 28 | 2.60E−04 |
| Q9UQ35 | 489.739 | 2 | 7 | 28.9 | 0.0047 |
| Q9UQ35 | 523.7805 | 2 | −5 | 36.5 | 0.0018 |
| Q9UQ35 | 433.8676 | 3 | −15 | 22.8 | 0.078 |
| O60232 | 639.9947 | 3 | −4.3 | 55.7 | 6.90E−06 |
| Q9BWW4 | 1146.555 | 2 | 4.5 | 22.9 | 0.0016 |
| Q9NQ55 | 831.9291 | 2 | −2.9 | 41 | 8.60E−08 |
| P28290 | 769.4176 | 2 | 1.3 | 41.8 | 0.0041 |
| Q76I76 | 792.3868 | 3 | −0.59 | 30.4 | 0.0021 |
| Q08945 | 912.4597 | 2 | −2.8 | 49.6 | 8.00E−06 |
| Q9ULZ2 | 640.9686 | 3 | −3.6 | 55.6 | 1.60E−05 |
| Q9ULZ2 | 635.637 | 3 | −3.7 | 57.2 | 3.90E−05 |
| O94804 | 1440.6692 | 4 | 1.1 | 25.8 | 2.10E−04 |
| Q9Y6E0 | 919.9206 | 2 | −18 | 54.6 | 3.10E−08 |
| Q9Y6E0 | 609.8011 | 4 | 1.4 | 32.3 | 0.0096 |
| Q9UEW8 | 799.3599 | 2 | 16 | 55.5 | 4.90E−04 |
| Q13043 | 1230.8882 | 3 | 1.3 | 33.7 | 2.40E−04 |
| Q13043 | 962.4368 | 4 | −5.5 | 22.6 | 0.025 |
| Q13043 | 801.4111 | 5 | 45 | 35 | 8.50E−05 |
| O43815 | 483.2445 | 2 | 1.9 | 32.5 | 0.0058 |
| O43815 | 694.8362 | 2 | −2.9 | 48.2 | 9.90E−04 |
| O43815 | 615.3103 | 3 | −1.1 | 43.5 | 4.70E−04 |
| O43815 | 493.7484 | 4 | −21 | 28.1 | 0.0056 |
| O60499 | 562.9101 | 3 | −1.1 | 23.4 | 3.30E−04 |
| O60499 | 550.2824 | 2 | 18 | 32.8 | 0.019 |
| Q86Y82 | 645.6447 | 3 | 5.4 | 62.6 | 2.30E−06 |
| P56962 | 585.3108 | 4 | 9.3 | 30.6 | 1.00E−04 |
| P56962 | 697.6675 | 3 | −5.2 | 53.4 | 8.10E−05 |
| O15400 | 905.4229 | 3 | −22 | 66.6 | 1.80E−08 |
| Q9Y2Z0 | 920.9676 | 2 | −14 | 26.6 | 0.0026 |
| Q96A49 | 537.5916 | 3 | 0.68 | 43.1 | 2.60E−04 |
| P07814 | 702.9106 | 2 | 3.1 | 52.2 | 0.0046 |
| O95926 | 567.9626 | 3 | 4.7 | 25.8 | 0.0053 |
| O95926 | 619.9912 | 3 | −4.1 | 51.6 | 2.40E−07 |
| P41250 | 716.8691 | 2 | −8.5 | 52.1 | 6.30E−05 |
| Q92797 | 524.2259 | 2 | 3.2 | 31.3 | 0.0031 |
| O43776 | 971.4463 | 2 | −0.63 | 31 | 8.20E−05 |
| Q8NF91 | 610.962 | 3 | 3.1 | 50.1 | 5.70E−07 |
| Q8WXH0 | 601.2927 | 2 | −2.1 | 44.7 | 2.40E−04 |
| P23381 | 775.8948 | 2 | −1.7 | 48.5 | 1.10E−05 |
| Q9NUM4 | 580.2535 | 2 | −4.4 | 37.4 | 3.10E−04 |
| Q9NUM4 | 572.2618 | 2 | 5.6 | 33.8 | 0.0046 |
| Q9BVX2 | 913.4464 | 3 | −20 | 31.1 | 0.0016 |
| P29083 | 605.0193 | 4 | 5.4 | 35.1 | 1.90E−04 |
| P29083 | 601.0209 | 4 | 5.9 | 44.9 | 1.80E−06 |
| P35269 | 1007.3983 | 2 | 1.3 | 55.5 | 1.30E−08 |
| P35269 | 999.4013 | 2 | 1.8 | 52.8 | 2.30E−07 |
| O75410 | 669.3194 | 2 | −1.3 | 24.8 | 3.40E−05 |
| O75410 | 635.2991 | 3 | 0.77 | 34.2 | 3.00E−05 |
| O75410 | 379.4883 | 3 | −31 | 22.4 | 0.0045 |
| O95359 | 459.5494 | 3 | −2.8 | 24.8 | 0.021 |
| Q9Y6A5 | 921.7929 | 3 | 5.9 | 31.8 | 3.90E−04 |
| Q9Y6A5 | 750.3785 | 2 | −2.1 | 34.1 | 0.0043 |
| Q96BN2 | 504.0201 | 4 | 1.7 | 31.8 | 3.90E−04 |
| Q15544 | 829.8834 | 2 | −9.7 | 39.6 | 3.50E−05 |
| Q15545 | 1032.492 | 2 | −2 | 30.2 | 0.0038 |
| Q71U36 P68363 Q9BQE3 Q13748 Q6PEY2 | 669.1185 | 5 | 4.2 | 56.2 | 1.60E−08 |
| Q71U36 P68363 Q9BQE3 Q13748 Q6PEY2 | 665.9205 | 5 | 5.7 | 62.1 | 1.10E−09 |
| Q71U36 P68363 Q9BQE3 Q13748 Q6PEY2 | 946.0852 | 3 | −11 | 51.1 | 1.30E−08 |
| Q71U36 P68363 Q9BQE3 Q13748 Q6PEY2 | 492.5025 | 4 | 5.7 | 42.9 | 6.80E−06 |
| Q71U36 P68363 Q9BQE3 Q13748 Q6PEY2 P68366 | 514.7216 | 2 | 0.51 | 34.3 | 0.035 |
| Q71U36 P68363 Q9BQE3 Q13748 Q6PEY2 P68366 Q9NY65 | 706.6535 | 3 | −5 | 27.8 | 0.0062 |
| Q71U36 P68363 Q9BQE3 Q13748 Q6PEY2 P68366 Q9NY65 | 744.7286 | 3 | 2.4 | 36.4 | 9.50E−06 |
| Q13885 Q9BVA1 P68371 Q13509 P07437 | 334.2091 | 3 | −2.1 | 22 | 0.071 |
| Q13885 Q9BVA1 P68371 Q13509 P07437 | 436.7664 | 2 | 6.4 | 30.8 | 0.087 |

TABLE 2-continued

Mass spectrometry statistics for identified caspase-derived peptides.

| Swiss-Prot acc # | m/z | z | Error ppm | score | E value |
|---|---|---|---|---|---|
| P68371 | 859.4191 | 5 | −15 | 41.1 | 1.90E−05 |
| P07437 | | | | | |
| Q15814 | 658.03 | 3 | 0.2 | 39.1 | 4.50E−07 |
| O60343 | 763.0459 | 3 | −3.5 | 55.2 | 3.30E−05 |
| O60343 | 672.0145 | 3 | −3.1 | 50.5 | 4.90E−05 |
| Q9BZK7 | 586.3129 | 3 | −20 | 32.1 | 0.0085 |
| Q9BZK7 | 691.336 | 2 | −9.6 | 43.6 | 0.016 |
| O60907 | | | | | |
| Q9BZK7 | 609.805 | 2 | 2.2 | 40.9 | 0.0013 |
| Q9BQ87 | | | | | |
| O60907 | 598.2951 | 2 | −1 | 39.3 | 0.032 |
| P23193 | 603.7908 | 2 | −3.8 | 27.3 | 0.0051 |
| Q9UGU0 | 1006.0216 | 3 | −1.5 | 48.2 | 3.60E−09 |
| Q9UGU0 | 954.2312 | 4 | −2.5 | 22.6 | 0.02 |
| Q9UGU0 | 548.7724 | 4 | −4 | 32.2 | 0.0013 |
| Q13428 | 935.4953 | 2 | −0.91 | 37 | 3.50E−07 |
| Q13428 | 927.4999 | 2 | 1.3 | 37.6 | 1.50E−07 |
| Q13428 | 958.0103 | 2 | 0.16 | 32.3 | 1.80E−06 |
| P50991 | 904.4691 | 3 | −13 | 38.6 | 6.50E−05 |
| P50991 | 525.2248 | 2 | 6.3 | 34.3 | 0.002 |
| P50991 | 517.2261 | 2 | 4 | 31.5 | 0.017 |
| P48643 | 872.7516 | 3 | −9.3 | 36 | 4.90E−04 |
| P48643 | 652.3692 | 3 | −6.7 | 48.5 | 7.30E−07 |
| P40227 | 676.3702 | 3 | 15 | 31.4 | 3.40E−04 |
| P13693 | 545.2834 | 2 | −1.3 | 29.7 | 0.0049 |
| O60522 | 686.3245 | 4 | 7.1 | 24.2 | 0.079 |
| Q8IWB9 | 575.7741 | 2 | −6.8 | 30.8 | 0.0014 |
| Q8IWB9 | 858.9738 | 2 | −7.4 | 24.2 | 4.90E−04 |
| Q00403 | 703.8401 | 2 | 7.7 | 31.8 | 0.0032 |
| Q00403 | 695.8365 | 2 | −0.95 | 37.1 | 0.029 |
| Q9NZI6 | 575.849 | 2 | 3.2 | 36.2 | 0.073 |
| Q12800 | | | | | |
| Q9NZI7 | | | | | |
| Q92664 | 697.7161 | 3 | −0.33 | 44.4 | 6.10E−05 |
| Q04206 | 721.3227 | 2 | −2.5 | 35.6 | 4.20E−06 |
| Q96RS0 | 428.8935 | 3 | 9 | 27.2 | 0.0093 |
| Q96RS0 | 720.6791 | 2 | −2 | 30.9 | 4.60E−05 |
| Q96RS0 | 709.9974 | 2 | −2.8 | 24.1 | 0.012 |
| Q86V81 | 715.8326 | 2 | 2.3 | 46.5 | 4.30E−07 |
| Q13769 | 440.2166 | 2 | 6.1 | 25.8 | 0.05 |
| P52888 | 687.3451 | 2 | −0.95 | 35.6 | 4.30E−05 |
| O15164 | 664.6242 | 3 | −5.5 | 36.4 | 1.30E−04 |
| Q13263 | 1426.8933 | 3 | 1.10E−04 | 38.5 | 3.70E−08 |
| Q13263 | 824.3788 | 2 | 2.4 | 42.8 | 4.30E−09 |
| Q13263 | 1010.0201 | 2 | −21 | 37.5 | 4.00E−04 |
| Q13263 | 577.788 | 2 | 0.019 | 43.1 | 0.002 |
| Q13263 | 456.2436 | 2 | −3.8 | 23.4 | 0.061 |
| Q9UNS1 | 972.4909 | 2 | 1.9 | 35.7 | 9.10E−06 |
| Q9BSI4 | 1033.9965 | 2 | −3.2 | 25.8 | 1.80E−04 |
| Q9BSI4 | 1026.0031 | 2 | 0.72 | 41.1 | 1.30E−05 |
| Q86UE8 | 934.4821 | 3 | −7.8 | 22.9 | 0.044 |
| Q9H0V1 | 731.0532 | 3 | −2.6 | 29.4 | 0.012 |
| Q6ZVM7 | 402.2346 | 3 | 7.9 | 22.8 | 0.0059 |
| Q9BVT8 | 608.9508 | 3 | −9.2 | 36.5 | 4.60E−04 |
| Q9BVT8 | 603.6198 | 3 | −8.2 | 44 | 4.50E−04 |
| Q8NFZ5 | 478.9161 | 3 | 7.9 | 44.1 | 9.40E−04 |
| Q8NDV7 | 782.8917 | 2 | −3.4 | 27.9 | 7.00E−04 |
| Q8NDV7 | 620.07 | 4 | 8.1 | 23.2 | 0.0096 |
| Q96GM8 | 1008.9917 | 2 | 2 | 42.9 | 1.30E−07 |
| Q96GM8 | 762.3608 | 2 | −13 | 32.7 | 6.70E−05 |
| Q5JTV8 | 938.495 | 2 | 3.1 | 37.6 | 3.00E−07 |
| Q5JTV8 | 448.9175 | 3 | 11 | 35.3 | 4.20E−05 |
| Q5JTV8 | 428.2089 | 3 | −12 | 34.5 | 8.60E−04 |
| Q9H0E2 | 620.6697 | 3 | 12 | 44.5 | 4.60E−07 |
| O60784 | 464.7612 | 2 | −6.4 | 38.2 | 0.08 |
| O60784 | 1207.2751 | 3 | −3.6 | 26 | 0.0021 |
| O60784 | 1360.34 | 3 | −3.7 | 28.4 | 6.00E−05 |
| O60784 | 482.5728 | 3 | −12 | 38.5 | 6.80E−04 |
| O60784 | 477.2509 | 3 | 8.7 | 34.5 | 0.0015 |
| Q02880 | 738.8719 | 2 | −0.28 | 41.4 | 0.0032 |
| Q12888 | 656.8251 | 4 | −0.49 | 46 | 1.30E−06 |
| Q12888 | 839.9387 | 4 | 30 | 34.3 | 3.70E−04 |
| Q12888 | 721.3541 | 2 | −4.2 | 52.6 | 0.023 |
| Q12888 | 507.7201 | 2 | 1.9 | 23.5 | 0.024 |
| Q12888 | 667.3603 | 2 | 1.7 | 30.1 | 0.0082 |
| O43399 | 721.8639 | 2 | −2 | 26.3 | 2.70E−04 |
| Q5T0D9 | 1006.5086 | 3 | −9.5 | 32.5 | 3.30E−04 |
| Q5T0D9 | 913.2612 | 5 | −16 | 22 | 0.07 |
| P12270 | 1124.0409 | 2 | 2.1 | 33.2 | 1.30E−05 |
| P12270 | 629.3242 | 3 | 1.3 | 60.4 | 5.40E−08 |
| Q9Y2W1 | 663.6706 | 3 | −3.2 | 53 | 4.60E−08 |
| Q15633 | 672.3055 | 3 | −4.1 | 48.2 | 1.30E−07 |
| Q96PN7 | 763.6944 | 3 | −13 | 32.8 | 1.80E−05 |
| Q9UPN9 | 583.8284 | 2 | −2.8 | 28.9 | 4.30E−04 |
| Q9UPN9 | 815.7195 | 3 | 2.2 | 28.2 | 0.0058 |
| Q9UPN9 | 810.3852 | 3 | −1.1 | 34.6 | 2.90E−04 |
| Q15650 | 557.6242 | 3 | −3.3 | 39.4 | 6.60E−04 |
| Q15650 | 848.3895 | 2 | 4 | 45.1 | 2.00E−04 |
| Q7Z2T5 | 1096.5593 | 3 | −4.9 | 54.4 | 3.00E−10 |
| Q9Y2L5 | 473.2404 | 3 | 12 | 43.7 | 0.0099 |
| Q92574 | 736.869 | 2 | −7.2 | 42.8 | 4.60E−04 |
| Q92574 | 656.089 | 4 | −0.31 | 26 | 0.0095 |
| Q92574 | 827.393 | 2 | −0.13 | 50 | 1.50E−04 |
| Q2NL82 | 604.2764 | 2 | −4.5 | 39.1 | 1.10E−06 |
| Q2NL82 | 560.285 | 3 | 0.83 | 48 | 3.30E−08 |
| Q2NL82 | 596.2769 | 2 | −8.1 | 39.6 | 3.20E−05 |
| Q2NL82 | 560.2876 | 3 | 5.6 | 37 | 1.10E−06 |
| Q2NL82 | 609.9619 | 3 | −8.5 | 42.7 | 8.30E−05 |
| Q99614 | 661.2932 | 3 | −8 | 41.5 | 2.00E−06 |
| O95801 | 612.3082 | 2 | −3 | 29.2 | 1.00E−04 |
| Q9UNY4 | 711.4294 | 2 | −5 | 22.4 | 0.0033 |
| Q9UNY4 | 517.3247 | 3 | 3.9 | 29 | 0.0014 |
| P63313 | 624.2846 | 2 | 0.51 | 41 | 0.0033 |
| P04818 | 426.731 | 2 | −3.2 | 23 | 0.0056 |
| P25490 | 1025.0097 | 4 | −13 | 33.5 | 3.20E−05 |
| Q13432 | 429.9161 | 3 | 4.5 | 42.9 | 2.20E−04 |
| A6NIH7 | 668.8739 | 4 | 0.24 | 40 | 2.50E−06 |
| P26368 | 692.6958 | 3 | −3.2 | 49.2 | 1.10E−07 |
| P26368 | 687.3638 | 3 | −3.7 | 58.5 | 4.20E−08 |
| Q3KQV9 | 1094.0704 | 2 | 1.9 | 43.5 | 2.00E−08 |
| Q13838 | 511.2687 | 2 | −1.2 | 32.2 | 0.049 |
| P22314 | 658.6626 | 3 | −0.22 | 36.1 | 9.70E−05 |
| Q8TBC4 | 715.3295 | 3 | 0.66 | 28.7 | 0.0019 |
| Q8TBC4 | 758.7929 | 2 | 1.8 | 48.6 | 7.10E−07 |
| Q5T6F2 | 759.3829 | 2 | −0.63 | 22.5 | 3.60E−04 |
| Q5T6F2 | 570.7653 | 2 | 2.8 | 30.8 | 4.90E−06 |
| Q5T6F2 | 597.2897 | 2 | 3 | 33 | 0.0015 |
| Q9C0C9 | 1065.1611 | 3 | −9.6 | 28.9 | 7.90E−04 |
| Q9C0C9 | 1059.8263 | 3 | −13 | 38.6 | 1.60E−04 |
| Q9C0C9 | 880.6616 | 4 | −13 | 26.6 | 0.0033 |
| Q9C0C9 | 1302.6199 | 3 | 5.3 | 30.6 | 0.0012 |
| Q9C0C9 | 420.5742 | 3 | 7 | 24.5 | 7.50E−04 |
| O14562 | 1090.4749 | 4 | −15 | 42.2 | 4.40E−08 |
| Q9NPG3 | 1143.0427 | 2 | −18 | 44.7 | 3.20E−07 |
| Q14694 | 753.6938 | 3 | −8 | 31.3 | 2.60E−04 |
| Q14694 | 458.2583 | 2 | 9.5 | 38 | 0.021 |
| Q14694 | 701.3464 | 3 | −7.4 | 39.1 | 3.10E−05 |
| P54578 | 513.7778 | 2 | 1.6 | 32 | 0.018 |
| P54578 | 622.2935 | 2 | −0.35 | 43.6 | 3.30E−05 |
| O94966 | 576.2896 | 3 | 2 | 28.2 | 0.0018 |
| Q14157 | 607.8398 | 2 | 6.9 | 22 | 0.0015 |
| Q14157 | 791.3962 | 3 | −15 | 48.8 | 7.20E−07 |
| Q14157 | 830.3892 | 2 | −9 | 31.8 | 2.80E−04 |
| Q70CQ2 | 463.2114 | 2 | 4 | 26.1 | 0.028 |
| Q70CQ2 | 706.8328 | 2 | 5.3 | 27.7 | 4.20E−04 |
| Q9P275 | 540.8051 | 2 | 8.6 | 27.9 | 0.016 |
| Q9H9J4 | 445.7561 | 2 | 12 | 37.4 | 8.80E−04 |
| P45974 | 625.7867 | 2 | −1.7 | 45 | 2.30E−06 |
| P45974 | 617.7907 | 2 | 0.68 | 30 | 3.50E−05 |
| P45974 | 480.615 | 3 | 6.2 | 32.1 | 1.80E−04 |
| P45974 | 623.837 | 2 | −9.9 | 36 | 0.033 |
| P45974 | 675.3514 | 2 | 0.65 | 33.6 | 9.00E−05 |
| Q93009 | 659.9335 | 3 | −0.98 | 45.6 | 2.80E−07 |
| Q93009 | 720.2814 | 3 | 2 | 50.9 | 7.00E−07 |
| Q9UMX0 | 870.4346 | 2 | 3.5 | 29.1 | 1.30E−06 |
| Q5T4S7 | 390.8701 | 3 | 8.1 | 35.6 | 1.60E−05 |
| O94888 | 540.5906 | 3 | −15 | 42.6 | 3.90E−04 |
| O94888 | 601.534 | 4 | −23 | 30 | 6.90E−04 |
| O94888 | 717.3751 | 2 | 11 | 34.3 | 1.10E−05 |
| Q16851 | 692.8494 | 2 | 4.3 | 54.5 | 0.063 |

TABLE 2-continued

Mass spectrometry statistics for identified caspase-derived peptides.

| Swiss-Prot acc # | m/z | z | Error ppm | score | E value |
|---|---|---|---|---|---|
| A0JNW5 | 859.4135 | 3 | −1.4 | 26.5 | 0.0025 |
| Q96T88 | 747.3409 | 3 | −4.2 | 42 | 2.50E−06 |
| Q96T88 | 797.411 | 4 | 48 | 60.3 | 1.00E−08 |
| Q86UX7 | 626.3471 | 2 | 3.1 | 42.8 | 0.011 |
| Q86UX7 | 443.9826 | 4 | −26 | 38.1 | 4.10E−04 |
| Q9NZ43 | 650.2803 | 2 | 0.97 | 33.5 | 6.70E−04 |
| Q15853 | 1464.7474 | 3 | −4.7 | 35.2 | 2.50E−05 |
| O60763 | 567.7412 | 2 | −4.8 | 25.5 | 0.0023 |
| P46939 | 634.8724 | 2 | 4.3 | 25.6 | 0.0021 |
| P63027 | 577.2989 | 3 | 25 | 30.6 | 4.10E−04 |
| Q15836 | | | | | |
| Q9Y5K8 | 630.3138 | 2 | −5 | 31.2 | 0.0048 |
| P08670 | 454.2513 | 2 | 7.7 | 27.6 | 0.019 |
| P08670 | 639.8444 | 2 | 1.1 | 23.8 | 2.50E−04 |
| P08670 | 651.8523 | 2 | −2.9 | 30.6 | 1.00E−04 |
| P08670 | 720.8728 | 2 | 0.96 | 41.1 | 1.10E−05 |
| P08670 | 604.6469 | 3 | −1.4 | 65 | 9.00E−08 |
| P08670 | 705.0226 | 3 | −1.3 | 52.9 | 4.50E−07 |
| P08670 | 376.4564 | 4 | 5.1 | 31.5 | 3.40E−04 |
| P08670 | 545.6313 | 3 | 2.9 | 37.2 | 2.90E−05 |
| P08670 | 502.0231 | 4 | −0.35 | 27.4 | 0.0011 |
| P08670 | 474.2526 | 3 | −25 | 44 | 3.20E−04 |
| P08670 | 448.502 | 4 | 5.7 | 27.1 | 0.0059 |
| Q5THJ4 | 679.3378 | 2 | −4.6 | 31.2 | 0.018 |
| Q9UN37 | 588.9353 | 3 | −0.85 | 47.2 | 5.10E−04 |
| Q9UN37 | 640.9725 | 3 | 4.7 | 27.1 | 0.0062 |
| Q99986 | 386.86 | 3 | 0.44 | 33.9 | 0.0011 |
| Q7Z5K2 | 476.2366 | 2 | 10 | 24.1 | 0.0055 |
| Q92558 | 779.7277 | 3 | 11 | 54 | 1.30E−05 |
| Q9Y6W5 | 1083.515 | 4 | 16 | 41.1 | 5.20E−06 |
| Q9Y6W5 | 633.0053 | 3 | −2.7 | 45.2 | 4.30E−05 |
| A8K0Z3 | 984.5248 | 4 | −17 | 52.7 | 2.40E−07 |
| Q9C0J8 | 435.7081 | 4 | 6.3 | 24.8 | 0.0035 |
| Q5JSH3 | 972.0395 | 2 | 8.3 | 37.9 | 8.50E−06 |
| Q9H6Y2 | 438.7174 | 2 | 3.7 | 27.6 | 0.027 |
| O43379 | 1109.2663 | 3 | −6 | 37.5 | 1.50E−05 |
| Q96MX6 | 912.9972 | 2 | 3.2 | 33 | 1.10E−06 |
| O76024 | 496.7763 | 2 | −7.2 | 31.2 | 0.0013 |
| O76024 | 730.6953 | 3 | −1.5 | 35.3 | 8.80E−04 |
| O43516 | 608.3255 | 4 | −3.5 | 45.9 | 1.80E−08 |
| Q9H4A3 | 707.815 | 4 | 4.7 | 34.3 | 2.70E−05 |
| Q9H4A3 | 1167.0025 | 2 | −3.4 | 50.4 | 3.30E−11 |
| Q9H4A3 | 563.2531 | 5 | 2.4 | 41 | 7.00E−07 |
| Q9H4A3 | 414.6975 | 4 | −5.4 | 37 | 3.30E−06 |
| Q9H4A3 | 932.4238 | 2 | 2.5 | 58 | 2.30E−06 |
| Q9H4A3 | 838.7054 | 3 | 23 | 56.8 | 1.00E−07 |
| Q96S55 | 622.6505 | 3 | 0.23 | 29.8 | 0.0039 |
| Q6AWC2 | 443.279 | 2 | −0.92 | 25 | 0.011 |
| P23025 | 747.3813 | 3 | −12 | 60 | 1.40E−07 |
| P46937 | 682.3796 | 2 | 5.7 | 23.4 | 6.30E−04 |
| P67809 | 855.4151 | 3 | 3.3 | 44.5 | 1.10E−06 |
| P67809 | 673.8279 | 4 | −10 | 47.1 | 1.30E−08 |
| P67809 | 863.0819 | 3 | −27 | 48.6 | 7.20E−08 |
| Q9GZM5 | 826.8774 | 2 | 0.15 | 32.9 | 6.80E−05 |
| Q6ZSR9 | 802.416 | 2 | −14 | 31.1 | 4.50E−04 |
| Q6ZSR9 | 585.8135 | 2 | −9.4 | 30 | 0.0073 |
| A8MX80 | 652.3391 | 3 | 0.68 | 22.5 | 0.028 |
| Q9H6S0 | 895.3569 | 2 | −0.24 | 53.6 | 4.40E−07 |
| Q9BYJ9 | 679.841 | 2 | 3.5 | 26.3 | 9.90E−05 |
| Q9BYJ9 | 726.6064 | 4 | 0.45 | 22.8 | 0.024 |
| Q9BYJ9 | 718.6071 | 4 | −2.2 | 39.8 | 9.40E−06 |
| Q9Y5A9 | 669.3386 | 4 | −8.1 | 46.5 | 3.20E−07 |
| Q9Y5A9 | 682.8468 | 2 | 4.3 | 30 | 7.20E−05 |
| Q9Y5A9 | 955.1275 | 3 | −14 | 62.1 | 4.20E−09 |
| Q9Y5A9 | 1012.2638 | 4 | 0.3 | 28.2 | 0.0086 |
| Q9Y5A9 | 857.4025 | 3 | −7.4 | 69.2 | 6.50E−09 |
| Q7Z739 | 926.4589 | 2 | −19 | 48 | 9.90E−07 |
| Q7Z739 | 722.8388 | 2 | −0.035 | 33.7 | 0.0014 |
| P43403 | 488.2466 | 2 | −3.6 | 33.3 | 7.70E−04 |
| Q8NCN2 | 730.3552 | 2 | 0.59 | 30.5 | 2.40E−04 |
| Q8NCP5 | 839.407 | 2 | −2.6 | 22.4 | 1.60E−04 |
| O75152 | 668.407 | 2 | −2.9 | 27.7 | 5.00E−05 |
| O75152 | 620.8188 | 4 | 2.3 | 40.1 | 2.20E−06 |
| Q9UPT8 | 759.8306 | 2 | −8.4 | 51 | 2.40E−05 |
| Q9UPT8 | 674.1222 | 4 | 32 | 35.5 | 6.20E−05 |
| Q5T200 | 497.2648 | 3 | −2.2 | 24.9 | 0.016 |
| Q5T200 | 505.5844 | 3 | 13 | 28.2 | 0.0013 |
| Q6PJT7 | 1304.925 | 3 | −1.4 | 27.4 | 3.80E−04 |
| Q7Z2W4 | 553.298 | 2 | 3.6 | 30.3 | 9.60E−05 |
| Q7Z2W4 | 663.3275 | 2 | −5 | 45.2 | 2.00E−04 |
| Q86VM9 | 741.0172 | 3 | 1.5 | 24.5 | 0.022 |
| Q9C0B9 | 620.3225 | 2 | 4 | 46.2 | 2.10E−05 |
| Q6NZY4 | 708.8519 | 2 | −0.04 | 36.9 | 6.20E−04 |
| P37275 | 869.06 | 3 | −2.6 | 44.5 | 5.20E−07 |
| O43829 | 785.3593 | 3 | −0.25 | 51.6 | 1.90E−07 |
| O43829 | 851.0337 | 3 | −3.8 | 57.4 | 4.40E−08 |
| Q6FIF0 | 1121.534 | 3 | 4.7 | 28.7 | 0.0043 |
| Q6FIF0 | 741.8363 | 2 | −3.6 | 48.5 | 4.00E−04 |
| O95159 | 1104.0579 | 4 | 0.9 | 22.8 | 0.035 |
| P17010 | 494.7613 | 2 | 2.1 | 26.2 | 0.043 |
| P17010 | 546.9704 | 3 | 2.5 | 26.4 | 0.003 |
| Q7Z3T8 | 877.9525 | 2 | −20 | 47 | 2.30E−04 |
| Q7Z3T8 | 804.889 | 2 | 1.3 | 26.5 | 3.00E−04 |
| Q7Z3T8 | 568.3072 | 3 | 1.5 | 40.9 | 4.00E−05 |
| Q14202 | 1161.5114 | 3 | 0.59 | 28.4 | 0.0011 |
| Q5VZL5 | 485.2796 | 3 | 5.6 | 31.4 | 2.50E−04 |
| P52747 | 679.3239 | 3 | −1.5 | 59.9 | 1.20E−07 |
| P52747 | 934.1298 | 3 | −9 | 47.4 | 1.30E−06 |
| P98182 | 963.9767 | 2 | −2.9 | 23.5 | 0.0016 |
| O43296 | 589.2808 | 2 | −7.4 | 38.2 | 5.50E−05 |
| Q9NRM2 | 758.3427 | 2 | 2.5 | 25.8 | 4.70E−05 |
| Q9UL40 | 741.8506 | 4 | −9.4 | 31.6 | 5.30E−04 |
| Q9H582 | 421.2414 | 3 | 16 | 22.1 | 0.01 |
| Q9H582 | 463.9373 | 3 | 9.1 | 39.6 | 4.60E−05 |
| O15015 | 930.9646 | 2 | 1.8 | 35.8 | 4.00E−07 |
| Q6DD87 | 1035.1812 | 3 | −26 | 56 | 5.80E−09 |
| Q96JM3 | 1185.6155 | 2 | 0.71 | 35.7 | 1.20E−05 |
| Q96JM3 | 625.3273 | 4 | −12 | 44.8 | 7.50E−05 |
| P17028 | 651.0446 | 3 | 4.2 | 49.2 | 1.80E−05 |
| P17028 | 867.4384 | 2 | −8.6 | 41.9 | 0.0017 |
| P36508 | 782.9207 | 2 | 0.71 | 27.4 | 1.80E−04 |
| Q9UHR6 | 833.909 | 2 | −17 | 45.4 | 6.50E−04 |
| Q9UHR6 | 1177.5831 | 3 | −0.27 | 28.7 | 0.0058 |
| Q15942 | 738.3417 | 2 | −12 | 29.9 | 9.80E−05 |
| Q15942 | 730.359 | 2 | 8.3 | 30.9 | 0.0068 |
| Q15942 | 572.7885 | 4 | 4.1 | 43.3 | 1.40E−06 |

"E value" is the expectation value.

TABLE 3

Caspase-like cleavage sites. P4-P4' indicates the eight amino acid residues spanning the cleavage site, which is located between the fourth and fifth residues of the sequence. P1 residue indicates the residue directly preceding the cleavage site. P1' indicates the residue directly following the cleavage site. P1 residue # indicates the residue number in the full-length protein sequence corresponding to the P1 residue. Entries separated by vertical bars indicate cleavage sites found in more than one homologous protein.

| Swiss-Prot ID | Swiss-Prot acc # | P1 residue # |
|---|---|---|
| 2A5G_HUMAN | Q13362 | 14 |
| 3MG_HUMAN | P29372 | 36 |
| 41_HUMAN | P11171 | 550 |
| 4EBP1_HUMAN | Q13541 | 25 |
| 4EBP2_HUMAN | Q13542 | 26 |
| AASD1_HUMAN | Q9BTE6 | 80 |
| ABL1_HUMAN | P00519 | 939 |
| ABLM1_HUMAN | O14639 | 567 |
| ACAP3_HUMAN | Q96P50 | 588 |
| ACINU_HUMAN | Q9UKV3 | 68 |
| ACINU_HUMAN | Q9UKV3 | 511 |
| ACINU_HUMAN | Q9UKV3 | 663 |
| ACOC_HUMAN | P21399 | 673 |
| ACSL3_HUMAN | O95573 | 571 |

TABLE 3-continued

Caspase-like cleavage sites. P4-P4' indicates the eight amino acid residues spanning the cleavage site, which is located between the fourth and fifth residues of the sequence. P1 residue indicates the residue directly preceding the cleavage site. P1' indicates the residue directly following the cleavage site. P1 residue # indicates the residue number in the full-length protein sequence corresponding to the P1 residue. Entries separated by vertical bars indicate cleavage sites found in more than one homologous protein.

| Swiss-Prot ID | Swiss-Prot acc # | P1 residue # |
|---|---|---|
| ACSL4_HUMAN | O60488 | 562 |
| ACTB_HUMAN | P60709 | 157 |
| ACTG_HUMAN | P63261 | |
| ACTN1_HUMAN | P12814 | 5 |
| ACTN1_HUMAN | P12814 | 22 |
| ACTN2_HUMAN | P35609 | 29 |
| ACTN3_HUMAN | Q08043 | 36 |
| ACTN4_HUMAN | O43707 | 41 |
| ADDA_HUMAN | P35611 | 633 |
| AEBP2_HUMAN | Q6ZN18 | 233 |
| AEDO_HUMAN | Q96SZ5 | 34 |
| AF1L2_HUMAN | Q8N4X5 | 312 |
| AF1L2_HUMAN | Q8N4X5 | 630 |
| AFTIN_HUMAN | Q6ULP2 | 339 |
| AGGF1_HUMAN | Q8N302 | 148 |
| AHNK_HUMAN | Q09666 | 575 |
| AHNK_HUMAN | Q09666 | 737 |
| AHNK_HUMAN | Q09666 | 739 |
| AHNK_HUMAN | Q09666 | 865 |
| AHNK_HUMAN | Q09666 | 919 |
| AHNK_HUMAN | Q09666 | 1168 |
| AHNK_HUMAN | Q09666 | 1424 |
| AHNK_HUMAN | Q09666 | 1583 |
| AHNK_HUMAN | Q09666 | 2711 |
| AHNK_HUMAN | Q09666 | 2882 |
| AHNK_HUMAN | Q09666 | 3464 |
| AHNK_HUMAN | Q09666 | 3493 |
| AHNK_HUMAN | Q09666 | 3718 |
| AHNK_HUMAN | Q09666 | 4358 |
| AHNK_HUMAN | Q09666 | 5580 |
| AHSA1_HUMAN | O95433 | 18 |
| AHSA1_HUMAN | O95433 | 254 |
| AHTF1_HUMAN | Q8WYP5 | 1367 |
| AIM1_HUMAN | Q9Y4K1 | 67 |
| AKA12_HUMAN | Q02952 | 451 |
| AKAP2_HUMAN | Q9Y2D5 | 472 |
| AKAP9_HUMAN | Q99996 | 1033 |
| AKNA_HUMAN | Q7Z591 | 799 |
| AKP13_HUMAN | Q12802 | 544 |
| AKP13_HUMAN | Q12802 | 829 |
| AKP13_HUMAN | Q12802 | 905 |
| AKP13_HUMAN | Q12802 | 1055 |
| AKP13_HUMAN | Q12802 | 1539 |
| AKP8L_HUMAN | Q9ULX6 | 108 |
| ALMS1_HUMAN | Q8TCU4 | 427 |
| ALMS1_HUMAN | Q8TCU4 | 590 |
| ALMS1_HUMAN | Q8TCU4 | 779 |
| ALO17_HUMAN | Q9HCF4 | 273 |
| AMPD3_HUMAN | Q01432 | 36 |
| AMPM1_HUMAN | P53582 | 12 |
| ANKH1_HUMAN | Q8IWZ3 | 4 |
| ANKH1_HUMAN | Q8IWZ3 | 1048 |
| ANKS6_HUMAN | Q68DC2 | 275 |
| ANS1A_HUMAN | Q92625 | 529 |
| ANXA2_HUMAN | P07355 | 16 |
| AXA2L_HUMAN | A6NMY6 | |
| AP1G1_HUMAN | O43747 | 689 |
| AP1G2_HUMAN | O75843 | 631 |
| AP2A2_HUMAN | O94973 | 690 |
| AP3B2_HUMAN | Q13367 | 843 |
| APBB2_HUMAN | Q92870 | 279 |
| APC_HUMAN | P25054 | 1498 |
| APMAP_HUMAN | Q9HDC9 | 22 |
| APTX_HUMAN | Q7Z2E3 | 141 |
| AR13B_HUMAN | Q3SXY8 | 241 |
| ARBK1_HUMAN | P25098 | 527 |
| ARBK1_HUMAN | P25098 | 481 |
| ARBK2_HUMAN | P35626 | |
| ARHG1_HUMAN | Q92888 | 292 |
| ARHG2_HUMAN | Q92974 | 626 |
| ARHGA_HUMAN | O15013 | 1246 |
| ARI1A_HUMAN | O14497 | 75 |
| ARI1A_HUMAN | O14497 | 606 |
| ARI4A_HUMAN | P29374 | 1030 |
| ARI4B_HUMAN | Q4LE39 | 1072 |
| ARID2_HUMAN | Q68CP9 | 625 |
| ARID2_HUMAN | Q68CP9 | 629 |
| ARM10_HUMAN | Q8N2F6 | 86 |
| ARMC6_HUMAN | Q6NXE6 | 82 |
| ARNT_HUMAN | P27540 | 151 |
| ARP2_HUMAN | P61160 | 161 |
| ARP21_HUMAN | Q9UBL0 | 494 |
| ARP3_HUMAN | P61158 | 59 |
| ARPC5_HUMAN | O15511 | 29 |
| ARPC5_HUMAN | O15511 | 32 |
| ARS2_HUMAN | Q9BXP5 | 161 |
| ASB13_HUMAN | Q8WXK3 | 51 |
| ASCC1_HUMAN | Q8N9N2 | 34 |
| ASCC2_HUMAN | Q9H1I8 | 621 |
| ASHWN_HUMAN | Q9BVC5 | 105 |
| ASPP2_HUMAN | Q13625 | 527 |
| ATAD5_HUMAN | Q96QE3 | 284 |
| ATD2B_HUMAN | Q9ULI0 | 77 |
| ATF1_HUMAN | P18846 | 46 |
| ATF4_HUMAN | P18848 | 65 |
| ATF7_HUMAN | P17544 | 43 |
| ATG3_HUMAN | Q9NT62 | 104 |
| ATRX_HUMAN | P46100 | 919 |
| ATX1L_HUMAN | P0C7T5 | 308 |
| ATX2_HUMAN | Q99700 | 842 |
| ATX2L_HUMAN | Q8WWM7 | 584 |
| ATX3_HUMAN | P54252 | 217 |
| AZI1_HUMAN | Q9UPN4 | 548 |
| BA2D1_HUMAN | Q9Y520 | 888 |
| BA2D1_HUMAN | Q9Y520 | 2189 |
| BAP1_HUMAN | Q92560 | 311 |
| BAP31_HUMAN | P51572 | 164 |
| BASP_HUMAN | P80723 | 165 |
| BASP_HUMAN | P80723 | 171 |
| BAT3_HUMAN | P46379 | 1001 |
| BAZ1A_HUMAN | Q9NRL2 | 499 |
| BCAP_HUMAN | Q6ZUJ8 | 148 |
| BCLF1_HUMAN | Q9NYF8 | 324 |
| BCLF1_HUMAN | Q9NYF8 | 382 |
| BCR_HUMAN | P11274 | 243 |
| BDP1_HUMAN | A6H8Y1 | 525 |
| BID_HUMAN | P55957 | 75 |
| BIG3_HUMAN | Q5TH69 | 292 |
| BIN1_HUMAN | O00499 | 301 |
| BIRC6_HUMAN | Q9NR09 | 461 |
| BL1S3_HUMAN | Q6QNY0 | 64 |
| BLNK_HUMAN | Q8WV28 | 177 |
| BNIP2_HUMAN | Q12982 | 83 |
| BPTF_HUMAN | Q12830 | 1625 |
| BRD1_HUMAN | O95696 | 921 |
| BRD4_HUMAN | O60885 | 337 |
| BRD8_HUMAN | Q9H0E9 | 560 |
| BTB14_HUMAN | Q96RE7 | 174 |
| BUB1_HUMAN | O43683 | 395 |
| BUD13_HUMAN | Q9BRD0 | 273 |
| C170L_HUMAN | Q96L14 | 50 |
| C1QBP_HUMAN | Q07021 | 185 |
| C2C2L_HUMAN | O14523 | 442 |
| C2D1A_HUMAN | Q6P1N0 | 30 |

TABLE 3-continued

Caspase-like cleavage sites. P4-P4' indicates the eight amino acid residues spanning the cleavage site, which is located between the fourth and fifth residues of the sequence. P1 residue indicates the residue directly preceding the cleavage site. P1' indicates the residue directly following the cleavage site. P1 residue # indicates the residue number in the full-length protein sequence corresponding to the P1 residue. Entries separated by vertical bars indicate cleavage sites found in more than one homologous protein.

| Swiss-Prot ID | Swiss-Prot acc # | P1 residue # |
|---|---|---|
| C2D1B_HUMAN | Q5T0F9 | 460 |
| CA059_HUMAN | Q5T8I9 | 13 |
| CA103_HUMAN | Q5T3J3 | 515 |
| CA163_HUMAN | Q96BR5 | 120 |
| CA165_HUMAN | Q7L4P6 | 103 |
| CA170_HUMAN | Q5SV97 | 42 |
| CA175_HUMAN | Q68CQ1 | 411 |
| CA1L1_HUMAN | Q08AD1 | 421 |
| CABL2_HUMAN | Q9BTV7 | 58 |
| CACO1_HUMAN | Q9P1Z2 | 134 |
| CADH2_HUMAN | P19022 | 799 |
| CAF1A_HUMAN | Q13111 | 110 |
| CAF1A_HUMAN | Q13111 | 614 |
| CALR_HUMAN | P27797 | 121 |
| CALR_HUMAN | P27797 | 258 |
| CALR_HUMAN | P27797 | 328 |
| CAMKV_HUMAN | Q8NCB2 | 407 |
| CAMLG_HUMAN | P49069 | 9 |
| CAMLG_HUMAN | P49069 | 115 |
| CAMP1_HUMAN | Q5T5Y3 | 751 |
| CAMP1_HUMAN | Q5T5Y3 | 1254 |
| CAPR1_HUMAN | Q14444 | 94 |
| CAPZB_HUMAN | P47756 | 149 |
| CASC3_HUMAN | O15234 | 389 |
| CASC5_HUMAN | Q8NG31 | 1194 |
| CASP_HUMAN | Q13948 | 387 |
| CUX1_HUMAN | P39880 | 376 |
| CASP3_HUMAN | P42574 | 28 |
| CASP3_HUMAN | P42574 | 175 |
| CASP7_HUMAN | P55210 | 198 |
| CATB_HUMAN | P07858 | 77 |
| CB044_HUMAN | Q9H6R7 | 508 |
| CBL_HUMAN | P22681 | 806 |
| CBWD1_HUMAN | Q9BRT8 | 184 |
| CBWD2_HUMAN | Q8IUF1 | 184 |
| CBWD3_HUMAN | Q5JTY5 | 184 |
| CBWD5_HUMAN | Q5RIA9 | 184 |
| CBWD6_HUMAN | Q4V339 | 184 |
| CBWD7_HUMAN | A6NM15 | 36 |
| CC104_HUMAN | Q96G28 | 141 |
| CC104_HUMAN | Q96G28 | 144 |
| CC124_HUMAN | Q96CT7 | 149 |
| CC131_HUMAN | O60293 | 335 |
| CC50A_HUMAN | Q9NV96 | 12 |
| CCD43_HUMAN | Q96MW1 | 16 |
| CCD53_HUMAN | Q9Y3C0 | 4 |
| CCD91_HUMAN | Q7Z6B0 | 99 |
| CCD97_HUMAN | Q96F63 | 52 |
| CCDC9_HUMAN | Q9Y3X0 | 299 |
| CCNT2_HUMAN | O60583 | 454 |
| CD2L1_HUMAN | P21127 | 405 |
| CD2L5_HUMAN | Q14004 | 1353 |
| CDC27_HUMAN | P30260 | 236 |
| CDC27_HUMAN | P30260 | 243 |
| CDC5L_HUMAN | Q99459 | 391 |
| CDCA7_HUMAN | Q9BWT1 | 39 |
| CDV3_HUMAN | Q9UKY7 | 122 |
| CDYL1_HUMAN | Q9Y232 | 210 |
| CE022_HUMAN | Q49AR2 | 196 |
| CE152_HUMAN | O94986 | 62 |
| CE170_HUMAN | Q5SW79 | 936 |
| CE170_HUMAN | Q5SW79 | 1324 |
| CEBPZ_HUMAN | Q03701 | 774 |
| CEBPZ_HUMAN | Q03701 | 917 |
| CEBPZ_HUMAN | Q03701 | 955 |
| CH041_HUMAN | Q6NXR4 | 4 |
| CH082_HUMAN | Q6P1X6 | 25 |
| CH60_HUMAN | P10809 | 111 |
| CH60_HUMAN | P10809 | 452 |
| CH60_HUMAN | P10809 | 504 |
| CHD3_HUMAN | Q12873 | 372 |
| CHD4_HUMAN | Q14839 | 363 |
| CHD5_HUMAN | Q8TDI0 | 336 |
| CHD4_HUMAN | Q14839 | 1233 |
| CHD7_HUMAN | Q9P2D1 | 2285 |
| CHM4A_HUMAN | Q9BY43 | 80 |
| CHM4B_HUMAN | Q9H444 | 83 |
| CHM4C_HUMAN | Q96CF2 | 83 |
| CI080_HUMAN | Q9NRY2 | 57 |
| CJ018_HUMAN | Q5VWN6 | 1207 |
| CJ047_HUMAN | Q86WR7 | 109 |
| CK059_HUMAN | Q6IAA8 | 72 |
| CL035_HUMAN | Q9HCM1 | 359 |
| CL035_HUMAN | Q9HCM1 | 501 |
| CL043_HUMAN | Q96C57 | 72 |
| CL043_HUMAN | Q96C57 | 204 |
| CLAP1_HUMAN | Q7Z460 | 1218 |
| CLCA_HUMAN | P09496 | 76 |
| CLCA_HUMAN | P09496 | 92 |
| CLIC1_HUMAN | O00299 | 141 |
| CLIP1_HUMAN | P30622 | 397 |
| CLSPN_HUMAN | Q9HAW4 | 563 |
| CND2_HUMAN | Q15003 | 170 |
| CND2_HUMAN | Q15003 | 199 |
| CND2_HUMAN | Q15003 | 366 |
| CND2_HUMAN | Q15003 | 380 |
| CNDH2_HUMAN | Q6IBW4 | 459 |
| CO6A3_HUMAN | P12111 | 2615 |
| COBL1_HUMAN | Q53SF7 | 983 |
| COPA_HUMAN | P53621 | 188 |
| COPA_HUMAN | P53621 | 856 |
| COPB2_HUMAN | P35606 | 854 |
| COR1A_HUMAN | P31146 | 394 |
| CP088_HUMAN | Q1ED39 | 182 |
| CP110_HUMAN | Q7Z7A1 | 801 |
| CP110_HUMAN | Q7Z7A1 | 1395 |
| CPIN1_HUMAN | Q6FI81 | 214 |
| CPNE1_HUMAN | Q99829 | 464 |
| CPNE3_HUMAN | O75131 | 428 |
| CPSF6_HUMAN | Q16630 | 54 |
| CPSF7_HUMAN | Q8N684 | 29 |
| CPSF7_HUMAN | Q8N684 | 33 |
| CPSF7_HUMAN | Q8N684 | 324 |
| CPZIP_HUMAN | Q6JBY9 | 272 |
| CQ056_HUMAN | Q96N21 | 380 |
| CQ085_HUMAN | Q53F19 | 157 |
| CQ085_HUMAN | Q53F19 | 231 |
| CR025_HUMAN | Q96B23 | 44 |
| CREB1_HUMAN | P16220 | 116 |
| CREB1_HUMAN | P16220 | 229 |
| CROCC_HUMAN | Q5TZA2 | 578 |
| CS043_HUMAN | Q9BQ61 | 62 |
| CS044_HUMAN | Q9H6X5 | 368 |
| CSN1_HUMAN | Q13098 | 94 |
| CSRN2_HUMAN | Q9H175 | 39 |
| CSTF3_HUMAN | Q12996 | 576 |
| CTBL1_HUMAN | Q8WYA6 | 66 |
| CTCF_HUMAN | P49711 | 46 |
| CTNB1_HUMAN | P35222 | 115 |
| CTND1_HUMAN | O60716 | 161 |
| CTR9_HUMAN | Q6PD62 | 1120 |
| CUL4B_HUMAN | Q13620 | 25 |
| CUTC_HUMAN | Q9NTM9 | 33 |
| CUX1_HUMAN | P39880 | 1339 |

TABLE 3-continued

Caspase-like cleavage sites. P4-P4' indicates the eight amino acid residues spanning the cleavage site, which is located between the fourth and fifth residues of the sequence. P1 residue indicates the residue directly preceding the cleavage site. P1' indicates the residue directly following the cleavage site. P1 residue # indicates the residue number in the full-length protein sequence corresponding to the P1 residue. Entries separated by vertical bars indicate cleavage sites found in more than one homologous protein.

| Swiss-Prot ID | Swiss-Prot acc # | P1 residue # |
|---|---|---|
| CYB5B_HUMAN | O43169 | 10 |
| DBPA_HUMAN | P16989 | 144 |
| DBPA_HUMAN | P16989 | 161 |
| DBPA_HUMAN | P16989 | 269 |
| DBPA_HUMAN | P16989 | 137 |
| YBOX1_HUMAN | P67809 | 105 |
| YBOX2_HUMAN | Q9Y2T7 | 140 |
| DCNL2_HUMAN | Q6PH85 | 42 |
| DCTN1_HUMAN | Q14203 | 302 |
| DD19A_HUMAN | Q9NUU7 | 4 |
| DDX1_HUMAN | Q92499 | 439 |
| DDX24_HUMAN | Q9GZR7 | 296 |
| DDX46_HUMAN | Q7L014 | 871 |
| DDX46_HUMAN | Q7L014 | 922 |
| DDX59_HUMAN | Q5T1V6 | 43 |
| DESM_HUMAN | P17661 | 264 |
| DFFA_HUMAN | O00273 | 6 |
| DFFA_HUMAN | O00273 | 221 |
| DGCR8_HUMAN | Q8WYQ5 | 248 |
| DGCR8_HUMAN | Q8WYQ5 | 396 |
| DGKH_HUMAN | Q86XP1 | 582 |
| DGKH_HUMAN | Q86XP1 | 698 |
| DGLB_HUMAN | Q8NCG7 | 548 |
| DHAK_HUMAN | Q3LXA3 | 362 |
| DHX30_HUMAN | Q7L2E3 | 206 |
| DHX37_HUMAN | Q8IY37 | 573 |
| DHX9_HUMAN | Q08211 | 96 |
| DHX9_HUMAN | Q08211 | 167 |
| DIAP1_HUMAN | O60610 | 648 |
| DIDO1_HUMAN | Q9BTC0 | 987 |
| DIDO1_HUMAN | Q9BTC0 | 1250 |
| DIDO1_HUMAN | Q9BTC0 | 1352 |
| DIDO1_HUMAN | Q9BTC0 | 1518 |
| DLG1_HUMAN | Q12959 | 412 |
| DNJC7_HUMAN | Q99615 | 8 |
| DNM1L_HUMAN | O00429 | 503 |
| DNM1L_HUMAN | O00429 | 579 |
| DNM3A_HUMAN | Q9Y6K1 | 438 |
| DOC10_HUMAN | Q96BY6 | 327 |
| DOHH_HUMAN | Q9BU89 | 8 |
| DOT1L_HUMAN | Q8TEK3 | 1333 |
| DP13A_HUMAN | Q9UKG1 | 444 |
| DPOD1_HUMAN | P28340 | 102 |
| DPOLA_HUMAN | P09884 | 83 |
| DPP9_HUMAN | Q86TI2 | 13 |
| DPYL4_HUMAN | O14531 | 456 |
| DREB_HUMAN | Q16643 | 340 |
| DREB_HUMAN | Q16643 | 477 |
| DSRAD_HUMAN | P55265 | 214 |
| DTL_HUMAN | Q9NZJ0 | 578 |
| DTX3L_HUMAN | Q8TDB6 | 217 |
| DYHC1_HUMAN | Q14204 | 4220 |
| DYHC1_HUMAN | Q14204 | 4367 |
| E400N_HUMAN | Q6ZTU2 | 183 |
| EP400_HUMAN | Q96L91 | 194 |
| E41L2_HUMAN | O43491 | 912 |
| EAP1_HUMAN | Q9H1B7 | 132 |
| EBP2_HUMAN | Q99848 | 211 |
| ECE1_HUMAN | P42892 | 33 |
| ECT2_HUMAN | Q9H8V3 | 628 |
| EDC4_HUMAN | Q6P2E9 | 57 |
| EDC4_HUMAN | Q6P2E9 | 485 |
| EDC4_HUMAN | Q6P2E9 | 490 |
| EDC4_HUMAN | Q6P2E9 | 662 |
| EDC4_HUMAN | Q6P2E9 | 796 |
| EDRF1_HUMAN | Q3B7T1 | 115 |
| EEA1_HUMAN | Q15075 | 127 |
| EEA1_HUMAN | Q15075 | 132 |
| EF1A1_HUMAN | P68104 | 403 |
| EF1A3_HUMAN | Q5VTE0 | |
| EF1B_HUMAN | P24534 | 102 |
| EF1D_HUMAN | P29692 | 158 |
| EF2_HUMAN | P13639 | 611 |
| EH1L1_HUMAN | Q8N3D4 | 1329 |
| EHBP1_HUMAN | Q8NDI1 | 274 |
| EHD1_HUMAN | Q9H4M9 | 415 |
| EHMT1_HUMAN | Q9H9B1 | 329 |
| EHMT1_HUMAN | Q9H9B1 | 481 |
| EHMT2_HUMAN | Q96KQ7 | 453 |
| EIF3B_HUMAN | P55884 | 184 |
| EIF3G_HUMAN | O75821 | 7 |
| EIF3J_HUMAN | O75822 | 50 |
| ELF1_HUMAN | P32519 | 145 |
| ENOA_HUMAN | P06733 | 203 |
| ENPL_HUMAN | P14625 | 28 |
| ENPL_HUMAN | P14625 | 59 |
| EP15_HUMAN | P42566 | 618 |
| EP15R_HUMAN | Q9UBC2 | 569 |
| EPC1_HUMAN | Q9H2F5 | 27 |
| EPN1_HUMAN | Q9Y6I3 | 460 |
| EPN2_HUMAN | O95208 | 339 |
| ERC6L_HUMAN | Q2NKX8 | 801 |
| ERCC6_HUMAN | Q03468 | 52 |
| ERF_HUMAN | P50548 | 191 |
| ERF3A_HUMAN | P15170 | 39 |
| ERIC1_HUMAN | Q86X53 | 276 |
| ESYT2_HUMAN | A0FGR8 | 759 |
| ETUD1_HUMAN | Q7Z2Z2 | 932 |
| EXDL2_HUMAN | Q9NVH0 | 198 |
| F101B_HUMAN | Q8N5W9 | 61 |
| F107B_HUMAN | Q9H098 | 5 |
| F117B_HUMAN | Q6P1L5 | 374 |
| F125A_HUMAN | Q96EY5 | 172 |
| F169A_HUMAN | Q9Y6X4 | 446 |
| FA13A_HUMAN | O94988 | 594 |
| FA21A_HUMAN | Q641Q2 | 1134 |
| FA21B_HUMAN | Q5SNT6 | 1046 |
| FA21C_HUMAN | Q9Y4E1 | 1113 |
| FA21D_HUMAN | Q5SRD0 | 101 |
| FA29A_HUMAN | Q7Z4H7 | 568 |
| FA44A_HUMAN | Q8NFC6 | 1483 |
| FA44A_HUMAN | Q8NFC6 | 1708 |
| FA44A_HUMAN | Q8NFC6 | 2044 |
| FAS_HUMAN | P49327 | 1165 |
| FETUA_HUMAN | P02765 | 133 |
| FIP1_HUMAN | Q6UN15 | 158 |
| FKB15_HUMAN | Q5T1M5 | 306 |
| FLI1_HUMAN | Q01543 | 20 |
| FLNA_HUMAN | P21333 | 25 |
| FLNA_HUMAN | P21333 | 1048 |
| FLNA_HUMAN | P21333 | 1336 |
| FLNA_HUMAN | P21333 | 1504 |
| FLNA_HUMAN | P21333 | 2536 |
| FLNA_HUMAN | P21333 | 34 |
| FLNB_HUMAN | O75369 | 7 |
| FLNC_HUMAN | Q14315 | 27 |
| FLNB_HUMAN | O75369 | 478 |
| FLNB_HUMAN | O75369 | 1021 |
| FLNB_HUMAN | O75369 | 1476 |
| FNBP1_HUMAN | Q96RU3 | 519 |
| FNBP4_HUMAN | Q8N3X1 | 153 |
| FNBP4_HUMAN | Q8N3X1 | 425 |
| FNBP4_HUMAN | Q8N3X1 | 777 |
| FOXJ2_HUMAN | Q9P0K8 | 212 |

TABLE 3-continued

Caspase-like cleavage sites. P4-P4' indicates the eight amino acid residues spanning the cleavage site, which is located between the fourth and fifth residues of the sequence. P1 residue indicates the residue directly preceding the cleavage site. P1' indicates the residue directly following the cleavage site. P1 residue # indicates the residue number in the full-length protein sequence corresponding to the P1 residue. Entries separated by vertical bars indicate cleavage sites found in more than one homologous protein.

| Swiss-Prot ID | Swiss-Prot acc # | P1 residue # |
|---|---|---|
| FOXK1_HUMAN | P85037 | 80 |
| FOXO3_HUMAN | O43524 | 54 |
| FOXP4_HUMAN | Q8IVH2 | 406 |
| FRAP_HUMAN | P42345 | 2459 |
| FRYL_HUMAN | O94915 | 1512 |
| FUBP1_HUMAN | Q96AE4 | 83 |
| FUBP1_HUMAN | Q96AE4 | 181 |
| FUBP1_HUMAN | Q96AE4 | 139 |
| FUBP2_HUMAN | Q92945 | 183 |
| FUBP2_HUMAN | Q92945 | 128 |
| FUBP3_HUMAN | Q96I24 | 34 |
| FUBP3_HUMAN | Q96I24 | 159 |
| FUS_HUMAN | P35637 | 355 |
| FXR2_HUMAN | P51116 | 561 |
| FYB_HUMAN | O15117 | 446 |
| FYB_HUMAN | O15117 | 655 |
| FYN_HUMAN | P06241 | 19 |
| FYTD1_HUMAN | Q96QD9 | 31 |
| THOC4_HUMAN | Q86V81 | 6 |
| FYV1_HUMAN | Q9Y2I7 | 989 |
| FYV1_HUMAN | Q9Y2I7 | 1607 |
| G3P_HUMAN | P04406 | 89 |
| GABP1_HUMAN | Q06547 | 303 |
| GABP2_HUMAN | Q8TAK5 | 304 |
| GALT_HUMAN | P07902 | 18 |
| GAPD1_HUMAN | Q14C86 | 1102 |
| GATA2_HUMAN | P23769 | 46 |
| GBF1_HUMAN | Q92538 | 368 |
| GCFC_HUMAN | Q9Y5B6 | 221 |
| GCP2_HUMAN | Q9BSJ2 | 772 |
| GCP60_HUMAN | Q9H3P7 | 15 |
| GCP60_HUMAN | Q9H3P7 | 343 |
| GDIR2_HUMAN | P52566 | 19 |
| GDIR2_HUMAN | P52566 | 55 |
| GELS_HUMAN | P06396 | 403 |
| GELS_HUMAN | P06396 | 639 |
| GEMI5_HUMAN | Q8TEQ6 | 1319 |
| GEMI8_HUMAN | Q9NWZ8 | 169 |
| GEN_HUMAN | Q17RS7 | 623 |
| GFPT1_HUMAN | Q06210 | 260 |
| GGA3_HUMAN | Q9NZ52 | 333 |
| GGA3_HUMAN | Q9NZ52 | 517 |
| GIT1_HUMAN | Q9Y2X7 | 418 |
| GIT1_HUMAN | Q9Y2X7 | 632 |
| GIT2_HUMAN | Q14161 | 625 |
| GLGB_HUMAN | Q04446 | 307 |
| GLRX3_HUMAN | O76003 | 101 |
| GLU2B_HUMAN | P14314 | 94 |
| GLU2B_HUMAN | P14314 | 101 |
| GLU2B_HUMAN | P14314 | 226 |
| GMIP_HUMAN | Q9P107 | 424 |
| GMIP_HUMAN | Q9P107 | 472 |
| GMIP_HUMAN | Q9P107 | 842 |
| GNL1_HUMAN | P36915 | 49 |
| GNL1_HUMAN | P36915 | 52 |
| GNL1_HUMAN | P36915 | 343 |
| GOGB1_HUMAN | Q14789 | 1245 |
| GOGB1_HUMAN | Q14789 | 1801 |
| GON4L_HUMAN | Q3T8J9 | 481 |
| GPKOW_HUMAN | Q92917 | 37 |
| GPKOW_HUMAN | Q92917 | 98 |
| GPN1_HUMAN | Q9HCN4 | 311 |
| GPTC8_HUMAN | Q9UKJ3 | 882 |
| GRDN_HUMAN | Q3V6T2 | 219 |
| GRDN_HUMAN | Q3V6T2 | 484 |
| GRIN1_HUMAN | Q7Z2K8 | 306 |
| GSDMD_HUMAN | P57764 | 87 |
| GSDMD_HUMAN | P57764 | 275 |
| GSTP1_HUMAN | P09211 | 91 |
| GTF2I_HUMAN | P78347 | 105 |
| H2AY_HUMAN | O75367 | 172 |
| H4_HUMAN | P62805 | 25 |
| H4_HUMAN | P62805 | 69 |
| HAP28_HUMAN | Q13442 | 24 |
| HBS1L_HUMAN | Q9Y450 | 29 |
| HCLS1_HUMAN | P14317 | 26 |
| HDAC4_HUMAN | P56524 | 8 |
| HDAC4_HUMAN | P56524 | 289 |
| HDAC6_HUMAN | Q9UBN7 | 1088 |
| HDAC7_HUMAN | Q8WUI4 | 412 |
| HDC_HUMAN | Q9UBI9 | 323 |
| HDGR2_HUMAN | Q7Z4V5 | 30 |
| HDGR2_HUMAN | Q7Z4V5 | 241 |
| HECD1_HUMAN | Q9ULT8 | 1492 |
| HELLS_HUMAN | Q9NRZ9 | 22 |
| HG2A_HUMAN | P04233 | 22 |
| HIRP3_HUMAN | Q9BW71 | 110 |
| HJURP_HUMAN | Q8NCD3 | 91 |
| HMHA1_HUMAN | Q92619 | 39 |
| HMHA1_HUMAN | Q92619 | 262 |
| HMHA1_HUMAN | Q92619 | 662 |
| HMOX2_HUMAN | P30519 | 251 |
| HNRH1_HUMAN | P31943 | 340 |
| HNRH2_HUMAN | P55795 | 340 |
| HNRH3_HUMAN | P31942 | 144 |
| HNRL1_HUMAN | Q9BUJ2 | 96 |
| HNRL2_HUMAN | Q1KMD3 | 126 |
| HNRLL_HUMAN | Q8WVV9 | 289 |
| HNRPD_HUMAN | Q14103 | 69 |
| HNRPF_HUMAN | P52597 | 251 |
| HNRPG_HUMAN | P38159 | 233 |
| HNRPG_HUMAN | P38159 | 283 |
| HNRPK_HUMAN | P61978 | 128 |
| HNRPK_HUMAN | P61978 | 346 |
| HNRPK_HUMAN | P61978 | 370 |
| HNRPL_HUMAN | P14866 | 284 |
| HNRPQ_HUMAN | O60506 | 468 |
| HOOK1_HUMAN | Q9UJC3 | 233 |
| HOOK2_HUMAN | Q96ED9 | 160 |
| HPS4_HUMAN | Q9NQG7 | 495 |
| HRX_HUMAN | Q03164 | 2384 |
| HRX_HUMAN | Q03164 | 2718 |
| HS105_HUMAN | Q92598 | 547 |
| HSP74_HUMAN | P34932 | 727 |
| HSP7C_HUMAN | P11142 | 80 |
| HTF4_HUMAN | Q99081 | 22 |
| HTSF1_HUMAN | O43719 | 33 |
| HTSF1_HUMAN | O43719 | 39 |
| HTSF1_HUMAN | O43719 | 80 |
| HUWE1_HUMAN | Q7Z6Z7 | 2017 |
| HUWE1_HUMAN | Q7Z6Z7 | 2359 |
| HUWE1_HUMAN | Q7Z6Z7 | 2473 |
| HUWE1_HUMAN | Q7Z6Z7 | 2930 |
| HUWE1_HUMAN | Q7Z6Z7 | 3079 |
| HUWE1_HUMAN | Q7Z6Z7 | 3664 |
| I2BP2_HUMAN | Q7Z5L9 | 495 |
| I5P2_HUMAN | P32019 | 263 |
| IASPP_HUMAN | Q8WUF5 | 294 |
| ICAL_HUMAN | P20810 | 233 |
| ICAL_HUMAN | P20810 | 348 |
| ICAL_HUMAN | P20810 | 513 |
| ICAL_HUMAN | P20810 | 659 |
| IF2BL_HUMAN | A6NK07 | 118 |
| IF2B_HUMAN | P20042 | |

TABLE 3-continued

Caspase-like cleavage sites. P4-P4' indicates the eight amino acid residues spanning the cleavage site, which is located between the fourth and fifth residues of the sequence. P1 residue indicates the residue directly preceding the cleavage site. P1' indicates the residue directly following the cleavage site. P1 residue # indicates the residue number in the full-length protein sequence corresponding to the P1 residue. Entries separated by vertical bars indicate cleavage sites found in more than one homologous protein.

| Swiss-Prot ID | Swiss-Prot acc # | P1 residue # |
|---|---|---|
| IF2P_HUMAN | O60841 | 20 |
| IF4A2_HUMAN | Q14240 | 21 |
| IF4B_HUMAN | P23588 | 50 |
| IF4B_HUMAN | P23588 | 59 |
| IF4G1_HUMAN | Q04637 | 414 |
| IF4G1_HUMAN | Q04637 | 532 |
| IF4G1_HUMAN | Q04637 | 665 |
| IF4G2_HUMAN | P78344 | 792 |
| IF4G3_HUMAN | O43432 | 478 |
| IF4H_HUMAN | Q15056 | 93 |
| IF5A1_HUMAN | P63241 | 96 |
| IF5A1_HUMAN | P63241 | 6 |
| IF5AL_HUMAN | Q6IS14 | |
| IF5A2_HUMAN | Q9GZV4 | 6 |
| IKBB_HUMAN | Q15653 | 159 |
| IKBL2_HUMAN | Q96HA7 | 498 |
| IKZF1_HUMAN | Q13422 | 367 |
| IKZF2_HUMAN | Q9UKS7 | 7 |
| IKZF5_HUMAN | Q9H5V7 | 225 |
| ILF3_HUMAN | Q12906 | 287 |
| ILF3_HUMAN | Q12906 | 439 |
| ILKAP_HUMAN | Q9H0C8 | 39 |
| IMA1_HUMAN | P52294 | 64 |
| IMA7_HUMAN | O60684 | 69 |
| IMDH2_HUMAN | P12268 | 172 |
| IN80D_HUMAN | Q53TQ3 | 678 |
| INF2_HUMAN | Q27J81 | 1051 |
| INF2_HUMAN | Q27J81 | 1146 |
| IPO9_HUMAN | Q96P70 | 963 |
| IQEC1_HUMAN | Q6DN90 | 234 |
| IQGA1_HUMAN | P46940 | 8 |
| IRF2_HUMAN | P14316 | 237 |
| IRS4_HUMAN | O14654 | 716 |
| ISY1_HUMAN | Q9ULR0 | 167 |
| IWS1_HUMAN | Q96ST2 | 347 |
| JHD3C_HUMAN | Q9H3R0 | 396 |
| JIP4_HUMAN | O60271 | 5 |
| JIP4_HUMAN | O60271 | 213 |
| JIP4_HUMAN | O60271 | 284 |
| JKIP1_HUMAN | Q96N16 | 17 |
| JMY_HUMAN | Q8N9B5 | 722 |
| JOSD3_HUMAN | Q9H5J8 | 10 |
| JSPR1_HUMAN | Q96MG2 | 12 |
| K0174_HUMAN | P53990 | 197 |
| K0232_HUMAN | Q92628 | 556 |
| K0515_HUMAN | Q5JSZ5 | 1082 |
| K0515_HUMAN | Q5JSZ5 | 1235 |
| K0831_HUMAN | Q6ZNE5 | 28 |
| K0831_HUMAN | Q6ZNE5 | 226 |
| K1462_HUMAN | Q9P266 | 1179 |
| K1543_HUMAN | Q9P1Y5 | 861 |
| K1627_HUMAN | Q9HCE5 | 29 |
| K1704_HUMAN | Q8IXQ4 | 88 |
| K1967_HUMAN | Q8N163 | 292 |
| K1967_HUMAN | Q8N163 | 618 |
| K1967_HUMAN | Q8N163 | 768 |
| KHDR1_HUMAN | Q07666 | 75 |
| KI67_HUMAN | P46013 | 173 |
| KI67_HUMAN | P46013 | 410 |
| KI67_HUMAN | P46013 | 2147 |
| KIF15_HUMAN | Q9NS87 | 1133 |
| KKCC1_HUMAN | Q8N5S9 | 32 |
| KLF12_HUMAN | Q9Y4X4 | 73 |
| KPYM_HUMAN | P14618 | 354 |
| KRI1_HUMAN | Q8N9T8 | 312 |
| KRR1_HUMAN | Q13601 | 38 |
| KS6A4_HUMAN | O75676 | 377 |
| KU86_HUMAN | P13010 | 455 |
| KU86_HUMAN | P13010 | 556 |
| LAGE3_HUMAN | Q14657 | 28 |
| LAMB1_HUMAN | P07942 | 1358 |
| LAP2A_HUMAN | P42166 | 441 |
| LAP2A_HUMAN | P42166 | 486 |
| LAP4_HUMAN | Q14160 | 501 |
| LAP4_HUMAN | Q14160 | 635 |
| LAP4_HUMAN | Q14160 | 1197 |
| LARP1_HUMAN | Q6PKG0 | 172 |
| LARP1_HUMAN | Q6PKG0 | 495 |
| LARP4_HUMAN | Q71RC2 | 573 |
| LARP5_HUMAN | Q92615 | 135 |
| LAT_HUMAN | O43561 | 167 |
| LCAP_HUMAN | Q9UIQ6 | 29 |
| LCORL_HUMAN | Q8N3X6 | 229 |
| LCOR_HUMAN | Q96JN0 | 80 |
| LIMA1_HUMAN | Q9UHB6 | 345 |
| LIN37_HUMAN | Q96GY3 | 23 |
| LIN7C_HUMAN | Q9NUP9 | 62 |
| LIPA1_HUMAN | Q13136 | 218 |
| LIPB2_HUMAN | Q8ND30 | 31 |
| LMNB1_HUMAN | P20700 | 146 |
| LMO7_HUMAN | Q8WWI1 | 962 |
| LMTK2_HUMAN | Q8IWU2 | 900 |
| LNP_HUMAN | Q9C0E8 | 368 |
| LPP_HUMAN | Q93052 | 403 |
| LRBA_HUMAN | P50851 | 1756 |
| LRBA_HUMAN | P50851 | 1784 |
| LRC47_HUMAN | Q8N1G4 | 525 |
| LRCH1_HUMAN | Q9Y2L9 | 405 |
| LRCH2_HUMAN | Q5VUJ6 | 603 |
| LRCH3_HUMAN | Q96II8 | 642 |
| LRCH4_HUMAN | O75427 | 358 |
| LRMP_HUMAN | Q12912 | 181 |
| LRRF1_HUMAN | Q32MZ4 | 415 |
| LRRF2_HUMAN | Q9Y608 | 531 |
| LSM11_HUMAN | P83369 | 305 |
| LSM3_HUMAN | P62310 | 6 |
| LSP1_HUMAN | P33241 | 102 |
| LTV1_HUMAN | Q96GA3 | 205 |
| LYRIC_HUMAN | Q86UE4 | 183 |
| M6PBP_HUMAN | O60664 | 9 |
| M6PBP_HUMAN | O60664 | 219 |
| M6PBP_HUMAN | O60664 | 222 |
| MA7D1_HUMAN | Q3KQU3 | 570 |
| MACF1_HUMAN | Q9UPN3 | 1523 |
| MACF1_HUMAN | Q9UPN3 | 1726 |
| MACF4_HUMAN | Q96PK2 | 2228 |
| MACF1_HUMAN | Q9UPN3 | 3020 |
| MACF4_HUMAN | Q96PK2 | 3522 |
| MADD_HUMAN | Q8WXG6 | 1177 |
| MAGD1_HUMAN | Q9Y5V3 | 222 |
| MAGG1_HUMAN | Q96MG7 | 41 |
| MAOM_HUMAN | P23368 | 379 |
| MAP1A_HUMAN | P78559 | 1884 |
| MAP4_HUMAN | P27816 | 8 |
| MAP4_HUMAN | P27816 | 46 |
| MAP4_HUMAN | P27816 | 151 |
| MAP4_HUMAN | P27816 | 249 |
| MAP4_HUMAN | P27816 | 327 |
| MAP9_HUMAN | Q49MG5 | 119 |
| MARE1_HUMAN | Q15691 | 116 |
| MARK1_HUMAN | Q9P0L2 | 22 |
| MATR3_HUMAN | P43243 | 187 |
| MATR3_HUMAN | P43243 | 452 |
| MATR3_HUMAN | P43243 | 680 |

TABLE 3-continued

Caspase-like cleavage sites. P4-P4' indicates the eight amino acid residues spanning the cleavage site, which is located between the fourth and fifth residues of the sequence. P1 residue indicates the residue directly preceding the cleavage site. P1' indicates the residue directly following the cleavage site. P1 residue # indicates the residue number in the full-length protein sequence corresponding to the P1 residue. Entries separated by vertical bars indicate cleavage sites found in more than one homologous protein.

| Swiss-Prot ID | Swiss-Prot acc # | P1 residue # |
|---|---|---|
| MATR3_HUMAN | P43243 | 703 |
| MATR3_HUMAN | P43243 | 763 |
| MAVS_HUMAN | Q7Z434 | 490 |
| MAX_HUMAN | P61244 | 48 |
| MBB1A_HUMAN | Q9BQG0 | 749 |
| MCM2_HUMAN | P49736 | 68 |
| MCM2_HUMAN | P49736 | 88 |
| MCM3_HUMAN | P25205 | 703 |
| MCM4_HUMAN | P33991 | 132 |
| MCM5_HUMAN | P33992 | 13 |
| MCM6_HUMAN | Q14566 | 274 |
| MDC1_HUMAN | Q14676 | 1035 |
| MDN1_HUMAN | Q9NU22 | 5127 |
| MED1_HUMAN | Q15648 | 930 |
| MED1_HUMAN | Q15648 | 1484 |
| MED14_HUMAN | O60244 | 994 |
| MED26_HUMAN | O95402 | 407 |
| MEF2C_HUMAN | Q06413 | 105 |
| METK2_HUMAN | P31153 | 39 |
| MEX3B_HUMAN | Q6ZN04 | 354 |
| MGAP_HUMAN | Q8IWI9 | 339 |
| MGAP_HUMAN | Q8IWI9 | 571 |
| MGAP_HUMAN | Q8IWI9 | 680 |
| MIA3_HUMAN | Q5JRA6 | 709 |
| MIER1_HUMAN | Q8N108 | 51 |
| MINT_HUMAN | Q96T58 | 1574 |
| MINT_HUMAN | Q96T58 | 2007 |
| MINT_HUMAN | Q96T58 | 2859 |
| MISSL_HUMAN | Q8NDC0 | 9 |
| MKL1_HUMAN | Q969V6 | 121 |
| MKL2_HUMAN | Q9ULH7 | 182 |
| MLL2_HUMAN | O14686 | 386 |
| MLL2_HUMAN | O14686 | 1865 |
| MLL3_HUMAN | Q8NEZ4 | 2188 |
| MOBL3_HUMAN | Q9Y3A3 | 34 |
| MOES_HUMAN | P26038 | 114 |
| MORC3_HUMAN | Q14149 | 664 |
| MORC3_HUMAN | Q14149 | 751 |
| MOT1_HUMAN | P53985 | 469 |
| MP2K1_HUMAN | Q02750 | 16 |
| MP2K1_HUMAN | Q02750 | 282 |
| MPP10_HUMAN | O00566 | 545 |
| MPP8_HUMAN | Q99549 | 19 |
| MPP8_HUMAN | Q99549 | 501 |
| MPP8_HUMAN | Q99549 | 516 |
| MRP_HUMAN | P49006 | 63 |
| MSPD2_HUMAN | Q8NHP6 | 274 |
| MTA70_HUMAN | Q86U44 | 334 |
| MYH10_HUMAN | P35580 | 1160 |
| MYH10_HUMAN | P35580 | 1309 |
| MYH11_HUMAN | P35749 | 1160 |
| MYH9_HUMAN | P35579 | 1153 |
| MYH9_HUMAN | P35579 | 1375 |
| MYO9B_HUMAN | Q13459 | 1703 |
| MYPT1_HUMAN | O14974 | 885 |
| N4BP1_HUMAN | O75113 | 490 |
| NACA_HUMAN | Q13765 | 42 |
| NADAP_HUMAN | Q9BWU0 | 537 |
| NAG_HUMAN | A2RRP1 | 636 |
| NAIF1_HUMAN | Q69YI7 | 102 |
| NARF_HUMAN | Q9UHQ1 | 272 |
| NARF_HUMAN | Q9UHQ1 | 291 |
| NASP_HUMAN | P49321 | 19 |
| NASP_HUMAN | P49321 | 32 |
| NCK1_HUMAN | P16333 | 88 |
| NCOA3_HUMAN | Q9Y6Q9 | 1012 |
| NCOA5_HUMAN | Q9HCD5 | 153 |
| NCOA5_HUMAN | Q9HCD5 | 380 |
| NCOA6_HUMAN | Q14686 | 1461 |
| NCOR1_HUMAN | O75376 | 385 |
| NCOR1_HUMAN | O75376 | 555 |
| NCOR1_HUMAN | O75376 | 1826 |
| NCOR2_HUMAN | Q9Y618 | 377 |
| NCOR2_HUMAN | Q9Y618 | 1926 |
| NDRG1_HUMAN | Q92597 | 9 |
| NEB2_HUMAN | Q96SB3 | 551 |
| NED4L_HUMAN | Q96PU5 | 345 |
| NEDD1_HUMAN | Q8NHV4 | 434 |
| NEDD4_HUMAN | P46934 | 279 |
| NEK1_HUMAN | Q96PY6 | 949 |
| NEK4_HUMAN | P51957 | 380 |
| NEK9_HUMAN | Q8TD19 | 841 |
| NELFA_HUMAN | Q9H3P2 | 299 |
| NFAC1_HUMAN | O95644 | 110 |
| NFAC2_HUMAN | Q13469 | 66 |
| NFKB2_HUMAN | Q00653 | 10 |
| NFRKB_HUMAN | Q6P4R8 | 5 |
| NFRKB_HUMAN | Q6P4R8 | 496 |
| NHERF_HUMAN | O14745 | 4 |
| NIPA_HUMAN | Q86WB0 | 295 |
| NIPA_HUMAN | Q86WB0 | 449 |
| NIPBL_HUMAN | Q6KC79 | 472 |
| NKTR_HUMAN | P30414 | 959 |
| NOL1_HUMAN | P46087 | 207 |
| NOL1_HUMAN | P46087 | 230 |
| NOL5_HUMAN | Q9Y2X3 | 124 |
| NOP14_HUMAN | P78316 | 319 |
| NP1L1_HUMAN | P55209 | 57 |
| NP1L1_HUMAN | P55209 | 183 |
| NP1L4_HUMAN | Q99733 | 8 |
| NP1L4_HUMAN | Q99733 | 46 |
| NP60_HUMAN | Q49A26 | 255 |
| NPAT_HUMAN | Q14207 | 733 |
| NPM_HUMAN | P06748 | 6 |
| NS1BP_HUMAN | Q9Y6Y0 | 238 |
| NSBP1_HUMAN | P82970 | 57 |
| NSUN2_HUMAN | Q08J23 | 108 |
| NSUN2_HUMAN | Q08J23 | 499 |
| NSUN2_HUMAN | Q08J23 | 664 |
| NU153_HUMAN | P49790 | 358 |
| NUCB2_HUMAN | P80303 | 237 |
| NUCB2_HUMAN | P80303 | 258 |
| NUCKS_HUMAN | Q9H1E3 | 29 |
| NUCL_HUMAN | P19338 | 636 |
| NUDC3_HUMAN | Q8IVD9 | 119 |
| NUDC3_HUMAN | Q8IVD9 | 125 |
| NUFP2_HUMAN | Q7Z417 | 451 |
| NUMA1_HUMAN | Q14980 | 1747 |
| NUMA1_HUMAN | Q14980 | 1829 |
| NUP43_HUMAN | Q8NFH3 | 58 |
| NUP50_HUMAN | Q9UKX7 | 126 |
| NUP93_HUMAN | Q8N1F7 | 157 |
| ODPB_HUMAN | P11177 | 37 |
| OFD1_HUMAN | O75665 | 853 |
| ORAV1_HUMAN | Q8WV07 | 9 |
| OSBL8_HUMAN | Q9BZF1 | 806 |
| OTU6B_HUMAN | Q8N6M0 | 80 |
| OTUD4_HUMAN | Q01804 | 9 |
| OXR1_HUMAN | Q8N573 | 449 |
| P4R3A_HUMAN | Q6IN85 | 692 |
| P66B_HUMAN | Q8WXI9 | 344 |
| PA24A_HUMAN | P47712 | 522 |
| PABP2_HUMAN | Q86U42 | 111 |
| PAIRB_HUMAN | Q8NC51 | 337 |

TABLE 3-continued

Caspase-like cleavage sites. P4-P4' indicates the eight amino acid residues spanning the cleavage site, which is located between the fourth and fifth residues of the sequence. P1 residue indicates the residue directly preceding the cleavage site. P1' indicates the residue directly following the cleavage site. P1 residue # indicates the residue number in the full-length protein sequence corresponding to the P1 residue. Entries separated by vertical bars indicate cleavage sites found in more than one homologous protein.

| Swiss-Prot ID | Swiss-Prot acc # | P1 residue # |
|---|---|---|
| PAK1_HUMAN | Q13153 | 90 |
| PAK2_HUMAN | Q13177 | 89 |
| PAK2_HUMAN | Q13177 | 148 |
| PALLD_HUMAN | Q8WX93 | 432 |
| PARG_HUMAN | Q86W56 | 256 |
| PARP1_HUMAN | P09874 | 72 |
| PARP1_HUMAN | P09874 | 214 |
| PAWR_HUMAN | Q96IZ0 | 131 |
| PAXI_HUMAN | P49023 | 5 |
| PAXI_HUMAN | P49023 | 102 |
| PAXI_HUMAN | P49023 | 335 |
| PB1_HUMAN | Q86U86 | 21 |
| PCBP1_HUMAN | Q15365 | 203 |
| PCBP1_HUMAN | Q15365 | 220 |
| PCBP1_HUMAN | Q15365 | 275 |
| PCBP2_HUMAN | Q15366 | 282 |
| PCF11_HUMAN | O94913 | 1288 |
| PCM1_HUMAN | Q15154 | 193 |
| PCM1_HUMAN | Q15154 | 1551 |
| PCNT_HUMAN | O95613 | 80 |
| PDIP3_HUMAN | Q9BY77 | 234 |
| PDLI1_HUMAN | O00151 | 54 |
| PDXD1_HUMAN | Q6P996 | 584 |
| PEBB_HUMAN | Q13951 | 120 |
| PFTK1_HUMAN | O94921 | 56 |
| PGK1_HUMAN | P00558 | 68 |
| PGK1_HUMAN | P00558 | 98 |
| PGK1_HUMAN | P00558 | 285 |
| PGK1_HUMAN | P00558 | 159 |
| PGK2_HUMAN | P07205 | |
| PHAR4_HUMAN | Q8IZ21 | 20 |
| PHF3_HUMAN | Q92576 | 1099 |
| PHF3_HUMAN | Q92576 | 1157 |
| PHF3_HUMAN | Q92576 | 1397 |
| PHF3_HUMAN | Q92576 | 1626 |
| PHTNS_HUMAN | Q6NYC8 | 495 |
| PI4KB_HUMAN | Q9UBF8 | 488 |
| PIAS1_HUMAN | O75925 | 100 |
| PICAL_HUMAN | Q13492 | 276 |
| PITM1_HUMAN | O00562 | 378 |
| PJA2_HUMAN | O43164 | 86 |
| PKHG1_HUMAN | Q9ULL1 | 435 |
| PKP4_HUMAN | Q99569 | 803 |
| PLCG1_HUMAN | P19174 | 770 |
| PLDN_HUMAN | Q9UL45 | 10 |
| POGZ_HUMAN | Q7Z3K3 | 27 |
| POMP_HUMAN | Q9Y244 | 12 |
| PP1RA_HUMAN | Q96QC0 | 293 |
| PP1RA_HUMAN | Q96QC0 | 366 |
| PP1RA_HUMAN | Q96QC0 | 376 |
| PP4R1_HUMAN | Q8TF05 | 444 |
| PPIA_HUMAN | P62937 | 9 |
| PPIL4_HUMAN | Q8WUA2 | 232 |
| PPR3D_HUMAN | O95685 | 31 |
| PR40A_HUMAN | O75400 | 133 |
| PRD15_HUMAN | P57071 | 1269 |
| PRKDC_HUMAN | P78527 | 3211 |
| PROF1_HUMAN | P07737 | 14 |
| PROF1_HUMAN | P07737 | 19 |
| PROF1_HUMAN | P07737 | 81 |
| PRP17_HUMAN | O60508 | 55 |
| PRP17_HUMAN | O60508 | 190 |
| PRP17_HUMAN | O60508 | 204 |
| PRP31_HUMAN | Q8WWY3 | 386 |
| PRR12_HUMAN | Q9ULL5 | 115 |
| PRR3_HUMAN | P79522 | 31 |
| PRS10_HUMAN | P62333 | 265 |
| PRS6A_HUMAN | P17980 | 27 |
| PRS6A_HUMAN | P17980 | 318 |
| PRS6B_HUMAN | P43686 | 297 |
| PRS8_HUMAN | P62195 | 252 |
| PSA5_HUMAN | P28066 | 71 |
| PSA7L_HUMAN | Q8TAA3 | 15 |
| PSA7_HUMAN | O14818 | 13 |
| PSB1_HUMAN | P20618 | 47 |
| PSB4_HUMAN | P28070 | 29 |
| PSB7_HUMAN | Q99436 | 53 |
| PSD12_HUMAN | O00232 | 19 |
| PSD4_HUMAN | Q8NDX1 | 82 |
| PSD4_HUMAN | Q8NDX1 | 535 |
| PSIP1_HUMAN | O75475 | 30 |
| PSIP1_HUMAN | O75475 | 433 |
| PSME3_HUMAN | P61289 | 77 |
| PTBP1_HUMAN | P26599 | 139 |
| PTBP1_HUMAN | P26599 | 172 |
| PTCA_HUMAN | Q14761 | 116 |
| PTCA_HUMAN | Q14761 | 120 |
| PTMA_HUMAN | P06454 | 7 |
| PTN3_HUMAN | P26045 | 471 |
| PUR2_HUMAN | P22102 | 205 |
| PUR2_HUMAN | P22102 | 225 |
| PUR2_HUMAN | P22102 | 443 |
| PUR6_HUMAN | P22234 | 26 |
| PUR6_HUMAN | P22234 | 319 |
| PUR9_HUMAN | P31939 | 339 |
| PUS7_HUMAN | Q96PZ0 | 22 |
| PUS7_HUMAN | Q96PZ0 | 50 |
| PWP2A_HUMAN | Q96N64 | 55 |
| PYR1_HUMAN | P27708 | 1138 |
| QKI_HUMAN | Q96PU8 | 74 |
| QN1_HUMAN | Q5TB80 | 247 |
| QSER1_HUMAN | Q2KHR3 | 1321 |
| QSK_HUMAN | Q9Y2K2 | 383 |
| R3HD1_HUMAN | Q15032 | 499 |
| RA1L3_HUMAN | P0C7M2 | 69 |
| ROA1_HUMAN | P09651 | |
| RA1L3_HUMAN | P0C7M2 | 157 |
| ROA1_HUMAN | P09651 | |
| RAD21_HUMAN | O60216 | 128 |
| RAD21_HUMAN | O60216 | 279 |
| RADIL_HUMAN | Q96JH8 | 841 |
| RANG_HUMAN | P43487 | 127 |
| RB_HUMAN | P06400 | 346 |
| RB3GP_HUMAN | Q15042 | 252 |
| RBBP4_HUMAN | Q09028 | 361 |
| RBBP7_HUMAN | Q16576 | 360 |
| RBBP6_HUMAN | Q7Z6E9 | 972 |
| RBBP6_HUMAN | Q7Z6E9 | 1267 |
| RBBP6_HUMAN | Q7Z6E9 | 1678 |
| RBBP7_HUMAN | Q16576 | 93 |
| RBBP7_HUMAN | Q16576 | 98 |
| RBBP8_HUMAN | Q99708 | 742 |
| RBM15_HUMAN | Q96T37 | 750 |
| RBM16_HUMAN | Q9UPN6 | 380 |
| RBM16_HUMAN | Q9UPN6 | 775 |
| RBM25_HUMAN | P49756 | 633 |
| RBM26_HUMAN | Q5T8P6 | 280 |
| RBM26_HUMAN | Q5T8P6 | 431 |
| RBM27_HUMAN | Q9P2N5 | 487 |
| RBM28_HUMAN | Q9NW13 | 244 |
| RBM33_HUMAN | Q96EV2 | 998 |
| RBM39_HUMAN | Q14498 | 331 |
| RBM8A_HUMAN | Q9Y5S9 | 6 |
| RBM8A_HUMAN | Q9Y5S9 | 55 |

TABLE 3-continued

Caspase-like cleavage sites. P4-P4' indicates the eight amino acid residues spanning the cleavage site, which is located between the fourth and fifth residues of the sequence. P1 residue indicates the residue directly preceding the cleavage site. P1' indicates the residue directly following the cleavage site. P1 residue # indicates the residue number in the full-length protein sequence corresponding to the P1 residue. Entries separated by vertical bars indicate cleavage sites found in more than one homologous protein.

| Swiss-Prot ID | Swiss-Prot acc # | P1 residue # |
|---|---|---|
| RBM9_HUMAN | O43251 | 102 |
| RBP2_HUMAN | P49792 | 1157 |
| RBP2_HUMAN | P49792 | 2490 |
| RBP2_HUMAN | P49792 | 2860 |
| RBP2_HUMAN | P49792 | 3131 |
| RBP2_HUMAN | P49792 | 2306 |
| RGPD1_HUMAN | Q68DN6 | 1315 |
| RGPD3_HUMAN | A6NKT7 | 1331 |
| RGPD4_HUMAN | Q7Z3J3 | 1331 |
| RGPD5_HUMAN | Q99666 | 1330 |
| RGPD6_HUMAN | Q53T03 | 1330 |
| RGPD8_HUMAN | O14715 | 320 |
| RBP2_HUMAN | P49792 | 2236 |
| RGPD3_HUMAN | A6NKT7 | 1261 |
| RGPD4_HUMAN | Q7Z3J3 | 1261 |
| RGPD5_HUMAN | Q99666 | 1260 |
| RGPD6_HUMAN | Q53T03 | 1260 |
| RGPD8_HUMAN | O14715 | 250 |
| RBP56_HUMAN | Q92804 | 140 |
| RBTN1_HUMAN | P25800 | 8 |
| RBY1B_HUMAN | A6NDE4 | 466 |
| RBY1F_HUMAN | Q15415 | 466 |
| RBY1H_HUMAN | Q15378 | 326 |
| RCC2_HUMAN | Q9P258 | 60 |
| RCN2_HUMAN | Q14257 | 203 |
| RCOR2_HUMAN | Q8IZ40 | 391 |
| RD23B_HUMAN | P54727 | 165 |
| RED_HUMAN | Q13123 | 108 |
| RED_HUMAN | Q13123 | 324 |
| REL_HUMAN | Q04864 | 86 |
| RENT1_HUMAN | Q92900 | 75 |
| REPS1_HUMAN | Q96D71 | 386 |
| REPS1_HUMAN | Q96D71 | 459 |
| REPS1_HUMAN | Q96D71 | 465 |
| REQU_HUMAN | Q92785 | 115 |
| REQU_HUMAN | Q92785 | 243 |
| REST_HUMAN | Q13127 | 941 |
| RFC1_HUMAN | P35251 | 167 |
| RFC1_HUMAN | P35251 | 723 |
| RFX7_HUMAN | Q2KHR2 | 479 |
| RGAP1_HUMAN | Q9H0H5 | 273 |
| RGPD1_HUMAN | Q68DN6 | 1499 |
| RGPD2_HUMAN | P0C839 | 764 |
| RGPD3_HUMAN | A6NKT7 | 1515 |
| RGPD4_HUMAN | Q7Z3J3 | 1515 |
| RGPD5_HUMAN | Q99666 | 1514 |
| RGPD6_HUMAN | Q53T03 | 1514 |
| RGPD8_HUMAN | O14715 | 504 |
| RGS10_HUMAN | O43665 | 12 |
| RGS10_HUMAN | O43665 | 14 |
| RHG04_HUMAN | P98171 | 403 |
| RHG25_HUMAN | P42331 | 387 |
| RHG25_HUMAN | P42331 | 397 |
| RHG30_HUMAN | Q7Z6I6 | 363 |
| RHG30_HUMAN | Q7Z6I6 | 592 |
| RHG30_HUMAN | Q7Z6I6 | 907 |
| RHGBA_HUMAN | Q6P4F7 | 256 |
| RHOA_HUMAN | P61586 | 90 |
| RHOC_HUMAN | P08134 | |
| RIF1_HUMAN | Q5UIP0 | 1809 |
| RIF1_HUMAN | Q5UIP0 | 2000 |
| RIMB1_HUMAN | O95153 | 44 |
| RIMB1_HUMAN | O95153 | 1807 |
| RING1_HUMAN | Q06587 | 31 |
| RIOK1_HUMAN | Q9BRS2 | 129 |
| RIPK1_HUMAN | Q13546 | 558 |
| RIR2_HUMAN | P31350 | 29 |
| RL17_HUMAN | P18621 | 110 |
| RL5_HUMAN | P46777 | 136 |
| RL5_HUMAN | P46777 | 168 |
| RN168_HUMAN | Q8IYW5 | 250 |
| RN213_HUMAN | Q63HN8 | 355 |
| RN219_HUMAN | Q5W0B1 | 433 |
| RN220_HUMAN | Q5VTB9 | 413 |
| RNF5_HUMAN | Q99942 | 8 |
| RNZ1_HUMAN | Q9H777 | 279 |
| ROA0_HUMAN | Q13151 | 62 |
| ROA0_HUMAN | Q13151 | 73 |
| ROA2_HUMAN | P22626 | 76 |
| ROA2_HUMAN | P22626 | 130 |
| ROA3_HUMAN | P51991 | 90 |
| ROA3_HUMAN | P51991 | 115 |
| ROA3_HUMAN | P51991 | 178 |
| ROCK1_HUMAN | Q13464 | 1113 |
| RPAP3_HUMAN | Q9H6T3 | 124 |
| RPAP3_HUMAN | Q9H6T3 | 451 |
| RPB9_HUMAN | P36954 | 4 |
| RPC4_HUMAN | P05423 | 131 |
| RPC5_HUMAN | Q9NVU0 | 543 |
| RPGF6_HUMAN | Q8TEU7 | 1282 |
| RREB1_HUMAN | Q92766 | 1173 |
| RRMJ3_HUMAN | Q8IY81 | 346 |
| RRP12_HUMAN | Q5JTH9 | 556 |
| RRP12_HUMAN | Q5JTH9 | 1161 |
| RRP1B_HUMAN | Q14684 | 275 |
| RS20_HUMAN | P60866 | 5 |
| RS23_HUMAN | P62266 | 88 |
| RS28_HUMAN | P62857 | 54 |
| RS3_HUMAN | P23396 | 32 |
| RSRC1_HUMAN | Q96IZ7 | 238 |
| RTF1_HUMAN | Q92541 | 140 |
| RTN4_HUMAN | Q9NQC3 | 84 |
| RTN4_HUMAN | Q9NQC3 | 905 |
| RU1C_HUMAN | P09234 | 10 |
| RU2A_HUMAN | P09661 | 45 |
| RUSD2_HUMAN | Q8IZ73 | 441 |
| RUXF_HUMAN | P62306 | 52 |
| S11IP_HUMAN | Q8N1F8 | 372 |
| S12A2_HUMAN | P55011 | 66 |
| S2546_HUMAN | Q96AG3 | 10 |
| S30BP_HUMAN | Q9UHR5 | 44 |
| SAFB1_HUMAN | Q15424 | 146 |
| SAFB1_HUMAN | Q15424 | 262 |
| SAFB2_HUMAN | Q14151 | 261 |
| SAFB1_HUMAN | Q15424 | 360 |
| SAFB2_HUMAN | Q14151 | 359 |
| SAFB1_HUMAN | Q15424 | 796 |
| SAFB2_HUMAN | Q14151 | 820 |
| SAFB2_HUMAN | Q14151 | 153 |
| SAFB2_HUMAN | Q14151 | 183 |
| SAHH2_HUMAN | O43865 | 5 |
| SAHH2_HUMAN | O43865 | 73 |
| SAHH2_HUMAN | O43865 | 83 |
| SAHH3_HUMAN | Q96HN2 | 109 |
| SAM4B_HUMAN | Q5PRF9 | 412 |
| SAP_HUMAN | P07602 | 312 |
| SAP_HUMAN | P07602 | 405 |
| SAPS1_HUMAN | Q9UPN7 | 358 |
| SASH3_HUMAN | O75995 | 55 |
| SASH3_HUMAN | O75995 | 115 |
| SATB1_HUMAN | Q01826 | 254 |
| SATT_HUMAN | P43007 | 12 |
| SC16A_HUMAN | O15027 | 341 |
| SC16A_HUMAN | O15027 | 837 |

TABLE 3-continued

Caspase-like cleavage sites. P4-P4' indicates the eight amino acid residues spanning the cleavage site, which is located between the fourth and fifth residues of the sequence. P1 residue indicates the residue directly preceding the cleavage site. P1' indicates the residue directly following the cleavage site. P1 residue # indicates the residue number in the full-length protein sequence corresponding to the P1 residue. Entries separated by vertical bars indicate cleavage sites found in more than one homologous protein.

| Swiss-Prot ID | Swiss-Prot acc # | P1 residue # |
|---|---|---|
| SC24B_HUMAN | O95487 | 295 |
| SCAM3_HUMAN | O14828 | 39 |
| SCMH1_HUMAN | Q96GD3 | 511 |
| SCO1_HUMAN | O75880 | 188 |
| SCOC_HUMAN | Q9UIL1 | 87 |
| SDCG1_HUMAN | O60524 | 779 |
| SEC13_HUMAN | P55735 | 14 |
| SEC20_HUMAN | Q12981 | 32 |
| SENP6_HUMAN | Q9GZR1 | 49 |
| SEPT9_HUMAN | Q9UHD8 | 282 |
| SETD2_HUMAN | Q9BYW2 | 647 |
| SETD2_HUMAN | Q9BYW2 | 1169 |
| SETX_HUMAN | Q7Z333 | 1534 |
| SF01_HUMAN | Q15637 | 448 |
| SF3A1_HUMAN | Q15459 | 32 |
| SF3A1_HUMAN | Q15459 | 503 |
| SF3B1_HUMAN | O75533 | 34 |
| SF3B2_HUMAN | Q13435 | 291 |
| SF3B2_HUMAN | Q13435 | 753 |
| SF3B4_HUMAN | Q15427 | 12 |
| SFPQ_HUMAN | P23246 | 525 |
| SFR14_HUMAN | Q8IX01 | 732 |
| SFR14_HUMAN | Q8IX01 | 901 |
| SFR14_HUMAN | Q8IX01 | 922 |
| SFRIP_HUMAN | Q99590 | 407 |
| SFRS2_HUMAN | Q01130 | 70 |
| SFRS2_HUMAN | Q01130 | 73 |
| SFRS3_HUMAN | P84103 | 4 |
| SFRS5_HUMAN | Q13243 | 52 |
| SFRS6_HUMAN | Q13247 | 167 |
| SGOL1_HUMAN | Q5FBB7 | 206 |
| SH2D3_HUMAN | Q8N5H7 | 375 |
| SHOT1_HUMAN | A0MZ66 | 129 |
| SIPA1_HUMAN | Q96FS4 | 814 |
| SIX4_HUMAN | Q9UIU6 | 296 |
| SKI_HUMAN | P12755 | 527 |
| SKT_HUMAN | Q5T5P2 | 609 |
| SLD5_HUMAN | Q9BRT9 | 6 |
| SLK_HUMAN | Q9H2G2 | 403 |
| SLMAP_HUMAN | Q14BN4 | 464 |
| SLU7_HUMAN | O95391 | 7 |
| SMC2_HUMAN | O95347 | 1116 |
| SMCA4_HUMAN | P51532 | 1381 |
| SMCE1_HUMAN | Q969G3 | 264 |
| SMHD1_HUMAN | A6NHR9 | 5 |
| SMRC2_HUMAN | Q8TAQ2 | 814 |
| SMRD2_HUMAN | Q92925 | 135 |
| SNPC4_HUMAN | Q5SXM2 | 1168 |
| SNX12_HUMAN | Q9UMY4 | 21 |
| SNX2_HUMAN | O60749 | 84 |
| SNX29_HUMAN | Q8TEQ0 | 182 |
| SNX3_HUMAN | O60493 | 32 |
| SNX6_HUMAN | Q9UNH7 | 10 |
| SOBP_HUMAN | A7XYQ1 | 298 |
| SODC_HUMAN | P00441 | 93 |
| SODC_HUMAN | P00441 | 102 |
| SON_HUMAN | P18583 | 153 |
| SON_HUMAN | P18583 | 352 |
| SON_HUMAN | P18583 | 1640 |
| SON_HUMAN | P18583 | 1718 |
| SP1_HUMAN | P08047 | 199 |
| SP110_HUMAN | Q9HB58 | 353 |
| SP3_HUMAN | Q02447 | 275 |
| SP3_HUMAN | Q02447 | 530 |
| SPAS2_HUMAN | Q86XZ4 | 145 |
| SPAST_HUMAN | Q9UBP0 | 470 |
| SPD2B_HUMAN | A1X283 | 682 |
| SPEC1_HUMAN | Q5M775 | 213 |
| SPEE_HUMAN | P19623 | 6 |
| SPF27_HUMAN | O75934 | 14 |
| SPF30_HUMAN | O75940 | 62 |
| SPG20_HUMAN | Q8N0X7 | 496 |
| SPS2L_HUMAN | Q9NUQ6 | 119 |
| SPT6H_HUMAN | Q7KZ85 | 1047 |
| SPTA2_HUMAN | Q13813 | 500 |
| SPTA2_HUMAN | Q13813 | 1478 |
| SPTN2_HUMAN | O15020 | 1752 |
| SR140_HUMAN | O15042 | 704 |
| SR140_HUMAN | O15042 | 712 |
| SR140_HUMAN | O15042 | 725 |
| SR140_HUMAN | O15042 | 737 |
| SRC_HUMAN | P12931 | 45 |
| SRCAP_HUMAN | Q6ZRS2 | 2275 |
| SRFB1_HUMAN | Q8NEF9 | 211 |
| SRP68_HUMAN | Q9UHB9 | 537 |
| SRPK1_HUMAN | Q96SB4 | 412 |
| SRRM2_HUMAN | Q9UQ35 | 147 |
| SRRM2_HUMAN | Q9UQ35 | 1149 |
| SSA27_HUMAN | O60232 | 81 |
| SSBP3_HUMAN | Q9BWW4 | 286 |
| SSF1_HUMAN | Q9NQ55 | 245 |
| SSFA2_HUMAN | P28290 | 627 |
| SSH2_HUMAN | Q76I76 | 963 |
| SSRP1_HUMAN | Q08945 | 173 |
| STAP1_HUMAN | Q9ULZ2 | 170 |
| STK10_HUMAN | O94804 | 332 |
| STK24_HUMAN | Q9Y6E0 | 325 |
| STK39_HUMAN | Q9UEW8 | 435 |
| STK4_HUMAN | Q13043 | 349 |
| STRN_HUMAN | O43815 | 35 |
| STRN_HUMAN | O43815 | 436 |
| STX10_HUMAN | O60499 | 138 |
| STX10_HUMAN | O60499 | 196 |
| STX12_HUMAN | Q86Y82 | 217 |
| STX17_HUMAN | P56962 | 201 |
| STX7_HUMAN | O15400 | 204 |
| SUGT1_HUMAN | Q9Y2Z0 | 20 |
| SYAP1_HUMAN | Q96A49 | 281 |
| SYEP_HUMAN | P07814 | 929 |
| SYF2_HUMAN | O95926 | 12 |
| SYG_HUMAN | P41250 | 56 |
| SYMPK_HUMAN | Q92797 | 28 |
| SYNC_HUMAN | O43776 | 409 |
| SYNE1_HUMAN | Q8NF91 | 8279 |
| SYNE2_HUMAN | Q8WXH0 | 4215 |
| SYWC_HUMAN | P23381 | 83 |
| T106B_HUMAN | Q9NUM4 | 19 |
| T106C_HUMAN | Q9BVX2 | 23 |
| T2EA_HUMAN | P29083 | 303 |
| T2FA_HUMAN | P35269 | 272 |
| TACC1_HUMAN | O75410 | 323 |
| TACC1_HUMAN | O75410 | 500 |
| TACC2_HUMAN | O95359 | 371 |
| TACC3_HUMAN | Q9Y6A5 | 21 |
| TACC3_HUMAN | Q9Y6A5 | 286 |
| TAD1L_HUMAN | Q96BN2 | 78 |
| TAF11_HUMAN | Q15544 | 34 |
| TAF7_HUMAN | Q15545 | 100 |
| TBA1A_HUMAN | Q71U36 | 33 |
| TBA1B_HUMAN | P68363 | |
| TBA1C_HUMAN | Q9BQE3 | |
| TBA3C_HUMAN | Q13748 | |
| TBA3E_HUMAN | Q6PEY2 | |
| TBA1A_HUMAN | Q71U36 | 245 |

TABLE 3-continued

Caspase-like cleavage sites. P4-P4' indicates the eight amino acid residues spanning the cleavage site, which is located between the fourth and fifth residues of the sequence. P1 residue indicates the residue directly preceding the cleavage site. P1' indicates the residue directly following the cleavage site. P1 residue # indicates the residue number in the full-length protein sequence corresponding to the P1 residue. Entries separated by vertical bars indicate cleavage sites found in more than one homologous protein.

| Swiss-Prot ID | Swiss-Prot acc # | P1 residue # |
|---|---|---|
| TBA1B_HUMAN | P68363 | |
| TBA1C_HUMAN | Q9BQE3 | |
| TBA3C_HUMAN | Q13748 | |
| TBA3E_HUMAN | Q6PEY2 | |
| TBA4A_HUMAN | P68366 | |
| TBA8_HUMAN | Q9NY65 | |
| TBB2A_HUMAN | Q13885 | 114 |
| TBB2B_HUMAN | Q9BVA1 | |
| TBB2C_HUMAN | P68371 | |
| TBB3_HUMAN | Q13509 | |
| TBB5_HUMAN | P07437 | |
| TBB2C_HUMAN | P68371 | 114 |
| TBB5_HUMAN | P07437 | |
| TBCC_HUMAN | Q15814 | 153 |
| TBCD4_HUMAN | O60343 | 272 |
| TBCD4_HUMAN | O60343 | 275 |
| TBL1R_HUMAN | Q9BZK7 | 152 |
| TBL1R_HUMAN | Q9BZK7 | 85 |
| TBL1X_HUMAN | O60907 | |
| TBL1R_HUMAN | Q9BZK7 | 152 |
| TBL1Y_HUMAN | Q9BQ87 | 162 |
| TBL1X_HUMAN | O60907 | 164 |
| TCEA1_HUMAN | P23193 | 124 |
| TCF20_HUMAN | Q9UGU0 | 1219 |
| TCOF_HUMAN | Q13428 | 1101 |
| TCOF_HUMAN | Q13428 | 1242 |
| TCPD_HUMAN | P50991 | 268 |
| TCPD_HUMAN | P50991 | 456 |
| TCPE_HUMAN | P48643 | 65 |
| TCPE_HUMAN | P48643 | 153 |
| TCPZ_HUMAN | P40227 | 404 |
| TCTP_HUMAN | P13693 | 25 |
| TDRD6_HUMAN | O60522 | 1918 |
| TEX2_HUMAN | Q8IWB9 | 96 |
| TEX2_HUMAN | Q8IWB9 | 356 |
| TF2B_HUMAN | Q00403 | 207 |
| TF2L1_HUMAN | Q9NZI6 | 22 |
| TFCP2_HUMAN | Q12800 | 42 |
| UBIP1_HUMAN | Q9NZI7 | 39 |
| TF3A_HUMAN | Q92664 | 18 |
| TF65_HUMAN | Q04206 | 97 |
| TGS1_HUMAN | Q96RS0 | 337 |
| TGS1_HUMAN | Q96RS0 | 343 |
| THOC4_HUMAN | Q86V81 | 93 |
| THOC5_HUMAN | Q13769 | 17 |
| THOP1_HUMAN | P52888 | 13 |
| TIF1A_HUMAN | O15164 | 784 |
| TIF1B_HUMAN | Q13263 | 105 |
| TIF1B_HUMAN | Q13263 | 148 |
| TIF1B_HUMAN | Q13263 | 685 |
| TIF1B_HUMAN | Q13263 | 688 |
| TIF1B_HUMAN | Q13263 | 726 |
| TIM_HUMAN | Q9UNS1 | 579 |
| TINF2_HUMAN | Q9BSI4 | 207 |
| TLK2_HUMAN | Q86UE8 | 132 |
| TM168_HUMAN | Q9H0V1 | 426 |
| TM1L2_HUMAN | Q6ZVM7 | 157 |
| TMUB1_HUMAN | Q9BVT8 | 60 |
| TNIP2_HUMAN | Q8NFZ5 | 194 |
| TNR6A_HUMAN | Q8NDV7 | 1542 |
| TOE1_HUMAN | Q96GM8 | 7 |
| TOE1_HUMAN | Q96GM8 | 373 |
| TOIP1_HUMAN | Q5JTV8 | 226 |
| TOIP1_HUMAN | Q5JTV8 | 304 |
| TOLIP_HUMAN | Q9H0E2 | 36 |
| TOM1_HUMAN | O60784 | 157 |
| TOM1_HUMAN | O60784 | 179 |
| TOM1_HUMAN | O60784 | 184 |
| TOM1_HUMAN | O60784 | 393 |
| TOP2B_HUMAN | Q02880 | 1470 |
| TP53B_HUMAN | Q12888 | 211 |
| TP53B_HUMAN | Q12888 | 317 |
| TP53B_HUMAN | Q12888 | 829 |
| TP53B_HUMAN | Q12888 | 1478 |
| TPR_HUMAN | P12270 | 1837 |
| TPR_HUMAN | P12270 | 2147 |
| TPRGL_HUMAN | Q5T0D9 | 9 |
| TR150_HUMAN | Q9Y2W1 | 574 |
| TRBP2_HUMAN | Q15633 | 234 |
| TREF1_HUMAN | Q96PN7 | 760 |
| TRI33_HUMAN | Q9UPN9 | 829 |
| TRIP4_HUMAN | Q15650 | 122 |
| TRIP4_HUMAN | Q15650 | 288 |
| TRM1L_HUMAN | Q7Z2T5 | 44 |
| TRS85_HUMAN | Q9Y2L5 | 853 |
| TSC1_HUMAN | Q92574 | 638 |
| TSR1_HUMAN | Q2NL82 | 332 |
| TTC1_HUMAN | Q99614 | 65 |
| TTC4_HUMAN | O95801 | 254 |
| TTF2_HUMAN | Q9UNY4 | 826 |
| TYB10_HUMAN | P63313 | 6 |
| TYSY_HUMAN | P04818 | 119 |
| TYY1_HUMAN | P25490 | 119 |
| U119A_HUMAN | Q13432 | 44 |
| U119B_HUMAN | A6NIH7 | 51 |
| U2AF2_HUMAN | P26368 | 128 |
| UAP1L_HUMAN | Q3KQV9 | 299 |
| UAP56_HUMAN | Q13838 | 25 |
| UBA1_HUMAN | P22314 | 427 |
| UBA3_HUMAN | Q8TBC4 | 25 |
| UBAP2_HUMAN | Q5T6F2 | 201 |
| UBAP2_HUMAN | Q5T6F2 | 262 |
| UBAP2_HUMAN | Q5T6F2 | 854 |
| UBE2O_HUMAN | Q9C0C9 | 437 |
| UBE2O_HUMAN | Q9C0C9 | 1225 |
| UBFD1_HUMAN | O14562 | 232 |
| UBN1_HUMAN | Q9NPG3 | 136 |
| UBP10_HUMAN | Q14694 | 125 |
| UBP10_HUMAN | Q14694 | 138 |
| UBP10_HUMAN | Q14694 | 217 |
| UBP14_HUMAN | P54578 | 76 |
| UBP14_HUMAN | P54578 | 227 |
| UBP19_HUMAN | O94966 | 619 |
| UBP2L_HUMAN | Q14157 | 298 |
| UBP2L_HUMAN | Q14157 | 411 |
| UBP2L_HUMAN | Q14157 | 850 |
| UBP34_HUMAN | Q70CQ2 | 3366 |
| UBP36_HUMAN | Q9P275 | 576 |
| UBP42_HUMAN | Q9H9J4 | 764 |
| UBP5_HUMAN | P45974 | 134 |
| UBP5_HUMAN | P45974 | 767 |
| UBP5_HUMAN | P45974 | 782 |
| UBP7_HUMAN | Q93009 | 50 |
| UBQL1_HUMAN | Q9UMX0 | 15 |
| UBR4_HUMAN | Q5T4S7 | 2903 |
| UBXN7_HUMAN | O94888 | 109 |
| UBXN7_HUMAN | O94888 | 400 |
| UGPA_HUMAN | Q16851 | 15 |
| UH1BL_HUMAN | A0JNW5 | 1173 |
| UHRF1_HUMAN | Q96T88 | 118 |
| URP2_HUMAN | Q86UX7 | 344 |
| USE1_HUMAN | Q9NZ43 | 129 |
| USF2_HUMAN | Q15853 | 120 |
| USO1_HUMAN | O60763 | 757 |

TABLE 3-continued

Caspase-like cleavage sites. P4-P4' indicates the eight amino acid residues spanning the cleavage site, which is located between the fourth and fifth residues of the sequence. P1 residue indicates the residue directly preceding the cleavage site. P1' indicates the residue directly following the cleavage site. P1 residue # indicates the residue number in the full-length protein sequence corresponding to the P1 residue. Entries separated by vertical bars indicate cleavage sites found in more than one homologous protein.

| Swiss-Prot ID | Swiss-Prot acc # | P1 residue # |
|---|---|---|
| UTRO_HUMAN | P46939 | 261 |
| VAMP2_HUMAN | P63027 | 68 |
| VAMP3_HUMAN | Q15836 | 51 |
| VATD_HUMAN | Q9Y5K8 | 117 |
| VIME_HUMAN | P08670 | 82 |
| VIME_HUMAN | P08670 | 85 |
| VIME_HUMAN | P08670 | 90 |
| VIME_HUMAN | P08670 | 257 |
| VIME_HUMAN | P08670 | 259 |
| VIME_HUMAN | P08670 | 331 |
| VIME_HUMAN | P08670 | 429 |
| VP13D_HUMAN | Q5THJ4 | 2610 |
| VPS4A_HUMAN | Q9UN37 | 230 |
| VRK1_HUMAN | Q99986 | 231 |
| WAPL_HUMAN | Q7Z5K2 | 154 |
| WASF1_HUMAN | Q92558 | 247 |
| WASF2_HUMAN | Q9Y6W5 | 242 |
| WASF2_HUMAN | Q9Y6W5 | 411 |
| WASH1_HUMAN | A8K0Z3 | 298 |
| WDR33_HUMAN | Q9C0J8 | 1183 |
| WDR44_HUMAN | Q5JSH3 | 83 |
| WDR55_HUMAN | Q9H6Y2 | 20 |
| WDR62_HUMAN | O43379 | 1301 |
| WDR92_HUMAN | Q96MX6 | 118 |
| WFS1_HUMAN | O76024 | 75 |
| WFS1_HUMAN | O76024 | 211 |
| WIPF1_HUMAN | O43516 | 181 |
| WNK1_HUMAN | Q9H4A3 | 652 |
| WNK1_HUMAN | Q9H4A3 | 1069 |
| WNK1_HUMAN | Q9H4A3 | 2025 |
| WRIP1_HUMAN | Q96S55 | 192 |
| WWC2_HUMAN | Q6AWC2 | 855 |
| XPA_HUMAN | P23025 | 5 |
| YAP1_HUMAN | P46937 | 111 |
| YBOX1_HUMAN | P67809 | 24 |
| YBOX1_HUMAN | P67809 | 112 |
| YIPF3_HUMAN | Q9GZM5 | 68 |
| YJ005_HUMAN | Q6ZSR9 | 117 |
| YJ005_HUMAN | Q6ZSR9 | 123 |
| YM017_HUMAN | A8MX80 | 223 |
| YTDC2_HUMAN | Q9H6S0 | 324 |
| YTHD1_HUMAN | Q9BYJ9 | 164 |
| YTHD2_HUMAN | Q9Y5A9 | 166 |
| YTHD2_HUMAN | Q9Y5A9 | 367 |
| YTHD3_HUMAN | Q7Z739 | 168 |
| ZAP70_HUMAN | P43403 | 290 |
| ZBT34_HUMAN | Q8NCN2 | 139 |
| ZBT44_HUMAN | Q8NCP5 | 157 |
| ZC11A_HUMAN | O75152 | 348 |
| ZC11A_HUMAN | O75152 | 530 |
| ZC3H4_HUMAN | Q9UPT8 | 67 |
| ZC3H4_HUMAN | Q9UPT8 | 741 |
| ZC3HD_HUMAN | Q5T200 | 159 |
| ZC3HE_HUMAN | Q6PJT7 | 523 |
| ZCCHV_HUMAN | Q7Z2W4 | 433 |
| ZCCHV_HUMAN | Q7Z2W4 | 491 |
| ZCH18_HUMAN | Q86VM9 | 361 |
| ZCHC2_HUMAN | Q9C0B9 | 234 |
| ZCHC8_HUMAN | Q6NZY4 | 343 |
| ZEB1_HUMAN | P37275 | 49 |
| ZF161_HUMAN | O43829 | 243 |
| ZFAN6_HUMAN | Q6FIF0 | 106 |
| ZFAN6_HUMAN | Q6FIF0 | 126 |
| ZFPL1_HUMAN | O95159 | 171 |
| ZFX_HUMAN | P17010 | 244 |
| ZFY16_HUMAN | Q7Z3T8 | 107 |
| ZFY16_HUMAN | Q7Z3T8 | 283 |
| ZFY16_HUMAN | Q7Z3T8 | 534 |
| ZMYM3_HUMAN | Q14202 | 255 |
| ZMYM4_HUMAN | Q5VZL5 | 928 |
| ZN143_HUMAN | P52747 | 151 |
| ZN143_HUMAN | P52747 | 182 |
| ZN200_HUMAN | P98182 | 188 |
| ZN264_HUMAN | O43296 | 159 |
| ZN277_HUMAN | Q9NRM2 | 6 |
| ZN346_HUMAN | Q9UL40 | 13 |
| ZN644_HUMAN | Q9H582 | 615 |
| ZN646_HUMAN | O15015 | 1005 |
| ZN787_HUMAN | Q6DD87 | 230 |
| ZN828_HUMAN | Q96JM3 | 585 |
| ZNF24_HUMAN | P17028 | 9 |
| ZNF76_HUMAN | P36508 | 13 |
| ZNHI2_HUMAN | Q9UHR6 | 144 |
| ZYX_HUMAN | Q15942 | 149 |

It is understood that the examples and embodiments described herein are for illustrative purposes only and that various modifications or changes in light thereof will be suggested to persons skilled in the art and are to be included within the spirit and purview of this application and scope of the appended claims. All publications, accession numbers, patents, and patent applications cited herein are hereby incorporated by reference in their entirety for all purposes.

What is claimed is:

1. A method of detecting a proteolytic polypeptide in a subject, the method comprising the steps of:
(a) obtaining a sample from a subject;
(b) contacting a proteolytic polypeptide with an antibody in said sample, wherein said antibody specifically binds said proteolytic polypeptide relative to a corresponding proteolytic cleavage junction of said proteolytic polypeptide; and
(c) detecting binding between said proteolytic polypeptide and said antibody;
wherein said proteolytic polypeptide is a sequence selected from the group consisting of SEQ ID NO:1 through SEQ ID NO:401.

2. The method of claim 1, wherein
step (b) comprises contacting a plurality of different proteolytic polypeptides with a plurality of different antibodies in said biological sample;
wherein said plurality of different proteolytic polypeptides are sequences selected from the group consisting of SEQ ID NO:1 through SEQ ID NO:401.

3. The method of claim 1, wherein said proteolytic polypeptide is selected from the group consisting of:
SISSQLGPIHPPPR (SEQ ID NO:63),
SFGGDAQADEGQAR (SEQ ID NOs:172 and 173),
GVPSDSVEAAKNASNTEK (SEQ ID NOs:198 and 199),
GVPLDATEDSKKNEPIFK (SEQ ID NO:300),
GSETPQLFTVLPEKR (SEQ ID NO:283),
GLPEEQPQTTK (SEQ ID NO:107),
GLGVARPHYGSVLDNER (SEQ ID NO:122 and 123),
GGGPGQVVDDGLEHR (SEQ ID NOs:87 and 412),
AYEPQGGSGYDYSYAGGR (SEQ ID NO:100),
ASSASSFLDSDELER (SEQ ID NOs:239 and 240),
ALYVACQGQPK (SEQ ID NO:177),
GFDVASVQQQR (SEQ ID NO:153),
GLAVTPTPVPVVGSQMTR (SEQ ID NO:349),
GQSDENKDDYTIPDEYR (SEQ ID NO:164),
GLVETPTGYIESLPR (SEQ ID NOs:195 and 196),
GVPSDSVEAAK (SEQ ID NOs:197, 198 and 199),
AINTEFK (SEQ ID NOs:366, 367, 369 and 370),
SLADAINTEFKNTR (SEQ ID NO:370),
GFDQNVNVK (SEQ ID NO:223),
GLGLSYLSSHIANVER (SEQ ID NO:73),
AINTEFKNTR (SEQ ID NOs:367 and 370),
ALKGTNESLER (SEQ ID NO:368),
AVTPGPQPTLEQLEEGGPRPLER (SEQ ID NOs:120 and 121),
AVSGQLPDPTTNPSAGKDGPSLLVVEQVR (SEQ ID NO:150),
GVPVPGSPFPLEAVAPTKPSK (SEQ ID NOs:58, 59 and 60),
GVPSDSVEAAKNASNTEKLTDQVMQNPR (SEQ ID NO:199), and
ATVGGPAPTPLLPPSATASVK (SEQ ID NO:136).

* * * * *

UNITED STATES PATENT AND TRADEMARK OFFICE
CERTIFICATE OF CORRECTION

PATENT NO. : 9,493,522 B2
APPLICATION NO. : 13/016710
DATED : November 15, 2016
INVENTOR(S) : James A. Wells et al.

It is certified that error appears in the above-identified patent and that said Letters Patent is hereby corrected as shown below:

In the Specification

Replace the Government Support clause in Column 1, Lines 19-22 of the instant patent with the following statement:

--This invention was made with Government support under grant nos. F32 GM074458, R01 GM081051 and R01 CA154802, awarded by the National Institutes of Health. The Government has certain rights in the invention.--

Signed and Sealed this
Twenty-fifth Day of April, 2017

Michelle K. Lee
*Director of the United States Patent and Trademark Office*